(12) United States Patent
Yoshino et al.

(10) Patent No.: US 7,192,968 B2
(45) Date of Patent: Mar. 20, 2007

(54) ETHYLENEDIAMINE DERIVATIVES

(75) Inventors: Toshiharu Yoshino, Tokyo (JP); Tsutomu Nagata, Tokyo (JP); Noriyasu Haginoya, Tokyo (JP); Kenji Yoshikawa, Tokyo (JP); Hideyuki Kanno, Tokyo (JP); Masatoshi Nagamochi, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/240,725

(22) PCT Filed: Apr. 5, 2001

(86) PCT No.: PCT/JP01/02945

§ 371 (c)(1),
(2), (4) Date: Jul. 30, 2003

(87) PCT Pub. No.: WO01/74774

PCT Pub. Date: Oct. 11, 2001

(65) Prior Publication Data

US 2004/0122063 A1 Jun. 24, 2004

(30) Foreign Application Priority Data

Apr. 5, 2000 (JP) ..................... 2000-108047

(51) Int. Cl.
| | |
|---|---|
| C07D 237/26 | (2006.01) |
| C07D 471/02 | (2006.01) |
| C07D 209/02 | (2006.01) |
| A61K 31/495 | (2006.01) |
| A61K 31/44 | (2006.01) |

(52) U.S. Cl. ............... 514/301; 514/302; 514/303; 514/248; 514/414; 514/416; 544/235; 544/236; 544/278; 548/113; 548/114; 548/115; 548/117; 548/118; 549/454

(58) Field of Classification Search ............... 514/414, 514/416, 301, 302, 303, 248; 548/454, 465, 548/492, 494; 544/235, 278, 236; 546/113, 546/114, 115, 117, 118

See application file for complete search history.

(56) References Cited

U.S. PATENT DOCUMENTS

| | | |
|---|---|---|
| 5,668,159 A | 9/1997 | Jin et al. |
| 5,707,994 A | 1/1998 | Ikeda et al. |
| 5,811,441 A | 9/1998 | Olson et al. |
| 5,849,736 A | 12/1998 | Wityak et al. |
| 5,852,045 A | 12/1998 | Askew et al. |
| 6,300,330 B1 | 10/2001 | Stocker et al. |
| 6,359,134 B1 | 3/2002 | Tawada et al. |
| 6,525,042 B1 | 2/2003 | Kobayashi et al. |
| 6,747,023 B1 | 6/2004 | Kobayashi et al. |

FOREIGN PATENT DOCUMENTS

| | | |
|---|---|---|
| EP | 0 937 711 | 8/1999 |
| EP | 0 937 723 | 8/1999 |
| EP | 1 102 766 | 5/2001 |
| JP | 6-174919 | 6/1994 |
| JP | 2000-86659 | 3/2000 |
| JP | 2000-086659 | 3/2000 |
| JP | 2000-302765 | 10/2000 |
| JP | 2001-11071 | 1/2001 |

(Continued)

OTHER PUBLICATIONS

Chemical Abstracts, vol. 129, Abstract No. 275469 RN=213460-06-1, etc., J. Org. Chem., vol. 63, No. 20, pp. 6762–6763 1998.
Tetrahedron Letters, vol. 39, No. 13, pp. 1713–1716 RN=205495-66-6 1998.
J. Am. Chem. Soc., vol. 119, No. 6, pp. 1484–1485 RN=187458-11-3 1997.
Tetrahedron Letters, vol. 37, No. 45, pp. 8165–8168 RN=183891-95-4, 183–97–6 1996.
J. Chromatogr., A, vol. 724, No. 1–2, pp. 79–90 RN=16191–60–6 Jun. 24, 1994.
J. Med. Chem., vol. 36, No. 23, pp. 3526–3532 RN=151227–27–9, 151226–77–6 1993.
J. Med. Chem., vol. 18, No. 11, pp. 1088–1094 RN=57154–72–0 1975.
Abstracts of Papers, Part 1, 218th ACS National Meeting, 0–8412–3685–2, Medi 29 and Medi 199, 3 pages, Aug. 22–26, 1999.
Abstracts of Papers, Part 2, 219th ACS National Meeting 0–8412–3731–X, Medi 187, 2 pages, Mar. 26–30, 2000.
Abstracts of Papers, Part 1, 220th ACS National Meeting, 0–8412–3749–2, Medi 289 and Medi 328, 3 pages, Aug. 20–24, 2000.
Abstracts of Papers, Part 2, 221st ACS National Meeting, 0–8412–3788–3, Medi 128 (with poster), 3 pages, Apr. 1–5, 2001.
Abstracts of Papers, Part 2, 226th ACS National Meeting, 0–8412–3889–8, Medi 79 (with poster), 3 pages, Sep. 7–11, 2003.

(Continued)

*Primary Examiner*—D. Margaret Seaman
(74) *Attorney, Agent, or Firm*—Oblon, Spivak, McClelland, Maier & Neustadt, P.C.

(57) ABSTRACT

The invention relates a compound represented by the formula (1):

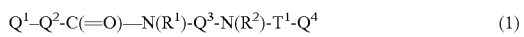

$$Q^1-Q^2-C(=O)-N(R^1)-Q^3-N(R^2)-T^1-Q^4 \quad (1)$$

wherein $R^1$ and $R^2$ represent H or the like; $Q^1$ represents an aromatic ring, heterocyclic ring or the like; $Q^2$ represents a single bond, aromatic ring, heterocyclic ring or the like; $Q^3$ represents a group

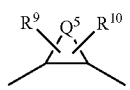

or the like, $Q^4$ represents an aromatic ring, heterocyclic ring or the like; and $T^1$ represents —CO— or —SO$_2$—, and a medicine which comprises the compound and is useful for thrombosis and embolism.

20 Claims, No Drawings

FOREIGN PATENT DOCUMENTS

| | | |
|---|---|---|
| WO | WO 93/10022 | 5/1993 |
| WO | 93/16038 | 8/1993 |
| WO | 94/20062 | 9/1994 |
| WO | WO 94/21599 | 9/1994 |
| WO | 95/11228 | 4/1995 |
| WO | 95/18111 | 7/1995 |
| WO | WO 96/10022 | 4/1996 |
| WO | 96/26187 | 8/1996 |
| WO | WO 96/26187 | 8/1996 |
| WO | WO 96/31501 | 10/1996 |
| WO | 96/37482 | 11/1996 |
| WO | 96/38426 | 12/1996 |
| WO | WO 96/40100 | 12/1996 |
| WO | WO 97/06802 | 2/1997 |
| WO | 97/14417 | 4/1997 |
| WO | WO 97/29104 | 8/1997 |
| WO | WO 97/38984 | 10/1997 |
| WO | 97/48395 | 12/1997 |
| WO | 98/6707 | 2/1998 |
| WO | WO 98/06705 | 2/1998 |
| WO | WO 98/21188 | 5/1998 |
| WO | WO 96/35956 | 8/1998 |
| WO | WO 98/35956 | 8/1998 |
| WO | 98/45262 | 10/1998 |
| WO | 98/46599 | 10/1998 |
| WO | WO 98/54164 | 12/1998 |
| WO | 98/57952 | 12/1998 |
| WO | WO 99/00121 | 1/1999 |
| WO | WO 99/00126 | 1/1999 |
| WO | WO 99/00127 | 1/1999 |
| WO | WO 99/06371 | 2/1999 |
| WO | WO 99/09027 | 2/1999 |
| WO | WO 99/16747 | 4/1999 |
| WO | 99/20606 | 4/1999 |
| WO | WO 99/20606 | 4/1999 |
| WO | 99/45939 | 9/1999 |
| WO | WO 99/57099 | 11/1999 |
| WO | WO 99/57112 | 11/1999 |
| WO | WO 99/57113 | 11/1999 |
| WO | 00/4001 | 1/2000 |
| WO | WO 00/06570 | 2/2000 |
| WO | 00/6570 | 2/2000 |
| WO | WO 00/09480 | 2/2000 |
| WO | 00/35900 | 6/2000 |
| WO | WO 00/39092 | 7/2000 |
| WO | WO 00/39111 | 7/2000 |
| WO | WO 00/39117 | 7/2000 |
| WO | WO 00/39118 | 7/2000 |
| WO | WO 00/47573 | 8/2000 |
| WO | 00/53264 | 9/2000 |
| WO | 00/59913 | 10/2000 |
| WO | WO 00/71516 | 11/2000 |
| WO | WO 00/76971 | 12/2000 |
| WO | WO 00/78749 | 12/2000 |
| WO | WO 01/17990 | 3/2001 |
| WO | WO 01/19788 | 3/2001 |
| WO | WO 01/19795 | 3/2001 |
| WO | WO 01/19798 | 3/2001 |
| WO | 01/27090 | 4/2001 |
| WO | WO 01/38309 | 5/2001 |
| WO | WO 01/64642 | 9/2001 |
| WO | WO 01/64643 | 9/2001 |
| WO | WO 02/02519 | 1/2002 |
| WO | 03/000657 | 3/2002 |
| WO | WO 02/26712 | 4/2002 |
| WO | WO 02/26720 | 4/2002 |
| WO | WO 02/26734 | 4/2002 |
| WO | WO 02/42270 | 5/2002 |
| WO | 03/000680 | 6/2002 |
| WO | 03/16302 | 8/2002 |
| WO | WO 02/060859 | 8/2002 |
| WO | WO 02/079145 | 10/2002 |
| WO | WO 02/102380 | 12/2002 |
| WO | WO 03/026652 | 4/2003 |
| WO | WO 03/045912 | 6/2003 |
| WO | WO 03/048081 | 6/2003 |
| WO | WO 03/048158 | 6/2003 |

OTHER PUBLICATIONS

S. M. Sheehan, et al., Bioorganic & Medicinal Chemistry Letters, vol. 13, pp. 2255-2259, "A Four Component Coupling Stategy for the Synthesis of D–Phenylglycinamide–Derived Non–Covalent Factor Xa Medi 289INHIBITORS", 2003.

Y. K. Yee, et al., J. Med. Chem., vol. 43, No. 5, pp. 873-882, "$N^2$–Aroylanthranilamide Inhibitores of Human Factor Xa", 2000.

D. K. Herron, et al., J. Med. Chem., vol. 43, No. 5, pp. 859-872, "1,2–Dibenzamidobenzene Inhibitors of Human Factor Xa", 2000.

C. Wu, et al., Bioorganic & Medicinal Chemistry, vol. 5, No. 10, pp. 1925-1934, "Stereochemical Influence on the Stability of Radio–Metal Complexes In Vivo. Synthesis and Evaluation of the Four Stereoisomers of 2–(p–Nitrobenzyl)–Trans–CyDTPA", 1997.

Y.–L. Chou, et al., Bioorganic & Medicinal Chemistry Letters, vol. 13, pp. 507-511, "Structure–Activity Relationships of Substituted Benzothiophene–Anthranilamide Factor Xa Inhibitors", 2003.

M. Adler, et al., Biochemistry, vol. 41, No. 52, pp. 15514-15523, "Crystal Structures of Two Potent Nonamidine Inhibitors Bound to Factors Xa", 2000.

J. J. Masters, et al., J. Med. Chem., vol. 43, No. 11, pp. 2087-2092, "Non–Amidine–Containing 1,2–Dibenzamidobenzene Inhibitors of Human Factor Xa with Potenet Anticoagulant and Antithrombotic Activity", 2000.

M. R. Wiley, et al., J. Med. Chem., vol. 43, No. 5, pp. 883-899, "Structure–Based Design of Potent, Amidine–Derived Inhibitors of Factor XA: Evaluation of Selectivity, Anticoagulant Activity, and Antithrombotic Activity", 2000.

Chemical Abstracts, vol. 129, Abstract No. 275469, RN=213460–06–1, etc., J. ORG. CHEM., vol. 63, No. 20, pages 6762-6763.

Tetrahedron Letters, vol. 39, No. 13, pages 1713-1716.

J. Am. Chem. Soc., vol. 119, No. 6, pages 1484-1485.

Tetrahedron Letters, vol. 37, No. 45, pages 6165-8168.

J. Chromatogr., A, vol. 724, No. 1-2, pages 79-90.

J. Med, Chem., vol. 36, No. 23, pages 3526-3532 RN=151227–27–9, 151226–77–6 1993.

J. Med. Chem., vol. 18, No. 11, pages 1088-1094 RN=57154–72–0.

U.S. Appl. No. 10/481,629, filed Dec. 22, 2003, Ohta, et al.

U.S. Appl. No. 10/481,262, filed Dec. 19, 2003, Ohta et al.

U.S. Appl. No. 10/240,725, filed Jul. 30, 2003, Yoshino et al., et al.

U.S. Appl. No. 10/733,344, filed Feb. 9, 2004, Ohta, et al.

U.S. Appl. No. 09/762,888, filed Feb. 12, 2001, Kobayashi, et al.

U.S. Appl. No. 10/240,725, filed Oct. 7, 2002, Yoshino, et al.

U.S. Appl. No. 10/240,725, filed Jul. 30, 2003, Yoshino, et al.

U.S. Appl. No. 10/539,995, filed Jun. 22, 2005, Nakamoto, et al.

U.S. Appl. No. 10/540,259, filed Jun. 23, 2005, Ohta, et al.

ETHYLENEDIAMINE DERIVATIVES

TECHNICAL FIELD

The present invention relates to novel compounds which inhibit activated blood coagulation factor X (hereinafter abbreviated as "FXa") to exhibit a strong anticoagulant effect and can be orally administered, and anticoagulants or agents for preventing and/or treating thrombosis or embolism, which comprise such a novel compound as an active ingredient.

BACKGROUND ART

In unstable angina, cerebral infarction, cerebral embolism, myocardial infarction, pulmonary infarction, pulmonary embolism, Buerger's disease, deep venous thrombosis, disseminated intravascular coagulation syndrome, thrombus formation after valve replacement, reocclusion after angioplasty and thrombus formation during extracorporeal circulation, hypercoagulable state is a pivotal factor. Therefore, there is a demand for development of excellent anticoagulants which have good dose responsiveness, long duration, low risk of hemorrhage and little side effects and fast onset of sufficient effects even by oral administration (Thrombosis Research, Vol. 68, pp. 507–512, 1992).

Based on the research of anticoagulants worked through various mechanism of action, it is suggested that FXa inhibitors are promising anticoagulants. A blood coagulation system comprises a series of reactions that a great amount of thrombin is produced through an amplification process by multi-stage enzyme reactions to form insoluble fibrin. In an endogenous system, activated factor IX activates into factor X on a phospholipid membrane in the presence of activated factor VIII and calcium ions after multi-stage reactions subsequent to activation of a contact factor. In an exogenous system, activated factor VII activates factor X in the presence of a tissue factor. More specifically, the activation of the factor X into FXa in the coagulation system is a crucial reaction in the formation of thrombin. The activated factor X (FXa) limitedly decomposes prothrombin to produce thrombin in the both systems. Since the produced thrombin activates coagulation factors in the upper stream, the formation of thrombin is more amplified. As described above, since the coagulation system in the upper stream of FXa is divided into the endogenous system and the exogenous system, production of FXa cannot be sufficiently inhibited by inhibiting enzymes in the coagulation system in the upper stream of FXa, leading to production of thrombin. Since the coagulation system comprises self-amplification reactions, inhibition of the coagulation system can be more efficiently achieved by inhibiting FXa in the upper stream of thrombin than the inhibition of thrombin (Thrombosis Research, Vol. 15, pp. 612–629, 1979).

An another excellent point of FXa inhibitors is a great difference between an effective dose in a thrombosis model and a dose elongating bleeding time in an experimental hemorrhagic model. From this experimental result, FXa inhibitors are considered to be anticoagulants having low risk of hemorrhage.

Various compounds have been reported as FXa inhibitors. It is known that antithrombin III and antithrombin III dependent pentasacchrides can generally not inhibit prothrombinase complexes which play a practical role in the thrombus formation in a living body (Thrombosis Research, Vol. 68, pp. 507–512, 1992; Journal of Clinical Investigation, Vol. 71, pp. 1383–1389, 1983; Mebio, Vol. 14, the August number, pp. 92–97). In addition, they do not exhibit effectiveness by oral administration. Tick anticoagulant peptide (TAP) (Science, Vol. 248, pp. 593–596, 1990) and antistasin (AST) (Journal of Biological Chemistry, Vol. 263, pp. 10162–10167, 1988) isolated from mites or leeches, which are bloodsuckers, also exhibit an anti-thrombotic effect. However, these compounds are high-molecular weight peptides and unavailable in oral administration. As described above, development of antithrombin III independent low-molecular weight FXa inhibitors which directly inhibit coagulation factors has been conducted.

It is therefore an object of the present invention to provide a novel compound which has a strong FXa-inhibiting effect and exhibits an anti-thrombotic effect quickly, sufficiently and persistently by oral administration.

DISCLOSURE OF THE INVENTION

The present inventors have investigated synthesis and pharmacological effects of novel FXa inhibitors. As a result, ethylenediamine derivatives, salts thereof, and solvates and N-oxides thereof, which exhibit strong FXa-inhibiting effect and anticoagulant effect, have been found. It has also been found that these compounds promptly, persistently and strongly inhibit FXa and exhibit strong anticoagulant effect and anti-thrombotic effect, and are hence useful as prophylactics and remedies for various diseases based on thromboembolism, thus leading to completion of the present invention.

This invention provides a compound represented by the general formula (1):

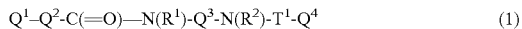

wherein $R^1$ and $R^2$, independently of each other, represent a hydrogen atom, hydroxyl group, alkyl group or alkoxy group;

$Q^1$ represents a saturated or unsaturated, 5- or 6-membered cyclic hydrocarbon group which may be substituted, a saturated or unsaturated, 5- or 6-membered heterocyclic group which may be substituted, a saturated or unsaturated, bicyclic or tricyclic fused hydrocarbon group which may be substituted, or a saturated or unsaturated, bicyclic or tricyclic fused heterocyclic group which may be substituted;

$Q^2$ represents a single bond, a linear or branched alkylene group having 1 to 6 carbon atoms, a linear or branched alkenylene group having 2 to 6 carbon atoms, a linear or branched alkynylene group having 2 to 6 carbon atoms, a group —$N(R^3)$—, in which $R^3$ means a hydrogen atom or alkyl group, a group —$N(R^4)$—$(CH_2)_m$—, in which $R^4$ means a hydrogen atom or alkyl group, and m is an integer of 1 to 6, a saturated or unsaturated, 5- or 6-membered divalent cyclic hydrocarbon group which may be substituted, a saturated or unsaturated, 5- or 6-membered divalent heterocyclic group which may be substituted, a saturated or unsaturated, divalent bicyclic or tricyclic fused hydrocarbon group which may be substituted, or a saturated or unsaturated, divalent bicyclic or tricyclic fused heterocyclic group which may be substituted;

$Q^3$ represents a group:

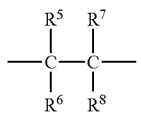

in which $R^5$, $R^6$, $R^7$ and $R^8$, independently of one another, mean a hydrogen atom, hydroxyl group, halogen atom, halogenoalkyl group, cyano group, cyanoalkyl group, acyl group, acylalkyl group, alkyl group, alkenyl group, alkynyl group, alkoxy group, alkoxyalkyl group, hydroxyalkyl group, carboxyl group, carboxyalkyl group, alkoxycarbonyl group, alkoxycarbonylalkyl group, carbamoyl group, N-alkylcarbamoyl group, N,N-dialkyl-carbamoyl group, carbamoylalkyl group, N-alkylcarbamoylalkyl group, N,N-dialkylcarbamoylalkyl group, aryl group, aralkyl group, heteroaryl group or heteroarylalkyl group, or the following group:

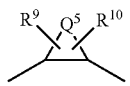

in which $Q^5$ means an alkylene group having 1 to 8 carbon atoms or an alkenylene group having 2 to 8 carbon atoms, and $R^9$ and $R^{10}$ are substituents on carbon atom(s) of a ring comprising $Q^5$ and are independently of each other a hydrogen atom, hydroxyl group, alkyl group, alkenyl group, alkynyl group, halogen atom, halogenoalkyl group, cyano group, cyanoalkyl group, amino group, aminoalkyl group, N-alkylaminoalkyl group, N,N-dialkylaminoalkyl group, acyl group, acylalkyl group, acylamino group which may be substituted, alkoxyimino group, hydroxyimino group, acylaminoalkyl group, alkoxy group, alkoxyalkyl group, hydroxyalkyl group, carboxyl group, carboxyalkyl group, alkoxycarbonyl group, alkoxycarbonylalkyl group, alkoxycarbonylalkylamino group, carboxyalkylamino group, alkoxycarbonylamino group, alkoxycarbonylaminoalkyl group, carbamoyl group, N-alkylcarbamoyl group which may have a substituent on the alkyl group, N,N-dialkylcarbamoyl group which may have a substituent on the alkyl group, N-alkenyl-carbamoyl group, N-alkenylcarbamoylalkyl group, N-alkenyl-N-alkylcarbamoyl group, N-alkenyl-N-alkylcarbamoylalkyl group, N-alkoxycarbamoyl group, N-alkyl-N-alkoxycarbamoyl group, N-alkoxycarbamoylalkyl group, N-alkyl-N-alkoxycarbamoylalkyl group, carbazoyl group which may be substituted by 1 to 3 alkyl groups, alkylsulfonyl group, alkylsulfonylalkyl group, 3- to 6-membered nitrogen-containing heterocyclic carbonyl group which may be substituted, 3- to 6-membered nitrogen-containing heterocyclic carbonylalkyl group which may be substituted, carbamoylalkyl group, N-alkylcarbamoylalkyl group which may have a substituent on the alkyl group, N,N-dialkylcarbamoylalkyl group which may have a substituent on the alkyl group, carbamoyloxyalkyl group, N-alkylcarbamoyloxyalkyl group, N,N-dialkylcarbamoyloxyalkyl group, 3- to 6-membered nitrogen-containing heterocyclic carbonyloxyalkyl group which may be substituted, aryl group, aralkyl group, heteroaryl group, heteroarylalkyl group, alkylsulfonylamino group, arylsulfonylamino group, alkylsulfonylaminoalkyl group, arylsulfonylaminoalkyl group, alkylsulfonylaminocarbonyl group, arylsulfonylaminocarbonyl group, alkylsulfonylaminocarbonylalkyl group, arylsulfonylaminocarbonylalkyl group, oxo group, carbamoyloxy group, aralkyloxy group, carboxyalkyloxy group, acyloxy group or acyloxyalkyl group, or $R^9$ and $R^{10}$, together with each other, denote an alkylene group having 1 to 5 carbon atoms, alkenylene group having 2 to 5 carbon atoms, alkylenedioxy group having 1 to 5 carbon atoms or carbonyldioxy group;

$Q^4$ represents an aryl group which may be substituted, an arylalkenyl group which may be substituted, a heteroaryl group which may be substituted, a heteroarylalkenyl group which may be substituted, a saturated or unsaturated, bicyclic or tricyclic fused hydrocarbon group which may be substituted, or a saturated or unsaturated, bicyclic or tricyclic fused heterocyclic group which may be substituted; and $T^1$ represents a carbonyl or sulfonyl group; a salt thereof, a solvate thereof, or an N-oxide thereof.

This invention also provides a medicine comprising the compound descried above, the salt thereof, the solvate thereof, or N-oxide thereof as an active ingredient.

This invention further provides a medicinal composition comprising the compound descried above, the salt thereof, the solvate thereof, or N-oxide thereof and a pharmaceutically acceptable carrier.

This invention still further provides use of the compound descried above, the salt thereof, the solvate thereof, or N-oxide thereof for preparation of a medicine.

This invention yet still further provides a method for treating thrombosis or embolism, which comprises administering the compound descried above, the salt thereof, the solvate thereof, or N-oxide thereof.

This invention yet still further provides a method for treating cerebral infarction, cerebral embolism, myocardial infarction, angina pectoris, pulmonary infarction, pulmonary embolism, Buerger's disease, deep venous thrombosis, disseminated intravascular coagulation syndrome, thrombus formation after valve or joint replacement, thrombus formation and reocclusion after angioplasty, systemic inflammatory reaction syndrome (SIRS), multiple organ disease syndrome (MODS), thrombus formation during extracorporeal circulation, or blood clotting upon blood gathering, which comprises administering the compound descried above, the salt thereof, the solvate thereof, or N-oxide thereof. This invention yet still further provides an intermediate useful for preparing the compound (1) according to the present invention.

BEST MODE FOR CARRYING OUT THE INVENTION

Substituents in the ethylenediamine derivatives according to the present invention represented by the general formula (1) will hereinafter be described.

<On Group $Q^4$>

The group $Q^4$ means an aryl group which may be substituted, an arylalkenyl group which may be substituted, a heteroaryl group which may be substituted, a heteroarylalkenyl group which may be substituted, a saturated or unsaturated, bicyclic or tricyclic fused hydrocarbon group which may be substituted, or a saturated or unsaturated, bicyclic or tricyclic fused heterocyclic group which may be substituted.

In the group $Q^4$, the aryl group may include aryl groups having 6 to 14 carbon atoms, for example, phenyl, naphthyl, anthryl and phenanthryl groups.

The arylalkenyl group means a group formed by an aryl group having 6 to 14 carbon atoms and an alkenylene group having 2 to 6 carbon atoms, and examples thereof may include a styryl group.

The heteroaryl group means a monovalent aromatic group having at least one heteroatom selected from oxygen, sulfur and nitrogen atoms, and examples thereof may include 5- or 6-membered heteroaryl groups, for example, pyridyl, furyl, thienyl, pyrimidinyl and tetrazolyl groups.

The heteroarylalkenyl group means a group formed by the above-described heteroaryl group and an alkenylene group having 2 to 6 carbon atoms, and examples thereof may include thienylethenyl and pyridylethenyl groups.

The saturated or unsaturated, bicyclic or tricyclic fused hydrocarbon group means a monovalent group derived from a saturated or unsaturated, bicyclic or tricyclic fused hydrocarbon. The saturated or unsaturated, bicyclic or tricyclic fused hydrocarbon denotes a bicyclic or tricyclic fused hydrocarbon formed by fusing 2 or 3 saturated or unsaturated, 5- or 6-membered cyclic hydrocarbons which are the same or different from each other. In this case, examples of the saturated or unsaturated, 5- or 6-membered cyclic hydrocarbons may include cyclopentane, cyclopentene, cyclohexane, cyclohexene, cyclohexadiene and benzene. Specific examples of the saturated or unsaturated, bicyclic or tricyclic fused hydrocarbon group may include indenyl, indanyl and tetrahydronaphthyl groups. Incidentally, the position of the saturated or unsaturated, bicyclic or tricyclic fused hydrocarbon group bonded to $T^1$ in the general formula (1) is not particularly limited.

The saturated or unsaturated, bicyclic or tricyclic fused heterocyclic group means a monovalent group derived from a saturated or unsaturated, bicyclic or tricyclic fused heterocyclic ring. The saturated or unsaturated, bicyclic or tricyclic fused heterocyclic ring denotes the following heterocyclic ring ①, ② or ③:

①: a bicyclic or tricyclic fused heterocyclic ring formed by fusing 2 or 3 saturated or unsaturated, 5- or 6-membered heterocyclic rings which are the same or different from each other;

②: a bicyclic or tricyclic fused heterocyclic ring formed by fusing a saturated or unsaturated, 5- or 6-membered heterocyclic ring with 1 or 2 saturated or unsaturated, 5- or 6-membered cyclic hydrocarbons; or ③: a tricyclic fused heterocyclic ring formed by fusing 2 saturated or unsaturated, 5- or 6-membered heterocyclic rings with a saturated or unsaturated, 5- or 6-membered cyclic hydrocarbon.

The position of the saturated or unsaturated, bicyclic or tricyclic fused heterocyclic group bonded to $T^1$ in the general formula (1) is not particularly limited.

The saturated or unsaturated, 5- or 6-membered heterocyclic ring denotes a heterocyclic ring having at least one heteroatom selected from oxygen, sulfur and nitrogen atoms, and specific examples thereof may include furan, pyrrole, thiophene, pyrazole, imidazole, oxazole, oxazolidine, thiazole, thiadiazole, furazane, pyrane, pyridine, pyrimidine, pyridazine, pyrrolidine, piperazine, piperidine, oxazine, oxadiazine, morpholine, thiazine, thiadiazine, thiomorpholine, tetrazole, triazole and triazine. The saturated or unsaturated, 5- or 6-membered cyclic hydrocarbon denotes the same saturated or unsaturated, 5- or 6-membered cyclic hydrocarbon as shown in the description of the saturated or unsaturated, bicyclic or tricyclic fused hydrocarbon group. Specific examples of the saturated or unsaturated, bicyclic or tricyclic fused heterocyclic group may include benzofuryl, benzothienyl, indolyl, indolinyl, isoindolyl, indazolyl, quinolyl, tetrahydroquinolyl, isoquinolyl, tetrahydroisoquinolyl, quinazolyl, dihydroquinazolyl, tetrahydroquinazolyl, quinoxalyl, tetrahydroquinoxalyl, cinnolyl, tetrahydrocinnolyl, indolizinyl, tetrahydroindolizinyl, benzothiazolyl, tetrahydrobenzothiazolyl, naphthyridinyl, tetrahydronaphthyridinyl, thienopyridyl, tetrahydrothienopyridyl, thiazolopyridyl, tetrahydrothiazolopyridyl, thiazolopyridazinyl, tetrahydrothiazolopyridazinyl, pyrrolopyridyl, tetrahydropyrrolopyridyl, pyrrolopyrimidinyl, dihydropyrrolopyrimidinyl, dihydropyridoquinazolyl, pyridopyrimidinyl, tetrahydropyridopyrimidinyl, pyranothiazolyl, dihydropyranothiazolyl, furopyridyl, tetrahydrofuropyridyl, oxazolopyridyl, tetrahydrooxazolopyridyl, oxazolopyridazinyl, tetrahydrooxazolopyridazinyl, pyrrolothiazolyl, dihydropyrrolothiazolyl, pyrrolooxazolyl and dihydropyrrolooxazolyl groups. No particular limitation is imposed on the fusing form of the fused heterocyclic group. For example, the naphthyridinyl group may be any of 1,5-, 1,6-, 1,7-, 1,8-, 2,6- and 2,7-naphthyridinyl groups, the thienopyridyl group may be any of thieno-[2,3-b]pyridyl, thieno[2,3-c]pyridyl, thieno[3,2-b]-pyridyl, thieno[3,2-c]pyridyl, thieno[3,4-b]pyridyl and thieno[3,4-c]pyridyl groups, the thiazolopyridyl group may be any of thiazolo[4,5-b]pyridyl, thiazolo[4,5-c]-pyridyl, thiazolo[5,4-b]pyridyl, thiazolo[5,4-c]pyridyl, thiazolo[3,4-a]pyridyl and thiazolo[3,2-a]pyridyl groups, the thiazolopyridazinyl group may be any of thiazolo-[4,5-c]pyridazinyl, thiazolo[4,5-d]pyridazinyl, thiazolo[5,4-c]pyridazinyl and thiazolo[3,2-b]-pyridazinyl groups, the pyrrolopyridyl may be any of pyrrolo[2,3-b]pyridyl, pyrrolo[2,3-c]pyridyl, pyrrolo[3,2-b]pyridyl, pyrrolo[3,2-c]pyridyl, pyrrolo-[3,4-b]pyridyl and pyrrolo[3,4-c]pyridyl group, the pyridopyrimidinyl group may be any of pyrido[2,3-d]-pyrimidinyl, pyrido[3,2-d]pyrimidinyl, pyrido[3,4-d]-pyrimidinyl, pyrido[4,3-d]pyrimidinyl, pyrido[1,2-c]pyrimidinyl and pyrido[1,2-a]pyrimidinyl groups, the pyranothiazolyl group may be any of pyrano[2,3-d]-thiazolyl, pyrano[4,3-d]thiazolyl, pyrano[3,4-d]-thiazolyl and pyrano[3,2-d]thiazolyl groups, the furopyridyl group may be any of furo[2,3-b]pyridyl, furo[2,3-c]pyridyl, furo[3,2-b]pyridyl, furo[3,2-c]-pyridyl, furo[3,4-b]pyridyl and furo[3,4-c]pyridyl groups, the oxazolopyridyl group may be any of oxazolo-[4,5-b]pyridyl, oxazolo[4,5-c]pyridyl, oxazolo[5,4-b]-pyridyl, oxazolo[5,4-c]pyridyl, oxazolo[3,4-a]pyridyl and oxazolo[3,2-a]pyridyl groups, the oxazolopyridazinyl group may be any of oxazolo[4,5-c]pyridazinyl, oxazolo[4,5-d]pyridazinyl, oxazolo[5,4-c]pyridazinyl and oxazolo[3,4-b]pyridazinyl groups, the pyrrolothiazolyl group may be any of pyrrolo[2,1-b]thiazolyl, pyrrolo-[1,2-c]thiazolyl, pyrrolo[2,3-d]thiazolyl, pyrrolo-[3,2-d]thiazolyl and pyrrolo[3,4-d]thiazolyl groups, and the pyrrolooxazolyl group may be any of pyrrolo[2,1-b]-oxazolyl, pyrrolo[1,2-c]oxazolyl, pyrrolo[2,3-d]oxazolyl, pyrrolo[3,2-d]oxazolyl and pyrrolo[3,4-d]oxazolyl groups. Other fusing forms than these may be allowed.

The above-described aryl groups, heteroaryl groups, arylalkenyl group, heteroarylalkenyl groups, saturated or unsaturated, bicyclic or tricyclic fused hydrocarbon groups and saturated or unsaturated, bicyclic or tricyclic fused heterocyclic groups may each have 1 to 3 substituents. Examples of the substituents may include a hydroxyl group, halogen atoms such as fluorine atom, chlorine atom, bromine atom and iodine atom, halogenoalkyl groups having 1 to 6 carbon atoms, and 1 to 3 halogen as substituents, an amino group, a cyano group, aminoalkyl groups, a nitro group, hydroxyalkyl groups (for example, hydroxymethyl group, 2-hydroxyethyl group, etc.), alkoxyalkyl groups (for example, methoxymethyl group, 2-methoxyethyl group, etc.), a carboxyl group, carboxyalkyl groups (for example, carboxymethyl group, 2-carboxyethyl group, etc.), alkoxycarbonylalkyl groups (for example, methoxycarbonylmethyl group, ethoxycarbonylmethyl group, etc.), acyl groups (for example, acetyl group, propionyl group, etc.), an amidino group, a hydroxyamidino group, linear, branched or cyclic alkyl groups (for example, methyl group, ethyl group, etc.) having 1 to 6 carbon atoms, linear, branched or cyclic alkoxy groups (for example, methoxy group, ethoxy group, etc.) having 1 to 6 carbon atoms, amidino groups (for example, methoxycarbonylamidino group, ethoxycarbonylamidino group, etc.) substituted by linear, branched or cyclic alkoxycarbonyl group having 2 to 7 carbon atoms, linear, branched or cyclic alkenyl groups (for example, vinyl group, allyl group, etc.) having 2 to 6 carbon atoms, linear or branched alkynyl groups (for example, ethynyl group, propynyl group, etc.) having 2 to 6 carbon atoms, linear, branched or cyclic alkoxycarbonyl groups (for example, methoxycarbonyl group, ethoxycarbonyl group, etc.) having 2 to 6 carbon atoms, a carbamoyl group, mono- or di-alkylamino groups (for example, ethylamino, dimethylamino and methylethylamino groups) substituted by 1 or 2 linear, branched or cyclic alkyl groups having 1 to 6 carbon atoms, and 5- or 6-membered nitrogen-containing heterocyclic groups (for example, pyrrolidino group, piperidino group, piperazino group, morpholino group, etc.).

As the group $Q^4$, are preferred the following 5 groups among the above-described groups. Namely,

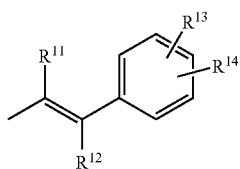

wherein $R^{11}$ and $R^{12}$, independently of each other, represent a hydrogen atom, cyano group, halogen atom, alkyl group, hydroxyalkyl group, alkoxy group, alkoxyalkyl group, carboxyl group, carboxyalkyl group, acyl group, alkoxycarbonyl group, alkoxycarbonylalkyl group, or phenyl group which may be substituted by a cyano group, hydroxyl group, halogen atom, alkyl group or alkoxy group, and $R^{13}$ and $R^{14}$, independently of each other, represent a hydrogen atom, hydroxyl group, nitro group, cyano group, halogen atom, alkyl group, alkenyl group, alkynyl group, halogenoalkyl group, hydroxyalkyl group, alkoxy group, alkoxyalkyl group, carboxyl group, carboxyalkyl group, carbamoyl group, alkoxycarbonyl group, amidino group or alkoxycarbonylalkyl group;

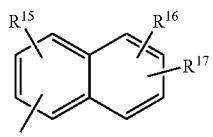

wherein $R^{15}$, $R^{16}$ and $R^{17}$, independently of one another, represent a hydrogen atom, hydroxyl group, nitro group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, alkoxycarbonyl group, amidino group or alkoxycarbonylalkyl group;

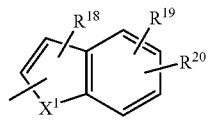

wherein $X^1$ represents $CH_2$, CH, NH, NOH, N, O or S, and $R^{18}$, $R^{19}$ and $R^{20}$, independently of one another, represent a hydrogen atom, hydroxyl group, nitro group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, alkoxycarbonyl group, amidino group or alkoxycarbonylalkyl group;

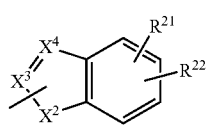

wherein $X^2$ represents NH, N, O or S, $X^3$ represents N, C or CH, $X^4$ represents N, C or CH, and $R^{21}$ and $R^{22}$, independently of each other, represent a hydrogen atom, hydroxyl group, nitro group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, alkoxycarbonyl group, amidino group or alkoxycarbonylalkyl group; and

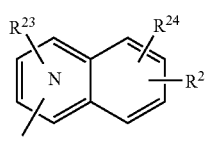

wherein N indicates that any one of carbon atoms of the ring substituted by $R^{23}$ has been substituted by a nitrogen atom, and $R^{23}$, $R^{24}$ and $R^{25}$, independently of one another, represent a hydrogen atom, hydroxyl group, nitro group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, alkoxycarbonyl group, amidino group or alkoxycarbonylalkyl group.

These groups will hereinafter be described.

In the description of $R^{11}$ to $R^{25}$, the halogen atom is a fluorine, chlorine, bromine or iodine atom, the alkyl group is a linear, branched or cyclic alkyl group having 1 to 6 carbon atoms, the alkenyl group is a linear, branched or cyclic alkenyl groups having 2 to 6 carbon atoms, the alkynyl group is a linear or branched alkynyl groups having 2 to 6 carbon atoms, the hydroxyalkyl group means the above-described alkyl group substituted by a hydroxyl group, the alkoxy group is a linear, branched or cyclic alkoxy group having 1 to 6 carbon atoms, the alkoxyalkyl group means the above-described alkyl group substituted by the above-described alkoxy group, the carboxyalkyl group means the above-described alkyl group substituted by a carboxyl group, the acyl group is an alkanoyl group having 1 to 6 carbon atom, an aroyl group such as a benzoyl or naphthoyl group, or an arylalkanoyl group with the above-described aryl group substituted on the above-described alkanoyl group, the alkoxycarbonyl group is a group composed of the above-described alkoxy group and a carbonyl group, the alkoxycarbonylalkyl group means the above-described alkyl group substituted by the above-described alkoxycarbonyl group, and the halogenoalkyl group means the above-described alkyl group substituted by 1 to 3 halogen atoms. Incidentally, in the above description, no particular limitation is imposed on the substituting position.

In the following group:

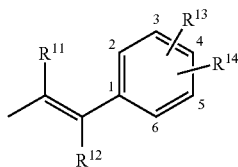

wherein $R^{11}$, $R^{12}$, $R^{13}$ and $R^{14}$ have the same meanings as defined above, and numerals 1 to 6 indicate positions, $R^{11}$ and $R^{12}$ are preferably hydrogen atoms or alkyl groups. In the case of the alkyl group, a methyl group is preferred. $R^{13}$ and $R^{14}$ are, independently of each other, preferably a hydrogen atom, cyano group, halogen atom, alkyl group, alkenyl group, alkynyl group or halogenoalkyl group. It is preferable that one of $R^{13}$ and $R^{14}$ is a hydrogen atom, and the other is a cyano group, halogen atom, alkyl group, alkenyl group, alkynyl group or halogenoalkyl group. Among others, it is particularly preferred that the other group be a halogen atom or alkynyl group. In this case, the halogen atom is preferably a fluorine, chlorine or bromine atom. As the alkynyl group, is particularly preferred an ethynyl group. As specific preferable examples of the group represented by the above formula, may be mentioned chlorostyryl, fluorostyryl, bromostyryl and ethynylstyryl groups. The position substituted by the halogen atom or alkynyl group is particularly preferably a 4-position in the above formula. As specific preferable examples thereof, may be mentioned 4-chlorostyryl, 4-fluorostyryl, 4-bromostyryl and 4-ethynylstyryl groups.

In the following group:

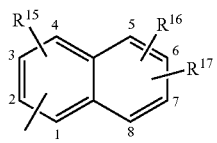

wherein $R^{15}$, $R^{16}$ and $R^{17}$ have the same meanings as defined above, and numerals 1 to 8 indicate positions, $R^{15}$, $R^{16}$ and $R^{17}$ are, independently of one another, preferably a hydrogen atom, cyano group, halogen atom, alkyl group, alkenyl group, alkynyl group or halogenoalkyl group. $R^{15}$ is preferably a hydrogen atom, alkyl group, halogen atom or hydroxyl group, with a hydrogen atom particularly preferred. It is preferable that one of $R^{16}$ and $R^{17}$ is a hydrogen atom, and the other is a cyano group, halogen atom, alkyl group, alkenyl group, alkynyl group or halogenoalkyl group. Among others, it is particularly preferred that the other group be a halogen atom or alkynyl group. In this case, the halogen atom is preferably a fluorine, chlorine or bromine atom. As the alkynyl group, is preferred an ethynyl group. In the naphthyl group, a 2-naphthyl group is preferred to a 1-naphthyl group. In the case of the 2-naphthyl group, a position substituted by a halogen atom or alkynyl group is preferably a 6- or 7-position in the above formula, with a 6-position being most preferred. These naphthyl groups are preferbly substituted by a chlorine, fluorine or bromine atom, an alkynyl group, or the like, with a group having a substituents such as a chlorine, fluorine or bromine atom, an alkynyl group, or the like at the above-described position in the above formula being particularly preferred. As specific preferable examples thereof, may be mentioned 6-chloro-2-naphthyl, 6-fluoro-2-naphthyl, 6-bromo-2-naphthyl, 6-ethynyl-2-naphthyl, 7-chloro-2-naphthyl, 7-fluoro-2-naphthyl, 7-bromo-2-naphthyl and 7-ethynyl-2-naphthyl groups.

In the following group:

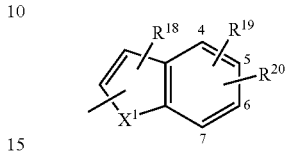

wherein $X^1$, $R^{18}$, $R^{19}$ and $R^{20}$ have the same meanings as defined above, and numerals 4 to 7 indicate positions, $X^1$ is preferably NH, NOH, N, O or S, with NH, O or S being particularly preferred. $R^{18}$ is preferably a hydrogen atom, and $R^{19}$ and $R^{20}$ are, independently of each other, preferably a hydrogen atom, cyano group, halogen atom, alkyl group, alkenyl group, alkynyl group or halogenoalkyl group. It is preferable that one of $R^{19}$ and $R^{20}$ is a hydrogen or a halogen atom, preferably fluorine atom, and the other is a cyano group, halogen atom, alkyl group, alkenyl group, alkynyl group or halogenoalkyl group. Among others, it is particularly preferred that the other group be a halogen atom, an alkyl or alkynyl group. In this case, the halogen atom is preferably a fluorine, chlorine or bromine atom. As the alkyl group, is preferred a methyl group. As the alkynyl group, is preferred an ethynyl group. The position substituted by the halogen atom, alkyl group or alkynyl group is preferably a 5- or 6-position in the above formula. As specific preferable examples of the group represented by the above formula, may be mentioned 5-chloroindolyl, 5-fluoroindolyl, 5-bromoindolyl, 5-ethynylindolyl, 5-methylindolyl, 5-chloro-4-fluoroindolyl, 6-chloroindolyl, 6-fluoroindolyl, 6-bromoindolyl, 6-ethynylindolyl, 6-methylindolyl, 5-chlorobenzothienyl, 5-fluorobenzothienyl, 5-bromobenzothienyl, 5-ethynylbenzothienyl, 5-methylbenzothienyl, 5-chloro-4-fluorobenzothienyl, 6-chlorobenzothienyl, 6-fluorobenzothienyl, 6-bromobenzothienyl, 6-ethynylbenzothienyl, 6-methylbenzothienyl, 5-chlorobenzofuryl, 5-fluorobenzofuryl, 5-bromobenzofuryl, 5-ethynylbenzofuryl, 5-methylbenzofuryl, 5-chloro-4-fluorobenzofuryl, 6-chlorobenzofuryl, 6-fluorobenzofuryl, 6-bromobenzofuryl, 6-ethynylbenzofuryl and 6-methylbenzofuryl groups. The position of the above-described substituent group bonded to $T^1$ is not particularly limited. More preferred are 5-chloroindol-2-yl, 5-fluoroindol-2-yl, 5-bromoindol-2-yl, 5-ethynylindol-2-yl, 5-methylindol-2-yl, 5-chloro-4-fluoroindol-2-yl, 6-chloroindol-2-yl, 6-fluoroindol-2-yl, 6-bromoindol-2-yl, 6-ethynylindol-2-yl, 6-methylindol-2-yl, 5-chloroindol-3-yl, 5-fluoroindol-3-yl, 5-bromoindol-3-yl, 5-ethynylindol-3-yl, 5-methylindol-3-yl, 5-chloro-4-fluoroindol-3-yl, 6-chloroindol-3-yl, 6-fluoroindol-3-yl, 6-bromoindol-3-yl, 6-ethynylindol-3-yl, 6-methylindol-3-yl, 5-chlorobenzothiophen-2-yl, 5-fluorobenzothiophen-2-yl, 5-bromobenzothiophen-2-yl, 5-ethynylbenzothiophen-2-yl, 5-methylbenzothiophen-2-yl, 5-chloro-4-fluorobenzothiophen-2-yl, 6-chlorobenzothiophen-2-yl, 6-fluorobenzothiophen-2-yl, 6-bromobenzothiophen-2-yl, 6-ethynylbenzothiophen-2-yl, 6-methylbenzothiophen-2-yl, 5-chlorobenzothiophen-3-yl, 5-fluorobenzothiophen-3-yl, 5-bromobenzothiophen-3-yl, 5-ethynylbenzothiophen-3-yl, 5-methylbenzothiophen-3-yl, 5-chloro-4-fluorobenzothiophen-3-yl, 6-chlorobenzothiophen-3-yl, 6-fluorobenzothiophen-3-yl, 6-bromobenzothiophen-3-yl, 6-ethynylbenzothiophen-3-yl, 6-methylbenzothiophen-3-yl, 5-chlorobenzofuran-2-yl, 5-fluorobenzofuran-2-yl, 5-bromobenzofuran-2-yl, 5-ethynylbenzofuran-2-yl, 5-methylbenzofuran-2-yl, 5-chloro-4-fluorobenzofuran-2-yl, 6-chlorobenzofuran-2-yl, 6-fluorobenzofuran-2-yl, 6-bromobenzofuran-2-yl, 6-ethynylbenzofuran-2-yl, 6-methylbenzofuran-2-yl, 5-chlorobenzofuran-3-yl, 5-fluorobenzofuran-3-yl, 5-bromobenzofuran-3-yl, 5-ethynylbenzofuran-3-yl, 5-methylbenzofuran-3-yl, 5-chloro-4-fluorobenzofuran-3-yl, 6-chlorobenzofuran-3-yl, 6-fluorobenzofuran-3-yl, 6-bromobenzofuran-3-yl, 6-ethynylbenzofuran-3-yl and 6-methylbenzofuran-3-yl groups, with 5-chloroindol-2-yl, 5-fluoroindol-2-yl, 5-bromoindol-2-yl, 5-ethynylindol-2-yl, 5-methyindol-2-yl, 5-chloro-4-fluoroindol-2-yl, 6-chloroindol-2-yl, 6-fluoroindol-2-yl, 6-bromoindol-2-yl, 6-ethynylindol-2-yl, 6-methyindol-2-yl, 5-chlorobenzothiophen-2-yl, 5-fluorobenzothiophen-2-yl, 5-bromobenzothiophen-2-yl, 5-ethynylbenzothiophen-2-yl, 5-methylbenzothiophen-2-yl, 5-chloro-4-fluorobenzothiophen-2-yl, 6-chlorobenzothiophen-2-yl, 6-fluorobenzothiophen-2-yl, 6-bromobenzothiophen-2-yl, 6-ethynylbenzothiophen-2-yl, 6-methylbenzothiophen-2-yl, 5-chlorobenzofuran-2-yl, 5-fluorobenzofuran-2-yl, 5-bromobenzofuran-2-yl, 5-ethynylbenzofuran-2-yl, 5-methylbenzofuran-2-yl, 5-chloro-4-fluorobenzofuran-2-yl, 6-chlorobenzofuran-2-yl, 6-fluorobenzofuran-2-yl, 6-bromobenzofuran-2-yl, 6-ethynylbenzofuran-2-yl and 6-methylbenzofuran-2-yl groups being particularly preferred.

In the following group:

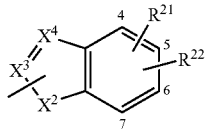

wherein $X^2$, $X^3$, $X^4$, $R^{21}$ and $R^{22}$ have the same meanings as defined above, and numerals 4 to 7 indicate positions, any one of $X^3$ and $X^4$ is preferably CH or C, particularly preferably C. $R^{21}$ and $R^{22}$ are, independently of each other, preferably a hydrogen atom, cyano group, halogen atom, alkyl group, alkenyl group, alkynyl group or halogenoalkyl group. It is preferable that one of $R^{21}$ and $R^{22}$ is a hydrogen atom, and the other is a cyano group, halogen atom, alkyl group, alkenyl group, alkynyl group or halogenoalkyl group. Among others, it is particularly preferred that the other group be a halogen atom or alkynyl group. In this case, the halogen atom is preferably a fluorine, chlorine or bromine atom. As the alkynyl group, is preferred an ethynyl group. The position substituted by the halogen atom or alkynyl group is preferably a 5- or 6-position in the above formula. As specific preferable examples of the group represented by the above formula, may be mentioned 5-chloroindazolyl, 5-fluoroindazolyl, 5-bromoindazolyl, 5-ethynylindazolyl, 6-chloroindazolyl, 6-fluoroindazolyl, 6-bromoindazolyl, 6-ethynylindazolyl, 5-chlorobenzimidazolyl, 5-fluorobenzimidazolyl, 5-bromobenzimidazolyl, 5-ethynylbenzimidazolyl, 6-chlorobenzimidazolyl, 6-fluorobenzimidazolyl, 6-bromobenzimidazolyl, 6-ethynylbenzimidazolyl, 5-chlorobenzothiazolyl, 5-fluorobenzothiazolyl, 5-bromobenzothiazolyl, 5-ethynylbenzothiazolyl, 6-chlorobenzothiazolyl, 6-fluorobenzothiazolyl, 6-bromobenzothiazolyl, 6-ethynylbenzothiazolyl, 5-chlorobenzoxazolyl, 5-fluorobenzoxazolyl, 5-bromobenzoxazolyl, 5-ethynylbenzoxazolyl, 6-chlorobenzoxazolyl, 6-fluorobenzoxazolyl, 6-bromobenzoxazolyl, 6-ethynylbenzoxazolyl, 5-chlorobenzisothiazolyl, 5-fluorobenzisothiazolyl, 5-bromobenzisothiazolyl, 5-ethynylbenzisothiazolyl, 6-chlorobenzisothiazolyl, 6-fluorobenzisothiazolyl, 6-bromobenzisothiazolyl, 6-ethynylbenzisothiazolyl, 5-chlorobenzisoxazolyl, 5-fluorobenzisoxazolyl, 5-bromobenzisoxazolyl, 5-ethynylbenzisoxazolyl, 6-chlorobenzisoxazolyl, 6-fluorobenzisoxazolyl, 6-bromobenzisoxazolyl and 6-ethynylbenzisoxazolyl groups. The position of the above-described substituent group bonded to $T^1$ is not particularly limited. More preferred are 5-chloroindazol-3-yl, 5-fluoroindazol-3-yl, 5-bromoindazol-3-yl, 5-ethynylindazol-3-yl, 6-chloroindazol-3-yl, 6-fluoroindazol-3-yl, 6-bromoindazol-3-yl, 6-ethynylindazol-3-yl, 5-chlorobenzimidazol-2-yl, 5-fluorobenzimidazol-2-yl, 5-bromobenzimidazol-2-yl, 5-ethynylbenzimidazol-2-yl, 6-chlorobenzimidazol-2-yl, 6-fluorobenzimidazol-2-yl, 6-bromobenzimidazol-2-yl, 6-ethynylbenzimidazol-2-yl, 5-chlorobenzothiazol-2-yl, 5-fluorobenzothiazol-2-yl, 5-bromobenzothiazol-2-yl, 5-ethynylbenzothiazol-2-yl, 6-chlorobenzothiazol-2-yl, 6-fluorobenzothiazol-2-yl, 6-bromobenzothiazol-2-yl, 6-ethynylbenzothiazol-2-yl, 5-chlorobenzoxazol-2-yl, 5-fluorobenzoxazol-2-yl, 5-bromobenzoxazol-2-yl, 5-ethynylbenzoxazol-2-yl, 6-chlorobenzoxazol-2-yl, 6-fluorobenzoxazol-2-yl, 6-bromobenzoxazol-2-yl, 6-ethynylbenzoxazol-2-yl, 5-chlorobenzisothiazol-3-yl, 5-fluorobenzisothiazol-3-yl, 5-bromobenzisothiazol-3-yl, 5-ethynylbenzisothiazol-3-yl, 6-chlorobenzisothiazol-3-yl, 6-fluorobenzisothiazol-3-yl, 6-bromobenzisothiazol-3-yl, 6-ethynylbenzisothiazol-3-yl, 5-chlorobenzisoxazol-3-yl, 5-fluorobenzisoxazol-3-yl, 5-bromobenzisoxazol-3-yl, 5-ethynylbenzisoxazol-3-yl, 6-chlorobenzisoxazol-3-yl, 6-fluorobenzisoxazol-3-yl, 6-bromobenzisoxazol-3-yl and 6-ethynylbenzisoxazol-3-yl groups, with 5-chlorobenzimidazol-2-yl, 5-fluorobenzimidazol-2-yl, 5-bromobenzimidazol-2-yl, 5-ethynylbenzimidazol-2-yl, 6-chlorobenzimidazol-2-yl, 6-fluorobenzimidazol-2-yl, 6-bromobenzimidazol-2-yl, 6-ethynylbenzimidazol-2-yl, 5-chlorobenzothiazol-2-yl, 5-fluorobenzothiazole-2-yl, 5-bromobenzothiazol-2-yl, 5-ethynylbenzothiazole-2-yl, 6-chlorobenzothiazol-2-yl, 6-fluorobenzothiazole-2-yl, 6-bromobenzothiazol-2-yl, 6-ethynylbenzothiazole-2-yl, 5-chlorobenzoxazol-2-yl, 5-fluorobenzoxazol-2-yl, 5-bromobenzoxazol-2-yl, 5-ethynylbenzoxazol-2-yl, 6-chlorobenzoxazol-2-yl, 6-fluorobenzoxazol-2-yl, 6-bromobenzoxazol-2-yl and 6-ethynylbenzoxazol-2-yl groups being particularly preferred.

In the following group:

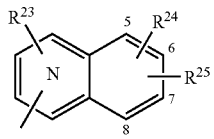

wherein N indicates that any one of carbon atoms of the ring substituted by $R^{23}$ has been substituted by a nitrogen atom, $R^{23}$, $R^{24}$ and $R^{25}$ have the same meanings as defined above, and numerals 5 to 8 indicate positions, $R^{23}$, $R^{24}$ and $R^{25}$ are, independently of each other, preferably a hydrogen atom, cyano group, halogen atom, alkyl group, alkenyl group, alkynyl group or halogenoalkyl group. $R^{23}$ is particularly preferably a hydrogen atom. It is preferable that one of $R^{24}$ and $R^{25}$ is a hydrogen atom, and the other is a cyano group, halogen atom, alkyl group, alkenyl group, alkynyl group or halogenoalkyl group. Among others, it is particularly preferred that the other group be a halogen atom or alkynyl group. In this case, the halogen atom is preferably a fluorine, chlorine or bromine atom. As the alkynyl group, is preferred an ethynyl group. The position substituted by the halogen atom or alkynyl group is preferably a 6- or 7-position in the above formula. As specific preferable examples thereof, may be mentioned quinolinyl and isoquinolinyl groups. More preferred are 6-chloroquinolinyl, 6-fluoroquinolinyl, 6-bromoquinolinyl, 6-ethynylquinolinyl, 6-chloroisoquinolinyl, 6-fluoroisoquinolinyl, 6-bromoisoquinolinyl and 6-ethynylisoquinolinyl groups, with 6-chloroquinolin-2-yl, 6-fluoroquinolin-2-yl, 6-bromoquinolin-2-yl, 6-ethynylquinolin-2-yl, 6-chloroquinolin-3-yl, 6-fluoroquinolin-3-yl, 6-bromoquinolin-3-yl, 6-ethynylquinolin-3-yl, 7-chloroquinolin-2-yl, 7-fluoroquinolin-2-yl, 7-bromoquinolin-2-yl, 7-ethynylquinolin-2-yl, 7-chloroquinolin-3-yl, 7-fluoroquinolin-3-yl, 7-bromoquinolin-3-yl, 7-ethynylquinolin-3-yl, 6-chloroisoquinolin-3-yl, 6-fluoroisoquinolin-3-yl, 6-bromoisoquinolin-3-yl, 6-ethynylisoquinolin-3-yl, 7-chloroisoquinolin-3-yl, 7-fluoroisoquinolin-3-yl, 7-bromoisoquinolin-3-yl and 7-ethynylisoquinolin-3-yl groups being particularly preferred.

<On Group $Q^1$>

In the present invention, $Q^1$ means a saturated or unsaturated, 5- or 6-membered cyclic hydrocarbon group which may be substituted, a saturated or unsaturated, 5- or 6-membered heterocyclic group which may be substituted, a saturated or unsaturated, bicyclic or tricyclic fused hydrocarbon group which may be substituted, or a saturated or unsaturated, bicyclic or tricyclic fused heterocyclic group which may be substituted.

As examples of the saturated or unsaturated, 5- or 6-membered cyclic hydrocarbon group, may be mentioned cyclopentyl, cyclopentenyl, cyclohexyl, cyclohexenyl and phenyl groups. Cyclopentyl, cyclohexyl and phenyl groups are preferred, with a phenyl group being particularly preferred.

The saturated or unsaturated, 5- or 6-membered heterocyclic group means a monovalent heterocyclic group having at least one heteroatom selected from oxygen, sulfur and nitrogen atoms, and examples thereof may include furyl, pyrrolyl, thienyl, pyrazolyl, imidazolyl, pyrazolinyl, oxazolyl, oxazolinyl, thiazolyl, thiazolinyl, thiadiazolyl, furazanyl, pyranyl, pyridyl, pyrimidyl, pyridazinyl, pyrrolidinyl, piperazinyl, piperidinyl, oxazinyl, oxadiazinyl, morpholinyl, thiazinyl, thiadiazinyl, thiomorpholinyl, tetrazolyl, triazolyl and triazinyl groups. Pyrazolyl, imidazolyl, oxazolyl, thiazolyl, thiadiazolyl, furazanyl, pyridyl, pyrimidyl, pyridazinyl, pyrrolidinyl, piperazinyl, piperidinyl, morpholinyl, thiadiazinyl and triazolyl groups are preferred, with pyrazolyl, imidazolyl, pyridyl, pyrimidyl, pyridazinyl, pyrrolidinyl, piperazinyl and piperidinyl groups being particularly preferred. Of these heterocyclic groups, the nitrogen-containing heterocyclic groups may be in the form of an N-oxide.

The saturated or unsaturated, bicyclic or tricyclic fused hydrocarbon group means the same saturated or unsaturated, bicyclic or tricyclic fused hydrocarbon group as described in the description of $Q^4$ in the general formula (1). As specific examples thereof, may be mentioned indenyl, indanyl, naphthyl, tetrahydronaphthyl, anthryl and phenanthryl groups, with indenyl, indanyl, naphthyl and tetrahydronaphthyl groups being preferred.

The saturated or unsaturated, bicyclic or tricyclic fused heterocyclic group means the same saturated or unsaturated, bicyclic or tricyclic fused heterocyclic group as described in the description of $Q^4$ in the general formula (1). As specific examples thereof, may be mentioned benzofuryl, benzothienyl, indolyl, indolinyl, isoindolyl, indazolyl, quinolyl, tetrahydroquinolyl, isoquinolyl, tetrahydroisoquinolyl, quinazolyl, dihydroquinazolyl, tetrahydroquinazolyl, quinoxalyl, tetrahydroquinoxalyl, cinnolyl, tetrahydrocinnolyl, indolizinyl, tetrahydroindolizinyl, benzothiazolyl, tetrahydrobenzothiazolyl, naphthyridinyl, thienopyridyl, tetrahydrothienopyridyl, thiazolopyridyl, tetrahydrothiazolopyridyl, tetrahydronaphthyridinyl, thiazolopyridazinyl, tetrahydrothiazolopyridazinyl, pyrrolopyridyl, dihydropyrrolopyridyl, tetrahydropyrrolopyridyl, pyrrolopyrimidinyl, dihydropyrrolopyrimidinyl, dihydro-pyridoquinazolyl, pyridopyrimidinyl, tetrahydropyrido-pyrimidinyl, pyranothiazolyl, dihydropyranothiazolyl, furopyridyl, tetrahydrofuropyridyl, oxazolopyridyl, tetrahydrooxazolopyridyl, oxazolopyridazinyl, tetrahydrooxazolopyridazinyl, pyrrolothiazolyl, dihydropyrrolothiazolyl, pyrrolooxazolyl, dihydropyrrolooxazolyl, pyrazolothiazolopyridazinyl, tetrahydropyrazolothiazolopyridazinyl and hexahydrothiazolopyridazinopyridazinyl groups. Preferred are benzothiazolyl, tetrahydrobenzothiazolyl, thienopyridyl, tetrahydrothienopyridyl, thiazolopyridyl, tetrahydrothiazolopyridyl, thiazolopyridazinyl, tetrahydrothiazolopyridazinyl, pyrrolopyrimidinyl, dihydropyrrolopyrimidinyl, pyranothiazolyl, dihydropyranothiazolyl, furopyridyl, tetrahydrofuropyridyl, oxazolopyridyl, tetrahydrooxazolopyridyl, pyrrolopyridyl, dihydropyrrolopyridyl, tetrahydropyrrolopyridyl, oxazolopyridazinyl, tetrahydrooxazolopyridazinyl, pyrrolothiazolyl, dihydropyrrolothiazolyl, pyrrolooxazolyl, dihydropyrrolooxazolyl, 4,5,6,7-tetrahydro-5,6-tetramethylenethiazolopyridazinyl and 5,6-trimethylene-4,5,6,7-tetrahydrothiazolopyridazinyl groups, with tetrahydrobenzothiazolyl, tetrahydrothienopyridyl, tetrahydrothiazolopyridyl, tetrahydrothiazolopyridazinyl, dihydropyrrolopyrimidinyl, dihydropyranothiazolyl, tetrahydrooxazolopyridyl, dihydropyrrolothiazolyl, 4,5,6,7-tetrahydro-5,6-tetramethylenethiazolopyridazinyl and 5,6-trimethylene-4,5,6,7-tetrahydrothiazolo-pyridazinyl groups being particularly preferred. No particular limitation is imposed on the fusing form of the fused heterocyclic groups. For example, thienopyridine may be any of thieno[2,3-b]pyridine, thieno[2,3-c]pyridine, thieno[3,2-b]pyridine, thieno[3,2-c]pyridine, thieno[3,4-b]pyridine and thieno[3,4-c]pyridine, with thieno[2,3-c]pyridine and thieno[3,2-c]pyridine being referred; thiazolopyridine may be any of thiazolo[4,5-b]pyridine, thiazolo[4,5-c]-pyridine, thiazolo[5,4-b]pyridine, thiazolo[5,4-c]-pyridine, thiazolo[3,4-a]pyridine and thiazolo[3,2-a]pyridine, with thiazolo[4,5-c]pyridine and thiazolo[5,4-c]pyridine being preferred; thiazolopyridazine may be any of thiazolo[4,5-c]pyridazine, thiazolo[4,5-d]-pyridazine, thiazolo[5,4-c]pyridazine and thiazolo[3,2-b]pyridazine, with thiazolo[4,5-d]pyridazine being preferred; pyrrolopyridine may be any of pyrrolo[2,3-b]pyridine, pyrrolo[2,3-c]pyridine, pyrrolo[3,2-b]pyridine, pyrrolo[3,2-c]pyridine, pyrrolo[3,4-d]pyridine and pyrrolo[3,4-c]pyridine, with pyrrolo[2,3-c]pyridine and pyrrolo[3,2-c]pyridine being preferred; pyrrolopyrimidine may be any of pyrrolo[3,4-d]pyrimidine, pyrrolo[3,2-d]pyrimidine and pyrrolo[2,3-d]pyrimidine, with pyrrolo[3,4-d]pyrimidine being preferred; pyridopyrimidine may be any of pyrido[2,3-d]pyrimidine, pyrido[3,2-d]pyrimidine, pyrido[3,4-d]pyrimidine, pyrido[4,3-d]pyrimidine, pyrido[1,2-c]pyrimidine and pyrido[1,2-a]pyrimidine, with pyrido[3,4-d]pyrimidine and pyrido[4,3-d]pyrimidine being preferred; pyranothiazole may be any of pyrano[2,3-d]thiazole, pyrano[4,3-d]thiazole, pyrano[3,4-d]thiazole and pyrano[3,2-d]thiazole, with pyrano[4,3-d]thiazole and pyrano[3,4-d]thiazole being preferred; furopyridine may be any of furo[2,3-b]pyridine, furo[2,3-c]pyridine, furo[3,2-b]pyridine, furo[3,2-c]pyridine, furo[3,4-b]-pyridine and furo[3,4-c]pyridine, with furo[2,3-c]-pyridine and furo[3,2-c]pyridine being preferred; oxazolopyridine may be any of oxazolo[4,5-b]pyridine, oxazolo[4,5-c]pyridine, oxazolo[5,4-b]pyridine, oxazolo[5,4-c]pyridine, oxazolo[3,4-a]pyridine and oxazolo[3,2-a]pyridine, with oxazolo[4,5-c]pyridine and oxazolo[5,4-c]pyridine being preferred; oxazolopyridazine may be any of oxazolo[4,5-c]pyridazine, oxazolo[4,5-d]pyridazine, oxazolo[5,4-c]pyridazine and oxazolo[3,4-b]pyridazine, with oxazolo[4,5-d]pyridazine being preferred; pyrrolothiazole may be any of pyrrolo[2,1-b]thiazole, pyrrolo[1,2-c]thiazole, pyrrolo[2,3-d]thiazole, pyrrolo[3,2-d]thiazole and pyrrolo[3,4-d]thiazole, with pyrrolo[3,4-d]thiazole being preferred; and pyrrolooxazole may be any of pyrrolo[2,1-b]oxazole, pyrrolo[1,2-c]oxazole, pyrrolo[2,3-d]oxazole, pyrrolo[3,2-d]oxazole and pyrrolo[3,4-d]oxazole, with pyrrolo[3,4-d]oxazole being preferred.

Of these heterocyclic groups, the nitrogen-containing heterocyclic groups may be in the form of an N-oxide. Incidentally, the position of the above substituent group bonded to $Q^2$ is not particularly limited.

The above-described saturated or unsaturated, 5- or 6-membered cyclic hydrocarbon groups, saturated or unsaturated, 5- or 6-membered heterocyclic groups, saturated or unsaturated, bicyclic or tricyclic fused hydrocarbon groups and saturated or unsaturated, bicyclic or tricyclic fused heterocyclic groups may each have 1 to 3 substituents. Examples of the substituents may include a hydroxyl group: halogen atoms of fluorine atom, chlorine atom, bromine atom and iodine atom; halogenomethyl groups having 1 to 3 halogen substituents; an amino group; a cyano group; an amidino group; a hydroxyamidino group; linear, branched or cyclic alkyl groups having 1 to 6 carbon atoms (hereinafter referred to as $C_1$–$C_6$ alkyl groups which mean linear, branched and cyclic alkyl groups; for example, linear or branched $C_1$–$C_6$ alkyl groups such as methyl, ethyl, isopropyl and tert-butyl; $C_3$–$C_6$ cycloalkyl groups such as cyclopropyl group, cyclobutyl group, cyclopentyl group and 1-methylcyclopropyl group; and $C_3$–$C_6$ cycloalkyl-$C_1$–$C_6$ alkyl groups such as cyclopropylmethyl group); hydroxy-$C_1$–$C_6$ alkyl groups (such as hydroxyethyl and 1,1-dimethyl-2-hydroxyethyl groups); $C_1$–$C_6$ alkoxy groups (for example, methoxy group, ethoxy group and the like); $C_1$–$C_6$ alkoxy-$C_1$–$C_6$ alkyl groups; a carboxyl group; $C_2$–$C_6$ carboxyalkyl groups (for example, carbocymethyl group and the like); $C_2$–$C_6$ alkoxycarbonyl-$C_1$–$C_6$ alkyl groups (for example, methoxycarbonylmethyl group, tert-butoxycarbonylmethyl group and the like); amidino groups substituted by a $C_2$–$C_6$ alkoxycarbonyl group; $C_2$–$C_6$ alkenyl groups (for example, vinyl group, allyl group and the like); $C_2$–$C_6$ alkynyl groups (for example, ethynyl group, propynyl group and the like); $C_2$–$C_6$ alkoxycarbonyl groups (for example, methoxycarbonyl group, ethoxycarbonyl group, tert-butoxycarbonyl group and the like); amino $C_1$–$C_6$ alkyl groups (for example, aminomethyl group, aminoethyl group and the like); $C_1$–$C_6$ alkylamino-$C_1$–$C_6$ alkyl groups (for example, N-methylaminomethyl group, N-ethylaminomethyl group and the like); $C_1$–$C_6$ dialkylamino-$C_1$–$C_6$ alkyl groups (for example, N,N-dimethylaminomethyl group, N,N-diethylaminomethyl group and the like); $C_2$–$C_6$ alkoxycarbonylamino-$C_1$–$C_6$ alkyl groups (for example, methoxycarbonylaminoethyl group, tert-butoxycarbonylaminoethyl group and the like); $C_1$–$C_6$ alkanoyl groups (for example, formyl group, acetyl group, methylpropionyl group, cyclopentanecarbonyl group and the like); $C_1$–$C_6$ alkanoylamino-$C_1$–$C_6$ alkyl groups (for example, acetylaminomethyl group and the like); $C_1$–$C_6$ alkylsulfonyl groups (for example, methanesulfonyl group and the like); $C_1$–$C_6$ alkylsulfonylamino-$C_1$–$C_6$ alkyl groups (for example, methanesulfonylaminomethyl group and the like); a carbamoyl group; $C_1$–$C_6$ alkylcarbamoyl groups (for example, methylcarbamoyl group, ethylcarbamoyl group, isopropylcarbamoyl group, tert-butylcarbamoyl group and the like); N,N-di($C_1$–$C_6$ alkyl)carbamoyl groups (for example, dimethylcarbamoyl group, diethylcarbamoyl group, methylethylcarbamoyl group and the like); $C_1$–$C_6$ alkylamino groups (for example, N-methylamino group, N-ethylamino group and the like); $C_1$–$C_6$ dialkylamino groups (for example, N,N-dimethylamino group, N,N-diethylamino group, N-methyl-N-ethylamino group and the like); 5- or 6-membered heterocyclic groups containing one of nitrogen, oxygen and sulfur or the same or different two atoms thereof (for example, pyrrolidinyl group, piperidinyl group, piperazinyl group, morpholinyl group, pyridyl group, pyrimidinyl group, tetrahydropyranyl group and the like); and groups composed of the above 5- or 6-membered heterocyclic group and a $C_1$–$C_4$ alkyl group (for example, morpholinomethyl group and the like). As specific examples of $Q^1$, may be mentioned bicyclic heterocyclic groups such as 5-methyl-4,5,6,7-tetrahydrothiazolo[5,4-c]pyridin-2-yl, 4,5,6,7-tetrahydrothiazolo[5,4-c]pyridin-2-yl, 5-cyclopropyl-4,5,6,7-tetrahydrothiazolo[5,4-c]pyridin-2-yl, 5-carboxymethyl-4,5,6,7-tetrahydrothiazolo[5,4-c]pyridin-2-yl, 5-butyl-4,5,6,7-tetrahydrothiazolo[5,4-c]pyridin-2-yl, 5-(4-pyridyl)-4,5,6,7-tetrahydrothiazolo[5,4-c]-pyridin-2-yl, 5-methyl-4,5,6,7-tetrahydrothiazolo[4,5-c]pyridin-2-yl, 6-methyl-4,5,6,7-tetrahydrothieno[2,3-c]pyridin-2-yl, 5-methyl-4,5,6,7-tetrahydroxazolo[5,4-c]pyridin-2-yl, 5-methyl-4,6-dihydro-5H-pyrrolo[3,4-d]-thiazol-2-yl, 5,7-dihydro-6-methylpyrrolo[3,4-d]-pyrimidin-2-yl, 5,6-dimethyl-4,5,6,7-tetrahydrothiazolo[4,5-d]pyridazin-2-yl, 5,6-dimethyl-4,5,6,7-tetrahydroxazolo[4,5-d]pyridazin-2-yl, 5-dimethylamino-4,5,6,7-tetrahydrobenzo[d]thiazol-2-yl, 5-(4-pyridyl)-4,5,6,7-tetrahydrothiazolo[5,4-c]pyridin-2-yl and 6,7-dihydro-4H-pyrano[4,3-d]thiazol-2-yl groups, and a 4-(4-pyridyl)phenyl group. Incidentally, $Q^1$ is not limited by these examples at all.

<On Group $Q^2$>

The group $Q^2$ means a single bond, a linear or branched alkylene group having 1 to 6 carbon atoms, a linear or branched alkenylene group having 2 to 6 carbon atoms, a linear or branched alkynylene group having 2 to 6 carbon atoms, a group —N($R^3$)—, in which $R^3$ means a hydrogen atom or alkyl group, a group —N($R^4$)—(CH$_2$)$_m$—, in which $R^4$ means a hydrogen atom or alkyl group, and m is an integer of 1 to 6, a saturated or unsaturated, 5- or 6-membered divalent cyclic hydrocarbon group which may be substituted, a saturated or unsaturated, 5- or 6-membered divalent heterocyclic group which may be substituted, a saturated or unsaturated, divalent bicyclic or tricyclic fused hydrocarbon group which may be substituted, or a saturated or unsaturated, divalent bicyclic or tricyclic fused heterocyclic group which may be substituted.

In the group $Q^2$, as examples of the linear or branched alkylene group having 1 to 6 carbon atoms, may be mentioned methylene, ethylene, trimethylene, propylene, tetramethylene, pentamethylene and hexamethylene groups.

As examples of the linear or branched alkenylene group having 2 to 6 carbon atoms, may be mentioned vinylene, propenylene, butenylene and pentenylene groups. No particular limitation is imposed on the position of the double bond thereof.

As examples of the linear or branched alkynylene group having 2 to 6 carbon atoms, may be mentioned ethynylene, propynylene, butynylene, pentynylene and hexynylene groups. No particular limitation is imposed on the position of the triple bond thereof.

$R^3$ in the group —N($R^3$)— is a hydrogen atom or alkyl group. The alkyl group means a linear, branched or cyclic alkyl group having 1 to 6 carbon atoms, and examples thereof may include methyl, ethyl, isopropyl and cyclopropyl groups.

$R^4$ in the group —N($R^4$)—(CH$_2$)$_m$— is a hydrogen atom or alkyl group. The alkyl group means a linear, branched or cyclic alkyl group having 1 to 6 carbon atoms, and examples thereof may include methyl, ethyl, isopropyl and cyclopropyl groups. m is an integer of 1 to 6, with an integer of 1 to 3 being preferred.

The saturated or unsaturated, 5- or 6-membered divalent cyclic hydrocarbon group means a divalent group derived from the saturated or unsaturated, 5- or 6-membered cyclic hydrocarbon described in the description of $Q^4$ in the general formula (1). As specific examples thereof, may be mentioned cyclohexylene, cyclohexenylene and phenylene groups, with cyclohexylene and phenylene groups being preferred.

The saturated or unsaturated, 5- or 6-membered divalent heterocyclic group means a divalent group derived from the saturated or unsaturated, 5- or 6-membered heterocyclic ring described in the description of $Q^4$ in the general formula (1). As specific examples thereof, may be mentioned divalent groups derived from furan, pyrrole, thiophene, pyrazole, imidazole, oxazole, oxazolidine, thiazole, thiadiazole, furazane, pyrane, pyridine, pyrimidine, pyridazine, pyrrolidine, piperazine, piperidine, oxazine, oxadiazine, morpholine, thiazine, thiadiazine, thiomorpholine, tetrazole, triazole and triazine. Particularly, divalent groups derived from pyrazole, imidazole, oxazole, thiazole, thiadiazole, furazane, pyridine, pyrimidine, pyridazine, pyrrolidine, piperazine, piperidine, triazole and triazine may be mentioned as preferable examples.

The saturated or unsaturated, divalent bicyclic or tricyclic fused hydrocarbon group means a divalent group derived from the saturated or unsaturated, bicyclic or tricyclic fused hydrocarbon described in the description of $Q^4$ in the general formula (1). As specific examples thereof, may be mentioned divalent groups derived from indene, indane, naphthalene, tetrahydronaphthalene, anthracene, phenanthrene and the like. As preferable examples thereof, may be mentioned divalent groups derived from indane and naphthalene.

The saturated or unsaturated, divalent bicyclic or tricyclic fused heterocyclic group means a divalent group derived from the saturated or unsaturated, bicyclic or tricyclic fused heterocyclic ring described in the description of $Q^4$ in the general formula (1). As specific examples thereof, may be mentioned divalent groups derived from benzofuran, benzothiophene, indole, isoindole, indazole, quinoline, tetrahydroquinoline, isoquinoline, tetrahydroisoquinoline, quinazoline, dihydroquinazoline, tetrahydroquinazoline, quinoxaline, tetrahydroquinoxaline, cinnoline, tetrahydrocinnoline, indolizine, tetrahydroindolizine, benzothiazole, tetrahydrobenzothiazole, naphthyridine, tetrahydronaphthyridine, thienopyridine, tetrahydrothienopyridine, thiazolopyridine, tetrahydrothiazolopyridine, thiazolopyridazine, tetrahydrothiazolopyridazine, pyrrolopyridine, dihydropyrrolopyridine, tetrahydropyrrolopyridine, pyrrolopyrimidine, dihydropyrrolopyrimidine, dihydropyridoquinazoline, pyranothiazole, dihydropyranothiazole, furopyridine, tetrahydrofuropyridine, oxazolopyridine, tetrahydrooxazolopyridine, oxazolopyridazine, tetrahydrooxazolopyridazine, pyrrolothiazole, dihydropyrrolothiazole, pyrrolooxazole and dihydropyrrolooxazole. As preferable examples thereof, may be mentioned divalent groups derived from benzofuran, benzothiophene, indole, indazole, quinoline, isoquinoline, tetrahydroisoquinoline, benzothiazole, naphthyridine, thienopyridine, thiazolopyridine, tetrahydrothiazolopyridine, thiazolopyridazine, pyrrolopyridine, tetrahydropyrrolopyridine, pyridopyrimidine, pyranothiazole, dihydropyranothiazole, furopyridine, oxazolopyridine, oxazolopyridazine, pyrrolothiazole, dihydropyrrolothiazole, pyrrolooxazole and dihydropyrrolooxazole. No particular limitation is imposed on the fusing form of the fused heterocyclic group. For example, naphthyridine may be any of 1,5-, 1,6-, 1,7-, 1,8-, 2,6- and 2,7-naphthyridine, thienopyridine may be any of thieno[2,3-b]pyridine, thieno[2,3-c]pyridine, thieno[3,2-b]pyridine, thieno[3,2-c]pyridine, thieno[3,4-b]pyridine and thieno[3,4-c]pyridine, thiazolopyridine may be any of thiazolo[4,5-b]pyridine, thiazolo[4,5-c]pyridine, thiazolo[5,4-b]pyridine, thiazolo[5,4-c]pyridine, thiazolo[3,4-a]pyridine and thiazolo[3,2-a]pyridine, thiazolopyridazine may be any of thiazolo[4,5-c]-pyridazine, thiazolo[4,5-d]pyridazine, thiazolo[5,4-c]-pyridazine and thiazolo[3,2-b]pyridazine, pyrrolopyridine may be any of pyrrolo[2,3-b]pyridine, pyrrolo[2,3-c]pyridine, pyrrolo[3,2-b]pyridine, pyrrolo[3,2-c]pyridine, pyrrolo[3,4-b]pyridine and pyrrolo[3,4-c]pyridine, pyrrolopyrimidine may be any of pyrrolo[3,4-d]pyrimidine, pyrrolo[3,2-d]pyrimidine and pyrrolo[2,3-d]pyrimidine, pyridopyrimidine may be any of pyrido[2,3-d]pyrimidine, pyrido[3,2-d]pyrimidine and pyrido[3,4-d]pyrimidine, pyranothiazole may be any of pyrano[2,3-d]thiazole, pyrano[4,3-d]thiazole, pyrano[3,4-d]thiazole and pyrano[3,2-d]thiazole, furopyridine may be any of furo[2,3-b]pyridine, furo[2,3-c]pyridine, furo[3,2-b]pyridine, furo[3,2-c]-pyridine, furo[3,4-b]pyridine and furo[3,4-c]pyridine, oxazolopyridine may be any of oxazolo[4,5-b]pyridine, oxazolo[4,5-c]pyridine, oxazolo[5,4-b]pyridine, oxazolo[5,4-c]pyridine, oxazolo[3,4-a]pyridine and oxazolo[3,2-a]pyridine, oxazolopyridazine may be any of oxazolo[4,5-c]pyridazine, oxazolo[4,5-d]pyridazine, oxazolo[5,4-c]pyridazine and oxazolo[3,4-b]pyridazine, pyrrolothiazole may be any of pyrrolo[2,1-b]thiazole, pyrrolo[1,2-c]thiazole, pyrrolo[3,2-d]thiazole and pyrrolo[3,4-d]thiazole, and pyrrolooxazole may be any of pyrrolo[2,1-b]oxazole, pyrrolo[1,2-c]oxazole, pyrrolo[2,3-d]oxazole, pyrrolo[3,2-d]oxazole and pyrrolo[3,4-d]oxazole. Other fusing forms than these may be allowed.

The above-described saturated or unsaturated, 5- or 6-membered divalent cyclic hydrocarbon groups, saturated or unsaturated, 5- or 6-membered divalent heterocyclic groups, saturated or unsaturated, divalent bicyclic or tricyclic fused hydrocarbon groups and saturated or unsaturated, divalent bicyclic or tricyclic fused heterocyclic groups may each have 1 to 3 substituents. Examples of the substituents may include a hydroxyl group, halogen atoms of a fluorine, chlorine, bromine and iodine atoms, halogenoalkyl groups having 1 to 3 halogen substituents, an amino group, a cyano group, aminoalkyl groups, an amidino group, a hydroxyamidino group, linear, branched or cyclic alkyl groups having 1 to 6 carbon atoms (for example, a methyl group, an ethyl group, etc.), linear, branched or cyclic alkoxy groups having 1 to 6 carbon atoms (for example, a methoxy group, an ethoxy group, etc.), amidino group substituted by linear, branched or cyclic alkoxycarbonyl groups having 2 to 7 carbon atoms (for example, a methoxycarbonylamidino group, an ethoxycarbonylamidino group, etc.), linear, branched or cyclic alkenyl groups having 2 to 6 carbon atoms (for example, a vinyl group, an allyl group, etc.), linear or branched alkynyl groups having 2 to 6 carbon atoms (for example, an ethynyl group, a propynyl group, etc.), linear, branched or cyclic alkoxycarbonyl group having 2 to 6 carbon atoms (for example, a methoxycarbonyl group, an ethoxycarbonyl group, etc.), and a carbamoyl group.

Preferable groups in $Q^2$ described above are a single bond, an alkylene group having 1 or 2 carbon atoms, an alkenylene group having 2 carbon atoms, an alkynylene group having 2 carbon atoms, group —NH—, group —N($R^4$)—(CH$_2$)$_2$—, a saturated or unsaturated, 5- or 6-membered divalent cyclic hydrocarbon group which may be substituted, a saturated or unsaturated, 5- or 6-membered divalent heterocyclic group which may be substituted, and a saturated or unsaturated, divalent bicyclic or tricyclic fused heterocyclic group which may be substituted. In particular, a single bond, saturated or unsaturated, divalent 5- or 6-membered cyclic hydrocarbon groups such as a cyclohexylene group and a phenylene group, and divalent groups derived from fused heterocyclic rings such as thiazole and piperidine are preferred.

When $Q^1$ is a saturated or unsaturated, bicyclic or tricyclic fused hydrocarbon group which may be substituted, or a saturated or unsaturated, bicyclic or tricyclic fused heterocyclic group which may be substituted, the group $Q^2$ is preferably a single bond. The fact that $Q^2$ is a single bond means that the general formula (1):

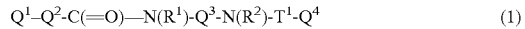

$$Q^1\text{-}Q^2\text{-}C(=O)\text{—}N(R^1)\text{-}Q^3\text{-}N(R^2)\text{-}T^1\text{-}Q^4 \qquad (1)$$

wherein $R^1$, $R^2$, $Q^1$, $Q^2$, $Q^3$, $Q^4$ and $T^1$ have the same meanings as defined above, comes to the following general formula (1'):

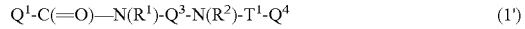

$$Q^1\text{-}C(=O)\text{—}N(R^1)\text{-}Q^3\text{-}N(R^2)\text{-}T^1\text{-}Q^4 \qquad (1')$$

wherein $Q^1$ represents the above bicyclic or tricyclic fused hydrocarbon group or bicyclic or tricyclic fused heterocyclic group, and $R^1$, $R^2$, $Q^3$, $Q^4$ and $T^1$ have the same meanings as defined above.

Specifically, are preferred those in which the group $Q^1$ is
a thienopyridyl group which may be substituted;
a tetrahydrothienopyridyl group which may be substituted;
a thiazolopyridyl group which may be substituted;
a tetrahydrothiazolopyridyl group which may be substituted;
a thiazolopyridazinyl group which may be substituted;
a tetrahydrothiazolopyridazinyl group which may be substituted;
a pyranothiazolyl group which may be substituted;
a dihydropyranothiazolyl group which may be substituted;
a furopyridyl group which may be substituted;
a tetrahydrofuropyridyl group which may be substituted;
an oxazolopyridyl group which may be substituted;
a tetrahydrooxazolopyridyl group which may be substituted;
a pyrrolopyridyl group which may be substituted;
a dihydropyrrolopyridyl group which may be substituted;
a tetrahydropyrrolopyridyl group which may be substituted;
a pyrrolopyrimidinyl group which may be substituted;
a dihydropyrrolopyrimidinyl group which may be substituted;
an oxazolopyridazinyl group which may be substituted;
a tetrahydrooxazolopyridazinyl group which may be substituted;
a pyrrolothiazolyl group which may be substituted;
a dihydropyrrolothiazolyl group which may be substituted;
a pyrrolooxazolyl group which may be substituted;
a dihydropyrrolooxazolyl group which may be substituted;
a benzothiazolyl group which may be substituted;
a tetrahydrobenzothiazolyl group which may be substituted;
a 4,5,6,7-tetrahydro-5,6-tetramethylenethiazolopyridazinyl group which may be substituted; or
a 5,6-trimethylene-4,5,6,7-tetrahydrothiazolo-pyridazinyl group which may be substituted, and $Q^2$ is a single bond.

When $Q^1$ is a saturated or unsaturated, 5- or 6-membered cyclic hydrocarbon group which may be substituted, or a saturated or unsaturated, 5- or 6-membered heterocyclic group which may be substituted, the group $Q^2$ is preferably a saturated or unsaturated, 5- or 6-membered divalent cyclic hydrocarbon group which may be substituted, or a saturated or unsaturated, 5- or 6-membered divalent heterocyclic group which may be substituted. On group $Q^1$-$Q^2$,5-(4-pyridyl)thiazolyl group, 1-(4-pyridyl)piperidyl group and the like are preffered.

<On Group $Q^3$>

The group $Q^3$ represents a group:

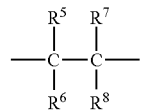

in which $R^5$, $R^6$, $R^7$ and $R^8$, independently of one another, mean a hydrogen atom, hydroxyl group, halogen atom, halogenoalkyl group, cyano group, cyanoalkyl group, acyl group, acylalkyl group, alkyl group, alkenyl group, alkynyl group, alkoxy group, alkoxyalkyl group, hydroxyalkyl group, carboxyl group, carboxyalkyl group, alkoxycarbonyl group, alkoxycarbonylalkyl group, carbamoyl group, N-alkylcarbamoyl group, N,N-dialkylcarbamoyl group, carbamoylalkyl group, N-alkylcarbamoylalkyl group, N,N-dialkylcarbamoylalkyl group, aryl group, aralkyl group, heteroaryl group or heteroarylalkyl group, or the following group:

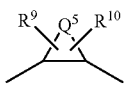

in which $Q^5$ means a alkylene group having 1 to 8 carbon atoms or a alkenylene group having 2 to 8 carbon atoms, and $R^9$ and $R^{10}$ are, independently of each other, substituents on a carbon atom of the ring comprising $Q^5$ and mean a hydrogen atom, hydroxyl group, alkyl group, alkenyl group, alkynyl group, halogen atom, halogenoalkyl group, cyano group, cyanoalkyl group, amino group, aminoalkyl group, N-alkylaminoalkyl group, N,N-dialkylaminoalkyl group, acyl group, acylalkyl group, acylamino group which may be substituted, alkoxyimino group, hydroxyimino group, acylaminoalkyl group, alkoxy group, alkoxyalkyl group, hydroxyalkyl group, carboxyl group, carboxyalkyl group, alkoxycarbonyl group, alkoxycarbonylalkyl group, alkoxycarbonylalkylamino group, carboxyalkylamino group, alkoxycarbonylamino group, alkoxycarbonylaminoalkyl group, carbamoyl group, N-alkylcarbamoyl group which may have an substituent on the alkyl group, N,N-dialkylcarbamoyl group which may have an substituent on the alkyl group, N-alkenylcarbamoyl group, N-alkenyl-carbamoylalkyl group, N-alkenyl-N-alkylcarbamoyl group, N-alkenyl-N-alkylcarbamoylalkyl group, N-alkoxycarbamoyl group, N-alkyl-N-alkoxycarbamoyl group, N-alkoxycarbamoylalkyl group, N-alkyl-N-alkoxycarbamoyl-alkyl group, carbazoyl group which may be substituted by 1 to 3 alkyl groups, alkylsulfonyl group, alkylsulfonylalkyl group, 3- to 6-membered nitrogen-containing heterocyclic carbonyl group which may be substituted, carbamoylalkyl group, N-alkylcarbamoylalkyl group which may have an substituent on the alkyl group, N,N-dialkylcarbamoylalkyl group which may have an substituent on the alkyl group, carbamoyloxyalkyl group, N-alkylcarbamoyloxyalkyl group, N,N-dialkylcarbamoyloxyalkyl group, 3- to 6-membered nitrogen-containing heterocyclic carbonylalkyl group which may be substituted, 3- to 6-membered nitrogen-containing heterocyclic carbonyloxyalkyl group which may be substituted, aryl group, aralkyl group, heteroaryl group, heteroarylalkyl group, alkylsulfonylamino group, arylsulfonylamino group, alkylsulfonylaminoalkyl group, arylsulfonylaminoalkyl group, alkylsulfonylaminocarbonyl group, arylsulfonylaminocarbonyl group, alkylsulfonylaminocarbonylalkyl group, arylsulfonylaminocarbonylalkyl group, oxo group, carbamoyloxy group, aralkyloxy group, carboxyalkyloxy group, acyloxy group or acyloxyalkyl group, or $R^9$ and $R^{10}$, together with each other, denote an alkylene group having 1 to 5 carbon atoms, alkenylene group having 2 to 5 carbon atoms, alkylenedioxy group having 1 to 5 carbon atoms or carbonyldioxy group.

The substituents $R^5$, $R^6$, $R^7$ and $R^8$ will be described in detail. The halogen atom means a fluorine, chlorine, bromine or iodine atom. Examples of the alkyl group include linear, branched or cyclic $C_1$–$C_6$ alkyl groups (for example, a methyl group, a cyclopropyl group, an isobutyl group and the like). Examples of the halogenoalkyl group include the 1 to 3 halogen-substituted alkyl groups (for example, a chloromethyl group, an 1-bromoethyl group, a trifluoromethyl group and the like). Examples of the cyanoalkyl group include the $C_1$–$C_6$ alkyl groups substituted with a cyano group (for example, a cyanomethyl group, a 1-cyanoethyl group and the like). Examples of the alkenyl group include linear or branched alkenyl groups having 2 to 6 carbon atoms and a double bond (for example, a vinyl group, an allyl group and the like). Examples of the alkynyl group include linear or branched alkynyl groups having 2 to 6 carbon atoms and a triple bond (for example, an ethynyl group, a propynyl group and the like) Examples of the acyl group include $C_1$–$C_6$ alkanoyl groups (for example, a formyl group, an acetyl group and the like), $C_7$–$C_{15}$ aroyl groups such as a benzoyl group and a naphthoyl group, and arylalkanoyl groups that are the $C_1$–$C_6$ alkanoyl groups substituted with the $C_6$–$C_{14}$ aryl group (for example, a phenacetyl group and the like). Examples of the acylalkyl group include the $C_1$–$C_6$ alkyl groups substituted with the acyl group (for example, an acethylmethyl group and the like). Examples of the alkoxy group include linear, branched or cyclic $C_1$–$C_6$ alkoxy groups (for example, a methoxy group, a cyclopropoxy group, an isopropoxy group and the like). Examples of the alkoxyalkyl group include the $C_1$–$C_6$ alkyl groups substituted with the $C_1$–$C_6$ alkoxy group (for example, a methoxymethyl group, an ethoxymethyl group and the like). Examples of the hydroxyalkyl group include the $C_1$–$C_6$ alkyl groups substituted with a hydroxyl group (for example, a hydroxymethyl group, a 1-hydroxyethyl group and the like). Examples of the carboxyalkyl group include the $C_1$–$C_6$ alkyl groups substituted with a carboxyl group (for example, a carboxymethyl group, a 1-carboxyethyl group and the like). Examples of the alkoxycarbonyl group include groups composed of the $C_1$–$C_6$ alkoxy group and a carbonyl group (for example, a methoxycarbonyl group, an ethoxycarbonyl group and the like). Examples of the alkoxycarbonylalkyl group include the $C_1$–$C_6$ alkyl groups substituted with the $C_1$–$C_6$ alkoxycarbonyl group (for example, a methoxycarbonylethyl group, an ethoxycarbonylethyl group and the like). Examples of the carbamoylalkyl group include the $C_1$–$C_6$ alkyl groups substituted a carbamoyl group (for example, a carbamoyl methyl group, a carbamoylethyl group and the like), Examples of the N-alkylcarbamoyl group include carbamoyl groups substituted with the $C_1$–$C_6$ alkyl group (for example, an N-methylcarbamoyl group, an N-isopropylcarbamoyl group, N-cyclopropylcarbamoyl group and the like). Examples of the N,N-dialkylcarbamoyl group include carbamoyl groups substituted with the two $C_1$–$C_6$ alkyl groups which are the same or different from each other (for example, an N,N-dimethylcarbamoyl group, an N-ethyl-N-methylcarbamoyl group and the like). The examples of the N-alkylcarbamoylalkyl group include the $C_1$–$C_6$ alkyl groups substituted with the N-alkylcarbamoyl group (for example, an N-methylcarbamoylmethyl group, an N-methylcarbamoylethyl group and the like). Examples of the N,N-dialkylcarbamoylalkyl group include the $C_1$–$C_6$ alkyl groups substituted with the N,N-dialkylcarbamoyl group (for example, an N,N-dimethylcarbamoylmethyl group, an N,N-dimethylcarbamoylethyl group and the like). Examples of the heteroaryl group include the same heteroaryl groups as described in the description of $Q^4$ in the general formula (1). Examples of the heteroarylalkyl group include the $C_1$–$C_6$ alkyl groups substituted with the heteroaryl group (for example, a thienylmethyl group,a pyridylethyl group and the like). Examples of the aryl group include aryl groups having 6 to 14 carbon atoms, such as a phenyl group and a naphthyl group. The aryl groups may have 1 to 3 substituents selected from the $C_1$–$C_6$ alkyl groups, the $C_1$–$C_6$ alkanoyl groups, a hydroxyl group, a nitro group, a cyano group, halogen atoms, the $C_2$–$C_6$ alkenyl groups, the $C_2$–$C_6$ alkynyl groups, the halogenoalkyl groups, the alkoxy groups, a carboxy group, a carbamoyl group, the alkoxycarbonyl groups and the like. Examples of the aralkyl group include $C_1$–$C_6$ alkyl groups substituted with the $C_6$–$C_{14}$ aryl groups (for example, a benzyl group, a phenetyl group and the like). Incidentally, in the above description, no particular limitation is imposed on the substituting position.

The following group will now be described in detail.

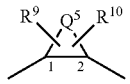

wherein $Q^5$, $R^9$ and $R^{10}$ have the same meaning as defined above, and numerals 1 and 2 indicate positions.

A portion of the cyclic structure having the group $Q^5$ is a 3- to 10-membered divalent cyclic hydrocarbon group which may have a double bond, preferably a 3- to 8-membered divalent cyclic hydrocarbon group, more preferably a 5- to 7-membered divalent cyclic hydrocarbon group. Among others, a group in which $Q^5$ is an alkylene group is preferred. This cyclic hydrocarbon group may have both cis and trans structures in the relation between position 1 and position 2. However, the trans-form is preferred in the case of the 5-membered ring, while both cis-form and trans-form are preferred in the 6- or 7-membered ring.

The substituents $R^9$ and $R^{10}$ will now be described in detail.

The alkyl group, alkenyl group, alkynyl group, halogen atom, halogenoalkyl group, cyanoalkyl group, acyl group, acylalkyl group, alkoxy group, alkoxyalkyl group, hydroxyalkyl group, carboxyalkyl group, alkoxycarbonyl group, alkoxycarbonylalkyl group, aryl group, aralkyl group, heteroaryl group and heteroarylalkyl group are the same as those described above in the description as to $R^5$, $R^6$, $R^7$ and $R^8$. Examples of the acylamino group which may be substituted include the amino groups substituted with the acyl group (for example, a formylamino group, an acetylamino group and the like) and besides acyl groups having 1 to several substituents selected from halogen atoms, a hydroxyl group, $C_1$–$C_6$ alkoxy groups, a amino group, N—$C_1$–$C_6$ alkylamino groups, N,N-di-$C_1$–$C_6$ alkylamino groups, a carboxyl group, $C_2$–$C_6$ alkoxycarbonyl groups and the like (for example, a 2-methoxyacetylamino group, a 3-aminopropionylamino group and the like). Examples of the acylaminoalkyl group include the $C_1$–$C_6$ alkyl groups substituted with the acylamino group (for example, a formylaminomethyl group, an acetylaminomethyl group and the like). Examples of the aminoalkyl group include the $C_1$–$C_6$ alkyl groups substituted with an amino group (for example, an aminomethyl group, a 1-aminoethyl group and the like). Examples of the N-alkylaminoalkyl group include the amino-$C_1$–$C_6$alkyl groups substituted with the $C_1$–$C_6$ alkyl group on the nitrogen atom (for example, an N-methylaminomethyl group, an N-methylaminoethyl group and the like). Examples of N,N-dialkylaminoalkyl group include the amino-$C_1$–$C_6$ alkyl groups respectively substituted with two $C_1$–$C_6$alkyl groups on the nitrogen atoms (for example, an N,N-dimethylaminomethyl group, an N-ethyl-N-methylaminoethyl group and the like). Examples of the N-alkenylcarbamoyl group include carbamoyl groups substituted with a linear or branched $C_2$–$C_6$ alkenyl group (for example, an allylcarbamoyl group and the like). Examples of the N-alkenylcarbamoylalkyl group include $C_1$–$C_6$ alkyl groups substituted with the N-alkenylcarbamoyl group (for example, an allylcarbamoylethyl group and the like). Examples of the N-alkenyl-N-alkylcarbamoyl group include the N-alkenylcarbamoyl groups substituted with a linear or branched $C_1$–$C_6$ alkyl group on the nitrogen atom (for example, an N-allyl-N-methylcarbamoyl group and the like). Example of the N-alkenyl-N-alkylcarbamoylalkyl group include the N-alkenylcarbamoylalkyl groups substituted with a linear or branched $C_1$–$C_6$ alkyl group on the nitrogen atom (for example, N-allyl-N-methylcarbamoylmethyl group and the like). Example of the N-alkoxycarbamoyl group include carbamoyl groups substituted with a linear or branched $C_1$–$C_6$ alkoxy group (for example, a methoxycarbamoyl group and the like). Examples of the N-alkoxycarbamoylalkyl group include linear or branched $C_1$–$C_6$ alkyl groups substituted with the N-alkoxycarbamoyl group (for example, a methoxycarbamoylmethyl group and the like). Examples of the N-alkyl-N-alkoxycarbamoyl group include carbamoyl groups substituted with linear or branched $C_1$–$C_6$ alkoxy group and $C_1$–$C_6$ alkyl group (for example, N-ethyl-N-methoxycarbamoyl group and the like). Examples of the N-alkyl-N-alkoxycarbomoylalkyl group include linear or branched $C_1$–$C_6$ alkyl groups substituted with the N-alkyl-N-alkoxycarbamoyl group (for example, an N-ethyl-N-methoxycarbamoylmethyl group and the like). Examples of the carbazoyl group which may be substituted by 1 to 3 alkyl groups include a carbazoyl group, and besides carbazoyl groups substituted with 1 to 3 linear or branched $C_1$–$C_6$ alkyl groups (for example, a 1-methylcarbazoyl group, a 1,2-dimethylcarbazoyl group and the like). Examples of the alkylsulfonyl group include linear or branched $C_1$–$C_6$ alkylsulfonyl groups (for example, a methanesulfonyl group and the like). Examples of the alkylsulfonylalkyl group include linear or branched $C_1$–$C_6$ alkyl groups substituted with the alkylsulfonyl group (for example, a methanesulfonylmethyl group and the like) Examples of the alkoxyimino group include $C_1$–$C_6$ alkoxyimino groups (for example, a methoxyimino group, an ethoxyimino group and the like). Examples of the alkoxycarbonylalkylamino group include amino groups substituted with the alkoxycarbonylalkyl group (for example, a methoxycarbonylmethylamino group, an ethoxycarbonylpropylamino group and the like). Examples of the carboxyalkylamino group include amino groups substituted with the carboxyalkyl group (for example, a carboxymethylamino group, a carboxyethylamino group and the like). Examples of the alkoxycarbonylamino group include amino groups substituted with the alkoxycarbonyl group (for example, a methoxycarbonylamino group, a tert-butoxycarbonylamino group and the like). Examples of the alkoxycarbonylaminoalkyl group include the alkyl groups substituted with the alkoxycarbonylamino group (for example, a methoxycarbonylaminomethyl group, a tert-butoxycarbonylaminoethyl group and the like). The N-alkylcarbamoyl group which may have a substituent on the alkyl group means a carbamoyl group substituted by a linear, branched or cyclic $C_1$–$C_6$ alkyl group which may be substituted by a hydroxyl group, amino group, N—$C_1$–$C_6$ alkylamino group, amidino group, halogen atom, carboxyl group, cyano group, carbamoyl group, $C_1$–$C_6$ alkoxy group, $C_1$–$C_6$ alkanoyl group, $C_1$–$C_6$ alkanoylamino group, $C_1$–$C_6$ alkyl-sulfonylamino group or the like, and examples thereof include N-methylcarbamoyl group, N-ethylcarbamoyl group, N-isopropylcarbamoyl group, N-cyclopropylcarbamoyl group, N-(2-hydroxyethyl)carbamoyl group, N-(2-fluoroethyl)-carbamoyl group, N-(2-cyanoethyl)carbamoyl group, N-(2-methoxyethyl) carbamoyl group, N-carboxymethylcarbamoyl group, N-(2-aminoethyl)carbamoyl group, N-(2-amidino-ethyl) carbamoyl group and the like. Examples of the N,N-dialkylcarbamoyl group which may have a substituent on the alkyl group means a carbamoyl group substituted by 2 linear, branched or cyclic $C_1$–$C_6$ alkyl groups which may be substituted by a hydroxyl group, amino group, N—$C_1$–$C_6$ alkylamino group, amidino group, halogen atom, carboxyl group, cyano group, carbamoyl group, $C_1$–$C_6$ alkoxy group, $C_1$–$C_6$ alkanoyl group, $C_1$–$C_6$ alkanoylamino group, $C_1$–$C_6$ alkylsulfonylamino group or the like, and examples thereof include N,N-dimethylcarbamoyl group, N,N-diethylcarbamoyl group, N-ethyl-N-methylcarbamoyl group, N-isopropyl-N-methylcarbamoyl group, N-(2-hydroxyethyl)-N-methylcarbamoyl group, N,N-bis(2-hydroxyethyl)-carbamoyl group, N,N-bis(2-fluoroethyl) carbamoyl group, N-(2-cyanoethyl)-N-methylcarbamoyl group, N-(2-methoxy-ethyl)-N-methylcarbamoyl group, N-carboxymethyl-N-methylcarbamoyl group, N,N-bis(2-aminoethyl)carbamoyl group and the like. N-alkylcarbamoylalkyl group which may have a substituent on the alkyl group include linear or branched $C_1$–$C_6$ alkyl group substituted with the N-alkylcarbamoyl group which may have a substituent on the alkyl group (for example, N-methylcarbamoylmethyl group, N-(2-hydroxyethyl)-carbamoylmethyl group and the like). Examples of the N,N-dialkylcarbamoylalkyl group which may have a substituent on the alkyl group include linear or branched $C_1$–$C_6$ alkyl groups substituted with the N,N-dialkylcarbamoyl group which may have a substituent on the alkyl group (for example, an N,N-dimethylcarbamoylmethyl group, an N-(2-hydroxyethyl)-N-methylmethylcarbamoylmethyl group and the like).

The 3- to 6-membered nitrogen-containing heterocyclic carbonyl group which may be substituted is a group composed of a saturated or unsaturated, nitrogen-containing heterocyclic ring and a carbonyl group. The nitrogen-containing heterocyclic ring means a 3- to 6-membered heterocyclic ring which at least containing 1 to 3 nitrogen atoms and may further contain an oxygen atom or sulfur atom. The heterocyclic ring may have a substituent such as a hydroxy group, halogen atom, amino group or $C_1$–$C_6$ alkyl group. As specific examples thereof, may be mentioned an azlidinylcarbonyl group, azetidinylcarbonyl group, 3-hydroxyazetidinylcarbonyl group, 3-methoxyazetidinylcarbonyl group, pyrrolidinylcarbonyl group, 3-hydroxypyrrolidinylcarbonyl group, 3-fluoropyrrolidinylcarbonyl group, piperidinylcarbonyl group, piperazinylcarbonyl group and morpholinylcarbonyl group.

Examples of the 3- to 6-membered nitrogen-containing heterocyclic carbonylalkyl group which may be substituted include the $C_1$–$C_6$ alkyl groups substituted with the 3- to 6-membered nitrogen-containing heterocyclic carbonyl group which may have be substituted (for example, an azetidinyl-carbonylmethyl group, a pyrrolidinylcarbonyl-ethyl group and the like).

Examples of the 3- to 6-membered nitrogen-containing heterocyclic carbonyloxyalkyl group which may be substituted include the $C_1$–$C_6$ alkyl groups substituted with the 3- to 6-membered nitrogen-containing heterocyclic carbonyloxy group which is composed of the 3- to 6-membered nitrogen-containing heterocyclic carbonyl group which may be substituted and an oxygen atom (for example, a piperidinylcarbonyloxyethyl group, morpholinylcarbonyloxymethyl group and the like).

Example of the carbamoylalkyl group include the $C_1$–$C_6$ alkyl groups substituted with a carbamoyl group (for example, a carbamoylmethyl group, a carbamoylethyl group and the like).

Examples of the carbamoyloxyalkyl group include the $C_1$–$C_6$ alkyl groups substituted with a carbamoyloxy group which is composed of a carbamoyl group and an oxygen atom (for example, a carbamoyloxymethyl group, a carbamoyloxyethyl group and the like).

Examples of the N-alkylcarbamoyloxyalkyl group include the $C_1$–$C_6$ alkyl groups substituted with the N-alkylcarbamoyloxy group which is composed of the N-alkylcarbamoyl group, which may have a substituent on the alkyl group, and an oxygen atom (for example, an N-methylcarbamoyloxymethyl group, an N-methylcarbamoyl-oxyethyl group and the like).

Examples of the N,N-dialkylcarbamoyloxyalkyl group include the $C_1$–$C_6$ alkyl groups substituted with the N,N-dialkylcarbamoyloxy group which is composed of the N,N-dialkylcarbamoyl group, which may have a substituent on the alkyl group, and an oxygen atom (for example, an N,N-dimethylcarbamoyloxymethyl group, an N-ethyl-N-methylcarbamoyloxyethyl group and the like).

Examples of the alkylsulfonylamino group include amino groups substituted with an alkylsulfonyl group having the $C_1$–$C_6$ alkyl group (for example, a methylsulfonylamino group, an isopropylsulfonylamino group and the like).

Examples of the arylsulfonylamino group include amino groups substituted with an arylsulfonyl group having the aryl group (for example, a phenylsulfonylamino group, a naphthylsulfonylamino group and the like).

Examples of the alkylsulfonylaminoalkyl group include the $C_1$–$C_6$ alkyl groups substituted with the $C_1$–$C_6$ alkylsulfonylamino group (for example, a methylsulfonylaminomethyl group, a methylsulfonylaminoethyl group and the like).

Examples of the arylsulfonylaminoalkyl group include the $C_1$–$C_6$ alkyl groups substituted with the arylsulfonylamino group (for example, a phenylsulfonylaminomethyl group, a naphthylsulfonylaminoethyl group and the like).

Examples of the alkylsulfonylaminocarbonyl group include groups composed of the $C_1$–$C_6$ alkylsulfonylamino group and a carbonyl group (for example, a methylsulfonylaminocarbonyl group, an isopropylsulfonylaminocarbonyl group and the like).

Examples of the arylsulfonylaminocarbonyl group include groups composed of the arylsulfonylamino group and a carbonyl group (for example, a phenylsulfonylaminocarbonyl group, a naphthylsulfonylaminocarbonyl group and the like).

Examples of the alkylsulfonylaminocarbonylalkyl group include the $C_1$–$C_6$ alkyl groups substituted with the $C_1$–$C_6$ alkylsulfonylaminocarbonyl group (for example, a methylsulfonylaminocarbonylmethyl group, an isopropylsulfonylaminocarbonylmethyl group and the like).

Examples of the arylsulfonylaminocarbonylalkyl group include the $C_1$–$C_6$ alkyl groups substituted with the arylsulfonylaminocarbonyl group (for example, a phenylsulfonylaminocarbonylmethyl group, a naphthylsulfonylaminocarbonylmethyl group and the like).

The acyloxy group means a group composed of the acyl group and an oxygen atom (for example, a formyloxy group, an acetyloxy group and the like).

Examples of the acyloxyalkyl group include the $C_1$–$C_6$ alkyl groups substituted with the acyloxy group (for example, a formyloxymethyl group, an acetyloxymethyl group and the like).

Examples of the aralkyloxy group include the alkoxy groups substituted with the aryl group (for example, a benzyloxy group, a naphthylmethoxy group and the like).

Examples of the carboxyalkyloxy group include the alkoxy groups substituted with a carboxyl group (for example, a carboxymethoxy group, a carboxyethoxy group and the like).

The alkylene group means a linear or branched alkylene group having 1 to 5 carbon atoms, and examples thereof include a methylene group, an ethylene group, a propylene group and the like.

The alkenylene group is an alkenylene group having 2 to 5 carbon atoms and a double bond, and examples thereof include a vinylene group, a propenylene group and the like. Examples of the alkylenedioxy group include those having 1 to 5 carbon atoms, such as a methylenedioxy group, an ethylenedioxy group and a propylenedioxy group.

The carbonyldioxy group is a group represented by —O—C(=O)—O—. Incidentally, no particular limitation is imposed on the substituting position in the above description.

Among these substituents represented by $R^9$ and $R^{10}$, the hydrogen atom, hydroxyl group, alkyl group, alkenyl group, alkynyl group, halogen atom, halogenoalkyl group, amino group, hydroxyimino group, alkoxyimino group, aminoalkyl group, N-alkylaminoalkyl group, N,N-dialkylaminoalkyl group, acyl group, acylalkyl group, acylamino group which may be substituted, acylaminoalkyl group, alkoxy group, alkoxyalkyl group, hydroxyalkyl group, carboxyl group, carboxyalkyl group, alkoxycarbonyl group, alkoxycarbonylalkyl group, alkoxycarbonylamino group, alkoxycarbonylaminoalkyl group, carbamoyl group, N-alkylcarbamoyl group which may have a substituent on the alkyl group, N,N-dialkylcarbamoyl group which may have a substituent on the alkyl groups, N-alkenylcarbamoyl group, N-alkenylcarbamoylalkyl group, N-alkenyl-N-alkylcarbamoyl group, N-alkenyl-N-alkylcarbamoylalkyl group, N-alkoxycarbamoyl group, N-alkyl-N-alkoxycarbamoyl group, N-alkoxycarbamoylalkyl group, N-alkyl-N-alkoxycarbamoylalkyl group, carbazoyl group which may be substituted by 1 to 3 alkyl groups, alkylsulfonyl group, alkylsulfonylalkyl group, 3- to 6-membered nitrogen-containing heterocyclic carbonyl group which may be substituted, 3- to 6-membered nitrogen-containing heterocyclic carbonyloxyalkyl group which may be substituted, carbamoylalkyl group, carbamoyloxyalkyl group, N-alkylcarbamoyloxyalkyl group, N,N-dialkylcarbamoyloxyalkyl group, N-alkylcarbamoylalkyl group which may have a substituent on the alkyl group, N,N-dialkylcarbamoylalkyl group which may have a substituent on the alkyl groups, alkylsulfonylamino group, alkylsulfonylaminoalkyl group, oxo group, acyloxy group, and acyloxyalkyl group are preferred. The alkylene group, alkenylene group, alkylenedioxy group and carbonyldioxy group which are formed by $R^9$ and $R^{10}$ together with each other are also preferred.

It is preferred that $R^9$ be a hydrogen atom, and $R^{10}$ is one of the substituents mentioned above as preferable groups. In this case, examples of a group more preferred as $R^{10}$ include the hydrogen atom, hydroxyl group, alkyl group, halogen atom, hydroxyimino group, N-alkylaminoalkyl group, N,N-dialkylaminoalkyl group, acyl group, acylamino group which may be substituted, acylaminoalkyl group, alkoxy group, alkoxyalkyl group, hydroxyalkyl group, carboxyl group, alkoxycarbonyl group, alkoxycarbonylalkyl group, alkoxycarbonylamino group, carbamoyl group, N-alkylcarbamoyl group which may have a substituent on the alkyl group, N,N-dialkylcarbamoyl group which may have a substituent on the alkyl groups, N-alkenylcarbamoyl group, N-alkenylcarbamoylalkyl group, N-alkenyl-N-alkylcarbamoyl group, N-alkenyl-N-alkylcarbamoylalkyl group, N-alkoxycarbamoyl group, N-alkyl-N-alkoxycarbamoyl group, N-alkyl-N-alkoxycarbamoylalkyl group, carbazoyl group which may be substituted by 1 to 3 alkyl groups, alkylsulfonyl group, alkylsulfonylalkyl group, 3- to 6-membered nitrogen-containing heterocyclic carbonyl group which may be substituted, 3- to 6-membered nitrogen-containing heterocyclic carbonyloxyalkyl group which may be substituted, carbamoylalkyl group, N,N-dialkylcarbamoyloxyalkyl group, N-alkylcarbamoylalkyl group which may have a substituent on the alkyl group, N,N-dialkylcarbamoylalkyl group which may have a substituent on the alkyl groups, alkylsulfonylamino group, alkylsulfonylaminoalkyl group, and acyloxy group.

Of these, as examples of $R^{10}$, are particularly preferred the hydrogen atom, hydroxyl group, alkyl group, N,N-dialkylaminoalkyl group, acylamino group which may be substituted, acylaminoalkyl group, alkoxy group, alkoxyalkyl group, hydroxyalkyl group, alkoxycarbonyl group, alkoxycarbonylamino group, carbamoyl group, N-alkylcarbamoyl group which may have a substituent on the alkyl group, N,N-dialkylcarbamoyl group which may have a substituent on the alkyl groups, N-alkenylcarbamoyl group, N-alkenylcarbamoylalkyl group, N-alkenyl-N-alkylcarbamoyl group, N-alkenyl-N-alkylcarbamoylalkyl group, N-alkyl-N-alkoxycarbamoyl group, carbazoyl group which may be substituted by 1 to 3 alkyl groups, alkylsulfonyl group, alkylsulfonylalkyl group, 3- to 6-membered nitrogen-containing heterocyclic carbonyl group which may be substituted, N,N-dialkylcarbamoyloxyalkyl group, N-alkylcarbamoylalkyl group which may have a substituent on the alkyl group, N,N-dialkylcarbamoylalkyl group which may have a substituent on the alkyl groups, alkylsulfonylamino group, alkylsulfonylaminoalkyl group, and acyloxy group.

As specific preferable examples of $R^9$ and $R^{10}$, may be mentioned a hydrogen atom, hydroxyl group, methyl group, ethyl group, isopropyl group, N,N-dimethylaminomethyl group, N,N-dimethylaminoethyl group, N,N-diethylaminomethyl group, acetylamino group, methoxyacetylamino group, acetylaminomethyl group, acetylaminoethyl group, methoxy group, ethoxy group, methoxymethyl group, methoxyethyl group, hydroxymethyl group, 2-hydroxyethyl group, 1-hydroxy-1-methylethyl group, methoxycarbonyl group, ethoxycarbonyl group, methoxycarbonylamino group, ethoxycarbonylamino group, N-allylcarbamoyl group, N-allylcarbamoylmethyl group, N-allyl-N-methylcarbamoyl group, N-allyl-N-methylcarbamoylmethyl group, N-methoxy-N-methylcarbamoyl group, N,N-dimethylcarbazoyl group, N,N,N'-trimethylcarbazoyl group, methanesulfonyl group, methanesulfonylmethyl group, ethanesulfonylmethyl group, N-methylcarbamoyl group, N-ethylcarbamoyl group, N-propylcarbamoyl group, N-isopropylcarbamoyl group, N-tert-butylcarbamoyl group, N-cyclopropylcarbamoyl group, N-cyclopropylmethylcarbamoyl group, N-(1-ethoxycarbonylcyclopropyl)carbamoyl group, N-(2-hydroxyethyl)carbamoyl group, N-(2-fluoroethyl)-carbamoyl group, N-(2-methoxyethyl)carbamoyl group, N-(carboxymethyl)carbamoyl group, N-(2-aminoethyl)-carbamoyl group, N-(2-amidinoethyl)carbamoyl group, N,N-dimethylcarbamoyl group, N,N-diethylcarbamoyl group, N-ethyl-N-methylcarbamoyl group, N-isopropyl-N-methyl-carbamoyl group, N-methyl-N-propylcarbamoyl group, N-(2-hydroxyethyl)-N-methylcarbamoyl group, N-(2-fluoroethyl)-N-methylcarbamoyl group, N,N-bis(2-hydroxyethyl)carbamoyl group, N,N-bis(2-fluoroethyl)carbamoyl group, N-(2-methoxyethyl)-N-methylcarbamoyl group, N-carboxymethyl-N-methylcarbamoyl group, N,N-bis(2-aminoethyl)carbamoyl group, azetidinocarbonyl group, 3-methoxyazetidinocarbonyl group, 3-hydroxyazetidinocarbonyl group, pyrrolidinocarbonyl group, 3-hydroxypyrrolidinocarbonyl group, 3-fluoropyrrolidinocarbonyl group, 3,4-dimethoxypyrrolidinocarbonyl group, piperidinocarbonyl group, piperazinocarbonyl group, morpholinocarbonyl group, N-methylcarbamoylmethyl group, N-methylcarbamoylethyl group, N-ethylcarbamoyl-methyl group, N-(2-fluoroethyl)carbamoylmethyl group, N-(2-methoxyethyl)carbamoylmethyl group, N,N-dimethylcarbamoylmethyl group, N,N-dimethylcarbamoylethyl group, N-(2-fluoroethyl)-N-methylcarbamoylmethyl group, N-(2-methoxyethyl)-N-methylcarbamoylmethyl group, N,N-dimethylcarbamoyloxymethyl group, 2-(N-ethyl-N-methylcarbamoyloxy)ethyl group, methylsulfonylamino group, ethylsulfonylamino group, methylsulfonylaminomethyl group and methylsulfonylaminoethyl group. As described above, it is preferred that $R^9$ be a hydrogen atom, and $R^{10}$ is one of these specified substituents. However, $R^9$ and $R^{10}$ are not limited to these specific substituents at all.

The group $T^1$ is a carbonyl group or sulfonyl group, and is preferably a carbonyl group when the group $Q^1$ is a bicyclic or tricyclic fused hydrocarbon group, or bicyclic or tricyclic fused heterocyclic group, and the group $Q^2$ is a single bond.

$R^1$ and $R^2$ are, independently of each other, a hydrogen atom, hydroxyl group, alkyl group or alkoxy group, preferably a hydrogen atom or alkyl group, more preferably a hydrogen atom.

Stereoisomers or optical isomers derived from an asymmetric carbon atom may be present in the compounds of the present invention represented by the general formula (1). However, these stereoisomers, optical isomers and mixtures thereof are all included in the present invention.

No particular limitation is imposed on salts of the compounds of the present invention represented by the general formula (1) so far as they are pharmaceutically acceptable salts. However, specific examples thereof include mineral acid salts such as hydrochlorides, hydrobromides, hydriodides, phosphates, nitrates and sulfates; benzoates; organic sulfonates such as methanesulfonates, 2-hydroxyethanesulfonates and p-toluenesulfonates; and organic carboxylates such as acetates, propanoates, oxalates, malonates, succinates, glutarates, adipates, tartrates, maleates, malates and mandelates. In the case where the compounds represented by the general formula (1) have an acidic group, they may be salts of alkali metal ions or alkaline earth metal ions. No particular limitation is imposed on the solvates thereof so far as they are pharmaceutically acceptable solvates. As specific examples thereof, however, may be mentioned hydrates and solvates with ethanol. When a nitrogen atom is present in the general formula (1), such a compound may be converted to an N-oxide thereof.

The preparation process of the ethylenediamine derivatives (1) according to the present invention will hereinafter be described.

[Preparation Process 1]

An ethylenediamine derivative represented by the general formula (1), a salt thereof, a solvate thereof, or an N-oxide thereof can be prepared in accordance with, for example, the following process:

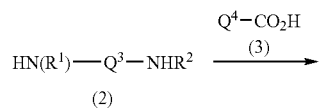

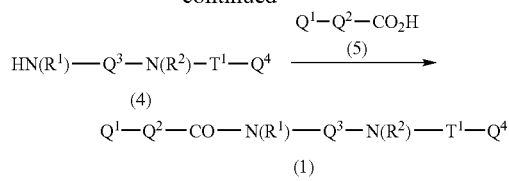

wherein $Q^1$, $Q^2$, $Q^3$, $Q^4$, $R^1$ and $R^2$ have the same meanings as defined above, and $T^1$ represents a carbonyl group.

A mixed acid anhydride, acid halide, activated ester or the like, which is derived from carboxylic acid (3), may react with diamine (2), giving compound (4). The resultant compound (4) may react with carboxylic acid (5) under the same conditions, giving compound (1) according to the present invention can be prepared. In the above reaction steps, reagents and conditions, which are generally used in peptide synthesis, may be applied. The mixed acid anhydride can be prepared by, for example, reaction of a chloroformate such as ethyl chloroformate or isobutyl chloroformate with carboxylic acid (3) in the presence of a base. The acid halide can be prepared by treating carboxylic acid (3) with an acid halide such as thionyl chloride or oxalyl chloride. The activated ester includes various kinds of esters. Such an ester can be prepared by, for example, reaction of a phenol such as p-nitrophenol, N-hydroxybenzotriazol, or N-hydroxysccinimide with carboxylic acid (3) using a condensing agent such as N,N'-dicyclohexylcarbodiimide or N-(3-dimethylaminopropyl)-N'-ethylcarbodiimide hydrochloride. The activated ester can also be prepared by reaction of carboxylic acid (3) with pentafluorophenyl trifluoroacetate or the like, reaction of carboxylic acid (3) with 1-benzotriazolyloxy-tripyrrolidinophosphonium hexafluorophosphite, reaction of carboxylic acid (3) with diethyl cyanophosphonate (Shioiri method), reaction of carboxylic acid (3) with triphenylphosphine and 2,2'-dipyridyl disulfide (Mukaiyama method) or the like. The thus-obtained mixed acid anhydride, acid halide or activated ester of carboxylic acid (3) may react with diamine (2) at −78° C. to 150° C. in the presence of a proper base in an inert solvent, giving compound (4). Thus-obtained compound (4) may react with a mixed acid anhydride, acid halide or activated ester of carboxylic acid (5) under the same conditions, giving compound (1) according to the present invention. The reagents and reaction conditions in the reaction of compound (4) with carboxylic acid (5) are the same as those in the reaction of diamine (2) with carboxylic acid (3).

As specific examples of the base used in each step, may be mentioned carbonates of alkali metals or alkaline earth metals, such as sodium carbonate and potassium carbonate, alkali metal alkoxides such as sodium ethoxide and potassium butoxide, alkali metal hydroxides such as sodium hydroxide and potassium hydroxide, and hydrides of alkali metals or alkaline earth metals, such as sodium hydride and potassium hydride; organic metal bases exemplified by alkyllithium such as n-butyllithium, and dialkylaminolithium such as lithium diisopropylamide; organic metal bases exemplified by bis(silyl)amine, such as lithium-bis(trimethylsilyl)-amide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

Examples of the inert solvent used in this reaction include alkyl halide type solvents such as dichloromethane, chloroform and carbon tetrachloride, etheric solvents such as tetrahydrofuran, 1,2-dimethoxyethane and dioxane, aromatic solvents such as benzene and toluene, amide solvents such as N,N-dimethylformamide, N,N-dimethylacetamide and N-methylpyrrolidin-2-one. In addition to these solvent, a sulfoxide solvent such as dimethyl sulfoxide or sulfolane, a ketone solvent such as acetone or methyl ethyl ketone, or the like may be used in some cases.

[Preparation Process 2]

Compound (1) according to the present invention can also be prepared in accordance with the following process:

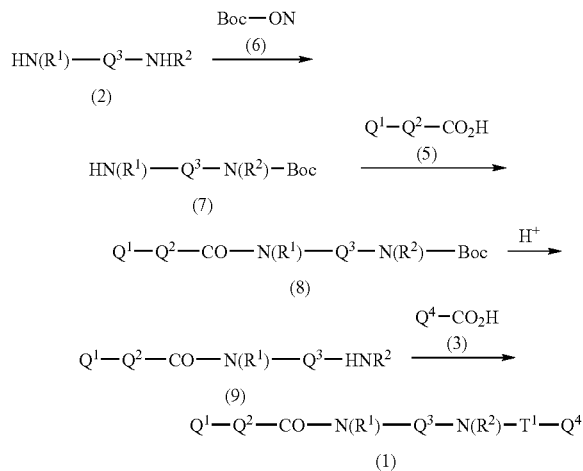

wherein $Q^1$, $Q^2$, $Q^3$, $Q^4$, $R^1$ and $R^2$ have the same meanings as defined above, $T^1$ represents a carbonyl group, Boc represents a tert-butoxycarbonyl group, and Boc-ON represents a 2-(tert-butoxycarbonyloxyimino)-2-phenylacetonitrile.

As described above, diamine (2) is treated with Boc-ON (6) to prepare compound (7) in which one of 2 amino groups has been protected with tert-butoxycarbonyl group. The resultant compound (7) reacts with carboxylic acid (5) and affords compound (8). Compound (8) is successively treated with an acid to give compound (9). Compound (9) then reacts with the carboxylic acid (3), giving compound (1) according to the present invention. Compound (7) can be prepared under the following conditions. The reaction is conducted at −10° C. to 40° C. in the presence of triethylamine in a solvent such as dichloromethane. Reaction of compound (7) with the mixed acid anhydride, acid halide or activated ester of the carboxylic acid (5) is carried out using the same reagents and reaction conditions as those described in Preparation Process 1, whereby compound (8) can be prepared. The resultant compound (8) is treated with trifluoroacetic acid or the like at −20° C. to 70° C., whereby amine (9) can be prepared. In the reaction of the resultant amine (9) with carboxylic acid (3), the same reagents and conditions as those described in Preparation Process 1 may be used.

By the way, the tert-butoxycarbonyl group of compound (7) may be replaced by other amino-protecting groups. In this case, reagent (6) is also changed to other reagents, and reaction conditions and the like according to the reagents must be used. As examples of other protecting groups for amino groups, may be mentioned ordinary acyl-type protecting groups, namely, alkanoyl groups such as an acetyl group, alkoxycarbonyl groups such as methoxycarbonyl and ethoxycarbonyl groups, arylmethoxycarbonyl groups such as benzyloxycarbonyl, p-methoxybenzyloxycarbonyl and p- or o-nitrobenzyloxycarbonyl groups, arylmethyl groups such as benzyl and triphenylmethyl groups, aroyl groups such as a benzoyl group, and arylsulfonyl groups such as 2,4-dinitrobenzenesulfonyl and o-nitrobenzenesulfonyl groups. These protecting groups may be chosen for use according to the nature and the like of the compound of which amino group is to be protected. Upon leaving such a protecting group, reagents and conditions may be employed according to the protecting group.

[Preparation Process 3]

Compound (1) according to the present invention can be prepared by reacting diamine (2) with sulfonyl halide (10).

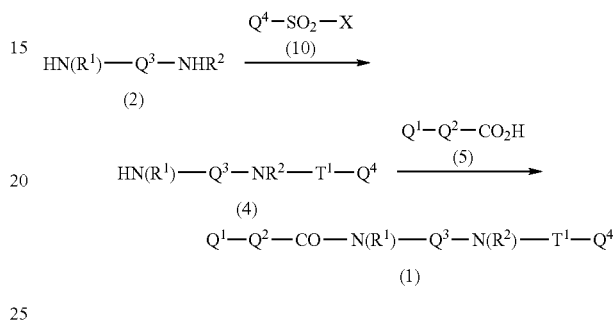

wherein $Q^1$, $Q^2$, $Q^3$, $Q^4$, $R^1$ and $R^2$ have the same meanings as defined above, $T^1$ represents a sulfonyl group, and X represents a halogen atom.

Diamine (2) reacts with sulfonyl halide (10) at −10° C. to 30° C. in the presence of a base such as triethylamine in an inert solvent, giving compound (4). The inert solvent and base may be suitably chosen for use from those described in Preparation Process 1. The resultant compound (4) is condensed with carboxylic acid (5) using the reagents and conditions described in Preparation Process 1, whereby compound (1) according to the present invention can be prepared. Sulfonyl halide (10) may be synthesized in a proper base in accordance with the publicly known process (WO96/10022, WO00/09480) or a process according to it.

[Preparation Process 4]

Compound (1) according to the present invention can also be prepared in accordance with the following process:

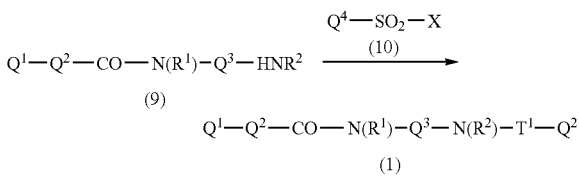

wherein $Q^1$, $Q^2$, $Q^3$, $Q^4$, $R^1$, $R^2$ and X have the same meanings as defined above, and $T^1$ represents a sulfonyl group.

More specifically, amine (9) may react with sulfonyl halide (10) at −10° C. to 30° C. in the presence of a base in an inert solvent, giving compound (1). The inert solvent and base may be suitably chosen for use from those described in Preparation Process 1.

[Preparation Process 5]

In the compounds (1) according to the present invention, geometrical isomers of trans-form and cis-form in the relation between position 1 and position 2 are present when $Q^3$ is the following group:

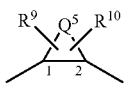

wherein $R^9$, $R^{10}$ and $Q^5$ have the same meanings as defined above, and numerals 1 and 2 indicate positions.

The preparation processes of the compounds (1) having the trans-form and the cis-form in $Q^3$ will hereinafter be described.

<Preparation Process of Trans-Form>

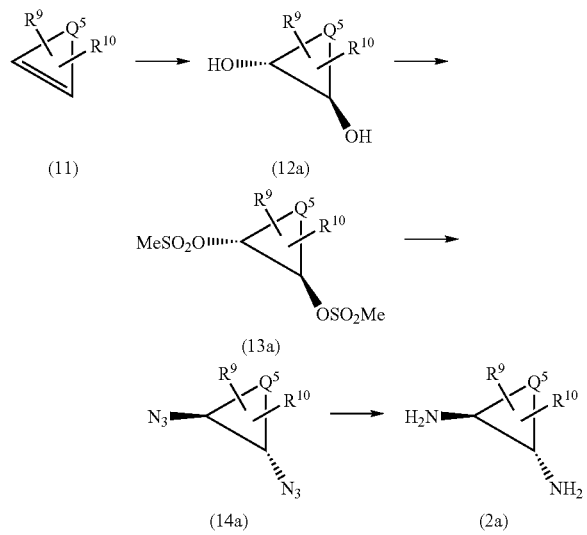

wherein $Q^5$, $R^9$ and $R^{10}$ have the same meanings as defined above.

As an example of preparation of trans-diol (12a) from cyclic alkene (11), conversion from, for example, cyclohexene to trans-cyclohexanediol (Organic Synthesis, 1995, Vol. III, p. 217) is known. As an example of preparation of trans-diamine (2a) from trans-diol (12a), conversion from trans-cyclopentanediol to trans-cyclopentanediamine (WO98/30574) is reported. Trans-diamine (2a) can be prepared from te cyclic alkene (11) according to these reports.

Trans-diamine (2a) prepared in accordance with the above-described process can be converted into trans-compound (1) by any of the above-described Preparation Processes 1 to 4.

<Preparation Process of Cis-Form>

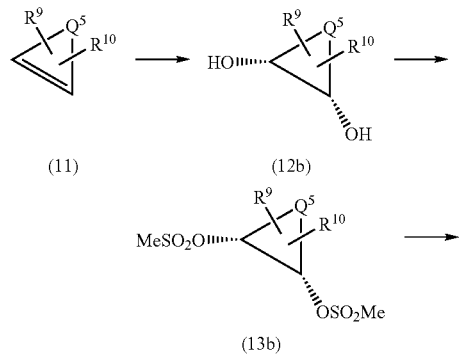

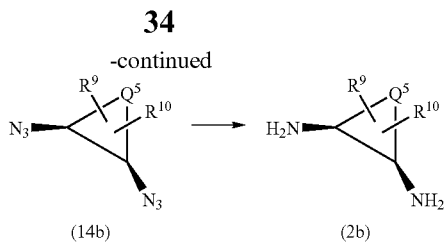

wherein $Q^5$, $R^9$ and $R^{10}$ have the same meanings as defined above.

As an example of preparation of cis-diol (12b) from cyclic alkene (11), conversion from cyclohexene to cis-cyclohexanediol (J. Org. Chem., 1998, Vol. 63, p. 6094) is known. As an example of preparation of cis-diamine (2b) from cis-diol (12a), conversion from cis-cyclopentanediol to cis-cyclopentanediamine (WO98/30574) is reported. Cis-diamine (2b) can be prepared from cyclic alkene (11) according to these reports.

Cis-diamine (2b) prepared in accordance with the above-described process can be converted into the cis-compound (1) by any of the above-described Preparation Processes 1 to 4.

[Preparation Process 6]

As described above, either cis-form or trans-form generated in $Q^3$ may be present in the compounds (1) according to the present invention, and so geometrical isomers are present. Further, optical isomers may be present in the respective geometrical isomers. The preparation process of an optically active compound will hereinafter be described.

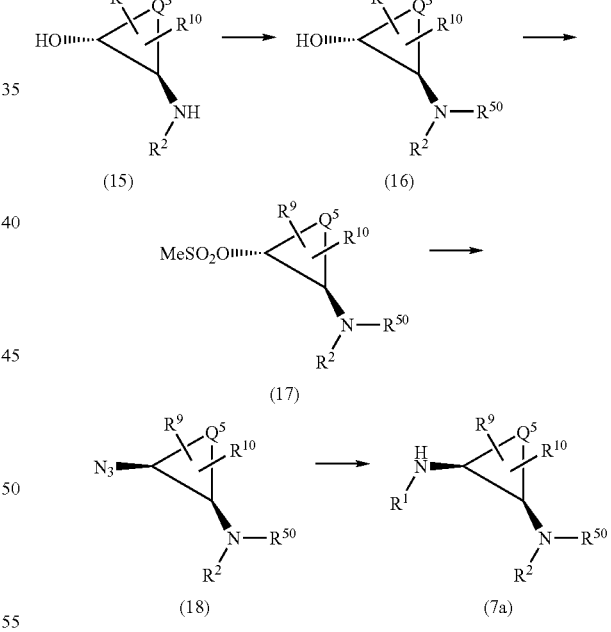

wherein $Q^5$, $R^1$, $R^2$, $R^9$ and $R^{10}$ have the same meanings as defined above, and $R^{50}$ represents a protecting group for amino group.

With respect to the preparation process of optically active aminoalcohol derivative (15) of 1,2-trans-form, for example, the preparation process of optically active 1,2-trans-2-aminocyclopentanol from cyclopentene oxide or the preparation process of optically active 1,2-trans-2-aminocyclohexanol from cyclohexene oxide is known (Tetrahedron: Asymmetry, 1996, Vol. 7, p. 843; J. Org. Chem., 1985, Vol. 50, p. 4154; J. Med. Chem., 1998, Vol. 41, p. 38). When the amino group of optically active aminoalcohol derivative (15) prepared by such an already known process or by applying such a process reacts with a proper protecting reagent, compound (16) can be produced. As a protecting group corresponding to $R^{50}$ in compound (16), is preferred, among the ordinary acyl type protecting groups, an alkoxycarbonyl group such as methoxycarbonyl, ethoxycarbonyl or tert-butoxycarbonyl group, an arylmethoxycarbonyl group such as benzyloxycarbonyl, p-methoxybenzyloxycarbonyl or p- or o-nitrobenzyloxycarbonyl group, or an arylsulfonyl group such as 2,4-dinitrobenzenesulfonyl or o-nitrobenzenesulfonyl group. When the amino group is protected with, for example, a tert-butoxycarbonyl group, aminoalcohol derivative (15) may react with di-tert-butyl dicarbonate at −78° C. to 50° C. in an inert solvent, giving compound (16). The inert solvent may be suitably chosen for use from those described in Preparation Process 1.

Compound (16) may react with methanesulfonyl chloride at −78° C. to 50° C. in the presence of a base in an inert solvent, giving compound (17). The inert solvent may be suitably chosen for use from those described in Preparation Process 1. As the base, is preferred an organic base such as pyridine, 2,6-lutidine, collidine, 4-dimethylaminopyridine, triethylamine, N-methyl-morpholine, diisopropylethylamine or diazabicyclo[5.4.0]-undec-7-ene (DBU).

Compound (17) may react with sodium azide at −10° C. to 150° C. in a proper solvent, giving compound (18). As the solvent, an amide solvent such as N,N-dimethyl-formamide, N,N-dimethylacetamide or N-methylpyrrolidin-2-on, an alcoholic solvent such as methanol or ethanol, an etheric solvent such as tetrahydrofuran, 1,2-dimethoxyethane or dioxane, benzenoid solvent such as toluene, a carbon halogenide such as dichloromethane, chloroform or carbon tetrachloride, acetone, dimethyl sulfoxide, or a mixed solvent of such a solvent with water is suitable.

As a process for converting azide derivative (18) into compound (7a), there are many processes such as a process of conducting hydrogenation with a palladium catalyst, Raney nickel catalyst or platinum catalyst, a reaction using a reducing agent such as lithium aluminum hydride, sodium borohydride or zinc borohydride, a reaction using zinc in the presence of nickel chloride or cobalt chloride, and a reaction using triphenylphosphine. Suitable reaction conditions may be selected according to the nature of the compound. For example, azide derivative (18) is hydrogenated at a temperature of −10° C. to 70° C. using 1 to 20% palladium on carbon as a catalyst in a proper solvent, whereby compound (7a) can be prepared. The hydrogen pressure may be raised higher than atmospheric pressure. As the solvent, an alcoholic solvent such as methanol or ethanol, an etheric solvent such as tetrahydrofuran, 1,2-dimethoxyethane or dioxane, an amide solvent such as N,N-dimethylformamide, N,N-dimethylacetamide or N-methylpyrrolidin-2-on, an ester solvent such as ethyl acetate, acetic acid, hydrochloric acid, water, or a mixed solvent thereof is suitable.

Optically active amine (7a) prepared in accordance with the above-described process can be converted to optically active compound (1) in accordance with the above-described Preparation Process 2. Antipode (1) of optically active substance (1) obtained from optically active amine (7a) may also be prepared in accordance with a similar process.

Optically active compound (1) may be prepared by separating racemic compound (1) through a column composed of an optically active carrier. It is also possible to separate intermediate (2), (4), (7), (8) or (9) for preparing racemic compound (1) through a column composed of an optically active carrier to isolate optically active intermediate (2), (4), (7), (8) or (9), and then prepare optically active compound (1) in accordance with any of Preparation Processes 1 to 4. As a process for isolating optically active intermediate (1), (2), (4), (7), (8) or (9), a process of fractionally crystallizing a salt with an optically active carboxylic acid, or a process of fractionally crystallizing a salt with an optically active base on the contrary may be used.

The following amines (4) used in the above-described Preparation Processes 1 to 4

$$HN(R^1)-Q^3-N(R^2)-T^1-Q^4 \qquad (4)$$

wherein $R^1$, $R^2$, $Q^3$, $Q^4$ and $T^1$ have the same meanings as defined above, or the following amines (9):

$$Q^1-Q^2-C(=O)-N(R^1)-Q^3-NHR^2 \qquad (9)$$

wherein $R^1$, $R^2$, $Q^1$, $Q^2$ and $Q^3$ have the same meanings as defined above, are useful compounds from a viewpoint of intermediates for preparing compounds (1) according to the present invention.

Optically active amines (7a) are also useful intermediates. In particular, the following amine (7b) can be converted into such an optically active compound (1a) as described below in accordance with the above Preparation Process 2. Compound (1a) can be further converted into derivatives having a carboxyl group, amide group or the like by converting the ester group on the cyclohexane ring of the compound.

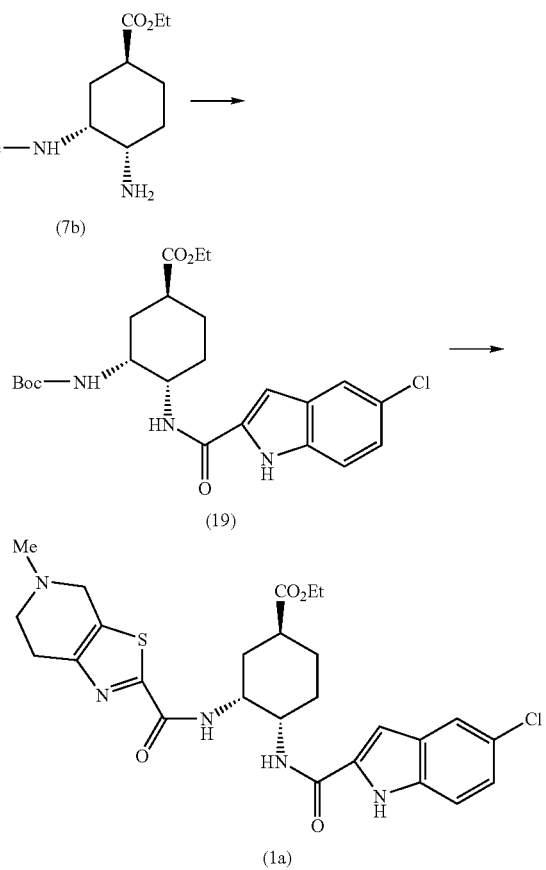

wherein Boc has the same meaning as defined above.

Specific preparation processes and FXa-inhibiting effects of the ethylenediamine derivatives according to the present invention will hereinafter be described.

EXAMPLES

In this embodiment, the ethylenediamine derivatives according to the present invention are named as substituted alkanediamines. For example, the following compound:

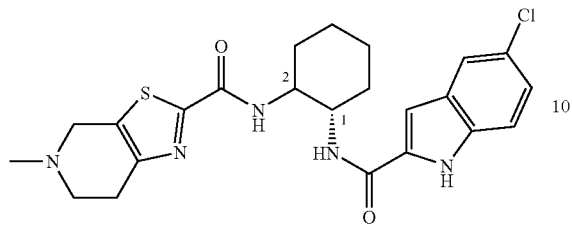

is named (±)-trans-$N^1$-[(5-chloroindol-2-yl)carbonyl]-$N^2$-[(5-methyl-4,5,6,7-(tetrahydrothiazolo[5,4-c]pyridin-2-yl)carbonyl]-1,2-cyclohexadiamine.

Referential Example 1

4-[(tert-Butoxycarbonyl)amino]pyridine

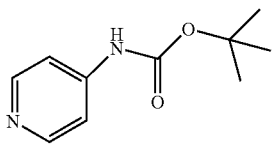

4-Aminopyridine (10 g) was dissolved in tetrahydrofuran (500 ml), di-tert-butyl dicarbonate (25.5 g) was added to the solution, and the mixture was stirred at room temperature for 10 minutes. The resultant reaction mixture was concentrated under reduced pressure, and deposited solids were washed with hexane to obtain the title compound (16.9 g) as a colorless solid.

$^1$H-NMR (CDCl$_3$) δ: 1.53(9H,s), 6.86(1H,br.s), 7.30(2H,dd,J=1.5, 4.9 Hz), 8.44(2H,dd,J=1.5, 4.9 Hz). MS (FAB) m/z: 195(M+H)$^+$.

Referential Example 2

4-[(tert-Butoxycarbonyl)amino]-3-mercaptopyridine

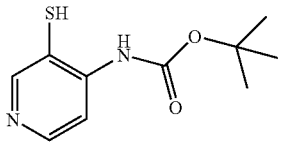

4-[(tert-Butoxycarbonyl)amino]pyridine (61.6 g) was dissolved in tetrahydrofuran (2,000 ml), and the solution was stirred at −78° C. for 10 minutes. A hexane solution (1.59 mol/l, 500 ml) of n-butyllithium was added dropwise to the solution, and the mixture was stirred for 10 minutes and then for 2 hours with ice cooling. After the reaction mixture was cooled to −78° C., sulfur powder (12.2 g) was added, and the resultant mixture was warmed to room temperature and stirred for 1 hour. Water (1,000 ml) was added to the reaction mixture to separate a water layer. After 3N hydrochloric acid was added to the water layer to adjust the pH of the water layer to 3 to 4, dichloromethane was added to separate an organic layer. The organic layer was dried over anhydrous sodium sulfate, and the solvent was distilled off under reduced pressure. The residue was purified by column chromatography on silica gel (dichloromethane:methanol=50:1) to obtain the title compound (33.2 g) as a pale yellow foamy substance.

$^1$H-NMR (DMSO-d$_6$) δ: 1.52(9H,s), 7.89(1H,d,J=6.4 Hz), 7.99(1H,d,J=6.4 Hz), 8.20(1H,s), 9.91(1H,br.s). MS (FAB) m/z: 227(M+H)$^+$.

Referential Example 3

Thiazolo[5,4-c]pyridine

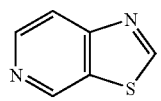

4-[(tert-Butoxycarbonyl)amino]-3-mercaptopyridine (33.2 g) was dissolved in formic acid (250 ml), and the solution was heated under reflux for 3 days. The reaction mixture was concentrated under reduced pressure, and a 5N aqueous solution (100 ml) of potassium hydroxide and ether were added to the residue to separate an organic layer. The organic layer was dried over anhydrous sodium sulfate, and the solvent was then distilled off under reduced pressure. The residue was purified by column chromatography on silica gel (dichloromethane:methanol=25:1) to obtain the title compound (9.03 g) as a colorless solid.

$^1$H-NMR (CDCl$_3$) δ: 8.05(1H,d,J=5.4 Hz), 8.70(1H,d,J=5.4 Hz), 9.23(1H,s), 9.34(1H,s). MS (FAB) m/z: 137(M+H)$^+$.

Referential Example 4

5-Methyl-4,5,6,7-tetrahydrothiazolo[5,4-c]pyridine

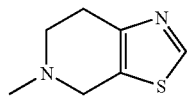

Thiazolo[5,4-c]pyridine (1.61 g) was dissolved in N,N-dimethylformamide (50 ml), and to the solution methyl iodide (1.50 ml) was added, the resultant mixture was stirred at 80° C. for 4 hours. The reaction mixture was concentrated under reduced pressure, and the residue was dissolved in methanol (100 ml), sodium borohydride (1.53 g) was added, and the resultant mixture was stirred at room temperature for 1 hour. The reaction mixture was concentrated under reduced pressure, and a saturated aqueous solution of potassium carbonate and ether were added to the residue to separate an organic layer. The organic layer was dried over anhydrous sodium sulfate, and the solvent was distilled off under reduced pressure. The residue was purified by column chromatography on silica gel (dichloromethane:methanol=25:1) to obtain the title compound (1.28 g) as a pale yellow oil.

$^1$H-NMR (CDCl$_3$) δ: 2.52(3H,s), 2.83(2H,t,J=5.9 Hz), 2.98(2H,t,J=5.9 Hz), 3.70(2H,s), 8.63(1H,s). MS (FAB) m/z: 155(M+H)$^+$.

Referential Example 5

Lithium 5-methyl-4,5,6,7-tetrahydrothiazolo[5,4-c]-pyridine-2-carboxylate

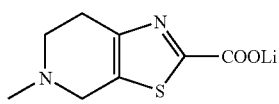

5-Methyl-4,5,6,7-tetrahydrothiazolo[5,4-c]pyridine (6.43 g) was dissolved in absolute tetrahydrofuran (200 ml), to the solution n-butyllithium (1.47N hexane solution, 34.0 ml) was added dropwise at −78° C., and the resultant mixture was stirred for 40 minutes. After carbon dioxide gas was blown into the reaction mixture at −78° C. for 1 hour, the reaction mixture was warmed to room temperature and then concentrated under reduced pressure to obtain the title compound (9.42 g) as pale brown foamy solids.

$^1$H-NMR (DMSO-$d_6$) δ: 2.37(3H,s), 2.64–2.77(4H,m), 3.54(2H,s). MS (FAB) m/z: 199(M+H)$^+$.

Referential Example 6

5-Ethoxycarbonyl-4,5,6,7-tetrahydrothiazolo[5,4-c]-pyridine

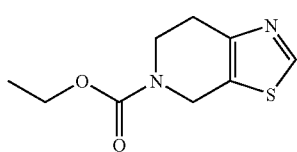

Phosphorus pentasulfide (500 g) was suspended in formamide (3,000 ml) with ice cooling, and the suspension was stirred overnight. Water and diethyl ether were added to the reaction mixture, and an organic layer was separated and dried over anhydrous magnesium sulfate, and the solvent was distilled off to obtain a yellow oil. After the oil was dissolved in n-butanol (350 ml), and 3-chloro-1-ethoxycarbonylpiperidin-4-one (150 g) synthesized according to the process described in literature (Tetrahedron, 1983, Vol. 39, p. 3767) was added to the solution, the resultant mixture was stirred at 100° C. for 2.5 hours. The reaction mixture was filtered through Celite. The resultant filtrate was washed with a saturated aqueous solution of sodium hydrogencarbonate and saturated saline, and then dried over anhydrous sodium sulfate. The solvent was distilled off under reduced pressure, and the residue was purified by column chromatography on silica gel (dichloromethane-ethyl acetate:hexane=1:2) to obtain the title compound (79.0 g) as a brown oil.

$^1$H-NMR (CDCl$_3$) δ: 1.30(3H,t,J=7.3 Hz), 2.96(2H,br.s), 3.82(2H,br.s), 4.19(2H,q,J=7.3 Hz), 4.73(2H,br.s), 8.68(1H, s). MS (FAB) m/z: 213(M+H)$^+$.

Referential Example 7

5-tert-Butoxycarbonyl-4,5,6,7-tetrahydrothiazolo[5,4-c]-pyridine

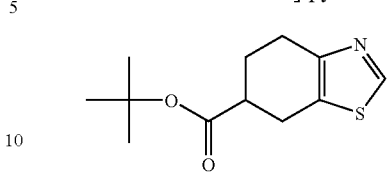

A 3.5N aqueous solution (250 ml) of sodium hydroxide was added to 5-ethoxycarbonyl-4,5,6,7-tetrahydrothiazolo [5,4-c]pyridine (33.5 g), and the mixture was heated under reflux overnight. After the reaction mixture was cooled to room temperature, di-tert-butyl dicarbonate (103 g) was added with ice cooling, and the mixture was stirred overnight at room temperature. After 3N hydrochloric acid was added to the reaction mixture to adjust the pH thereof to 1 to 2, dichloromethane was added. After separation of an organic layer, the organic layer was washed successively with an aqueous solution of sodium hydrogencarbonate and saturated saline and then dried-over anhydrous sodium sulfate. After the organic layer was concentrated under reduced pressure, the resultant residue was purified by column chromatography on silica gel (ethyl acetate:hexane=1:2) to obtain the title compound (21.1 g) as a pale brown oil.

$^1$H-NMR (CDCl$_3$) δ: 1.49(9H,s), 2.94(2H,br.s), 3.76(2H, br.s), 4.68(2H,s), 8.67(1H,s). MS (FAB) m/z: 241(M+H)$^+$.

Referential Example 8

5-tert-Butoxycarbonyl-4,5,6,7-tetrahydrothiazolo[5,4-c]-pyridine-2-carboxylic acid

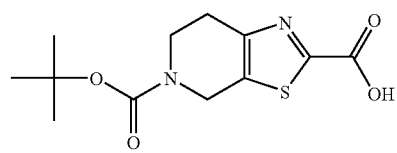

To a solution of 5-tert-butoxycarbonyl-4,5,6,7-tetrahydrothiazolo[5,4-c]pyridine (845 mg) in absolute tetrahydrofuran (20 ml), n-butyllithium (1.65N hexane solution, 2.13 ml) was added dropwise at −78° C., and the mixture was stirred for 30 minutes with ice cooling. After passing carbon dioxide gas into the reaction mixture at −78° C. for 1 hour, the reaction mixture was warmed to room temperature. A 5N aqueous solution of sodium hydroxide and diethyl ether were added to the reaction mixture to separate a water layer. 6N Hydrochloric acid was added to the water layer to adjust the pH thereof to 1 to 2. After addition of dichloromethane, an organic layer separated was washed with saturated saline and dried over anhydrous sodium sulfate. The solvent was distilled off under reduced pressure to obtain the title compound (562 mg) as a pale yellow foamy substance.

$^1$H-NMR (CDCl$_3$) δ: 1.50(9H,s), 3.00(2H,br.s), 3.78(2H, br.s), 4.74(2H,br.s). MS (FAB) m/z: 241(M+H)$^+$.

Referential Example 9

2-Amino-5-tert-butoxycarbonyl-4,5,6,7-tetrahydrothiazolo[5,4-c]pyridine

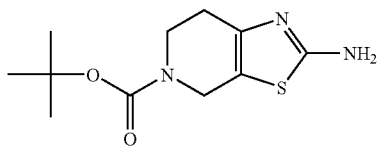

1-tert-Butoxycarbonyl-4-piperidone (40.0 g) was dissolved in cyclohexane (80 ml), and to the solution p-toluenesulfonic acid monohydrate (191 mg) and pyrrolidine (17.6 ml) were added. The mixture was heated under reflux for 2 hours while removing water using a Dean-Stark trap. After the reaction mixture was concentrated under reduced pressure, the residue was dissolved in methanol (60 ml), and sulfur powder (6.42 g) was added. A methanol solution (10 ml) of cyanamide (8.44 g) was slowly added dropwise with ice cooling, and the mixture was stirred at room temperature for 5 hours. Precipitated solid materials were collected by filtration to obtain the title compound (31.0 g) as a pale yellow solid.

$^1$H-NMR (DMSO-$d_6$) δ: 1.41(9H,s), 2.40–2.46(2H,m), 3.57(2H,t,J=5.6 Hz), 4.29(2H,s), 6.79(2H,s). MS (EI) m/z: 255(M$^+$).

Referential Example 10

2-Bromo-5-tert-butoxycarbonyl-4,5,6,7-tetrahydrothiazolo[5,4-c]pyridine

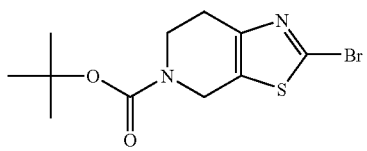

Copper(II) bromide (1.05 g) was suspended in N,N-dimethylformamide, and tert-butyl nitrite (0.696 ml) was added. After 2-amino-5-tert-butoxycarbonyl-4,5,6,7-tetrahydrothiazolo[5,4-c]pyridine (1.00 g) was added with ice cooling, the reaction mixture was heated and stirred at 40° C. for 30 minutes. The reaction mixture was concentrated under reduced pressure, and the residue was purified by column chromatography on silica gel (ethyl acetate:hexane=1:5) to obtain the title compound (568 mg) as a yellow solid.

$^1$H-NMR (CDCl$_3$) δ: 1.48(9H,s), 2.85(2H,br.s), 3.72(2H, t,J=5.6 Hz), 4.56(2H,br.s). MS (FAB) m/z: 319(M+H)$^+$.

Referential Example 11

2-Bromo-4,5,6,7-tetrahydrothiazolo[5,4-c]pyridine trifluoroacetate

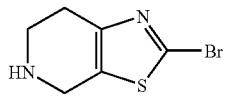

2-Bromo-5-tert-butoxycarbonyl-4,5,6,7-tetrahydrothiazolo[5,4-c]pyridine (890 mg) was dissolved in dichloromethane (2 ml), and to the solution trifluoroacetic acid (15 ml) was added, and the mixture was stirred at room temperature for 1 minute. The reaction mixture was concentrated under reduced pressure, and diethyl ether was added to the residue. Precipitated solid materials were collected by filtration to obtain the title compound (867 mg) as a colorless solid.

$^1$H-NMR (DMSO-$d_6$) δ: 2.98(2H,t,J=6.1 Hz), 3.72(2H,t, J=6.1 Hz), 4.35(2H,s), 9.53(2H,br.s). MS (FAB) m/z: 219 (M+H)$^+$.

Referential Example 12

2-Bromo-5-methyl-4,5,6,7-tetrahydrothiazolo[5,4-c]-pyridine

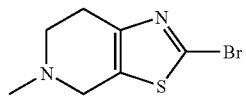

2-Bromo-4,5,6,7-tetrahydrothiazolo[5,4-c]pyridine trifluoroacetate (422 mg) was suspended in dichloromethane (10 ml), triethylamine (0.356 ml) was added, and the mixture was stirred at room temperature for 15 minutes. Acetic acid (0.216 ml) and an aqueous solution (35% solution, 0.202 ml) of formaldehyde were added to the reaction mixture, and the resultant mixture was stirred at room temperature for 2 minutes. Sodium triacetoxyborohydride (428 mg) was added to the reaction mixture, and the resultant mixture was stirred at room temperature for 1 hour. A 1N aqueous solution (10 ml) of sodium hydroxide was added to the reaction mixture and an organic layer was separated. After the organic layer was dried over anhydrous sodium sulfate, the solvent was distilled off under reduced pressure. The residue was purified by column chromatography on silica gel (dichloromethane:methanol=100:1) to obtain the title compound (286 mg) as a pale brown oil.

$^1$H-NMR (CDCl$_3$) δ: 2.49(3H,s), 2.79(2H,t,J=5.8 Hz), 2.88–2.93(2H,m), 3.58(2H,s). MS (FAB) m/z: 233(M+H)$^+$.

Referential Example 13

Lithium 5-methyl-4,5,6,7-tetrahydrothiazolo[5,4-c]-pyridine-2-carboxylate

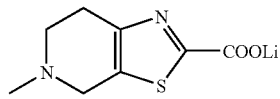

2-Bromo-5-methyl-4,5,6,7-tetrahydrothiazolo-[5,4-c] pyridine (531 mg) was dissolved in absolute diethyl ether (20 ml), n-butyllithium (1.54N hexane solution, 1.63 ml) was added dropwise at −78° C., and the mixture was stirred for 30 minutes with ice cooling. After passing carbon dioxide into the reaction mixture at −78° C. for 1 hour, the mixture was warmed to room temperature. The reaction mixture was concentrated under reduced pressure to obtain the title compound (523 mg) as a pale brown solid.

$^1$H-NMR (DMSO-$d_6$) δ: 2.37(3H,s), 2.64–2.77(4H,m), 3.54(2H,s). MS (FAB) m/z: 199(M+H)$^+$.

Referential Example 14

4-Ethoxycarbonyl-2-(trans-styryl)oxazole

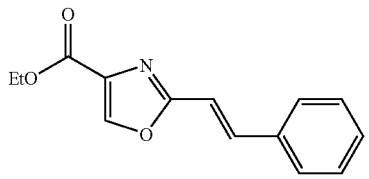

Synthesis was conducted in accordance with the report (J. Org. Chem., 1996, Vol. 61, p. 6496) by Panek et al. Sodium hydrogencarbonate (22.8 g) and ethyl bromopyruvate (10.5 ml) were added to a solution of cinnamamide (10.0 g) in tetrahydrofuran (250 ml) at room temperature, and the mixture was heated under reflux for 48 hours. The reaction mixture was allowed to cool to room temperature, filtered through Celite and then concentrated under reduced pressure to obtain residue. Trifluoroacetic anhydride (30 ml) was added to a solution of this residue in tetrahydrofuran (30 ml) at 0° C., and the mixture was gradually warmed to room temperature. After the mixture was stirred for 63 hours, a saturated aqueous solution (500 ml) of sodium hydrogencarbonate and ethyl acetate (150 ml) were added to the reaction mixture, and an organic layer was separated. The water layer was extracted with ethyl acetate (150 ml). The organic layers were combined, washed with saturated saline (150 ml), dried over anhydrous sodium sulfate and then concentrated under reduced pressure. The residue was purified by column chromatography on silica gel (hexane:ethyl acetate=5:1→3:1) to obtain the title compound (10.9 g) as a colorless solid.

$^1$H-NMR (CDCl$_3$) δ: 1.41(3H,t,J=7.0 Hz), 4.42(2H,q,J=7.0 Hz), 6.96(1H,d,J=16.6 Hz), 7.30–7.40(3H,m), 7.53(2H,d,J=6.8 Hz), 7.63(1H,d,J=16.6 Hz), 8.20(1H,s).

Referential Example 15

4-Formyl-2-(trans-styryl)oxazole

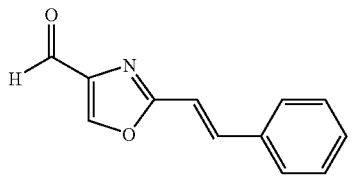

Diisobutylaluminum hydride (1.0N hexane solution, 66 ml) was added dropwise to a solution of 4-ethoxycarbonyl-2-(trans-styryl)oxazole (8.57 g) in dichloromethane (80 ml) at −78° C. After 15 minutes, methanol (11 ml) was added dropwise, and the mixture was warmed to room temperature over 1 hour. The reaction mixture was filtered through Celite, and the resultant pasty substance was dissolved in ethyl acetate (200 ml) and a saturated aqueous solution (200 ml) of ammonium chloride was added, and an organic layer was separated. The water layer was then extracted with dichloromethane (2×100 ml). The resultant organic layers were collected and washed with a saturated aqueous solution (100 ml) of sodium hydrogencarbonate and saturated saline (100 ml), combined with the filtrate obtained by the filtration through Celite and then dried over anhydrous sodium sulfate, and the solvent was distilled off under reduced pressure. The residue was purified by column chromatography on silica gel (dichloromethane:ethyl acetate=5:1→dichloromethane:methanol=10:1) to obtain the title compound (5.86 g) as colorless needle crystals.

$^1$H-NMR (CDCl$_3$) δ: 6.96(1H,d,J=16.6 Hz), 7.35–7.45 (3H,m), 7.56(2H,d,J=6.4 Hz), 7.67(1H,d,J=16.6 Hz), 8.26 (1H,s), 9.98(1H,s). MS (FAB) m/z: 200(M+H)$^+$.

Referential Example 16

2-(trans-Styryl)-4-vinyloxazole

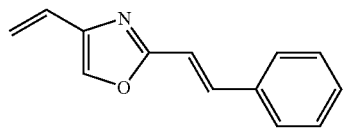

n-Butyllithium (1.54N hexane solution, 14.2 ml) was added dropwise to a solution of methyltriphenylphosphonium bromide (8.16 g) in tetrahydrofuran (80 ml) at 0° C., and the mixture was stirred at room temperature for 30 minutes. The reaction mixture was cooled again to 0° C., a solution of 4-formyl-2-(trans-styryl) oxazole (3.64 g) in tetrahydrofuran (20 ml) was added, and the mixture was warmed to room temperature. After stirring for 2 hours, water (200 ml) and ethyl acetate (100 ml) were added and an organic layer was separated. The water layer was extracted with ethyl acetate (50 ml). After the organic layers were combined, washed with saturated saline (100 ml) and dried over anhydrous sodium sulfate, the solvent was distilled off under reduced pressure. The residue was purified by column chromatography on silica gel (hexane:ethyl acetate=4:1→3:1) to obtain the title compound (2.84 g) as a pale yellow oil.

$^1$H-NMR (CDCl$_3$) δ: 5.33(1H,dd,J=1.5, 10.7 Hz), 5.98 (1H,dd,J=1.5, 17.6 Hz), 6.56(1H,dd,J=10.7, 17.6 Hz), 6.95 (1H,d,J=16.6 Hz), 7.31–7.42(3H,m), 7.49–7.56(4H,m). MS (FAB) m/z: 198(M+H)$^+$.

Referential Example 17

4-(2-Hydroxyethyl)-2-(trans-styryl)oxazole

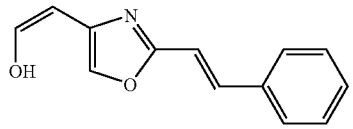

9-Borabicyclo[3.3.1]nonane (0.5N tetrahydrofuran solution, 158 ml) was added to a solution of 2-(trans-styryl)-4-vinyloxazole (13.0 g) in tetrahydrofuran (500 ml) at 0° C., and the mixture was stirred at room temperature for 15 hours. Water (10 ml), a 3N aqueous solution (80 ml) of sodium hydroxide and aqueous hydrogen peroxide (80 ml) were successively added dropwise to the reaction mixture at 0° C., and the mixture was stirred at room temperature for 6 hours. After water (600 ml) and ethyl acetate (200 ml) were added to the resultant reaction mixture to separate an organic layer, the water layer was extracted with ethyl acetate (200 ml). After the organic layers were collected, washed with saturated saline (200 ml) and dried over anhydrous sodium sulfate, the solvent was distilled off under reduced pressure. The residue was purified by column chromatography on silica gel (hexane:ethyl acetate=

2:1→ethyl acetate alone) to obtain the title compound (14.1 g) as a colorless solid.

$^1$H-NMR (CDCl$_3$) δ: 2.69(1H,br.s), 2.80(2H,t,J=5.6 Hz), 3.90–3.97(2H,m), 6.91(1H,d,J=16.6 Hz), 7.30–7.42(4H,m), 7.43–7.56(3H,m). MS (FAB) m/z: 216(M+H)$^+$.

Referential Example 18

N-[2-[2-(trans-Styryl)oxazol-4-yl]ethyl]phthalimide

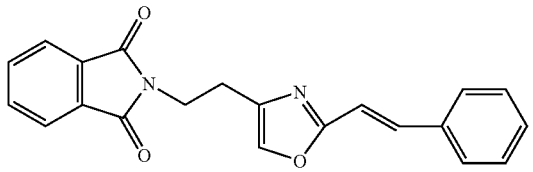

Phthalimide (200 mg), triphenylphosphine (357 mg) and diethyl azodicarboxylate (0.214 ml) were added to a solution of 4-(2-hydroxyethyl)-2-(trans-styryl)oxazole (292 mg) in tetrahydrofuran (15 ml) at room temperature, and the mixture was stirred for 4 hours. The solvent of the reaction mixture was distilled off under reduced pressure. The residue was purified by column chromatography on silica gel (hexane:ethyl acetate=3:1) to obtain the title compound (447 mg) as a colorless solid.

$^1$H-NMR (CDCl$_3$) δ: 2.98(2H,t,J=7.2 Hz), 4.03(2H,t,J=7.2 Hz), 6.88(1H,d,J=16.6 Hz), 7.28–7.45(5H,m), 7.48(2H,d,J=7.3 Hz), 7.71(2H,dd,J=2.9, 5.4 Hz), 7.84(2H,dd,J=2.9, 5.4 Hz). MS (FAB) m/z: 345(M+H)$^+$.

Referential Example 19

4-[2-(tert-Butoxycarbonylamino)ethyl]-2-(trans-styryl)oxazole

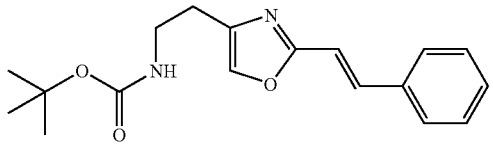

After hydrazine monohydrate (1.50 ml) was added to a solution of N-[2-[2-(trans-styryl)oxazol-4-yl]-ethyl] phthalimide (6.40 g) in ethanol (150 ml) at room temperature, and the mixture was stirred for 1 hour, hydrazine monohydrate (0.500 ml) was added again at room temperature, and the mixture was stirred for 2 hours. Dichloromethane (150 ml), a saturated solution (150 ml) of sodium hydrogencarbonate and di-tert-butyl dicarbonate (13.4 g) were added to the reaction mixture at room temperature. After stirring for 30 minutes, a water layer was separated and extracted with dichloromethane (50 ml). The resultant organic layers were combined and dried over anhydrous sodium sulfate, and the solvent was then distilled off under reduced pressure. The residue was purified by column chromatography on silica gel (hexane:ethyl acetate= 2:1→1:1) to obtain the title compound (5.06 g) as a colorless solid.

$^1$H-NMR (CDCl$_3$) δ: 1.45(9H,s), 2.75(2H,t,J=6.6 Hz), 3.46(2H,dt,J=5.9, 6.6 Hz), 4.92(1H,br.s), 6.91(1H,d,J=16.6 Hz), 7.29–7.45(4H,m), 7.48(1H,d,J=16.6 Hz), 7.52(2H,d,J=7.3 Hz). MS (FAB) m/z: 315(M+H)$^+$, 259(M-isobutene+H)$^+$, 315(M-Boc+H)$^+$.

Referential Example 20

5-(tert-Butoxycarbonyl)-2-(trans-styryl)-4,5,6,7-tetrahydrooxazolo[5,4-c]pyridine

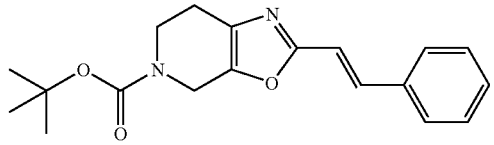

Paraformaldehyde (54.5 mg) and p-toluenesulfonic acid (7.2 mg) were added to a solution of 4-[2-(tert-butoxycarbonylamino)ethyl]-2-(trans-styryl)oxazole (190 mg) in toluene (15 ml) at room temperature. After heating under reflux for 1 hour, the reaction mixture was allowed to cool, and ethyl acetate (15 ml) and a saturated aqueous solution (15 ml) of sodium hydrogen-carbonate were added to the reaction mixture to separate an organic layer. After the water layer was extracted with ethyl acetate (10 ml), the resultant organic layers were combined and dried over anhydrous sodium sulfate, and the solvent was distilled off under reduced pressure. The residue was purified by column chromatography on silica gel (hexane:ethyl acetate= 3:1→2:1) to obtain the title compound (153 mg) as a colorless oil.

$^1$H-NMR (CDCl$_3$) δ: 1.50(9H,s), 2.67(2H,br.s), 3.73(2H, br.s), 4.55(2H,s), 6.90(1H,d,J=16.1 Hz), 7.29–7.42(3H,m), 7.46(1H,d,J=16.1 Hz), 7.52(2H,d,J=7.3 Hz). MS (FAB) m/z: 327(M+H)$^+$, 271(M-isobutene+H)$^+$, 227(M-Boc+H)$^+$.

Referential Example 21

5-(tert-Butoxycarbonyl)-2-formyl-4,5,6,7-tetrahydrooxazolo[5,4-c]pyridine

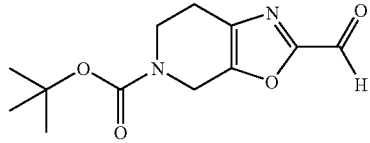

Acetone (8.0 ml), water (4.0 ml), N-methyl-morpholine oxide (577 mg) and osmium tetroxide (0.039 M, 3.20 ml) were added to a solution of 5-(tert-butoxy-carbonyl)-2-(trans-styryl)-4,5,6,7-tetrahydrooxazolo-[5,4-c]pyridine (803 mg) in tetrahydrofuran (16 ml) at room temperature, and the mixture was stirred overnight. Ethyl acetate (50 ml) and a 10% aqueous solution (50 ml) of sodium thiosulfate were added to the reaction mixture to separate an organic layer. The water layer was then extracted with ethyl acetate (30 ml). After the resultant organic layers were combined and dried over anhydrous sodium sulfate, the solvent was distilled off under reduced pressure. Methanol (8.0 ml), water (8.0 ml) and sodium metaperiodate (790 mg) were added to a solution of the residue in tetrahydrofuran (16 ml). After stirring for 3 hours, ethyl acetate (30 ml) and water (50 ml) were added to the reaction mixture to separate an organic layer. The water layer was extracted with ethyl acetate (20 ml). After the resultant organic layers were combined, washed with a saturated solution (50 ml) of sodium hydrogencarbonate and dried over anhydrous sodium sulfate, the solvent was distilled off under reduced pressure. The residue was purified by column chromatography on silica gel (hexane:ethyl acetate=4:1→2:1) to obtain the title compound (234 mg) as a colorless amorphous substance. Since this aldehyde was unstable, it was immediately used in the next reaction.

$^1$H-NMR (CDCl$_3$) δ: 1.49(9H,s), 2.77(2H,br.s), 3.77(2H, br.s), 4.62(2H,s), 9.70(1H,s).

Referential Example 22

5-(tert-Butoxycarbonyl)-2-methoxycarbonyl-4,5,6,7-tetrahydrooxazolo[5,4-c]pyridine

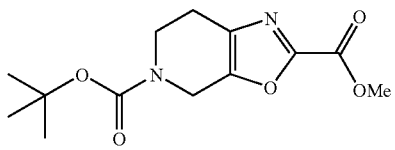

Sodium cyanide (220 mg) and manganese dioxide (780 mg) were added to a solution of 5-(tert-butoxycarbonyl)-2-formyl-4,5,6,7-tetrahydrooxazolo[5,4-c]pyridine (225 mg) in methanol (9.0 ml) at room temperature. After stirring for 30 minutes, the reaction mixture was filtered through Celite with ethyl acetate. The filtrate was washed with water (50 ml) and saturated saline (50 ml) and dried over anhydrous sodium sulfate. The solvent was then distilled off under reduced pressure, and the residue was purified by column chromatography on silica gel (hexane:ethyl acetate= 3:2→1:1) to obtain the title compound (120 mg) as a colorless amorphous substance.

$^1$H-NMR (CDCl$_3$) δ: 1.49(9H,s), 2.73(2H,br.s), 3.74(2H, br.s), 4.01(3H,s), 4.59(2H,s). MS (FAB) m/z: 283(M+H)$^+$.

Referential Example 23

2-Methoxycarbonyl-5-methyl-4,5,6,7-tetrahydrooxazolo-[5,4-c]pyridine

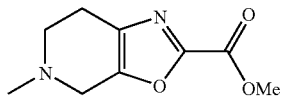

Trifluoroacetic acid (15 ml) was added to a solution of 5-(tert-butoxycarbonyl)-2-methoxycarbonyl-4,5,6,7-tetrahydrooxazolo[5,4-c]pyridine (500 mg) in dichloromethane (15 ml) at room temperature, and the mixture was stirred for 10 minutes. The reaction mixture was concentrated under reduced pressure, and dichloromethane (20 ml), triethylamine (0.495 ml), acetic acid (205 ml), formalin (0.230 ml) and sodium triacetoxyborohydride (570 mg) were added to the resultant residue at room temperature. After stirring for 15 minutes, dichloromethane (20 ml) and a saturated aqueous solution (50 ml) of sodium hydrogencarbonate were added to separate an organic layer. The water layer was extracted with dichloromethane (3×20 ml). After the resultant organic layers were combined and dried over anhydrous sodium sulfate, the solvent was distilled off under reduced pressure. The residue was purified by column chromatography on silica gel (chloroform:methanol= 20:1→10:1) to obtain the title compound (257 mg) as a colorless oil.

$^1$H-NMR (CDCl$_3$) δ: 2.52(3H,s), 2.72–2.78(2H,m), 2.78–2.83(2H,m), 3.61(2H,t,J=1.7 Hz), 4.00(3H,s). MS (FAB) m/z: 197(M+H)$^+$, 165(M-OCH$_3$)$^+$.

Referential Example 24

Lithium 5-methyl-4,5,6,7-tetrahydrooxazolo[5,4-c]-pyridine-2-carboxylate

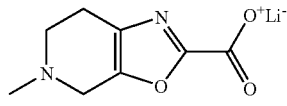

Water (6.0 ml) and lithium hydroxide (99.7 mg) were added to a solution of 2-methoxycarbonyl-5-methyl-4,5,6,7-tetrahydrooxazolo[5,4-c]pyridine (800 mg) in tetrahydrofuran (24 ml) at room temperature, and the mixture was stirred for 10 minutes. The reaction mixture was concentrated under reduced pressure to obtain the title compound (825 mg).

$^1$H-NMR (DMSO-d$_6$) δ: 2.37(3H,s), 2.47(2H,t,J=5.6 Hz), 2.64(2H,t,J=5.6 Hz), 3.43(2H,s).

Referential Example 25

5-Chlorobenzo[b]thiophene-2-carboxylic acid

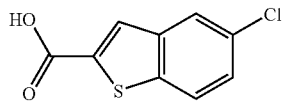

After 5-chlorobenzo[b]thiophene (2.53 g) was dissolved in absolute ether (40 ml), and the interior of a vessel was purged with argon, the solution was cooled to −78° C. tert-Butyllithium (1.54N hexane solution, 9.74 ml) was added dropwise to the solution, and the mixture was stirred at the same temperature for 1 hour in total. The reaction mixture was heated to 0° C. and stirred for 1.5 hours. The reaction mixture was cooled again to −78° C. and stirred for 1.5 hours while blowing carbon dioxide into the interior of the vessel. The temperature was returned to room temperature, 0.3N hydrochloric acid (100 ml) and ethyl acetate were added to the reaction mixture to separate an organic layer. The solvent was distilled off under reduced pressure, and ether was added to the residue. Precipitates were collected by filtration to obtain the title compound (2.67 g) as a colorless solid.

$^1$H-NMR (DMSO-d$_6$) δ: 7.53(1H,dd,J=8.5, 2.2 Hz), 8.07–8.11(3H,m), 13.65(1H,br.s). MS (FAB) m/z: 213(M+ H)$^+$.

Referential Example 26

Methyl 5-chloro-6-fluoroindole-2-carboxylate

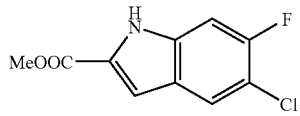

A mixture of methyl 3-chloro-4-fluoro-α-azidocinnamate (Japanese Patent Application Laid-Open No. 149723/1995) (1.85 g) and xylene (140 ml) was heated under reflux for 1 hour, and the solvent was then distilled off. The residue was purified by column chromatography on silica gel (dichloromethane) to obtain the title compound (491 mg) as colorless powder.

¹H-NMR (CDCl₃) δ: 3.95(3H,s), 7.13–7.15(1H,m), 7.20 (1H,dd,J=9.3, 0.49 Hz), 7.71(1H,d,J=7.3 Hz), 8.93(1H,br.s). MS (FAB) m/z: 227(M⁺).

Referential Example 27

5-Chloro-6-fluoroindole-2-carboxylic acid

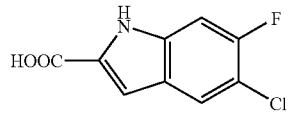

Methyl 5-chloro-6-fluoroindole-2-carboxylate (461 mg) was dissolved in a mixed solvent of tetrahydrofuran (15 ml), methanol (10 ml) and water (10 ml), lithium hydroxide (283 mg) was added at room temperature, and the mixture was stirred for 4 hours. The solvent was distilled off under reduced pressure, and 1N hydrochloric acid was added to the residue to weakly acidify it. The resultant powder was collected by filtration and dried to obtain the title compound (422 mg) as colorless powder.

¹H-NMR (CDCl₃) δ: 7.08–7.10(1H,m), 7.34(1H,d,J=9.5 Hz), 7.88(1H,d,J=7.6 Hz), 12.04(1H,s), 13.16(1H,s). MS (FAB) m/z: 213(M⁺).

Referential Example 28

5-(4-Pyridyl)-4,5,6,7-tetrahydrothiazolo[5,4-c]-pyridine

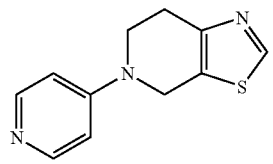

Trifluoroacetic acid (25 ml) was added to a solution of 5-(tert-butoxycarbonyl)-4,5,6,7-tetrahydrothiazolo[5,4-c] pyridine (5.00 g) in dichloromethane (25 ml) at room temperature. After stirring for 10 minutes, the reaction mixture was concentrated under reduced pressure, and 4-bromopyridine (5.20 g), N,N-dimethylformamide (30 ml) and triethylamine (15.5 ml) were added to the residue at room temperature, and the mixture was stirred at 150° C. for 2 days and then allowed to cool to room temperature. Colorless precipitates were separated by filtration, and the filtrate was concentrated under reduced pressure. Thereafter, dichloromethane (50 ml) and a saturated aqueous solution (100 ml) of sodium hydrogencarbonate were added to the residue, and the resultant water layer was saturated with sodium chloride. After separation of an organic layer, the resultant water layer was extracted with dichloromethane (5×30 ml). After the resultant organic layers were combined and dried over anhydrous sodium sulfate, the solvent was distilled off under reduced pressure. The residue was purified by column chromatography on silica gel (dichloromethane:methanol=20:1→8:1) to obtain the title compound (2.97 g) as a brown solid.

¹H-NMR (CDCl₃) δ: 3.07(2H,t,J=5.9 Hz), 3.81(2H,t,J=5.9 Hz), 4.61(2H,s), 6.74(2H,t,J=6.5 Hz), 8.30(2H,t,J=6.5 Hz), 8.70(1H,s). MS (ESI) m/z: 218(M+H)⁺.

Referential Example 29

Methyl 5-(4-pyridyl)thiazole-2-carboxylate

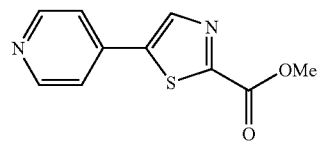

1-Hydroxybenzotriazole monohydrate (805 mg) and 1-(3-dimethylaminopropyl)-3-ethylcarbodiimide hydrochloride (1.71 g) were added to a solution of lithium 5-(4-pyridyl) thiazole-2-carboxylate (632 mg) in methanol (5.0 ml) at room temperature. After stirring for 4 days, the reaction mixture was concentrated under reduced pressure, and dichloromethane (20 ml), a saturated aqueous solution (100 ml) of sodium hydrogencarbonate and water (100 ml) were added to the residue to separate an organic layer. The water layer was then extracted with dichloromethane (2×20 ml). After the resultant organic layers were combined and dried over anhydrous sodium sulfate, the solvent was distilled off under reduced pressure. The residue was then purified by column chromatography on silica gel (dichloromethane:acetone=5:1→2:1) to obtain the title compound (353 mg) as a colorless solid.

¹H-NMR (CDCl₃) δ: 4.05(3H,s), 7.51(2H,d,J=6.1 Hz), 8.32(1H,s), 8.71(2H,d,J=6.1 Hz). MS (ESI) m/z: 221(M+H)⁺.

Referential Example 30

(±)-cis-N-[(5-Chloroindol-2-yl)carbonyl]-1,2-cyclopropanediamine

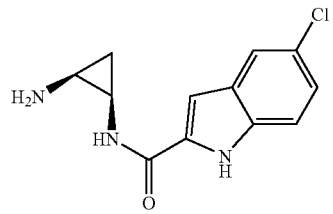

1-Hydroxybenzotriazole monohydrate (377 mg), 1-(3-dimethylaminopropyl)-3-ethylcarbodiimide hydrochloride (642 mg) and diisopropylethylamine (1.95 ml) were added to cis-1,2-cyclopropanediamine hydrochloride (J. Med. Chem., 1998, Vol. 41, pp. 4723–4732) (405 mg) and a solution of 5-chloroindole-2-carboxylic acid (546 mg) in N,N-dimethylformamide (10 ml) at room temperature, and the mixture was stirred for 50 hours. After the reaction mixture was concentrated under reduced pressure, dichloromethane (50 ml) and a saturated solution (200 ml) of sodium hydrogencarbonate were added to separate colorless solid deposited by filtration. An organic layer of the filtrate was separated and the water layer was extracted with dichloromethane. After the resultant organic layers were combined and dried over anhydrous sodium sulfate, the solvent was distilled off under reduced pressure to obtain residue. The residue was purified by medium-pressure flash column chromatography on silica gel (dichloromethane:methanol=100:7→10:1) to obtain the title compound (110 mg) as a colorless solid.

¹H-NMR (DMSO-d₆) δ: 0.44(1H,dd,J=10.7, 4.4 Hz), 1.11(1H,dd,J=14.0, 7.4 Hz), 2.63–2.70(1H,m), 3.07–3.16

(1H,m), 6.77(1H,s), 6.97(1H,br.s), 7.23(1H,dd,J=8.9, 1.8 Hz), 7.36(1H,d,J=8.9 Hz), 7.60(1H,s), 9.32(1H,s). MS (FAB) m/z: 250(M+H)⁺.

Referential Example 31

2-Chloro-6,7-dihydro-4H-pyrano[4,3-d]thiazole

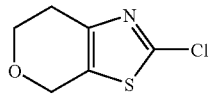

1) Tetrahydro-4H-pyran-4-one (5.0 g) was dissolved in cyclohexane (20 ml), and to the solution pyrrolidine (4.35 ml) and p-toluenesulfonic acid monohydrate (48 mg) were added, and the mixture was heated under reflux for 70 minutes while removing water by a Dean-Stark trap. The reaction mixture was cooled to room temperature, and the solvent was decanted, and the resulting solvent was concentrated under reduced pressure. The residue was dissolved in methanol (15 ml), and sulfur powder (1.60 g) was added with ice cooling. After 15 minutes, a methanol solution (10 ml) of cyanamide (2.10 g) was added dropwise over 20 minutes, and the mixture was stirred for 3 days. The solvent was distilled off under reduced pressure, and the residue was purified by column chromatography on silica gel (dichloromethane:methanol=20:1→10:1→4:1) to obtain 2-amino-6,7-dihydro-4H-pyrano[4,3-d]-thiazole (3.97 g) as a brown amorphous substance.

¹H-NMR (CDCl₃) δ: 2.66–2.70(2H,m), 3.97(2H,t,J=5.6 Hz), 4.63(2H,s), 4.94(2H,br.s). MS (FAB) m/z: 157(M+H)⁺.

2) Copper(II) chloride (4.10 g) was dissolved in acetonitrile (50 ml), and to the solution tert-butyl nitrite (3.93 g) was added in one portion with ice cooling. After 10 minutes, the compound (3.97 g) obtained in the above-described reaction was added to the mixture over about 1 hour, and the reaction mixture was stirred at room temperature for 1 hour. The reaction mixture was heated to 65° C. and continuously stirred for 2 hours. After silica gel (20 g) was added to the reaction mixture, the solvent was distilled off under reduced pressure, and the residue was purified by column chromatography on silica gel (hexane:ethyl acetate=3:1) to obtain the title compound (1.78 g) as a yellow oil.

¹H-NMR (CDCl₃) δ: 2.85–2.89(2H,m), 4.02(2H,t,J=5.6 Hz), 4.73(2H,s). MS (FAB) m/z: 175(M+H)⁺.

Referential Example 32

Lithium 6,7-dihydro-4H-pyrano[4,3-d]thiazole-2-carboxylate

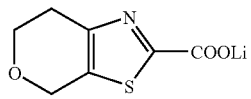

1) 2-Chloro-6,7-dihydro-4H-pyrano[4,3-d]thiazole (1.78 g) was dissolved in methanol (30 ml), and to the solution 10% palladium on carbon (300 mg) and sodium acetate (830 mg) were added. The mixture was stirred for 5 days in a hydrogen stream of 5 atm. After the catalyst was separated by filtration, the filtrate was concentrated, and the residue was subjected to column chromatography on silica gel (hexane:ethyl acetate=2:1) to obtain 6,7-dihydro-4H-pyrano[4,3-d]thiazole (1.14 g) as a colorless oil.

¹H-NMR (CDCl₃) δ: 2.97–3.01(2H,m), 4.04(2H,t,J=5.6 Hz), 4.87(2H,s), 8.69(1H,s). MS (FAB) m/z: 142(M+H)⁺.

2) After the product (1.14 g) obtained above was dissolved in diethyl ether (30 ml) and cooled to −78° C., 1.6 M butyllithium (6.6 ml) was added to the solution, and the mixture was stirred. After 20 minutes, bubbling was conducted with carbon dioxide for 15 minutes. The reaction mixture was warmed to room temperature and concentrated under reduced pressure to obtain the title compound (1.65 g) as a colorless amorphous substance.

¹H-NMR (DMSO-d₆) δ: 2.83(2H,t,J=5.6 Hz), 3.92(2H,t, J=5.6 Hz), 4.73(2H,s).

Referential Example 33

(±)-cis-N-[(5-Chloroindol-2-yl)carbonyl]-1,2-cyclobutanediamine

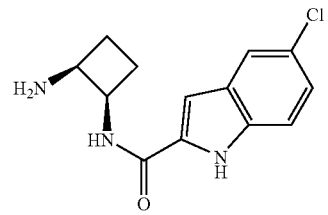

The title compound was obtained from cis-1,2-cyclobutanediamine hydrochloride (J. Am. Chem. Soc., 1942, Vol. 64, pp. 2696–2700) in a similar manner to Referential Example 30.

¹H-NMR (DMSO-d₆) δ: 1.55–2.20(4H,m), 3.52–3.62 (1H,m), 4.35–4.50(1H,m), 7.16(1H,dd,J=8.7, 2.1 Hz), 7.19 (1H,s), 7.42(1H,d,J=8.7 Hz), 7.70(1H,d,J=2.1 Hz), 8.36(1H, d,J=7.8 Hz), 11.77(1H,br.s). MS (ESI) m/z: 264(M+H)⁺.

Referential Example 34

(±)-cis-N-tert-Butoxycarbonyl-1,2-cyclopentanediamine

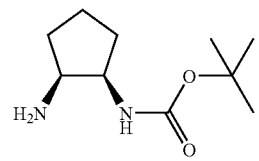

cis-1,2-Cyclopentanediamine (WO98/30574) (692 mg) was dissolved in dichloromethane (10 ml), to which triethylamine (1.1 ml) and 2-(tert-butoxycarbonyloxy-imino)-2-phenylacetonitrile (493 mg) were added, and the mixture was stirred at 0° C. for 1 hour. Thereafter, 2-(tert-butoxycarbonyloxyimino)-2-phenylacetonitrile (493 mg) were additionally added, and the mixture was stirred at room temperature for 7 hours. Water was added to the reaction mixture to separate an organic layer. The organic layer was washed with saturated saline and dried over anhydrous sodium sulfate. The residue was purified by flash column chromatography on silica gel (dichloromethane:methanol= 9:1) to obtain the title compound (395 mg) as a pale yellow oil.

¹H-NMR (CDCl₃) δ: 1.46(9H,s), 1.55–2.00(6H,m), 3.45–3.52(1H,m), 3.83–3.90(1H,m), 5.27(1H,br.s). MS (ESI) m/z: 201(M+H)⁺.

Referential Example 35 trans-N-[(5-Chloroindol-2-yl)carbonyl]-1,2-cyclopentanediamine hydrochloride

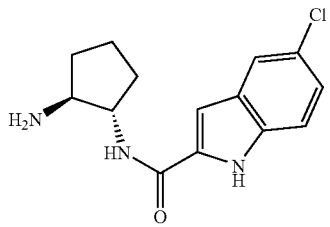

trans-N-tert-Butoxycarbonyl-1,2-cyclopentane-diamine (1.40 g) was dissolved in N,N-dimethylformamide (15 ml), and to the solution 5-chloroindole-2-carboxylic acid (1.64 g), 1-(3-dimethylaminopropyl)-3-ethylcarbodiimide hydrochloride (2.68 g) and 1-hydroxybenzotriazole monohydrate (473 mg) were added. The mixture was stirred at room temperature for 23 hours. The solvent was distilled off under reduced pressure, and dichloromethane and a saturated solution of sodium hydrogencarbonate were added to the residue to collect precipitates by filtration. The precipitates were washed with ethyl acetate, dichloromethane and methanol. On the other hand, the filtrate was separated to give an organic layer, which was taken out and dried over anhydrous sodium sulfate, and the solvent was then distilled off under reduced pressure. The residue was purified by medium-pressure flash column chromatography on silica gel (dichloromethane:methanol=19:1) to obtain a pale yellow solid. This pale yellow solid was combined with the precipitates obtained by the filtration and dissolved in dichloromethane (10 ml), and trifluoroacetic acid (10 ml) was added to stir the mixture at room temperature for 3 hours. The solvent was distilled off under reduced pressure, and dichloromethane and a 1N aqueous solution of sodium hydroxide were added to the residue to collect precipitate by filtration. The organic layer of the filtrate was separated and dried over anhydrous sodium sulfate. The precipitates collected by the filtration were added to this solution, and a 4N dioxane solution (20 ml) of hydrochloric acid was further added. The solvent was distilled off under reduced pressure, and dichloromethane (10 ml) and a 4N dioxane solution (10 ml) of hydrochloric acid were added to the residue. The solvent was distilled off again under reduced pressure. Ethyl acetate was added to the residue to collect precipitates by filtration, thereby obtaining the title compound (1.83 g) as a gray solid.

$^1$HNMR (DMSO-$d_6$) δ: 1.60–1.75(4H,m), 2.05–2.10(2H,m), 3.49(1H,q,J=7.6 Hz), 4.27(4H,quintet,J=7.6 Hz), 7.17 (1H,d,J=8.6 Hz), 7.19(1H,s), 7.42(1H,d,J=8.6 Hz), 7.70(1H,s), 8.24(3H,br.s), 8.85(1H,d,J=7.3 Hz), 11.91(1H,s) MS (ESI) m/z: 278(M+H)$^+$.

Referential Example 36

(±)-trans-N-tert-Butoxycarbonyl-1,2-cyclopentanediamine

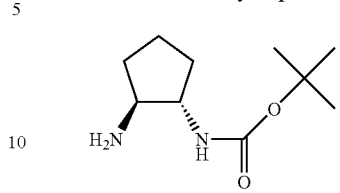

The title compound was obtained from trans-1,2-cyclopentanediamine (WO98/30574) in a similar manner to Referential Example 34.

$^1$H-NMR (CDCl$_3$) δ: 1.25–1.40(2H,m), 1.49(9H,s), 1.59–1.77(2H,m), 1.92–2.08(1H,m), 2.10–2.17(1H,m), 2.98 (1H,q,J=7.2 Hz), 3.48–3.53(1H,m), 4.49(1H,br.s). MS (ESI) m/z: 201(M+H)$^+$.

Referential Example 37

(±)-trans-N-[(5-Methyl-4,5,6,7-tetrahydrothiazolo-[5,4-c]pyridin-2-yl)carbonyl]-1,2-cyclopentanediamine hydrochloride

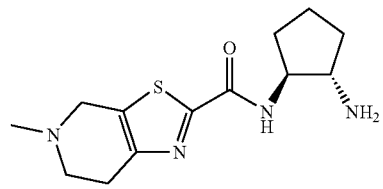

(±)-trans-N-tert-Butoxycarbonyl-1,2-cyclopentane-diamine (175 mg) was dissolved in N,N-dimethylformamide (3 ml), and to the solution lithium 5-methyl-4,5,6,7-tetrahydrothiazolo[5,4-c]pyridine-2-carboxylate (purity: 90%, 258 mg), 1-(3-dimethylaminopropyl)-3-ethyl-carbodiimide hydrochloride (252 mg) and 1-hydroxybenzotriazole monohydrate (60 mg) were added. The mixture was stirred at room temperature for 2 days. The solvent was distilled off under reduced pressure using a pump, and dichloromethane and a saturated solution of sodium hydrogencarbonate were added to the residue to separate an organic layer. The resultant organic layer was washed with saturated saline and dried over anhydrous sodium sulfate, and the solvent was distilled off under reduced pressure. The residue was purified by medium-pressure flash column chromatography on silica gel (dichloromethane:methanol=47:3). The resultant pale yellow oil was dissolved in a saturated ethanol solution (5 ml) of hydrochloric acid, and the solution was stirred at room temperature for 1 hour. Ethyl acetate was then added, and the solvent was distilled off under reduced pressure. Ethyl acetate was added to the residue to collect precipitate by filtration, thereby obtaining the title compound (120 mg) as a pale yellow solid.

$^1$H-NMR (DMSO-$d_6$) δ: 1.63–1.73(4H,m), 1.99–2.06 (2H,m), 2.91(3H,s), 3.09–3.14(1H,m), 3.25–3.70(4H,m), 4.27–4.32(1H,m), 4.42–4.46(1H,m), 4.68–4.71(1H,m), 8.20–8.23(3H,m), 9.09(1H,d,J=8.3 Hz), 11.82–12.01(1H,m). MS (ESI) m/z: 281(M+H)$^+$.

Referential Example 38

(±)-cis-N-(5-Chloro-1-phenylsulfonylindole-2-sulfonyl)-1,2-cyclopentanediamine

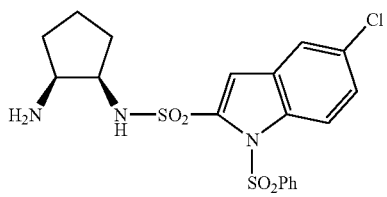

cis-1,2-Cyclopentanediamine (WO98/30574) (348 mg) was dissolved in dichloromethane (10 ml), and to the solution triethylamine (1 ml) and 5-chloro-1-phenylsulfonylindole-2-sulfonyl chloride (390 mg) were added at 0° C. with stirring. After 15 minutes and 1 hour, 5-chloro-1-phenylsulfonylindole-2-sulfonyl chloride (156 mg) was additionally added. After stirring for 15 minutes, 5-chloro-1-phenylsulfonylindole-2-sulfonyl chloride (78 mg) was further added, and the mixture was stirred at room temperature for 2 hours. Water was added to the reaction mixture to separate an organic layer. The resultant organic layer was washed with a saturated solution of sodium hydrogencarbonate and dried over anhydrous sodium sulfate. The residue was purified by flash column chromatography on silica gel (chloroform:methanol=23:2) to obtain the title compound (739 mg) as a pale yellow solid.

$^1$H-NMR (CDCl$_3$) δ: 1.38–1.91(8H,m), 3.27–3.31(1H,m), 3.41–3.45(1H,m), 7.42–7.50(4H,m), 7.58–7.61(2H,m), 8.11–8.15(3H,m). MS (ESI) m/z: 454(M+H)$^+$.

Referential Example 39

(±)-trans-N-tert-Butoxycarbonyl-1,2-cyclohexanediamine

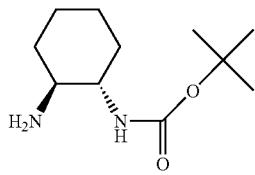

The title compound was obtained from (±)-trans-1,2-cyclohexanediamine in a similar manner to Referential Example 34.

mp 79–81° C. $^1$H-NMR (CDCl$_3$) δ: 1.05–1.34(4H,m), 1.45(9H,s), 1.68–1.75(2H,m), 1.92–2.02(2H,m), 2.32(1H, dt,J=10.3, 3.9 Hz), 3.08–3.20(1H,m), 4.50(1H,br.s). MS (FAB) m/z: 215(M+H)$^+$.

Referential Example 40

(±)-trans-N-[(5-Methyl-4,5,6,7-tetrahydrothiazolo-[5,4-c]pyridin-2-yl)carbonyl]-1,2-cyclohexanediamine trifluoroacetate

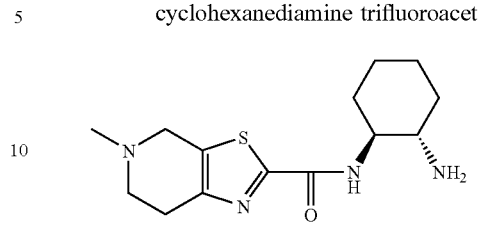

The title compound was obtained from (±)-trans-N-tert-butoxycarbonyl-1,2-cyclohexanediamine in a similar manner to Referential Example 37.

$^1$H-NMR (DMSO-d$_6$) δ: 1.10–1.80(7H,m), 1.95–2.05 (1H,m), 2.97(3H,s), 3.00–3.20(3H,m), 3.63(2H,br.s), 3.72–3.88(1H,m), 4.61(2H,br.s), 7.98(3H,s), 8.89(1H,d,J= 9.2 Hz). MS (FAB) m/z: 295(M+H)$^+$.

Referential Example 41

(±)-cis-N-tert-Butoxycarbonyl-1,2-cyclohexanediamine

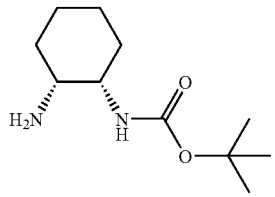

The title compound was obtained from cis-1,2-cyclohexanediamine in a similar manner to Referential Example 34.

$^1$H-NMR (CDCl$_3$) δ: 1.30–1.70(17H,m), 2.98–3.05(1H,m), 3.60(1H,br.s), 4.98(1H,br.s). MS (FAB) m/z: 215(M+H)$^+$.

Referential Example 42

(±)-trans-N-[(5-methyl-4,5,6,7-tetrahydrothiazolo-[5,4-c]pyridin-2-yl)carbonyl]-1,2-cyclohexanediamine trifluoroacetate

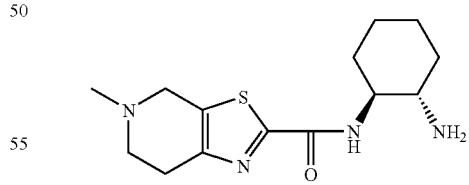

(±)-trans-N-tert-Butoxycarbonyl-1,2-cyclohexanediamine (642 mg) was dissolved in N,N-dimethylformamide (20 ml), and to the solution lithium 5-methyl-4,5,6,7-tetrahydrothiazolo[5,4-c]pyridine-2-carboxylate (795 mg), 1-hydroxybenzotriazole monohydrate (46 mg) and 1-(3-dimethylaminopropyl)-3-ethylcarbodiimide hydrochloride (2.30 g) were added, and the mixture was stirred overnight at room temperature. After the reaction mixture was concentrated under reduced pressure, and dichloromethane and water were added to the residue, the organic layer was taken out and dried over anhydrous sodium sulfate. The solvent was distilled off under reduced pressure, and the residue was purified by column chromatography on silica gel (dichloromethane:methanol=100:3) to obtain a pale yellow foamy substance. This substance was dissolved in dichloromethane (5 ml), and trifluoroacetic acid (30 ml) was added, and the mixture was stirred at room temperature for 1 minute. The reaction mixture was concentrated under reduced-pressure to obtain the title compound (731 mg) as a pale brown foamy substance.

$^1$H-NMR (DMSO-$d_6$) δ: 1.10–1.80(7H,m), 1.95–2.05 (1H,m), 2.97(3H,s), 3.00–3.20(3H,m), 3.63(2H,br.s), 3.72–3.88(1H,m), 4.61(2H,br.s), 7.98(3H,s), 8.89(1H,d,J= 9.2 Hz) MS (FAB) m/z: 295(M+H)$^+$.

Referential Example 43

Isolation of Optically Active Substances of (±)-cis-N$^1$-[(5-methyl-4,5,6,7-tetrahydrothiazolo[5,4-c] pyridin-2-yl)carbonyl]-1,2-cyclohexanediamine (±)-cis-N-[(5-Methyl-4,5,6,7-tetrahydrothiazolo-[5,4-c] pyridin-2-yl)carbonyl]-1,2-cyclohexanediamine (900 mg) was dissolved in isopropyl alcohol (6 ml), and the solution was purified in 11 portions by HPLC. As a column, CHIRALPAK AD (Daicel Chemical Industries, Ltd.; 2.0 in diameter×25 cm) was used to conduct elution at a flow rate of 6 ml/min using a solvent of hexane: isopropyl alcohol:diethylamine=68:32:0.5. Fractions eluted after 24.8 minutes and 33.4 minutes were separately collected and concentrated under reduced pressure to obtain Isomer A (320 mg) and Isomer B (390 mg) as brown amorphous substances.

Isomer A:
$^1$H-NMR (CDCl$_3$) δ: 1.30–1.90(8H,m), 2.51(3H,s), 2.82 (2H,t,J=5.9 Hz), 2.90–3.00(2H,m), 3.10–3.15(1H,m), 3.71 (2H,s), 4.00–4.20(1H,m), 7.55–7.75(1H,m). MS (FD$^+$)m/z: 295(M+H)$^+$.

Isomer B:
$^1$H-NMR (CDCl$_3$) δ: 1.30–1.90(8H,m), 2.51(3H,s), 2.82 (2H,t,J=5.9 Hz), 2.90–3.00(2H,m), 3.10–3.15(1H,m), 3.71 (2H,s), 4.00–4.20(1H,m), 7.55–7.75(1H,m). MS (FD$^+$) m/z: 295(M+H)$^+$.

In Referential Example 49, which will be described subsequently, Isomer B was identified as (1R,2S)-N$^1$-[(5-methyl-4,5,6,7-tetrahydrothiazolo[5,4-c]pyridin-2-yl) carbonyl]-1,2-cyclohexanediamine, and Isomer A as (1S, 2R)-N$^1$-[(5-methyl-4,5,6,7-tetrahydrothiazolo[5,4-c]-pyridin-2-yl)carbonyl]-1,2-cyclohexanediamine.

Referential Example 44

(1S,2S)-2-tert-Butoxycarbonylamino-1-cyclohexanol

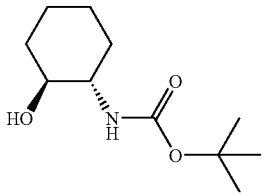

(1S,2S)-2-Amino-1-cyclohexanol (J. Med. Chem., 1998, Vol. 41, p. 38) (0.83 g) was dissolved in dichloromethane (10 ml), and to the solution di-tert-butyl dicarbonate (1.64 g) was added, and the mixture was stirred at room temperature for 2 hours. The solvent was distilled off under reduced pressure, and the resultant solids were recrystallized from hexane:ethyl acetate=20:1 to obtain the title compound (1.33 g) as colorless needle crystals.

mp: 103–105° C. [α]$_D$ –5.48° (19.8° C., C=1.01, CHCl$_3$).
$^1$H-NMR (CDCl$_3$) δ: 1.05–1.50(4H,m), 1.45(9H,s), 1.65–1.75(2H,m), 1.90–2.10(2H,m), 3.10–3.30(3H,m), 4.51 (1H,br.s).

Referential Example 45

(1S,2S)-1-tert-Butoxycarbonylamino-2-methanesulfonyloxy-cyclohexane

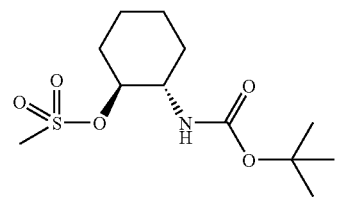

(1S,2S)-2-tert-Butoxycarbonylamino-1-cyclohexanol (646 mg) was dissolved in pyridine (4 ml), methane-sulfonyl chloride (378 mg) was added with ice cooling, and the mixture was stirred for 5 hours. After diethyl ether was added to the reaction mixture and washed 5 times with water, the resultant organic layer was dried over anhydrous sodium sulfate. The solvent was distilled off under reduced pressure to obtain the title compound (630 mg) as colorless crystals.

mp 123–124° C. [α]$_D$+7.16° (19.8° C., C=1.01, CHCl$_3$).
$^1$H-NMR (CDCl$_3$) δ: 1.20–1.40(3H,m), 1.44(9H,s), 1.55–1.70(2H,m), 1.70–1.80(1H,m), 2.03–2.23(2H,m), 3.03 (3H,s), 3.58(1H,br.s), 4.44(1H,td,J=9.8, 4.2 Hz), 4.67(1H, br.s)

Referential Example 46

(1R,2S)-1-Azido-2-(tert-butoxycarbonylamino) cyclohexane

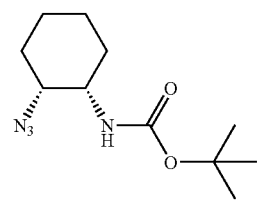

(1S,2S)-1-(tert-Butoxycarbonylamino)-2-methane-sulfonyloxycyclohexane (475 mg) was dissolved in N,N-dimethylformamide (6 ml), sodium azide (156 mg) was added, and the mixture was stirred for 2 hours at 60° C. and then for 24 hours at 80° C. After diethyl ether was added to the reaction mixture to conduct water washing twice, the resultant organic layer was dried over anhydrous sodium sulfate. The solvent was distilled off under reduced pressure, and the residue was purified by column chromatography on silica gel (dichloromethane) to obtain the title compound (184 mg) as a colorless solid.

Mp 69–70° C. [α]$_D$–105.14° (19.8° C., C=1.01, CHCl$_3$).
$^1$H-NMR (CDCl$_3$) δ: 1.20–1.80(7H,m), 1.45(9H,s), 1.90–2.00(1H,m), 3.61(1H,br.s), 3.95(1H,br.s), 4.70(1H, br.s). MS (FAB) m/z: 241(M+H)$^+$.

Referential Example 47

(1S,2R)-N¹-tert-Butoxycarbonyl-1,2-cyclohexanediamine

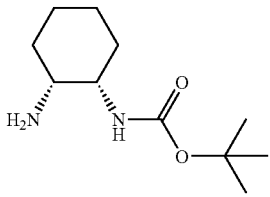

(1R,2S)-1-Azido-2-(tert-butoxycarbonylamino)-cyclohexane (174 mg) was dissolved in methanol (10 ml), and to the solution 10% palladium on carbon (120 mg) was added to conduct catalytic reduction under atmospheric pressure. The catalyst was separated by filtration, and the filtrate was concentrated to obtain a crude title compound (145 mg) as a colorless amorphous substance. This compound was used in the next reaction without purifying it.

Referential Example 48

(1S,2R)-N¹-tert-Butoxycarbonyl-N²-[(5-methyl-4,5,6,7-tetrahydrothiazolo[5,4-c]pyridin-2-yl)carbonyl]-1,2-cyclohexanediamine

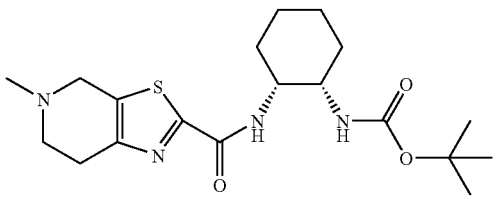

Crude (1S,2R)-N¹-tert-butoxycarbonyl-1,2-cyclohexanediamine (145 mg) was dissolved in N,N-dimethylformamide (3 ml), lithium 5-methyl-4,5,6,7-tetrahydrothiazolo[5,4-c]pyridine-2-carboxylate (180 mg), 1-hydroxybenzotriazole monohydrate (13 mg) and 1-(3-dimethylaminopropyl)-3-ethylcarbodiimide hydrochloride (770 mg) were added, and the mixture was stirred at room temperature for 22 hours. After the reaction mixture was concentrated under reduced pressure, and dichloromethane and water were added to the residue to conduct liquid separation, the resultant organic layer was dried over anhydrous potassium carbonate. The solvent was distilled off under reduced pressure, and the residue was purified by column chromatography on silica gel (dichloromethane:methanol=40:1) to obtain a pale yellow foamy substance (126 mg).

$[\alpha]_D$ –19.96° (19.7° C., C=0.51, CHCl₃). ¹H-NMR (CDCl₃) δ: 1.20–1.90(7H,m), 1.56(9H,s), 2.50(3H,s), 2.75–2.85(2H,m), 2.85–2.95(2H,m), 3.71(2H,s), 3.88–4.00 (1H,m), 4.22(1H,br.s), 4.91(1H,br.s), 7.48(1H,br.s).

Referential Example 49

(1R,2S)-N¹-[(5-Methyl-4,5,6,7-tetrahydrothiazolo[5,4-c]-pyridin-2-yl)carbonyl]-1,2-cyclohexanediamine

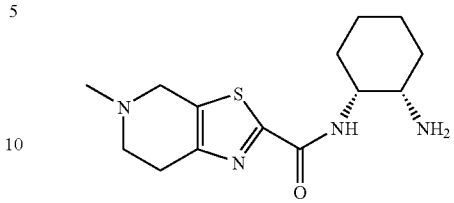

(1S,2R)-N¹-tert-Butoxycarbonyl-N²-[(5-methyl-4,5,6,7-tetrahydrothiazolo[5,4-c]pyridin-2-yl)carbonyl]-1,2-cyclohexanediamine (120 mg) was dissolved in methanol (1 ml), 1N ethanolic hydrochloric acid (3 ml) was added, and the mixture was stirred at 50° C. for 2 hours. The reaction mixture was concentrated under reduced pressure, and diethyl ether was added to the residue to form powder. The powder is collected by filtration to obtain the hydrochloride (106 mg) of the title compound as pale yellow powder.

¹H-NMR (DMSO-d₆) δ: 1.30–1.90(8H,m), 2.92(3H,s), 3.05–3.79(5H,m), 4.24(1H,br.s), 4.34–4.79(2H,m), 7.85–8.20(3H,m), 8.30–8.49(1H,m), 11.50–12.10(1H,m). MS (FAB) m/z: 295(M+H)⁺.

Dichloromethane and a saturated aqueous solution of sodium hydrogencarbonate were added to a part of the hydrochloride of the title compound to conduct liquid separation. The resultant organic layer was dried over anhydrous sodium sulfate, and the solvent was then distilled off under reduced pressure. The residue was analyzed by HPLC (solvent:hexane:isopropyl alcohol:diethylamine=80:20:0.5; flow rate: 2 ml/min) making use of CHIRALPAK AD (Daicel Chemical Industries, Ltd.; 0.46 in diameter×25 cm). As a result, the title compound was eluted in 9.5 minutes. Isomer A and Isomer B shown in Referential Example 43 were eluted in 7.2 minutes and 9.5 minutes, respectively, under such conditions. Therefore, Isomer B was identified as (1R,2S)-N¹-[(5-methyl-4,5,6,7-tetrahydrothiazolo[5,4-c]-pyridin-2-yl)carbonyl]-1,2-cyclohexanediamine.

¹H-NMR (CDCl₃) δ: 1.30–1.90(8H,m), 2.51(3H,s), 2.82 (2H,t,J=5.6 Hz), 2.93(2H,t,J=5.6 Hz), 3.10–3.15(1H,m), 3.70(2H,s), 4.00–4.20(1H,m), 7.63(1H,d,J=8.1 Hz).

Referential Example 50

(±)-trans-N-[(5-Methyl-4,5,6,7-tetrahydrothiazolo[5,4-c]pyridin-2-yl)carbonyl]-1,2-cyclohexanediamine hydrochloride

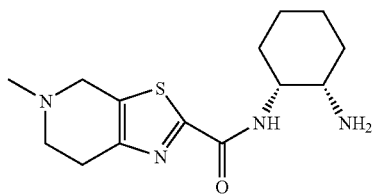

The title compound was obtained from (±)-trans-N-tert-butoxycarbonyl-1,2-cyclohexanediamine in a similar manner to Referential Example 37.

¹H-NMR (DMSO-d₆) δ: 1.10–2.17(8H,m), 2.92(3H,s), 3.00–3.93(6H,m), 4.38–4.60(1H,m), 4.64–4.77(1H,m), 8.00–8.19(3H,m), 8.82–8.96(1H,m), 11.95–11.30(1H,m). MS (FAB) m/z: 295(M+H)⁺.

Referential Example 51

(±)-cis-N-[(5-Methyl-4,5,6,7-tetrahydrothiazolo [5,4-c]pyridin-2-yl)carbonyl]-1,2-cyclohexanediamine hydrochloride

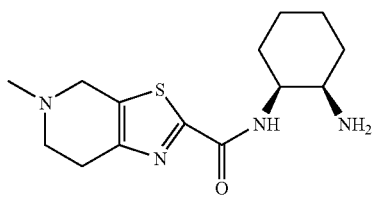

The title compound was obtained from (±)-cis-N-tert-butoxycarbonyl-1,2-cyclohexanediamine in a similar manner to Referential Example 37.

$^1$H-NMR (DMSO-d$_6$) δ: 1.30–1.90(8H,m), 2.92(3H,s), 3.05–3.79(5H,m), 4.23(1H,br.s), 4.34–4.79(2H,m), 8.01–8.34(3H,m), 8.30–8.49(1H,m), 11.90–12.30(1H,m). MS (FAB) m/z: 295(M+H)$^+$.

Referential Example 52

(±)-trans-N$^1$-(tert-Butoxycarbonyl)-N$^2$-[(5-chloroindol-2-yl)carbonyl]-1,2-cyclohexanediamine

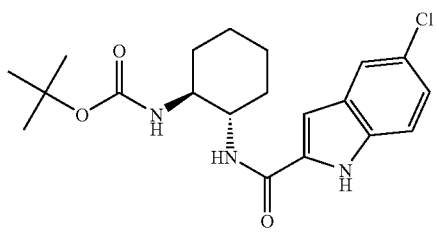

5-Chloroindole-2-carboxylic acid (2.88 g), 1-hydroxybenzotriazole monohydrate (2.08 g) and 1-(3-dimethylaminopropyl)-3-ethylcarbodiimide hydrochloride (2.95 g) were added to a solution of (±)-trans-N-tert-butoxycarbonyl-1,2-cyclohexanediamine (3.00 g) in N,N-dimethylformamide (10 ml) at room temperature. After stirring for 3 days, the reaction mixture was concentrated under reduced pressure, and dichloromethane (30 ml), a saturated aqueous solution (150 ml) of sodium hydrogencarbonate and water (150 ml). were added to the residue. After collecting colorless precipitate formed was collected by filtration and dried to obtain the title compound (5.21 g) as a colorless solid.

$^1$H-NMR (DMSO-d$_6$) δ: 1.10–1.45(4H,m), 1.21(9H,s), 1.68(2H,d,J=8.1 Hz), 1.86(2H,t,J=16.2 Hz), 3.22–3.42(1H,m), 3.69(1H,br.s), 6.66(1H,d,J=8.5 Hz), 7.02(1H,s), 7.15 (1H,dd,J=8.5, 2.0 Hz), 7.41(1H,d,J=8.5 Hz), 7.67(1H,d,J= 2.0 Hz), 8.15(1H,d,J=8.1 Hz), 11.73(1H,br.s). MS (ESI) m/z: 392(M+H)$^+$.

Referential Example 53

(±)-cis-N$^1$-(tert-Butoxycarbonyl)-N$^2$-[(5-chloroindol-2-yl)carbonyl]-1,2-cyclohexanediamine

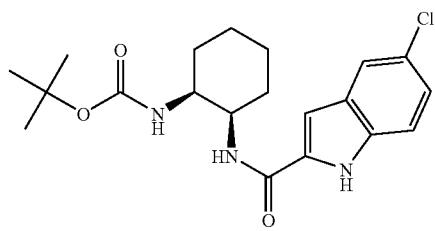

The title compound was obtained from (±)-cis-N-(tert-butoxycarbonyl)-1,2-cyclohexanediamine in a similar manner to Referential Example 52.

$^1$H-NMR (DMSO-d$_6$) δ: 1.20–1.45(11H,m), 1.45–1.70 (4H,m), 1.70–1.85(2H,m), 3.76(1H,br.s), 4.08(1H,br.s), 6.64 (1H,d,J=7.6 Hz), 7.12(1H,s), 7.16(1H,dd,J=8.8, 2.0 Hz), 7.43(1H,d,J=8.8 Hz), 7.69(1H,d,J=2.0 Hz), 7.85(1H,d,J=6.9 Hz), 11.80(1H,br.s). MS (ESI) m/z: 392(M+H)$^+$.

Referential Example 54

(±)-trans-N-[(5-Chloroindol-2-yl)carbonyl]-1,2-cyclohexanediamine hydrochloride

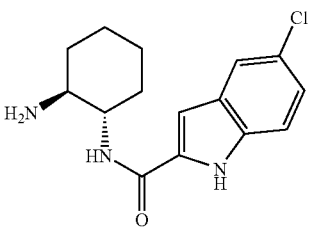

A saturated ethanol solution (100 ml) of hydrochloric acid was added to a solution of (±)-trans-N$^1$-(tert-butoxycarbonyl)-N$^2$-[(5-chloroindol-2-yl)-carbonyl]-1,2-cyclohexanediamine (5.18 g) in dichloromethane (100 ml) at room temperature. After stirring for 2 days, the reaction mixture was concentrated under reduced pressure, diethyl ether (300 ml) was added to the resultant residue, and colorless precipitate formed was collected by filtration and dried to obtain the title compound (4.30 g) as a colorless solid.

$^1$H-NMR (DMSO-d$_6$) δ: 1.20–1.36(2H,m), 1.36–1.50 (2H,m), 1.60(2H,br.s), 1.90(1H,d,J=13.0 Hz), 2.07(1H,d,J= 13.7 Hz), 3.06(1H,br.s), 3.83–3.96(1H,m), 7.15–7.24(2H, m), 7.45(1H,d,J=8.6 Hz), 7.73(1H,s), 8.00(3H,br.s), 8.60 (1H,d,J=8.3 Hz), 11.86(1H,s). MS (ESI) m/z: 292(M+H)$^+$.

Referential Example 55

(±)-cis-N-[(5-Chloroindol-2-yl)carbonyl]-1,2-cyclohexanediamine

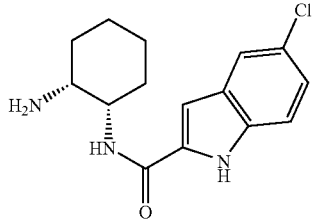

The title compound was obtained from (±)-cis-N$^1$-(tert-butoxycarbonyl)-N$^2$-[(5-chloroindol-2-yl)-carbonyl]-1,2-cyclohexanediamine in a similar manner to Referential Example 54.

$^1$H-NMR (DMSO-d$_6$) δ: 1.30–1.50(2H,m), 1.55–1.95 (6H,m), 3.41(1H,br.s), 4.32(1H,br.s), 7.19(1H,dd,J=8.7, 2.0 Hz), 7.33(1H,s), 7.45(1H,d,J=8.7 Hz), 7.60–7.90(4H,m), 8.17(1H,d,J=7.1 Hz), 1.91(1H,s). MS (FAB) m/z: 292(M+H)$^+$.

Referential Example 56

(±)-cis-N$^1$-Benzyl-N$^2$-tert-butoxycarbonyl-1,2-cyclohexanediamine

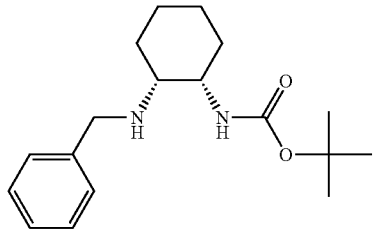

(±)-cis-N-tert-Butoxycarbonyl-1,2-cyclohexanediamine (3.78 g) was dissolved in acetonitrile (80 ml), and to the solution triethylamine (2.44 ml) and benzyl bromide (2.10 ml) were added, and the mixture was stirred at room temperature for 13 hours. The solvent was distilled off under reduced pressure, dichloromethane and water was added to the residue to separate an organic layer. The organic layer was dried over anhydrous sodium sulfate and then concentrated under reduced pressure. The residue was purified by flash column chromatography on silica gel (hexane:ethyl acetate=1:1) to obtain the title compound (3.08 g) as a pale orange oil.

$^1$H-NMR (CDCl$_3$) δ: 1.35–1.63(17H,m), 2.75–2.79(1H, m), 3.71–3.83(3H,m), 5.17(1H,br.s), 7.22–7.33(5H,m). MS (FAB) m/z: 305(M+H)$^+$.

Referential Example 57

(±)-cis-N$^1$-Benzyl-N$^2$-tert-butoxycarbonyl-N$^1$-methyl-1,2-cyclohexanediamine

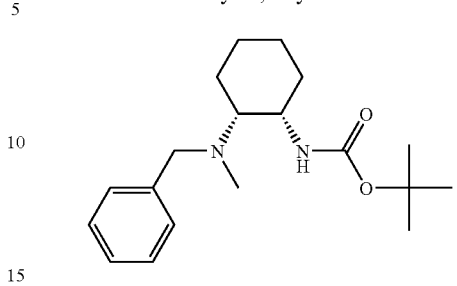

(±)-cis-N$^1$-Benzyl-N$^2$-tert-butoxycarbonyl-1,2-cyclohexanediamine (3.24 g) was dissolved in methanol (30 ml), and to the solution an aqueous solution (35%, 0.909 ml) of formaldehyde was added, and the mixture was stirred at room temperature for 10 minutes. Sodium cyanoborohydride (666 mg) was added to this mixture, and the resultant mixture was stirred at room temperature for 6 hours. Thereafter, a saturated aqueous solution of sodium hydrogencarbonate was added, and the solvent was concentrated under reduced pressure. Dichloromethane was added to the residue to separate an organic layer. The organic layer was dried over anhydrous sodium sulfate, and the solvent was distilled off under reduced pressure. The residue was purified by flash column chromatography on silica gel (hexane:ethyl acetate=3:1) to obtain the title compound (1.98 g) as a yellow oil.

$^1$H-NMR (CDCl$_3$) δ: 1.24–1.50(14H,m), 1.76–1.79(1H, m), 1.93–1.98(1H,m), 2.15(3H,s), 2.16–2.21(1H,m), 2.30–2.35(1H,m), 3.34(1H,d,J=13.4 Hz), 3.78(1H,d,J=13.4 Hz), 4.08(1H,br.s), 5.09(1H,br.s), 7.20–7.32(5H,m). MS (ESI): 319(M+H)$^+$.

Referential Example 58

(±)-cis-N$^1$-tert-Butoxycarbonyl-N$^2$-methyl-1,2-cyclohexane-diamine

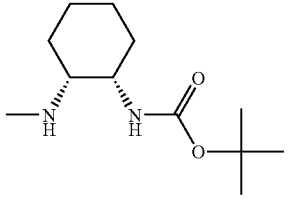

(±)-cis-N$^1$-Benzyl-N$^2$-tert-butoxycarbonyl-N$^1$-methyl-1,2-cyclohexanediamine (1.92 g) was added to methanol (50 ml), 10% palladium on carbon (containing 50% of water, 900 mg) was added, and the mixture was stirred for 20 hours in a hydrogen atmosphere. After separating the catalyst by filtration, the filtrate was concentrated to obtain the title compound (1.27 g) as a colorless oil.

$^1$H-NMR (CDCl$_3$) δ: 1.37–1.60(17H,m), 2.39(3H,s), 2.58–2.59(1H,m), 3.48–3.49(1H,m), 3.72(1H,br.s), 5.10 (1H,br.s). MS (ESI) m/z: 229(M+H)$^+$.

Referential Example 59

(±)-cis-N[1]-[(5-Chloroindol-2-yl)carbonyl]-N[1]-methyl-1,2-cyclohexanediamine trifluoroacetate

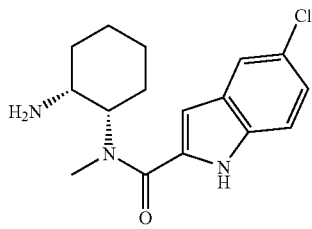

(±)-cis-N[1]-tert-Butoxycarbonyl-N[2]-methyl-1,2-cyclohexanediamine (629 mg), 5-chloroindole-2-carboxylic acid (647 mg), 1-(3-dimethylaminopropyl)-3-ethylcarbodiimide hydrochloride (792 mg) and 1-hydroxybenzotriazole monohydrate (186 mg) were dissolved in N,N-dimethylformamide (20 ml) and stirred at room temperature for 4 days. The solvent was distilled off under reduced pressure by using a pump, and dichloromethane and a saturated aqueous solution of sodium hydrogencarbonate were added to the residue to separate an organic layer. The organic layer was washed with an saturated aqueous solution of sodium hydrogencarbonate and dried over anhydrous sodium sulfate, and the solvent was distilled off under reduced pressure. The residue was purified by flash column chromatography on silica gel (hexane:ethyl acetate=1:1). The resultant pale yellow solid was dissolved in a mixed solvent of dichloromethane (5 ml) and trifluoroacetic acid (5 ml) and stirred at room temperature for 1 hour. The solvent was distilled off under reduced pressure, and dichloromethane and a saturated aqueous solution of sodium hydrogencarbonate were added to separate an organic layer. The organic layer was concentrated under reduced pressure, and ethyl acetate was added to the residue. Precipitate formed was collected by filtration to obtain the title compound (786 mg) as a pale yellow solid.

$^1$H-NMR (CDCl$_3$) δ: 1.37–1.55(3H,m), 1.72–1.96(4H, m), 2.09–2.19(1H,m), 3.23(3H,s), 3.76(1H,br.s), 4.34–4.39 (1H,m), 6.92(1H,d,J=1.7 Hz), 7.20(1H,dd,J=8.8, 2.0 Hz), 7.46(1H,d,J=8.8 Hz), 7.69(1H,d,J=2.0 Hz), 8.08(3H,br.s), 11.74(1H,br.s). MS (ESI) m/z: 306(M+H)$^+$.

Referential Example 60

(±)-cis-N[1]-(tert-Butoxycarbonyl)-N[2]-methyl-N[2]-[(5-methyl-4,5,6,7-tetrahydrothiazolo[5,4-c]pyridin-2-yl)carbonyl]-1,2-cyclohexanediamine

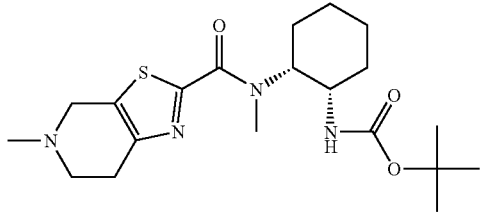

Lithium 5-methyl-4,5,6,7-tetrahydrothiazolo-[5,4-c]pyridine-2-carboxylate (613 mg) was suspended in dichloromethane (10 ml), to which a 1N ethanol solution (3.0 ml) of hydrochloric acid was added, and the mixture was stirred at room temperature for several minutes. The solvent was distilled off under reduced pressure, chloroform (15 ml), N,N-dimethylformamide (one drop) and thionyl chloride (5 ml) were added to the residue, and the mixture was stirred at 60° C. for 4 hours. The solvent was distilled off under reduced pressure, and pyridine (10 ml) and dichloromethane (10 ml) were added to the residue, to which a solution (5 ml) of (±)-cis-N[1]-(tert-butoxycarbonyl)-N[2]-methyl-1,2-cyclohexanediamine (455 mg) in dichloromethane (5 ml) was added. After the mixture was stirred at room temperature for 2 hours, water was added to separate an organic layer. After the resultant organic layer was washed with water and saturated saline and dried over anhydrous sodium sulfate, the solvent was distilled off under reduced pressure. The residue was purified by flash column chromatography on silica gel (dichloromethane:methanol=47:3) to obtain the title compound (324 mg) as a pale brown solid.

MS (ESI) m/z: 409(M+H)$^+$.

Referential Example 61

(±)-trans-1,2-Cycloheptanediol

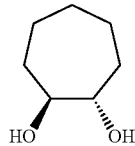

Cycloheptene (3.85 g) was added portionwise to 30% aqueous hydrogen peroxide (45 ml) and 88% formic acid (180 ml), and the mixture was stirred at 40 to 50° C. for 1 hour and then at room temperature for a night. The solvent was distilled off under reduced pressure, and a 35% aqueous solution of sodium hydroxide was added to the residue to alkalify it. After this residue was stirred at 40 to 50° C. for 10 minutes, ethyl acetate was added to conduct liquid separation. The resultant water layer was extracted 4 times with ethyl acetate. The resultant organic layers were collected and dried over anhydrous sodium sulfate, and the solvent was distilled off under reduced pressure to obtain the title compound (4.56 g) as a colorless oil.

$^1$H-NMR (CDCl$_3$) δ: 1.44–1.56(6H,m), 1.63–1.70(2H, m), 1.83–1.91(2H,m), 2.91(2H,br.s), 3.40–3.44(2H,m). MS (FAB) m/z: 131(M+H)$^+$.

Referential Example 62

(±)-trans-1,2-Cycloheptanediamine hydrochloride

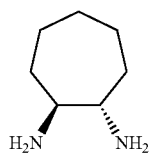

(±)-trans-1,2-Cycloheptanediol (4.56 g) was dissolved in dichloromethane (35 ml), triethylamine (29 ml) was added, and the mixture was cooled to −78° C. Methanesulfonyl chloride (8.13 ml) was added dropwise thereto. Since precipitate was formed to make it difficult to stir, dichloromethane (10 ml) was slowly added, and the mixture was stirred for 20 minutes at the same temperature and then for 1.5 hours at 0° C. Water was added to the reaction mixture to conduct liquid separation, and the resultant organic layer was washed with a saturated aqueous solution of sodium hydrogencarbonate and dried over anhydrous sodium sulfate. The solvent was distilled off under reduced pressure to obtain a brown oil.

This oil was dissolved in N,N-dimethylformamide (90 ml), sodium azide (13.65 g) was added, and the mixture was stirred at 65° C. for 18 hours. Ether and water was added to the reaction mixture to conduct liquid separation. The resultant ether layer was washed with a saturated aqueous solution of sodium hydrogencarbonate and saturated saline and dried over anhydrous sodium sulfate. The solvent was distilled off under reduced pressure to obtain a yellow oil.

This oil was dissolved in ethanol (70 ml), 10% palladium on carbon (containing 50% of water, 4 g) was added, and the mixture was stirred for 4 days in a hydrogen (3.5 atm) atmosphere. After separating the palladium on carbon by filtration, a 1N ethanol solution (70 ml) of hydrochloric acid was added to the filtrate, and the solvent was distilled off under reduced pressure. The residue was dissolved in methanol, ethyl acetate was added, and the solvent was distilled off under reduced pressure again. Precipitate formed was collected by filtration to obtain the title compound (3.57 g) as a colorless solid.

$^1$H-NMR (DMSO) δ: 1.44(4H,br.s), 1.73–1.81(6H,m), 3.43(2H,br.s), 8.63(6H,br.s). MS (ESI) m/z: 129(M+H)$^+$.

Referential Example 63

(±)-trans-N-[(5-Chloroindol-2-yl)carbonyl]-1,2-cycloheptanediamine

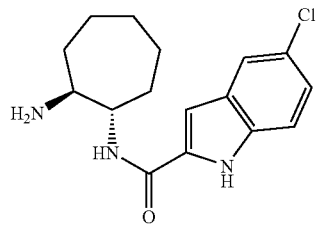

The title compound was obtained from (±)-trans-1,2-cycloheptanediamine in a similar manner to Referential Example 30.

$^1$H-NMR (DMSO-d$_6$) δ: 1.49–1.52(4H,m), 1.72–1.91 (6H,m), 4.04–4.10(1H,m), 7.17–7.23(2H,m), 7.44(1H,d,J= 8.8 Hz), 7.72(1H,d,J=2.0 Hz), 7.96(2H,br.s), 8.75(1H,d,J= 8.5 Hz), 11.89(1H,br.s) MS (ESI) m/z: 306(M+H)$^+$.

Referential Example 64 cis-1,2-Cycloheptanediol

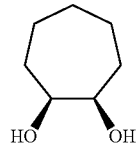

Cycloheptene (3.85 g) was dissolved in acetonitrile (45 ml) and water (15 ml), and to the solution N-methylmorpholine N-oxide (5.15 g), microcapsulated osmium tetroxide (1 g, containing 10% osmium tetroxide) was added, and the mixture was stirred at 40 to 50° C. for 21 hours. Insoluble microcapsulated osmium tetroxide was removed by filtration, and the insoluble substance was washed with acetonitrile and the filtrate was concentrated under reduced pressure. The residue was purified by flash column chromatography on silica gel (hexane:ethyl acetate= 1:1) to obtain the title compound (4.77 g) as a colorless solid.

$^1$H-NMR (CDCl$_3$) δ: 1.34–1.84(10H,m), 2.31(2H,m), 3.86(2H,d,J=7.1 Hz). MS (FAB) m/z: 131(M+H)$^+$.

Referential Example 65 cis-1,2-Cycloheptanediazide

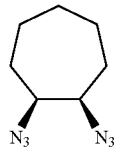

Triethylamine (30 ml) was added to the solution of cis-1,2-cycloheptanediol (4.76 g) in dichloromethane (50 ml), after the interior of a vessel was purged with argon, the mixture was cooled to −78° C., and methanesulfonyl chloride (8.5 ml) was added dropwise thereto. The mixture was stirred for 1 hour at the same temperature and then for 2 hours at 0° C. Water was added to the reaction mixture to conduct liquid separation, and the resultant organic layer was washed with a saturated aqueous solution of sodium hydrogencarbonate and dried over anhydrous sodium sulfate. The solvent was distilled off under reduced pressure, and the residue was dissolved in N,N-dimethylformamide (90 ml), sodium azide (14.28 g) was added, and the mixture was stirred at 65° C. for 21 hours. Ether and water was added to the reaction mixture to conduct liquid separation. The resultant ether layer was washed with a saturated aqueous solution of sodium hydrogencarbonate and saturated saline and dried over anhydrous sodium sulfate. The solvent was distilled off under reduced pressure, and the residue was purified by flash column chromatography on silica gel (hexane:ethyl acetate=2:1) to obtain the title compound (3.57 g) as a colorless oil.

$^1$H-NMR (DMSO) δ: 1.46–1.80(8H,m), 1.89–1.98(2H, m), 3.71(2H,dd,J=6.7, 2.3 Hz).

Referential Example 66 cis-1,2-Cycloheptanediamine hydrochloride

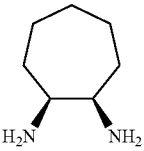

cis-1,2-Cycloheptanediazide (6.35 g) was dissolved in ethanol (75 ml), to the solution 10% palladium on carbon (containing 50% of water, 4.2 g) was added, and the mixture was stirred for 3 days in a hydrogen (3.5 atm) atmosphere. After separating the 10% palladium on carbon by filtration, a 1N ethanol solution (70.5 ml) of hydrochloric acid was added to the filtrate, and the solvent was distilled off under reduced pressure. Ethyl acetate was added to the residue, and the solvent was distilled off under reduced pressure again. Precipitate formed was collected by filtration and washed with ethyl acetate to obtain the title compound (5.28 g) as a colorless solid.

$^1$H-NMR (DMSO) δ: 1.44–1.68(6H,m), 1.79–1.93(4H, m), 3.68(2H,dd,J=6.8, 3.9 Hz), 8.62(6H,br.s). MS (ESI) m/z: 129(M+H)$^+$.

Referential Example 67

(±)-cis-N-[(5-Chloroindol-2-yl)carbonyl]-1,2-cycloheptanediamine

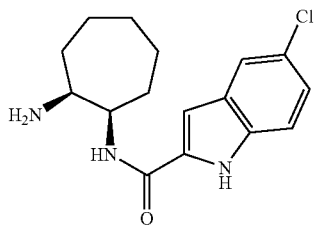

The title compound was obtained from cis-1,2-cycloheptanediamine in a similar manner to Referential Example 30.

MS (ESI) m/z: 306(M+H)$^+$.

Referential Example 68 cis-1,2-Cyclooctanediol

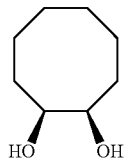

Cyclooctene (4.41 g) was dissolved in acetonitrile (45 ml) and water (15 ml), and to the solution N-methylmorpholine N-oxide (5.15 g) and microcapsulated osmium tetroxide (1 g, containing 10% osmium tetroxide) were added, and the mixture was stirred at 40 to 50° C. for 21 hours. Insoluble microcapsulated osmium tetroxide was removed by filtration, and was washed with acetonitrile, and the filtrate was concentrated under reduced pressure. The residue was purified by flash column chromatography on silica gel (hexane:ethyl acetate=1:1) to obtain the title compound (4.97 g) as a colorless solid.

$^1$H-NMR (CDCl$_3$) δ: 1.48–1.58(6H,m), 1.64–1.75(4H, m), 1.86–1.96(2H,m), 2.28(2H,d,J=2.9 Hz), 3.90(2H,d,J= 8.3 Hz). MS (FAB) m/z: 145(M+H)$^+$.

Referential Example 69 cis-1,2-Cyclooctanediazide

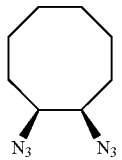

cis-1,2-cyclooctanediol (4.82 g) was dissolved in dichloromethane (60 ml), and to the solution triethylamine (27.7 ml) was added. After the interior of a vessel was purged with argon, the mixture was cooled to −78° C., and methanesulfonyl chloride (7.7 ml, 100 mmol) was added dropwise thereto. The mixture was stirred for 1 hour at the same temperature and then for 1 hour at 0° C. Water was then added to the reaction mixture to conduct liquid separation, and the resultant organic layer was washed with water, 0.5N hydrochloric acid, water and a saturated aqueous solution of sodium hydrogencarbonate and dried over anhydrous sodium sulfate. The solvent was distilled off under reduced pressure, and the residue was dissolved in N,N-dimethylformamide (80 ml), and to the solution sodium azide (13.0 g) was added, and the mixture was stirred at 65° C. for 19 hours. Ether and water was added to the reaction mixture to conduct liquid separation. The resultant ether layer was washed with a saturated aqueous solution of sodium hydrogencarbonate and saturated saline and dried over anhydrous sodium sulfate. The solvent was distilled off under reduced pressure, and the residue was purified by flash column chromatography on silica gel (hexane:ethyl acetate= 6:1) to obtain the title compound (4.85 g) as a colorless oil.

$^1$H-NMR (CDCl$_3$) δ: 1.49–1.64(6H,m), 1.67–1.78(2H, m), 1.81–1.97(4H,m), 3.74–3.76(2H,m).

Referential Example 70 cis-1,2-Cyclooctanediamine hydrochloride

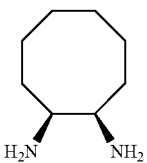

cis-1,2-Cyclooctanediazide (4.85 g) was dissolved in ethanol (55 ml), to the solution 10% palladium on carbon (containing 50% of water, 3.0 g) was added, and the mixture was stirred for 21 hours in a hydrogen (4.5 atm) atmosphere. After separating the catalyst by filtration, a 1N ethanol solution (50 ml) of hydrochloric acid was added to the filtrate, and the solvent was distilled off under reduced pressure. Ethyl acetate was added to the residue, and precipitate formed was collected by filtration to obtain the title compound (4.14 g) as a pale yellow solid.

$^1$H-NMR (DMSO) δ: 1.51(6H,br.s), 1.69(2H,br.s), 1.79–1.99(4H,m), 3.68–3.70(2H,m), 8.66(6H,br.s). MS (ESI) m/z: 143(M+H)$^+$.

Referential Example 71

(±)-cis-N-[(5-Chloroindol-2-yl)carbonyl]-1,2-cyclooctanediamine

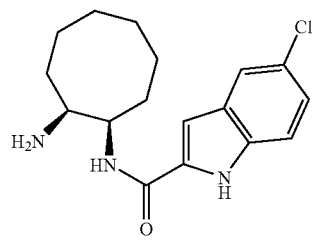

The title compound was obtained from cis-1,2-cyclooctanediamine in a similar manner to Referential Example 30.

MS (ESI) m/z: 320(M+H)$^+$.

Referential Example 72

N¹-tert-Butoxycarbonyl-N²-[(5-methyl-4,5,6,7-tetrahydrothiazolo[5,4-c]pyridin-2-yl)carbonyl]-1,2-ethylenediamine

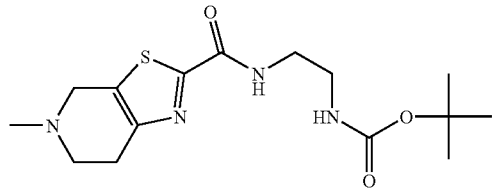

tert-Butyl N-(2-aminoethyl)carbamate (1.0 g) was dissolved in N,N-dimethylformamide, and to the solution lithium 5-methyl-4,5,6,7-tetrahydrothiazolo[5,4-c]-pyridine-2-carboxylate (purity: 90%, 1.13 g), 1-(3-dimethylaminopropyl)-3-ethylcarbodiimide hydrochloride (1.79 g) and 1-hydroxybenzotriazole monohydrate (422 mg) were added, and the mixture was stirred at room temperature for 23 hours. The solvent was distilled off under reduced pressure using a vacuum pump, and dichloromethane and a saturated solution of sodium hydrogencarbonate were added to the residue to conduct liquid separation. The resultant water layer was extracted with dichloromethane, the resultant organic layers were collected and dried over anhydrous sodium sulfate, and the solvent was distilled off under reduced pressure. The residue was purified by flash column chromatography on silica gel (dichloromethane:methanol= 91:9) to obtain the title compound (1.26 g) as a pale yellow solid.

$^1$H-NMR (CDCl$_3$) δ: 1.43(9H,s), 2.51(3H,m), 2.81–2.84 (2H,m), 2.91–2.95(2H,m), 3.35–3.40(2H,m), 3.53–3.57(2H, m), 3.71(2H,s), 5.30(1H,br.s), 7.47(1H,br.s). MS (FAB) m/z: 341(M+H)⁺.

Referential Example 73

N¹-tert-Butoxycarbonyl-N²-[(1-phenylsulfonyl-5-chloroindol-2-yl)sulfonyl]-1,2-ethylenediamine

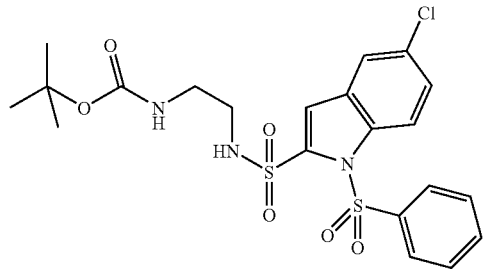

tert-Butyl N-(2-aminoethyl)carbamate (1.0 g) was dissolved in dichloromethane, to the solution 5-chloro-1-phenylsulfonyl-indole-2-sulfonyl chloride (2.44 g) and triethylamine (1.73 ml) were added, and the mixture was stirred overnight at room temperature. Water was added to the reaction mixture to conduct liquid separation, and the resultant water layer was extracted with dichloromethane. The resultant organic layers were collected and dried over anhydrous sodium sulfate, and the solvent was distilled off under reduced pressure. The residue was purified by flash column chromatography on silica gel (hexane:ethyl acetate= 4:1→3:2) to obtain the title compound (2.83 g) as a colorless solid.

$^1$H-NMR (CDCl$_3$) δ: 1.43(9H,s), 3.17–3.21(2H,m), 3.28–3.31(2H,m), 4.89(1H,br.s), 5.97–6.00(1H,m), 7.42–7.51(4H,m), 7.59–7.65(2H,m), 8.11–8.16(3H,m). MS (FAB) m/z: 514(M+H)⁺.

Referential Example 74

N¹-tert-Butoxycarbonyl-N¹-methyl-1,2-ethylenediamine

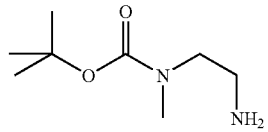

Synthesis was performed in accordance with literature (J. Med. Chem., 1990, Vol. 33, p. 97). N-methyl-1,2-ethylenediamine (5.57 ml) was dissolved in dichloromethane (80 ml), and a solution of di-tert-butyl dicarbonate (4.37 g) in dichloromethane (20 ml) was added at 0° C. The mixture was stirred overnight at room temperature. Saturated saline was added to the reaction mixture to conduct liquid separation. The resultant organic layer was washed with saturated saline and dried over anhydrous sodium sulfate. The thus-obtained product was purified by column chromatography on silica gel (chloroform:methanol=9:1→4:1) to obtain the title compound (2.96 g) as a pale yellow oil from an initial eluate.

$^1$H-NMR (DMSO-d$_6$) δ: 1.37(9H,s), 2.63(2H,t,J=6.7 Hz), 2.77(3H,s), 3.12(2H,t,J=6.7 Hz). MS (ESI) m/z: 175(M+H)⁺.

Further, N¹-tert-butoxycarbonyl-N²-methyl-1,2-ethylenediamine (339 mg) was obtained as a pale yellow oil from the next eluate.

$^1$H-NMR (DMSO-d$_6$) δ: 1.36(9H,s), 2.24(3H,s), 2.46(2H, t,J=6.5 Hz), 2.97(2H,q,J=6.5 Hz), 6.68(1H,br.s). MS (ESI) m/z: 175(M+H)⁺.

Referential Example 75

N¹-Methyl-N²-[(5-methyl-4,5,6,7-tetrahydrothiazolo-[5,4-c]pyridin-2-yl)carbonyl]-1,2-ethylenediamine hydrochloride

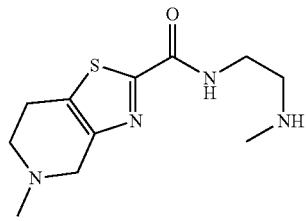

N¹-tert-Butoxycarbonyl-N¹-methyl-1,2-ethylene-diamine (1.05 g) was dissolved in N,N-dimethylformamide (30 ml), to which lithium 5-methyl-4,5,6,7-tetrahydrothiazolo[5,4-c] pyridine-2-carboxylate (157 mg), 1-ethyl-3-(3-dimethylaminopropyl)carbodiimide hydrochloride (181 mg) and 1-hydroxybenzotriazole monohydrate (42 mg) were added, and the mixture was stirred overnight at room temperature. The solvent was distilled off under reduced pressure using a vacuum pump, and dichloromethane and a saturated solution of sodium hydrogencarbonate were added to the residue to conduct liquid separation. The resultant water layer was extracted with dichloromethane, the resultant organic layers were collected and dried over anhydrous sodium sulfate, and the solvent was distilled off under reduced pressure. The residue was purified by flash column chromatography on silica gel (dichloromethane:methanol= 23:2), and the resultant compound was dissolved in a small amount of dichloromethane, to which a saturated ethanol solution (8 ml) of hydrochloric acid was added, and the mixture was stirred at room temperature for 1 hour. After the solvent was distilled off under reduced pressure, ethyl acetate was added, and precipitate formed was collected by filtration to obtain the title compound (697 mg) as a pale yellow solid.

$^1$H-NMR (DMSO-$d_6$) δ: 2.54(3H,s), 2.89(3H,s), 3.02–3.28(4H,m), 3.43–3.74(4H,brm), 4.45(1H,br.s), 4.66 (1H,br.s), 8.79(2H,br.s), 9.04(1H,t,J=5.9 Hz), 11.88(1H, br.s). MS (FAB) m/z: 255(M+H)$^+$.

Referential Example 76

N$^1$-[(5-Chloroindol-2-yl)carbonyl]-N$^2$-methyl-1,2-ethylenediamine hydrochloride

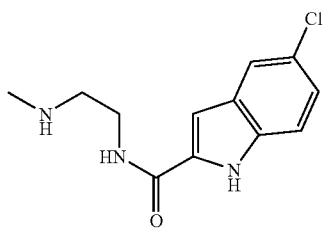

N$^1$-tert-Butoxycarbonyl-N$^1$-methyl-1,2-ethylene-diamine (348 mg) was dissolved in N,N-dimethylformamide (5 ml), to which 5-chloroindole-2-carboxylic acid (391 mg), 1-ethyl-3-(3-dimethylaminopropyl)carbodiimide hydrochloride (575 mg) and 1-hydroxybenzotriazole monohydrate (135 mg) were added, and the mixture was stirred at room temperature for 3 days. The solvent was distilled off under reduced pressure, and dichloromethane and a saturated solution of sodium hydrogencarbonate were added to the residue to conduct liquid separation. The resultant organic layer was dried over anhydrous sodium sulfate, and the solvent was distilled off under reduced pressure. The residue was purified by flash column chromatography on silica gel (dichloromethane:methanol=47:3), and the resultant pale yellow solid was dissolved in dichloromethane (10 ml) and methanol (10 ml), to which a saturated ethanol solution (10 ml) of hydrochloric acid was added, and the mixture was stirred at room temperature for 1 hour. After the solvent was distilled off under reduced pressure, ethyl acetate was added, and precipitate formed was collected by filtration to obtain the title compound (288 mg) as a pale yellow solid.

$^1$H-NMR (DMSO-$d_6$) δ: 2.59(3H,t,J=5.4 Hz), 3.11(2H, quint,J=5.9 Hz), 3.61(2H,q,J=5.9 Hz), 7.19(1H,dd,J=8.8, 2.2 Hz), 7.22(1H,d,J=1.2 Hz), 7.44(1H,d,J=8.8 Hz), 7.71(1H,d, J=2.2 Hz), 9.00(1H,t,J=5.9 Hz), 9.03(2H,br.s), 11.89(1H, br.s). MS (ESI) m/z: 252(M+H)$^+$.

Referential Example 77

N$^1$-tert-Butoxycarbonyl-N$^1$,N$^2$-dimethyl-1,2-ethylene-diamine

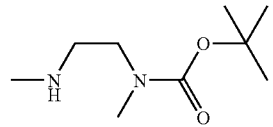

N,N'-Dimethyl-1,2-ethylenediamine (1.07 ml) was dissolved in dichloromethane, and to the solution di-tert-butyl dicarbonate (2.18 g) was added at room temperature, and the mixture was stirred overnight. The solvent was distilled off under reduced pressure, and the residue was purified by column chromatography on silica gel (dichloromethane:methanol=4:1) to obtain the title compound (678 mg) as a yellow oil.

$^1$H-NMR (CDCl$_3$) δ: 1.46(9H,s), 2.48(3H,br.s), 2.78(2H, br.s), 2.89(3H,s), 3.37(2H,br.s). MS (ESI) m/z: 189(M+H)$^+$.

Referential Example 78

4-(2-Pyridyl)benzoic acid

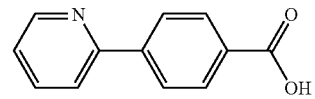

2-(p-Toluyl)pyridine (17.2 g) was suspended in water (200 ml), and to the suspension potassium permanganate (21.0 g) was added. The mixture was heated under reflux for 18 hours. After the reaction mixture was allowed to cool, and insoluble matter was removed by filtration, dichloromethane was added to the filtrate, and the resultant water layer was separated and acidified with 2N hydrochloric acid. The solution was concentrated, and precipitate was collected by filtration to obtain the title compound (7.07 g) as a white solid.

$^1$H-NMR (DMSO-$d_6$) δ: 7.60(1H,t,J=5.9 Hz), 8.08(2H,d, J=7.8 Hz), 8.17(2H,m), 8.21(2H,d,J=7.8 Hz), 8.78(1H,d,J= 4.9 Hz). MS (EI) m/z: 199(M$^+$).

Referential Example 79

Thiazolo[4,5-c]pyridine

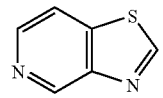

3-(tert-Butoxycarbonylamino)-4-mercaptopyridine (Japanese Patent Application Laid-Open No. 321691/1992) (9.20 g) was dissolved in formic acid (60 ml) and heated under reflux for 4 hours. The reaction mixture was concentrated under reduced pressure, and a 4N aqueous solution (100 ml) of potassium hydroxide and ether were added to the residue to conduct liquid separation. The resultant organic layer was dried over anhydrous sodium sulfate, and the solvent was distilled off under reduced pressure. Ether was added to the residue, and solids deposited were collected by filtration to obtain the title compound (3.97 g) as a colorless solid.

¹H-NMR (CDCl₃) δ: 7.93(1H,d,J=5.4 Hz), 8.60(1H,d,J=5.4 Hz); 9.07(1H,s), 9.46(1H,s).

Referential Example 80

5-Methyl-4,5,6,7-tetrahydrothiazolo[4,5-c]pyridine

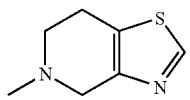

The title compound was obtained from thiazolo-[4,5-c]pyridine in a similar manner to Referential Example 4.

¹H-NMR (CDCl₃) δ: 2.52(3H,s), 2.77(2H,t,J=5.4 Hz), 2.92–3.00(2H,m), 3.69(2H,t,J=2.0 Hz), 8.61(1H,s). MS (FAB) m/z: 155(M+H)⁺.

Referential Example 81

Lithium 5-methyl-4,5,6,7-tetrahydrothiazolo[4,5-c]-pyridine-2-carboxylate

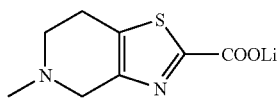

The title compound was obtained from 5-methyl-4,5,6,7-tetrahydrothiazolo[4,5-c]pyridine in a similar manner to Referential Example 5.

¹H-NMR (DMSO-d₆) δ: 2.38(3H,s), 2.64(2H,br.s), 2.80 (2H,br.s), 3.44(2H,br.s). MS (FD) m/z: 199(M+H)⁺.

Referential Example 82

6-Methyl-4,5,6,7-tetrahydrothieno[2,3-c]pyridine

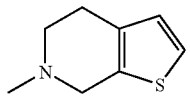

A 35% aqueous solution (6 ml) of formaldehyde was added to 3-[(2-amino)ethyl]thiophene (Arkiv för kemi, 1971, Vol. 32, p. 217) (4.50 g) with ice cooling, and the mixture was heated and stirred at 90° C. 3 hours. The reaction mixture was cooled back to room temperature and extracted with benzene. The resultant organic layer was washed with water and then dried over anhydrous magnesium sulfate. The solvent was distilled off under reduced pressure, and 7N hydrochloric acid was added to the residue to stir the mixture overnight at room temperature. The reaction mixture was concentrated under reduced pressure, and a 3N aqueous solution (100 ml) of sodium hydroxide and dichloromethane were added to conduct liquid separation. After the resultant organic layer was dried over anhydrous magnesium sulfate, and the solvent was distilled off under reduced pressure, the residue was dissolved in dichloromethane (200 ml), and a 35% aqueous solution (2 ml) of formaldehyde, acetic acid (2 ml) and sodium triacetoxyborohydride (11.24 g) were added to stir the mixture at room temperature for 1 hour. A 3N aqueous solution (100 ml) of sodium hydroxide was added to the reaction mixture, and the resultant organic layer was separated and then dried over anhydrous magnesium sulfate. The solvent was distilled off under reduced pressure, and the residue was distilled under reduced pressure (0.3 mmHg, 45 to 47° C.) to obtain the title compound (1.82 g) as a colorless oil.

¹H-NMR (CDCl₃) δ: 2.49(3H,s), 2.70–2.80(4H,m), 3.64 (2H,s), 6.78(1H,d,J=4.9 Hz), 7.09(1H,d,J=4.9 Hz). MS (FAB) m/z: 154(M+H)⁺.

Referential Example 83

Lithium 6-methyl-4,5,6,7-tetrahydrothieno[2,3-c]-pyridine-2-carboxylate

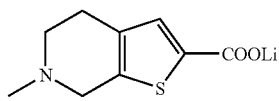

The title compound was obtained from 6-methyl-4,5,6,7-tetrahydrothieno[2,3-c]pyridine in a similar manner to Referential Example 5.

¹H-NMR (DMSO-d₆) δ: 2.48–2.70(4H,m), 3.30–3.50 (3H,m), 3.61(1H,s), 7.01(1H,s). MS (FD) m/z: 198(M+H)⁺.

Referential Example 84

2-Chloro-5-(N,N-dimethylamino)-4,5,6,7-tetrahydrobenzo-[d]thiazole

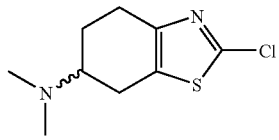

2-Chloro-5-oxo-4,5,6,7-tetrahydrobenzo[d]thiazole (Helv. Cim. Acta., 1994, Vol. 77, p. 1256) (2.0 g) was dissolved in methanol (100 ml), and ammonium acetate (8.2 g) and sodium cyanoborohydride (4.0 g) were added to heat the mixture under reflux. After 20 hours, the reaction was stopped, hydrochloric acid was added to decompose excessive sodium cyanoborohydride before the solvent was distilled off under reduced pressure. The residue was alkalified with a 1N solution of sodium hydroxide and then extracted with dichloromethane. The resultant organic layer was dried over anhydrous magnesium sulfate, and the solvent was distilled off under reduced pressure to obtain a pale yellow oil. This oil was dissolved in methanol (50 ml), and an aqueous solution (4.29 g) of formaldehyde and sodium cyanoborohydride (3.49 g) were added to stir the mixture at room temperature for 12 hours. The solvent was distilled off under reduced pressure, and methylene chloride was added to the residue, the organic layer was washed with a saturated aqueous solution of sodium hydrogencarbonate and dried over anhydrous magnesium sulfate. The solvent was distilled off under reduced pressure, and the residue was purified by column chromatography on silica gel (dichloromethane:methanol=10:1) to obtain the title compound (740 mg) as a pale yellow oil.

¹H-NMR (CDCl₃) δ: 1.71–1.78(1H,m), 2.10–2.19(1H, m), 2.35(6H,s), 2.66–2.94(5H,m). MS (FAB) m/z: 217(M+H)⁺.

Referential Example 85

Lithium [5-(N,N-dimethylamino)-4,5,6,7-tetrahydrobenzo-[d]thiazol-2-yl]carboxylate

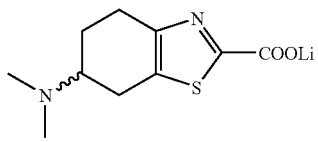

After 2-chloro-5-(N,N-dimethylamino)-4,5,6,7-tetrahydrobenzo[d]thiazole (750 mg) was dissolved in ether (15 ml), and the solution was cooled to −78° C., 1.5N t-butyllithium (3.5 ml) was added, and the mixture was stirred. After 20 minutes, carbon dioxide was bubbled, and the bubbling was stopped after about 15 minutes. The reaction mixture was warmed to room temperature and concentrated under reduced pressure to obtain the title compound as a pale yellow amorphous substance.

$^1$H-NMR (DMSO-$d_6$) δ: 1.75–1.78(1H,m), 1.98–2.07(1H,m), 2.50(6H,s), 2.64–2.88(5H,m).

Referential Example 86

4-(Morpholinomethyl)thiazole

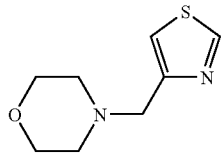

4-Methylthiazole (1.98 g), N-bromosuccinimide (3.56 g) and α,α'-azobisisobutyronitrile (164 mg) were dissolved in carbon tetrachloride (200 ml), and the solution was heated under reflux for 2 hours. After completion of the reaction, insoluble matter was removed by filtration, N,N-dimethylformamide (20 ml) was added to the filtrate, and carbon tetrachloride was distilled off under reduced pressure to obtain an N,N-dimethylformamide solution (about 20 ml) of 4-(bromomethyl)thiazole. Morpholine (871 μl), triethylamine (2.79 ml) and N,N-dimethylformamide (10 ml) were successively added to this N,N-dimethyl-formamide solution (about 10 ml) of 4-(bromomethyl)-thiazole, and the mixture was stirred overnight at room temperature. The solvent was distilled off under reduced pressure, dichloromethane and a saturated aqueous solution of sodium hydrogen carbonate were added to the residue and an organic layer was separated. The organic layer was dried over anhydrous sodium sulfate. The solvent was distilled off under reduced pressure, and the residue was purified by column chromatography on silica gel (methanol:dichloromethane=1:19) to obtain the title compound (700 mg) as a yellow oil.

$^1$H-NMR (CDCl$_3$) δ: 2.45–2.60(4H,br), 3.65–3.90(6H,br), 7.21(1H,s), 8.79(1H,s). MS (ESI) m/z: 185(M+H)$^+$.

Referential Example 87

5-[(N,N-Dimethylamino)methyl]thiazole

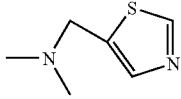

An N,N-dimethylformamide solution of 5-(bromomethyl)thiazole was prepared by using 5-methylthiazole (5.00 g), N-bromosuccinimide (8.97 g) and α,α'-azobisisobutyronitrile (414 mg) in a similar manner to Referential Example 86, and morpholine (2.20 ml) and triethylamine (7.02 ml) were reacted with this solution to obtain the title compound (1.76 g) as a yellow oil.

1H-NMR (CDCl$_3$) δ: 2.27(6H,s), 3.68(2H,s), 7.70(1H,s), 8.75(1H,s). MS (ESI) m/z: 143(M+H)$^+$.

Referential Example 88

Lithium 4-(morpholinomethyl)thiazole-2-carboxylate

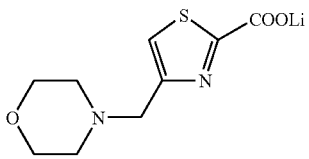

4-(Morpholinomethyl)thiazole (640 mg) was dissolved in diethyl ether (5 ml) in an argon atmosphere, and n-butyllithium (1.54N hexane solution, 2.50 ml) was added dropwise at −78° C. The reaction mixture was stirred for 10 minutes under ice cooling, and cooled again to −78° C. After blowing carbon dioxide into the reaction mixture for 20 minutes, it was heated to room temperature. The reaction mixture was concentrated under reduced pressure to obtain the title compound (873 mg) as crude yellow powder.

$^1$H-NMR (DMSO-$d_6$) δ: 2.40(4H,br.s), 3.50–3.70(6H,m), 7.34(1H,s).

Referential Example 89

Lithium 5-[(N,N-dimethylamino)methyl]thiazole-2-carboxylate

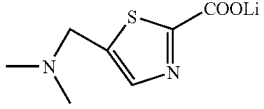

The title compound (2.34 g) was obtained as violet powder from 5-[(N,N-dimethylamino)methyl]thiazole (1.81 g) in a similar manner to Referential Example 5.

$^1$H-NMR (DMSO-$d_6$) δ: 2.14(6H,br.s), 3.56(2H,br.s), 7.51(1H,s).

Referential Example 90

2-Amino-5-tert-butoxycarbonyl-4,6-dihydro-5H-pyrrolo-[3,4-d]thiazole

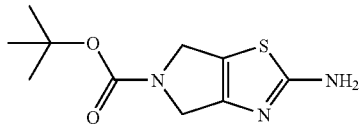

1-tert-Butoxycarbonyl-3-pyrrolidone (1.58 g) was dissolved in cyclohexane (10 ml), p-toluenesulfonic acid monohydrate (8.12 mg) and pyrrolidine (607 mg) were added, and the mixture was heated under reflux for 1.5 hours while dewatering by a Dean-Stark trap. After a supernatant was taken out and concentrated under reduced pressure, the residue was dissolved in methanol (5 ml), and sulfur powder (274 mg) was added. The mixture was stirred for 15 minutes under ice cooling. A methanol solution (2 ml) of cyanamide (377 mg) was slowly added dropwise to the reaction mixture, and the mixture was stirred overnight at room temperature. Then the mixture was heated under reflux for 2 hours, the reaction mixture was concentrated, and dichloromethane and a saturated aqueous solution of sodium hydrogen carbonate were added. The resultant organic layer was dried over anhydrous sodium sulfate. The solvent was distilled off under reduced pressure, and the residue was purified by column chromatography on silica gel (methanol:dichloromethane=1:39) to obtain the title compound (248 mg) as a yellow oil.

$^1$H-NMR (CDCl$_3$) δ: 1.50(9H,s), 4.34–4.37(1H,m), 4.40–4.45(1H,m), 4.49–4.55(2H,m), 4.99(2H,m).

Referential Example 91

2-Bromo-5-tert-butoxycarbonyl-4,6-dihydro-5H-pyrrolo-[3,4-d]thiazole

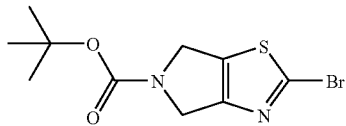

Copper(II) bromide (445 mg) was suspended in N,N-dimethylformamide, and tert-butyl nitrite (256 mg) was added dropwise at room temperature. After an N,N-dimethylformamide solution (1 ml) of 2-amino-5-tert-butoxycarbonyl-4,6-dihydro-5H-pyrrolo[3,4-d]thiazole (400 mg) was added under ice cooling, the reaction mixture was heated and stirred at 60° C. for 1.5 hours. Diethyl ether and saturated saline were added to the reaction mixture, and the resultant organic layer was dried over anhydrous magnesium sulfate and concentrated under reduced pressure. The residue was purified by column chromatography on silica gel (ethyl acetate:hexane=1:4) to obtain the title compound (174 mg) as pale yellow powder.

$^1$H-NMR (CDCl$_3$) δ: 1.51(9H,s), 4.52–4.55(1H,m), 4.57–4.67(3H,m) MS (FAB) m/z: 305(M+H)$^+$.

Referential Example 92

5-(Benzenesulfonyl)-4,6-dihydro-5H-pyrrolo[3,4-d]-thiazole

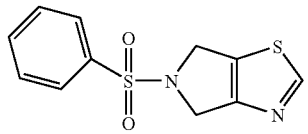

1) 4,5-Dimethylthiazole (5.00 g), N-bromo-succinimide (15.7 g) and α,α'-azobisisobutyronitrile (362 mg) were dissolved in dichloroethane (500 ml) at room temperature, and the solution was heated under reflux for 1 hour. The solvent was distilled off, and the residue was purified by column chromatography on silica gel (hexane:diethyl ether= 1:4) to obtain 4,5-bis(bromomethyl)thiazole (5.24 g) as a pale yellow oil.

$^1$H-NMR (CDCl$_3$) δ: 4.64(2H,s), 4.74(2H,s), 8.75(1H,s).

2) Benzenesulfonamide (638 mg) and 4,5-bis(bromomethyl)thiazole (1.10 g) were dissolved in dimethylformamide (10 ml), 60% sodium hydride in oil (357 mg) was added at a time, and the mixture was stirred at room temperature for 3 hours. Water and dichloromethane were added to conduct liquid separation. After the resultant oil layer was dried over anhydrous sodium sulfate, the solvent was distilled off, and the residue was purified by column chromatography on silica gel (dichloromethane:ethylacetate=9:1) to obtain the title compound (137 mg) as colorless powder.

$^1$H-NMR (CDCl$_3$) δ: 4.60–4.63(2H,m), 4.70–4.73(2H, m), 7.52–7.64(3H,m), 7.88–7.92(2H,m), 8.71(1H,s). MS (FAB) m/z: 267(M+H)$^+$.

Referential Example 93

4,6-Dihydro-5H-pyrrolo[3,4-d]thiazole hydrobromide

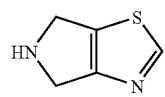

A mixture of 5-(benzenesulfonyl)-4,6-dihydro-5H-pyrrolo[3,4-d]thiazole (800 mg), phenol (800 μl) and 47% hydrobromic acid (5.00 ml) was heated under reflux for 2 hours. After the reaction mixture was cooled to room temperature, ethyl acetate and water were added to conduct liquid separation. The resultant water layer was concentrated under reduced pressure. Ethyl acetate was added to the residue, colorless powder deposited was collected by filtration to obtain the title compound (521 mg).

$^1$H-NMR (DMSO-d$_6$) δ: 4.42(2H,br.s), 4.56(2H,br.s), 9.14(1H,s). MS (FAB) m/z: 127(M+H)$^+$.

Referential Example 94

5-Methyl-4,6-dihydro-5H-pyrrolo[3,4-d]thiazole

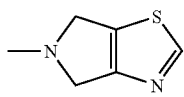

The title compound was obtained from 4,6-dihydro-5H-pyrrolo[3,4-d]thiazole hydrobromide and formalin in a similar manner to Referential Example 12.

$^1$H-NMR (CDCl$_3$) δ: 2.67(3H,s), 3.95–3.99(2H,m), 4.01–4.05(2H,m), 8.69(1H,s). MS (ESI) m/z: 141(M+H)$^+$.

Referential Example 95

Lithium 5-methyl-4,6-dihydro-5H-pyrrolo[3,4-d]thiazole-2-carboxylate

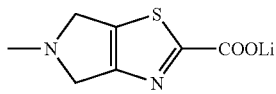

5-Methyl-4,6-dihydro-5H-pyrrolo[3,4-d]thiazole (771 mg) was dissolved in tetrahydrofuran (10 ml) in an argon atmosphere, and the solution was cooled to −78° C. tert-Butyllithium (1.54N pentane solution, 3.93 ml) was added dropwise to this reaction mixture. The reaction mixture was stirred for 1 hour under ice cooling, and cooled again to −78° C. After blowing carbon dioxide into the reaction mixture for 20 minutes, it was heated to room temperature. The reaction mixture was concentrated under reduced pressure to obtain the title compound (1.08 g) as crude brown powder.

$^1$H-NMR (DMSO-d$_6$) δ: 2.52(3H,s), 3.73(2H,t,J=3.2 Hz), 3.87(2H,t,J=3.2 Hz).

Referential Example 96

2-Bromo-5-isopropyl-4,5,6,7-tetrahydrothiazolo[5,4-c]-pyridine

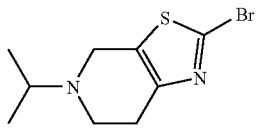

2-Bromo-4,5,6,7-tetrahydrothiazolo[5,4-c]pyridine trifluoroacetate (5.00 g) was suspended in dichloromethane (200 ml), and to the suspension triethylamine (4.16 ml) was added, and the mixture was stirred at room temperature into a solution. Acetic acid (2.55 ml) and acetone (17 ml) were added to the reaction mixture, and the mixture was stirred at room temperature for 2 minutes. Sodium triacetoxyborohydride (19.1 g) was added to the reaction mixture, and the resultant mixture was stirred at room temperature for 5 hours. A 3N aqueous solution (200 ml) of sodium hydroxide was added to the reaction mixture to separate an organic layer. After the organic layer was dried over anhydrous sodium sulfate, the solvent was distilled off under reduced pressure. The residue was purified by column chromatography on silica gel (dichloromethane:methanol=100:1) to obtain the title compound (3.45 g) as a yellow oil.

$^1$H-NMR (CDCl$_3$) δ: 1.13(6H,d,J=6.6 Hz), 2.86(4H,s), 2.92–3.01(1H,m), 3.70(2H,s). MS (FAB) m/z: 261(M$^+$).

Referential Example 97

Lithium 5-isopropyl-4,5,6,7-tetrahydrothiazolo[5,4-c]-pyridine-2-carboxylate

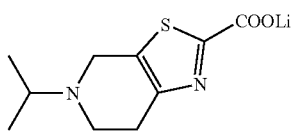

The title compound was obtained from 2-bromo-5-isopropyl-4,5,6,7-tetrahydrothiazolo[5,4-c]pyridine in a similar manner to Referential Example 13.

$^1$H-NMR (DMSO-d$_6$) δ: 0.90–1.20(6H,m), 2.60–3.03 (5H,m), 3.58–4.00(2H,m).

Referential Example 98

Lithium 5-tert-butoxycarbonyl-4,5,6,7-tetrahydrothiazolo[5,4-c]pyridine-2-carboxylate

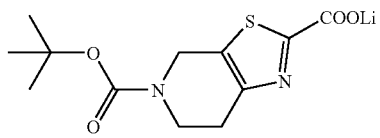

The title compound was obtained from 2-bromo-5-tert-butoxycarbonyl-4,5,6,7-tetrahydrothiazolo[5,4-c]-pyridine in a similar manner to Referential Example 13.

$^1$H-NMR (DMSO-d$_6$) δ: 1.42(9H,s), 2.69–2.77(2H,m), 3.60–3.68(2H,m), 4.51–4.58(2H,m). MS (FAB) m/z: 285 (M+H)$^+$.

Referential Example 99

Methyl 2-bromo-5-methoxycarbonylthiazole-4-acetate

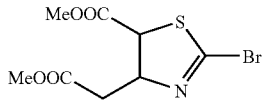

Copper(II) chloride (26.8 g) was added to a solution of tert-butyl nitrite (15.5 g) in acetonitrile (500 ml) at a time under ice cooling. A solution of methyl 2-amino-5-methoxycarbonylthiazole-4-acetate (Yakugaku Zasshi, 1966, Vol. 86, p. 300) (23.0 g) in acetonitrile (500 ml) was added dropwise over 45 minutes, and the mixture was stirred for 1 hour under ice cooling and for 30 minutes at room temperature. The solvent was concentrated, and 10% hydrochloric acid and diethyl ether were added to the residue to separate an organic layer. The organic layer was dried over anhydrous magnesium sulfate. The solvent was distilled off under reduced pressure, and the residue was purified by column chromatography on silica gel (ethyl acetate:hexane= 1:4) to obtain the title compound (25.9 g) as a yellow solid.

$^1$H-NMR (CDCl$_3$) δ: 3.73(3H,s), 3.87(3H,s), 4.21(2H,s).

Referential Example 100

4-(2-Hydroxyethyl)-5-hydroxymethylthiazole

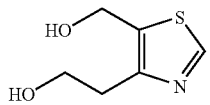

A solution of methyl 2-bromo-5-methoxycarbonyl-thiazole-4-acetate (23.4 g) in tetrahydrofuran (500 ml) was added dropwise over 1 hour to a suspension of lithium aluminum hydride (9.03 g) in tetrahydrofuran (500 ml) under ice cooling. After stirring for additional 1 hour under ice cooling, water (9 ml), a 35% aqueous solution (9 ml) of sodium hydroxide and water (27 ml) were successively added, and the mixture was stirred at room temperature for 1 hour. After anhydrous magnesium sulfate was added to the reaction mixture, and the resultant mixture was stirred, insoluble matter was removed by filtration with Celite, and the filtrate was concentrated. The residue was purified by column chromatography on silica gel (methanol:dichloromethane=7:93) to obtain the title compound (8.64 g) as a yellow oil.

$^1$H-NMR (CDCl$_3$) δ: 3.01(2H,t,J=5.5 Hz), 3.30(1H,br.s), 3.57(1H,br.s), 3.90(2H,br.s), 4.75(2H,br.s), 8.66(1H,s). MS (ESI) m/z: 160(M+H)$^+$.

Referential Example 101

4-(2-Methanesulfonyloxyethyl)-5-(methanesulfonyloxy-methyl)thiazole

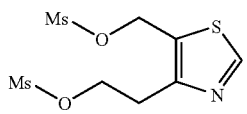

A dichloromethane solution of methanesulfonyl chloride (12.6 ml) was added dropwise to a solution of 4-(2-hydroxyethyl)-5-(hydroxymethyl)thiazole (8.64 g) and triethylamine (45.4 ml) dissolved in dichloromethane (500 ml) over 20 minutes at −78° C. After stirring the reaction mixture for 15 minutes at −78° C. and 1 hour at 0° C., water was added to separate an organic layer. The organic layer was dried over anhydrous sodium sulfate. The solvent was distilled off under reduced pressure to obtain the title compound (13.4 g) as a crude pale yellow oil.

$^1$H-NMR (CDCl$_3$) δ: 2.93(3H,s), 3.03(3H,s), 3.28(2H,t, J=6.3 Hz), 4.61(2H,t,J=6.3 Hz), 5.44(2H,s), 8.84(1H,s).

Referential Example 102

5-(1-Methylcyclopropyl)-4,5,6,7-tetrahydrothiazolo-[5,4-c]pyridine

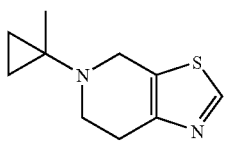

1-Methylcyclopropylamine hydrochloride (J. Org. Chem., 1989, Vol. 54, p. 1815) (1.89 g) was added to dichloromethane (20 ml) containing 4-(2-methanesulfonyloxyethyl)-5-methanesulfonyloxymethylthiazole (4.46 g) under ice cooling, and the mixture was stirred overnight at room temperature. 1-Methylcyclopropylamine hydrochloride (1.89 g) was additionally added, and the mixture was stirred for 20 hours at room temperature and 5 hours under refluxing. Dichloromethane and water were added to the reaction mixture to separate an organic layer. The organic layer was dried over anhydrous sodium sulfate. The solvent was distilled off under reduced pressure, and the residue was purified by column chromatography on silica gel (methanol:dichloromethane=1:49) to obtain the title compound (944 mg) as a pale yellow oil.

$^1$H-NMR (CDCl$_3$) δ: 0.40–0.50(2H,m), 0.68–0.73(2H, m), 1.16(3H,s), 2.88–2.94(2H,m), 3.03(2H,t,J=5.7 Hz), 3.89 (2H,br.s), 8.60(1H,s). MS (ESI) m/z: 195(M+H)$^+$.

Referential Example 103

Lithium 5-(1-methylcyclopropyl)-4,5,6,7-tetrahydrothiazolo[5,4-c]pyridine-2-carboxylate

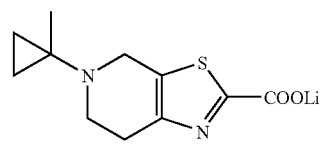

The title compound was obtained from 5-(1-methyl-cyclopropyl)-4,5,6,7-tetrahydrothiazolo[5,4-c]pyridine in a similar manner to Referential Example 5.

$^1$H-NMR (DMSO-d$_6$) δ: 0.39(2H,br.s), 0.56(2H,br.s), 1.10(3H,br.s), 2.66(2H,br.s), 2.89(2H,br.s), 3.75(2H,br.s).

Referential Example 104

5-tert-Butyl-4,5,6,7-tetrahydrothiazolo[5,4-c]pyridine

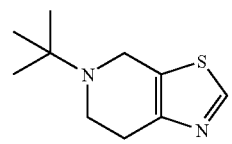

The title compound was obtained from 4-(2-methanesulfonyloxyethyl)-5-(methanesulfonyloxy-methyl)thiazole and tert-butylamine in a similar manner to Referential Example 102.

$^1$H-NMR (CDCl$_3$) δ: 1.20(9H,s), 2.87–2.96(4H,m), 3.87 (2H,s), 8.59(1H,s). MS (ESI) m/z: 197(M+H)$^+$.

Referential Example 105

Lithium 5-tert-butyl-4,5,6,7-tetrahydrothiazolo[5,4-c]-pyridine-2-carboxylate

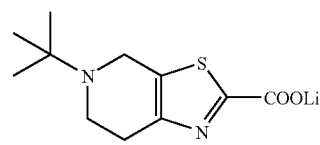

The title compound was obtained from 5-tert-butyl-4,5, 6,7-tetrahydrothiazolo[5,4-c]pyridine in a similar manner to Referential Example 5.

¹H-NMR (DMSO-d₆) δ: 1.09(9H,br.s), 2.65(2H,br.s), 2.75–2.85(2H,m), 3.71(2H,br.s).

Referential Example 106

5-(1,1-Dimethyl-2-hydroxyethyl)-4,5,6,7-tetrahydrothiazolo[5,4-c]pyridine

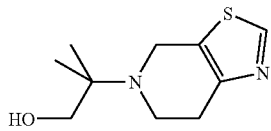

The title compound was obtained from 4-(2-methanesulfonyloxyethyl)-5-(methanesulfonyloxy-methyl)thiazole and 2-amino-2-methyl-1-propanol in a similar manner to Referential Example 102.

¹H-NMR (CDCl₃) δ: 1.15(6H,s), 2.91(4H,s), 3.45(2H,s), 3.87(2H,s), 8.63(1H,s).

Referential Example 107

5-[2-(tert-Butyldiphenylsilyloxy)-1,1-dimethylethyl]-4,5,6,7-tetrahydrothiazolo[5,4-c]pyridine

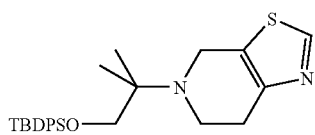

tert-Butylchlorodiphenylsilane (1.93 g) and imidazole (994 mg) were added to a solution of 5-(1,1-dimethyl-2-hydroxyethyl)-4,5,6,7-tetrahydrothiazolo-[5,4-c]pyridine (1.24 g) in N,N-dimethylformamide (5 ml) at room temperature, and the mixture was stirred overnight. Water and diethyl ether were added to the reaction mixture to separate an organic layer. The organic layer was dried over anhydrous magnesium sulfate. The solvent was distilled off under reduced pressure, and the residue was purified by column chromatography on silica gel (hexane:ethyl acetate=1:2) to obtain the title compound (2.46 g) as a colorless oil.

¹H-NMR (CDCl₃) δ: 1.07(9H,s), 1.15(6H,s), 2.83–2.90 (2H,m), 2.93–3.00(2H,m), 3.63(2H,s), 3.97(2H,s), 7.35–7.48(6H,m), 7.63–7.70(4H,m), 8.58(1H,s). MS (ESI) m/z: 451(M+H)⁺.

Referential Example 108

Lithium 5-[2-(tert-butyldiphenylsilyloxy)-1,1-dimethyl-ethyl]-4,5,6,7-tetrahydrothiazolo[5,4-c]pyridine-2-carboxylate

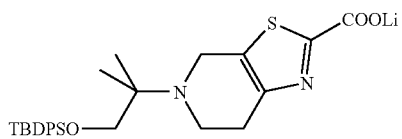

The title compound was obtained from 5-[2-(tert-butyldiphenylsilyloxy)-1,1-dimethylethyl]-4,5,6,7-tetrahydrothiazolo[5,4-c]pyridine in a similar manner to Referential Example 5.

¹H-NMR (DMSO-d₆) δ: 1.01(9H,s), 1.11(6H,s), 2.55–2.65(2H,m), 2.80–2.90(2H,m), 3.57(2H,s), 3.80(2H, br.s), 7.40–7.52(6H,m), 7.60–7.65(4H,m).

Referential Example 109

4,5,6,7-Tetrahydro-5,6-trimethylenethiazolo[4,5-d]-pyridazine

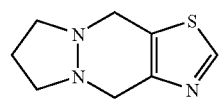

1) 4,5-Dimethylthiazole (5.00 g), N-bromo-succinimide (15.7 g) and α,α'-azobisisobutyronitrile (362 mg) were dissolved in ethylene dichloride (500 ml) at room temperature, and the solution was heated under reflux for 1 hour. The solvent was distilled off, and the residue was purified by column chromatography on silica gel (hexane:diethyl ether=1:4) to obtain 4,5-bis(bromomethyl) thiazole (5.24 g) as a pale yellow oil.

¹H-NMR (CDCl₃) δ: 4.64(2H,s), 4.74(2H,s), 8.75(1H,s).

2) 4,5-Bis(bromomethyl)thiazole (1.37 g) and 1,2-trimethylenehydrazine hydrochloride (WO9532965) (732 mg) were suspended in ethanol (15 ml) under ice cooling, and triethylamine (2.82 ml) was added dropwise over 5 minutes. After stirring the mixture at room temperature for 2 hours, the solvent was distilled off, and dichloromethane and a saturated aqueous solution of sodium hydrogencarbonate were added to the residue to separate an organic layer. The organic layer was dried over anhydrous sodium sulfate. The solvent was distilled off under reduced pressure, and the residue was purified by column chromatography on silica gel (methanol:dichloromethane=3:47) to obtain the title compound (358 mg) as yellow powder.

¹H-NMR (CDCl₃) δ: 2.10–2.25(2H,m), 3.01(4H,br.s), 3.95(2H,s), 3.99(2H,br.s), 8.64(1H,s). MS (FAB) m/z: 182 (M+H)⁺.

Referential Example 110

4,5,6,7-Tetrahydro-5,6-tetramethylenethiazolo[4,5-d]-pyridazine

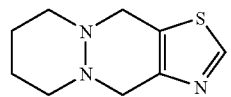

The title compound was obtained from 4,5-bis (bromomethyl)thiazole (2.20 g) and 1,2-tetramethylenehydrazine hydrochloride (U.S. Pat. No. 5,726,126) in a similar manner to Referential Example 109.

¹H-NMR (CDCl₃) δ: 1.77(4H,br.s), 2.20–3.50(4H,br), 3.92(4H,br.s), 8.65(1H,s). MS (FAB) m/z: 196(M+H)⁺.

Referential Example 111

Lithium 4,5,6,7-tetrahydro-5,6-trimethylenethiazolo-[4,5-d]pyridazine-2-carboxylate

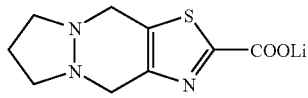

The title compound was obtained from 4,5,6,7-tetrahydro-5,6-trimethylenethiazolo[4,5-d]pyridazine in a similar manner to Referential Example 5.

$^1$H-NMR (DMSO-$d_6$) δ: 1.90–2.10(2H,m), 2.60–3.10 (4H,br.s), 3.65–4.00(4H,m).

Referential Example 112

Lithium 4,5,6,7-tetrahydro-5,6-tetramethylenethiazolo-[4,5-d]pyridazine-2-carboxylate

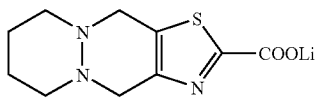

The title compound was obtained from 4,5,6,7-tetrahydro-5,6-tetramethylenethiazolo[4,5-d]pyridazine in a similar manner to Referential Example 5.

Referential Example 113

6-(tert-Butoxycarbonyl)-5,7-dihydro-2-methylthiopyrrolo-[3,4-d]pyrimidine

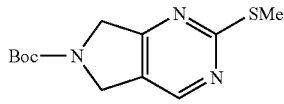

1-tert-Butoxycarbonyl-3-pyrrolidone (4.57 g) was added to N,N-dimethylformamide dimethyl acetal (30 ml) at room temperature, and the mixture was heated for 1 hour at 140° C. After allowing the reaction mixture to cool to room temperature, it was concentrated under reduced pressure. Hexane was added to the residue, and yellow powder deposited was collected by filtration. This powder was dissolved in ethanol (100 ml), and methylisothiourea sulfate (9.24 g) and sodium ethoxide (4.52 g) were added to the resultant solution at room temperature, and the mixture was heated under reflux for 24 hours. Saturated saline was added to the reaction mixture to separate an organic layer. The organic layer was dried over anhydrous sodium sulfate and concentrated under reduced pressure, and the residue was purified by column chromatography on silica gel (methanol:dichloromethane=1:99) to obtain the title compound (1.10 g) as pale yellow powder.

$^1$H-NMR (CDCl$_3$) δ: 1.51(9H,s), 2.57(3H,m), 4.15–4.45 (4H,m), 8.39(1/2H,s), 8.43(1/2H,s). MS (FAB) m/z: 268(M+H)$^+$.

Referential Example 114

6-(tert-Butoxycarbonyl)-5,7-dihydro-2-methylsulfonyl-pyrrolo[3,4-d]pyrimidine

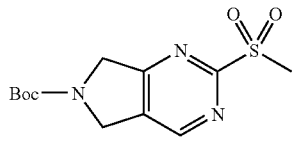

m-Chloroperbenzoic acid (1.99 g) was added to a dichloromethane solution (20 ml) of 6-(tert-butoxy-carbonyl)-5,7-dihydro-2-methylthiopyrrolo[3,4-d]-pyrimidine (1.08 g) under ice cooling, and the mixture was stirred for 5 hours. A saturated aqueous solution of sodium sulfite, a saturated aqueous solution of sodium hydrogen carbonate and dichloromethane were added to separate an organic layer. The organic layer was then dried over anhydrous sodium sulfate. The solvent was distilled off under reduced pressure, hexane was added to the residue, and powder deposited was collected by filtration to obtain the title compound (1.09 g) as colorless powder.

$^1$H-NMR (CDCl$_3$) δ: 1.53(9H,s), 3.36(3H,m), 4.77–4.90 (4H,m), 8.77(1/2H,s), 8.81(1/2H,s). MS (FAB) m/z: 300(M+H)$^+$.

Referential Example 115

6-(tert-Butoxycarbonyl)-2-cyano-5,7-dihydropyrrolo-[3,4-d]pyrimidine

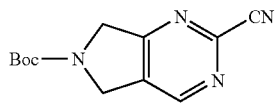

Tetrabutylammonium cyanide (1.04 g) was added to a solution of 6-(tert-butoxycarbonyl)-5,7-dihydro-2-methylsulfonylpyrrolo[3,4-d]pyrimidine (1.05 g) in dichloromethane (30 ml) at room temperature, and the mixture was stirred at room temperature for 1 hour. 1N sodium hydroxide was added to the reaction mixture to separate an organic layer, and the organic layer was dried over anhydrous sodium sulfate. The solvent was distilled off under reduced pressure, and the residue was purified by column chromatography on silica gel (dichloromethane:acetone=20:1) to obtain the title compound (776 mg) as colorless powder.

$^1$H-NMR (CDCl$_3$) δ: 1.52(9H,s), 4.70–4.85(4H,m), 8.68–8.77(1H,m). MS (FAB) m/z: 247(M+H)$^+$.

Referential Example 116

6-(tert-Butoxycarbonyl)-5,7-dihydro-2-methoxycarbonyl-pyrrolo[3,4-d]pyrimidine

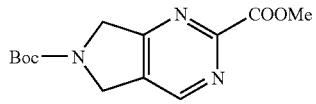

Concentrated hydrochloric acid (5 ml) was added to a solution of 6-(tert-butoxycarbonyl)-2-cyano-5,7-dihydropyrrolo[3,4-d]pyrimidine (776 mg) in methanol (10 ml) at room temperature, and the mixture was stirred at 100° C. for 1 hour. After allowing to cool, the reaction mixture was concentrated under reduced pressure, and the residue was dissolve in methanol (10 ml). Triethylamine (2.20 ml) and di-tert-butyl dicarbonate (1.37 g) were added to the solution at room temperature and stirred for 1 hour. The reaction mixture was concentrated under reduced pressure, and dichloromethane and saturated saline were added to the residue to separate an organic layer, and the organic layer was dried over anhydrous sodium sulfate. The solvent was distilled off under reduced pressure, and the residue was purified by column chromatography on silica gel (methanol:dichloromethane=3:97) to obtain the title compound (317 mg) as colorless powder.

$^1$H-NMR (CDCl$_3$) δ: 1.53(9H,s), 4.09(3H,s), 4.75–4.85 (4H,m), 8.81(1/2H,s), 8.85(1/2H,s). MS (FAB) m/z: 280(M+H)$^+$.

Referential Example 117

Lithium 1-isopropylpiperidine-4-carboxylate

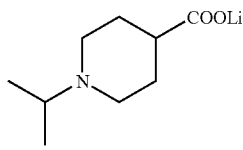

Ethyl 1-isopropylpiperidine-4-carboxylate (Farmaco., 1993, Vol. 48, p. 1439) (3.43 g) was dissolved in tetrahydrofuran (60 ml), and water (15 ml) and lithium hydroxide (421 mg) were added at room temperature to stir the mixture overnight. The reaction mixture was concentrated under reduced pressure to obtain the title compound (3.05 g) as a white solid.

$^1$H-NMR (CD$_3$OD) δ: 1.05(6H,d,J=6.6 Hz), 1.65–1.78 (2H,m), 1.83–1.94(2H,m), 2.07(1H,tt,J=11.4, 3.9 Hz), 2.20 (2H,dt,J=2.7, 11.6 Hz), 2.60–2.72(1H,m), 2.84–2.95(2H,m).

Referential Example 118 p-Nitrophenyl 5-chloroindole-2-carboxylate

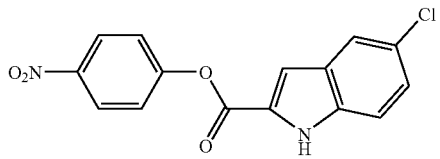

After 5-chloroindole-2-carboxylic acid (20 g) was suspended in dichloromethane (1500 ml), and N,N-dimethylformamide (2 ml) was added, thionyl chloride (11 ml) was added dropwise at room temperature. The reaction mixture was heated overnight under reflux and then concentrated under reduced pressure. The residue was dissolved in dichloromethane (1000 ml), and triethylamine (84.7 ml) was added to stir the mixture at room temperature for 1 hour. The reaction mixture was concentrated under reduced pressure, and ethyl acetate and 0.2N hydrochloric acid were added to the residue to separate an organic layer. The organic layer was successively washed with a saturated aqueous solution of sodium hydrogencarbonate and saturated saline and then dried over anhydrous sodium sulfate. The solvent was distilled off under reduced pressure to obtain the title compound (29.9 g) as a pale brown solid.

$^1$H-NMR (CDCl$_3$) δ: 7.35(1H,dd,J=9.0, 1.7 Hz), 7.39–7.42(2H,m), 7.45(2H,dd,J=7.3, 1.7 Hz), 7.73(1H,d,J=1.0 Hz), 8.35(2H,dd,J=7.3, 1.7 Hz), 9.09(1H,br.s). MS (FD) m/z: 316(M$^+$).

Referential Example 119

6-Chloro-4-hydroxynaphthalene-2-carboxylic acid

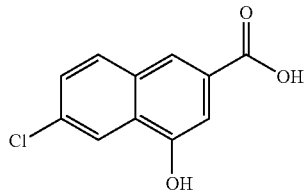

6-Chloro-4-hydroxy-2-methoxycarbonylnaphthalene (J. Chem. Research (S), 1995, p. 638) (473 mg) was dissolved in ethanol (10 ml), and a 1N aqueous solution (4.0 ml) of sodium hydroxide was added to stir the mixture for 24 hours at room temperature. Thereafter, the reaction mixture was stirred for 1 hour at 60° C. and 6 hours at 70° C., and the solvent was distilled off under reduced pressure. An 1N aqueous solution of hydrochloric acid and ethyl acetate were added to separate an organic layer. The organic layer was dried over anhydrous magnesium sulfate, and the solvent was distilled off under reduced pressure to obtain the title compound (442 mg) as a pale yellow solid.

$^1$H-NMR (DMSO-d$_6$) δ: 7.43(1H,d,J=1.2 Hz), 7.58(1H, dd,J=8.8, 2.2 Hz), 8.07–8.09(2H,m), 8.13(1H,d,J=2.2 Hz), 10.69(1H,s), 12.99(1H,br.s). MS (ESI) m/z: 223(M+H)$^+$.

Referential Example 120

Isolation of Optically Active Substances of (±)-trans-N-[(5-methyl-4,5,6,7-tetrahydrothiazolo[5,4-c]pyridin-2-yl)carbonyl]-1,2-cyclopentanediamine

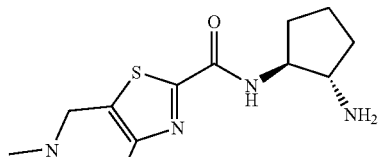

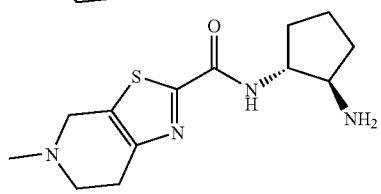

(±)-trans-N-[(5-Methyl-4,5,6,7-tetrahydrothiazolo-[5,4-c]pyridin-2-yl)carbonyl]-1,2-cyclopentanediamine (1.83 g) was dissolved in 2-propanol (15 ml), and the solution was purified by HPLC. As a column, CHIRALPAK AD was used to conduct elution at a flow rate of 6 ml/min using a solvent of hexane:2-propanol:diethylamine=75:25:0.5. Fractions eluted after 32 minutes and 45 minutes were separately collected to obtain (1S,2S)-form (675 mg) as an orange oil and (1R,2R)-form (673 mg) as a brown oil.

Referential Example 121

1,2-Epoxy-4-methoxycarbonylcyclopentane

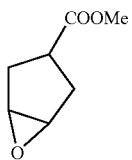

3-Cyclopentenecarboxylic acid (J. Org. Chem., 1984, Vol. 49, p. 928) (2.42 g) was dissolved in methanol (8 ml) and 2,2-dimethoxypropane (32 ml), and trimethylsilyl chloride (253 µl) was added dropwise to stir the mixture at room temperature for 6.5 hours. The solvent was distilled off under reduced pressure, and the residue was dissolved in dichloromethane (50 ml), to which m-chloroperbenzoic acid (70%, 4.93 g) was added under ice cooling. After the mixture was heated to room temperature and stirred for 5 hours, a saturated aqueous solution of sodium hydrogencarbonate was added to separate an organic layer. The organic layer was washed with a saturated aqueous solution of sodium hydrogencarbonate and then dried over anhydrous sodium sulfate. The organic layer was concentrated under reduced pressure, and the residue was purified by column chromatography on silica gel (hexane:ethyl acetate=2:1) to obtain the title compound (1.59 g) as a colorless oil.

$^1$H-NMR (CDCl$_3$) δ: 1.86–1.92(2H,m), 2.32–2.38(2H, m), 2.61–2.70(1H,m), 3.53(2H,s), 3.68(3H,s).

Referential Example 122

(1R*,2R*)-1,2-Dihydroxy-4-methoxycarbonylcyclopentane

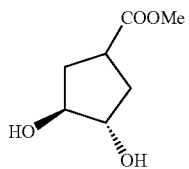

1,2-Epoxy-4-methoxycarbonylcyclopentane (37.7 g) was dissolved in a mixed solvent of tetrahydrofuran (500 ml) and water (500 ml), and sulfuric acid (13.3 ml) was added dropwise under ice cooling to stir the mixture at room temperature for 4 hours. Sodium carbonate and sodium hydrogencarbonate were added to the reaction mixture to make the mixture neutral or weakly alkaline, and the solvent was distilled off under reduced pressure. The residue was extracted with dichloromethane and ethyl acetate, insoluble matter was removed by filtration, and the filtrate was concentrated under reduced pressure to obtain the title compound (35.5 g) as a pale yellow oil.

$^1$H-NMR (CDCl$_3$) δ: 1.81–1.93(2H,m), 2.20–2.37(2H, m), 2.84(1H,br.s), 2.99–3.07(1H,m), 3.70(3H,s), 3.97–4.01 (1H,s), 4.08–4.12(1H,m), 4.56(1H,br.s).

Referential Example 123

(1R*,2R*)-1,2-Bis(methanesulfonyloxy)-4-methoxycarbonyl-cyclopentane

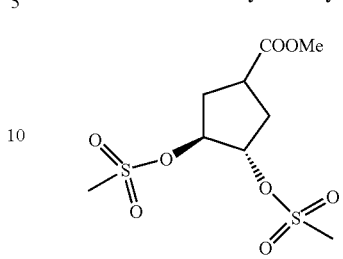

(1R*,2R*)-1,2-Dihydroxy-4-methoxycarbonylcyclopentane (700 mg) was dissolved in dichloromethane (10 ml), and triethylamine (3.63 ml) was added. After purging with argon, the mixture was cooled to −78° C. and methanesulfonyl chloride (1.01 ml) was added dropwise. After the mixture was heated to 0° C. and stirred for 2 hours, water was added to conduct liquid separation. An organic layer was separated and dried over anhydrous sodium sulfate, and the solvent is distilled off under reduced pressure. The residue was purified by flash column chromatography on silica gel (ethyl acetate:hexane=1:1) to obtain the title compound (521 mg) as a pale yellow oil.

$^1$H-NMR (CDCl$_3$) δ: 2.21–2.29(2H,m), 2.42–2.63(2H, m), 3.02–3.14(7H,m), 3.72(3H,s), 5.07–4.11(1H,m), 5.13–5.17 (1H,m). MS (FAB) m/z: 317(M+H)$^+$.

Referential Example 124

(1R*,2R*)-1,2-Diazido-4-methoxycarbonylcyclopentane

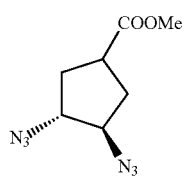

(1R*,2R*)-1,2-Bis (methanesulfonyloxy)-4-methoxycarbonylcyclopentane (27.3 g) was dissolved in N,N-dimethylformamide (200 ml), and sodium azide (33.7 g) was added to stir the mixture at 75° C. for 16 hours. After allowing the reaction mixture to cool, water was added, and the reaction mixture was extracted with ether. The resultant organic layer was washed with a saturated aqueous solution of sodium hydrogen carbonate and saturated saline and then dried over anhydrous sodium sulfate. The solvent was distilled off under reduced pressure, and the residue was purified by column chromatography on silica gel (hexane:ethyl acetate=2:1) to obtain the title compound (11.53 g) as a pale yellow oil.

$^1$H-NMR (CDCl$_3$) δ: 1.92–2.02(2H,m), 2.34–2.43(2H, m), 2.96–3.04(1H,m), 3.72(3H,s), 3.75–3.80(1H,m), 3.85–3.90(1H,m).

Referential Example 125

(1R*,2R*)-N¹-[(5-Chloroindol-2-yl)carbonyl]-4-methoxycarbonyl-1,2-cyclopentanediamine (Mixture of Stereoisomers)

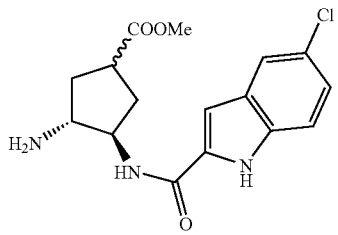

trans-1,2-Diazido-4-methoxycarbonylcyclopentane (10.6 g) was dissolved in tetrahydrofuran (200 ml), and 10% palladium on carbon (3 g) was added to stir the mixture at room temperature for 13 hours in a hydrogen atmosphere. The catalyst was removed by filtration, and the solvent was distilled off under reduced pressure. A solution of p-nitrophenyl 5-chloroindole-2-carboxylate (13.6 g) in N,N-dimethylformamide (100 ml) was added dropwise to the residue under ice cooling. The mixture was stirred for 2 hours at 0° C. and then 11 hours at room temperature. A saturated aqueous solution of sodium hydrogencarbonate was added to the reaction mixture to conduct extraction with dichloromethane. The resultant organic layer was washed with a saturated aqueous solution of sodium hydrogencarbonate and then dried over anhydrous sodium sulfate. The solvent was distilled off under reduced pressure, and the residue was purified by column chromatography on silica gel (dichloromethane:methanol=19:1→9:1) to obtain the title compound (4.22 g) as a pale yellow solid.

$^1$H-NMR (DMSO-d$_6$) δ: 1.51–1.81(2H,m), 2.05–2.34 (2H,m), 2.93–3.04(1H,m), 3.15–3.22(1H,m), 3.62,3.63(3H, each s), 3.87–3.94(1H,m), 7.15–7.19(2H,m), 7.43(1H,d,J= 8.8 Hz), 7.70(1H,d,J=2.0 Hz), 8.37–8.42(1H,m), 11.74(1H, br.s). MS (FAB) m/z: 336(M+H)$^+$.

Referential Example 126

(1R*,2R*)-1,2-Dihydroxy-4-methoxycyclopentane

60% Sodium hydride (800 mg) was added portionwise to a solution with 3-cyclopentene-1-ol (1.68 g) and methyl iodide (1.25 ml) dissolved in tetrahydrofuran (20 ml) under ice cooling, and the mixture was stirred overnight at room temperature. Water and diethyl ether was added to the reaction mixture to separate an organic layer, the organic layer was dried over anhydrous magnesium sulfate, and the solvent was distilled off under reduced pressure cooling with ice to obtain crude 4-methoxy-1-cyclopentene.

88% Formic acid (90 ml) and 30% hydrogen peroxide (3.17 ml) were added to 4-methoxy-1-cyclopentene thus obtained, and the mixture was stirred overnight at room temperature. The reaction mixture was concentrated under reduced pressure, and a 35% aqueous solution of sodium hydroxide was added to the residue to alkalify the reaction mixture, followed by stirring at 50° C. for 10 minutes. The reaction mixture was cooled to room temperature and extracted with ethyl acetate to dry the organic layer over anhydrous magnesium sulfate. The solvent was distilled off, and the residue was purified by column chromatography on silica gel (methanol:dichloromethane=5:95) to obtain the title compound (1.21 g) as a colorless oil.

$^1$H-NMR (CDCl$_3$) δ: 1.65–1.85(2H,m), 2.15–2.30(2H, m), 3.28(3H,s), 3.90–4.00(2H,m), 4.26(1H,br.s).

Referential Example 127

(1R*,2R*)-1,2-Diazido-4-methoxycyclopentane

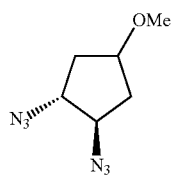

(1R*,2R*)-1,2-Dihydroxy-4-methoxycyclopentane (1.21 g) and triethylamine (7.66 ml) were dissolved in dichloromethane (20 ml), and methanesulfonyl chloride (2.13 ml) was added dropwise over 20 minutes at −78° C. After completion of drop addition, the mixture was warmed to 0° C. and stirred for 80 minutes to obtain crude (1R*,2R*)-1, 2-bis (methanesulfonyloxy)-4-methoxy-cyclopentane. This product was dissolved in N,N-dimethylformamide (20 ml), and sodium azide (3.57 g) was added. The mixture was stirred at 65° C. for 22 hours. Sodium azide (3.57 g) was additionally added to stir the mixture at 70° C. for 2 days. The reaction mixture was allowed to cool, and water and diethyl ether was added to separate an organic layer. The organic layer was dried over anhydrous magnesium sulfate. The solvent was distilled off, and the residue was purified by column chromatography on silica gel (hexane:ethyl acetate= 2:1) to obtain the title compound (584 mg) as a colorless liquid.

$^1$H-NMR (CDCl$_3$) δ: 1.65–1.80(2H,m), 2.05–2.18(1H, m), 2.25–2.40(1H,m), 3.21(3H,s), 3.55–3.65(1H,m), 3.75–3.90(2H,m).

Referential Example 128

(1R*,2R*)-4-Methoxycyclopentane-1,2-diamine hydrochloride

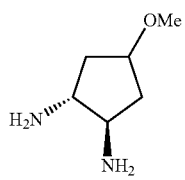

(1R*,2R*)-1,2-Diazido-4-methoxycyclopentane (584 mg) was dissolved in ethanol, and 10% palladium on carbon (321 mg) was added to conduct hydrogenation at normal temperature and normal pressure for 2 days. After removing the catalyst by filtration, the reaction mixture was concentrated, and a 1N ethanol solution of hydrochloric acid and ethyl acetate were added to the residue. The mixture was concentrated to obtain the title compound (488 mg).

$^1$H-NMR (CDCl$_3$) δ: 1.72–1.83(1H,m), 1.91–2.03(1H,m), 2.07–2.18(1H,m), 2.37–2.50(1H,m), 3.19(3H,s), 3.55–3.75(2H,br), 3.85–3.95(1H,m), 8.60–8.90(6H,br). MS (ESI) m/z: 261(2M+H)$^+$.

Referential Example 129 trans-4-Benzyloxy-1,2-dihydroxycyclopentane

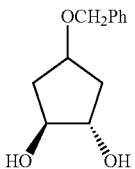

The title compound was obtained by benzylating 3-cyclopentene-1-ol with benzyl bromide and then treating the product with formic acid-hydrogen peroxide in a similar manner to Referential Example 126.

$^1$H-NMR (CDCl$_3$) δ: 1.62(1H,br.s), 1.75–1.95(2H,m), 2.21(1H,d.t,J=14.2 and 5.9 Hz), 2.33(1H,d.d,J=14.7 and 6.9 Hz), 2.57(1H,br.s), 3.96(1H,s), 4.15(1H,s), 4.30(1H,s), 4.48(2H,s), 7.20–7.40(5H,m).

Referential Example 130 trans-4-Benzyloxy-1,2-diazidocyclopentane

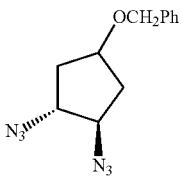

The title compound was obtained from trans-4-benzyloxy-1,2-dihydroxycyclopentane in a similar manner to Referential Example 127.

$^1$H-NMR (CDCl$_3$) δ: 1.75–1.90(2H,m), 2.15–2.30(1H,m), 2.35–2.50(1H,m), 3.67(1H,d.d,J=14.9 and 6.8 Hz), 3.96(1H,d.d,J=15.2 and 6.8 Hz), 4.00–4.10(1H,m), 4.44(1H,d.d,J=11.8 Hz), 4.48(1H,d.d,J=11.8 Hz), 7.20–7.40(5H,m).

Referential Example 131 trans-4-Benzyloxy-1,2-cyclopentanediamine

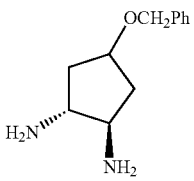

Lithium aluminum hydride (2.0 g) was suspended in tetrahydrofuran (50 ml), and a tetrahydrofuran solution (30 ml) of trans-1,2-diazido-4-benzyloxycyclopentane (6.74 g) was added dropwise over 70 minutes under an argon atmosphere. After 1 hour, the reaction mixture was cooled with ice, and water (2 ml), a 15% aqueous solution (2 ml) of sodium hydroxide and water (3 ml) were slowly added dropwise. After the mixture was stirred at room temperature for 2 hours, insoluble thereof. matter was removed by filtration, and the filtrate was concentrated to obtain the title compound (5.37 g) as a crude pale yellow oil.

$^1$H-NMR (CDCl$_3$) δ: 120–1.80(6H,m), 2.18(1H,d.d,J=13.9 and 7.1 Hz), 2.41(1H,d.t,J=13.5 and 7.1 Hz), 2.71(1H,q,J=7.6 Hz), 3.04(1H,q,J=7.6 Hz), 3.95–4.05(1H,m), 4.45(2H,s), 7.20–7.40(5H,m). MS (ESI) m/z: 207(M+H)$^+$.

Referential Example 132

Mixture of (1R*,2R*,4R*)-4-benzyloxy-N$^1$-[(5-chloroindol-2-yl)carbonyl]-1,2-cyclopentanediamine and (1R*,2R*,4S*)-4-benzyloxy-N$^1$-[(5-chloroindol-2-yl)carbonyl]-1,2-cyclopentanediamine

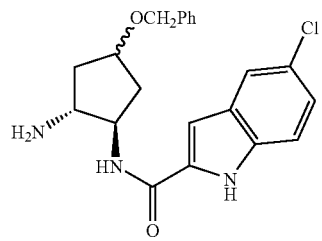

The title compound was obtained from (±)-trans-4-benzyloxy-1,2-cyclopentanediamine and 5-chloroindole-2-carboxylic acid in a similar manner to Referential Example 30

$^1$H-NMR (CDCl$_3$) δ: 1.60–2.20(4H,m), 3.30–3.60(3H,m), 3.95–4.45(2H,m), 4.43,4.45(total 2H,each s), 7.10–7.50(8H,m), 7.68,7.70(total 1H,each s), 8.67,8.69(total 1H,d,J=8.3 Hz), 11.87(1H,br.s). MS (ESI) m/z: 384(M+H)$^+$.

Referential Example 133

(1R*,2R*)-4-Benzyloxymethyl-1,2-cyclopentanediol

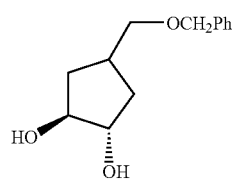

The title compound was obtained by benzylating (1R*,2R*)-4-hydroxymethyl-1-cyclopentene. (J. Heterocycl. Chem., 1989, Vol. 26, p. 451) with benzyl bromide and then reacting the product with formic acid-hydrogen peroxide in a similar manner to Referential Example 126.

$^1$H-NMR (CDCl$_3$) δ: 1.44–1.52(1H,m), 1.77–1.85(1H,m), 1.89–1.97(1H,m), 2.25–2.35(1H,m), 2.46–2.58(1H,m), 3.40–3.50(2H,m), 3.89(1H,br.s), 4.08(1H,br.s), 4.54(2H,s), 7.27–7.39(5H,m). MS (FAB) m/z: 223(M+H)$^+$.

Referential Example 134

(1R*,2R*)-4-Benzyloxymethyl-1,2-cyclopentanediamine

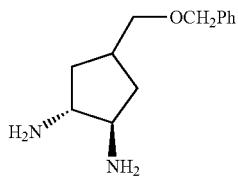

(1R*,2R*)-4-Benzyloxymethyl-1,2-diazidocyclopentane was obtained from (1R*,2R*)-4-benzyloxymethyl-1,2-cyclopentanediol in a similar manner to Referential Example 127. The title compound was obtained in a similar manner to Referential Example 128 without purifying this product.

Referential Example 135

(1R*,2R*)-4-Benzyloxymethyl-$N^1$-[(5-chloroindol-2-yl)carbonyl]-1,2-cyclopentanediamine

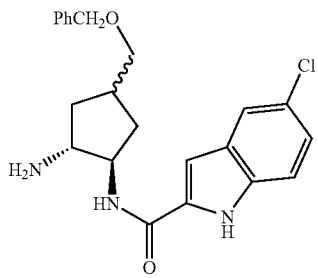

The title compound was obtained from (1R*,2R*)-4-benzyloxymethyl-1,2-cyclopentanediamine in a similar manner to Referential Example 125.

$^1$H-NMR (DMSO-$d_6$) δ: 1.07–1.15(0.5H,m), 1.26–1.35 (0.5H,m), 1.47–1.55(0.5H,m), 1.61–1.79(1H,m), 1.83–1.92 (0.5H,m), 1.99–2.10(0.5H,m), 2.12–2.20(0.5H,m), 2.27–2.40(1H,m), 3.10–3.20(1H,m), 3.33–3.39(2H,m), 3.81–3.92(1H,m), 4.48(2H,s), 7.13–7.20(2H,m), 7.22–7.39 (5H,m), 7.43(1H,d,J=8.5 Hz), 7.69(1H,d,J=2.2 Hz), 8.34 (1H,t,J=7.1 Hz). MS (FAB) m/z: 398(M+H)$^+$.

Referential Example 136

(±)-trans-4,4-Bis(methoxymethyl)-1,2-dihydroxycyclopentane

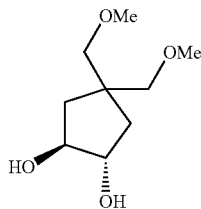

The title compound was obtained from 1,1-bis(hydroxymethyl)-3-cyclopentene (J. Med., Chem., 1991, Vol. 34, p. 3316) in a similar manner to Referential Example 126.

$^1$H-NMR (CDCl$_3$) δ: 1.57(2H,d,J=14.7 Hz), 2.16(2H,dd, J=14.7, 4.9 Hz), 3.23(4H,s), 3.40(6H,s), 3.90–3.98(1H,m) MS (FAB) m/z: 191(M+H)$^+$.

Referential Example 137

(±)-trans-4,4-Bis(methoxymethyl)-1,2-cyclopentanediamine

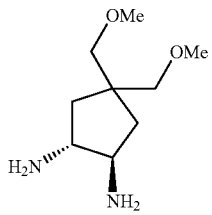

(±)-trans-4,4-Bis(methoxymethyl)-1,2-diazidocyclopentane was obtained from (±)-trans-4,4-bis(methoxymethyl)-1,2-dihydroxycyclopentane in a similar manner to Referential Example 127. The title compound was obtained in a similar manner to Referential Example 128 without purifying this product.

$^1$H-NMR (CDCl$_3$) δ: 1.19–1.25(2H,m), 1.89(2H,dd,J= 13.2, 6.6 Hz), 2.70–2.77(2H,m), 3.20(4H,s), 3.33(6H,s). MS (FAB) m/z: 189(M+H)$^+$.

Referential Example 138

(±)-trans-4,4-Bis(methoxymethyl)-$N^1$-[(5-chloroindol-2-yl)carbonyl]-1,2-cyclopentanediamine

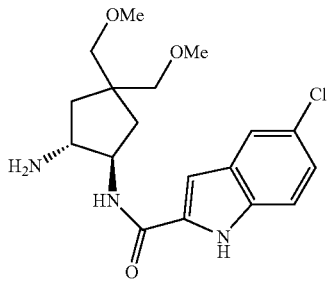

The title compound was obtained from (±)-trans-4,4-bis(methoxymethyl)-1,2-clopentanediamine in a similar manner to Referential Example 125.

$^1$H-NMR (CDCl$_3$) δ: 1.42(1H,dd,J=14.0, 3.5 Hz), 1.58 (1H,dd,J=14.0, 3.5 Hz), 2.05(1H,dd,J=14.0, 6.9 Hz), 3.31 (1H,dd,J=14.0, 6.9 Hz)., 3.25–3.55(11H,m), 4.16–4.23(1H, m), 6.69(1H,s), 7.19(1H,dd,J=8.8, 1.7 Hz), 7.36(1H,d,J=8.8 Hz), 7.58(1H,s), 7.65(1H,d,J=7.6 Hz). MS (FAB) m/z: 366 (M+H)$^+$.

Referential Example 139

(±)-trans-4,4-Bis(benzyloxymethyl)-1,2-cyclopentanediol

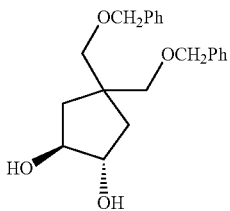

The title compound was obtained by benzylating 1,1-bis(hydroxymethyl)-3-cyclopentene (J. Med., Chem., 1991, Vol. 34, p. 3316) with benzyl bromide and then treating the product with formic acid-hydrogen peroxide in a similar manner to Referential Example 126.

$^1$H-NMR (CDCl$_3$) δ: 1.58–1.65(2H,m), 2.21(2H,dd,J=14.5, 4.9 Hz), 3.27–3.34(4H,m), 3.93(2H,dd,J=7.5, 4.9 Hz), 4.55(4H,s), 7.27–7.39(10H,m). MS (FAB) m/z: 343(M+H)$^+$.

Referential Example 140

(±)-trans-4,4-Bis(benzyloxymethyl)-1,2-cyclopentane-diamine

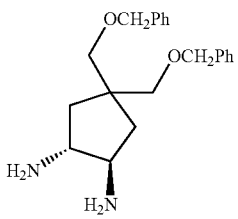

(±)-trans-4,4-Bis(benzyloxymethyl)-1,2-diazidocyclopentane was obtained from (±)-trans-4,4-bis(benzyloxymethyl)-1,2-cyclopentanediol in a similar manner to Referential Example 127. The title compound was obtained in a similar manner to Referential Example 128.

$^1$H-NMR (CDCl$_3$) δ: 1.20–1.28(2H,m), 1.96(2H,dd,J=13.2, 6.6 Hz), 2.69–2.78(2H,m), 3.32(4H,s), 4.50(4H,s), 7.27–7.38(10H,m). MS (FAB) m/z: 341(M+H)$^+$.

Referential Example 141

(±)-trans-4,4-Bis (benzyloxymethyl)-N$^1$-[(5-Chloroindol-2-yl)carbonyl]-1,2-cyclopentanediamine

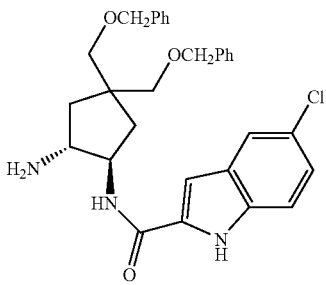

The title compound was obtained from (±)-trans-4,4-bis(benzyloxymethyl)-1,2-cyclopentanediamine and 5-chloroindole-2-carboxylic acid in a similar manner to Referential Example 30.

$^1$H-NMR (DMSO-d$_6$) δ: 1.33–1.41(1H,m), 1.45–1.54(1H,m), 1.86–2.00(2H,m), 3.15–3.23(1H,m), 3.26–3.38(4H,m), 3.98–4.07(1H,m), 4.51(2H,d,J=4.2 Hz), 7.14(1H,s), 7.17(1H,dd,J=8.8, 2.0 Hz), 7.25–7.39(11H,m), 7.43(1H,d,J=8.5 Hz), 7.70(1H,d,J=2.0 Hz), 8.41(1H,d, J=7.5 Hz) MS (FAB) m/z: 518(M+H)$^+$.

Referential Example 142

Lithium 5,6-dimethyl-4,5,6,7-tetrahydrothiazolo[4,5-d]-pyridazine-2-carboxylate

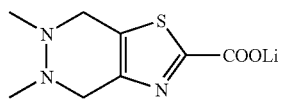

1) After 4,5-bis(bromomethyl)thiazole (600 mg) synthesized in 1) of Referential Example 109 was dissolved in ethanol (20 ml), and 1,2-dimethylhydrazine hydrochloride (294 mg) was added under ice cooling, triethylamine (1.23 ml) was added at a time, and the mixture was stirred for 30 minutes at room temperature and 30 minutes at 50° C. The solvent was distilled off, and the residue was purified by column chromatography on silica gel (methanol:dichloromethane=1:19) to obtain 5,6-dimethyl-4,5,6,7-tetrahydrothiazolo[4,5-d]-pyridazine (90 mg) as a colorless oil.

$^1$H-NMR (CDCl$_3$) δ: 2.43(3H,s), 2.56(3H,s), 3.92(2H,s), 4.06(2H,br.s), 8.68(1H,s). MS (FAB) m/z: 170(M+H)$^+$.

2) The title compound was obtained from 5,6-dimethyl-4,5,6,7-tetrahydrothiazolo[4,5-d]pyridazine in a similar manner to Referential Example 5.

$^1$H-NMR (DMSO-d$_6$) δ: 2.28(3H,s), 2.39(3H,s), 3.66(2H,br.s), 3.88(2H,br.s).

Referential Example 143

Lithium 5-tert-butyl-4,6-dihydro-5H-pyrrolo[3,4-d]-thiazole-2-carboxylate

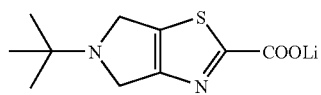

1) 4,5-bis(bromomethyl)thiazole (1.50 g) synthesized in 1) of Referential Example 109 was dissolved in dioxane (30 ml), and a dioxane solution (10 ml) of tert-butylamine (2.03 ml) was added dropwise to the solution over 1 hour at room temperature. After stirring at room temperature for 5 hours, the reaction mixture was concentrated, and dichloromethane and a saturated aqueous solution of sodium hydrogencarbonate were added to the residue to separate an organic layer. The organic layer was dried over anhydrous sodium sulfate. The solvent was distilled off under reduced pressure, and the residue was purified by column chromatography on silica gel (methanol:dichloromethane=1:19) to obtain 5-tert-butyl-4,6-dihydro-5H-pyrrolo[3,4-d]thiazole (407 mg) as a pale yellow oil.

$^1$H-NMR (CDCl$_3$) δ: 1.19(9H,s), 4.05–4.07(2H,m), 4.10–4.14(2H,br.s.), 8.68(1H,s). MS (ESI) m/z: 183(M+H)$^+$.

2) The product (407 mg) formed above was dissolved in diethyl ether (3 ml), and n-butyllithium (1.53N hexane solution, 1.60 ml) was added dropwise at −78° C. in an argon atmosphere to stir the mixture for 30 minutes under ice cooling. The reaction mixture was cooled again to −78° C. After blowing carbon dioxide into the reaction mixture for 20 minutes, it was heated to room temperature. The reaction mixture was concentrated under reduced pressure to obtain the title compound (580 mg) as crude brown powder.

Referential Example 144

1-(tert-Butoxycarbonyl)-4-(methoxycarbonylethynyl)-piperidine

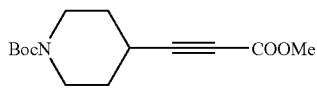

n-Butyllithium (1.57N hexane solution, 3.11 ml) was added dropwise to a solution with 1-(tert-butoxycarbonyl)-4-(2,2-dibromovinyl)piperidine (WO9806720) (900 mg) dissolved in tetrahydrofuran (16 ml) at −78° C., and the mixture was stirred for 1 hour. Methyl chlorocarbonate (377 μl) was added to the reaction mixture to heat the mixture to room temperature in 1 hour. Diethyl ether (30 ml) and a saturated aqueous A solution (50 ml) of ammonium chloride were added to the reaction mixture to separate an organic layer. The organic layer was dried over anhydrous sodium sulfate. The solvent was distilled off under reduced pressure, and the residue was purified by column chromatography on silica gel (hexane:ethyl acetate=4:1) to obtain the title compound (634 mg) as a colorless transparent oil.

$^1$H-NMR (CDCl$_3$) δ: 1.45(9H,s), 1.58–1.70(2H,m), 1.78–1.88(2H,m), 2.68–2.76(1H,m), 3.14–3.23(2H,m), 3.67–3.77(2H,m), 3.77(3H,s). MS (ESI) m/z: 268(M+H)$^+$.

Referential Example 145

1-(tert-Butoxycarbonyl)-4-hydroxy-4-(methoxycarbonyl-ethynyl)piperidine

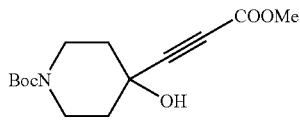

n-Butyllithium (1.57N hexane solution, 6.4 ml) was added dropwise to a solution of methyl propionate (893 μl) in tetrahydrofuran (50 ml) at −78° C. After stirring for 30 minutes, a solution of 1-(tert-butoxycarbonyl)-4-piperidone (2.0 g) in tetrahydrofuran (10 ml) was added, and the mixture was gradually warmed to room temperature and stirred overnight. A saturated aqueous solution (50 ml) of ammonium chloride and ethyl acetate (50 ml) were added to the reaction mixture to separate an organic layer. The organic layer was dried over anhydrous sodium sulfate. The solvent was distilled off under reduced pressure, and the residue was purified by column chromatography on silica gel (hexane:ethyl acetate=3:1) to obtain the title compound (1.78 g) as a pale yellow caramel-like substance.

$^1$H-NMR (CDCl$_3$) δ: 1.46(9H,s), 1.72–1.82 (2H,m), 1.90–2.00(2H,m), 2.39(1H,br.s), 3.30–3.38(2H,m), 3.67–3.77(2H,m), 3.79(3H,s). MS (ESI) m/z: 284(M+H)$^+$.

Referential Example 146

1-(tert-Butoxycarbonyl)-4-(methoxycarbonylethynyl)-1,2,3,6-tetrahydropyridine

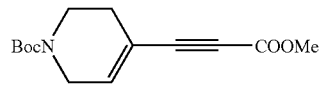

Pyridine (1.12 ml) and trifluoromethanesulfonic anhydride (875 μl) were added dropwise to a solution of 1-(tert-butoxycarbonyl)-4-hydroxy-4-(methoxycarbonyl-ethynyl) piperidine (490 mg) in dichloromethane (15 ml) at −78° C. After heating the mixture to room temperature in 1 hour, a saturated aqueous solution (50 ml) of sodium hydrogencarbonate and dichloromethane (10 ml) were added to the reaction mixture to separate an organic layer. The organic layer was dried over anhydrous sodium sulfate. The solvent was distilled off under reduced pressure, and the residue was purified by column chromatography on silica gel (hexane:ethyl acetate=5:1→2:1) to obtain the title compound (249 mg) as a pale yellow oil.

$^1$H-NMR (CDCl$_3$) δ: 1.48(9H,s), 2.26–2.33(2H,m), 3.51 (2H,t,J=5.6 Hz), 3.79(3H,s), 4.00–4.05(2H,m), 6.36(1H, br.s).

Referential Example 147 cis-N$^1$,N$^2$-Bis(tert-butoxycarbonyl)-1,2-cyclohexanediamine

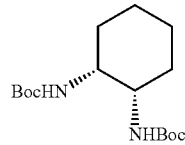

cis-1,2-Cyclohexanediamine (4.79 ml) was dissolved in dichloromethane (200 ml), and di-tert-butyl carbonate (18.3 g) and a 1N aqueous solution (100 ml) of sodium hydroxide were added to stir the mixture at room temperature for 2 hours. An organic layer was separated, washed with saturated saline and then dried over anhydrous sodium sulfate. The solvent was distilled off under reduced pressure to obtain the title compound (17.2 g) as a white solid.

$^1$H-NMR (CDCl$_3$) δ: 1.40–1.71(26H,m), 3.79(2H,br.s), 4.84–4.86(2H,m). MS (ESI) m/z: 315(M+H)$^+$.

Referential Example 148 cis-N$^1$,N$^2$-Bis(tert-butoxycarbonyl)-N$^1$,N$^2$-dimethyl-1,2-cyclohexanediamine

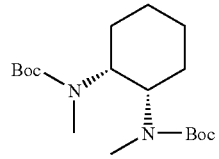

N,N-Dimethylformamide (20 ml) was cooled to 0° C., and 60% sodium hydride (800 mg) was added. cis-N$^1$,N$^2$-Bis(tert-butoxycarbonyl)-1,2-cyclohexanediamine (3.14 g)

was added to the reaction mixture, and the mixture was stirred for 30 minutes at the same temperature and then 4 hours at room temperature. A saturated aqueous solution of sodium hydrogencarbonate was added to the reaction mixture to conduct extraction with hexane. The resultant extract was dried over anhydrous sodium sulfate. The solvent was distilled off under reduced pressure to obtain the title compound (2.16 g) as a pale yellow solid.

$^1$H-NMR (CDCl$_3$) δ: 1.43–1.83(26H,m), 2.89(6H,br.s), 4.35(2H,br.s). MS (ESI) m/z: 343(M+H)$^+$.

Referential Example 149 cis-N$^1$,N$^2$-Dimethyl-1,2-cyclohexanediamine hydrochloride

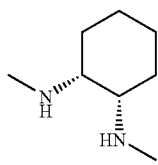

cis-N$^1$,N$^2$-Bis(tert-butoxycarbonyl)-N$^1$,N$^2$-dimethyl-1,2-cyclohexanediamine (2.15 g) was dissolved in a saturated ethanol solution of hydrochloric acid, and the solution was stirred at room temperature for 30 minutes. The solvent was distilled off under reduced pressure, ethyl acetate was added to the residue, and solids were collected by filtration to obtain the title compound (1.19 g) as a pale yellow solid.

$^1$H-NMR (DMSO-d$_6$) δ: 1.40–1.41(2H,m), 1.71–1.92 (6H,m), 2.65(6H,s), 3.61(2H,br.s) MS (ESI) m/z: 143(M+H)$^+$.

Referential Example 150 cis-N$^1$-[(1-Benzenesulfonyl-5-chloroindol-2-yl)carbonyl]-N$^1$,N$^2$-dimethyl-1,2-cyclohexanediamine

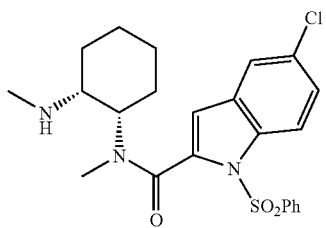

1-Benzenesulfonyl-5-chloroindole-2-carboxylic acid (890 mg) was dissolved in chloroform (20 ml), and thionyl chloride (2 ml) and N,N-dimethylformamide (one drop) were added to stir the mixture at 65° C. for 45 minutes. The solvent was distilled off under reduced pressure, and dichloromethane (10 ml) and pyridine (10 ml) were added to the residue. A solution (10 ml) of cis-N$^1$,N$^2$-dimethyl-1,2-cyclohexanediamine hydrochloride (855 mg) in a 1:1 mixed solution (10 ml) of dichloromethane and pyridine was added to the reaction mixture, and the mixture was stirred at room temperature for 3 days. The reaction mixture was heated and stirred at 55° C. for additional 4 hours, and water was added to separate an organic layer. The organic layer was washed with water and dried over anhydrous sodium sulfate. The solvent was distilled off under reduced pressure, and the residue was purified by flash column chromatography on silica gel (hexane:ethyl acetate=2:1) to obtain the title compound (738 mg) as an ocher solid.

MS (ESI) m/z: 460(M+H)$^+$.

Referential Example 151

(1R,2S)-N$^1$-tert-Butoxycarbonyl-1,2-cyclohexanediamine

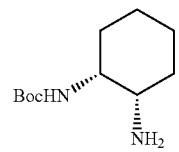

The title compound was synthesized from (1R,2S)-2-amino-1-cyclohexanol (J. Org. Chem., 1985, Vol. 50, p. 4154) in a similar manner to Referential Examples 44 to 47.

$^1$H-NMR (CDCl$_3$) δ: 1.00–1.70(8H,m), 1.45(9H, s), 2.95–3.05(1H,m), 3.60(1H,br.s), 5.00(1H,br.s). MS (FAB) m/z: 215(M+H)$^+$.

Referential Example 152

(1S,2R)-N$^1$-[(5-Chloroindol-2-yl)carbonyl]-1,2-cyclohexanediamine hydrochloride

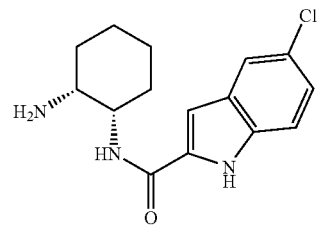

(1R,2S)-N$^1$-(tert-Butoxycarbonyl)-N$^2$-[(5-chloroindol-2-yl)carbonyl]-1,2-cyclohexanediamine was obtained from (1R,2S)-N$^1$-(tert-butoxycarbonyl)-1,2-cyclohexanediamine in a similar manner to Referential Example 52, and deprotection was then conducted with a saturated ethanol solution of hydrochloric acid in a similar manner to Referential Example 54 to obtain the title compound.

$^1$H-NMR (DMSO-d$_6$) δ: 1.30–1.50(2H,m), 1.55–1.95 (6H,m), 3.02(1H,br.s), 3.90–3.97(1H,br.s), 7.15–7.19(2H, m), 7.43(1H,d,J=8.8 Hz), 7.68(1H,d,J=2.0 Hz), 7.90(1H,d, J=8.1 Hz)

Referential Example 153

(±)-cis-N$^1$-[(5-Chloroindol-2-yl)carbonyl]-4-cyclohexene-1,2-diamine

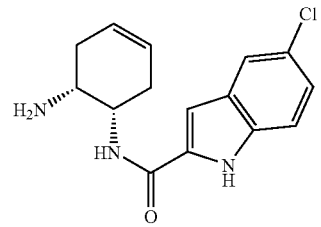

The title compound was obtained from cis-4-cyclohexene-1,2-diamine hydrochloride (EP 154788) and 5-chloroindole-2-carboxylic acid in a similar manner to Referential Example 30.

¹H-NMR (DMSO-d₆) δ: 1.93(m,1H), 2.05(m,1H), 2.36 (m,2H), 2.91(dt,1H,J=5.6, 10.3 Hz), 3.82(m,1H), 5.60(s, 2H), 7.17(m,2H), 7.43(d,1H,J=8.8 Hz), 7.69(d,1H,J=1.7 Hz), 8.32(d,1H,J=8.6 Hz).

Referential Example 154

Ethyl (1R*,3R*,4S*)-3,4-epoxycyclohexane-1-carboxylate

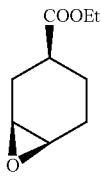

(1R*,4R*,5R*)-4-Iodo-6-oxabicyclo [3.2.1]octan-7-one (J. Org. Chem., 1996, Vol. 61, p. 8687) (14.3 g) was dissolved in ethanol (130 ml), a 2N aqueous solution (34.5 ml) of sodium hydroxide was added under ice cooling, and the mixture was then stirred at room temperature for 7 hours. After the solvent was distilled off under reduced pressure, and water was added to the residue to conduct extraction with dichloromethane, the extract was dried over anhydrous sodium sulfate. The solvent was distilled off under reduced pressure, and the residue was purified by column chromatography on silica gel (hexane:ethyl acetate=83:17) to obtain the title compound (6.54 g) as a colorless oil.

¹H-NMR (CDCl₃) δ: 1.25 (3H,t, J=7.1 Hz), 1.50–1.70 (2H,m), 1.71–1.82(1H,m), 2.08–2.28(4H,m), 3.16(2H,s), 4.12 (2H,q, J=7.1 Hz)

Referential Example 155

Ethyl (1R*,3S*,4S*)-3-azido-4-hydroxycyclohexane-1-carboxylate

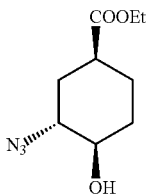

Ethyl (1R*,3R*,4S*)-3,4-epoxycyclohexane-1-carboxylate (13.6 g) was dissolved in N,N-dimethylformamide (100 ml), ammonium chloride (6.45 g) and sodium azide (7.8 g) were successively added at room temperature, and the mixture was then stirred at 75° C. for 12 hours. The solvent was concentrated to about 1/3, and the residue was diluted with water and ethyl acetate to conduct stirring for 3 minutes. The resultant organic layer was washed with water and saturated saline and dried over anhydrous magnesium sulfate. The solvent was distilled off under reduced pressure, and the residue was purified by column chromatography on silica gel (ethyl acetate:hexane= 1:4) to obtain the title compound (15.8 g) as a colorless oil.

¹H-NMR (CDCl₃) δ: 1.28(3H,t,J=7.1 Hz), 1.37–1.67(2H, m), 1.86–1.95(1H,m), 2.04–2.18(2H,m), 2.32–2.43(1H,m), 2.68–2.78(1H,m), 3.40–3.60(2H,m), 4.17(2H,q,J=7.1 Hz).

Referential Example 156

Ethyl (1R*,3S*,4S*)-3-(tert-butoxycarbonylamino)-4-hydroxycyclohexane-1-carboxylate

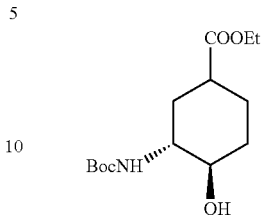

Ethyl (1R*,3S*,4S*)-3-azido-4-hydroxycyclohexane-1-carboxylate (100 mg) and di-tert-butyl dicarbonate (133 mg) were dissolved in ethyl acetate (12 ml) and a catalytic amount of 10% palladium on carbon was added to stir the mixture at room temperature for 12 hours in a hydrogen atmosphere. After insoluble matter was removed by filtration, the solvent was distilled off under reduced pressure, and the residue was purified by column chromatography on silica gel (hexane:ethyl acetate=3:1) to obtain the title compound (145 mg) as a colorless solid.

¹H-NMR (CDCl₃) δ: 1.28 (3H,t, J=7.1 Hz), 1.45(9H,s), 1.38–1.57(2H,m), 1.86–1.95(1H,m), 2.05–2.17(1H,m), 2.29–2.39(2H,m), 2.61–2.68(1H,m), 3.25–3.66(3H,m), 4.17 (2H,q,J=7.1 Hz), 4.53(1H,br.s).

Referential Example 157

Ethyl (1R*,3S*,4R*)-4-azido-3-(tert-butoxycarbonylamino)-cyclohexane-1-carboxylate and ethyl (1R*,3S*,4S*)-4-azido-3-(tert-butoxycarbonylamino)cyclohexane-1-carboxylate

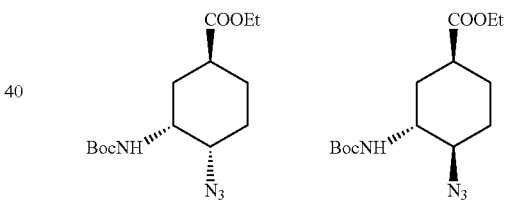

After ethyl (1R*,3S*,4S*)-3-tert-butoxycarbonylamino-4-hydroxycyclohexane-1-carboxylate (16 g) and triethylamine (38 ml) were dissolved in dichloromethane (150 ml), and the solution was cooled to −78° C., methanesulfonyl chloride (13 ml) was added dropwise at the same temperature. After stirring for 15 minutes at the same temperature, the mixture was heated to 0° C. and stirred for 30 minutes and then 2 hours at room temperature. After 0.1N hydrochloric acid was added, and the mixture was diluted with dichloromethane, the resultant organic layer was separated, washed with a saturated aqueous solution of sodium hydrogencarbonate and saturated saline and dried over anhydrous magnesium sulfate. The solvent was distilled off under reduced pressure to obtain crude ethyl (1R*,3S*,4S*)-3-tert-butoxycarbonylamino-4-methanesulfonyloxycyclohexane-1-carboxylate.

The product obtained above was dissolved in N,N-dimethylformamide (100 ml), and sodium azide (18 g) was added at room temperature. The mixture was heated to 75° C. and stirred for 12 hours. The solvent was concentrated to about ⅓, and the residue was diluted with water and ethyl acetate to conduct stirring for 3 minutes. The resultant organic layer was separated, washed with saturated saline and dried over anhydrous magnesium sulfate. The solvent was distilled off under reduced pressure, and the residue was purified by column chromatography on silica gel (ethyl acetate:hexane=1:4) to obtain the title compounds [(1R*,3S*,4R*)-form (6.74 g) and (1R*,3S*,4S*)-form (1.32 g)] as colorless solids.

(1R*, 3S*, 4R*)-form:
$^1$H-NMR (CDCl$_3$) δ: 1.26(3H,t,J=7.1 Hz), 1.45(9H,s), 1.38–2.33(6H,m), 2.57–2.68(1H,m), 3.77–4.20(4H,m), 4.63 (1H,br.s).

(1R*,3S*,4S*)-form:
$^1$H-NMR (CDCl$_3$) δ: 1.27(3H,t,J=7.1 Hz), 1.46(9H,s), 1.53–2.30(6H,m), 2.50–2.65(1H,m), 3.42–3.72(2H,m), 4.15 (2H,q,J=7.1 Hz), 4.67(1H,br.s).

Referential Example 158

(1R*,2S*,4R*)-N$^2$-tert-Butoxycarbonyl-4-ethoxycarbonyl-1,2-cyclohexanediamine

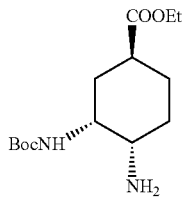

Ethyl (1R*,3S*,4R*)-4-azido-3-(tert-butoxycarbonylamino)cyclohexane-1-carboxylate (5.4 g) was dissolved in a mixed solvent of ethanol (10 ml) and ethyl acetate (10 ml), and a catalytic amount of 10% palladium on carbon was added to stir the mixture at room temperature for 20 hours in a hydrogen atmosphere. After insoluble matter was removed by filtration, the solvent was distilled off under reduced pressure to obtain the title compound (4.7 g) as a pale yellow oil.

Referential Example 159

(1R*,2S*,4R*)-N$^2$-tert-Butoxycarbonyl-N$^1$-[(5-chloroindol-2-yl)carbonyl]-4-ethoxycarbonyl-1,2-cyclohexanediamine

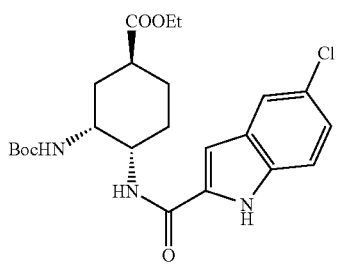

(1R*,2S*,4R*)-N$^2$-tert-Butoxycarbonyl-4-ethoxycarbonyl-1,2-cyclohexanediamine (4.62 g) was dissolved in dichloromethane (50 ml), 5-chloroindole-2-carboxylic acid (3.63 g), 1-hydroxybenzotriazole monohydrate (2.43 g) and 1-(3-dimethylaminopropyl)-3-ethylcarbodiimide hydrochloride (3.45 g) were added at room temperature, and the mixture was stirred for 12 hours. After 0.1N hydrochloric acid was added, and the mixture was extracted with dichloromethane, the resultant organic layer was washed with a saturated aqueous solution of sodium hydrogencarbonate and saturated saline and dried over anhydrous magnesium sulfate. The solvent was distilled off under reduced pressure, and the residue was purified by column chromatography on silica gel (ethyl acetate:hexane=2:3) to obtain the title compound (5.3 g) as a colorless solid.

$^1$H-NMR (CDCl$_3$) δ: 1.26(3H,t, J=7.1 Hz), 1.43 (9H,s), 1.35–2.46(7H,m), 3.91–4.02(1H,m), 4.10–4.22(2H,m), 4.79 (1H,br.s), 6.79(1H,s), 7.18–7.40(2H,m), 7.59(1H,s), 8.00 (1H,br.s), 9.13(1H,br.s).

Referential Example 160

(1R*,2R*,4S*)-N$^2$-tert-Butoxycarbonyl-N$^1$-[(5-chloroindol-2-yl)carbonyl]-4-ethoxycarbonyl-1,2-cyclohexanediamine

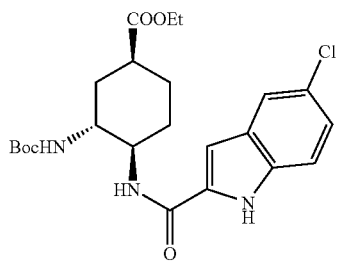

1) (1R*,2R*,4S*)-N$^2$-tert-Butoxycarbonyl-4-ethoxycarbonyl-1,2-cyclohexanediamine was obtained from ethyl (1R*,3S*,4S*)-4-azido-3-(tert-butoxycarbonylamino)-cyclohexane-1-carboxylate obtained in Referential Example 157 in a similar manner to Referential Example 158.

2) The title compound was obtained from the product described above in a similar manner to Referential Example 159.

$^1$H-NMR (CDCl$_3$) δ: 1.22–1.72(6H,m), 1.34(9H,3), 2.15–2.28(2H,m), 2.41–2.49(1H,m), 2.85(1H,brs), 3.62–3.75(1H,m), 3.78–3.92(1H,m), 4.12–4.28(2H,m), 4.56–4.63(1H,m), 6.88(1H,brs), 7.20(1H,dd,J=8.8 and 2.0 Hz), 7.33(1H,d,J=8.8 Hz), 7.52–7.57(1H,m), 7.59(1H,d,J= 2.0 Hz), 9.24(1H,s). MS (ESI) m/z: 464(M+H)$^+$.

Referential Example 161

Ethyl (1S,3S,4R)-3,4-epoxycyclohexane-1-carboxylate (1S,4S,5S)-4-Iodo-6-oxabicyclo[3.2.1]octan-7-on (J. Org. Chem., 1996, Vol. 61, p. 8687) (89.3 g) was dissolved in ethanol (810 ml), a 2N aqueous solution (213 ml) of sodium hydroxide was added, and the mixture was then stirred at room temperature for 3 hours. After the solvent was distilled off under reduced pressure, and water was added to the residue to conduct extraction with dichloromethane, the extract was dried over anhydrous magnesium sulfate. The solvent was distilled off under reduced pressure, and the residue was purified by column chromatography on silica gel (hexane:ethyl acetate=17:3) to obtain the title compound (41.2 g) as a pale yellow oil.

[α]$_D$–58° (C=1.0, chloroform).

Referential Example 162

Ethyl (1S,3R,4R)-3-azido-4-hydroxycyclohexane-1-carboxylate

Ethyl (1S,3S,4R)-3,4-epoxycyclohexane-1-carboxylate (41 g) was dissolved in N,N-dimethylformamide (300 ml), ammonium chloride (19.3 g) and sodium azide (23.5 g) were successively added at room temperature, and the mixture was then stirred at 75° C. for 13 hours. The reaction mixture was filtered, the filtrate was concentrated to distill off 400 ml of the solvent, the product captured by the filter was put in the residue, and water was added to dissolve the collected product. The solution was extracted with ethyl acetate. The resultant organic layer was washed with water and saturated saline and dried over anhydrous magnesium sulfate. The solvent was distilled off under reduced pressure to obtain the title compound (51.5 g) as an oil.

$[\alpha]_D$+8° (C=1.0, chloroform).

Referential Example 163

Ethyl (1S,3R,4R)-3-(tert-butoxycarbonylamino)-4-hydroxycyclohexane-1-carboxylate Ethyl (1S,3R,4R)-3-azido-4-hydroxycyclohexane-1-carboxylate (51.2 g) and di-tert-butyl dicarbonate (68.1 g) were dissolved in ethyl acetate (1000 ml), and 5% palladium on carbon was added to stir the mixture for 16 hours at room temperature under a hydrogen pressure of 5 kg/cm². After insoluble matter was removed by filtration, the solvent was distilled off under reduced pressure, the residue was purified by column chromatography on silica gel (hexane:ethyl acetate=4:1), and hexane was added to solidify it to obtain the title compound (53.6 g) as colorless crystals.

$[\alpha]_D$+25 (C=1.0, chloroform).

Referential Example 164

Ethyl (1S,3R,4S)-4-azido-3-(tert-butoxycarbonylamino)-cyclohexane-1-carboxylate and ethyl (1S,3R,4R)-4-azido-3-(tert-butoxycarbonylamino)cyclohexane-1-carboxylate Ethyl (1S,3R,4R)-3-(tert-butoxycarbonylamino)-4-hydroxycyclohexane-1-carboxylate (53.5 g) and triethylamine (130 ml) were dissolved in dichloromethane (500 ml), and methanesulfonyl chloride (42 ml) was added dropwise while cooling the solution to −10° C. to −15° C. After stirring for 20 minutes at the same temperature, the mixture was heated to room temperature over 30 minutes and further stirred for 2 hours. The reaction mixture was cooled to 0° C., 0.5N hydrochloric acid (800 ml) was added dropwise, and the mixture was extracted with dichloromethane. The resultant organic layer was washed with a saturated aqueous solution of sodium hydrogencarbonate and saturated saline and dried over anhydrous magnesium sulfate. The solvent was distilled off under reduced pressure to obtain crude ethyl (1S,3R,4R)-3-(tert-butoxycarbonylamino)-4-(methanesulfonyloxy)cyclohexane-1-carboxylate.

The crude ethyl (1S,3R,4R)-3-(tert-butoxycarbonylamino)-4-(methanesulfonyloxy)cyclohexane-1-carboxylate obtained above was dissolved in N,N-dimethylformamide (335 ml), and sodium azide (60.5 g) was added to stir the mixture at 68 to 73° C. for 16 hours. The reaction mixture was filtered, the filtrate was concentrated to distill off 250 ml of the solvent, the product captured by the filter was put in the residue, and the collected product was dissolved in water and extracted with ethyl acetate. The resultant organic layer was washed with saturated saline and dried over anhydrous magnesium sulfate. The solvent was distilled off under reduced pressure, and the residue was purified by column chromatography on silica gel (ethyl acetate:hexane=1:4) to obtain the title compounds [(1S,3R,4S)-form (18.4 g) and (1S,3R,4R)-form (3.3 g)] as colorless solids.

(1S,3R,4S)-form: $[\alpha]_D$+62° (C=1.0, chloroform) (1S,3R,4R)-form: $[\alpha]_D$−19° (C=1.0, chloroform)

Referential Example 165

(1S,2R,4S)-N²-tert-Butoxycarbonyl-4-ethoxycarbonyl-1,2-cyclohexanediamine

Ethyl (1S,3R,4S)-4-azido-3-(tert-butoxycarbonylamino)cyclohexane-1-carboxylate (4.0 g) was dissolved in a mixed solvent of ethanol (150 ml) and ethyl acetate (150 ml), and 5% palladium on carbon (0.5 g) was added to stir the mixture at room temperature for 17 hours in a hydrogen atmosphere. After insoluble matter was removed by filtration, the solvent was distilled off under reduced pressure to obtain the title compound (4.2 g) as a pale yellow oil.

Referential Example 166

(1S,2R,4S)-N²-tert-Butoxycarbonyl-N¹-[(5-chloroindol-2-yl)carbonyl]-4-ethoxycarbonyl-1,2-cyclohexanediamine (1S,3R,4S)-N²-tert-Butoxycarbonyl-4-ethoxycarbonyl-1,2-cyclohexanediamine (4.2 g) was dissolved in dichloromethane (50 ml), 5-chloroindole-2-carboxylic acid (3.33 g), 1-hydroxybenzotriazole monohydrate (2.52 g) and 1-(3-dimethylaminopropyl)-3-ethylcarbodiimide hydrochloride (3.15 g) were added at room temperature, and the mixture was stirred for 12 hours. After 0.1N hydrochloric acid was added to the reaction mixture, and the mixture was extracted with dichloromethane, the resultant organic layer was washed with a saturated aqueous solution of sodium hydrogencarbonate and saturated saline and dried over anhydrous magnesium sulfate. The solvent was distilled off under reduced pressure, and the residue was purified by column chromatography on silica gel (ethyl acetate:hexane=1:1) to obtain the title compound (4.36 g) as a colorless solid.

$[\alpha]_D$−27° (C=1.0, chloroform)

Referential Example 167

(1S,2R,4S)-N²-tert-Butoxycarbonyl-4-ethoxycarbonyl-N¹-[(5-fluoroindol-2-yl)carbonyl]-1,2-cyclohexanediamine

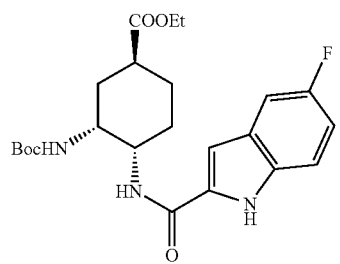

Ethyl (1S,3R,4R)-4-azido-3-(N-tert-butoxycarbonylamino)cyclohexane-1-carboxylate (500 mg) was dissolved in methanol (10 ml), and 10% palladium on carbon (50 mg) was added to stir the mixture in a hydrogen atmosphere. After 3 hours, the reaction was stopped to remove the catalyst by filtration, and the reaction mixture was concentrated under reduced pressure. The residue was dissolved in dichloromethane (10 ml) and N,N-dimethylformamide (10 ml), and 5-fluoroindole-2-carboxylic acid (345 mg), 1-ethyl-3-(3-dimethylaminopropyl)carbodiimide hydrochloride (460 mg), 1-hydroxybenzotriazole monohydrate (325 mg) and N-methylmorpholine (485 mg) were added to stir the mixture at room temperature for 15 hours. After the solvent was distilled off under reduced pressure, dichloromethane was added, and the resultant organic layer was washed with a saturated aqueous solution of sodium hydrogencarbonate and dried over anhydrous magnesium sulfate. The solvent was distilled off under reduced pressure, and the residue was purified by column chromatography on silica gel (methanol:dichloromethane=1:50) to obtain the title compound (740 mg) as a pale yellow amorphous substance.

$^1$H-NMR (CDCl$_3$) δ: 1.26(3H,t,J=7.1 Hz), 1.52(9H,s), 1.67–2.41(7H,m), 3.97(1H,br.s), 4.15(2H,q,J=7.1 Hz), 4.08–4.22(1H,m), 6.83(1H,s), 7.00–7.05(1H,m), 7.32–7.36 (1H,m), 8.02(1H,s), 9.51(1H,s). MS (FAB) m/z: 448(M+H)$^+$.

Referential Example 168

(1R*,2S*,4R*)-N$^2$-(tert-Butoxycarbonyl)-4-ethoxycarbonyl-N$^1$-[(5-methyl-4,5,6,7-tetrahydrothiazolo[5,4-c]pyridin-2-yl)carbonyl]-1,2-cyclohexanediamine

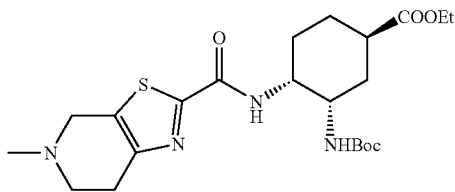

The title compound was obtained from (1R*,2S*,4R*)-N$^2$-tert-butoxycarbonyl-4-ethoxycarbonyl-1,2-cyclohexanediamine and lithium 5-methyl-4,5,6,7-tetrahydrothiazolo[5,4-c]pyridine-2-carboxylate in a similar manner to Referential Example 48.

Referential Example 169

Benzyl (±)-3-cyclohexene-1-carboxylate

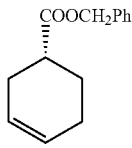

(±)-3-Cyclohexene-1-carboxylic acid (50 g) was dissolved in N,N-dimethylformamide (550 ml), and triethylamine (170 ml) and benzyl bromide (61 ml) were added under ice cooling to stir the mixture at room temperature for 12 hours. Water was added, extraction was conducted with ethyl acetate, and the resultant organic layer was washed with saturated saline and then dried over anhydrous magnesium sulfate. The solvent was distilled off under reduced pressure, and the residue was purified by column chromatography on silica gel (hexane:ethyl acetate=3:1) to obtain the title compound (70.8 g) as a reddish brown oil.

$^1$H-NMR (CDCl$_3$) δ: 1.66–1.76(1H,m), 2.00–2.13(3H, m), 2.27–2.29(2H,m), 2.58–2.65(1H,m), 5.13(2H,s), 5.66 (2H,br.s), 7.29–7.38(5H,m).

Referential Example 170

Benzyl (1R*,3S*,4R*)-3,4-epoxycyclohexane-1-carboxylate

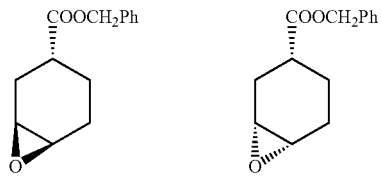

Benzyl (±)-3-cyclohexene-1-carboxylate (40 g) was dissolved in dichloromethane (500 ml), and m-chloroperbenzoic acid (86 g) was added under ice cooling to stir the mixture for 2 hours. After a 10% aqueous solution of sodium thiosulfate was added to conduct stirring for 20 minutes, an organic layer was separated, washed with a saturated aqueous solution of sodium hydrogencarbonate and saturated saline and then dried over anhydrous magnesium sulfate. The solvent was distilled off under reduced pressure, and the residue was purified by column chromatography on silica gel (ethyl acetate:hexane=1:9) to obtain the title compound (23.4 g) and benzyl (1R*,3R*,4S*)-3,4-epoxycyclohexane-1-carboxylate (12.1 g) as colorless oils.

$^1$H-NMR (CDCl$_3$) δ: 1.39–1.49(1H,m), 1.75–1.82(1H, m), 1.90–2.04(3H,m), 2.30(1H,dd,J=14.9, 4.9 Hz), 2.54–2.61(1H,m), 3.12–3.14(1H,m), 3.22–3.24(1H,m), 5.12 (2H,s), 7.30–7.39(5H,m). MS (FAB) m/z: 233(M+H)$^+$.

Referential Example 171

Benzyl (1R*,3S*,4S*)-4-azido-3-hydroxycyclohexane-1-carboxylate

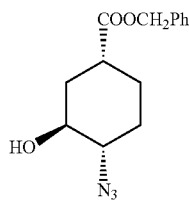

Benzyl (1R*,3S*, 4R*)-3,4-epoxycyclohexane-1-carboxylate (52.3 g) was dissolved in N,N-dimethylformamide (1000 ml), ammonium chloride (21.9 g) and sodium azide (18.1 g) were added, and the mixture was heated to 70° C. and stirred for 24 hours. The solvent was distilled off under reduced pressure, and water was added to conduct extraction with ethyl acetate. The resultant organic layer was washed with saturated saline and dried over anhydrous magnesium sulfate. The solvent was distilled off under reduced pressure to obtain the title compound (61.8 g) as a colorless oil.

$^1$H-NMR (CDCl$_3$) δ: 1.51–1.66(2H,m), 1.91–1.98(1H, m), 2.07–2.10(1H,m), 2.27–2.32(1H,m), 2.51–2.52(1H,m), 2.81–2.86(1H,m), 3.30–3.36(1H,m), 3.70–3.75(1H,m), 5.13 (2H,s), 7.30–7.39(5H,m).

Referential Example 172

Benzyl (1R*,3S*,4S*)-4-(N-tert-butoxycarbonyl)amino-3-hydoxycyclohexane-1-carboxylate

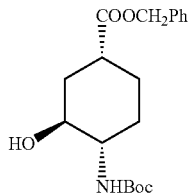

Benzyl (1R*,3S*,4S*)-4-azido-3-hydroxycyclohexane-1-carboxylate (5.27 g) was dissolved in tetrahydrofuran (25 ml), and triphenylphosphine (5.53 g) and water (0.55 ml) were added to stir the mixture at room temperature for 20 hours. Di-tert-butyl dicarbonate (4.82 g) was added to the reaction mixture to continue stirring for additional 2 hours. The solvent was distilled off under reduced pressure, and the residue was purified by column chromatography on silica gel (hexane:ethyl acetate=2:1) to obtain the title compound (6.22 g) as a colorless oil.

$^1$H-NMR (CDCl$_3$) δ: 1.44(9H,s), 1.59–1.66(2H,m), 1.88–2.00(2H,m), 2.29–2.32(1H,m), 2.80–2.85(1H,m), 3.02 (1H,br.s), 3.42(1H,br.s), 3.59–3.65(1H,m), 4.56(1H,br.s), 5.12(2H,q,J=12.5 Hz), 7.30–7.38(5H,m). MS (FAB) m/z: 350(M+H)$^+$.

Referential Example 173

Methyl (1R*,3S*,4S*)-4-N-(tert-butoxycarbonylamino)-3-hydroxycyclohexane-1-carboxylate

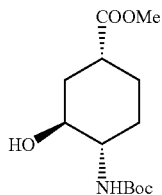

Benzyl (1R*,3S*,4S*)-4-N-(tert-butoxy-carbonylamino)-3-hydroxycyclohexane-1-carboxylate (2.54 g) was dissolved in ethyl acetate (15 ml), and a catalytic amount of 10% palladium on charcoal was added to the solution. The mixture was stirred in a hydrogen stream at room temperature for 20 hours. After the catalyst was filtered off, the filtrate was concentrated under reduced pressure to give (1R*,3S*,4S*)-4-N-(tert-butoxycarbonylamino)-3-hydroxycyclohexane-1-carboxylic acid as a colorless oil. The oil was dissolved in a mixture of methanol (8 ml) and toluene (15 ml), to which 2N trimethylsilyldiazomethane solution (10 ml) was added, and the resulting mixture was stirred for 30 minutes at room temperature. After removal of the solvent under reduced pressure, the resulting residue was purified by column chromatography on silica gel (hexane:ethyl acetate=1:1) to obtain the title compound (1.82 g) as an colorless oil.

$^1$H-NMR (CDCl$_3$) δ: 1.44 (9H,s), 1.36–2.32(7H,m), 2.74–2.82 (1H,m), 3.04 (1H,br.s), 3.33–3.47(1H,m), 3.55–3.65(1H,m), 3.68(3H,s), 4.56(1H,br.s). MS (FAB) m/z: 274 (M+H)$^+$.

Referential Example 174

Methyl (1R*,3R*,4S*)-3-azido-4-N-(tert-butoxycarbonylamino)cyclohexane-1-carboxylate and methyl (1R*,3R*,4R*)-3-azido-4-N-(tert-butoxycarbonyl-amino)cyclohexane-1-carboxylate

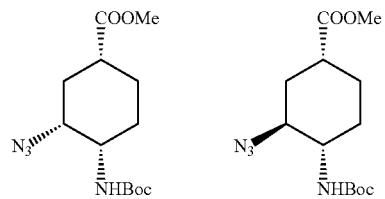

Methyl (1R*,3S*,4S*)-4-(N-tert-butoxycarbonyl-amino)-3-hydroxycyclohexane-1-carboxylate (1.81 g) was dissolved in dichloromethane (36 ml), and triethylamine (4.6 ml) and methanesulfonyl chloride (1.63 ml) were added at −78° C. After 30 minutes, the mixture was heated to 0° C. and stirred for 30 minutes. 1N Hydrochloric acid was added, extraction was conducted with dichloromethane, and the resultant organic layer was washed with saturated saline and dried over anhydrous magnesium sulfate. The solvent was distilled off under reduced pressure to obtain crude methyl (1R*,3S*,4S*)-4-N-tert-butoxycarbonylamino-3-methanesulfonyloxycyclohexane-1-carboxylate.

The crude methyl (1R*,3S*,4S*)-4-N-tert-butoxycarbonylamino-3-methanesulfonyloxycyclohexane-1-carboxylate was dissolved in N,N-dimethylformamide (23 ml), sodium azide (1.29 g) was added, and the mixture was heated to 70° C. and stirred for 12 hours. Water was added to the reaction mixture, extraction was conducted with ethyl acetate, and the resultant organic layer was washed with saturated saline and dried over anhydrous magnesium sulfate. The solvent was distilled off under reduced pressure, and the residue was purified by flash column chromatography on silica gel (ethyl acetate:hexane=3:17) to obtain methyl (1R*,3R*,4R*)-3-azido-4-(N-tert-butoxycarbonylamino)cyclohexane-1-carboxylate (85 mg) and methyl (1R*,3R*,4S*)-3-azido-4-(N-tert-butoxycarbonylamino)cyclohexane-1-carboxylate (590 mg) as colorless oils.

(1R*,3R*,4S*)-form: $^1$H-NMR (CDCl$_3$) δ: 1.45(9H,s), 1.35–2.35(7H,m), 2.45–2.55(1H,m), 3.73(3H,s), 3.67–3.84 (2H,m), 4.70(1H,br.s). MS (FAB) m/z: 299(M+H)$^+$.

(1R*,3R*,4R*)-form: $^1$H-NMR (CDCl$_3$) δ: 1.45(9H,s), 1.56–2.25(7H,m), 2.68–2.80(1H,m), 3.70(3H,s), 3.48–3.68 (2H,m), 4.56(1H,br.s). MS (FAB) m/z: 299(M+H)$^+$.

Referential Example 175

(1R*,2S*,4S*)-N$^1$-tert-butoxycarbonyl-4-methoxycarbonyl-1,2-cyclohexanediamine

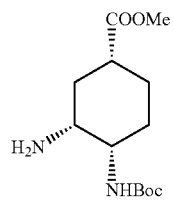

Methyl (1R*,3R*,4S*)-3-azido-4-(N-tert-butoxycarbonylamino)cyclohexane-1-carboxylate (230 mg)

was dissolved in ethyl acetate (8 ml), and a catalytic amount of 10% palladium on carbon was added to stir the mixture at room temperature for 20 hours in a hydrogen atmosphere. Insoluble matter was removed by filtration, and the filtrate was concentrated under reduced pressure to obtain the title compound (220 mg) as a pale yellow oil.

Referential Example 176

(1R*,2S*,4S*)-N$^1$-tert-Butoxycarbonyl-4-methoxycarbonyl-N$^2$-[(5-methyl-4,5,6,7-tetrahydrothiazolo[5,4-c]pyridin-2-yl)carbonyl]-1,2-cyclohexanediamine

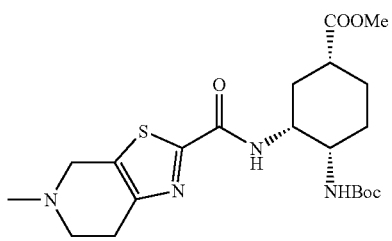

The title compound was obtained from (1R*,2S*,4S*)-N$^1$-tert-butoxycarbonyl-4-methoxycarbonyl-1,2-cyclohexanediamine and lithium 5-methyl-4,5,6,7-tetrahydrothiazolo[5,4-c]pyridine-2-carboxylate in a similar manner to Referential Example 48.

$^1$H-NMR (CDCl$_3$) δ: 1.46(9H,s), 1.53–1.95(5H,m), 2.17–2.24(1H,m), 2.50(3H,s), 2.50–2.53(1H,m), 2.80–2.96 (4H,m), 3.67(3H,s), 3.69–3.74(1H,m), 4.10(2H,br.s), 4.88 (1H,br.s). MS (FAB) m/z: 453(M+H)$^+$.

Referential Example 177

(1R*,2S*,4S*)-N$^1$-tert-Butoxycarbonyl-4-methoxycarbonyl-N$^2$-[(5-chloroindol-2-yl)carbonyl]-1,2-cyclohexanediamine

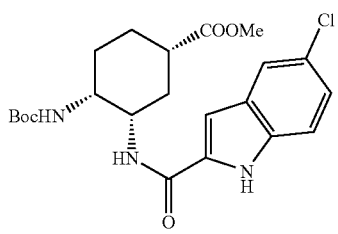

The title compound was obtained from (1R*,2S*,4S*)-N$^1$-tert-butoxycarbonyl-4-methoxycarbonyl-1,2-cyclohexanediamine and 5-chloroindole-2-carboxylic acid in a similar manner to Referential Example 159.

$^1$H-NMR (CDCl$_3$) δ: 1.33(9H,s), 1.42–2.47(6H,m), 2.78–2.88(1H,m), 3.70(3H,s), 3.86–4.15(2H,m), 4.65–4.75 (1H,m), 6.86(1H,br.s), 7.18–7.38(2H,m), 7.57–7.61(1H,m), 8.32(1H,br.s). MS (ESI) m/z: 450(M+H)$^+$.

Referential Example 178

Benzyl (1R,3S,4R)-3,4-epoxycyclohexane-1-carboxylate

1) Benzyl (1R)-3-cyclohexene-1-carboxylate was obtained from (1R)-3-cyclohexene-1-carboxylic acid (J. Am. Chem. Soc., 1978, Vol. 100, p. 5199) in a similar manner to Referential Example 169.

2) The title compound was obtained from the above-described product in a similar manner to Referential Example 170. MS (FAB) m/z: 233(M+H)$^+$.

Referential Example 179

Benzyl (1R,3S,4S)-4-(N-tert-butoxycarbonylamino)-3-hydroxycyclohexane-1-carboxylate 1) Benzyl (1R,3S,4S)-4-azido-3-hydroxycyclohexane-1-carboxylate was obtained from benzyl (1R,3S,4R)-3,4-epoxycyclohexane-1-carboxylate in a similar manner to Referential Example 171.

2) The title compound was obtained from the above-described product in a similar manner to Referential Example 172. MS (FAB) m/z: 350(M+H)$^+$.

Referential Example 180

Benzyl (1R,3R,4S)-3-azido-4-(N-tert-butoxycarbonylamino)cyclohexane-1-carboxylate

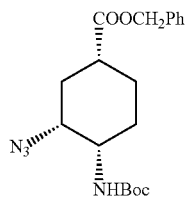

The title compound was obtained from benzyl (1R,3S,4S)-4-(N-tert-butoxycarbonylamino)-3-hydroxycyclohexane-1-carboxylate in a similar manner to Referential Example 174.

$^1$H-NMR (CDCl$_3$) δ: 1.45(9H,s), 1.52–1.66(2H,m), 1.83–2.01(3H,m), 2.20–2.28(1H,m), 2.51–2.54(1H,m), 3.77 (2H,br.s), 4.70(1H,br.s), 5.15(2H,ABq,J=12.2 Hz), 7.33–7.38(5H,m). MS (FAB) m/z: 375(M+H)$^+$.

Referential Example 181

Methyl (1R,3R,4S)-3-azido-4-(N-tert-butoxycarbonyl-amino)cyclohexane-1-carboxylate

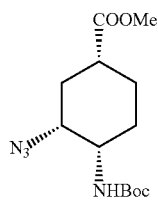

Benzyl (1R,3R,4S)-3-azido-4-(N-tert-butoxycarbonylamino)cyclohexane-1-carboxylate (3.5 g) was dissolved in tetrahydrofuran (130 ml) and water (16 ml), and lithium hydroxide (291 mg) was added under ice cooling. After 10 minutes, the mixture was heated to room temperature to continue stirring. After 20 hours, the reaction was stopped, the solvent was distilled off under reduced pressure, and the resultant residue was subjected to column chromatography on silica gel (methanol:dichloromethane= 1:20) to obtain (1R,3R,4S)-3-azido-4-(N-tert-butoxycarbonylamino)cyclohexane-1-carboxylic acid (3.34 g) as a pale yellow oil. This product was dissolved in methanol (18 ml) and toluene (64 ml), trimethylsilyldiazomethane (2 M solution, 6.1 ml) was added under ice cooling, and the mixture was heated to room temperature and stirred. After 2 hours, the reaction was stopped, the solvent was distilled off under reduced pressure, and the residue was purified by column chromatography on silica gel (ethyl acetate:hexane=1:4) to obtain the title compound (3.35 g) as a colorless oil.

$^1$H-NMR (CDCl$_3$) δ: 1.45 (9H, s), 1.57–1.63(2H,m), 1.82–1.85(1H,m), 1.95–1.99(2H,m), 2.20–2.28(1H,m), 2.48–2.51(1H,m), 3.73(3H,s), 3.78(2H,br.s), 4.70–4.72(1H, m). MS (FAB) m/z: 299(M+H)$^+$.

Referential Example 182

(1S,2R, 4R)-N$^1$-tert-Butoxycarbonyl-4-methoxycarbonyl-N$^2$-[(5-methyl-4,5,6,7-tetrahydrothiazolo[5,4-c]pyridin-2-yl)carbonyl]-1,2-cyclohexanediamine 1) (1S,2R,4R)-N$^1$-tert-Butoxycarbonyl-4-methoxycarbonyl-1,2-cyclohexanediamine was obtained from methyl (1R,3R,4S)-3-azido-4-(N-tert-butoxycarbonylamino)cyclohexane-1-carboxylate in a similar manner to Referential Example 175.

2) The title compound was obtained from the above-described product and lithium 5-methyl-4,5,6,7-tetrahydrothiazolo[5,4-c]pyridine-2-carboxylate in a similar manner to Referential Example 176. MS (FAB) m/z: 453 (M+H)$^+$.

Referential Example 183

Mixture of dimethyl (1R*,2S*,4S*,5R*)-4,5-dihydroxy-1,2-cyclohexanedicarboxylate and dimethyl (1R*,2S*,4R*,5S*)-4,5-dihydroxy-1,2-cyclohexanedicarboxylate

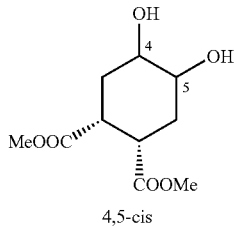

4,5-cis

Dimethyl (±)-cis-4-cyclohexene-1,2-dicarboxylate (20 g) was dissolved in a mixed solvent of water (30 ml) and acetonitrile (90 ml), N-methylmorpholine N-oxide (18 g) and microcapsulated osmium (1.0 g) were added, and the mixture was stirred at room temperature for 17 hours. After the reaction mixture was heated to 40° C. and stirred for 5 hours, N-methylmorpholine N-oxide (11 g) was added, and the mixture was stirred at 40° C. for 41 hours. The microcapsulated osmium was removed by filtration, and the filtrate was concentrated under reduced pressure. The residue was purified by column chromatography on silica gel (hexane:ethyl acetate=1:4), and the raw materials (5.0 g) were recovered to obtain the title compound (6.2 g) as a colorless oil.

$^1$H-NMR (CDCl$_3$) δ: 2.09–2.13(4H,br.s), 3.13 (2H,br.s), 3.68(6H,s), 3.90(2H, br.s) MS (FAB) m/z: 233(M+H)$^+$.

Referential Example 184

Dimethyl (1R*,2S*,4R*,5S* or 1R*,2S*,4S*,5R*)-4,5-diazido-1,2-cyclohexanedicarboxylate

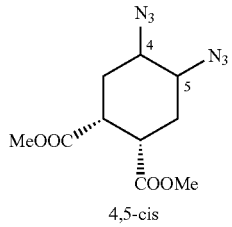

4,5-cis

The title compound was obtained as a main product from a mixture of dimethyl (1R*,2S*,4S*,5R*)-4,5-dihydroxy-1,2-cyclohexanedicarboxylate and dimethyl (1R*,2S*,4R*,5S*)-4,5-dihydroxy-1,2-cyclohexanedicarboxylate in a similar manner to Referential Example 127.

$^1$H-NMR (CDCl$_3$) δ: 1.81–3.13(6H,m), 3.64–3.71(2H, m), 3.73 (6H,s)

Referential Example 185

Dimethyl (1R*,2S*,4R*,5S* or 1R*,2S*,4S*,5R*)-4,5-bis-(tert-butoxycarbonylamino)-1,2-cyclohexanedicarboxylate

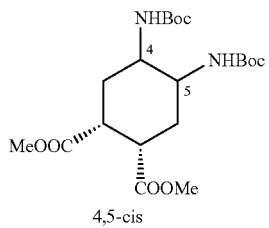

4,5-cis

Dimethyl (1R*,2S*,4R*,5S* or 1R*,2S*,4S*,5R*)-4,5-diazido-1,2-cyclohexanedicarboxylate (900 mg) was dissolved in tetrahydrofuran (100 ml), and di-tert-butyl dicarbonate (3 g) and 10% palladium on carbon (180 mg) were added to stir the mixture for 22 hours in a hydrogen atmosphere. After the catalyst was removed by filtration, di-tert-butyl dicarbonate (1.5 g) and 10% palladium on carbon (90 mg) were added to the filtrate to conduct a reaction for 5 hours in a hydrogen atmosphere. The catalyst was removed by filtration, the filtrate was concentrated, the residue was purified by column chromatography on silica gel (hexane:ethyl acetate=1:1→2:3) to obtain the title compound (570 mg) as white powder.

$^1$H-NMR (CDCl$_3$) δ: 1.44(18H,s), 2.08(4H,br.s), 2.87 (2H,br.s), 3.69(6H,s), 3.83(2H,br.s), 4.98(2H,br.s) MS (FAB) m/z: 431(M+H)$^+$.

Referential Example 186

(1R*,2S*,4R*)-N²-(tert-Butoxycarbonyl)-4-carbomoyl-N¹-[(5-chloroindol-2-yl)carbonyl]-1,2-cyclohexanediamine

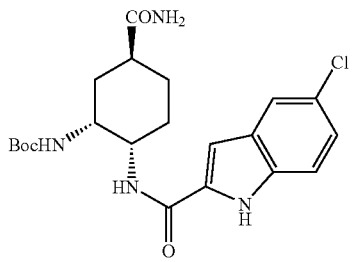

(1R*,2S*,4R*)-N²-(tert-Butoxycarbonyl)-N¹-[(5-chloroindol-2-yl)carbonyl]-4-ethoxycarbonyl-1,2-cyclohexanediamine (590 mg) was dissolved in a mixed solvent of ethanol (3 ml) and tetrahydrofuran (6 ml), a 1N aqueous solution (2.5 ml) of sodium hydroxide was added at room temperature, and the mixture was stirred for 12 hours. The solvent was distilled off to obtain the sodium salt of (1R*,2S*,4R*)-N²-(tert-butoxycarbonyl)-4-carboxy-N¹-[(5-chloroindol-2-yl)carbonyl]-1,2-cyclohexanediamine. This product was suspended in N,N-dimethylformamide (4 ml), di-tert-butyl dicarbonate (654 mg) and ammonium hydrogencarbonate (1 g) were added at room temperature, and the mixture was stirred for 18 hours. The solvent was distilled off under reduced pressure, and water was added to conduct extraction with chloroform. The resultant organic layer was washed with saturated saline and dried over anhydrous magnesium sulfate. The solvent was distilled off under reduced pressure, and the residue was purified by column chromatography on silica gel (methylene chloride:methanol=47:3) to obtain the title compound (82 mg) as a colorless solid. MS (ESI) m/z: 435(M+H)⁺.

Referential Example 187

(1S,2R,4S)-N²-(tert-Butoxycarbonyl)-N¹-[(5-chloroindol-2-yl)carbonyl]-4-(N,N-dimethylcarbamoyl)-1,2-cyclohexanediamine

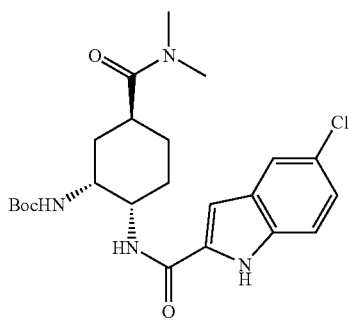

(1S,2R,4S)-N²-(tert-Butoxycarbonyl)-N¹-[(5-chloroindol-2-yl)carbonyl]-4-(ethoxycarbonyl)-1,2-cyclohexanediamine (1.5 g) was dissolved in tetrahydrofuran (10 ml) and ethanol (10 ml), a 5N aqueous solution (1.29 ml) of sodium hydroxide was added, and the mixture was stirred at room temperature for 18 hours. A 10% aqueous solution of citric acid was added to the reaction mixture to weakly acidify it. The reaction mixture was concentrated under reduced pressure and extracted with ethyl acetate, and the resultant organic layer was washed with saturated saline and dried over anhydrous sodium sulfate. The solvent was distilled off under reduced pressure, the residue was dissolved in N,N-dimethylformamide (20 ml), and dimethylamine hydrochloride (791 mg), 1-(3-dimethylaminopropyl)-3-ethylcarbodiimide hydrochloride (806 mg), 1-hydroxybenzotriazole monohydrate (644 mg) and triethylamine (2.24 ml) were added to stir the mixture at room temperature for 7 hours. Dimethylamine hydrochloride (527 mg), 1-(3-dimethylaminopropyl)-3-ethylcarbodiimide hydrochloride (620 mg), 1-hydroxybenzotriazole monohydrate (495 mg) and triethylamine (896 ml) were additionally added, and the mixture was stirred at room temperature for 15 hours. The reaction mixture was concentrated, an aqueous solution of sodium hydrogencarbonate was added to conduct extraction with ethyl acetate, and the resultant organic layer was washed with a saturated saline and dried over anhydrous sodium sulfate. The solvent was distilled off under reduced pressure, and the residue was purified by column chromatography on silica gel (dichloromethane:methanol=95:5) to obtain the title compound (1.49 g) as a pale yellow amorphous solid.

¹H-NMR (CDCl₃) δ: 1.52(9H,s), 1.71(1H,m), 1.89(2H,m), 2.13(1H,m), 2.30(1H,m), 2.65(1H,s), 2.89(3H,s), 3.07(3H,s), 4.01(1H,br.s), 4.20(1H,s), 4.82(1H,br.s), 6.79(1H,d, J=2.0 Hz), 7.23(1H,dd,J=8.5, 2.0 Hz), 7.35(1H,d,J=8.5 Hz), 7.59(1H,s), 8.02(1H,s), 9.54(1H,s). MS (ESI) m/z: 462(M+H)⁺.

Referential Example 188

(1S,2R,4S)-1-Azido-2-(N-tert-butoxycarbonylamino)-4-[N-(tert-butyl)carbamoyl]cyclohexane

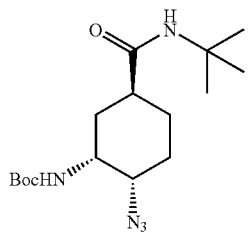

(1S,2R,4S)-1-Azido-2-(N-tert-butoxycarbonylamino)-4-methoxycarbonylcyclohexane (509 mg) was dissolved in tetrahydrofuran (40.0 ml), lithium hydroxide (111 mg) and water (5.0 ml) were successively added under ice cooling, and the mixture was stirred at room temperature for 36.5 hours. The solvent was distilled off under reduced pressure, water and 1N hydrochloric acid (4.64 ml) were added to the residue, and the solvent was distilled off again under reduced pressure to obtain crude (1S,2R,4S)-1-azido-2-(N-tert-butoxycarbonylamino)-4-carboxycyclohexane. Dichloromethane (25 ml) and N,N-dimethylformamide (260 μl) were added to this crude product, and the mixture was stirred under ice cooling. Further, oxalyl chloride (216 μl) was added to continuously stir the mixture at room temperature for 1 hour. tert-Butylamine (1130 μl) was added to the reaction mixture under ice cooling to stir the mixture at room temperature for 14 hours. After water and dichloromethane were added to the reaction mixture to conduct liquid separation, the resultant organic layer was dried over anhydrous sodium sulfate, and the solvent was distilled off under reduced pressure. The residue was purified by flash column chromatography on silica gel (hexane:ethyl acetate=2:1) to obtain the title compound (197 mg) as a pale yellow amorphous substance.

$^1$H-NMR (CDCl$_3$) δ: 1.25–1.35(9H,m), 1.35–1.45(9H, m), 1.55–2.00(6H,m), 2.20–2.30(1H,m), 3.70–4.80(3H,m), 5.30–5.45(1H,m). MS (FAB) m/z: 340(M+H)$^+$.

Referential Example 189

(1S,2R,4S)-N$^2$-(tert-butoxycarbonyl)-4-[N-(tert-butyl)carbamoyl]-1,2-cyclohexanediamine

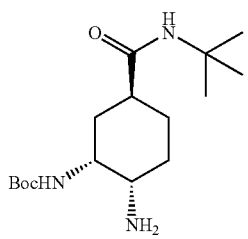

The title compound was obtained from (1S,2R,4S)-1-azido-2-(tert-butoxycarbonylamino)-4-[N-(tert-butyl)carbamoyl]cyclohexane in a similar manner to Referential Example 47.

$^1$H-NMR (CDCl$_3$) δ: 1.20–1.35(9H,m), 1.44(9H,s), 1.50–2.20(9H,m), 2.90–3.00(1H,m), 3.84(1H,br), 4.94(1H, br), 5.34(1H,br).

Referential Example 190

(1S,2R,4S)-N$^2$-(tert-Butoxycarbonyl)-4-[N-(tert-butyl)carbamoyl]-N$^1$-[(5-chloroindol-2-yl)carbonyl]-1,2-cyclohexanediamine

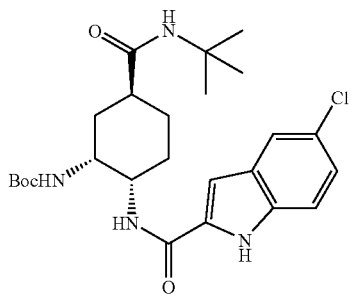

The title compound was obtained from (1S,2R,4S)-N$^2$-(tert-butoxycarbonyl)-4-[N-(tert-butyl)carbamoyl]-1,2-cyclohexanediamine and 5-chloroindole-2-carboxylic acid in a similar manner to Referential Example 159.

$^1$H-NMR (CDCl$_3$) δ: 1.33(9H,s), 1.35–2.30(16H,m), 3.90–4.05(1H,m), 4.15–4.25(1H,m), 5.04(1H,br), 5.42(1H, br), 6.65–6.90(1H,m), 7.19(1H,dd,J=8.8, 1.7 Hz), 7.37(1H, d,J=8.8 Hz), 7.59(1H,br), 8.13(1H,br), 10.51(1H,s). MS (ESI) m/z: 491(M+H)$^+$.

Referential Example 191

(3R)-1-Benzyl-3-(tert-butyldiphenylsilyloxy)pyrrolidine

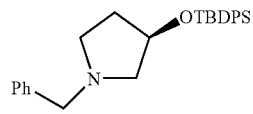

(3R)-1-Benzyl-3-hydroxypyrrolidine (500 μl) and imidazole (466 mg) were dissolved in N,N-dimethylformamide (15 ml), tert-butyldiphenylsilyl chloride (1.57 ml) was added under ice cooling, and the mixture was stirred at room temperature for 9 days. After the solvent was distilled off under reduced pressure, and dichloromethane and water were added to the residue to conduct liquid separation, the resultant organic layer was dried over anhydrous sodium sulfate, and the solvent was distilled off under reduced pressure. The residue was subjected to flash column chromatography on silica gel (hexane:ethyl acetate=3:1) to obtain the title compound (1.27 g) as a yellow oil.

$^1$H-NMR (CDCl$_3$) δ: 1.05(9H,s), 1.70–1.85(1H,m), 1.90–2.00(1H,m), 2.45–2.65(3H,m), 2.70–2.80(1H,m), 3.50–3.70(2H,m), 4.35–4.45(1H,m), 7.20–7.45(11H,m), 7.60–7.70(4H,m). MS (ESI) m/z: 416(M+H)$^+$.

Referential Example 192

1-Benzhydryl-3-(tert-butyldiphenylsilyloxy)azetidine

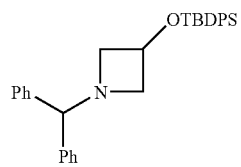

The title compound was obtained from 1-benzhydryl-3-hydroxyazetidine hydrochloride in a similar manner to Referential Example 191.

$^1$H-NMR (CDCl$_3$) δ: 1.01(9H,s), 2.90–3.00(2H,m), 3.40–3.50(2H,m), 4.36(1H,s), 4.40–4.50(1H,m), 7.10–7.20 (2H,m), 7.20–7.30(4H,m), 7.30–7.40(10H,m), 7.55–7.65 (4H,m) MS (ESI) m/z: 478(M+H)$^+$.

Referential Example 193 cis-N$^1$,N$^2$-Bis(benzyloxycarbonyl)-4-cyclohexene-1,2-diamine

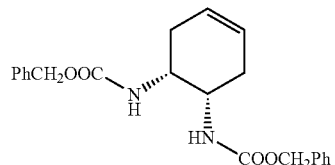

4-Cyclohexene-1,2-diamine hydrochloride (4.0 g) was dissolved in a mixed solvent of water (20 ml) and acetonitrile (20 ml), and benzyl chloroformate (7.66 ml) and potassium carbonate (14.9 g) were added, and the mixture was stirred at room temperature for 3 days. Water was poured into the reaction mixture to conduct extraction with methylene chloride, and the resultant organic layer was washed with saturated saline. The solvent was distilled off under reduced pressure, and the residue was purified by column chromatography on silica gel (dichloromethane) to obtain the title compound (8.22 g) as a colorless solid.

$^1$H-NMR (CDCl$_3$) δ: 2.03(2H,m), 2.53(2H,d,J=17.1 Hz), 3.77(2H,m), 5.03(2H,q,J=12.3 Hz), 5.09(2H,q,J=12.3 Hz), 5.59(2H,s), 7.32(10H,m). MS (ESI) m/z: 381(M+H)$^+$.

Referential Example 194

(1R*,2S*)-N$^1$,N$^2$-Bis(benzyloxycarbonyl)-4-hydroxy-1,2-cyclohexanediamine

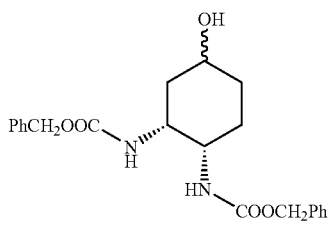

cis-N$^1$,N$^2$-Bis(benzyloxycarbonyl)-4-cyclohexene-1,2-diamine (10 g) was dissolved in absolute tetrahydrofuran (70 ml), borane-dimethyl sulfide complex (7.4 ml) was added at 0° C., and the mixture was gradually heated to room temperature and stirred for 14 hours. Ice was added to the reaction mixture to decompose excessive borane, and a 1N aqueous solution (80 ml) of sodium hydroxide and 30% aqueous hydrogen peroxide (80 ml) were added to stir the mixture for 1 hour. The reaction mixture was extracted with ethyl acetate, and the resultant organic layer was washed with saturated saline and dried over anhydrous sodium sulfate. The solvent was distilled off under reduced pressure, and the residue was purified by column chromatography on silica gel (ethyl acetate:hexane=2:1) to obtain the title compound (9.2 g) as a colorless wax.

$^1$H-NMR (CDCl$_3$) δ: 1.98(1H,m), 2.08(1H,m), 2.30(1H,m), 3.43(2H,m), 3.73(1H,m), 5.06(6H,m), 7.32(10H,s). MS (ESI) m/z: 399(M+H)$^+$.

Referential Example 195

(±)-cis-N$^1$,N$^2$-Bis(benzyloxycarbonyl)-4-oxo-1,2-cyclohexanediamine

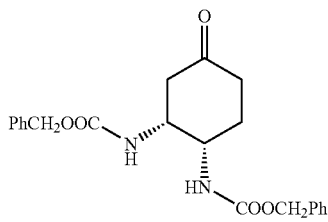

Dimethylsulfoxide (8.2 ml) was added to a solution of oxalyl chloride (9.9 ml) in dichloromethane (90 ml) at −60° C., and a solution of (1R*,2S*)-N$^1$,N$^2$-bis(benzyloxycarbonyl)-4-hydroxy-1,2-cyclohexanediamine (9.2 g) in tetrahydrofuran (90 ml) was added to the mixture in one portion. After 1 hour, the temperature of the mixture was raised to −40° C., and triethylamine (26 ml) was added in one portion. The mixture was heated to room temperature as it is, and stirred for 3 hours. The reaction mixture was poured into water and extracted with methylene chloride. The resultant organic layer was washed with saturated saline and then dried over anhydrous sodium sulfate. The solvent was distilled off under reduced pressure, and the residue was purified by column chromatography on silica gel (ethyl acetate:hexane=1:1) to obtain the title compound (8.0 g) as a pale yellow solid.

$^1$H-NMR (CDCl$_3$) δ: 2.27–2.43(4H,m), 2.78(1H,dd,J=14.4, 3.9 Hz), 3.86(2H,m), 5.08(4H,m), 5.22(2H,m), 7.32 (10H,m). MS (ESI) m/z: 397(M+H)$^+$.

Referential Example 196

(±)-cis-N$^1$,N$^2$-Bis(benzyloxycarbonyl)-4,4-dimethoxy-1,2-cyclohexanediamine

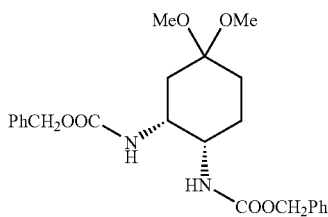

(±)-cis-N$^1$,N$^2$-Bis(benzyloxycarbonyl)-4-oxo-1,2-cyclohexanediamine (3.89 g) was dissolved in a mixed solvent of methanol (15 ml) and tetrahydrofuran (15 ml), 2,2-dimethoxypropane (10.7 ml) and p-toluenesulfonic acid (187 mg) were added, and the mixture was stirred at room temperature for 3 hours. The solvent was concentrated, and a saturated aqueous solution of sodium hydrogencarbonate was added to conduct extraction with ethyl acetate. After the resultant organic layer was washed with saturated saline and dried over anhydrous sodium sulfate, the solvent was distilled off under reduced pressure, and the residue was purified by column chromatography on silica gel (ethyl acetate:hexane=1:2) to obtain the title compound (3.54 g) as a colorless amorphous solid.

$^1$H-NMR (CDCl$_3$) δ: 1.30–1.41(4H,m), 1.93(1H,m), 2.38 (1H,m), 3.19(6H,s), 3.46(1H,m), 3.59(1H,m), 5.03(2H,q,J= 12.5 Hz), 5.09(2H,q,J=12.5 Hz), 7.32(10H,s).

Referential Example 197

(±)-cis-N$^1$-[5-Chloroindol-2-yl)carbonyl]-4,4-dimethoxy-1,2-cyclohexanediamine and (±)-cis-N$^2$-[(5-chloroindol-2-yl)carbonyl]-4,4-dimethoxy-1,2-cyclohexanediamine

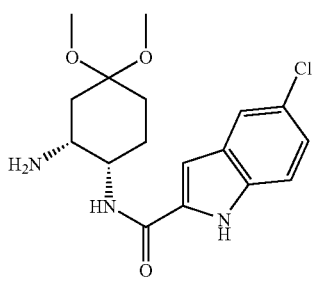

(±)-cis-N$^1$,N$^2$-Bis(benzyloxycarbonyl)-4,4-dimethoxy-1,2-cyclohexanediamine (1.45 g) was dissolved in methanol (12 ml), and 10% palladium on carbon (290 mg) was added to stir the mixture at room temperature for 20 hours in a hydrogen atmosphere. 10% Palladium on carbon (290 mg) and methanol (10 ml) were additionally added to stir the mixture for 8 hours. The reaction mixture was filtered through Celite, and mother liquor was concentrated, and the residue was dissolved in N,N-dimethylformamide (10 ml). 5-Chloroindole-2-carboxylic acid (320 mg), 1-(3-dimethylaminopropyl)-3-ethylcarbodi-imide hydrochloride (377 mg), 1-hydroxybenzotriazole monohydrate (301 mg) and N-methylmorpholine (360 ml) were added, and the mixture was stirred at room temperature for 14 hours. The reaction mixture was poured into an aqueous solution of sodium hydrogencarbonate and extracted with ethyl acetate. The resultant organic layer was washed with saturated saline and then dried over anhydrous sodium sulfate, the solvent was distilled off under reduced pressure, and the residue was isolated and purified by preparative thin-layer chromatography on silica gel (dichloromethane:methanol=93:7) to obtain (±)-cis-$N^1$ (or $N^2$)-[(5-chloroindol-2-yl)carbonyl]-4,4-dimethoxy-1,2-cyclohexanediamine (98 mg) and (±)-cis-$N^2$(or $N^1$)-[(5-chloroindol-2-yl)carbonyl]-4,4-dimethoxy-1,2-cyclohexanediamine (105 mg).

(±)-cis-$N^1$ (or $N^2$)-[(5-Chloroindol-2-yl)carbonyl]-4,4-dimethoxy-1,2-cyclohexanediamine $^1$H-NMR (CDCl$_3$) δ: 1.48(2H,m), 2.08(2H,m), 2.34(1H, d,J=13.1 Hz), 2.78(1H,dt,J=2.9, 13.1 Hz), 3.18(3H,s), 3.23 (,3H,s), 3.76(1H,m), 6.24(1H,d,J=8.3 Hz), 6.79(1H,s), 7.23 (1H,dd,J=8.8, 2.0 Hz), 7.35(1H,d,J=8.8 Hz), 7.60(1H,d,J=8.8 Hz), 9.53(1H,br.s). MS (ESI) m/z: 352(M+H)$^+$.

(±)-cis-$N^2$(or $N^1$)-[(5-Chloroindol-2-yl)carbonyl]-4,4-dimethoxy-1,2-cyclohexanediamine $^1$H-NMR (CDCl$_3$) δ: 1.85(1H,m), 1.99(1H,m), 2.39(1H, br,J=13.2 Hz), 2.88(1H,m), 3.26(10H,m), 4.00(1H,m), 6.77 (1H,s), 7.23(1H,d,J=8.5 Hz), 7.37(1H,d,J=8.5 Hz), 7.61(1H, s),9.49(1H,br.s). MS (ESI) m/z: 352(M+H)$^+$.

Referential Example 198

(±)-cis-$N^1$,$N^2$-Bis(benzyloxycarbonyl)-4,4-(1,2-ethylenedioxy)-1,2-cyclohexanediamine

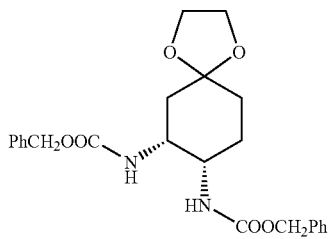

(±)-cis-$N^1$,$N^2$-Bis(benzyloxycarbonyl)-4-oxo-1,2-cyclohexanediamine (4.0 g) was dissolved in absolute tetrahydrofuran (30 ml), and ethylene glycol (5.6 ml) and p-toluenesulfonic acid (192 mg) were added to stir the mixture at room temperature for 17 hours. The reaction mixture was poured into a saturated aqueous solution of sodium hydrogencarbonate and extracted with ethyl acetate. The resultant organic layer was washed with saturated saline and then dried over anhydrous sodium sulfate, the solvent was distilled off under reduced pressure, and the residue was purified by column chromatography on silica gel (ethyl acetate:hexane=1:1) to obtain the title compound (4.23 g) as a pale yellow solid.

$^1$H-NMR (CDCl$_3$) δ: 1.65–1.71(4H,m), 2.00(1H,m), 2.11 (1H,m), 3.49(1H,m), 3.73(1H,m), 3.93(4H,s), 5.03(2H,q,J= 12.2 Hz), 5.08(2H,q,J=12.2 Hz), 7.32(10H,s). MS (ESI) m/z: 441(M+H)$^+$.

Referential Example 199

(±)-cis-$N^1$-[(5-chloroindol-2-yl)carbonyl]-4,4-(1,2-ethylenedioxy)-1,2-cyclohexanediamine and (±)-cis-$N^2$-[(5-chloroindol-2-yl)carbonyl]-4,4-(1,2-ethylenedioxy)-1,2-cyclohexanediamine

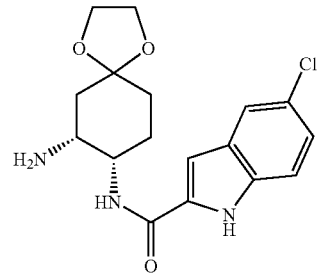

(±)-cis-$N^1$ (or $N^2$)-[(5-Chloroindol-2-yl)carbonyl]-4,4-(1,2-ethylenedioxy)-1,2-cyclohexanediamine and (±)-cis-$N^2$ (or $N^1$)-[(5-chloroindol-2-yl)carbonyl]-4,4-(1,2-ethylenedioxy)-1,2-cyclohexanediamine were obtained from (±)-cis-$N^1$,$N^2$-bis(benzyloxycarbonyl)-4,4-(1,2-ethylenedioxy)-1,2-cyclohexanediamine in a similar manner to Referential Example 197.

(±)-cis-$N^1$(or $N^2$)-[(5-Chloroindol-2-yl)carbonyl]-4,4-(1,2-ethylenedioxy)-1,2-cyclohexanediamine $^1$H-NMR (CDCl$_3$) δ: 1.68–1.81(4H,m), 2.11(2H,m), 2.87 (1H,td,J=3.9, 11.2 Hz), 3.77(1H,m), 3.97(4H,s), 6.27(1H,d, J=7.6 Hz), 6.80(1H,s), 7.24(1H,d,J=9.0 Hz), 7.35(1H,d,J= 9.0 Hz), 7.61(1H,s), 9.47(br.s,1H). MS (ESI) m/z: 350(M+H)$^+$.

(±)-cis-$N^2$(or $N^1$)-[(5-Chloroindol-2-yl)carbonyl]-4,4-(1,2-ethylenedioxy)-1,2-cyclohexanediamine $^1$H-NMR (CDCl$_3$) δ: 1.65(2H,m), 1.88(1H,m), 1.96(1H, m), 2.31(1H,dd,J=12.9, 3.2 Hz), 2.96(1H,m), 3.98(1H,m), 4.02(4H,s), 4.12(1H,m), 6.77(1H,s), 7.06(1H,br.s), 7.23(1H, dd,J=8.8, 2.0 Hz), 7.37(1H,d,J=8.8 Hz), 7.62(1H,d, J=2.0 Hz), 9.49(1H,br.s). MS (ESI) m/z: 350(M+H)$^+$.

Referential Example 200 cis-$N^1$,$N^2$-Bis(tert-butoxycarbonyl)-4-cyclohexene-1,2-diamine

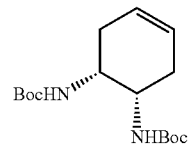

cis-4-Cyclohexene-1,2-diamine hydrochloride (4.0 g) was dissolved in a mixed solvent of water (40 ml) and acetonitrile (40 ml), and di-tert-butoxy carbonate (11.8 g) and triethylamine (12 ml) were added, and the mixture was stirred at room temperature for 4.5 hours. The reaction mixture was poured into water to conduct extraction with dichloromethane, and the resultant dichloromethane layer was washed with saturated saline and then dried over anhydrous sodium sulfate. The solvent was distilled off under reduced pressure, and the residue was purified by column chromatography on silica gel (ethyl acetate:hexane= 1:4) to obtain the title compound (6.12 g) as a colorless solid.

$^1$H-NMR (CDCl$_3$) δ: 1.44(18H,s), 1.98(2H,dd,J=9.3, 15.9 Hz), 2.48(2H,br.d,J=15.9 Hz), 3.66(2H,br.s), 4.88(2H,br.s), 5.58(2H,d,J=2.7 Hz).

Referential Example 201

(1R*,2S*)-N$^1$,N$^2$-Bis(tert-butoxycarbonyl)-4-hydroxy-1,2-cyclohexanediamine (mixture of stereoisomers)

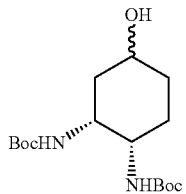

cis-N$^1$,N$^2$-Bis (tert-butoxycarbonyl)-4-cyclohexene-1,2-diamine (6.1 g) was dissolved in absolute tetrahydrofuran (40 ml), and borane-dimethyl sulfide complex (2.22 ml) was added by a syringe under ice cooling. The mixture was stirred for 16 hours while gradually heating the mixture to room temperature as it is. Ice was added to the reaction mixture, and a 1N aqueous solution of sodium hydroxide and 30% aqueous hydrogen peroxide (50 ml) were added to stir the mixture at room temperature for 2 hours as it is. The reaction mixture was extracted with ethyl acetate, and the resultant organic layer was washed with saturated saline and dried over anhydrous sodium sulfate. The solvent was distilled off under reduced pressure, and the residue was purified by column chromatography on silica gel (ethyl acetate:hexane=1:2→2:1) to obtain the title compound (6.1 g) as a colorless oil.

$^1$H-NMR (CDCl$_3$) δ: 1.42(9H,s), 1.43(9H,s), 1.83–1.67 (5H,m), 2.15(1H,m), 2.22(1H,s), 3.34(1H,m), 3.78(1H,m), 4.15(1H,s), 4.98(1H,q,J=9.0 Hz), 5.02(1H,q,J=9.0 Hz). MS (ESI) m/z: 331(M+H)$^+$.

Referential Example 202 cis-N$^1$,N$^2$-Bis(tert-butoxycarbonyl)-4-oxo-1,2-cyclohexanediamine

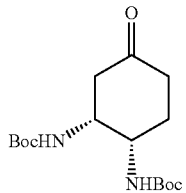

Dimethylsulfoxide (6.8 ml) was added to a solution of oxalyl chloride (8.2 ml) in dichloromethane (100 ml) at −60° C., and a solution of (1R*,2S*)-N$^1$,N$^2$N-bis(tert-butoxycarbonyl)-4-hydroxy-1,2-cyclohexanediamine (mixture of stereoisomers) (6.32 g) in tetrahydrofuran (80 ml) was added at a time, and the mixture was stirred for 1 hour. The temperature of the mixture was raised to −40° C., and triethylamine (21 ml) was added. The mixture was heated to room temperature. After 3 hours, the reaction mixture was poured into water and extracted with dichloromethane. The resultant organic layer was washed with saturated saline and then dried over anhydrous sodium sulfate. The solvent was distilled off under reduced pressure, and the residue was purified by column chromatography on silica gel (ethyl acetate:hexane=1:1) to obtain the title compound (3.8 g) as a pale yellow solid.

1H-NMR (CDCl$_3$) δ: 1.43(9H,s), 1.44(9H,s), 2.36–2.24 (3H,)m, 2.39–2.44(2H,m), 2.75(1H,dd,J=14.6, 2.9 Hz), 3.66–3.81(2H,m), 4.95–4.90(1H,m), 4.97–5.03(1H,m). MS (ESI) m/z: 329(M+H)$^+$.

Referential Example 203

(±)-cis-N$^1$,N$^2$-Bis(tert-butoxycarbonyl)-4-methoxyimino-1,2-cyclohexanediamine

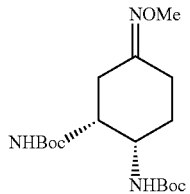

cis-N$^1$,N$^2$-Bis(tert-butoxycarbonyl)-4-oxo-1,2-cyclohexanediamine (1.5 g) was dissolved in methanol (30 ml), and O-methylhydroxylamine hydrochloride (572 mg) and pyridine (737 ml) were added to stir the mixture at room temperature for 17 hours. After the reaction mixture was concentrated, water was added to conduct extraction with ethyl acetate. The resultant organic layer was washed with saturated saline and then dried over anhydrous sodium sulfate. The solvent was distilled off under reduced pressure, and the residue was purified by column chromatography on silica gel (ethyl acetate:hexane=1:4) to obtain the title compound (1.52 g) as a colorless solid.

$^1$H-NMR (CDCl$_3$) δ: 1.44(18H,s), 1.64(1H,m), 2.16(2H, m), 2.44(1H,m), 3.45–3.63(3H,m), 3.82(3H,s), 4.93(1H,m). MS (ESI) m/z: 358(M+H)$^+$.

Referential Example 204

(1R*,2S*,4R*(or 4S*))-N$^1$,N$^2$-Bis(tert-butoxycarbonyl)-4-tert-butyldiphenylsilyloxy-1,2-cyclohexanediamine (Stereoisomer A)

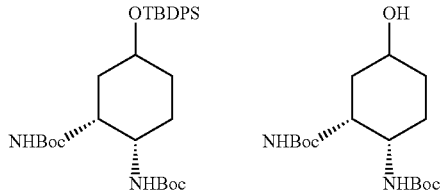

The title compound was obtained from (1R*,2S*)-N$^1$,N$^2$-bis(tert-butoxycarbonyl)-4-hydroxy-1,2-cyclohexanediamine (mixture of stereoisomers) in a similar manner to Referential Example 191.

$^1$H-NMR (CDCl$_3$) δ: 1.03(9H,s), 1.39(9H,s), 1.40(9H,s), 1.72(1H,m), 1.86(1H,m), 2.13(1H,m), 3.24(2H,m), 3.65 (1H,m), 4.83(1H,m), 7.37(10H,m).

Referential Example 205

(1R*,2S*)-4-Acetoxy-N¹,N²-bis(tert-butoxycarbonyl)-1,2-cyclohexanediamine (Stereoisomer B)

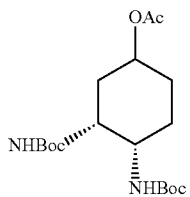

(1R*,2S*)-N¹,N²-Bis(tert-butoxycarbonyl)-4-hydroxy-1,2-cyclohexanediamine (Stereoisomer B) (1.74 g) was dissolved in pyridine (15 ml), and acetic anhydride (5 ml) was added to stir the mixture at room temperature for 4 days. 1N Hydrochloric acid was added to the reaction mixture, extraction was conducted with ethyl acetate, and the resultant organic layer was successively washed with 1N hydrochloric acid, a saturated aqueous solution of sodium hydrogencarbonate and saturated saline, and then dried over anhydrous sodium sulfate. The solvent was distilled off under reduced pressure, and the residue was purified by column chromatography on silica gel (ethyl acetate:hexane=1:3) to obtain the title compound (1.96 g) as a colorless oil.

$^{1}$H-NMR (CDCl$_{3}$) δ: 1.43(18H,s), 1.89(2H,m), 2.10(3H, s), 2.19(1H,m), 3.35(1H,m), 3.69(1H,m), 4.86(1H,d,J=8.3 Hz), 5.00(1H,d,J=8.3 Hz), 5.11(1H,s). MS (ESI) m/z: 373 (M+H)$^{+}$.

Referential Example 206

(1R*,2S*)-N¹,N²-Bis(benzyloxycarbonyl)-4-hydroxy-4-methyl-1,2-cyclohexanediamine

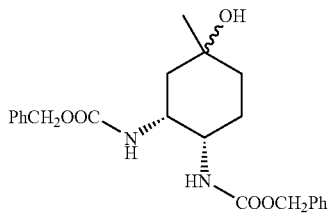

Anhydrous cerium chloride (6.4 g) was suspended in tetrahydrofuran (50 ml), and the suspension was cooled to −78° C. in an argon atmosphere. A methyllithium solution (1.14N diethyl ether solution, 22.5 ml) was added to the suspension, and the mixture was stirred at −78° C. for 30 minutes. A tetrahydrofuran solution (50 ml) of (±)-cis-N¹,N²-bis(benzyloxycarbonyl)-4-oxo-1,2-cyclohexanediamine (3.0 g) was added dropwise at −78° C., and the mixture was stirred for 30 minutes. The reaction mixture was poured into a 3% aqueous solution (100 ml) of acetic acid, and diethyl ether (50 ml) was added to stir the mixture at room temperature for 10 minutes. The reaction mixture was extracted with ethyl acetate, and the resultant organic layer was washed with a saturated aqueous solution of sodium hydrogencarbonate and saturated saline and then dried over anhydrous sodium sulfate. The solvent was distilled off under reduced pressure, and the residue was purified twice by medium-pressure column chromatography on silica gel (methanol:chloroform=0:100–1:19) to obtain the title compound (Stereoisomer A) (780 mg) as a colorless foamy compound and the title compound (Stereoisomer B) (1.1 g) as white powder.

Stereoisomer A:
$^{1}$H-NMR (CDCl$_{3}$) δ: 1.26(3H,s), 1.27–2.08(6H,m), 3.48 (1H,br.s), 3.59(1H,br.s), 5.02–5.09(5H,m), 5.33(1H,br.s), 7.30–7.32(10H,s) MS (FAB) m/z: 413(M+H)$^{+}$.

Stereoisomer B:
$^{1}$H-NMR (CDCl$_{3}$) δ: 1.25(3H,s), 1.29–2.07(6H,m), 3.39 (1H,br.s), 3.82(1H,br.s), 5.02–5.23(6H,m), 7.30(10H,s) MS(FAB) m/z: 413(M+H)$^{+}$.

Referential Example 207

(1R*,2S*)-4-Hydroxy-4-methyl-1,2-cyclohexanediamine (Stereoisomer A)

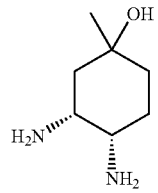

10% Palladium on carbon (350 mg) was suspended in a methanol solution (100 ml) of (1R*,2S*)-N¹,N²-bis(benzyloxycarbonyl)-4-hydroxy-4-methyl-1,2-cyclohexanediamine (Stereoisomer A) (780 mg), and the suspension was stirred for 5 hours in a hydrogen atmosphere. The catalyst was removed by filtration, and the filtrate was concentrated under reduced pressure. After the residue was dissolved in dichloromethane (100 ml), and the solution was dried over anhydrous sodium sulfate, the solvent was distilled off to obtain the title compound (Stereoisomer A) (190 mg) as a colorless oil.

$^{1}$H-NMR (CDCl$_{3}$) δ: 1.22(3H,s), 1.25–2.48(11H,m), 2.62 (1H,br.s), 2.78(1H,br.s).

Referential Example 208

(1R*,2S*)-4-Hydroxy-4-methyl-1,2-cyclohexanediamine (Stereoisomer B)

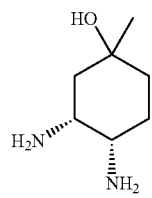

The title compound was obtained from (1R*,2S*)-N¹,N²-bis(benzyloxycarbonyl)-4-hydroxy-4-methyl-1,2-cyclohexanediamine (Stereoisomer B) in a similar manner to Referential Example 207.

$^{1}$H-NMR (CDCl$_{3}$) δ: 1.17(3H,s), 1.39–1.79(11H,m), 2.10–2.18(1H,m), 2.55–2.61(1H,m)

Referential Example 209

Mixture of (1R*,2S*)-N¹-[(5-chloroindol-2-yl)carbonyl]-4-hydroxy-4-methyl-1,2-cyclohexanediamine (Stereoisomer A) and (1R*,2S*)-N²-[(5-chloroindol-2-yl)carbonyl]-4-hydroxy-4-methyl-1,2-cyclohexanediamine (Stereoisomer A)

The title compound was obtained from (1R*,2S*)-4-hydroxy-4-methyl-1,2-cyclohexanediamine (Stereoisomer A) and 5-chloroindole-2-carboxylic acid in a similar manner to Referential Example 30.

¹H-NMR (CDCl₃) δ: 1.32(3H,s), 1.34–2.29(6H,m), 4.42–4.70(4H,br), 7.13(2H,s), 7.50(2H,s), 8.00(1H,s), 11.0 (1H,br)

Referential Example 210

(1R*,2S*)-N¹(or N²)-[(5-chloroindol-2-yl)carbonyl]-4-hydroxy-4-methyl-1,2-cyclohexanediamine (Stereoisomer B)

The title compound was obtained from (1R*,2S*)-4-hydroxy-4-methyl-1,2-cyclohexanediamine (Stereoisomer B) and 5-chloroindole-2-carboxylic acid in a similar manner to Referential Example 125.

¹H-NMR (DMSO-d₆) δ: 1.18(3H,s), 1.23–1.96(6H,m), 4.12–5.60(4H,br), 7.11–8.59(5H,m), 11.8(1H,br) MS (FAB) m/z: 322(M+H)⁺.

Referential Example 211

(1R*,2S*)-4-(tert-Butyldiphenylsilyloxymethyl)-1,2-cyclohexanediol

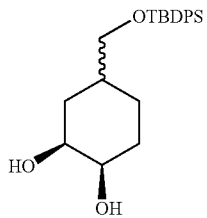

1) 3-Cyclohexene-1-methanol (5.0 g) was dissolved in N,N-dimethylformamide (50 ml), and imidazole (3.93 g) and tert-butylchlorodiphenylsilane (14 ml) were added to stir the mixture for 22 hours. After adding methanol, the solvent was distilled off under reduced pressure, and water was added to the residue to conduct extraction with ethyl acetate. The extract was dried over anhydrous sodium sulfate. The solvent was distilled off under reduced pressure, and the residue was purified by column chromatography on silica gel (hexane:ethyl acetate=30:1) to obtain (±)-4-(tert-butyldiphenylsilyloxymethyl)-1-cyclohexene (16.1 g) as a colorless oil.

¹H-NMR (CDCl₃) δ: 1.05(9H,s), 1.20–1.35(2H,m), 1.70–1.90(3H,m), 2.05–2.20(2H,m), 3.55(2H,d,J=5.9 Hz), 5.67(2H,s), 7.35–7.50(6H,m), 7.65–7.75(4H,m). MS (FAB) m/z: 351(M+H)⁺.

2) The title compound was obtained from (±)-4-(tert-butyldiphenylsilyloxymethyl)-1-cyclohexene in a similar manner to Referential Example 183.

¹H-NMR (CDCl₃)δ: 1.04, 1.05(total 9H,each s), 1.29–2.09(7H,m), 2.05(2H,s), 3.44–3.51(2H,m), 3.52–3.67 (1H,m), 4.00, 3.96(total 1H,each br.s), 7.35–7.44(6H,m), 7.63–7.66(4H,m). MS (FAB) m/z: 385(M+H)⁺.

Referential Example 212

(1R*,2S*)-4-(tert-Butyldiphenylsilyloxymethyl)-1,2-bis(methanesulfonyloxy)cyclohexane

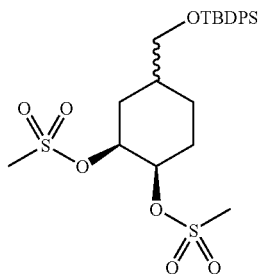

Methanesulfonyl chloride (2.5 ml) was added dropwise to a dichloromethane solution (300 ml) of (1R*,2S*)-4-(tert-butyldiphenylsilyloxymethyl)-1,2-cyclohexanediol (4.2 g) and triethylamine (9.1 ml) at 0° C., and the mixture was stirred for 1.5 hours. Water was added to conduct extraction with dichloromethane, and the resultant organic layer was washed with a saturated aqueous solution of sodium hydrogencarbonate and saturated saline and then dried over anhydrous sodium sulfate. The solvent was distilled off under reduced pressure, and the residue was purified by medium-pressure column chromatography on silica gel (hexane:ethyl acetate 3:2) to obtain the title compound (4.9 g) as a pale yellow oil.

¹H-NMR (CDCl₃) δ: 1.04, 1.05(total 9H,each s), 1.31–2.29(7H,m), 3.07,3.08(total 3H,each s), 3.09,3.10(total 3H,each s), 4.11(2H,dt,J=7.1, 0.73 Hz), 4.65–4.72(1H,m), 5.11,5.08(total 1H,each br.s), 7.39–7.43(6H,m), 7.61–7.64 (4H,m).

Referential Example 213

(1R*, 2S*,)-4-(tert-Butyldiphenylsilyloxymethyl)-1,2-diazidocyclohexane (Stereoisomer A and Stereoisomer B)

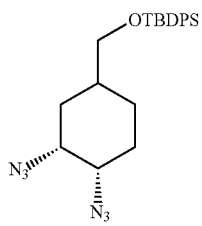

The respective title compounds (Stereoisomer A and Stereoisomer B) were obtained from (1R*,2S*)-4-(tert-butyldiphenylsilyloxymethyl)-1,2-bis(methanesulfonyloxy)cyclohexane in a similar manner to Referential Example 127.

Stereoisomer A:
¹H-NMR (CDCl₃) δ: 0.88(1H,m), 1.06(9H,s), 1.24–1.30 (2H,m), 1.63–1.66(1H,m), 1.89–1.92(2H,m), 2.00–2.05(1H, m), 3.37–3.42(1H,m), 3.52(2H,br.t,J=6.0 Hz), 3.92(1H,br.s), 7.37–7.45(6H,m), 7.63–7.65(4H,m).

Stereoisomer B:
¹H-NMR (CDCl₃) δ: 0.88(1H,m), 1.05(9H,s), 1.13–1.43 (2H,m), 1.79–1.84(3H,m), 2.02–2.06(1H,m), 3.34–3.38(1H, m), 3.47–3.51(2H,m), 3.94(1H,br.d,J=2.9 Hz), 7.37–7.45 (6H,m), 7.62–7.64(4H,m)

Referential Example 214

(1R*,2S*)-4-(tert-Butyldiphenylsilyloxymethyl)-1,2-cyclohexanediamine (Stereoisomer A)

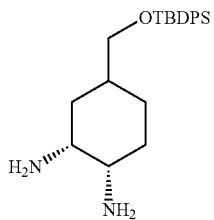

The title compounds was obtained from (1R*,2S*)-4-(tert-butyldiphenylsilyloxymethyl)-1,2-diazidocyclohexane (Stereoisomer A) in a similar manner to Referential Example 128.

$^1$H-NMR (CDCl$_3$) δ: 1.05(9H,s), 1.09–1.76(7H,m), 2.76–2.79(1H,m), 2.98(1H,br.s), 3.48–3.49(2H,m), 7.36–7.41(6H,m), 7.64–7.66(4H,m).

Referential Example 215

(1R*,2S*)-4-tert-Butyldiphenylsilyloxymethyl-1,2-cyclohexanediamine (Stereoisomer B)

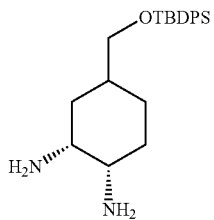

The title compounds was obtained from (1R*,2S*)-4-(tert-butyldiphenylsilyloxymethyl)-1,2-diazidocyclohexane (Stereoisomer B) in a similar manner to Referential Example 128.

$^1$H-NMR (CDCl$_3$) δ: 1.05(9H,s), 1.42–1.79(7H,m), 2.70–2.73(1H,m), 3.01–3.03(1H,m), 3.44–3.49(2H,m), 7.37–7.42(6H,m), 7.64–7.66(4H,m)

Referential Example 216

(1R,3S,4S)-3-Azido-4-(N-tert-butoxycarbonyl-amino)cyclohexane-1-carboxylic acid

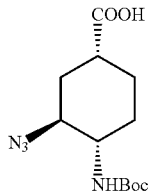

Benzyl (1R,3S,4S)-3-azido-4-(N-tert-butoxycarbonylamino)cyclohexane-1-carboxylate (4.4 g) was dissolved in tetrahydrofuran (160 ml) and water (20 ml), and lithium hydroxide (366 mg) was added under ice cooling. After 10 minutes, the mixture was heated to room temperature to continue stirring. After 20 hours, the solvent was distilled off under reduced pressure, and the residue was purified by column chromatography on silica gel (methanol:dichloromethane=1:10) to obtain the title compound (1.86 g) as a pale yellow oil.

$^1$H-NMR (CDCl$_3$) δ: 1.47(9H,s), 1.72–1.73(2H,m), 1.82–1.90(3H,m), 2.05–2.10(1H,m), 2.77–2.80(1H,m), 3.49–3.65(2H,m). MS (FAB)m/z: 285(M+H)$^+$.

Referential Example 217

(1R,3S,4S)-3-Azido-4-(N-tert-butoxycarbonylamino)-1-(hydroxymethyl)cyclohexane

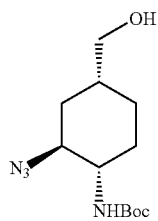

(1R,3S,4S)-3-Azido-4-(N-tert-butoxycarbonylamino)cyclohexane-1-carboxylic acid (1.86 g) was dissolved in dimethoxyethane (20 ml), and to the solution isobutyl chloroformate (1.02 ml) and N-methylmorpholine (860 mg) were added at −15° C. The mixture was stirred for 10 minutes at the same temperature. The hydrochloride of N-morpholine deposited was separated by filtration, and an aqueous solution (4 ml) of sodium borohydride (370 mg) was added to the filtrate to stir the mixture for 10 minutes. After water was added, and the solvent was distilled off under reduced pressure, the residue was extracted with dichloromethane and dried over anhydrous magnesium sulfate. The solvent was distilled off under reduced pressure, and the residue was purified by column chromatography on silica gel (ethyl acetate:hexane=1:1) to obtain the title compound (1.35 g) as a colorless oil.

$^1$H-NMR (CDCl$_3$) δ: 1.46(9H,s), 1.33–2.20(7H,m), 3.52–3.55(2H,m), 3.64–3.81(2H,m). MS(FAB) m/z: 271 (M+H)$^+$.

Referential Example 218

(1R,3S,4S)-3-Azido-4-(N-tert-butoxycarbonylamino)-1-(tert-butyldiphenylsilyloxymethyl)cyclohexane

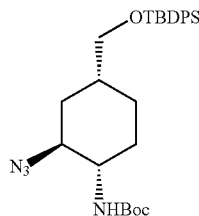

The title compounds was obtained from (1R,3S,4S)-3-azido-4-(N-tert-butoxycarbonylamino)-1-(hydroxymethyl)cyclohexane in a similar manner to Referential Example 107.

$^1$H-NMR (CDCl$_3$) δ: 1.06(9H,s), 1.45(9H,s), 1.53–2.16 (7H,m), 3.51(2H,d,J=6.4 Hz), 3.61(2H,br.s), 7.36–7.46(6H, m), 7.63–7.66(4H,m). MS(FAB) m/z: 509(M+H)$^+$.

Referential Example 219

(1S,2S,4R)-N$^1$-tert-Butoxycarbonyl-4-(tert-butyldiphenylsilyloxymethyl)-N$^2$-[(5-methyl-4,5,6, 7-tetrahydrothiazolo[5,4-c]pyridin-2-yl)carbonyl]-1, 2-cyclohexanediamine

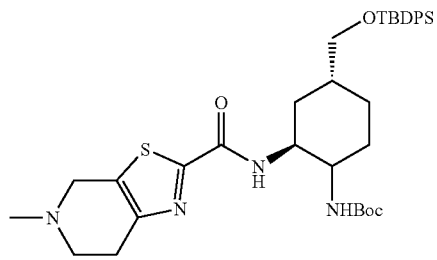

1) (1R,3S,4S)-3-Azido-4-(N-tert-butoxycarbonyl-amino)-1-(tert-butyldiphenylsilyloxymethyl)cyclohexane (2.59 g) was dissolved in methanol (50 ml), and 10% palladium on carbon (200 mg) was added to stir the mixture for 20 hours in a hydrogen atmosphere. After the catalyst was removed by filtration, the solvent was distilled off under reduced pressure, and the residue was purified by column chromatography on silica gel (methanol:dichloromethane= 1:20→1:10) to obtain (1S,2S,4R)-N$^1$-tert-butoxycarbonyl-4-(tert-butyldiphenylsilyloxymethyl)-1,2-cyclohexanediamine (1.66 g) as a pale yellow oil.

2) The title compound was obtained from (1S,2S,4R)-N$^1$-tert-butoxycarbonyl-4-(tert-butyldiphenyl-silyloxymethyl)-1,2-cyclohexanediamine and lithium 5-methyl-4,5,6,7-tetrahydrothiazolo[5,4-c]pyridine-2-carboxylate in a similar manner to Referential Example 48.

$^1$H-NMR (CDCl$_3$) δ: 1.05(9H,s), 1.29(9H,s), 1.56–1.58 (3H,m), 1.80–1.84(2H,m), 2.00–2.05(2H,m), 2.49(3H,s), 2.80–2.81(2H,m), 2.90–3.00(2H,m), 3.48(1H,br.s), 3.58–3.69(4H,m), 3.84(1H,br.s), 7.35–7.44(6H,m), 7.63–7.65 (4H,m). MS (FAB) m/z: 663(M+H)$^+$.

Referential Example 220

(1S,2S,4R)-N$^1$-tert-Butoxycarbonyl-4-hydroxymethyl-N$^2$-[(5-methyl-4,5,6,7-tetrahydrothiazolo[5,4-c]pyridin-2-yl)carbonyl]-1,2-cyclohexanediamine

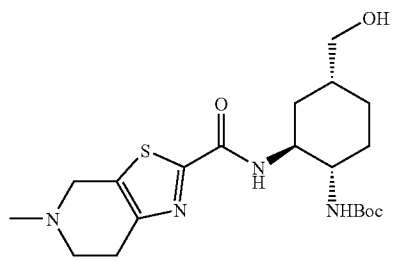

(1S,2S,4R)-N$^1$-tert-Butoxycarbonyl-4-(tert-butyldiphenylsilyloxymethyl)-N$^2$-[(5-methyl-4,5,6,7-tetrahydrothiazolo[5,4-c]pyridin-2-yl)carbonyl]-1,2-cyclohexanediamine (1.25 g) was dissolved in tetrahydrofuran (30 ml), and tetrabutylammonium fluoride (1 M solution, 2.5 ml), and the mixture was stirred at room temperature for 3 days. After the solvent was distilled off under reduced pressure, dichloromethane was added, and the reaction mixture was washed with water, the resultant organic layer was dried over anhydrous magnesium sulfate. The solvent was distilled off under reduced pressure, and the residue was purified by column chromatography on silica gel (methanol:dichloromethane=1:20–1:10) to obtain the title compound (540 mg) as a pale yellow amorphous substance.

$^1$H-NMR (CDCl$_3$) δ: 1.31(9H,s), 1.37–2.37(7H,m), 2.50 (3H,s), 2.76–2.82(2H,m), 2.89–2.98(2H,m), 3.56–3.75(5H, m), 3.91–3.94(1H,m), 4.80–4.82(1H,m). MS (FAB) m/z: 425(M+H)$^+$.

Referential Example 221

(1R*,2R*,4S*)-N$^2$(tert-Butoxycarbonyl)-N-$^1$[(5-chloroindol-2-yl)carbonyl]-4-hydroxymethyl-1,2-cyclohexanediamine

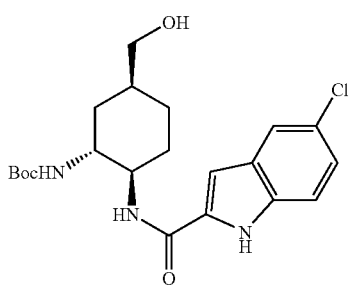

(1R*,2R*,4S*)-N$^2$-(tert-Butoxycarbonyl)-N$^1$-[(5-chloroindol-2-yl)carbonyl]-4-ethoxycarbonyl-1,2-cyclohexanediamine (735 mg) was dissolved in dichloromethane (10 ml), a 1N hexane solution (5 ml) of isobutyllithium hydride was added at −78° C., and the mixture was stirred for 3 hours and then 30 minutes at 0° C. A saturated aqueous solution of ammonium chloride was added at −78° C., the mixture was extracted with dichloromethane, and the resultant organic layer was washed with a saturated aqueous solution of sodium bicarbonate and saturated saline and then dried over anhydrous magnesium sulfate. The solvent was distilled off under reduced pressure, and the residue was purified by column chromatography on silica gel (dichloromethane:methanol= 19:1) to obtain the title compound (480 mg) as a colorless solid.

$^1$H-NMR (CDCl$_3$) δ: 1.20–2.30(7H,m), 3.60–3.86(4H, m), 4.64(1H,br.s), 6.87(1H,s), 7.20–7.48(3H,m), 9.15(1H, br.s). MS(ESI) m/z: 422(M+H)$^+$.

Referential Example 222

(1R,2R,4S)-N²-(tert-Butoxycarbonyl)-N¹-[(5-chloroindol-2-yl)carbonyl]-4-hydroxymethyl-1,2-cyclohexanediamine

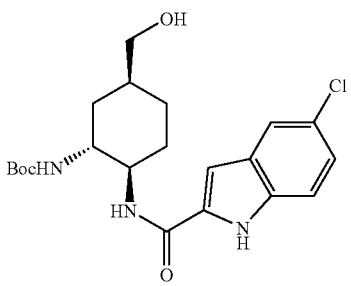

The title compound was obtained from (1R,2R,4S)-N²-(tert-butoxycarbonyl)-N¹-[(5-chloroindol-2-yl)carbonyl]-4-ethoxycarbonyl-1,2-cyclohexanediamine in a similar manner to Referential Example 221.

MS(ESI) m/z:. 422(M+H)⁺.

Referential Example 223

(1R*,2S*,4R*)-N²-tert-Butoxycarbonyl-N¹-[(5-chloroindol-2-yl)carbonyl]-4-(1-hydroxy-1-methylethyl)-1,2-cyclohexanidiamine

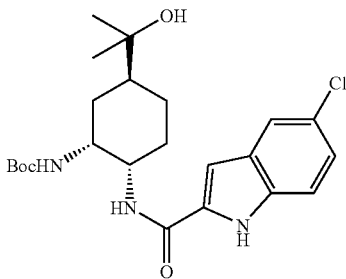

Methyllithium (1.14N solution, 2.27 ml) was added to a tetrahydrofuran solution (10 ml) of (1R*,2S*,4R*)-N²-tert-butoxycarbonyl-N¹-[(5-chloroindol-2-yl)carbonyl]-4-ethoxycarbonyl-1,2-cyclohexanediamine (200 mg) at −78° C., and the mixture was stirred for 1 hour and then 2 hours under ice cooling. An aqueous solution of ammonium chloride was added to the reaction mixture to extract the reaction mixture with chloroform, and the resultant organic layer was washed with saturated saline and then dried over anhydrous magnesium sulfate. The solvent was distilled off under reduced pressure, and the residue was purified by column chromatography on silica gel (hexane:ethyl acetate=1:3) to obtain the title compound (115 mg) as a colorless solid.

¹H-NMR (DMSO-d₆) δ: 1.04(6H,s), 1.33(9H,s), 0.97–2.05(7H,m), 3.80–4.02(2H,m), 6.43(1H,m), 7.01(1H, br.s), 7.16(1H,brd,J=8.8 Hz), 7.41(1H,d,J=8.8 Hz), 7.68(1H, s), 8.03–8.14(2H,m). MS (ESI) m/z: 450(M+H)⁺.

Referential Example 224

(1R*,2S*,4R*)-N¹-[(5-Chloroindol-2-yl)carbonyl]-4-(1-hydroxy-1-methylethyl)-1,2-cyclohexanediamine hydrochloride

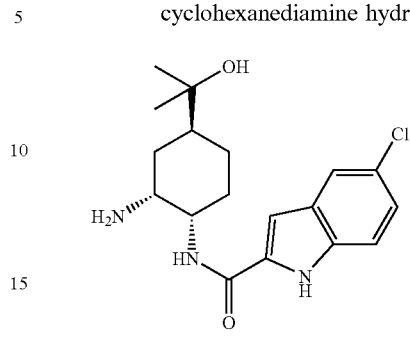

A 4N hydrogen chloride solution in dioxane (10 ml) was added to an ethanol solution (5 ml) of (1R*,2S*,4R*)-N²tert-butoxycarbonyl-N¹-[(5-Chloroindol-2-yl)carbonyl]-4-(1-hydroxy-1-methylethyl)-1,2-cyclohexanediamine, and the mixture was stirred at room temperature for 12 hours. The solvent was distilled off under reduced pressure to obtain the title compound (100 mg) as a colorless oil.

¹H-NMR (DMSO-d⁶) δ: 1.07(3H,s), 1.08(3H,s), 1.10–2.08(7H,s), 3.60–4.06(2H,m), 7.19(1H,dd,J=8.8 and 1.6 Hz), 7.27(1H,br.s), 7.44(1H,d,J=8.8 Hz), 7.72(1H,br.s), 7.92(1H,br.s), 8.43(1H,d,J=6.8 Hz). MS (ESI) m/z: 350(M+H)⁺.

Referential Example 225

(1R*,2S*,4S*)-1,2-Epoxy-4-methoxymethylcyclohexane

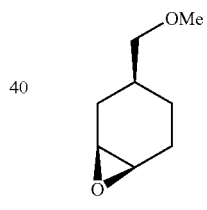

1) (1R*,3R*,4R*)-4-Iodo-6-oxabicyclo[3.2.1]octan-7-one (2.8 g) was dissolved in a mixed solvent of tetrahydrofuran (27 ml) and water (3 ml), concentrated hydrochloric acid (0.1 ml) was added, and the mixture was heated under reflux for 1 hour. The solvent was distilled off under reduced pressure to obtain (1R*,3R*,4R*)-3-hydroxy-4-iodocyclohexane-1-carboxylic acid (3.23 g) as a colorless solid.

2) The product (3.22 g) obtained by the reaction described above was dissolved in tetrahydrofuran (50 ml), borane-dimethyl sulfide complex (2 M tetrahydrofuran solution, 47 ml) was added under ice cooling, and the mixture was stirred at room temperature for 12 hours. The solvent was distilled off under reduced pressure, the residue was dissolved in isopropanol (10 ml), a 1N aqueous solution (12 ml) of sodium hydroxide was added, and the mixture was stirred for 12 hours. After the solvent was concentrated to about 1/5, the reaction mixture was diluted with water and dichloromethane to stir it for 10 minutes. An organic layer was separated, successively washed with a saturated aqueous solution of ammonium chloride and saturated saline and dried over anhydrous magnesium sulfate. The solvent was distilled off under reduced pressure, and the residue was purified by column chromatography on silica gel (ethyl acetate:hexane=1:2) to obtain (1R*,2S*,4S*)-1,2-epoxy-4-hydroxymethylcyclohexane (1.25 g) as a colorless oil.

3) The product (4.63 g) obtained by the reaction in 2) was dissolved in tetrahydrofuran (50 ml), potassium bis(trimethylsilyl)amide (0.5N toluene solution, 80 ml) was added, and methyl iodide (2.93 ml) was then added. After heating the mixture to 0° C., it was stirred for 1 hour, quenched with a saturated aqueous solution of ammonium chloride and then diluted with diethyl ether. An organic layer was separated, washed with saturated saline and dried over anhydrous magnesium sulfate. The solvent was distilled off under reduced pressure, and the residue was purified by column chromatography on silica gel (ethyl acetate:hexane=1:4) to obtain the title compound (3.7 g) as a colorless oil.

$^1$H-NMR (CDCl$_3$) δ: 0.89–1.63(5H,m), 1.80–2.05(2H,m), 1.89–3.06(4H,m), 3.16(3H,s).

Referential Example 226

(1R*,2R*,4S*)-2-Azido-4-methoxymethyl-1-cyclohexanol

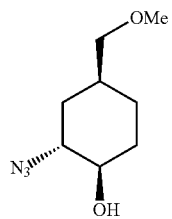

The title compound was obtained from (1R*,2S*,4S*)-1,2-epoxy-4-methoxymethylcyclohexane in a similar manner to Referential Example 155.

$^1$H-NMR (CDCl$_3$) δ: 1.45–1.70(5H,m), 1.77–1.95(2H,m), 1.98–2.08(1H,m), 3.30(2H,d,J=6.8 Hz), 3.35(3H,s), 3.45–3.65(2H,m).

Referential Example 227

(1R*,2R*,4S*)-2-(tert-Butoxycarbonylamino)-4-methoxy-methyl-1-cyclohexanol

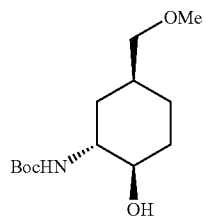

The title compound was obtained from (1R*,2R*,4S*)-2-azido-4-methoxymethyl-1-cyclohexanol in a similar manner to Referential Example 156.

$^1$H-NMR (CDCl$_3$) δ: 1.35–2.01(16H,m), 3.05(1H,br.s), 3.32(2H,d,J=7.1 Hz), 3.34(3H,s), 3.44–3.62(2H,m), 4.59 (1H,br.s).

Referential Example 228

(1R*,2S*,4R*)-1-Azido-2-(tert-butoxycarbonylamino)-4-methoxymethylcyclohexane

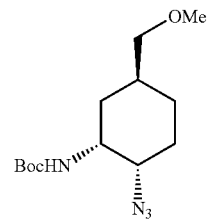

The title compound was obtained from (1R*,2R*,4S*)-2-(tert-butoxycarbonylamino)-4-methoxy-methyl-1-cyclohexanol in a similar manner to Referential Example 157.

$^1$H-NMR (CDCl$_3$) δ: 1.31–1.93(16H,m), 3.27(2H,d,J=6.4 Hz), 3.32(3H,s), 3.57–3.70(1H,m), 3.67(1H,br.s), 3.95(1H,br.s).

Referential Example 229

(1R*,2S*,4R*)-N$^2$-(tert-Butoxycarbonyl)-4-methoxymethyl-1,2-cyclohexanediamine

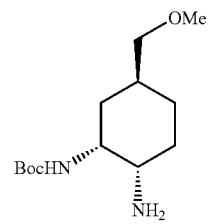

The title compound was obtained from (1R*,2S*,4R*)-1-azido-2-(tert-butoxycarbonylamino)-4-methoxymethylcyclohexane in a similar manner to Referential Example 47.

Referential Example 230

(1R*,2S*,4R*)-N$^2$ (tert-Butoxycarbonyl)-N$^1$-[(5-chloroindol-2-yl)carbonyl]-4-methoxymethyl-1,2-cyclohexanediamine

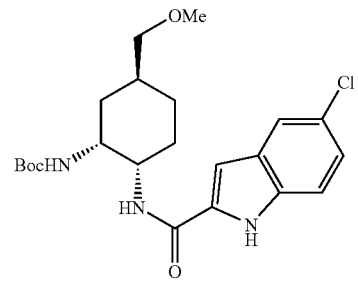

The title compound was obtained from (1R*,2S*,4R*)-N$^2$-(tert-butoxycarbonyl)-4-methoxymethyl-1,2-cyclohexanediamine and 5-chloroindole-2-carboxylic acid in a similar manner to Referential Example 159.

$^1$H-NMR (CDCl$_3$) δ: 1.12–2.31(16H,m), 3.14–3.30(2H,m), 3.34(3H,s), 3.92(1H,br.s), 4.13(1H,br.s), 4.88(1H,br.s), 6.82(1H,s), 7.21(1H,br.d,J=8.8 Hz), 7.33(1H,d,J=8.8 Hz), 7.60(1H,s), 8.09(1H,br.s), 9.42(1H,br.s). MS (ESI) m/z: 436(M+H)$^+$.

Referential Example 231

Mixture of (1R*,2S*,4R*,5S*)-N$^1$,N$^2$-bis(benzyloxy-carbonyl)-4,5-dihydroxy-1,2-cyclohexanediamine and (1R*,2S*,4S*,5R*)-N$^1$,N$^2$-bis(benzyloxycarbonyl)-4,5-dihydroxy-1,2-cyclohexanediamine

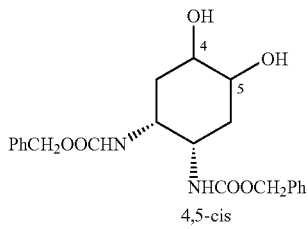

4,5-cis

The title compound was obtained from cis-N$^1$,N$^2$-bis(benzyloxycarbonyl)-4-cyclohexene-1,2-diamine in a similar manner to Referential Example 183.

Referential Example 232

Mixture of (1R*,2S*,4R*,5S*)-N$^1$,N$^2$-bis(benzyloxy-carbonyl)-4,5-isopropylidenedioxy-1,2-cyclohexanediamine and (1R*,2S*,4S*,5R*)-N$^1$,N$^2$-bis(benzyloxycarbonyl)-4,5-isopropylidenedioxy-1,2-cyclohexanediamine

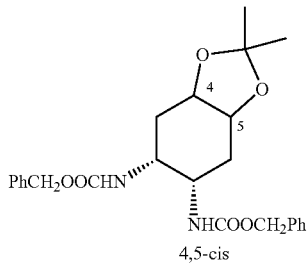

4,5-cis

The mixture (1.0 g) of (1R*,2S*,4R*,5S*)-N$^1$,N$^2$-bis-(benzyloxycarbonyl)-4,5-dihydroxy-1,2-cyclohexanediamine and (1R*,2S*,4S*,5R*)-N$^1$,N$^2$-bis(benzyloxycarbonyl)-4,5-dihydroxy-1,2-cyclohexanediamine was dissolved in tetrahydrofuran (20 ml), and 2,2-dimethoxypropane (443 ml) and pyridinium p-toluenesulfonate (61 mg) were added to stir the mixture at room temperature for 2 hours. After 2,2-dimethoxypropane (2 ml) was additionally added, and the mixture was stirred for 16 hours, saturated saline was added to the reaction mixture to extract it with ethyl acetate. After the resultant organic layer was washed with saturated saline and dried over anhydrous sodium sulfate, the solvent was distilled off under reduced pressure, and the residue was purified by column chromatography on silica gel (ethyl acetate:hexane= 1:2–1:1) to obtain the title compound (1.10 g) as a colorless amorphous solid.

$^1$H-NMR (CDCl$_3$) δ: 1.50(3H,s), 1.54–1.64(2H,m), 1.66 (3H,s), 2.16–2.19(1H,m), 2.39(1H,br.d,J=14.2 Hz), 3.47–3.49(1H,m), 3.80–3.82(1H,m), 4.16–4.19(1H,m), 4.25 (1H,s), 4.95(1H,d,J=8.1 Hz), 5.03(2H,d,J=12.0 Hz), 5.08 (2H,d,J=12.0 Hz), 5.21(1H,d,J=8.1 Hz), 7.31(10H,s).

Referential Example 233

Mixture of (1R*,2S*,4R*,5S*)-N$^1$-[(5-chloroindol-2-yl)-carbonyl]-4,5-isopropylidenedioxy-1,2-cyclohexanediamine and (1R*,2S*,4S*,5R*)-N$^1$-[(5-chloroindol-2-yl)-carbonyl]-4,5-isopropylidenedioxy-1,2-cyclohexanediamine

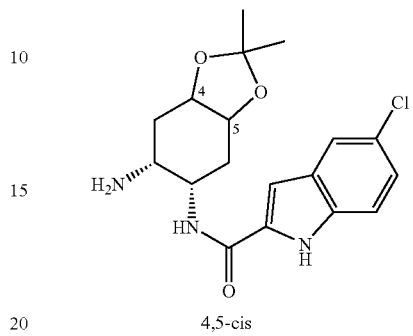

4,5-cis

The title compound was obtained from the mixture of (1R*,2S*,4R*,5S*)-N$^1$,N$^2$-bis(benzyloxycarbonyl)-4,5-isopropylidenedioxy-1,2-cyclohexanediamine and (1R*,2S*,4S*,5R*)-N$^1$,N$^2$-bis(benzyloxycarbonyl)-4,5-isopropylidenedioxy-1,2-cyclohexanediamine in a similar manner to Referential Example 197.

$^1$H-NMR (DMSO-d$_6$) δ: 1.44(3H,s), 1.47(3H,s), 1.59–1.72(2H,m), 1.93–1.96(1H,m), 2.23–2.26(2H,m), 2.66–2.69(1H,m), 2.93–2.95(1H,m), 3.60–3.62(1H,m), 4.15–4.16(1H,m), 4.22(1H,s), 7.15(1H,s), 7.17(1H,dd,J= 8.5, 2.0 Hz), 7.43(1H,d,J=8.5 Hz), 7.70(1H,s), 8.27(1H,s), 11.76(1H,s).

Referential Example 234

Mixture of dimethyl (1R*,2S*,4R*,5S*)-4,5-dimethoxy-cyclohexane-1,2-dicarboxylate and dimethyl (1R*,2S*,4S*,5R*)-4,5-dimethoxycyclohexane-1,2-dicarboxylate

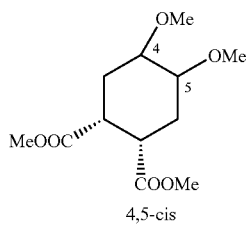

4,5-cis

Under argon atmosphere, methyl iodide (2.00 ml) and sodium hydride (60% oil suspension, 1.29 g) were successively added to a tetrahydrofuran solution (25 ml) of a mixture (3.74 g) of (1R*,2S*,4R*,5S*)-4,5-dihydroxycyclohexane-1,2-dicarboxylic acid and (1R*,2S*, 4S*,5R*)-4,5-dihydroxy-cyclohexane-1,2-dicarboxylic acid under ice cooling, and the mixture was stirred overnight at room temperature. Diethyl ether and water was added to the reaction mixture to conduct liquid separation. The resultant oil layer was dried over anhydrous magnesium sulfate. The solvent was distilled off under reduced pressure, and the residue was purified by column chromatography on silica gel (hexane:ethyl acetate=2:1) to obtain the title compound (2.64 g) as a colorless oil.

$^1$H-NMR (CDCl$_3$) δ: 1.35–1.45(1H,m), 1.80–1.90(1H, m), 2.10–2.16(1H,m), 2.34–2.40(1H,m), 2.65–2.75(1H,m), 2.93–3.01(1H,m), 3.20–3.26(1H,m), 3.35–3.45(7H,s), 3.69 (6H,s). MS (ESI) m/z: 261(M+H)⁺.

Referential Example 235

Mixture of (1R*,2S*,4R*,5S*)-4,5-dimethoxycyclohexane-1,2-dicarboxydihydrazide and (1R*,2S*,4S*,5R*)-4,5-dimethoxycyclohexane-1,2-dicarboxydihydrazide

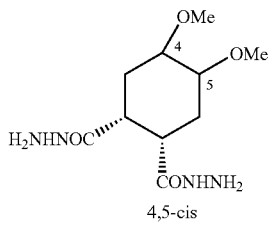

4,5-cis

Hydrazine monohydrate (1.97 ml) was added dropwise to an ethanol solution (10 ml) of the mixture (2.64 g) of dimethyl (1R*,2S*,4R*,5S*)-4,5-dimethoxycyclohexane-1,2-dicarboxylate and dimethyl (1R*,2S*,4S*,5R*)-4,5-dimethoxycyclohexane-1,2-dicarboxylate, and the resultant mixture was heated overnight under reflux. After the reaction mixture was cooled to room temperature, it was concentrated, and diethyl ether was added to the residue to solidify the residue, thereby obtaining the title compound (1.07 g).

¹H-NMR (DMSO-d₆) δ: 1.25–1.35(1H,m), 1.55–1.70 (2H,m), 1.91–2.00(1H,m), 2.40–2.50(1H,m), 2.55–2.70(1H, m), 3.12–3.20(1H,m), 3.20–3.40(6H,m), 3.64(1H,br.s), 4.06 (4H,br.s), 8.85(1H,br.s), 8.97(1H,br.s). MS (FAB) m/z: 261 (M+H)⁺.

Referential Example 236

Mixture of (1R*,2S*,4R*,5S*)-4,5-dimethoxy-1,2-cyclohexanediamine hydrochloride and (1R*,2S*,4S*,5R*)-4,5-dimethoxy-1,2-cyclohexanediamine hydrochloride

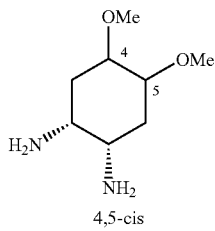

4,5-cis

Ice (3.7 g), concentrated hydrochloric acid (1.9 ml) and diethyl ether (4.1 ml) were successively added to the mixture (1.07 g) of (1R*,2S*,4R*,5S*)-4,5-dimethoxy-cyclohexane-1,2-dicarboxydihydrazide and (1R*,2S*,4S*, 5R*)-4,5-dimethoxycyclohexane-1,2-dicarboxydihydrazide. While stirring under ice cooling, water (1.6 ml) containing sodium nitrite (709 mg) was added dropwise over 10 minutes. The mixture was stirred for 5 minutes under ice cooling to separate a diethyl ether layer, and the ether layer was dried over calcium chloride. Toluene (10 ml) was added to the solution, only diethyl ether was carefully distilled off under reduced pressure, and the resultant toluene solution was heated at 120° C. for 1 hour. The reaction mixture was added dropwise to concentrated hydrochloric acid (3 ml) heated to 60° C., and the mixture was stirred at 60° C. for 1 hour. After the reaction mixture was cooled to room temperature, it was concentrated, and ethanol was added to the residue. The mixture was concentrated. Ethyl acetate was added, and powder deposited was collected by filtration to obtain the title compound (745 mg).

¹H-NMR (DMSO-d₆) δ: 1.50–1.60(1H,m), 1.75–1.87 (1H,m), 2.05–2.15(1H,m), 2.31–2.40(1H,m), 3.20–3.40(9H, m), 3.75(1H,br.s), 8.67(6H,br.s). MS (FAB) m/z: 175(M+H)⁺.

Referential Example 237

(1R*,2S*,4R*)-N²-(tert-Butoxycarbonyl)-N¹-[(5-chloroindol-2-yl)carbonyl]-4-hydroxymethyl-1,2-cyclohexanediamine

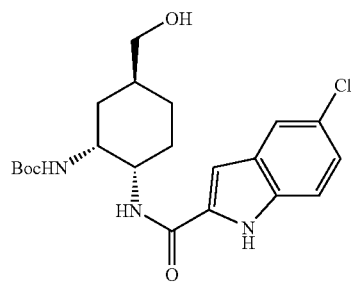

The title compound was obtained from (1R*,2S*,4R*)-N²-(tert-butoxycarbonyl)-N¹-[(5-chloroindol-2-yl) carbonyl]-4-ethoxycarbonyl-1,2-cyclohexanediamine in a similar manner to Referential Example 221.

¹H-NMR (CDCl₃) δ: 0.78–2.30(16H,m), 3.41–3.59(3H, m), 3.86–3.95(1H,m), 4.12–4.20(1H,m), 4.82–4.91(1H,m), 6.81(1H,s), 7.17–7.40(2H,m), 7.60(1H,s), 8.03(1H,br.s), 9.18(1H,br.s). MS (ESI) m/z: 422(M+H)⁺.

Referential Example 238

(1R*,2S*,4R*)-4-Azidomethyl-N²-(tert-butoxycarbonyl)-N¹-[(5-chloroindol-2-yl)carbonyl]-1,2-cyclohexanediamine

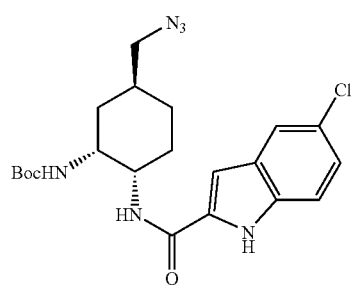

The title compound was obtained from (1R*,2S*,4R*)-N²-(tert-butoxycarbonyl)-N¹-[(5-chloroindol-2-yl) carbonyl]-4-hydroxymethyl-1,2-cyclohexanediamine in a similar manner to Referential Example 127.

Referential Example 239

(1R*,2S*)-N,N-Bis(tert-butoxycarbonyl)-4-[(1-ethoxycarbonyl)cyclopropan-1-yl]amino-1,2-cyclohexanediamine (Stereoisomer A and Stereoisomer B)

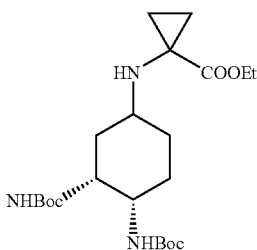

Ethyl 1-aminocyclopropanecarboxylate hydrochloride (1.63 g) was dissolved in dichloromethane (60 ml), and (1R*,2S*)-N,N-bis(tert-butoxycarbonyl)-4-oxo-1,2-cyclohexanediamine (3.0 g) and sodium triacetoxyborohydride (2.51 g) were added to stir the mixture at room temperature for 3 hours. An aqueous solution of sodium hydrogencarbonate was added to separate an organic layer. The organic layer was dried over anhydrous sodium sulfate. The solvent was distilled off under reduced pressure, and the residue was purified by column chromatography on silica gel (hexane:ethyl acetate=3:1→1:1) to obtain the title compounds (Stereoisomer A: 1.43 g and Stereoisomer B: 2.17 g) as colorless amorphous solids.

Stereoisomer A $^1$H-NMR (CDCl$_3$) δ: 0.90–1.00(1H,m), 1.05–1.15(1H,m), 1.20–1.85(29H,m), 2.00–2.10(1H,m), 3.20–3.35(2H,m), 3.65–3.75(1H,m), 4.11(2H,q,J=7.1 Hz), 4.75–4.95(2H,m). MS (FAB) m/z: 442(M+H)$^+$.

Stereoisomer B $^1$H-NMR (CDCl$_3$) δ: 0.90–1.70(29H,m), 1.85–1.95(1H,m), 1.95–2.10(1H,m), 2.20–2.30(1H,m), 2.85–2.95(1H,m), 3.20–3.45(2H,m), 4.13(2H,q,J=7.1 Hz), 4.80–4.95(2H,m). MS (FAB) m/z: 442(M+H)$^+$.

Referential Example 240

(1R*,2S*)-N$^2$-[(5-Chloroindol-2-yl)carbonyl]-4-[(1-ethoxycarbonyl)cyclopropan-1-yl]amino-1,2-cyclohexanediamine (Stereoisomer A) and (1R*,2S*)-N$^1$-[(5-chloroindol-2-yl)carbonyl]-4-[(1-ethoxycarbonyl)-cyclopropan-1-yl]amino-1,2-cyclohexanediamine (Stereoisomer A)

(1R*,2S*)-N,N-Bis(tert-butoxycarbonyl)-4-[(1-ethoxycarbonyl)cyclopropan-1-yl]amino-1,2-cyclohexanediamine (Stereoisomer A) (1.34 g) was dissolved in dichloromethane (20 ml), a saturated ethanol solution (20 ml) of hydrochloric acid was added, and the mixture was stirred for 90 minutes. The solvent was distilled off under reduced pressure to obtain (1R*,2S*)-4-[(1-ethoxycarbonyl)cyclopropan-1-yl]amino-1,2-cyclohexanediamine hydrochloride (Stereoisomer A) (1.07 g) as a colorless solid.

The above-described product was treated in the same manner as in Referential Example 125 to obtain the title compound.

One Title Compound:

$^1$H-NMR (CDCl$_3$+CD$_3$OD) δ: 0.95–1.05(2H,m), 1.20–1.35(6H,m), 1.45(1H,m), 1.50–1.90(4H,m), 2.00–2.10 (1H,m), 3.05(1H,m), 3.30(1H,m), 3.76(1H,m), 4.13(2H,q, J=7.1 Hz), 6.98(1H,d,J=2.2 Hz), 7.21(1H,dd,J=8.8, 2.2 Hz), 7.35(1H,d,J=8.8 Hz), 7.60(1H,d,J=1.5 Hz). MS (FAB) m/z: 419(M+H)$^+$.

The Other Title Compound:

$^1$H-NMR (CDCl$_3$+CD$_3$OD) δ: 0.99(1H,m), 1.20–1.35 (6H,m), 1.35–1.90(6H,m), 2.15–2.25(1H,m), 2.61(1H,m), 3.36(1H,m), 4.05–4.20(3H,m), 6.88(1H,s), 7.22(1H,dd, J=8.8, 2.0 Hz), 7.35(1H,d,J=8.8 Hz), 7.60(1H,d,J=2.0 Hz). MS (FAB) m/z: 419(M+H)$^+$.

Referential Example 241

4-(tert-Butoxycarbonylamino)-1-cyclohexene

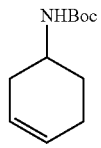

3-Cyclohexene-1-carboxylic acid (25.3 g) was dissolved in tert-butanol (250 ml), triethylamine (28 ml) and diphenylphosphorylazide (43.0 ml) were added, and the mixture was stirred for 1 hour at room temperature and 2 days at 90° C. The solvent was distilled off under reduced pressure, and the residue was purified by column chromatography on silica gel (dichloromethane) and then repurified by column chromatography on silica gel (hexane:ethyl acetate=20:1) to obtain the title compound (24.9 g) as colorless crystals.

$^1$H-NMR (CDCl$_3$) δ: 1.45(9H,s), 1.45–1.60(1H,m), 1.80–1.90(2H,m), 2.05–2.20(2H,m), 2.35–2.45(1H,m), 3.78 (1H,br), 4.56(1H,br), 5.55–5.65(1H,m), 5.65–5.75(1H,m).

Referential Example 242

(1R*,2S*)-4-(tert-Butoxycarbonylamino)-1,2-dihydroxy-cyclohexane

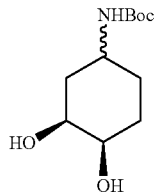

The title compound was obtained from 4-(tert-butoxycarbonylamino)-1-cyclohexene in a similar manner to Referential Example 183.

$^1$H-NMR (CDCl$_3$) δ: 1.15–1.30(1/2H,m), 1.35–2.00(15H, m), 2.15–2.30(3/2H,m), 2.40–2.60(1H,m), 3.64(1H,br), 3.75–3.90(3/2H,m), 4.00(1/2H,br). MS (FAB) m/z: 232(M+H)$^+$.

Referential Example 243

(1R*,2S*)-4-(tert-Butoxycarbonylamino)-1,2-diazidocyclohexane (Stereoisomer A and Stereoisomer B)

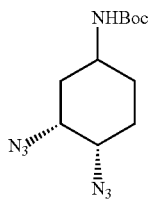

The respective title compounds were obtained from (1R*,2S*)-4-(tert-butoxycarbonylamino)-1,2-dihydroxycyclohexane in a similar manner to Referential Example 127.

Stereoisomer A
$^1$H-NMR (CDCl$_3$) δ: 1.45(9H,s), 1.40–1.55(1H,m), 1.55–1.80(3H,m), 1.95–2.15(2H,m), 3.53(1H,m), 3.59(1H,br), 3.80(1H,m), 4.70(1H,br).

Stereoisomer B
$^1$H-NMR (CDCl$_3$) δ: 1.27(1H,m), 1.44(9H,s), 1.40–1.55(1H,m), 1.80–2.00(2H,m), 2.00–2.15(1H,m), 2.21(1H,m), 3.48(1H,m), 3.77(1H,br), 3.89(1H,br), 4.34(1H,br).

Referential Example 244

4-(4-Pyridyl)benzoic acid hydrochloride

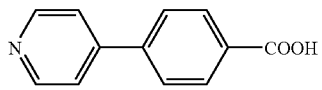

4-Bromopyridine hydrochloride (11.7 g) and 4-carboxyphenylboric acid (10.0 g) were dissolved in a mixed solvent of toluene (250 ml) and water (250 ml), tetrakis(triphenylphosphine)palladium(0) (5.0 g) and anhydrous sodium carbonate (25.4 g) were successively added, and the mixture was heated under reflux at 120° C. for 19 hours. After the reaction mixture was cooled to room temperature, ethyl acetate was added to the reaction mixture to extract it with water. Concentrated hydrochloric acid was added to the water layer to acidify it. The water layer was washed with ethyl acetate and then concentrated, and solids deposited were collected to obtain the title compound (8.37 g) as a colorless solid.

$^1$H-NMR (DMSO-d$_6$) δ: 8.11(2H,d,J=8.8 Hz), 8.14(2H,d,J=8.8 Hz), 8.35(2H,d,J=6.6 Hz), 8.97(2H,d,J=6.6 Hz). MS (FAB) m/z: 200(M+H)$^+$.

Referential Example 245

Methyl 4-(4-pyridyl)benzoate

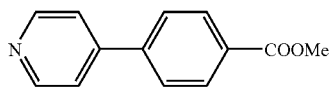

4-(4-Pyridyl)benzoic acid hydrochloride (12.4 g) was dissolved in methanol (200 ml), concentrated sulfuric acid (5 ml) was added at room temperature, and the mixture was heated under reflux for 3 hours. After completion of the reaction, the solvent was distilled off, and a saturated aqueous solution of sodium hydrogencarbonate was added to the residue to extract it with ethyl acetate. The extract was dried over anhydrous sodium sulfate, the solvent was distilled off, and hexane was added to the residue to solidify it, thereby obtaining the title compound (9.86 g) as colorless powder.

$^1$H-NMR (CDCl$_3$) δ: 3.96(3H,s), 7.54(2H,d,J=5.9 Hz), 7.71(2H,dJ=8.3 Hz), 8.16(2H,d,J=8.3 Hz), 8.71(2H,d,J=5.9 Hz).

Referential Example 246

4-(4-Methoxycarbonylphenyl)pyridine N-oxide

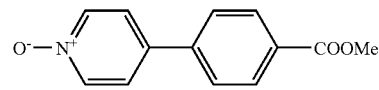

Methyl 4-(4-pyridyl)benzoate (1.49 g) was dissolved in dichloromethane (30 ml), 70% m-chloroperbenzoic acid (3.46 g) was added, and the mixture was stirred at room temperature for 1 hour. An aqueous solution of sodium sulfite was added to conduct liquid separation. The resultant organic layer was washed with a saturated aqueous solution of sodium hydrogencarbonate and then dried over anhydrous sodium sulfate. The solvent was distilled off to obtain the title compound (1.33 g) as white powder.

$^1$H-NMR (DMSO) δ: 3.88(3H,s), 7.86(2H,d,J=7.2 Hz), 7.94(2H,d,J=8.3 Hz), 8.05(2H,d,J=8.3 Hz), 8.30(2H,d,J=7.2 Hz). MS (FAB) m/z: 230(M+H)$^+$.

Referential Example 247

4-(4-Carboxyphenyl)pyridine N-oxide

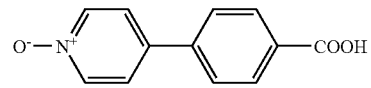

4-(4-Carboxyphenyl)pyridine N-oxide (802 mg) was dissolved in dioxane (20 ml), a 1N aqueous solution (5 ml) of sodium hydroxide was added, and the mixture was refluxed for 1 hour and then stirred at room temperature for 2 hours. 1N Hydrochloric acid (5 ml) was added to neutralize it. Further, water (5 ml) was added, and precipitate formed was collected by filtration to obtain the title compound (627 mg) as a white solid.

$^1$H-NMR (DMSO) δ: 7.85(2H,d,J=7.2 Hz), 7.91(2H,d,J=8.3 Hz), 8.03(2H,d,J=8.3 Hz), 8.30(2H,d,J=7.2 Hz).

Referential Example 248

2-(4-Carboxyphenyl)pyridine N-oxide

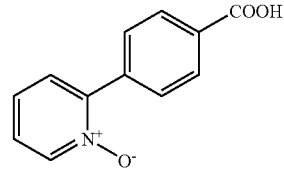

2-(4-Ethoxycarbonylphenyl)pyridine N-oxide (260 mg) synthesized from 4-(2-pyridyl)benzoic acid in the same manner as in the above Referetnial Example was dissolved in 1,4-dioxane (10 ml), a 1N aqueous solution (2.00 ml) of sodium hydroxide was added, and the mixture was heated under reflux for 2 hours. The reaction mixture was concentrated under reduced pressure, 1N hydrochloric acid (6 ml) was added to the residue, and precipitate formed was collected by filtration to obtain the title compound (202 mg) as a colorless amorphous solid.

$^1$H-NMR (DMSO-$d_6$) δ: 7.41–7.45(2H,m), 7.65–7.69(1H,m), 7.94(2H,d,J=8.3 Hz), 8.02(2H,d,J=8.3 Hz), 8.34–8.38(1H,m), 13.09(1H,s). MS (FAB) m/z: 216(M+H)$^+$.

Referential Example 249

(1R,2R,4S)-N$^2$-(tert-Butoxycarbonyl)-N$^1$-(5-chloroindol-2-yl)carbonyl-4-ethoxycarbonyl-1,2-cyclohexanediamine

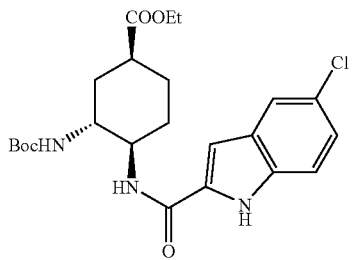

1) (1R,2R,4S)-N$^2$-tert-Butoxycarbonyl-4-ethoxycarbonyl-1,2-cyclohexanediamine was obtained as a pale brown oil from ethyl (1S,3R,4R)-4-azido-3-(tert-butoxycarbonylamino)cyclohexane-1-carboxylate in a similar manner to Referential Example 158.

2) The title compound was obtained as a colorless solid from the product described above in a similar manner to Referential Example 159.

$^1$H-NMR (CDCl$_3$) δ: 1.22–1.72(5H,m), 2.15–2.28(2H,m), 2.41–2.49(1H,m), 2.85(1H,brs), 3.62–3.75(1H,m), 3.78–3.92(1H,m), 4.12–4.28(2H,m), 4.56–4.63(1H,m), 6.88(1H,brs), 7.20(1H,dd,J=8.8 and 2.0 Hz), 7.33(1H,d,J=8.8 Hz), 7.52–7.57(1H,m), 7.59(1H,d,J=2.0 Hz), 9.24(1H,s). MS (ESI) m/z: 464(M+H)$^+$.

Referential Example 250

6-Chloro-2-cyanoquinoline

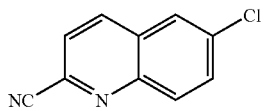

6-Chloroquinoline (2.50 g) was dissolved in dichloromethane (25 ml), and m-chloroperbenzoic acid (3.71 g) was added under ice cooling to stir the mixture at room temperature for 1 hour. After the reaction mixture was diluted with dichloromethane, the diluted mixture was washed with an aqueous solution of sodium thiosulfate and an aqueous solution of sodium hydroxide and dried over anhydrous sodium sulfate. The solvent was distilled off under reduced pressure, and the residue was dissolved in dichloromethane (40 ml), and trimethylsilyl cyanide (2.0 ml) and N,N-dimethylcarbamoyl chloride (1.50 ml) were added to heat the resultant mixture for 9 hours under reflux. After trimethylsilyl cyanide (2.0 ml) and N,N-dimethylcarbamoyl chloride (1.50 ml) were additionally added, and the mixture was heated for 16 hours under reflux, the reaction mixture was diluted with dichloromethane, and a 10% aqueous solution (40 ml) of potassium carbonate was added to stir the mixture for 30 minutes. After an organic layer was separated and dried over anhydrous sodium sulfate, the solvent was distilled off under reduced pressure. Dichloromethane was added to the residue, and crystals deposited were collected by filtration to obtain the title compound (1.77 g) as colorless crystals. Further, a mother liquor was purified by column chromatography on silica gel (dichloromethane) to obtain the title compound (0.80 g) as pale yellow crystals.

$^1$H-NMR (DMSO-$d_6$) δ: 7.94(1H,dd,J=9.0, 2.2 Hz), 8.09(1H,d,J=8.5 Hz), 8.15(1H,d,J=9.0 Hz), 8.29(1H,d,J=2.2 Hz), 8.63(1H,d,J=8.5 Hz). MS (FAB) m/z: 189(M+H)$^+$.

Referential Example 251

6-Chloroquinoline-2-carboxylic acid

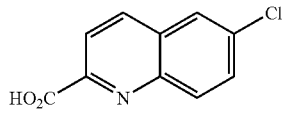

6-Chloro-2-cyanoquinoline (1.73 g) was dissolved in concentrated hydrochloric acid (40 ml), and the solution was heated for 19 hours under reflux. The reaction mixture was cooled to room temperature, and deposits were collected by filtration and then washed with water to obtain the title compound (1.81 g) as a colorless solid.

$^1$H-NMR (DMSO-$d_6$) δ: 7.87(1H,dd,J=9.0, 2.4 Hz), 8.10–8.20(2H,m), 8.24(1H,d,J=2.2 Hz), 8.52(1H,d,J=8.5 Hz). MS (FAB) m/z: 208(M+H)$^+$.

Referential Example 252

(1S,2R,4S)-N$^1$-Benzyloxycarbonyl-N$^2$-(tert-butoxycarbonyl)-4-ethoxycarbonylcyclohexanediamine

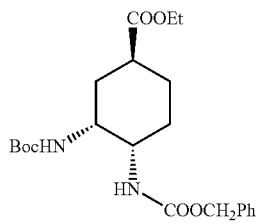

(1S,2R,4S)-N$^2$-(tert-Butoxycarbonyl)-4-ethoxycarbonylcyclohexanediamine (3.10 g) was dissolved in tetrahydrofuran (50 ml), and a saturated aqueous solution (50 ml) of sodium hydrogencarbonate waa added. After benzyloxycarbonyl chloride (1.71 ml) was added dropwise to the reaction mixture under ice cooling, the mixture was stirred at room temperature for 3 days. Ethyl acetate (200 ml) and water (200 ml) were added to the reaction mixture to conduct liquid separation. After the resultant organic layer was dried over anhydrous sodium sulfate, the solvent was distilled off under reduced pressure. Solids deposited were collected by filtration to obtain the title compound (3.24 g) as a colorless solid.

$^1$H-NMR (CDCl$_3$) δ: 1.24 (3H,t,J=7.1 Hz), 1.29–1.44(1H,m), 1.51–1.64(1H,m), 1.72–2.02(4H,m), 2.27–2.40(1H, m), 3.60–3.73(1H, m), 4.00–4.15(3H, m), 4.59(1H,br.s), 5.01–5.13(2H,m), 5.26(1H, br.s), 7.27–7.38(5H, m).

Referential Example 253

(1S,2R,4S)-4-Carboxy-N¹-benzyloxycarbonyl-N²-(tert-butoxycarbonyl)-1,2-cyclohexanediamine

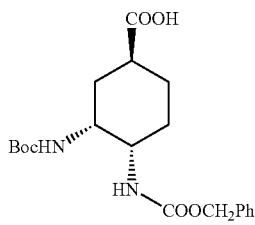

(1S,2R,4S)-N¹-Benzyloxycarbonyl-N²-(tert-butoxycarbonyl)-4-ethoxycarbonyl-1,2-cyclohexanediamine (620 mg) was dissolved in tetrahydrofuran (10 ml), and an aqueous solution (5.0 ml) of lithium hydroxide monohydrate (93 mg) was added to stir the mixture at room temperature for 16 hours. After lithium hydroxide monohydrate (221 mg) was additionally added to the reaction mixture, and the mixture was stirred at room temperature for 2 hours, the reaction mixture was neutralized with 1N hydrochloric acid and extracted with methylene chloride. An organic layer was washed with saturated saline and then dried over anhydrous sodium sulfate. The solvent was distilled off under reduced pressure to obtain the title compound (580 mg) as a colorless foamy substance.

¹H-NMR (CDCl₃) δ: 1.22–2.02(6H, m), 1.44(9H,s), 2.27–2.45(1H,br), 3.71–3.76(1H,br), 4.09(1H,br), 4.66–4.71(1H,br), 5.10(2H,s), 5.26(1H,br), 6.15(1H,br), 7.35(5H,s). MS (FAB m/z: 393(M+H)⁺.

Referential Example 254

(1S,2R,4S)-N¹-Benzyloxycarbonyl-N²-(tert-butoxycarbonyl)-4-(N,N-dimethylcarbamoyl)-1,2-cyclohexanediamine

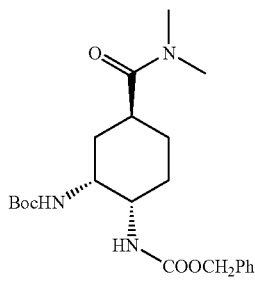

(1S,2R,4S)-4-Carboxy-N¹-benzyloxycarbonyl-N²-(tert-butoxycarbonyl)-1,2-cyclohexanediamine was dissolved in dichloromethane (50 ml), and dimethylamine hydrochloride (240 mg), triethylamine (0.41 ml), 3-(3-dimethylaminopropyl)-1-ethylcarbodiimide hydrochloride (420 mg) and 1-hydroxybenzotriazole monohydrate (340 mg) were added to stir the mixture at room temperature for 1 hour. Dimethylamine hydrochloride (480 mg) and triethylamine (0.82 ml) were additionally added to the reaction mixture to stir the mixture at room temperature for additional 18 hours. The reaction mixture was poured into water to separate an organic layer. After the organic layer was washed with 1N hydrochloric acid and saturated saline and dried over anhydrous sodium sulfate. The solvent was distilled off under reduced pressure, and the residue was purified by column chromatography on silica gel (methanol:methylene chloride=3:47→2:23) to obtain the title compound (620 mg) as a colorless foamy substance.

¹H-NMR (CDCl₃) δ: 1.26–1.98 (6H,m), 1.44 (9H,s), 2.57–2.63(1H,m), 2.93(3H,s), 3.02(3H,s), 3.70(1H,br.s), 4.14 (1H,br.s), 4.65(1H,br.s), 5.10(2H,s), 5.05–5.13(1H,br), 7.35(5H,s). MS (FAB) m/z=420(M+H)⁺.

Referential Example 255

(1S,2R,4S)-N²-(tert-Butoxycarbonyl)-4-(N,N-dimethylcarbamoyl)-1,2-cyclohexanediamine

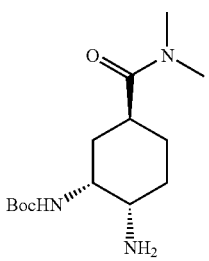

(1S,2S,4R)-N¹-Benzyloxycarbonyl-N²-(tert-butoxycarbonyl)-4-(N,N-dimethylcarbamoyl)-1,2-cyclohexanediamine (560 mg) was dissolved in tetrahydrofuran (100 ml), and 10% palladium on carbon (220 mg) was added to stir the mixture for 17 hours in a hydrogen atmosphere. After the catalyst was removed by filtration, the filtrate was concentrated to obtain the title compound (370 mg) as a colorless oil.

¹H-NMR (CDCl₃) δ: 1.21–1.87(6H,m), 1.45(9H,s), 2.64–2.75(1H,m), 2.92(3H,s), 3.02(3H,s), 3.73–3.78(2H, br.s), 4.93(1H,br.s). MS (FAB) m/z: 286(M+H)⁺.

Referential Example 256

(1S,2R,4S)-N²-(tert-Butoxycarbonyl)-N¹-[(6-chloroquinolin-2-yl)carbonyl]-4-(N,N-dimethylcarbamoyl)-1,2-cyclohexanediamine

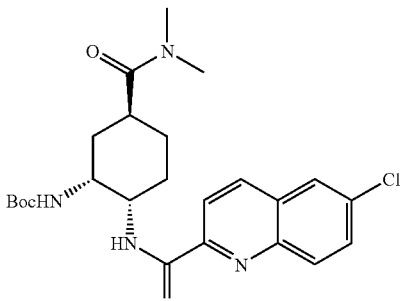

The title compound was obtained from (1S,2R,4S)-N²-(tert-butoxycarbonyl)-4-(N,N-dimethylcarbamoyl)-1,2-cyclohexanediamine and 6-chloroquinoline-2-carboxylic acid in a similar manner to Referential Example 159.

¹H-NMR (CDCl₃) δ: 1.41(9H,br), 1.50–1.70(1H,m), 1.75–1.95(2H,m), 1.95–2.25(3H,m), 2.65–2.80(1H,m), 2.96 (3H,s), 3.07(3H,s), 4.15–4.30(1H,m), 4.30–4.40(1H,m), 4.95(1H,br), 7.66(1H,d,J=8.8 Hz), 7.84(1H,s), 8.00(1H,d,J= 8.8 Hz), 8.19(1H,d,J=8.6 Hz), 8.30(1H,d,J=8.6 Hz) MS (FAB) m/z: 475(M+H)⁺.

Referential Example 257

(±)-N-Formyl-(4-chlorophenyl)alanine methyl ester

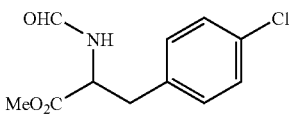

(±)-(4-Chlorophenyl)alanine methyl ester hydrochloride (2.00 g) was suspended in dichloromethane (20 ml), and 3-(3-dimethylaminopropyl)-1-ethylcarbodiimide hydrochloride (1.60 g), 1-hydroxybenzotriazole monohydrate (1.23 g), N-methylmorpholine (1.90 ml) and formic acid (0.30 ml) were added to stir the mixture for 15 minutes. After a process in which formic acid (0.30 ml) was additionally added to stir the mixture for 15 minutes was repeated 3 times, the reaction mixture was diluted with dichloromethane. After an ogranic layer was washed with water and then dried over anhydrous sodium sulfate, the solvent was distilled off under reduced pressure. The residue was purified by column chromatography on silica gel (dichloromethane methanol=40:1) to obtain the title compound (1.21 g) as a yellow oil.

$^1$H-NMR (CDCl$_3$) δ: 3.10(1H,dd,J=13.9, 5.6 Hz), 3.18 (1H,dd,J=13.9, 5.9 Hz), 3.75(3H,s), 4.95(1H,m), 6.07(1H, br), 7.05(2H,d,J=8.3 Hz), 7.27(2H,d,J=8.3 Hz), 8.18(1H,s). MS (FAB) m/z: 242(M+H)$^+$.

Referential Example 258

Methyl 7-chloroisoquinoline-3-carboxylate

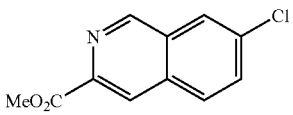

(±)-N-Formyl-(4-chlorophenyl)alanine methyl ester (1.45 g) was dissolved in dichloromethane (40 ml), and oxalyl chloride (0.57 ml) was added dropwise. After the mixture was stirred at room temperature for 30 minutes, ferric chloride (1.17 g) was added at an ambient temperature of about −10° C. to stir the mixture at room temperature for 4 days. 1N Hydrochloric acid was added, and the resultant mixture was diluted with dichloromethane to separate an organic layer. The organic layer was dried over anhydrous sodium sulfate. The solvent was distilled off under reduced pressure, and the residue was dissolved in methanol (38 ml), and concentrated sulfuric acid (2 ml) was added to heat the mixture for 20 hours under reflux. An aqueous solution of sodium hydrogencarbonate was added to the reaction mixture, the resultant mixture was extracted with dichloromethane, and the extract was dried over anhydrous sodium sulfate. The solvent was distilled off under reduced pressure, and the residue was purified by column chromatography on silica gel (hexane:ethyl acetate=2:1→ethyl acetate) to obtain the title compound (0.25 g) as colorless crystals.

$^1$H-NMR (CDCl$_3$) δ: 4.07(3H,s), 7.74(1H,dd,J=8.8, 2.0 Hz), 7.94(1H,d,J=8.8 Hz), 8.06(1H,d,J=2.0 Hz), 8.59(1H,s), 9.28(1H,s).

Referential Example 259

7-Chloroisoquinoline-3-carboxylic acid hydrochloride

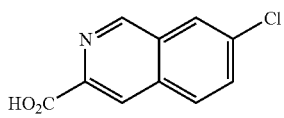

Methyl 7-chloroisoquinoline-3-carboxylate (0.23 g) was dissolved in concentrated hydrochloric acid (10 ml) to heat the mixture for 18 hours under reflux. The temperature of the reaction mixture was dropped to room temperature, and deposits were collected by filtration and then washed with water to obtain the title compound (0.21 g) as a colorless solic.

$^1$H-NMR (DMSO-d$_6$) δ: 7.96(1H,m), 8.29(1H,d,J=8.5 Hz), 8.44(1H,s), 8.72(1H,s), 9.45(1H,d,J=6.6 Hz). MS (FAB) m/z: 208(M+H)$^+$.

Referential Example 260

(1S,2R,4S)-N$^2$-(tert-Butoxycarbonyl)-N$^1$-[(7-chloroisoquinolin-3-yl)carbonyl]-4-(N,N-dimethylcarbamoyl)-1,2-cyclohexanediamine

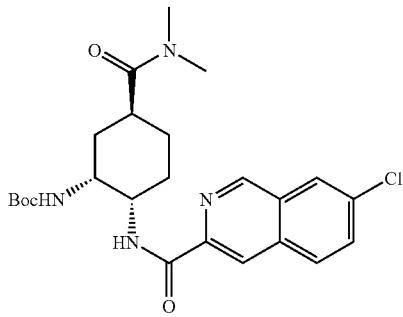

The title compound was obtained from (1S,2R,4S)-N$^2$-(tert-butoxycarbonyl)-4-(N,N-dimethylcarbamoyl)-1,2-cyclohexanediamine and 7-chloroisoquinoline-2-carboxylic hydrochloride in a similar manner to Referential Example 159.

$^1$H-NMR (CDCl$_3$) δ: 1.30–1.65(10H,br), 1.75–1.90(2H, m), 1.90–2.25(3H,m), 2.65–2.90(1H,br), 2.96(3H,s), 3.08 (3H,s), 4.20–4.30(1H,m), 4.30–4.40(1H,m), 4.93(1H,br), 7.68(1H,m), 7.90(1H,br), 7.99(1H,s), 8.35–8.70(2H,m), 9.01(1H,br). MS (FAB) m/z: 475(M+H)$^+$.

Example 1

(±)-cis-$N^1$-[(5-Chloroindol-2-yl)carbonyl]-$N^2$-[(5-methyl-4,5,6,7-tetrahydrothiazolo[5,4-c]pyridin-2-yl)carbonyl]-1,2-cyclopropanediamine hydrochloride

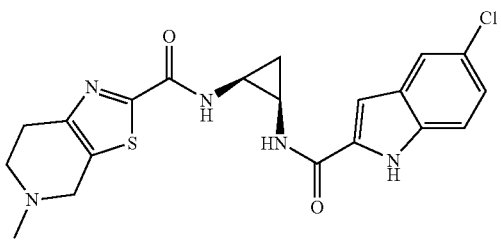

1-Hydroxybenzotriazole monohydrate (71 mg) and 1-(3-dimethylaminopropyl)-3-ethylcarbodiimide hydrochloride (100 mg) were added to a solution with (±)-cis-N-[(5-chloroindol-2-yl)carbonyl]-1,2-cyclopropanediamine (108 mg) and lithium 5-methyl-4,5,6,7-tetrahydrothiazolo[5,4-c]pyridine-2-carboxylate (124 mg) dissolved in N,N-dimethylformamide (3 ml) at room temperature, and the mixture was stirred for 8 days. After concentrating the reaction mixture under reduced pressure using a vacuum pump, water (50 ml) and a saturated aqueous solution (50 ml) of sodium hydrogencarbonate were added to the residue to conduct extraction with dichloromethane. The resultant organic layers were collected and dried over anhydrous sodium sulfate, the solvent was distilled off under reduced pressure, and the residue was purified by preparative thin-layer chromatography on silica gel (dichloromethane:methanol=10:1). After 1N hydrochloric acid, dichloromethane and methanol were added to the thus-obtained amorphous substance, the mixture was concentrated to obtain the title compound (72 mg) as a colorless solid.

$^1$H-NMR (DMSO-$d_6$) δ: 1.15–1.35(2H,m), 2.88(3H,s), 2.95–3.25(4H,m), 3.35–3.75(2H,m), 4.32–4.45(1H,m), 4.68 (1H,br,J=15.4 Hz), 7.08(1H,s), 7.17(1H,dd,J=8.6, 2.1 Hz), 7.41(1H,d,J=8.6 Hz), 7.70(1H,s), 8.50(1H,br,J=11.0 Hz), 8.56(1H,br.s), 11.56(1H,br,J=19.3 Hz), 11.86(1H,s). MS (FAB) m/z: 430(M+H)$^+$.

Example 2

(±)-cis-$N^1$-[(5-Chloroindol-2-yl)carbonyl]-$N^2$-[(5-methyl-4,5,6,7-tetrahydrothiazolo[5,4-c]pyridin-2-yl)carbonyl]-1,2-cyclobutanediamine hydrochloride

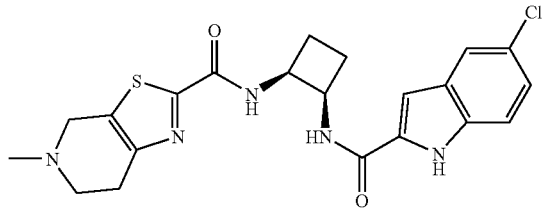

Lithium 5-methyl-4,5,6,7-tetrahydrothiazolo-[5,4-c]pyridine-2-carboxylate (136 mg), 1-(3-dimethylaminopropyl)-3-ethylcarbodiimide hydrochloride (255 mg) and 1-hydroxybenzotriazole monohydrate (90 mg) were added to a solution with (±)-cis-N-[(5-chloroindol-2-yl)carbonyl]-1,2-cyclobutanediamine (117 mg) dissolved in N,N-dimethylformamide (5 ml), and the mixture was stirred overnight at room temperature. The solvent was then distilled off under reduced pressure using a vacuum pump, and dichloromethane and a saturated aqueous solution of sodium hydrogencarbonate were added to the residue to conduct liquid separation. The resultant organic layer was washed with saturated saline and dried over anhydrous sodium sulfate, the solvent was distilled off under reduced pressure, and the residue was purified by flash column chromatography on silica gel (methanol:dichloromethane=7:93). After ethyl acetate and a 1N ethanol solution of hydrochloric acid were added to the thus-obtained compound to acidify it, and the solvent was distilled off under reduced pressure. Ethyl acetate was added again, and precipitate formed was collected by filtration and dried to obtain the title compound (56 mg) as a colorless powder.

$^1$H-NMR (DMSO-$d_6$) δ: 2.00–2.35(4H,m), 2.88(3H,m), 3.10(2H,br.s), 3.20–3.75(3H,m), 4.20–4.85(3H,m), 7.09 (1H,s), 7.16(1H,d,J=8.8 Hz), 7.38(1H,d,J=8.8 Hz), 7.71(1H, s), 8.63(1H,d,J=8.3 Hz), 8.85(1H,d,J=8.6 Hz), 10.85–11.20 (1H,br), 11.81(1H,s). MS (FAB) m/z: 444(M+H)$^+$.

Example 3

(±)-trans-$N^1$-[(5-Chloroindol-2-yl)carbonyl]-$N^2$-[(5-methyl-4,5,6,7-tetrahydrothiazolo[5,4-c]pyridin-2-yl)carbonyl]-1,2-cyclopentanediamine hydrochloride

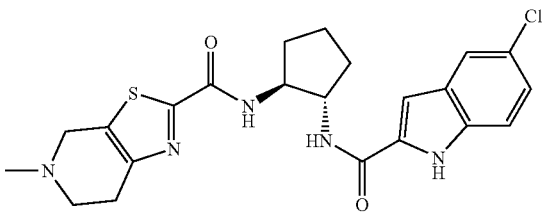

5-Chloroindole-2-carboxylic acid (80 mg), 1-(3-dimethylaminopropyl)-3-ethylcarbodiimide hydrochloride (98 mg), 1-hydroxybenzotriazole monohydrate (23 mg) and triethylamine (141 µl) were added to a solution with (±)-trans-N-[(5-methyl-4,5,6,7-tetrahydrothiazolo-[5,4-c]pyridin-2-yl)carbonyl]-1,2-cyclopentanediamine hydrochloride (120 mg) dissolved in N,N-dimethylformamide (5 ml), and the mixture was stirred at room temperature for 3 days. The solvent was distilled off under reduced pressure, and dichloromethane and a saturated aqueous solution of sodium hydrogencarbonate were added to the residue to conduct liquid separation. The resultant organic layer was dried over anhydrous sodium sulfate, the solvent was distilled off under reduced pressure, and the residue was purified by flash column chromatography on silica gel (dichloromethane:methanol=93:7). After dichloromethane (5 ml) and a 1N ethanol solution (282 µl) of hydrochloric acid were added to the thus-obtained pale yellow solid. Ethyl acetate was added, solvent was distilled off under reduced pressure and precipitate formed was collected by filtration to obtain the title compound (109 mg) as a pale yellow solid.

$^1$H-NMR (DMSO-$d_6$) δ: 1.64–1.74(4H,m), 1.98–2.02 (2H,m), 2.89(3H,s), 3.14(2H,br.s), 3.47–3.65(2H,m), 4.29–4.63(4H,m), 7.10(1H,d,J=1.5 Hz), 7.14(1H,dd,J=8.5, 2.0 Hz), 7.38(1H,d,J=8.5 Hz), 7.68(1H,d,J=2.0 Hz), 8.55 (1H,d,J=8.5 Hz), 8.91(1H,d,J=8.5 Hz), 11.49(1H,br.s), 11.76 (1H,s). MS (ESI) m/z: 458(M+H)$^+$.

Example 4

(±)-cis-N$^1$-[(5-Chloroindol-2-yl)sulfonyl]-N$^2$-[(5-methyl-4,5,6,7-tetrahydrothiazolo[5,4-c]pyridin-2-yl)carbonyl]-1,2-cyclopentanediamine hydrochloride

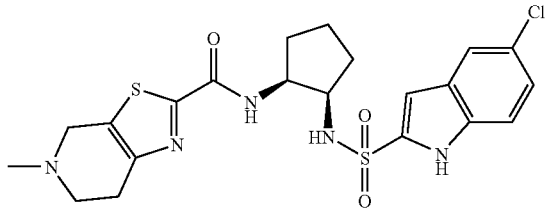

The title compound (182 mg) was obtained as a pale yellow solid by dissolving (±)-cis-N-[(5-chloro-1-phenylsulfonylindol-2-yl)sulfonyl]-1,2-cyclopentanediamine (409 mg), lithium 5-methyl-4,5,6,7-tetrahydrothiazolo[5,4-c]pyridine-2-carboxylate (250 mg) and 1-hydroxybenzotriazole monohydrate (61 mg) in N,N-dimethyl-formamide (7 ml) and causing 1-(3-dimethylaminopropyl)-3-ethylcarbodiimide hydrochloride (259 mg) to react as a condensing agent in a similar manner to Example 2.

$^1$H-NMR (DMSO-d$_6$) δ: 1.43–1.85(6H,m), 2.94(3H,s), 3.15(2H,br.s), 3.49–3.84(3H,m), 4.23(1H,t,J=7.5 Hz), 4.35–4.63(2H,brm), 6.78(1H,s), 7.22(1H,dd,J=8.8, 2.0 Hz), 7.30(1H,br.s), 7.54(1H,br.s), 7.88,7.90(1H, each s), 8.15 (1H,br,J=8.3 Hz), 11.55–11.75(1H,brm), 12.01(1H,br.s). MS (ESI) m/z: 494(M+H)$^+$.

Example 5

(±)-cis-N$^1$-[(5-Chloroindol-2-yl)sulfonyl]-N$^2$-[(5-methyl-4,5,6,7-tetrahydrothiazolo[5,4-c]pyridin-2-yl)carbonyl]-1,2-cyclohexanediamine hydrochloride

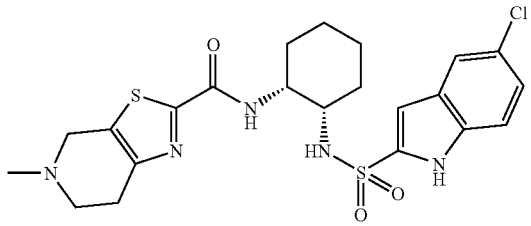

(±)-cis-N-[(5-methyl-4,5,6,7-tetrahydrothiazolo-[5,4-c]pyridin-2-yl)carbonyl]-1,2-cyclohexanediamine trifluoroacetate (400 mg) was suspended in dichloromethane (10 ml), triethylamine (0.514 ml) and 5-chloro-1-phenylsulfonylindole-2-sulfonyl chloride (Japanese Patent Application Laid-Open No. 2000-119253) (319 mg) were added, and the mixture was stirred at room temperature for 15 minutes. After water was added to the reaction mixture to conduct liquid separation, the resultant organic layer was dried over anhydrous sodium sulfate. The solvent was distilled off under reduced pressure, and the residue was purified by column chromatography on silica gel (dichloromethane:methanol=100:3) to obtain a pale yellow foamy substance. This substance was dissolved in tetrahydrofuran (3 ml), and methanol (2 ml) and a 1N aqueous solution (1.5 ml) of sodium hydroxide were added to heat the mixture under reflux for 2 hours. The reaction mixture was concentrated under reduced pressure, and dichloromethane and 1N hydrochloric acid were added to the residue to conduct liquid separation. After the resultant organic layer was dried over anhydrous sodium sulfate, the solvent was distilled off under reduced pressure, and the residue was purified by column chromatography on silica gel (dichloromethane:methanol=100:3) to obtain a pale yellow foamy substance. This substance was added to 1N hydrochloric acid (1 ml), and the mixture was concentrated under reduced pressure to obtain the title compound (108 mg) as a pale yellow foamy substance.

$^1$H-NMR (DMSO-d$_6$) δ: 1.20–1.78(8H,m), 2.94(3H,s), 3.13(2H,br.s), 3.22–3.40(1H,m), 3.44–3.70(3H,m), 3.83–3.95(1H,m), 4.20–4.70(1H,m), 6.78(1H,s), 7.18–7.30 (2H,m), 7.44(1H,s), 7.69(1H,br.s), 8.09(1H,br.s), 11.92(1H, s). MS (FAB) m/z: 508(M+H)$^+$.

Example 6

(±)-trans-N$^1$-[(5-Chloroindol-2-yl)carbonyl]-N$^2$-[(5-methyl-4,5,6,7-tetrahydrothiazolo[5,4-c]pyridin-2-yl)carbonyl]-1,2-cyclohexanediamine hydrochloride

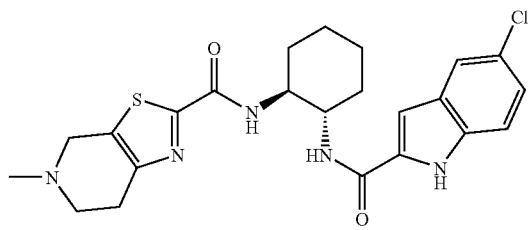

5-Chloroindole-2-carboxylic acid (109 mg), 1-hydroxybenzotriazole monohydrate (9 mg), 1-(3-dimethylaminopropyl)-3-ethylcarbodiimide hydrochloride (321 mg) and triethylamine (0.232 ml) were added to a solution with (±)-trans-N-[(5-methyl-4,5,6,7-tetrahydrothiazolo[5,4-c]pyridin-2-yl)carbonyl]-1,2-cyclohexanediamine trifluoroacetate (300 mg) dissolved in N,N-dimethylformamide (20 ml), and the mixture was stirred overnight at room temperature. The reaction mixture was concentrated under reduced pressure using a vacuum pump, and dichloromethane and water were added to the residue to conduct liquid separation. The resultant organic layer was dried over anhydrous sodium sulfate, the solvent was distilled off under reduced pressure, and the residue was purified by column chromatography on silica gel (dichloromethane:methanol=25:1) to obtain a colorless foamy substance. 1N hydrochloric acid (1 ml) was added to this substance and the solvent was distilled off under reduced pressure to obtain the title compound (203 mg) as a pale brown foamy substance.

$^1$H-NMR (DMSO-d$_6$) δ: 1.25–1.40(2H,m), 1.46–1.81 (4H,m), 1.88–1.98(2H,m), 2.89(3H,s), 3.00–3.76(5H,m), 3.86–3.97(1H,m), 4.00–4.10(1H,m), 4.25–4.72(1H,m), 7.03 (1H,s), 7.12(1H,dd,J=8.5, 1.2 Hz), 7.38(1H,d,J=8.5 Hz), 7.64(1H,s), 8.28(1H,d,J=8.5 Hz), 8.54(1H,d,J=8.5 Hz), 11.70(1H,s) MS (FAB) m/z: 472(M+H)$^+$.

Example 7

(±)-cis-$N^1$-[(5-Chloroindol-2-yl)carbonyl]-$N^2$-[(5-methyl-4,5,6,7-tetrahydrothiazolo[5,4-c]pyridin-2-yl)carbonyl]-1,2-cyclohexanediamine hydrochloride

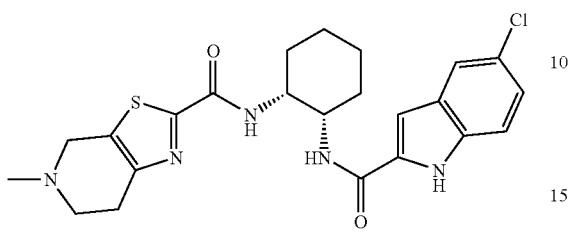

The title compound was obtained from (±)-cis-N-[(5-methyl-4,5,6,7-tetrahydrothiazolo[5,4-c]pyridin-2-yl)carbonyl]-1,2-cyclohexanediamine trifluoroacetate in a similar manner to Example 6.

$^1$H-NMR (DMSO-$d_6$) δ: 1.35–1.70(6H,m), 1.80–2.06 (2H,m), 2.89(3H,s), 3.00–3.27(2H,m), 3.35–3.51(1H,m), 3.57–3.82(1H,m), 4.15–4.30(2H,m), 4.32–4.48(1H,m), 4.60–4.74(1H,m), 7.15(1H,s), 7.17(1H,dd,J=8.8, 2.0 Hz), 7.41(1H,d,J=8.6 Hz), 7.70(1H,d,J=2.0 Hz), 8.14(1H,br.s), 8.36–8.48(1H,m), 11.51(1H,br.s), 11.86(1H,s). MS (FAB) m/z: 472(M+H)$^+$.

Example 8

(1S,2R)-$N^1$-[(5-Chloroindol-2-yl)carbonyl]-$N^2$-[(5-methyl-4,5,6,7-tetrahydrothiazolo[5,4-c]pyridin-2-yl)carbonyl]-1,2-cyclohexanediamine

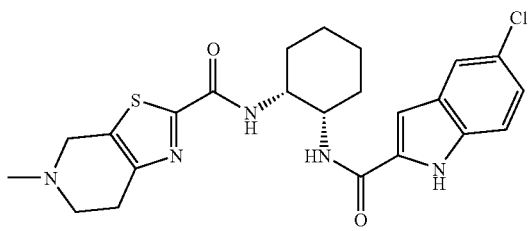

The title compound was obtained from (1R,2S)-$N^1$-[(5-methyl-4,5,6,7-tetrahydrothiazolo[5,4-c]pyridin-2-yl)carbonyl]-1,2-cyclohexanediamine (Isomer B) in a similar manner to Example 6.

[α]$_D$ −128.7° (20.8° C., C=0.5, CHCl$_3$). $^1$H-NMR (DMSO-$d_6$) δ: 1.38–1.52(2H,m), 1.55–1.70(4H,m), 1.89–2.07(2H,m), 2.38(3H,s), 2.70–2.77(2H,m), 2.78–2.87 (2H,m), 3.63(2H,s), 4.20–4.30(2H,m), 7.12(1H,s), 7.14(1H, d,J=8.8 Hz), 7.41(1H,d,J=8.8 Hz), 7.67(1H,s), 8.10(1H,d,J= 6.9 Hz), 8.30(1H,d,J=8.1 Hz), 11.77(1H,s). MS (FAB) m/z: 472(M+H)$^+$.

Example 9

(1R,2S)-$N^1$-[(5-Chloroindol-2-yl)carbonyl]-$N^2$-[(5-methyl-4,5,6,7-tetrahydrothiazolo[5,4-c]pyridin-2-yl)-carbonyl]-1,2-cyclohexanediamine

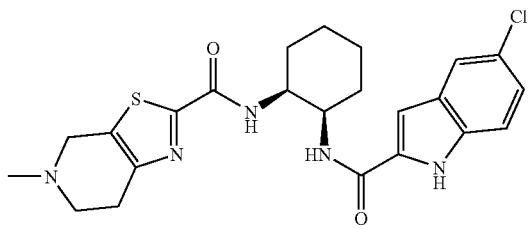

The title compound was obtained from (1S,2R)-$N^1$-[(5-methyl-4,5,6,7-tetrahydrothiazolo[5,4-c]pyridin-2-yl)carbonyl]-1,2-cyclohexanediamine (Isomer A) in a similar manner to Example 6.

[α]$_D$ +125.7° (20.8° C., C=0.5, CHCl$_3$). $^1$H-NMR (DMSO-$d_6$) δ: 1.38–1.52(2H,m), 1.55–1.70(4H,m), 1.89–2.07(2H,m), 2.37(3H,s), 2.70–2.76(2H,m), 2.78–2.86 (2H,m), 3.63(2H,s), 4.20–4.30(2H,m), 7.13(1H,s), 7.15(1H, d,J=8.8 Hz), 7.41(1H,d,J=8.8 Hz), 7.67(1H,s), 8.10(1H,d,J= 6.9 Hz), 8.30(1H,d,J=8.1 Hz), 11.78(1H,s). MS (FAB) m/z: 472(M+H)$^+$.

Example 10

(±)-cis-$N^1$-[(6-Chloronaphthalen-2-yl)carbonyl]-$N^2$-[(5-methyl-4,5,6,7-tetrahydrothiazolo[5,4-c]pyridin-2-yl)-carbonyl]-1,2-cyclohexanediamine hydrochloride

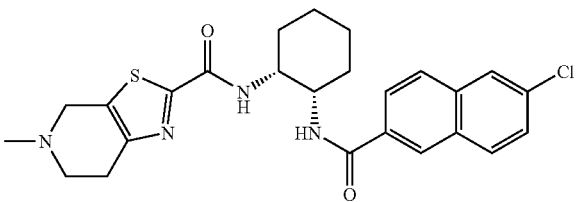

The title compound (186 mg) was obtained as a pale brown foamy substance by dissolving (±)-cis-N-[(5-methyl-4,5,6,7-tetrahydrothiazolo[5,4-c]pyridin-2-yl)carbonyl]-1,2-cyclohexanediamine hydrochloride (275 mg), 6-chloronaphthalene-2-carboxylic acid (Eur. J. Chem.-Chim. Ther., 1984, Vol. 19, pp. 205–214) (148 mg), triethylamine (0.298 ml) and 1-hydroxybenzotriazole monohydrate (11 mg) in N,N-dimethylformamide (20 ml) and causing 1-(3-dimethylaminopropyl)-3-ethylcarbodiimide hydrochloride (412 mg) to react as a condensing agent in a similar manner to Example 6.

$^1$H-NMR (DMSO-$d_6$) δ: 1.40–1.56(2H,m), 1.57–1.77 (4H,m), 1.90–2.10(2H,m), 2.90(3H,s), 3.13(2H,br.s), 3.28–3.74(2H,m), 4.26(2H,br.s), 4.30–4.74(2H,m), 7.59 (1H,d,J=8.6 Hz), 7.90(1H,d,J=8.6 Hz), 7.98(1H,d,J=8.3 Hz), 8.03–8.11(2H,m), 8.25–8.58(3H,m), 11.52(1H,br.s). MS (FAB) m/z: 483(M+H)$^+$.

Example 11

(±)-trans-N¹-[(6-Chlorobenzo[b]thiophen-2-yl)carbonyl]-N²-[(5-methyl-4,5,6,7-tetrahydrothiazolo[5,4-c]pyridin-2-yl)carbonyl]-1,2-cyclohexanediamine hydrochloride

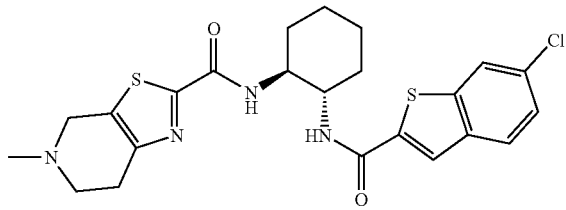

The title compound (239 mg) was obtained as a pale brown foamy substance by dissolving (±)-trans-N-[(5-methyl-4,5,6,7-tetrahydrothiazolo[5,4-c]pyridin-2-yl)carbonyl]-1,2-cyclohexanediamine hydrochloride (255 mg, 0.665 mmol), 6-chlorobenzo[b]thiophene-2-carboxylic acid (Japanese Patent Application Laid-Open No. 2000-119253) (141 mg), triethylamine (0.276 ml) and 1-hydroxybenzotriazole monohydrate (10 mg) in N,N-dimethylformamide (20 ml) and causing 1-(3-dimethylaminopropyl)-3-ethylcarbodiimide hydrochloride (382 mg) to react as a condensing agent in a similar manner to Example 6.

¹H-NMR (DMSO-$d_6$) δ: 1.20–1.98(8H,m), 2.88(3H,s), 3.00–3.72(4H,m), 3.84–4.09(2H,m), 4.20–4.75(2H,m), 7.41 (1H,dd,J=8.6, 1.7 Hz), 7.91(1H,d,J=8.6 Hz), 7.99(1H,s), 8.12(1H,s), 8.54–8.67(2H,m), 11.53(1H,br.s). MS (FAB) m/z: 489(M+H)⁺.

Example 12

(±)-trans-N¹-[(5-Fluoroindol-2-yl)carbonyl]-N²-[(5-methyl-4,5,6,7-tetrahydrothiazolo[5,4-c]pyridin-2-yl)carbonyl]-1,2-cyclohexanediamine hydrochloride

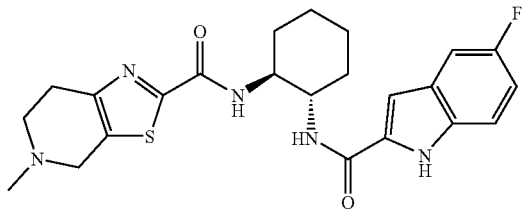

The title compound was obtained from (±)-trans-N-[(5-methyl-4,5,6,7-tetrahydrothiazolo[5,4-c]pyridin-2-yl)carbonyl]-1,2-cyclohexanediamine hydrochloride and 5-fluoroindole-2-carboxylic acid in a similar manner to Example 6.

¹H-NMR (DMSO-$d_6$) δ: 1.20–1.38(2H,m)., 1.40–1.57 (1H,m), 1.54–1.68(1H,m), 1.71(2H,d,J=7.3 Hz), 1.88(2H,d, J=12.0 Hz), 2.86(3H,s), 2.95–3.24(2H,m), 3.40(1H,br.s), 3.63(1H,br.s), 3.90(1H,br.s), 3.97–4.10(1H,m), 4.20–4.44 (1H,m), 4.53–4.70(1H,m), 6.98(1H,dd,J=9.2, 2.3 Hz), 7.01 (1H,s), 7.31–7.39(2H,m), 8.26(1H,d,J=8.6 Hz), 8.59(1H,d, J=8.4 Hz), 11.21(1/2H,br.s), 11.42(1/2H,br.s), 11.60(1H,s). MS (ESI) m/z: 456(M+H)⁺.

Example 13

(±)-cis-N¹-[(5-Fluoroindol-2-yl)carbonyl]-N²-[(5-methyl-4,5,6,7-tetrahydrothiazolo[5,4-c]pyridin-2-yl)carbonyl]-1,2-cyclohexanediamine hydrochloride

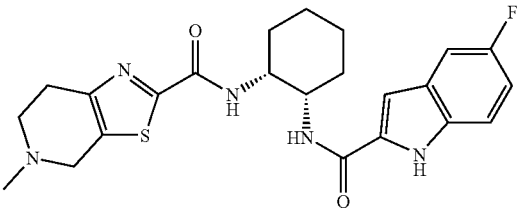

The title compound was obtained from (±)-cis-N-[(5-methyl-4,5,6,7-tetrahydrothiazolo[5,4-c]pyridin-2-yl)carbonyl]-1,2-cyclohexanediamine hydrochloride and 5-fluoroindole-2-carboxylic acid in a similar manner to Example 6.

¹H-NMR (DMSO-$d_6$) δ: 1.43(2H,br.s), 1.61(4H,br.s), 1.82–2.08(2H,m), 2.89(3H,s), 3.00–3.23(2H,m), 3.44(1H, br.s), 3.65(1H,br.s), 4.23(1H,d,J=16.2 Hz), 4.26(1H,br.s), 4.41(1H,br.s), 4.68(1H,d,J=16.2 Hz), 6.98–7.07(1H,m), 7.14(1H,s), 7.37–7.43(2H,m), 8.01(1H,br.s), 8.35–8.52(1H, br), 11.37(1H,br.s), 11.74(1H,s). MS (ESI) m/z: 456(M+H)⁺.

Example 14

(±)-trans-N¹-[(5-Chloro-6-fluoroindol-2-yl)carbonyl]-N²-[(5-methyl-4,5,6,7-tetrahydrothiazolo[5,4-c]pyridin-2-yl)carbonyl]-1,2-cyclohexanediamine hydrochloride

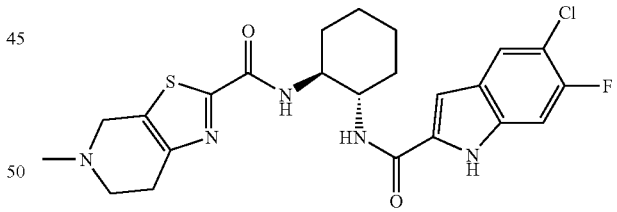

The title compound was obtained from (±)-trans-N-[(5-methyl-4,5,6,7-tetrahydrothiazolo[5,4-c]pyridin-2-yl)carbonyl]-1,2-cyclohexanediamine hydrochloride and 5-chloro-6-fluoroindole-2-carboxylic acid in a similar manner to Example 6.

¹H-NMR (DMSO-$d_6$) δ: 1.20–1.40(2H,m), 1.40–1.80 (4H,m), 1.80–2.00(2H,m), 2.87(3H,s), 3.01(2H,br.s), 3.30–3.80(2H,m), 3.81–3.97(2H,m), 4.20–4.80(2H,m), 7.06 (1H,s), 7.28(1H,d,J=10.0 Hz), 7.86(1H,d,J=7.3 Hz), 8.32 (1H,d,J=8.5 Hz), 8.59(1H,d,J=8.5 Hz), 11.77(1H,s). MS (FAB) m/z: 490(M+H)⁺.

Example 15

(±)-cis-$N^1$-[(5-Bromoindol-2-yl)carbonyl]-$N^2$-[(5-methyl-4,5,6,7-tetrahydrothiazolo[5,4-c]pyridin-2-yl)carbonyl]-1,2-cyclohexanediamine hydrochloride

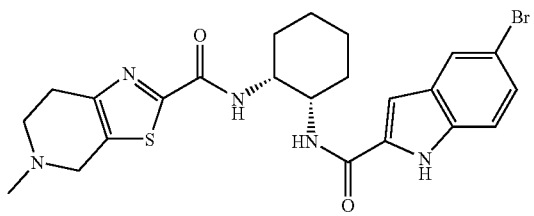

The title compound was obtained from (±)-cis-N-[(5-methyl-4,5,6,7-tetrahydrothiazolo[5,4-c]pyridin-2-yl)carbonyl]-1,2-cyclohexanediamine hydrochloride and 5-bromoindole-2-carboxylic acid in a similar manner to Example 6.

$^1$H-NMR (DMSO-$d_6$) δ: 1.43(2H,br.s), 1.61(4H,br.s), 1.80–2.10(2H,m), 2.88(3H,s), 3.00–3.26(2H,m), 3.40(1H,br.s), 3.65(1H,br.s), 4.22(1H,br.s), 4.26(1H,br.s), 4.41(1H,br.s), 4.67(1H,d,J=15.6 Hz), 7.14(1H,s), 7.28(1H,d,J=8.7 Hz), 7.37(1H,d,J=8.7 Hz), 7.84(1H,s), 8.13(1H,br.s), 8.33–8.52(1H,m), 11.51(1H,br.s), 11.86(1H,s). MS (ESI) m/z: 515(M$^+$).

Example 16

(±)-cis-$N^1$-[(5-Ethynylindol-2-yl)carbonyl]-$N^2$-[(5-methyl-4,5,6,7-tetrahydrothiazolo[5,4-c]pyridin-2-yl)carbonyl]-1,2-cyclohexanediamine

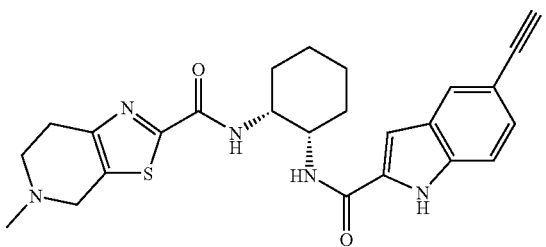

Triethylamine (6 ml), N,N-dimethylformamide (5 ml), trimethylsilylacetylene (0.250 ml) and palladium acetate (20 mg) were added to a tetrahydrofuran solution (2 ml) of (±)-cis-$N^1$-[(5-bromoindol-2-yl)carbonyl]-$N^2$-[(5-methyl-4,5,6,7-tetrahydrothiazolo[5,4-c]pyridin-2-yl)carbonyl]-1,2-cyclohexanediamine (300 mg) and triphenylphosphine (70 mg) at room temperature. After stirring at 90° C. for 2 hours, the reaction mixture was allowed to cool to room temperature, and dichloromethane (20 ml) and a saturated aqueous solution (30 ml) of sodium hydrogencarbonate were added to conduct liquid separation. The resultant water layer was extracted with dichloromethane (3×10 ml), the organic layers were collected and dried over anhydrous sodium sulfate, and the solvent was distilled off under reduced pressure to obtain residue. The resultant residue was purified by preparative thin-layer chromatography on silica gel (dichloromethane:acetone:methanol=10:10:1) to obtain a mixture mainly containing (±)-cis-$N^1$-[(5-methyl-4,5,6,7-tetrahydrothiazolo[5,4-c]pyridin-2-yl)carbonyl]-$N^2$-[[5-(trimethylsilylethynyl)indol-2-yl]carbonyl]-1,2-cyclohexanediamine as a colorless solid. This product was dissolved in methanol (6 ml), potassium carbonate (120 mg) was added, and the mixture was stirred for 1 hour. Dichloromethane (20 ml) and water (20 ml) were added to the reaction mixture to conduct liquid separation. The resultant water layer was extracted with dichloromethane (2×15 ml), the organic layers were collected and dried over anhydrous sodium sulfate, and the solvent was distilled off under reduced pressure. The resultant residue was purified by preparative thin-layer chromatography on silica gel (dichloromethane:acetone:methanol=10:10:1) and dissolved in water-methanol-dichloromethane. The resultant solution was then concentrated to obtain the title compound (72 mg) as a pale yellow solid.

$^1$H-NMR (CDCl$_3$) δ: 1.50–2.25(8H,m), 2.53(3H,s), 2.85 (2H,br.s), 2.93(2H,br.s), 3.01(1H,s), 3.74(1H,d,J=14.1 Hz), 3.77(1H,d,J=14.1 Hz), 4.21(1H,br.s), 4.45(1H,br.s), 6.91 (1H,s), 7.25–7.42(2H,m), 7.61(1H,br.s), 7.80–7.97(2H,m), 9.72(1H,s). MS (FAB) m/z: 462(M+H)$^+$.

Example 17

(±)-cis-$N^1$-[(6-Bromonaphthalen-2-yl)carbonyl]-$N^2$-[(5-methyl-4,5,6,7-tetrahydrothiazolo[5,4-c]pyridin-2-yl)carbonyl]-1,2-cyclohexanediamine hydrochloride

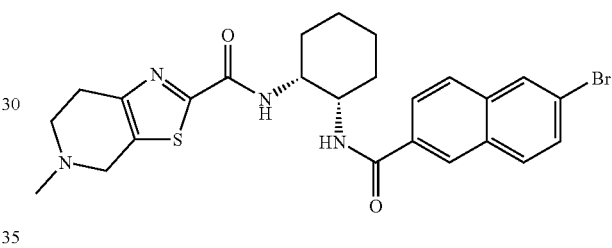

The title compound was obtained from (±)-cis-N-[(5-methyl-4,5,6,7-tetrahydrothiazolo[5,4-c]pyridin-2-yl)carbonyl]-1,2-cyclohexanediamine hydrochloride and 6-bromonaphthalene-2-carboxylic acid in a similar manner to Example 6.

$^1$H-NMR (DMSO-$d_6$) δ: 1.45(2H,br.s), 1.62(4H,br.s), 1.96(2H,br.s), 2.88(3H,s), 2.93–3.25(2H,m), 3.40(1H,br.s), 3.64(1H,br.s), 4.25(2H,br.s), 4.41(1H,br.s), 4.66(1H,br.s), 7.72(1H,br.s), 7.90(1H,br.s), 7.99(2H,br.s), 8.20–8.55(4H, m), 11.46(1H,br.s). MS (ESI) m/z: 526(M$^+$,Br$^{79}$), 528(M$^+$, Br$^{81}$).

Example 18

(±)-cis-$N^1$-[(6-Ethynylnaphthalen-2-yl)carbonyl]-$N^2$-[(5-methyl-4,5,6,7-tetrahydrothiazolo[5,4-c]pyridin-2-yl)carbonyl]-1,2-cyclohexanediamine

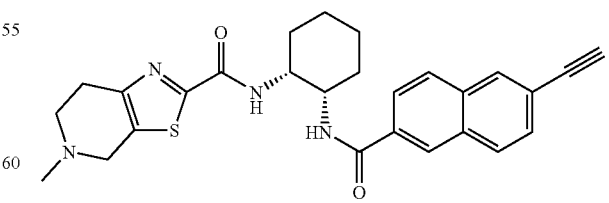

The title compound was obtained from (±)-cis-$N^1$-[(6-bromonaphthalen-2-yl)carbonyl]-$N^2$-[(5-methyl-4,5,6,7-tetrahydrothiazolo[5,4-c]pyridin-2-yl)carbonyl]-1,2-cyclohexanediamine in a similar manner to Example 16.

$^1$H-NMR (CDCl$_3$) δ: 1.53–1.68(3H,m), 1.72(1H,br.s), 1.80(1H,br.s), 1.93(2H,br.s), 2.17(1H,br.s), 2.59(3H,s), 2.94 (2H,br.s), 2.96–3.04(2H,m), 3.19(1H,s), 3.78–3.90(2H,m), 4.27(1H,br.s), 4.48(1H,d,J=3.7 Hz), 7.55(1H,dd,J=8.4, 1.3 Hz), 7.62(1H,d,J=7.8 Hz), 7.71(1H,d,J=5.9 Hz), 7.83(1H,d, J=8.5 Hz), 7.87(1H,d,J=8.4 Hz), 7.89(1H,dd,J=8.5, 1.7 Hz), 8.02(1H,s), 8.31(1H,s). MS (FAB) m/z: 473(M+H)$^+$.

Example 19

(±)-cis-N$^1$-[(5-Chloroindol-2-yl)carbonyl]-N$^2$-[(5,6-dimethyl-4,5,6,7-tetrahydrothiazolo[4,5-d]pyridazin-2-yl)carbonyl]-1,2-cyclohexanediamine hydrochloride

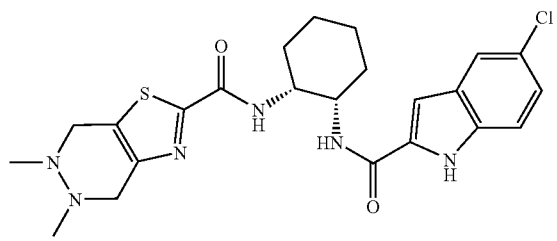

The title compound was obtained from (±)-cis-N-[(5-chloroindol-2-yl)carbonyl]-1,2-cyclohexanediamine and lithium 5,6-dimethyl-4,5,6,7-tetrahydrothiazolo[4,5-d]-pyridazine-2-carboxylate in a similar manner to Example 2.

$^1$H-NMR (DMSO-d$_6$) δ: 1.35–1.50(2H,m), 1.50–1.75 (4H,m), 1.80–2.10(2H,m), 2.70(3H,br.s), 2.79(3H,br.s), 4.10–4.70(6H,m), 7.10–7.27(2H,m), 7.41(1H,d,J=8.8 Hz), 7.70(1H,s), 8.12(1H,d,J=6.8 Hz), 8.47(1H,d,J=7.6 Hz), 11.85(1H,s). MS (FAB) m/z: 487(M+H)$^+$.

Example 20

(±)-cis-N$^1$-[(5-Chloroindol-2-yl)carbonyl]-N$^2$-[(6,7-dihydro-4H-pyrano[4,3-d]thiazol-2-yl)carbonyl]-1,2-cyclohexanediamine

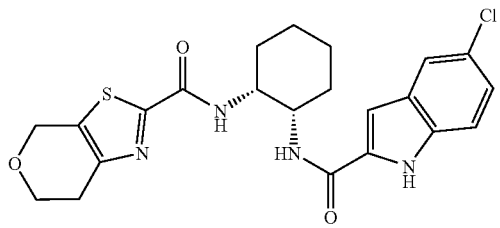

The title compound was obtained from (±)-cis-N-[(5-chloroindol-2-yl)carbonyl]-1,2-cyclohexanediamine hydrochloride and lithium 6,7-dihydro-4H-pyrano[4,3-d]-thiazole-2-carboxylate in a similar manner to Example 2.

$^1$H-NMR (DMSO-d$_6$) δ: 1.36–1.72(6H,m), 1.90–2.10 (2H,m), 2.80–2.87(2H,m), 3.93(2H,t,J=5.6 Hz), 4.20–4.32 (2H,m), 4.81(2H,s), 7.12(1H,s), 7.15(1H,dd, J=8.8, 2.0 Hz), 7.41(1H,d,J=8.8 Hz), 7.67(1H,d,J=1.7 Hz), 8.11(1H,d,J=6.6 Hz), 8.36(1H,d,J=8.3 Hz), 11.78(1H,s). MS (FAB) m/z: 459(M+H)$^+$.

Example 21

(±)-cis-N$^1$-[(5-Chloroindol-2-yl)carbonyl]-N$^2$-[(5-methyl-4,5,6,7-tetrahydrothiazolo[4,5-c]pyridin-2-yl)carbonyl]-1,2-cyclohexanediamine hydrochloride

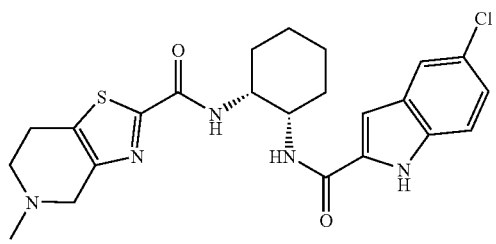

The title compound was obtained from (±)-cis-N-[(5-chloroindol-2-yl)carbonyl]-1,2-cyclohexanediamine hydrochloride and lithium 5-methyl-4,5,6,7-tetrahydrothiazolo[4,5-c]pyridine-2-carboxylate in a similar manner to Example 2.

$^1$H-NMR (DMSO-d$_6$) δ: 1.32–1.74(6H,m), 1.82–2.10 (2H,m), 2.92(3H s), 3.12–3.50(3H,m), 3.69(1H,br.s), 4.13–4.39(3H,m), 4.51(1H,br.s), 7.10–7.19(2H,m), 7.41 (1H,d,J=8.6 Hz), 7.68(1H,s), 8.10(1H,br.s), 8.40(1H,br.s), 11.41(1H,br.s), 11.87(1H,s). MS (FAB) m/z: 472(M+H)$^+$.

Example 22

(±)-trans-N$^1$-[(5-Chloroindol-2-yl)carbonyl]-N$^2$-[(5-methyl-4,5,6,7-tetrahydrooxazolo[5,4-c]pyridin-2-yl)carbonyl]-1,2-cyclohexanediamine hydrochloride

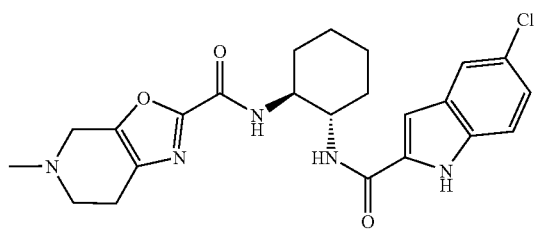

The title compound was obtained from (±)-trans-N-[(5-chloroindol-2-yl)carbonyl]-1,2-cyclohexanediamine hydrochloride and lithium 5-methyl-4,5,6,7-tetrahydrooxazolo[5,4-c]pyridine-2-carboxylate in a similar manner to Example 2.

$^1$H-NMR (DMSO-d$_6$) δ: 1.23–1.39(2H,m), 1.40–1.81 (4H,m), 1.82–1.98(2H,m), 2.60–3.00(5H,m), 3.20–3.70(2H, m), 3.87–3.96(1H,m), 3.98–4.10(1H,m), 4.12–4.70(2H,m), 7.04(1H,d,J=1.5 Hz), 7.12(1H,dd,J=8.8, 2.0 Hz), 7.38(1H, d,J=8.8 Hz), 7.65(1H,d,J=2.0 Hz), 8.33(1H,d,J=8.6 Hz), 8.72(1H,d,J=8.6 Hz), 11.61(1H,br.s), 11.72(1H,s). MS (FAB) m/z: 456(M+H)$^+$.

Example 23

(±)-cis-N¹-[(5-Chloroindol-2-yl)carbonyl]-N²-[(5-methyl-4,5,6,7-tetrahydrooxazolo[5,4-c]pyridin-2-yl)carbonyl]-1,2-cyclohexanediamine hydrochloride

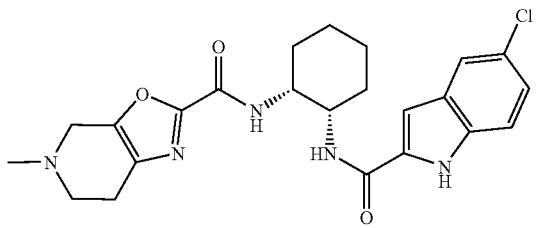

The title compound was obtained from (±)-cis-N-[(5-chloroindol-2-yl)carbonyl]-1,2-cyclohexanediamine hydrochloride and lithium 5-methyl-4,5,6,7-tetrahydrooxazolo[5,4-c]pyridine-2-carboxylate in a similar manner to Example 2.

$^1$H-NMR (DMSO-$d_6$) δ: 1.33–1.72(6H,m), 1.86–2.06 (2H,m), 2.70–3.05(5H,m), 3.30–3.77(2H,m), 4.17–4.32(2H, m), 4.33–4.70(2H,m), 7.12–7.20(2H,m), 7.41(1H,d,J=8.8 Hz), 7.68(1H,s), 8.08(1H,d,J=6.9 Hz), 8.54(1H,br.s), 11.61 (1H,br.s), 11.85(1H,s). MS (FAB) m/z: 456(M+H)$^+$.

Example 24

(±)-cis-N¹-[(5-Chloroindol-2-yl)carbonyl]-N²-[(6-methyl-4,5,6,7-tetrahydrothieno[2,3-c]pyridin-2-yl)carbonyl]-1,2-cyclohexanediamine hydrochloride

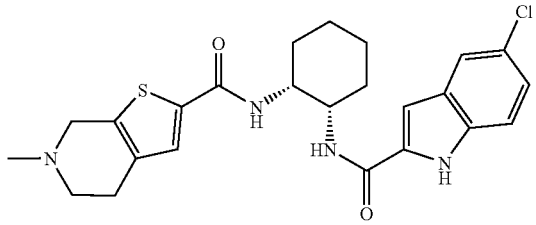

The title compound was obtained from (±)-cis-N-[(5-chloroindol-2-yl)carbonyl]-1,2-cyclohexanediamine hydrochloride and lithium 6-methyl-4,5,6,7-tetrahydrothieno[2,3-c]pyridine-2-carboxylate in a similar manner to Example 2.

$^1$H-NMR (DMSO-$d_6$) δ: 1.41(2H,br.s), 1.51–1.74(4H,m), 1.99(2H,br.s), 2.85–3.10(5H,m), 3.25–3.50(1H,m), 3.60 (1H,br.s), 4.10–4.37(3H,m), 4.53–4.67(1H,m), 7.15(1H,dd, J=8.6, 2.0 Hz), 7.23(1H,s), 7.41(1H,d,J=8.6 Hz), 7.65(1H,s), 7.80(1H,s), 8.10–8.30(2H,m), 10.84(1H,br.s), 11.90 (1H, s). MS (FAB) m/z: 471(M+H)$^+$.

Example 25

(±)-cis-N¹-[(5-Chloroindol-2-yl)carbonyl]-N²-[(4,5,6,7-tetrahydrothieno[3,2-c]pyridin-2-yl)carbonyl]-1,2-cyclohexanediamine hydrochloride

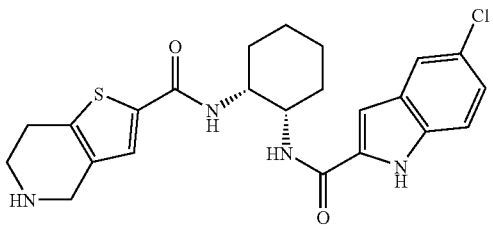

The title compound was obtained by dissolving (±)-cis-N-[(5-chloroindol-2-yl)carbonyl]-1,2-cyclohexanediamine hydrochloride (164 mg), 5-tert-butoxycarbonyl-4,5,6,7-tetrahydrothieno[3,2-c]pyridine-2-carboxylic acid (WO94/21599) (140 mg) and 1-hydroxybenzotriazole monohydrate (76 mg) in N,N-dimethylformamide (20 ml), causing 1-(3-dimethylaminopropyl)-3-ethylcarbodiimide hydrochloride (192 mg) to react as a condensing agent and then conducting a treatment with hydrochloric acid to deprotect in a similar manner to Example 2.

$^1$H-NMR (DMSO-$d_6$) δ: 1.42(2H,br.s), 1.56–1.76(4H,m), 1.98–2.11(2H,m), 3.04(2H,br.s), 3.32–3.45(2H,m), 4.15 (3H,br.s), 4.26(1H,br.s), 7.14(1H,dd,J=8.8, 2.0 Hz), 7.23 (1H,s), 7.41(1H,d,J=8.8 Hz), 7.62(1H,s), 7.77(1H,s), 8.18–8.30(2H,m), 9.42(2H,br.s), 11.92(1H,s). MS (FAB) m/z: 457(M+H)$^+$.

Example 26

(±)-cis-N¹-[(5-Chloroindol-2-yl)carbonyl]-N²-[(5-methyl-4,5,6,7-tetrahydrothieno[3,2-c]pyridin-2-yl)carbonyl]-1,2-cyclohexanediamine hydrochloride

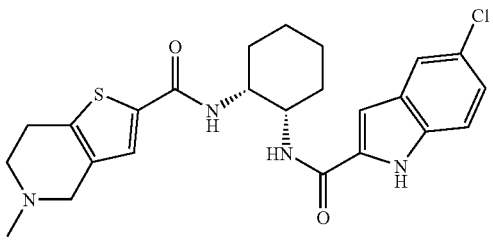

(±)-cis-N¹-[(5-Chloroindol-2-yl)carbonyl]-N²-[(4,5,6,7-tetrahydrothieno[3,2-c]pyridin-2-yl)carbonyl]-1,2-cyclohexanediamine hydrochloride (171 mg) was suspended in dichloromethane (10 ml), and triethylamine (0.104 ml) was added to stir the mixture at room temperature for 10 minutes. After acetic acid (0.059 ml) was added to the reaction mixture, a 35% aqueous formaldehyde solution (0.070 ml) and sodium triacetoxyborohydride (118 mg) were added, and the mixture was stirred at room temperature for 30 minutes. After a 1N aqueous solution (3 ml) of sodium hydroxide was added to the reaction mixture, water was added to conduct liquid separation. After the resultant organic layer was dried over anhydrous sodium sulfate, the solvent was then distilled off under reduced pressure, and the residue was purified by column chromatography on silica gel (dichloromethane:methanol=50:3) to obtain a colorless foamy substance. This substance was suspended in 1N hydrochloric acid, and the suspension was concentrated under reduced pressure to obtain the title compound (85 mg) as a colorless foamy substance.

$^1$H-NMR (DMSO-$d_6$) δ: 1.40(2H,br.s), 1.50–1.71(4H,m), 1.97–2.05(2H,m), 2.87(3H,s), 2.98–3.20(1H,m), 3.30–3.38 (2H,m), 3.54–3.70(1H,m), 4.05–4.42(4H,m), 7.14(1H,d,J=8.6 Hz), 7.23(1H,s), 7.40(1H,d,J=8.6 Hz), 7.63(1H,s), 7.77 (1H,s), 8.17–8.27(2H,m), 10.83(1H,br.s), 11.92(1H,s). MS (FAB) m/z: 471(M+H)$^+$.

Example 27 cis-$N^1$-[(5-Chloroindol-2-yl)carbonyl]-$N^2$-[[5-(N,N-dimethylamino)-4,5,6,7-tetrahydrobenzo[d]thiazol-2-yl)carbonyl]-1,2-cyclohexanediamine hydrochloride

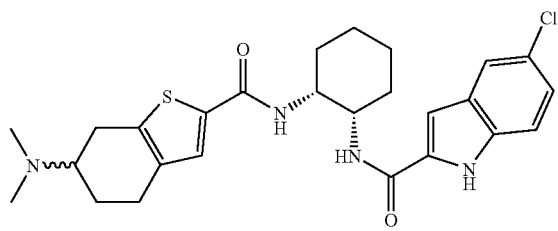

The title compound was obtained from (±)-cis-N-[(5-chloroindol-2-yl)carbonyl]-1,2-cyclohexanediamine hydrochloride and lithium [5-(N,N-dimethylamino)-4,5,6,7-tetrahydrobenzo[d]thiazole-2-carboxylate in a similar manner to Example 2.

$^1$H-NMR (DMSO-$d_6$) δ: 1.44(2H,br.s), 1.52–1.68(4H,m), 1.87–2.08(3H,m), 2.30–2.40(1H,m), 2.65–2.75(1H,m), 2.77 (6H,s), 2.95–3.17(2H,m), 3.30–3.70(2H,m), 4.15–4.30(2H,m), 7.10–7.20(2H,m), 7.41(1H,d,J=8.6 Hz), 7.69(1H,s), 8.11(1H,d,J=5.1 Hz), 8.34(1H,d,J=8.1 Hz), 10.95(1H,br.s), 11.83(1H,s). MS (FAB) m/z: 500(M+H)$^+$.

Example 28

(±)-cis-$N^1$-[(6-Chloroindol-2-yl)carbonyl]-$N^2$-[[5-(4-pyridyl)-4,5,6,7-tetrahydrothiazolo[5,4-c]pyridin-2-yl)carbonyl]-1,2-cyclohexanediamine hydrochloride

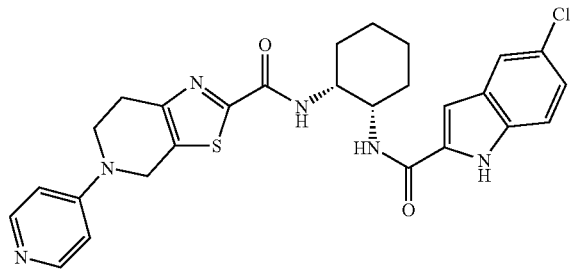

n-Butyllithium (1.60N hexane solution, 0.704 ml) was added dropwise to a solution of 5-(4-pyridyl)-4,5,6,7-tetrahydrothiazolo[5,4-c]pyridine (204 mg) in tetrahydrofuran 3 ml) at −78° C. and the mixture was stirred at 0° C. for 30 minutes. After the reaction mixture was cooled to −78° C. again, it was heated to room temperature in 20 minutes while blowing carbon dioxide, and the reaction mixture was concentrated under reduced pressure. (±)-cis-N-[(5-Chloroindol-2-yl)carbonyl]-1,2-cyclohexanediamine hydrochloride (400 mg), 1-hydroxybenzotriazole monohydrate (254 mg), 1-(3-dimethylaminopropyl)-3-ethylcarbodiimide hydrochloride (360 mg) and diisopropylamine (0.491 ml) were added to a solution of the resultant residue in N,N-dimethylformamide (6 ml) at room temperature. After stirring for 3 days, the reaction mixture was concentrated under reduced pressure, and dichloromethane (30 ml), a saturated aqueous solution (100 ml) of sodium hydrogencarbonate and water (100 ml) were added to the residue to conduct liquid separation. The resultant water layer was extracted with dichloromethane (4×15 ml), the organic layers were collected and dried over anhydrous sodium sulfate, and the solvent was distilled off under reduced pressure. The resultant residue was purified by column chromatography on silica gel (dichloromethane:methanol=20:1→10:1) and dissolved in 1N hydrochloric acid-methanol-dichloromethane. The resultant solution was then concentrated to obtain the title compound (245 mg) as a pale yellow solid.

$^1$H-NMR (DMSO-$d_6$) δ: 1.42(2H,br.s), 1.60(4H,br.s), 1.84–1.94(1H,m), 1.94–2.08(1H,m), 2.97(2H,br.s), 3.97–4.13(2H,m), 4.19(1H,br.s), 4.27(1H,br.s), 5.03(2H,s), 7.13(1H,br.s), 7.16(1H,dd,J=8.8, 2.0 Hz), 7.32(2H,br.s), 7.40(1H,d,J=8.8 Hz), 7.68(1H,d,J=2.0 Hz), 8.15(1H,br,J=7.3 Hz), 8.31(2H,d,J=5.9 Hz), 8.39(1H,d,J=8.1 Hz), 11.90 (1H,s), 14.03(1H,br.s). MS (ESI) m/z: 535(M+H)$^+$.

Example 29

(±)-cis-$N^1$-[(5-Chloroindol-2-yl)carbonyl]-$N^2$-[4-(4-pyridyl)benzoyl]-1,2-cyclohexanediamine hydrochloride

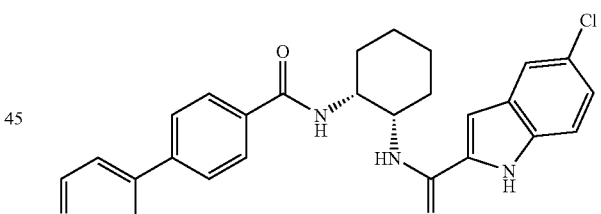

The title compound was obtained from (±)-cis-N-[(5-chloroindol-2-yl)carbonyl]-1,2-cyclohexanediamine hydrochloride and 4-(4-pyridyl)benzoic acid hydrochloride in a similar manner to Example 2.

$^1$H-NMR (DMSO-$d_6$) δ: 1.40–1.52(2H,m), 1.60–1.80 (4H,m), 1.96–2.10(2H,m), 4.24–4.39(2H,m), 7.15(1H,dd,J=8.8, 2.0 Hz), 7.21(1H,s), 7.40(1H,d,J=8.8 Hz), 7.64(1H,d,J=2.0 Hz), 8.06(4H,s), 8.18(1H,J=7.3 Hz), 8.34–8.42(3H,m), 8.94(2H,d,J=6.9 Hz), 11.91(1H,s). MS (FAB) m/z: 473 (M+H)$^+$.

Example 30

(±)-4-[4-[N-[cis-2-[[(5-Chloroindol-2-yl)carbonyl]-amino]cyclohexyl]carbamoyl]phenyl]pyridine N-oxide

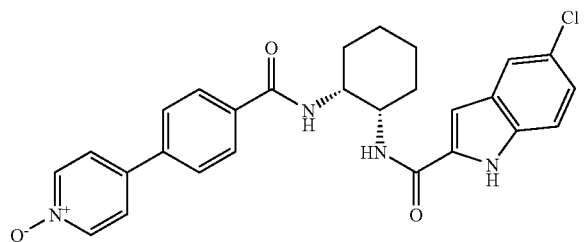

The title compound was obtained from (±)-cis-N-[(5-chloroindol-2-yl)carbonyl]-1,2-cyclohexanediamine hydrochloride and 4-(4-carboxyphenyl)pyridine N-oxide in a similar manner to Example 2.

$^1$H-NMR (DMSO-$d_6$) δ: 1.40–1.52(2H,m), 1.60–1.80 (4H,m), 1.88–2.00(2H,m), 4.21–4.36(2H,m), 7.12–7.18(2H, m), 7.41(1H,d,J=8.6 Hz), 7.66(1H,s), 7.80–7.87(4H,m), 7.91(2H,d,J=8.3 Hz), 8.01(1H,d,J=7.6 Hz), 8.09(1H,d,J=7.3 Hz), 8.27(2H,d,J=6.6 Hz), 11.79(1H,s). MS (FAB) m/z: 489(M+H)$^+$.

Example 31

(±)-cis-N$^1$-[(5-Chloroindol-2-yl)carbonyl]-N$^2$-[4-(2-pyridyl)benzoyl]-1,2-cyclohexanediamine hydrochloride

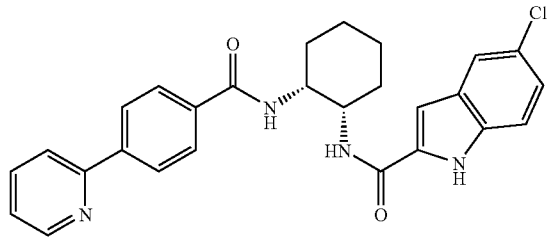

The title compound was obtained from (±)-cis-N-[(5-chloroindol-2-yl)carbonyl]-1,2-cyclohexanediamine hydrochloride and 4-(2-pyridyl)benzoic acid (Japanese Patent Application Laid-Open No. 2000-119253) in a similar manner to Example 2.

$^1$H-NMR (DMSO-$d_6$) δ: 1.39–1.51(2H,m), 1.60–1.80 (4H,m), 1.89–2.00(2H,m), 4.24–4.38(2H,m), 7.12–7.16(2H, m), 7.36–7.39(1H,m), 7.42(1H,d,J=8.8 Hz), 7.66(1H,d,J= 2.0 Hz), 7.87–7.90(1H,m), 7.92(2H,d,J=8.3 Hz), 7.98–8.11 (3H,m), 8.15(2H,d,J=8.3 Hz), 8.69(1H,d,J=4.6 Hz), 11.80 (1H,s). MS (FAB) m/z: 473(M+H)$^+$.

Example 32

(±)-2-[4-[N-[cis-2-[[(5-Chloroindol-2-yl)carbonyl]-amino]cyclohexyl]carbamoyl]phenyl]pyridine N-oxide

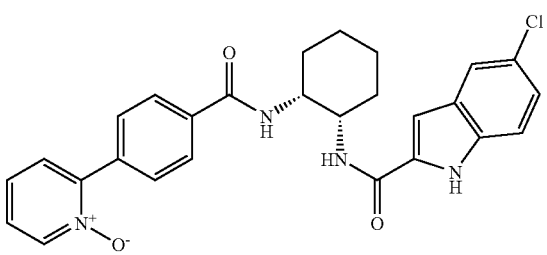

The title compound was obtained from (±)-cis-N-[(5-chloroindol-2-yl)carbonyl]-1,2-cyclohexanediamine hydrochloride and 2-(4-carboxyphenyl)pyridine N-oxide in a similar manner to Example 2.

$^1$H-NMR (DMSO-$d_6$) δ: 1.39–1.51(2H,m), 1.60–1.79 (4H,m), 1.89–2.00(2H,m), 4.23–4.37(2H,m), 7.12–7.17(2H, m), 7.39–7.43(3H,m), 7.61–7.64(1H,m), 7.67(1H,d,J=2.0 Hz), 7.89(4H,s), 8.00–8.06(1H.m), 8.08–8.02(1H,m), 8.32–8.35(1H,m), 11.79(1H,s). MS (FAB) m/z: 489(M+H)$^+$.

Example 33

(±)-trans-N$^1$-[(5-Chloroindol-2-yl)carbonyl]-N$^2$-[[5-(4-pyridyl)thiazol-2-yl)carbonyl]-1,2-cyclohexanediamine hydrochloride

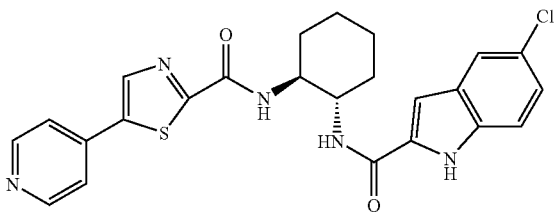

The title compound was obtained from (±)-trans-N-[(5-chloroindol-2-yl)carbonyl]-1,2-cyclohexanediamine and lithium 5(4-pyridyl)thiazole-2-carboxylate in a similar manner to Example 2.

$^1$H-NMR (DMSO-$d_6$) δ: 1.44(2H,br.s), 1.65(4H,br.s), 1.85–2.06(2H,m), 4.23(1H,br.s), 4.30(1H,br.s), 7.14–7.23 (2H,m), 7.41(1H,d,J=8.8 Hz), 7.69(1H,s), 8.04–8.13(2H,m), 8.13(1H,d,J=8.8 Hz), 8.59(1H,d,J=8.0 Hz), 8.75–8.87(3H, m), 11.83(1H,s). MS (ESI) m/z: 480(M+H)$^+$.

Example 34

(±)-cis-N$^1$-[(5-Chloroindol-2-yl)carbonyl]-N$^1$-methyl-N$^2$-[(5-methyl-4,5,6,7-tetrahydrothiazolo[5,4-c]pyridin-2-yl)carbonyl]-1,2-cyclohexanediamine hydrochloride

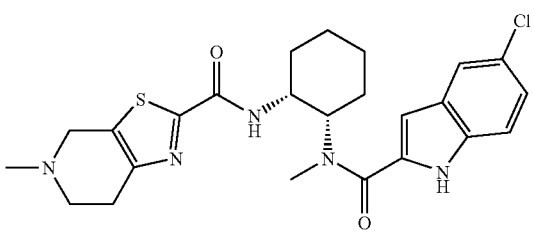

The title compound was obtained from (±)-cis-N$^1$-[(5-chloroindol-2-yl)carbonyl]-N$^1$-methyl-1,2-cyclohexanediamine and lithium 5-methyl-4,5,6,7-tetrahydrothiazolo[5,4-c]pyridine-2-carboxylate in a similar manner to Example 2.

$^1$H-NMR (DMSO-d$_6$) δ: 1.42–1.90(7H,m), 2.23–2.32 (1H,m), 2.90(3H,s), 3.11(3H,br.s), 3.19(2H,br.s), 3.45–3.67 (2H,brm), 4.41–4.72(4H,m), 6.76(1H,s), 7.17(1H,dd,J=8.8, 2.0 Hz), 7.43(1H,d,J=8.8 Hz), 7.64(1H,br.s), 8.52(1H,br,J= 8.5 Hz), 11.46(1H,br.s), 11.71(1H,s). MS (ESI) m/z: 500 (M+H)$^+$.

Example 35

(±)-cis-N$^1$-[(5-Chloroindol-2-yl)carbonyl]-N$^2$-methyl-N$^2$-[(5-methyl-4,5,6,7-tetrahydrothiazolo[5,4-c]pyridin-2-yl)carbonyl]-1,2-cyclohexanediamine hydrochloride

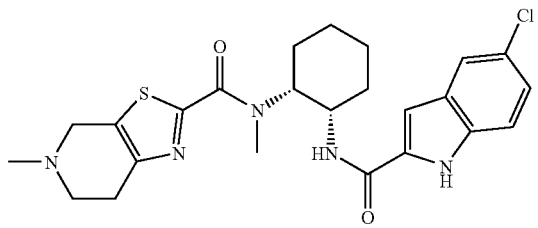

A saturated ethanol solution (5 ml) of hydrochloric acid was added to (±)-cis-N$^1$-(tert-butoxycarbonyl)-N$^2$-methyl-N$^2$-[(5-methyl-4,5,6,7-tetrahydrothiazolo[5,4-c]pyridin-2-yl)carbonyl]-1,2-cyclohexanediamine (324 mg), the mixture was stirred at room temperature for 30 minutes, and the solvent was distilled off under reduced pressure. The residue was dissolved in N,N-dimethylformamide (5 ml), and triethylamine (1 ml), 5-chloroindole-2-carboxylic acid (279 mg), 1-(3-dimethylaminopropyl)-3-ethylcarbodiimide hydrochloride (458 mg) and 1-hydroxybenzotriazole monohydrate (108 mg) were added to the solution. The resultant mixture was stirred at room temperature for 7 days. The solvent was distilled off under reduced pressure using a pump, and dichloromethane and a saturated aqueous solution of sodium hydrogencarbonate were added to the residue to conduct liquid separation. The resultant organic layer was dried over anhydrous sodium sulfate, and the solvent was then distilled off under reduced pressure. The resultant residue was purified by flash column chromatography on silica gel (dichloromethane:methanol=93:7) to obtain a pale yellow solid (176 mg). After this product was dissolved in methanol (5 ml), and a 1N ethanol solution (362 μl) of hydrochloric acid was added, the solvent was concentrated under reduced pressure, and ethyl acetate was added to the residue. Precipitate thus formed was collected by filtration to obtain the title compound (164 mg) as a pale yellow solid.

$^1$H-NMR (DMSO-d$_6$) δ: 1.43–1.90(7H,m), 2.26–2.31 (1H,m), 2.90(3H,s), 3.11–3.19(5H,m), 3.48–3.68(2H,m), 4.42–4.72(4H,m), 6.76(1H,d,J=1.5 Hz), 7.17(1H,dd,J=8.8, 2.1 Hz), 7.43(1H,d,J=8.8 Hz), 7.64(1H,br.s), 8.52(1H,br,J= 7.6 Hz), 11.45(1H,br.s), 11.71(1H,br.s). MS (ESI) m/z: 486(M+H)$^+$.

Example 36

(±)-trans-N$^1$-[(5-Chloroindol-2-yl)carbonyl]-N$^2$-[(5-methyl-4,5,6,7-tetrahydrothiazolo[5,4-c]pyridin-2-yl)carbonyl]-1,2-cycloheptanediamine hydrochloride

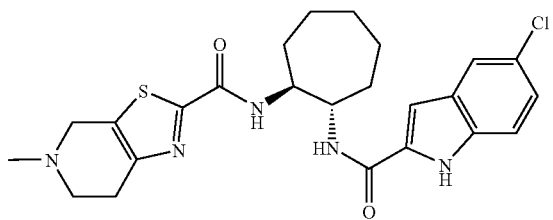

The title compound was obtained from (±)-trans-N-[(5-chloroindol-2-yl)carbonyl]-1,2-cycloheptanediamine and lithium 5-methyl-4,5,6,7-tetrahydrothiazolo[5,4-c]pyridine-2-carboxylate in a similar manner to Example 2.

$^1$H-NMR (DMSO-d$_6$) δ: 1.51–1.55(4H,m), 1.75–1.80 (6H,m), 2.88(3H,s), 3.12(1H,br.s), 3.35–3.63(4H,m), 4.10–4.13(1H,m), 4.29–4.61(2H,m), 7.06(1H,s), 7.14(1H, dd,J=8.8, 2.0 Hz), 7.39(1H,d,J=8.8 Hz), 7.67(1H,d,J=2.0 Hz), 8.46(1H,d,J=8.3 Hz), 8.77(1H,d,J=8.3 Hz), 11.21–11.35(1H,m), 11.71(1H,s). MS (ESI) m/z: 486(M+ H)$^+$.

Example 37

(±)-cis-N$^1$-[(5-Chloroindol-2-yl)carbonyl]-N$^2$-[(5-methyl-4,5,6,7-tetrahydrothiazolo[5,4-c]pyridin-2-yl)carbonyl]-1,2-cyclooctanediamine hydrochloride

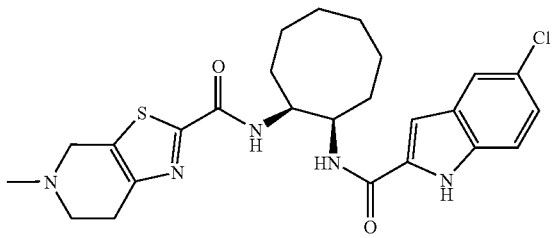

The title compound was obtained from (±)-cis-N-[(5-chloroindol-2-yl)carbonyl]-1,2-cyclooctanediamine and lithium 5-methyl-4,5,6,7-tetrahydrothiazolo[5,4-c]pyridine-2-carboxylate in a similar manner to Example 2.

$^1$H-NMR (DMSO-d$_6$) δ: 1.61–2.06(12H,m), 2.90(3H,s), 3.08–3.17(2H,m), 3.43–3.45(1H,m), 3.67(1H,br.s), 4.43 (3H,br.s), 4.67(1H,br.s), 7.16–7.18(2H,m), 7.42(1H,d,J=8.8 Hz), 7.70(1H,s), 8.24(1H,br.s), 8.58(1H,d,J=8.3 Hz), 11.43, 11.63(1H,each br.s), 11.80(1H,s). MS (ESI) m/z: 500(M+ H)$^+$.

Example 38

N$^1$-[(5-Chloroindol-2-yl)carbonyl]-N$^2$-[(5-methyl-4,5,6,7-tetrahydrothiazolo[5,4-c]pyridin-2-yl)carbonyl]-1,2-ethylenediamine hydrochloride

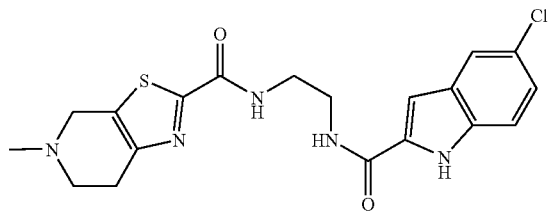

The title compound was obtained from N$^1$-tert-butoxycarbonyl-N$^2$-[(5-methyl-4,5,6,7-tetrahydrothiazolo[5,4-c]pyridin-2-yl)carbonyl]-1,2-ethylenediamine in a similar manner to Example 35.

$^1$H-NMR (DMSO-d$_6$) δ: 2.91(3H,s), 3.17(2H,br.s), 3.47 (4H,br.s), 3.56(2H,br.s), 4.53(2H,br.s), 7.08(1H,d,J=1.7 Hz), 7.17(1H,dd,J=8.8, 2.0 Hz), 7.42(1H,d,J=8.8 Hz), 7.69(1H, d,J=2.0 Hz), 8.69(1H,br.s), 9.00(1H,br.s), 11.62(1H,br.s), 11.79(1H,br.s). MS (FAB) m/z: 418(M+H)$^+$.

Example 39

N$^1$-[(5-Chloroindol-2-yl)carbonyl]-N$^1$-methyl-N$^2$-[(5-methyl-4,5,6,7-tetrahydrothiazolo[5,4-c]pyridin-2-yl)carbonyl]-1,2-ethylenediamine hydrochloride

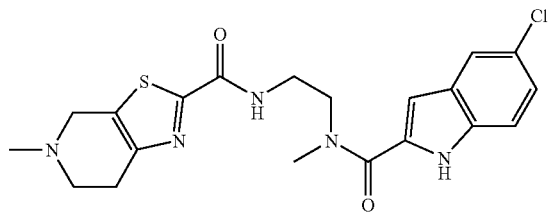

The title compound was obtained from N$^1$-methyl-N$^2$-[(5-methyl-4,5,6,7-tetrahydrothiazolo[5,4-c]pyridin-2-yl)carbonyl]-1,2-ethylenediamine and 5-chloroindole-2-carboxylic acid in a similar manner to Example 2.

$^1$H-NMR (DMSO-d$_6$) δ: 2.91(3H,s), 3.15–3.73(11H,m), 4.46–4.61(2H,m), 6.86(1H,d,J=2.0 Hz), 7.18(1H,dd,J=8.8, 2.0 Hz), 7.41(1H,d,J=8.8 Hz), 7.65(1H,br.s), 9.06(1H,t,J= 5.7 Hz), 11.48(1H,br.s), 11.72(1H,br.s). MS (ESI) m/z: 432(M+H)$^+$.

Example 40

N$^1$-[(5-Chloroindol-2-yl)sulfonyl]-N$^2$-[(5-methyl-4,5,6,7-tetrahydrothiazolo[5,4-c]pyridin-2-yl)carbonyl]-1,2-ethylenediamine hydrochloride

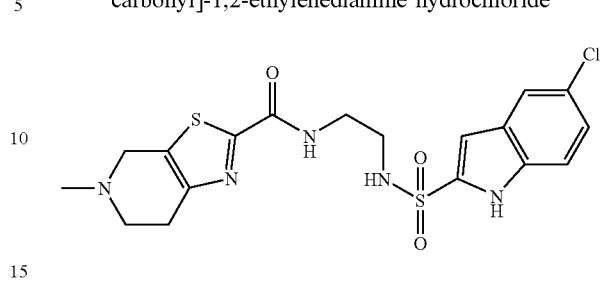

The title compound was obtained by eliminating the tert-butoxy group of N$^1$-[(5-chloro-1-phenylsulfonylindol-2-yl)sulfonyl]-N$^2$-(tert-butoxycarbonyl)-1,2-ethylenediamine and then reacting it with lithium 5-methyl-4,5,6,7-tetrahydrothiazolo[5,4-c]pyridine-2-carboxylate in a similar manner to Example 35.

$^1$H-NMR (DMSO-d$_6$) δ: 2.92(3H,m), 3.06–3.12(4H,m), 3.31–3.37(2H,m), 3.44–3.74(2H,m), 4.38–4.75(2H,m), 6.92 (1H,d,J=1.2 Hz), 7.27(1H,dd,J=8.8, 1.7 Hz), 7.43(1H,d,J= 8.8 Hz), 7.70(1H,d,J=1.7 Hz), 7.90(1H,t,J=5.8 Hz), 8.81 (1H,t,J=5.8 Hz), 11.25(1H,br.s), 12.14(1H,br.s). MS (FAB) m/z: 454(M+H)$^+$.

Example 41

(±)-cis-N$^1$-[(5-Chloroindol-2-yl)carbonyl]-N$^2$-[(5-methyl-4,6-dihydro-5H-pyrrolo[3,4-d]thiazol-2-yl)carbonyl]-1,2-cyclohexanediamine hydrochloride

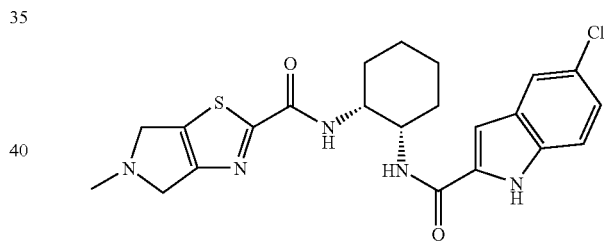

5-Methyl-4,6-dihydro-5H-pyrrolo[3,4-d]thiazole (155 mg) was dissolved in tetrahydrofuran (7 ml) in an argon atmosphere, and the solution was cooled to −78° C., to which tert-butyllithium (1.54N pentane solution, 0.792 ml) was added dropwise. The reaction mixture was stirred for 1 hour under ice cooling and cooled again to −78° C. After blowing carbon dioxide into the reaction mixture for 20 minutes, it was heated to room temperature. The reaction mixture was concentrated under reduced pressure to obtain crude lithium 5-methyl-4,6-dihydro-5H-pyrrolo[3,4-d]thiazole-2-carboxylate. This product was dissolved in N,N-dimethylformamide (20 ml), and to this solution, were added (±)-cis-N-[(5-chloroindol-2-yl)carbonyl]-1,2-cyclohexanediamine hydrochloride (364 mg), 1-hydroxybenzotriazole monohydrate (150 mg) and 1-(3-dimethylaminopropyl)-3-ethylcarbodiimide hydrochloride (426 mg). After the resultant mixture was stirred overnight, the solution was concentrated, and dichloromethane and a saturated aqueous solution of sodium hydrogencarbonate were added to the residue to conduct liquid separation. The resultant organic layer was dried over anhydrous sodium sulfate, and the solvent was then distilled off under reduced pressure. The resultant residue was purified by column chromatography on silica gel (methanol:dichloromethane= 7:93). A 1N ethanol solution of hydrochloric acid and ethyl acetate were added to the thus-obtained product, and powder deposited was collected by filtration to obtain the title compound (343 mg) as colorless powder.

$^1$H-NMR (DMSO-d$_6$) δ: 1.35–1.53(2H,m), 1.64(4H,br.s), 1.82–2.05(2H,m), 3.03(3H,br.s), 4.15–5.00(6H,m), 7.15 (1H,d,J=1.9 Hz), 7.18(1H,dd,J=8.7, 1.9 Hz), 7.42(1H,d,J= 8.7 Hz), 7.71(1H,d,J=1.9 Hz), 8.11(1H,d,J=7.6 Hz), 8.46 (1H,d,J=7.1 Hz), 11.85(1H,br.s), 12.26(1H,br.s). MS (FAB) m/z: 458(M+H)$^+$.

Example 42

(1R,2R)-N$^1$-(5-Chloroindol-2-yl)carbonyl]-N$^2$-[(5-methyl-4,5,6,7-tetrahydrothiazolo[5,4-c]pyridin-2-yl)carbonyl]-1,2-cyclopentanediamine hydrochloride

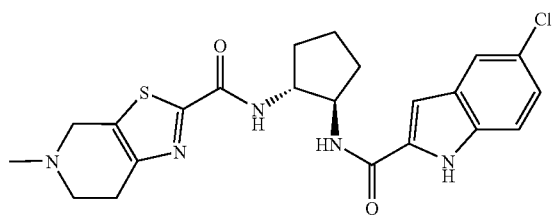

The title compound was obtained from (1R,2R)-N-[(5-methyl-4,5,6,7-tetrahydrothiazolo[5,4-c]pyridin-2-yl) carbonyl]-1,2-cyclopentanediamine hydrochloride in a similar manner to Example 6. The absolute structure was determined by X-ray analysis.

MS (ESI) m/z: 458(M+H)$^+$. [α]$_D$ −181.59° (C=1.02, dimethyl sulfoxide).

Example 43

(±)-trans-N$^1$-[(5-Bromoindol-2-yl)carbonyl]-N$^2$-[(5-methyl-4,5,6,7-tetrahydrothiazolo[5,4-c]pyridin-2-yl)carbonyl]-1,2-cyclopentanediamine hydrochloride

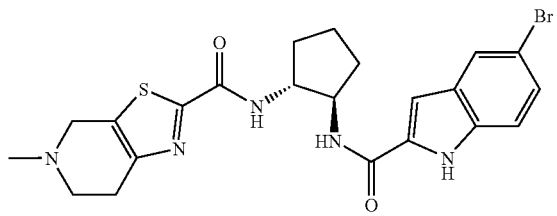

The title compound was obtained from (±)-trans-N-[(5-methyl-4,5,6,7-tetrahydrothiazolo[5,4-c]pyridin-2-yl) carbonyl]-1,2-cyclopentanediamine hydrochloride and 5-bromoindole-2-carboxylic acid in a similar manner to Example 6.

$^1$H-NMR (DMSO-d$_6$) δ: 1.65–1.76(4H,m), 2.00–2.03 (2H,m), 2.91(3H,s), 3.13–3.19(2H,br.s), 3.47(1H,br.s), 3.68 (1H,br.s), 4.30–4.67(4H,m), 7.11(1H,d,J=1.5 Hz), 7.27(1H, dd,J=8.8, 2.0 Hz), 7.35(1H,d,J=8.8 Hz), 7.84(1H,d,J=1.5 Hz), 8.56(1H,d,J=8.5 Hz), 8.93(1H,d,J=8.8 Hz), 11.44(1H, br.s), 11.78(1H,br.s). MS (ESI) m/z: 502(M+H)$^+$.

Example 44

(±)-trans-N$^1$-(5-Chloroindol-2-yl)carbonyl]-N$^2$-[(4,5,6,7-tetrahydrothiazolo[5,4-c]pyridin-2-yl)carbonyl]-1,2-cyclopentanediamine hydrochloride

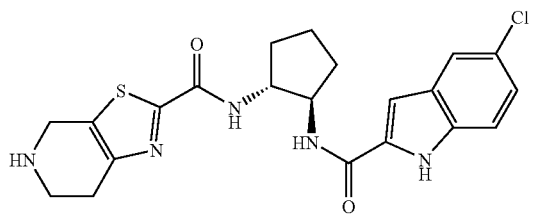

The title compound was obtained by subjecting a product obtained by the reaction of (±)-trans-N-[(5-chloroindol-2-yl)carbonyl]-1,2-cyclopentanediamine with lithium 5-tert-butoxycarbonyl-4,5,6,7-tetrahydrothiazolo[5,4-c]pyridine-2-carboxylate to a deprotecting treatment in a similar manner to Example 2.

$^1$H-NMR (DMSO-d$_6$) δ: 1.60–1.82(4H,m), 1.91–2.15 (2H,m), 3.08(2H,s), 3.37–3.49(2H,m), 4.28–4.56(4H,m), 7.13(1H,s), 7.15(1H,d,J=8.8 Hz), 7.40(1H,d,J=8.8 Hz), 7.69 (1H,s), 8.61(1H,d,J=8.3 Hz), 8.88(1H,d,J=8.3 Hz), 10.05 (2H,br.s), 11.82(1H,s). MS (FAB) m/z: 444(M+H)$^+$.

Example 45

(±)-trans-N$^1$-(5-Chloroindol-2-yl)carbonyl]-N$^2$-[(5-isopropyl-4,5,6,7-tetrahydrothiazolo[5,4-c]pyridin-2-yl)carbonyl]-1,2-cyclopentanediamine hydrochloride

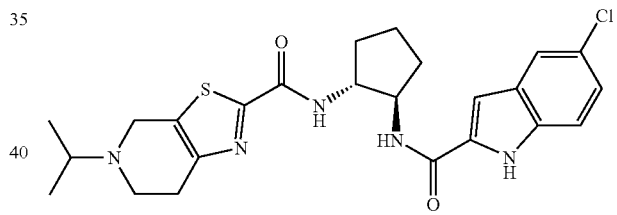

(±)-trans-N$^1$-[(5-Chloroindol-2-yl)carbonyl]-N$^2$-[(4,5,6, 7-tetrahydrothiazolo[5,4-c]pyridin-2-yl)carbonyl]-1,2-cyclopentanediamine hydrochloride (30 mg) was suspended in dichloromethane (20 ml), and triethylamine (260 μl) was added to stir the mixture at room temperature for 15 minutes. Acetic acid (179 μl) and acetone (920 μl) were added to the reaction mixture, and the resultant mixture was stirred at room temperature for 2 minutes. Sodium triacetoxyborohydride (796 mg) was added to the reaction mixture to stir them at room temperature for 5 hours. A 1N aqueous solution (10 ml) of sodium hydroxide was added to the reaction mixture to conduct liquid separation. The resultant organic layer was dried over anhydrous sodium sulfate, and the solvent was distilled off under reduced pressure. The residue was purified by column chromatography on silica gel (dichloromethane:methanol=100:3) to obtain a colorless foamy substance. This product was dissolved in dichloromethane, and a 1N ethanol solution (1 ml) of hydrochloric acid was added. The solution was concentrated under reduced pressure to obtain the title compound (205 mg) as a pale yellow foamy substance.

$^1$H-NMR (DMSO-d$_6$) δ: 1.27–1.39(6H,m), 1.58–1.80 (4H,m), 1.95–2.10(2H,m), 3.00–3.12(1H,m), 3.25–3.45(2H, m), 3.59–3.77(2H,m), 4.25–4.39(1H,m), 4.40–4.55(2H,m), 4.57–4.65(1H,m), 7.10(1H,s), 7.14(1H,d,J=8.8 Hz), 7.38 (1H,d,J=8.8 Hz), 7.68(1H,s), 8.56(1H,d,J=8.8 Hz), 8.90(1H, d,J=8.8 Hz), 11.39(1H,br.s), 11.76(0.5H,s), 11.80(0.5H,s). MS (FAB) m/z: 486(M+H)⁺.

Example 46

(±)-trans-N¹-(5-Chloroindol-2-yl)carbonyl]-N²-[[5-(2,3,5,6-tetrahydro-4H-pyran-4-yl)-4,5,6,7-tetrahydrothiazolo[5,4-c]pyridin-2-yl]carbonyl]-1,2-cyclopentanediamine hydrochloride

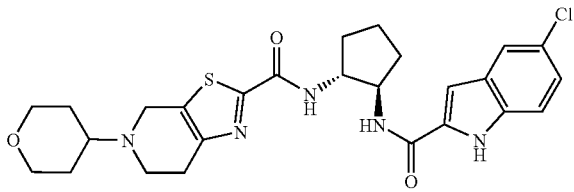

The title compound was obtained from (±)-trans-N¹-[(5-chloroindol-2-yl)carbonyl]-N ²-[(4,5,6,7-tetrahydrothiazolo [5,4-c]pyridin-2-yl)carbonyl]-1,2-cyclopentanediamine hydrochloride by using tetrahydro-4H-pyran-4-one in place of acetone in Example 45.

¹H-NMR (DMSO-d₆) δ: 1.60–2.20(10H,m), 3.08–3.18 (1H,m), 3.21–3.70(5H,m), 3.72–3.91(1H,m), 3.93–4.04(2H, m), 4.27–4.42(1H,m), 4.45–4.60(2H,m), 4.62–4.77(1H,m), 7.12(1H,s), 7.15(1H,dd,J=8.8, 2.0 Hz), 7.39(1H,d,J=8.8 Hz), 7.69(1H,d,J=1.7 Hz), 8.56(1H,d,J=8.3 Hz), 8.91(1H,d, J=8.3 Hz), 11.77(1H,s), 11.79(1H,s). MS (FAB) m/z: 528 (M+H)⁺.

Example 47

(±)-trans-N¹-(5-Chloroindol-2-yl)carbonyl]-N²-[(5-cyclopropyl-4,5,6,7-tetrahydrothiazolo[5,4-c] pyridin-2-yl)carbonyl]-1,2-cyclopentanediamine hydrochloride

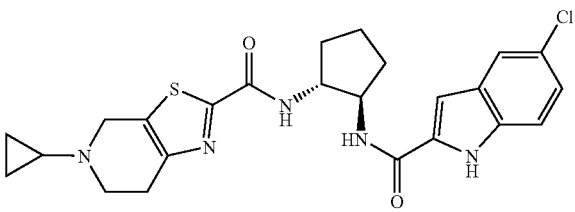

Acetic acid (0.1 ml), molecular sieve 4A powder (1 g) and [(1-ethoxycyclopropyl)oxy]trimethylsilane (0.173 ml) and successively sodium cyanoborohydride (43.2 mg) were added to a solution of (±)-trans-N¹-(5-chloroindol-2-yl) carbonyl]-N²-[(4,5,6,7-tetrahydrothiazolo[5,4-c]-pyridin-2-yl)carbonyl]-1,2-cyclopentanediamine hydrochloride (82.8 mg) in methanol (30 ml), and the mixture was heated under reflux for 18.5 hours. After allowing the reaction mixture to cool, it was filtered, and the filtrate was concentrated under reduced pressure. The residue was dissolved in ethyl acetate, the solution was washed with a 2N aqueous solution of sodium hydroxide and saturated saline and dried over anhydrous sodium sulfate. The solvent was distilled off under reduced pressure, and the residue was purified by column chromatography on silica gel (methanol:dichloromethane= 3:97) to obtain a pale yellow amorphous substance (52 mg).

A mixture of ethanol and hydrochloric acid was added to this product and then methanol and dichloromethane were added to obtain the title compound as solid.

¹H-NMR (DMSO-d₆) δ: 0.86(2H,d,J=6.8 Hz), 1.16–1.23 (3H,m), 1.62–1.76(4H,m), 2.01–2.04(2H,m), 3.00(1H,br), 3.19(2H,br), 3.68(2H,br), 4.30–4.34(1H,m), 4.47–4.51(1H, m), 4.64(1H,br), 7.10(1H,d,J=1.4 Hz), 7.14(1H,dd,J=8.7, 2.1 Hz), 7.39(1H,d,J=8.7 Hz), 7.67(1H,d,J=1.9 Hz), 8.53 (1H,d,J=8.3 Hz), 8.89(1H,d,J=8.5 Hz), 11.74(1H,s). MS (FAB) m/z: 484(M+H)⁺.

Example 48

(±)-trans-N¹-(5-Chloroindol-2-yl)carbonyl]-N²-[[5-(1-methylcyclopropyl)-4,5,6,7-tetrahydrothiazolo[5, 4-c]-pyridin-2-yl]carbonyl]-1,2-cyclopentanediamine hydrochloride

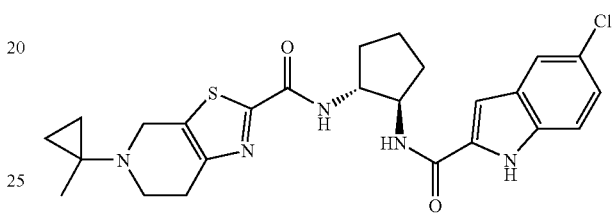

The title compound was obtained from (±)-trans-N-[(5-chloroindol-2-yl)carbonyl]-1,2-cyclopentanediamine hydrochloride and lithium 5-(1-methylcyclopropyl)-4,5,6,7-tetrahydrothiazolo[5,4-c]pyridine-2-carboxylate in a similar manner to Example 2.

¹H-NMR (DMSO-d₆) δ: 0.81(2H,br.s), 1.20–1.55(5H,br), 1.55–1.80(4H,m), 1.95–2.12(2H,m), 3.05–3.40(2H,br), 3.60–3.80(2H,br), 4.25–4.80(4H,m), 7.10(1H,s), 7.16(1H,d, J=8.8 Hz), 7.39(1H,d,J=8.8 Hz), 7.69(1H,s), 8.53(1H,d,J= 8.6 Hz), 8.85–8.95(1H,m), 10.60–10.90(1H,br), 11.73(1H, br.s). MS (FAB) m/z: 498(M+H)⁺.

Example 49

(±)-trans-N¹-[[5-(tert-Butyl)-4,6-dihydro-5H-pyrrolo-[3,4-d]thiazol-2-yl]carbonyl]-N²-[(5-chloroindol-2-yl)carbonyl]-1,2-cyclopentanediamine hydrochloride

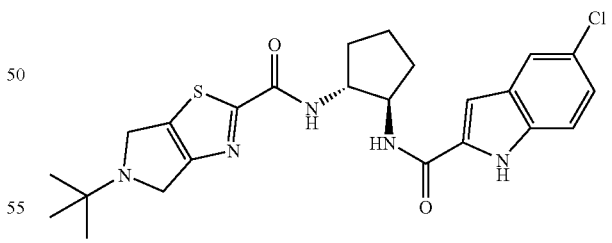

The title compound was obtained from (±)-trans-N-[(5-chloroindol-2-yl)carbonyl]-1,2-cyclopentanediamine hydrochloride and lithium 5-(tert-butyl)-4,6-dihydro-5H-pyrrolo [3,4-d]thiazole-2-carboxylate in a similar manner to Example 2.

¹H-NMR (DMSO-d₆) δ: 1.40(9H,s), 1.60–1.80(4H,m), 1.95–2.10(2H,m), 4.25–4.40(1H,m), 4.40–4.55(2H,m), 4.60–4.85(3H,m), 7.11(1H,s), 7.16(1H,d,J=8.8 Hz), 7.39 (1H,d,J=8.8 Hz), 7.69(1H,s), 8.54(1H,d,J=8.5 Hz), 8.95–9.05(1H,m), 11.70–11.80(1H,m), 12.45–12.65(1H,m). MS (FAB) m/z: 486(M+H)+.

Example 50

(±)-trans-$N^1$-[[5-(tert-Butyl)-4,5,6,7-tetrahydrothiazolo-[5,4-c]pyridin-2-yl]carbonyl]-$N^2$-[(5-chloroindol-2-yl)carbonyl]-1,2-cyclopentanediamine hydrochloride

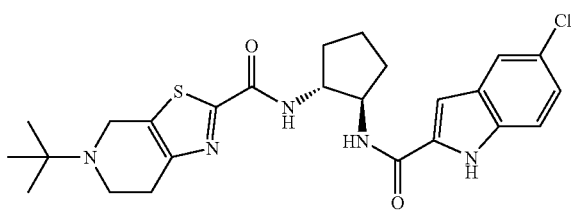

The title compound was obtained from (±)-trans-N-[(5-chloroindol-2-yl)carbonyl]-1,2-cyclopentanediamine hydrochloride and lithium (5-tert-butyl)-4,5,6,7-tetrahydrothiazolo[5,4-c]pyridine-2-carboxylate in a similar manner to Example 2.

$^1$H-NMR (DMSO-$d_6$) δ: 1.43(9H,s), 1.55–1.85(4H,m), 1.95–2.10(2H,m), 3.05–3.40(3H,m), 3.85–3.95(1H,m), 4.25–4.40(1H,m),4.40–4.55(2H,m), 4.70–4.85(1H,m), 7.11 (1H,s), 7.16(1H,dd,J=8.8, 2.0 Hz), 7.39(1H,d,J=8.8 Hz), 7.70(1H,d,J=2.0 Hz), 8.50–8.58(1H,m), 8.92(1H,d,J=8.5 Hz), 10.78(1H,br.s), 11.73–11.79(1H,m). MS (FAB) m/z: 500(M+H)+.

Example 51

(±)-trans-$N^1$-[(5-Chloroindol-2-yl)carbonyl]-$N^2$-[[5-(1,1-dimethyl-2-hydroxyethyl)-4,5,6,7-tetrahydrothiazolo-[5,4-c]pyridin-2-yl]carbonyl]-1,2-cyclopentanediamine hydrochloride

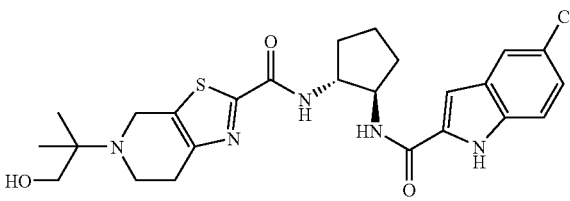

A 1 M tetrahydrofuran solution (5.0 ml) of tetrabutylammonium fluoride was added to (±)-trans-$N^1$-[[5-[2-(tert-butyldiphenylsilyloxy)-1,1-dimethylethyl]-4,5,6,7-tetrahydrothiazolo[5,4-c]pyridin-2-yl]carbonyl]-$N^2$-[(5-chloroindol-2-yl)carbonyl]-1,2-cyclopentanediamine (757 mg) obtained by the reaction of (±)-trans-N-[(5-chloroindol-2-yl)carbonyl]-1,2-cyclopentanediamine hydrochloride (393 mg) with lithium 5-[2-(tert-butyldiphenylsilyloxy)-1,1-dimethylethyl]-4,5,6,7-tetrahydrothiazolo[5,4-c]pyridine-2-carboxylate (812 mg) in a similar manner to Example 2, and the mixture was stirred overnight at room temperature. Dichloromethane and saturated saline were added to the reaction mixture to separate an organic layer, and the organic layer was dried over anhydrous magnesium sulfate. The solvent was distilled off, and the residue was purified by column chromatography on silica gel (methanol:dichloromethane=1:19) to obtain yellow powder. This product was dissolved in dichloromethane, and a 1N ethanol solution of hydrochloric acid and ethyl acetate were added to the solution. After the mixture was concentrated, ethyl acetate was added to solidify the residue, thereby obtaining the title compound (328 mg) as colorless powder.

$^1$H-NMR (DMSO-$d_6$) δ: 1.30(3H,s), 1.39(3H,s), 1.55–1.80(4H,m), 1.95–2.10(2H,m), 3.05–3.95(6H,m), 4.75–4.25(4H,m), 5.80(1H,br.s), 7.10(1H,s), 7.16(1H,d,J= 8.6 Hz), 7.39(1H,d,J=8.6 Hz), 7.69(1H,s), 8.52(1H,d,J=8.3 Hz), 8.90(1H,d,J=8.3 Hz), 9.92(1H,br.s), 11.72(1H,br.s). MS (FAB) m/z: 516(M+H)+.

Example 52

(±)-trans-$N^1$-[(5-Chloroindol-2-yl)carbonyl]-$N^2$-[(5-ethyl-4,5,6,7-tetrahydrothiazolo[5,4-c]pyridin-2-yl)carbonyl]-1,2-cyclopentanediamine hydrochloride

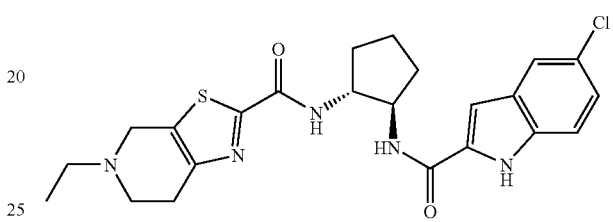

(±)-trans-$N^1$-[(5-Chloroindol-2-yl)carbonyl]-$N^2$-[(4,5,6,7-tetrahydrothiazolo[5,4-c]pyridin-2-yl)carbonyl]-1,2-cyclopentanediamine hydrochloride (500 mg) was dissolved in N,N-dimethylformamide (10 ml), and triethylamine (576 µl) and ethyl iodide (329 µl) were added to stir the mixture overnight at room temperature. The reaction mixture was concentrated under reduced pressure, and water was added to the residue to collect insoluble matter by filtration. This product was purified by column chromatography on silica gel (dichloromethane:methanol=100:3) to obtain a pale brown foamy substance. This substance was suspended in 1N hydrochloric acid (2 ml), and the suspension was concentrated under reduced pressure to obtain the title compound (180 mg) as a pale yellow foamy substance.

$^1$H-NMR (DMSO-$d_6$) δ: 1.32(3H,t,J=7.1 Hz), 1.60–1.80 (4H,m), 1.96–2.10(2H,m), 3.20–3.39(5H,m), 3.70–3.80(1H, m), 4.26–4.58(3H,m), 4.68–4.79(1H,m), 7.11(1H,s), 7.15 (1H,dd,J=8.8, 2.0 Hz), 7.39(1H,d,J=8.8 Hz), 7.69(1H,d,J= 1.5 Hz), 8.55(1H,d,J=8.5 Hz), 8.92(1H,d,J=8.5 Hz), 11.38 (1H,br.s), 11.70–11.80(1H,m). MS (FAB) m/z: 472(M+H)+.

Example 53

(±)-trans-$N^1$-[(5-Chloroindol-2-yl)carbonyl]-$N^2$-[[5-(2-methoxyethyl)-4,5,6,7-tetrahydrothiazolo[5,4-c]pyridin-2-yl]carbonyl]-1,2-cyclopentanediamine hydrochloride

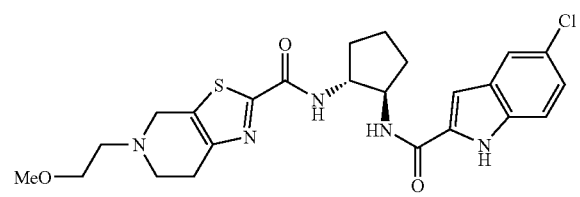

The title compound was obtained from (±)-trans-$N^1$-[(5-chloroindol-2-yl)carbonyl]-$N^2$-[(4,5,6,7-tetrahydrothiazolo[5,4-c]pyridin-2-yl)carbonyl]-1,2-cyclopentanediamine hydrochloride and 2-methoxyethyl bromide in a similar manner to Example 52.

$^1$H-NMR (DMSO-$d_6$) δ: 1.58–1.80(4H,m), 1.96–2.09 (2H,m), 3.05–3.28(2H,m), 3.31(3H,s), 3.41–3.57(3H,m), 3.70–3.85(3H,m), 4.26–4.38(1H,m), 4.40–4.57(2H,m), 4.66–4.80(1H,m), 7.10(1H,s), 7.15(1H,d,J=8.8 Hz), 7.38 (1H,d,J=8.8 Hz), 7.69(1H,s), 8.56(1H,d,J=8.3 Hz), 8.93(1H, d,J=8.3 Hz), 11.20(1H,br.s), 11.77(1H,s). MS (FAB) m/z: 502(M+H)$^+$.

Example 54

(±)-trans-N$^1$-[[5-(tert-Butoxycarbonylmethyl)-4,5,6, 7-tetrahydrothiazolo[5,4-c]pyridin-2-yl)carbonyl]- N$^2$-[(5-chloroindol-2-yl)carbonyl]-1,2- cyclopentanediamine

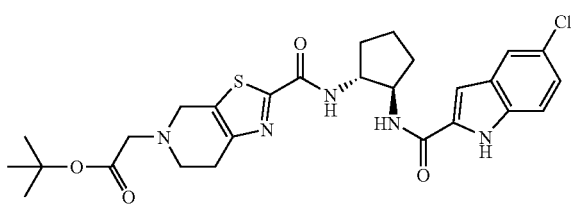

The title compound was obtained from (±)-trans-N$^1$-[(5-chloroindol-2-yl)carbonyl]-N$^2$-(4,5,6,7-tetrahydrothiazolo [5,4-c]pyridin-2-yl)carbonyl]-1,2-cyclopentanediamine hydrochloride and tert-butyl bromoacetate in a similar manner to Example 52.

$^1$H-NMR (CDCl$_3$) δ: 1.47(9H,s), 1.60–1.95(4H,m), 2.19–2.28(1H,m), 2.45–2.55(1H,m), 2.87–3.07(4H,m), 3.36 (2H,s), 3.88(1H,d,J=15.4 Hz), 3.97(1H,d,J=15.4 Hz), 4.09–4.18(1H,m), 4.38–4.49(1H,m), 6.90(1H,d,J=2.0 Hz), 7.18(1H,dd,J=8.8, 2.0 Hz), 7.31(1H,d,J=8.8 Hz), 7.49(1H, d,J=7.8 Hz), 7.61(1H,s), 7.71(1H,d,J=5.6 Hz), 9.57(1H,s). MS (FAB) m/z: 558(M+H)$^+$.

Example 55

(±)-trans-N$^1$-[[5-(Carboxymethyl)-4,5,6,7- tetrahydrothiazolo[5,4-c]pyridin-2-yl)carbonyl]-N$^2$- [(5-chloroindol-2-yl)carbonyl]-1,2- cyclopentanediamine

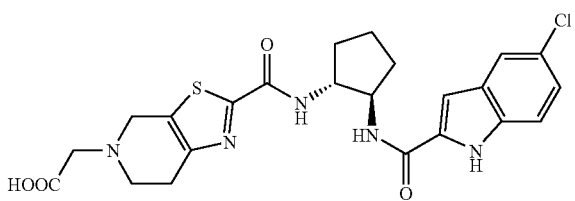

The compound (170 mg) obtained in Example 54 was dissolved in dichloromethane (1 ml), and trifluoroacetic acid (5 ml) was added to stir the mixture at room temperature for 2 hours. The reaction mixture was concentrated under reduced pressure, and diethyl ether was added to the residue to collect precipitate deposited by filtration, thereby obtaining the title compound (127 mg) as a colorless foamy substance.

$^1$H-NMR (DMSO-$d_6$) δ: 1.65–1.80(4H,m), 2.00–2.12 (2H,m), 3.02–3.10(2H,m), 3.40–3.55(2H,m), 3.98–4.08(2H, m), 4.30–4.59(4H,m), 7.10(1H,s), 7.17(1H,dd,J=8.6, 2.0 Hz), 7.39(1H,d,J=8.6 Hz), 7.69(1H,s), 8.53(1H,d,J=8.6 Hz), 8.99(1H,d,J=9.0 Hz), 11.73(1H,s). MS (FAB) m/z: 502(M+H)$^+$.

Example 56

(1R*,2R*)-N$^1$-[(5-Chloroindol-2-yl)carbonyl]-4- methoxycarbonyl-N$^2$-[(5-methyl-4,5,6,7- tetrahydrothiazolo[5,4-c]pyridin-2-yl)carbonyl]-1,2- cyclopentanediamine hydrochloride (Stereoisomer A and Stereoisomer B)

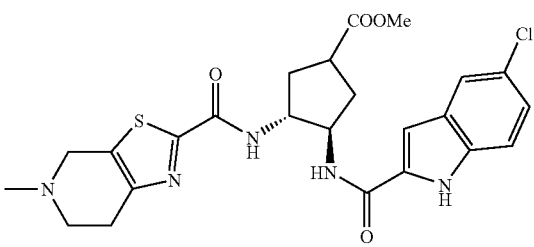

(1R*,2R*)-N$^1$-[(5-Chloroindol-2-yl)carbonyl]-4- methoxycarbonyl-1,2-cyclopentanediamine (mixture of stereoisomers) (3.42 g) was dissolved in N,N-dimethylformamide (20 ml), and lithium 5-methyl-4,5,6,7-tetrahydrothiazolo[5,4-c]pyridine-2-carboxylate (3.12 g), 1-hydroxybenzotriazole monohydrate (689 mg) and 1-(3-dimethylaminopropyl)-3-ethylcarbodiimide hydrochloride (4.89 g) were added to stir the mixture overnight at room temperature. The reaction mixture was concentrated under reduced pressure, and a saturated aqueous solution of sodium hydrogencarbonate and dichloromethane were added to the residue to conduct liquid separation. The resultant water layer was extracted with dichloromethane. The resultant organic layers were collected and dried over anhydrous sodium sulfate. The solvent was distilled off under reduced pressure, and the residue was purified by flash column chromatography on silica gel (dichloromethane:methanol=97:3→19:1) to obtain Stereoisomer A (585 mg) and Stereoisomer B (1.31 g). Each stereoisomer was dissolved in methanol, and a 1N ethanol solution of hydrochloric acid was added thereto. After the solvent was distilled off under reduced pressure, ethyl acetate was added to the residue. Precipitate formed was collected by filtration to obtain the title compounds [Stereoisomer A (573 mg) and Stereoisomer B (1.26 g)] as pale yellow solids.

Hydrochloride of Stereoisomer A:

$^1$H-NMR (DMSO-$d_6$) δ: 1.91–2.02(2H,m), 2.23–2.27 (2H,m), 2.90(3H,s), 3.06–3.14(3H,m), 3.46–3.64(5H,m), 4.38–4.64(4H,m), 7.10(1H,d,J=1.5 Hz), 7.16(1H,dd,J=8.7, 2.0 Hz), 7.39(1H,d,J=8,7 Hz), 7.70(1H,d,J=2.0 Hz), 8.64 (1H,d,J=8.3 Hz), 9.02(1H,d,J=8.6 Hz), 11.41(1H,br.s), 11.79 (1H,br.s). MS (FAB) m/z: 516(M+H)$^+$.

Hydrochloride of Stereoisomer B:

$^1$H-NMR (DMSO-$d_6$) δ: 1.91–2.02(2H,m), 2.19–2.33 (2H,m), 2.90(3H,s), 3.05–3.17(3H,m), 3.46–3.68(5H,m), 4.39–4.64(4H,m), 7.11(1H,d,J=1.5 Hz), 7.15(1H,dd,J=8.8, 2.0 Hz), 7.38(1H,d,J=8,8 Hz), 7.70(1H,d,J=2.0 Hz), 8.63 (1H,d,J=8.6 Hz), 9.01(1H,d,J=8.8 Hz), 11.42(1H,br.s), 11.78 (1H,br.s). MS (FAB) m/z: 516(M+H)$^+$.

Example 57

(1R*,2R*)-4-Carboxy-N¹-[(5-chloroindol-2-yl)carbonyl]-N²-[(5-methyl-4,5,6,7-tetrahydrothiazolo[5,4-c]pyridin-2-yl)carbonyl]-1,2-cyclopentanediamine (Stereoisomer B)

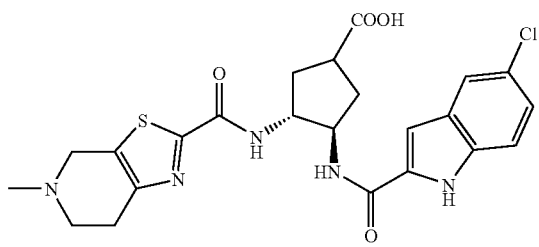

Stereoisomer B (900 mg) obtained in Example 56 was dissolved in methanol (10 ml) and water (3 ml), and lithium hydroxide (84 mg) was added to stir the mixture at room temperature for 3 hours. The reaction mixture was neutralized, the solvent was concentrated under reduced pressure, and water was added to the residue. Insoluble matter was collected by filtration to obtain the title compound (1.03 g) as a crude pale yellow solid.

$^1$H-NMR (DMSO-$d_6$) δ: 1.86–1.99(2H,m), 2.20–2.30 (2H,m), 2.38(3H,s), 2.76(2H,br.s), 2.84(2H,br.s), 2.95–3.03 (1H,m), 3.66(2H,br.s), 4.37–4.42(1H,m), 4.56–4.60(1H,m), 7.11(1H,s), 7.16(1H,d,J=8.5 Hz), 7.40(1H,d,J=8,5 Hz), 7.70 (1H,s), 8.58(1H,d,J=8.1 Hz), 8.81(1H,d,J=8.3 Hz), 11.73 (1H,br.s). MS (FAB) m/z: 502(M+H)$^+$.

Example 58

(1R*,2R*)-N¹-[(5-Chloroindol-2-yl)carbonyl]-4-(N-methylcarbamoyl)-N²-[(5-methyl-4,5,6,7-tetrahydrothiazolo[5,4-c]pyridin-2-yl)carbonyl]-1,2-cyclopentanediamine hydrochloride (Stereoisomer B)

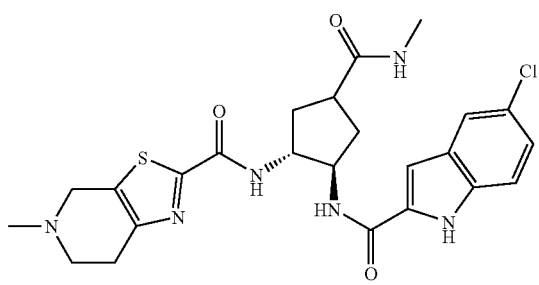

Stereoisomer B (195 mg) obtained in Example 57 was dissolved in N,N-dimethylformamide (5 ml), and 1-hydroxybenzotriazole monohydrate (26 mg), 1-(3-dimethylaminopropyl)-3-ethylcarbodiimide hydrochloride (149 mg), methylamine hydrochloride (52 mg) and triethylamine (107 μl) were added to stir the mixture at room temperature for 24 hours. The solvent was distilled off under reduced pressure, and a saturated aqueous solution of sodium hydrogencarbonate was added to the residue to conduct extraction with dichloromethane. The resultant organic layer was dried over anhydrous sodium sulfate, and the solvent was then distilled off under reduced pressure. The residue was purified by flash column chromatography on silica gel (dichloromethane:methanol=9:1). The thus-obtained pale yellow solid was dissolved in methanol, a 1N ethanol solution (276 μl) of hydrochloric acid was added, the solvent was concentrated under reduced pressure, and ethyl acetate was added to the residue. Precipitate formed was collected by filtration to obtain the title compound (140 mg) as a pale yellow solid.

$^1$H-NMR (DMSO-$d_6$) δ: 1.83–1.91(2H,m), 2.09–2.19 (2H,m), 2.59,2.60(3H,each s), 2.82–2.90(4H,m), 3.15(2H, br.s), 3.44–3.67(2H,br.s), 4.34–4.63(4H,m), 7.12(1H,d,J= 1.2 Hz), 7.16(1H,dd,J=8.8, 2.1 Hz), 7.39(1H,d,J=8,8 Hz), 7.69(1H,d,J=2.1 Hz), 7.88,7.89(1H,each s), 8.81(1H,d,J=8.6 Hz), 8.97(1H,d,J=8.6 Hz), 11.37(1H,br.s), 11.76(1H,br.s). MS (ESI) m/z: 515(M+H)$^+$.

Example 59

(1R*,2R*)-N¹-[(5-Chloroindol-2-yl)carbonyl]-4-(N,N-dimethylcarbamoyl)-N²-[(5-methyl-4,5,6,7-tetrahydrothiazolo[5,4-c]pyridin-2-yl)carbonyl]-1,2-cyclopentanediamine hydrochloride (Stereoisomer B)

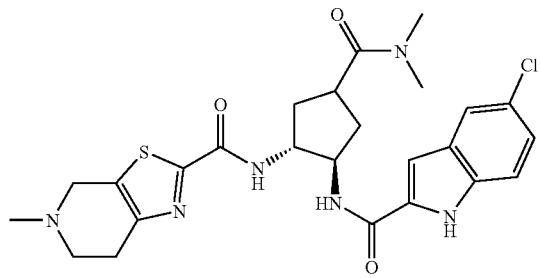

The title compound was obtained from Stereoisomer B obtained in Example 57 in a similar manner to Example 58.

$^1$H-NMR (DMSO-$d_6$) δ: 1.84–1.95(2H,m), 2.12–2.22 (2H,m), 2.85(3H,s), 2.88(3H,s), 3.01(3H,s), 3.05–3.10(1H, m), 3.15(2H,br.s), 3.29–3.53(2H,m), 4.34–4.63(4H,m), 7.11 (1H,s), 7.15(1H,dd,J=8.7, 1.7 Hz), 7.38(1H,d,J=8.7 Hz), 7.69(1H,d,J=1.7 Hz), 8.64(1H,d,J=8.6 Hz), 8.97(1H,d,J=8.8 Hz), 11.39(1H,br.s), 11.76(1H,s). MS (ESI) m/z: 529(M+H)$^+$.

Example 60

(1R*,2R*)-4-Methoxy-N¹-[(5-chloroindol-2-yl)carbonyl]-N²-[(5-methyl-4,5,6,7-tetrahydrothiazolo[5,4-c]pyridin-2-yl)carbonyl]-1,2-cyclopentanediamine hydrochloride (Stereoisomer A and Stereoisomer B)

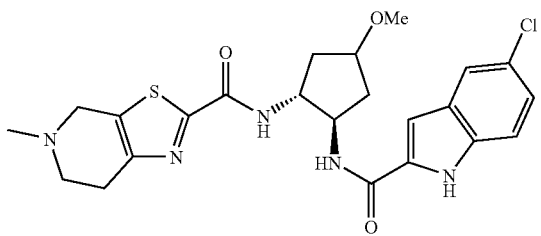

1) (1R*,2R*)-4-Methoxy-1,2-cyclopentanediamine hydrochloride (470 mg) was suspended in N,N-dimethylformamide (5 ml), and triethylamine (0.966 ml) and p-nitrophenyl 5-chloroindole-2-carboxylate (805 mg) were added to stir the mixture at room temperature for 4 days. The solvent was distilled off under reduced pressure, and a saturated aqueous solution of sodium hydrogencarbonate and dichloromethane were added to the residue to conduct liquid separation. The resultant organic layers was dried over anhydrous sodium sulfate. The solvent was distilled off under reduced pressure, and the residue was purified by column chromatography on silica gel (methanol:dichloromethane=1:9) to obtain (1R*,2R*)-4-methoxy-N$^1$-[(5-chloroindol-2-yl)carbonyl]-1,2-cyclopentanediamine (mixture of stereoisomers at 4-position) (268 mg) as yellow powder.

2) A mixture of stereoisomers A and B of the title compound was synthesized from the product (268 mg) obtained above in a similar manner to Example 2, and the isomers were isolated by column chromatography on silica gel in the same manner as in Example 56 and then converted into hydrochlorides to obtain the title compounds [Stereoisomer A (75 mg) and Stereoisomer B (70 mg)].
Stereoisomer A:
$^1$H-NMR (DMSO-d$_6$) δ: 1.70–2.15(4H,m), 2.90(3H,s), 3.00–3.90(8H,m), 4.10–4.80(4H,m), 7.08(1H,s), 7.16(1H,d, J=8.8 Hz), 7.38(1H,d,J=8.8 Hz), 7.69(1H,s), 8.56(1H,d,J= 8.8 Hz), 8.88(1H,d,J=8.3 Hz), 10.96(1H,br.s), 11.75(1H, br.s) MS (FAB) m/z: 488(M+H)$^+$.
Stereoisomer B:
$^1$H-NMR (DMSO-d$_6$) δ: 1.60–2.10(4H,m), 2.89(3H,s), 3.00–3.70(7H,m), 3.70–3.90(1H,m), 4.20–4.80(4H,m), 7.05–7.20(2H,m), 7.38(1H,d,J=8.8 Hz), 7.68(1H,s), 8.59 (1H,d,J=8.3 Hz), 8.90(1H,d,J=8.5 Hz), 11.26(1H,br.s), 11.74 (1H,br.s). MS (FAB) m/z: 488(M+H)$^+$.

Example 61

(1R*,2R*)-4-Benzyloxy-N$^1$-[(5-chloroindol-2-yl) carbonyl]-N$^2$-[(5-methyl-4,5,6,7-tetrahydrothiazolo [5,4-c]pyridin-2-yl)carbonyl]-1,2-cyclopentanediamine (Stereoisomer A and Stereoisomer B)

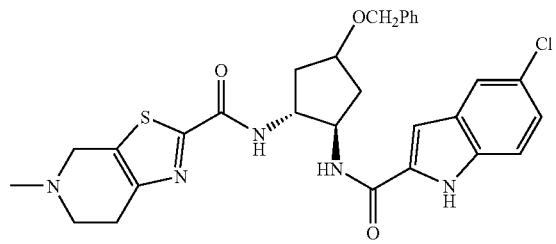

Stereoisomers A and B of the title compound were obtained from a mixture of (1R*,2R*,4R*)- and (1R*,2R*, 4S*)-4-benzyloxy-N$^1$-[(5-chloroindol-2-yl)-carbonyl]-1,2-cyclopentanediamines, and they were respectively isolated by column chromatography on silica gel to obtain the title compounds, Stereoisomers A and B.
Stereoisomer A:
$^1$H-NMR (CDCl$_3$) δ: 1.75–1.95(2H,m), 2.50(3H,s), 2.60–2.70(1H,m), 2.70–2.90(5H,m), 3.65(1H,d,J=15.4 Hz), 3.74(1H,d,J=15.6 Hz), 4.10–4.20(1H,m), 4.30–4.45(2H,m), 4.47(1H,d,J=11.7 Hz), 4.58(1H,d,J=12.0 Hz), 6.88(1H,d,J= 2.2 Hz), 7.20(1H,d.d,J=8.6 and 2.0 Hz), 7.30–7.40(6H,m), 7.50(1H,d,J=5.4 Hz), 7.58(1H,d,J=7.3 Hz), 7.63(1H,d,J=2.0 Hz), 9.19(1H,br.s). MS (FAB) m/z: 564(M+H)$^+$.
Stereoisomer B:
$^1$H-NMR (CDCl$_3$) δ: 1.80–2.00(2H,m), 2.45–2.55(1H, m), 2.49(3H,s), 2.70–2.90(5H,m), 3.65(1H,d,J=15.8 Hz), 3.72(1H,d,J=15.2 Hz), 4.15–4.30(2H,m), 4.48(1H,d,J=11.3 Hz), 4.52(1H,d,J=11.5 Hz), 4.55–4.70(1H,m), 6.68(1H,d,J= 1.7 Hz), 7.18(1H,d.d,J=8.7 and 2.0 Hz), 7.20–7.35(6H,m), 7.42(1H,d,J=7.8 Hz), 7.56(1H,d,J=1.7 Hz), 7.60(1H,d,J=6.4 Hz), 9.31(1H,br.s). MS (FAB) m/z: 564(M+H)$^+$.

Example 62

(1R*,2R*)-N$^1$-[(5-Chloroindol-2-yl)carbonyl]-4-hydroxy-N$^2$-[(5-methyl-4,5,6,7-tetrahydrothiazolo[5, 4-c]pyridin-2-yl)carbonyl]-1,2-cyclopentanediamine (Stereoisomer B) hydrochloride

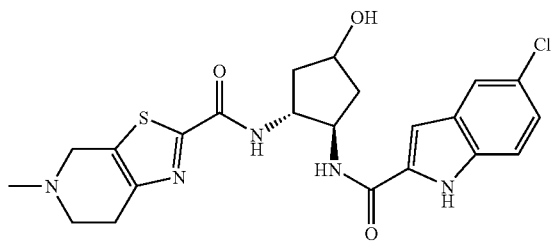

Dimethyl sulfide (8 ml) and anhydrous aluminum chloride (2.0 g) were dissolved in dichloromethane (100 ml), and Stereoisomer B (1.20 g) obtained in Example 61 was added to stir the mixture at room temperature for 8.5 hours. The reaction mixture was concentrated under reduced pressure, and diluted hydrochloric acid was added to the residue to acidify it. This solution was alkalified with a saturated aqueous solution of sodium hydrogencarbonate and extracted with dichloromethane. The extract was dried over anhydrous magnesium sulfate, and the solvent was then distilled off under reduced pressure. The residue was purified by column chromatography on silica gel (dichloromethane:methanol=9:1) to obtain yellow powder (0.93 g). A 1N ethanol solution of hydrochloric acid was added to this powder (100 mg) into a solution, and the solution was concentrated under reduced pressure to obtain the title compound (84 mg) as pale yellow powder.
$^1$H-NMR (DMSO-d$_6$) δ: 1.55–1.70(1H,m), 1.85–1.95 (2H,m), 2.25–2.35(1H,m), 2.93(3H,s), 3.00–3.20(2H,m), 3.35–3.70(2H,m), 4.15–4.25(1H,m), 4.30–4.75(3H,m), 7.13 (1H,d,J=2.2 Hz), 7.15(1H,d.d,J=8.8 and 2.2 Hz), 7.38(1H, d,J=9.3 Hz), 7.67(1H,s), 8.57(1H,d,J=8.1 Hz), 8.88(1H,d,J= 8.3 Hz), 10.79(1H,br.s), 11.72(1H,s). MS (FAB) m/z: 474 (M+H)$^+$.

Example 63

(1R*,2R*)-4-Acetoxy-N$^1$-[(5-chloroindol-2-yl) carbonyl]-N$^2$-[(5-methyl-4,5,6,7-tetrahydrothiazolo [5,4-c]pyridin-2-yl)carbonyl]-1,2-cyclopentanediamine (Stereoisomer B)

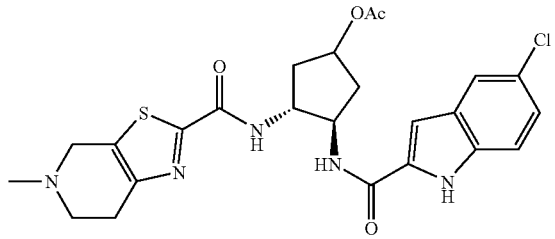

Stereoisomer B (208 mg) obtained in Example 62 was dissolved in pyridine (3 ml), and acetyl chloride (35.5 μl)

was added at room temperature to stir the mixture for 3.5 hours. The reaction mixture was concentrated under reduced pressure, and the residue was alkalified with a saturated aqueous solution of sodium hydrogencarbonate and extracted with dichloromethane. The extract was dried over anhydrous magnesium sulfate, and the solvent was then distilled off under reduced pressure. The residue was purified by column chromatography on silica gel (dichloromethane:hexane=1:1) to obtain the title compound (180 mg) as powder.

$^1$H-NMR (CDCl$_3$) δ: 1.70–1.85(1H,m), 2.00–2.15(1H, m), 2.06(3H,s), 2.20–2.35(1H,m), 2.50(3H,s), 2.70–3.10 (5H,m), 3.66(1H,d,J=15.1 Hz), 3.73(1H,d,J=15.4 Hz), 4.05–4.20(1H,m), 4.60–4.75(1H,m), 5.15–5.30(1H,m), 6.90 (1H,d,J=1.2 Hz), 7.21(1H,d.d,J=8.8 and 2.0 Hz), 7.31(1H, d,J=8.5 Hz), 7.48(1H,d,J=7.8 Hz), 7.63(1H,d,J=2.0 Hz), 7.67(1H,d,J=5.4 Hz), 9.30(1H,br.s). MS (FAB) m/z: 516 (M+H)$^+$.

Example 64

(1R*,2R*)-N$^1$-[(5-Chloroindol-2-yl)carbonyl]-4-hydroxymethyl-N$^2$-[(5-methyl-4,5,6,7-tetrahydrothiazolo[5,4-c]pyridin-2-yl)carbonyl]-1,2-cyclopentanediamine hydrochloride
(Stereoisomer A)

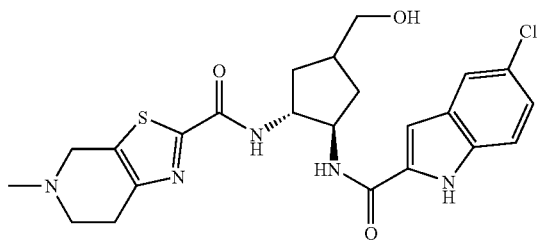

1) (1R*,2R*)-4-Benzyloxymethyl-N$^1$-[(5-chloroindol-2-yl)carbonyl]-1,2-cyclopentanediamine (794 mg) was dissolved in N,N-dimethylformamide (150 ml), and lithium 5-methyl-4,5,6,7-tetrahydrothiazolo[5,4-c]pyridine-2-carboxylate (694 mg), 1-hydroxybenzotriazole monohydrate (61 mg) and 1-(3-dimethylaminopropyl)-3-ethyl-carbodiimide hydrochloride (1.15 g) were added to stir the mixture overnight at room temperature. The reaction mixture was concentrated under reduced pressure, and water was added to the residue to conduct extraction with dichloromethane. The resultant organic layer was dried over anhydrous sodium sulfate. The solvent was distilled off under reduced pressure, and the residue was purified by preparative thin-layer chromatography (dichloromethane:acetone=2:1) to obtain Stereoisomer A (378 mg) and Stereoisomer B (354 mg) of (1R*,2R*)-4-benzyloxymethyl-N$^1$-[(5-chloroindol-2-yl)carbonyl]-N$^2$-[(5-methyl-4,5,6,7-tetrahydrothiazolo[5,4-c]pyridin-2-yl) carbonyl]-1,2-cyclopentanediamine.
Stereoisomer A:

$^1$H-NMR (CDCl$_3$) δ: 1.50–1.53(1H,m), 1.76–1.84(1H, m), 2.31–2.40(2H,m), 2.49(3H,s), 2.51–2.59(1H,m), 2.72–2.93(4H,m), 3.38–3.50(2H,m), 3.66(1H,d,J=15.4 Hz), 3.73(1H,d,J=15.4 Hz), 4.10–4.19(1H,m), 4.38–4.47(1H,m), 4.55(2H,s), 6.88(1H,s), 7.20(1H,dd,J=8.8, 1.5 Hz), 7.25–7.37(6H,m), 7.55(1H,d,J=6.3 Hz), 7.64(1H,s), 9.16 (1H,s). MS (FAB) m/z: 578(M+H)$^+$.
Stereoisomer B:

$^1$H-NMR (CDCl$_3$) δ: 1.40–1.51(1H,m), 1.83–1.92(1H, m), 2.10–2.18(1H,m), 2.49(3H,s), 2.51–2.68(2H,m), 2.73–2.94(4H,m), 3.39–3.49(2H,m), 3.63(1H,d,J=15.4 Hz), 3.72(1H,d,J=15.4 Hz), 4.14–4.23(1H,m), 4.41–4.50(2H,m), 4.54(2H,s), 6.72(1H,d,J=1.7 Hz), 7.17(1H,dd,J=8.8, 2.0 Hz), 7.27–7.42(6H,m), 7.57(1H,d,J=1.7 Hz), 7.66(1H,d,J= 6.1 Hz), 9.41(1H,s). MS (FAB) m/z: 578(M+H)$^+$.

2) The benzyl group of the above Stereoisomer A was eliminated in the same manner as in Example 62 to obtain the title compound (269 mg).

$^1$H-NMR (DMSO-d$_6$) δ: 1.41–1.52(1H,m), 1.69–1.90 (2H,m), 2.03–2.30(2H,m), 2.90(3H,s), 3.09–3.19(2H,m), 3.40–3.73(5H,m), 4.40–4.74(4H,m), 7.11(1H,s), 7.15(1H, dd,J=8.6, 2.0 Hz), 7.38(1H,d,J=8.6 Hz), 7.69(1H,J=1.7 Hz), 8.52(1H,J=8.6 Hz), 8.88(1H,J=8.6 Hz), 11.07(1H,br.s), 11.74(1H,s). MS (FAB) m/z: 488(M+H)$^+$.

Example 65

(1R*,2R*)-N$^1$-[(5-Chloroindol-2-yl)carbonyl]-4-hydroxymethyl-N$^2$-[(5-methyl-4,5,6,7-tetrahydrothiazolo[5,4-c]pyridin-2-yl)carbonyl]-1,2-cyclopentanediamine hydrochloride
(Stereoisomer B)

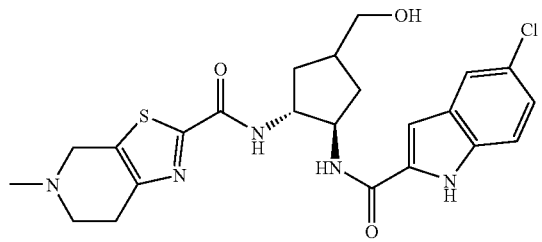

The title compound was obtained from Stereoisomer B obtained in 1) of Example 64 in a similar manner to 2) of Example 64.

$^1$H-NMR (DMSO-d$_6$) δ: 1.35–1.40(1H,m), 1.78–1.90 (2H,m), 2.01–2.11(1H,m), 2.19–2.30(1H,m), 2.91(3H,s), 3.10–3.77(7H,m), 4.27–4.78(4H,m), 7.09(1H,s), 7.15(1H,d, J=8.8 Hz), 7.38(1H,d,J=8.8 Hz), 7.69(1H,s), 8.52(1H,d,J= 8.3 Hz), 8.90(1H,d,J=8.3 Hz.), 10.97(1H,br.s), 11.73(1H,s). MS (FAB) m/z: 488(M+H)$^+$.

Example 66

Isolation of Optically Active Compound of (1R*, 2R*)-N$^1$-[(5-chloroindol-2-yl)carbonyl]-4-hydroxymethyl-N$^2$-[(5-methyl-4,5,6,7-tetrahydrothiazolo[5,4-c]pyridin-2-yl)carbonyl]-1,2-cyclopentanediamine (Stereoisomer A)

Stereoisomer A obtained in Example 64 was divided into optically active compound by HPLC (hexane:isopropyl alcohol:diethylamine=80:20:0.5; flow rate 12 ml/min) making use of CHIRALPAK AD (Daicel Chemical Industries, Ltd.) to obtain Optically Active Compound A1 eluted in 45 minutes and Optically Active Compound A2 eluted in 62 minutes. After 1N hydrochloric acid (1 ml) was added to the respective optically active compounds to suspend them, each suspension was concentrated under reduced pressure to obtain the hydrochloride (92 mg) of Optically Active Compound A1 and the hydrochloride (74 mg) of Optically Active Compound A2 as pale brown foamy substances.
Hydrochloride of Optically Active Compound A1:

$^1$H-NMR (DMSO-d$_6$) δ: 1.41–1.52(1H,m), 1.69–1.90 (2H,m), 2.03–2.30(2H,m), 2.90(3H,s), 3.09–3.19(2H,m), 3.40–3.73(5H,m), 4.40–4.74(4H,m), 7.11(1H,s), 7.15(1H, dd,J=8.6, 2.0 Hz), 7.38(1H,d,J=8.6 Hz), 7.69(1H,J=1.7 Hz), 8.52(1H,J=8.6 Hz), 8.88(1H,J=8.6 Hz), 11.07(1H,br.s), 11.74(1H,s). MS (FAB) m/z: 488(M+H)⁺.

Hydrochloride of Optically Active Compound A2:
¹H-NMR (DMSO-d₆) δ: 1.41–1.52(1H,m), 1.69–1.90 (2H,m), 2.03–2.30(2H,m), 2.90(3H,s), 3.09–3.19(2H,m), 3.40–3.73(5H,m), 4.40–4.74(4H,m), 7.11(1H,s), 7.15(1H, dd,J=8.6, 2.0 Hz), 7.38(1H,d,J=8.6 Hz), 7.69(1H,J=1.7 Hz), 8.52(1H,J=8.6 Hz), 8.88(1H,J=8.6 Hz), 11.07(1H,br.s), 11.74(1H,s). MS (FAB) m/z: 488(M+H)⁺.

Example 67

(1R*,2R*)-N¹-[(5-Chloroindol-2-yl)carbonyl]-4-hydroxymethyl-N²-[(5-isopropyl-4,5,6,7-tetrahydrothiazolo[5,4-c]pyridin-2-yl)carbonyl]-1,2-cyclopentanediamine hydrochloride
(Stereoisomer A)

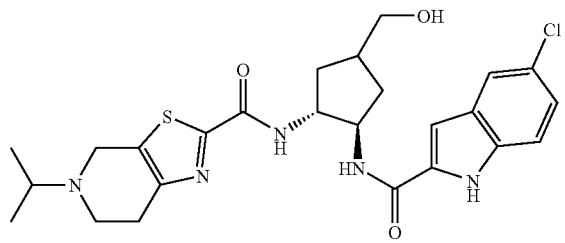

1) Stereoisomers A and B of (1R*,2R*)-4-benzyloxymethyl-N¹-[(5-chloroindol-2-yl)carbonyl]-4-hydroxymethyl-N²-[(5-isopropyl-4,5,6,7-tetrahydrothiazolo[5,4-c]pyridin-2-yl)carbonyl]-1,2-cyclopentanediamine were obtained from (1R*,2R*)-4-benzyloxymethyl-N¹-[(5-chloroindol-2-yl)carbonyl]-1,2-cyclopentanediamine and lithium 5-isopropyl-4,5,6,7-tetrahydrothiazolo[5,4-c]pyridin-2-yl)-2-carboxylate in a similar manner to 1) of Example 64.

Stereoisomer A:
¹H-NMR (CDCl₃) δ: 1.12(6H,d,J=6.4 Hz), 1.53–1.63(1H, m), 1.75–1.85(1H,m), 2.29–2.39(2H,m), 2.47–2.58(1H,m), 2.78–3.02(5H,m), 3.37–3.49(2H,m), 3.76(1H,d,J=15.1 Hz), 3.83(1H,d,J=15.1 Hz), 4.15–4.23(1H,m), 4.40–4.50(1H,m), 4.54(2H,s), 6.88(1H,d,J=1.7 Hz), 7.16(1H,dd,J=8.8, 2.0 Hz), 7.27–7.38(6H,m), 7.58(1H,d,J=7.3 Hz), 7.60(1H,s), 7.64(1H,d,J=5.6 Hz), 9.56(1H,s). MS (FAB) m/z: 606(M+H)⁺.

Stereoisomer B:
¹H-NMR (CDCl₃) δ: 1.12(1H,d,J=6.6 Hz), 1.42–1.52(1H, m), 1.82–1.92(1H,m), 2.10–2.20(1H,m), 2.48–2.68(2H,m), 2.80–3.02(5H,m), 3.40–3.49(2H,m), 3.77(1H,d,J=15.5 Hz), 3.83(1H,d,J=15.5 Hz), 4.15–4.25(1H,m), 4.42–4.52(1H,m), 4.53(1H,d,J=1.0 Hz), 6.74(1H,d,J=1.5 Hz), 7.17(1H,dd,J=8.8, 2.0 Hz), 7.27–7.37(6H,m), 7.41(1H,d,J=7.8 Hz), 7.57 (1H,d,J=2.0 Hz), 7.68(1H,d,J=6.1 Hz), 9.51(1H,s). MS (FAB) m/z: 606(M+H)⁺.

2) The title compound was obtained from the above Stereoisomer A in a similar manner to 2) of Example 64.
¹H-NMR (DMSO-d₆) δ: 1.30–1.40(6H,m), 1.43–1.53 (1H,m), 1.71–1.91(2H,m), 2.09–2.16(1H,m), 2.19–2.31(1H, m), 3.04–3.15(1H,m), 3.34–3.77(7H,m), 4.30–4.67(4H,m), 7.12(1H,s), 7.16(1H,d,J=8.8 Hz), 7.40(1H,d,J=8.8 Hz), 7.69 (1H,s), 8.56(1H,d,J=8.3 Hz), 8.85(1H,d,J=8.3 Hz), 11.42 (1H,br.s), 11.77(0.5H,s),11.80(0.5H,s). MS (FAB) m/z: 516 (M+H)⁺.

Example 68

(1R*,2R*)-N¹-[(5-Chloroindol-2-yl)carbonyl]-4-hydroxymethyl-N²-[(5-isopropyl-4,5,6,7-tetrahydrothiazolo[5,4-c]pyridin-2-yl)carbonyl]-1,2-cyclopentanediamine hydrochloride
(Stereoisomer B)

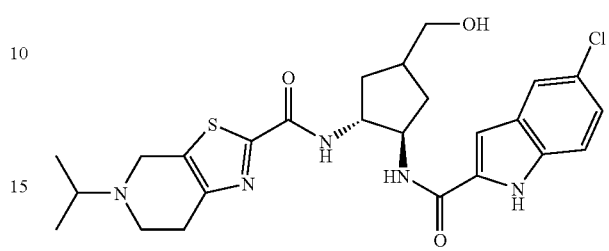

The title compound was obtained from the Stereoisomer B obtained in 1) of Example 67 in a similar manner to 2) of Example 67.
¹H-NMR (DMSO-d₆) δ: 1.30–1.39(6H,m), 1.40–1.54 (1H,m), 1.75–1.90(2H,m), 2.02–2.11(1H,m), 2.18–2.30(1H, m), 3.05–3.15(1H,m), 3.30–3.55(5H,m), 3.60–3.79(2H,m), 4.29–4.38(1H,m), 4.41–4.67(3H,m), 7.10(1H,s), 7.15(1H,d, J=8.8 Hz), 7.39(1H,d,J=8.8 Hz), 7.69(1H,s), 8.54(1H,d,J= 8.5 Hz), 8.87(1H,d,J=8.5 Hz), 11.29(1H,br.s), 11.75(0.5H,s), 11.78(0.5H,s). MS (FAB) m/z: 516(M+H)⁺.

Example 69

(1R*,2R*)-N¹-[(5-Chloroindol-2-yl)carbonyl]-N²-[[5-(1,1-dimethyl-2-hydroxyethyl)-4,5,6,7-tetrahydrothiazolo-[5,4-c]pyridin-2-yl)carbonyl]-4-hydroxymethyl-1,2-cyclopentanediamine hydrochloride (Stereoisomer A)

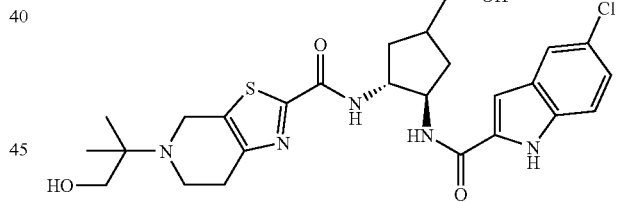

1) Stereoisomers A and B of (1R*,2R*)-4-benzyloxymethyl-N¹-[[5-[2-(tert-butyldiphenylsilyloxy)-1,1-dimethylethyl]-4,5,6,7-tetrahydrothiazolo[5,4-c]-pyridin-2-yl]carbonyl]-N²-[(5-chloroindol-2-yl)carbonyl]-1,2-cyclopentanediamine were obtained from (1R*,2R*)-4-benzyloxymethyl-N¹-[(5-chloroindol-2-yl)carbonyl]-1,2-cyclopentanediamine and lithium 5-[2-(tert-butyldiphenylsilyloxy)-1,1-dimethylethyl]-4,5,6,7-tetrahydrothiazolo[5,4-c]pyridin-2-yl)-2-carboxylate in a similar manner to Example 2.

Stereoisomer A:
¹H-NMR (CDCl₃) δ: 1.05(9H,s), 1.168, 1.171(6H,each s), 1.53–1.61(1H,m), 1.76–1.88(1H,m), 2.30–2.37(2H,m), 2.78–2.79(2H,m), 2.87–2.90(1H,m), 2.96–3.00(1H,m), 3.37–3.47(2H,m), 3.58(2H,s), 3.96(1H,q,J=13.1 Hz), 4.41–4.45(1H,m), 4.51–4.57(2H,m), 6.88(1H,d,J=1.5 Hz), 7.17(1H,dd,J=8.8, 2.0 Hz), 7.23–7.43(12H,m), 7.52(1H,d, J=7.6 Hz), 9.37(1H,br.s).

Stereoisomer B:

$^1$H-NMR (CDCl$_3$) δ: 1.05(9H,s), 1.17(6H,s), 1.43–1.47 (1H,m), 1.85–1.88(1H,m), 2.09–2.14(1H,m), 2.58–2.63(1H, m), 2.78–2.79(2H,m), 2.86–2.90(1H,m), 2.96–3.00(1H,m), 3.38–3.46(2H,m), 3.59(2H,s), 3.95(1H,q,J=13.3 Hz), 4.15–4.20(1H,m), 4.45–4.56(3H,m), 6.74(1H,d,J=2.0 Hz), 7.16(1H,dd,J=8.8, 2.0 Hz), 7.27–7.43(12H,m), 7.57(1H,d, J=2.0 Hz), 9.48(1H,br.s).

2) The above Stereoisomer A (288 mg) was suspended in dichloromethane (20 ml), and dimethyl sulfide (1.15 ml) and anhydrous aluminum chloride (350 mg) were added to stir the mixture at room temperature for 1 hour. A 1N aqueous solution (10 ml) of sodium hydroxide was added to the reaction mixture, and the mixture was extracted with dichloromethane. The resultant organic layer was dried over anhydrous sodium sulfate. The solvent was distilled off under reduced pressure, and the residue was purified by flash column chromatography on silica gel (dichloromethane:methanol=9:1) to obtain (1R*,2R*)-N$^1$-[[5-[2-(tert-butyldiphenylsilyloxy)-1,1-dimethylethyl]-4,5,6,7-tetrahydrothiazolo[5,4-c]pyridin-2-yl]carbonyl]-N$^2$-[(5-chloroindol-2-yl)carbonyl]-4-hydroxymethyl-1,2-cyclopentanediamine (Stereoisomer A) (184 mg) as a pale yellow solid.

$^1$H-NMR (CDCl$_3$) δ: 1.04(9H,s), 1.15(6H,s), 1.54–1.62 (1H,m), 1.73–1.81(1H,m), 1.99–2.25(2H,m), 2.34–2.38(2H, m), 2.67–2.85(3H,m), 2.92–2.97(1H,m), 3.48–3.62(4H,m), 3.93(1H,q,J=15.6 Hz), 4.20–4.28(1H,m), 4.47–4.56(1H,m), 6.89(1H,s), 7.11–7.18(1H,m), 7.24–7.27(1H,m), 7.32–7.43 (6H,m), 7.54(1H,d,J=1.7 Hz), 7.63(4H,dd,J=7.8, 1.5 Hz), 7.90–7.92(2H,m), 10.13(1H,br.s). MS (FAB) m/z: 784(M+H)$^+$.

3) Stereoisomer A (180 mg) obtained in the step 2) described above was dissolved in a 1N tetrahydrofuran solution (2 ml) of tetrabutylammonium fluoride, and the solution was stirred overnight at room temperature. Dichloromethane, a 1N aqueous solution of sodium hydroxide and sodium chloride were added to the reaction mixture to conduct liquid separation. The resultant organic layer was dried over anhydrous sodium sulfate. The solvent was distilled off under reduced pressure, and the residue was purified by flash column chromatography on silica gel (dichloromethane:methanol=19:1). The thus-obtained powder was dissolved in methanol, and a 1N ethanol solution (229 µl) of hydrochloric acid was added, to which ethyl acetate was added. The solvent was concentrated under reduced pressure to obtain the title compound (63 mg) as a pale brown solid.

$^1$H-NMR (DMSO-d$_6$) δ: 1.33–1.50(8H,m), 1.70–1.91 (2H,m), 2.07–2.14(1H,m), 2.23–2.24(1H,m), 3.04–3.10(1H, m), 3.27–3.44(4H,m), 3.57–3.70(2H,m), 3.92–3.95(1H,m), 4.29–4.72(4H,m), 5.81(1H,br.s), 7.11(1H,s), 7.15(1H,dd,J= 8.6, 2.0 Hz), 7.39(1H,d,J=8.6 Hz), 7.68(1H,d,J=2.0 Hz), 8.53–8.56(1H,m), 8.83(1H,d,J=8.3 Hz), 10.36(1H,br.s), 11.75,11.77(1H, each s). MS (ESI) m/z: 546(M+H)$^+$.

Example 70

(1R*,2R*)-N$^1$-[(5-Chloroindol-2-yl)carbonyl]-N$^2$-[[5-(1-dimethyl-2-hydroxyethyl)-4,5,6,7-tetrahydrothiazolo-[5,4-c]pyridin-2-yl)carbonyl]-4-hydroxymethyl-1,2-cyclopentanediamine hydrochloride (Stereoisomer B)

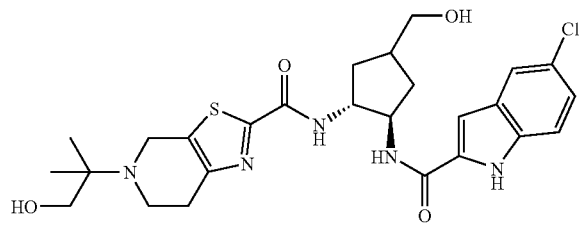

The title compound was obtained by eliminating the benzyl group of (1R*,2R*)-4-benzyloxymethyl-N$^1$-[(5-chloroindol-2-yl)carbonyl]-N 2-[5-[2-(tert-butyldiphenylsilyl)oxy-1,1-dimethylethyl]-4,5,6,7-tetrahydrothiazolo[5,4-c]pyridin-2-yl)carbonyl]-1,2-cyclopentanediamine (Stereoisomer B) obtained in 1) of Example 69 and then eliminating the tert-butyldiphenylsilyl group in the same manner as in 3) of Example 69.

$^1$H-NMR (DMSO-d$_6$) δ: 1.32–1.46(8H,m), 1.78–1.91 (2H,m), 2.03–2.10(1H,m), 2.24(1H,m), 3.05–3.11(1H,m), 3.26–3.37(3H,m), 3.58–3.69(2H,m), 3.92(1H,br.s), 4.29–4.36(1H,m), 4.52–4.72(4H,m), 5.80–5.81(1H,m), 7.10 (1H,s), 7.15(1H,d,J=8.8 Hz), 7.39(1H,d,J=8.8 Hz), 7.69(1H, s), 8.53(1H,d,J=7.6 Hz), 8.86(1H,d,J=8.1 Hz), 10.28(1H, br.s), 11.75,11.76(1H,each s). MS (ESI) m/z: 546(M+H)$^+$.

Example 71

(1R*,2R*)-4-Carbamoyloxymethyl-N$^1$-[(5-chloroindol-2-yl)carbonyl]-N$^2$-[(5-methyl-4,5,6,7-tetrahydrothiazolo-[5,4-c]pyridin-2-yl)carbonyl]-1,2-cyclopentanediamine (Stereoisomer A)

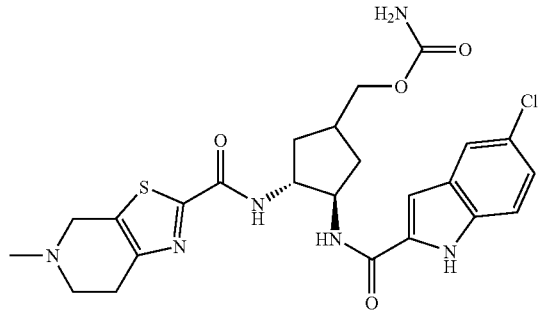

(1R*,2R*)-N$^1$-[(5-Chloroindol-2-yl)carbonyl]-4-hydroxymethyl-N$^2$-[(5-methyl-4,5,6,7-tetrahydrothiazolo-[5,4-c]pyridin-2-yl)carbonyl]-1,2-cyclopentanediamine (Stereoisomer A) (200 mg) was suspended in tetrahydrofuran (80 ml), and pyridine (100 µl) was added, and phenyl chloroformate (156 µl) was then added to stir the mixture at room temperature for 10 minutes. A saturated methanol solution (10 ml) of ammonia was added to the reaction mixture, and the mixture was left to stand overnight at room temperature. The reaction mixture was concentrated under reduced pressure, and a 1:9 mixed solvent (100 ml) of methanol and dichloromethane and a 1N aqueous solution (50 ml) of sodium hydroxide were added to the residue to conduct liquid separation. The resultant organic layer was then dried over anhydrous sodium sulfate. The solvent was distilled off under reduced pressure, and the residue was purified by column chromatography on silica gel (dichloromethane:methanol=10:1). The thus-obtained colorless amorphous solid was suspended in 1N hydrochloric acid (1 ml), and the suspension was concentrated under reduced pressure to obtain the title compound (151 mg) as a pale yellow solid.

$^1$H-NMR (DMSO-d$_6$) δ: 1.44–1.56(1H,m), 1.70–1.90 (2H,m), 2.05–2.15(1H,m), 2.35–2.45(1H,m), 3.02–3.26(2H, m), 3.39–3.72(2H,m), 3.80–3.92(2H,m), 4.30–4.42(2H,m), 4.49–4.59(1H,m), 4.60–4.70(1H,m), 6.46(2H,br.s), 7.10 (1H,s), 7.14(1H,dd,J=8.8, 2.0 Hz), 7.38(1H,d,J=8.8 Hz), 7.68(1H,s), 8.57(1H,J=8.3 Hz), 8.91(1H,J=8.3 Hz), 11.48 (1H,br.s), 11.75(1H,s). MS (FAB) m/z: 531(M+H)$^+$.

Example 72

(1R*,2R*)-N$^1$-[(5-Chloroindol-2-yl)carbonyl]-4-(N, N-dimethylcarbamoyl)oxymethyl-N$^2$-[(5-methyl-4,5, 6,7-tetrahydrothiazolo[5,4-c]pyridin-2-yl)carbonyl]-1,2-cyclopentanediamine (Stereoisomer A)

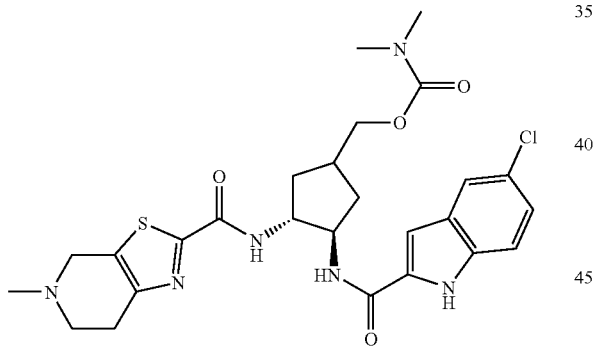

The title compound was obtained from (1R*,2R*)-N$^1$-[(5-chloroindol-2-yl)carbonyl]-4-hydroxymethyl-N$^2$-[(5-methyl-4,5,6,7-tetrahydrothiazolo[5,4-c]pyridin-2-yl) carbonyl]-1,2-cyclopentanediamine (Stereoisomer A) in a similar manner to Example 71.

$^1$H-NMR (DMSO-d$_6$) δ: 1.50–1.60(1H,m), 1.76–1.90 (2H,m), 2.06–2.15(1H,m), 2.39–2.46(1H,m), 2.75–2.93(9H, m), 3.14(2H,br.s), 3.38–3.73(2H,m), 3.89–3.90(1H,m), 4.28–4.71(4H,m), 7.09(1H,s), 7.15(1H,dd,J=8.6, 2.0 Hz), 7.37(1H,d,J=8.6 Hz), 7.68(1H,s), 8.57(1H,d,J=8.3 Hz), 8.94 (1H,d,J=8.3 Hz), 11.42(1H,br.s), 11.74(1H,s). MS (FAB) m/z: 559(M+H)$^+$.

Example 73

(1R*,2R*)-N$^1$-[(5-Chloroindol-2-yl)carbonyl]-N$^2$-[(5-methyl-4,5,6,7-tetrahydrothiazolo[5,4-c]pyridin-2-yl)carbonyl]-4-morpholinocarbonyloxymethyl-1,2-cyclopentanediamine (Stereoisomer B)

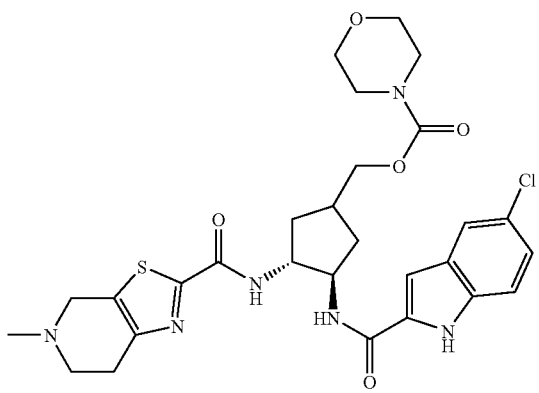

The title compound was obtained from (1R*,2R*)-N$^1$-[(5-chloroindol-2-yl)carbonyl]-4-hydroxymethyl-N$^2$-[(5-methyl-4,5,6,7-tetrahydrothiazolo[5,4-c]pyridin-2-yl) carbonyl]-1,2-cyclopentanediamine (Stereoisomer B) in a similar manner to Example 71.

$^1$H-NMR (DMSO-d$_6$) δ: 1.43–1.52(1H,m), 1.80–1.90 (2H,m), 2.07–2.17(2H,m), 2.85(3H,s), 3.12(2H,br.s), 3.25–3.65(1OH,m), 3.91–4.04(2H,m), 4.32–4.65(6H,m), 7.08(1H,s), 7.14(1H,d,J=8.8 Hz), 7.37(1H,d,J=8.8 Hz), 7.68 (1H,s), 8.54(1H,d,J=8.6 Hz), 8.93(1H,d,J=8.6 Hz), 11.40 (1H,br.s), 11.75(1H,s). MS (FAB) m/z: 601(M+H)$^+$.

Example 74

(±)-trans-4,4-Bis(methoxymethyl)-N$^1$-[(5-chloroindol-2-yl)carbonyl]-N$^2$-[(5-isopropyl-4,5,6,7-tetrahydrothiazolo-[5,4-c]pyridin-2-yl)carbonyl]-1,2-cyclopentanediamine hydrochloride

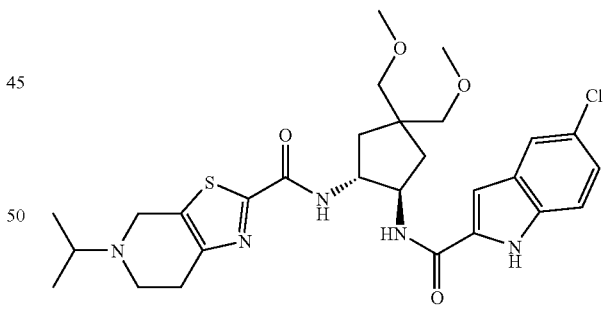

The title compound (300 mg) was obtained as a pale yellow foamy substance by dissolving (±)-trans-4,4-bis (methoxymethyl)-N-[(5-chloroindol-2-yl)carbonyl]-1,2-cyclopentanediamine (365 mg), lithium 5-isopropyl-4,5,6, 7-tetrahydrothiazolo[5,4-c]pyridin-2-yl)carboxylate (395 mg) and 1-hydroxybenzotriazole monohydrate (31 mg) in N,N-dimethylformamide (50 ml) and causing 1-(3-dimethylaminopropyl)-3-ethylcarbodiimide hydrochloride (575 mg) to react as a condensing agent in a similar manner to Example 2.

$^1$H-NMR (DMSO-d$_6$) δ: 1.33(6H,br.s), 1.59–1.72(1H,m), 1.80–1.95(1H,m), 3.01–3.14(1H,m), 3.18–3.45(12H,m), 3.60–3.80(2H,m), 4.30–4.69(4H,m), 7.11(1H,s), 7.15(1H, dd,J=8.5, 2.0 Hz), 7.39(1H,d,J=8.5 Hz), 7.69(1H,d,J=2.0 Hz), 8.49(1H,d,J=8.3 Hz), 8.80(1H,d,J=8.3 Hz), 11.11(1H, br.s), 11.69–11.80(1H,m). MS (FAB) m/z: 574(M+H)+.

Example 75

(±)-trans-4,4-Bis(hydroxymethyl)-$N^1$-[(5-chloroindol-2-yl)carbonyl]-$N^2$-[(5-isopropyl-4,5,6,7-tetrahydrothiazolo-[5,4-c]pyridin-2-yl)carbonyl]-1,2-cyclopentanediamine

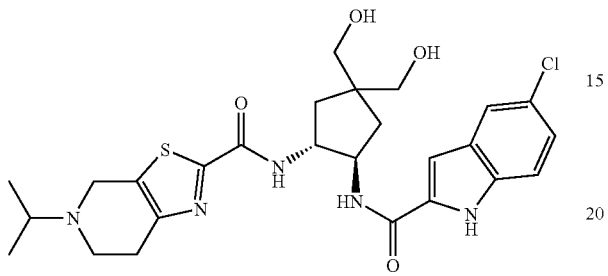

1) (±)-trans-4,4-Bis(benzyloxymethyl)-$N^1$-[(5-chloroindol-2-yl)carbonyl]-$N^2$-[(5-isopropyl-4,5,6,7-tetrahydrothiazolo[5,4-c]pyridin-2-yl)carbonyl]-1,2-cyclopentanediamine was obtained from (±)-trans-4,4-bis(benzyloxymethyl)-$N^1$-[(5-chloroindol-2-yl)carbonyl]-1,2-cyclopentanediamine and lithium 5-isopropyl-4,5,6,7-tetrahydrothiazolo[5,4-c]pyridin-2-yl)carboxylate in a similar manner to Example 2.

$^1$H-NMR (DMSO-$d_6$) δ: 1.01(6H,d,J=6.6 Hz), 1.60–1.72 (2H,m), 1.89–1.99(2H,m), 2.76(4H,br.s), 2.85–2.95(1H,m), 3.32–3.43(4H,m), 3.69–3.74(2H,m), 4.32–4.44(1H,m), 4.48–4.60(5H,m), 7.07(1H,s), 7.13(1H,dd,J=8.8, 2.0 Hz), 7.23–7.40(11H,m), 7.67(1H,d,J=1.7 Hz), 8.45(1H,d,J=8.6 Hz), 8.65(1H,d,J=8.6 Hz), 11.69(1H,s). MS (FAB) m/z: 726(M+H)+.

2) The title compound was obtained by eliminating the benzyl group of the product obtained above in the same manner as in Example 62.

$^1$H-NMR (DMSO-$d_6$) δ: 1.22–1.39(6H,m), 1.44–1.60 (2H,m), 1.85–1.98(2H,m), 3.00–3.78(9H,m), 4.25–4.80(4H, m), 7.09(1H,s), 7.14(1H,d,J=8.8 Hz), 7.37(1H,d,J=8.8 Hz), 7.67(1H,s), 8.48(1H,d,J=8.5 Hz), 8.73(1H,d,J=8.5 Hz), 10.82(1H,br.s), 11.72(1H,s). MS (FAB) m/z: 546(M+H)+.

Example 76

(±)-cis-$N^1$-[(5-Chloroindol-2-yl)carbonyl]-$N^2$-[(thiophen-2-yl)sulfonyl]-1,2-cyclohexanediamine

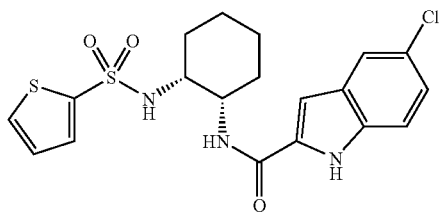

(±)-cis-N-[(5-Chloroindol-2-yl)carbonyl]-1,2-cyclohexanediamine hydrochloride (200 mg) was dissolved in N,N-dimethylformamide (1 ml), and triethylamine (0.28 ml) and 2-thiophenesulfonyl chloride (111 mg) were added to stir the mixture for 75 minutes. Water was added to the reaction mixture, and deposit was collected by filtration and recrystallized from methanol to obtain the title compound (198 mg) as colorless crystals.

$^1$H-NMR (DMSO-$d_6$) δ: 1.20–1.80(8H,m), 3.52(1H,br.s), 3.97(1H,br.s), 6.86(1H,t,J=4.5 Hz), 7.01(1H,s), 7.17(1H,dd, J=8.3, 2.2 Hz), 7.43(1H,d,J=8.6 Hz), 7.51(1H,s), 7.60–7.70 (2H,m), 7.73(1H,s), 7.80(1H,d,J=8.3 Hz), 11.71(1H,s) MS (FAB)m/z: 437(M+H)+.

Example 77

(±)-cis-$N^1$-[(5-Chloroindol-2-yl)carbonyl]-$N^2$-(2-butynoyl)-1,2-cyclohexanediamine

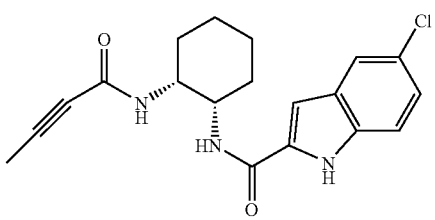

The title compound was obtained from (±)-cis-N-[(5-chloroindol-2-yl)carbonyl]-1,2-cyclohexanediamine hydrochloride and tetrolic acid in a similar manner to Example 2.

$^1$H-NMR (CDCl$_3$) δ: 1.40–1.81(6H,m), 1.81–1.92(1H, m), 1.99(3H,s), 2.08–2.17(1H,m), 4.11(1H,br.s), 4.29(1H, br.s), 6.22(1H,br,J=6.8 Hz), 6.87(1H,d,J=2.0 Hz), 7.22(1H, dd,J=8.8, 2.0 Hz), 7.34(1H,d,J=8.8 Hz), 7.61(1H,s), 7.70 (1H,br.s), 9.31(1H,s). MS (ESI)m/z: 358(M+H)+.

Example 78

(±)-cis-$N^1$-[(5-Chloroindol-2-yl)carbonyl]-$N^2$-phenylpropioloyl-1,2-cyclohexanediamine

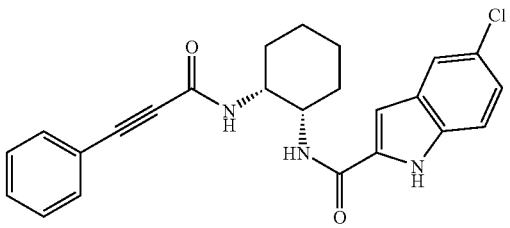

The title compound was obtained from (±)-cis-N-[(5-chloroindol-2-yl)carbonyl]-1,2-cyclohexanediamine hydrochloride and phenylptopiolic acid in a similar manner to Example 2.

$^1$H-NMR (CDCl$_3$) δ: 1.40–2.00(7H,m), 2.09–2.10(1H, m), 4.17(1H,br.s), 4.36(1H,br.s), 6.45(1H,br,J=5.6 Hz), 6.90 (1H,d,J=2.0 Hz), 7.10–73(9H,m), 9.50(1H,s). MS (ESI) m/z: 420(M+H)+.

Example 79

(±)-cis-N$^1$-[(5-Chloroindol-2-yl)carbonyl]-N$^2$-[(pyridin-4-yl)carbonyl]-1,2-cyclohexanediamine hydrochloride

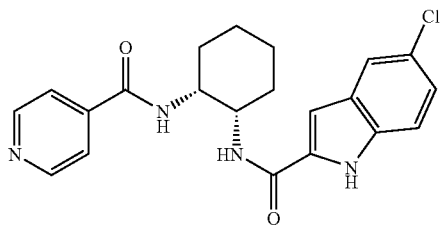

The title compound was obtained from (±)-cis-N-[(5-chloroindol-2-yl)carbonyl]-1,2-cyclohexanediamine hydrochloride and isonicotinic acid in a similar manner to Example 2.

$^1$H-NMR (DMSO-d$_6$) δ: 1.04(2H,br.s), 1.62(2H,d,J=10.2 Hz), 1.74(2H,br.s), 1.99(2H,d,J=4.6 Hz), 4.23–4.35(2H,m), 7.16(2H,dd,J=8.8, 1.8 Hz), 7.23(1H,s), 7.40(1H,d,J=8.8 Hz), 7.63(1H,d,J=1.8 Hz), 8.25(2H,d,J=6.1 Hz), 8.33(1H,br, J=7.3 Hz), 8.88(1H,br,J=6.6 Hz), 8.94(2H,d,J=6.1 Hz), 11.93(1H,s). MS (ESI)m/z: 397(M+H)$^+$.

Example 80

(±)-cis-N$^1$-[(5-Chloroindol-2-yl)carbonyl]-N$^2$-(4-dimethylaminobenzoyl)-1,2-cyclohexanediamine hydrochloride

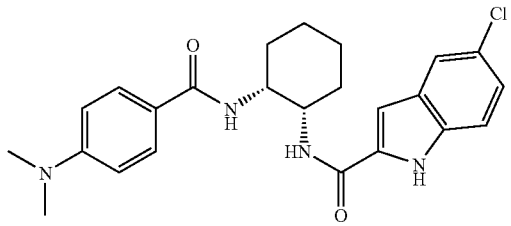

The title compound was obtained from (±)-cis-N-[(5-chloroindol-2-yl)carbonyl]-1,2-cyclohexanediamine hydrochloride and 4-dimethylaminobenzoic acid in a similar manner to Example 2.

$^1$H-NMR (DMSO-d$_6$) δ: 1.40(2H,br.s), 1.61(4H,br.s), 1.97(2H,br.s), 2.96(6H,s), 4.13–4.25(2H,m), 6.88(2H,d,J=8.5 Hz), 7.16(1H,dd,J=8.8, 2.0 Hz), 7.17(1H,s), 7.40(1H,d,J=8.8 Hz), 7.65(1H,d,J=2.0 Hz), 7.77(2H,d,J=8.5 Hz), 7.90 (1H,br,J=6.8 Hz), 8.18(1H,br,J=6.8 Hz), 11.91(1H,s). MS (ESI)m/z: 439(M+H)$^+$.

Example 81

(±)-cis-N$^1$-[(5-Chloroindol-2-yl)carbonyl]-N$^2$-[3-(4-pyridyl)acryloyl]-1,2-cyclohexanediamine hydrochloride

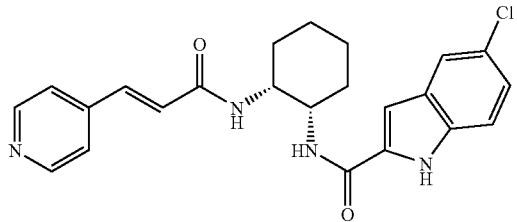

The title compound was obtained from (±)-cis-N-[(5-chloroindol-2-yl)carbonyl]-1,2-cyclohexanediamine hydrochloride and 3-(4-pyridyl)acrylic acid in a similar manner to Example 2.

$^1$H-NMR (DMSO-d$_6$)δ: 1.21(2H,br.s),1.50–1.67(3H,m), 1.67–1.80(1H,m),1.80–1.96(2H,m),4.11–4.30(2H,m), 7.15 (1H,dd,J=8.8, 1.7 Hz),7.21(1H,s),7.40(1H,d,J=8.8 Hz), 7.42 (1H,d,J=16.0 Hz),7.53(1H,d,J=16.0 Hz), 7.62(1H,d,J=1.7 Hz), 8.06(2H,d,J=6.0 Hz), 8.27(1H,br,J=7.6 Hz), 8.50(1H, br,J=7.6 Hz), 8.87(2H,d,J=6.0 Hz), 11.86(1H,s). MS (ESI) m/z:423(M+H)$^+$.

Example 82

(±)-cis-N$^1$-[(5-Chloroindol-2-yl)carbonyl]-N$^2$-[(1-isopropylpiperidin-4-yl)carbonyl]-1,2-cyclohexanediamine hydrochloride

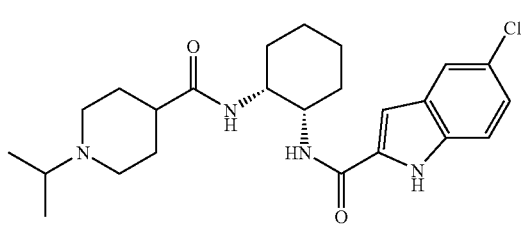

The title compound was obtained from (±)-cis-N-[(5-chloroindol-2-yl)carbonyl]-1,2-cyclohexanediamine hydrochloride and lithium 1-isopropylpiperidine-4-carboxylate in a similar manner to Example 2.

$^1$H-NMR (DMSO-d$_6$) δ: 0.94–2.10(1H,m), 1.22(6H,d,J= 6.1 Hz), 2.60–2.94(4H,m), 2.98–3.50(4H,m), 4.01(1H,br.s), 4.12(1H,br.s), 7.16(1H,d,J=8.4 Hz), 7.20(1H,s), 7.42(1H,d, J=8.4 Hz), 7.65(1H,s),7.93(1H,br,J=7.1 Hz), 8.17(1H,br,J= 7.8 Hz), 9.59(1H,br.s), 11.91(1H,s). MS (ESI)m/z: 445(M+ H)$^+$.

Example 83

(±)-cis-N$^1$-[(5-Chloroindol-2-yl)carbonyl]-N$^2$-[[(E)-3-(1-methylpiperidin-4-yl)acryloyl]-1,2-cyclohexanediamine hydrochloride

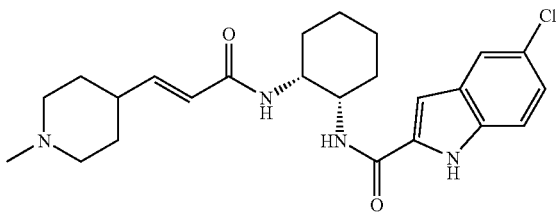

1) Water (1 ml) and lithium hydride (10 mg) were added to a solution with 1-(tert-butoxycarbonyl)-4-[(E)-2-(methoxycarbonyl)ethenyl]piperidine (J. Med. Chem., 1998, Vol. 41, p. 2492) (110 mg) dissolved in tetrahydrofuran (4.0 ml) at room temperature, and the mixture was stirred for 3 days. The reaction mixture was concentrated under reduced pressure, and the residue was dissolved in N,N-dimethylformamide (3 ml), to which (±)-cis-N-[(5-chloroindol-2-yl)carbonyl]-1,2-cyclohexane-diamine hydrochloride (134 mg), 1-hydroxybenzotriazole monohydrate (111 mg), 1-(3-dimethylaminopropyl)-3-ethylcarbodiimide hydrochloride (157 mg) and diisopropylethylamine (286 μl) were added at room temperature, and the mixture was stirred for 7 days. The reaction mixture was concentrated under reduced pressure, and dichloromethane (20 ml), water (50 ml) and a saturated aqueous solution (50 ml) of sodium hydrogencarbonate were added to the residue to separate an organic layer. The organic layer was dried over anhydrous sodium sulfate. The solvent was distilled off under reduced pressure, and the residue was purified by column chromatography on silica gel (dichloromethane acetone=10:1→2:1) to obtain (±)-cis-N$^1$-[[(E)-3-[1-(tert-butoxycarbonyl)piperidin-4-yl]acryloyl]-N$^2$-[(5-chloroindol-2-yl)carbonyl]-1,2-cyclohexanediamine (215 mg) as a white solid.

$^1$H-NMR (CDCl$_3$) δ: 1.24–1.80(10H,m), 1.47(9H,s), 1.85–1.97(1H,m), 2.10–2.20(1H,m), 2.22–2.36(1H,m), 2.68–2.74(2H,m), 4.12(3H,brs), 4.29(1H,br.s), 5.84(1H,d,J=15.2 Hz), 6.06(1H,br.s), 6.89(1H,s), 6.92(1H,dd,J=15.2, 6.4 Hz), 7.23(1H,dd,J=8.8, 1.7 Hz), 7.35(1H,d,J=8.8 Hz), 7.64 (1H,d,J=1.7 Hz), 8.04(1H,br.s), 9.41(1H,s). MS (ESI) m/z: 529(M+H)$^+$.

2) Trifluoroacetic acid (1 ml) was added to a solution with the product (210 mg) obtained above dissolved in dichloromethane (1 ml) at room temperature, and the mixture was stirred for 30 minutes. The reaction mixture was concentrated under reduced pressure, and the residue was dissolved in dichloromethane (5 ml), to which triethylamine (111 μl), acetic acid (68 μl), 35% formalin (51 μl) and sodium triacetoxyborohydride (126 mg) were added at room temperature. The resultant mixture was stirred for 4 hours. Dichloromethane (10 ml) and saturated aqueous solution (10 ml) of sodium hydrogencarbonate were added to the reaction mixture to separate an organic layer. The organic layer was dried over anhydrous sodium sulfate. The solvent was distilled off under reduced pressure, and the residue was purified by reversed phase HPLC (aqueous solution of formic acid-acetonitrile system). Solids thus obtained were dissolved in 1N hydrochloric acid-dichloromethane system, and the solution was concentrated to obtain the title compound (12 mg) as a white solid.

$^1$H-NMR (DMSO-d$_6$) δ: 1.30–1.93(12H,m), 2.25–2.38 (1H,m), 2.70(3H,d,J=4.9 Hz), 2.87–2.–3.00(2H,m), 3.34–3.44(2H,m), 4.13(2H,br.s), 6.20(1H,d,J=15.5 Hz), 6.55(1H,dd,J=15.5, 5.9 Hz), 7.18(1H,dd,J=8.8, 2.1 Hz), 7.20 (1H,d,J=1.5 Hz), 7.43(1H,d,J=8.8 Hz), 7.67(1H,d,J=2.1 Hz), 8.01(1H,br,J=7.6 Hz), 8.29(1H,br,J=7.1 Hz), 10.40(1H,br.s), 11.89(1H,s). MS (ESI) m/z: 443(M+H)$^+$.

Example 84

(±)-cis-N$^1$-[(5-Chloroindol-2-yl)carbonyl]-N$^2$-[3-(1-methylpiperidin-4-yl)propionyl]-1,2-cyclohexanediamine hydrochloride

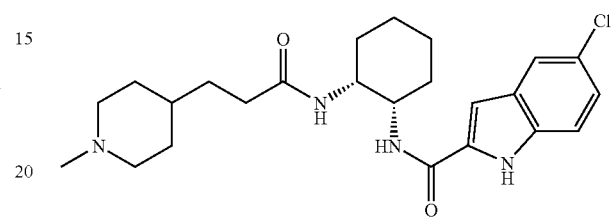

1) (±)-cis-N$^1$-[3-[1-(tert-Butoxycarbonyl)piperidin-4-yl] propionyl]-N$^2$-[(5-chloroindol-2-yl)carbonyl]-1,2-cyclohexanediamine was obtained from 1-(tert-butoxycarbonyl)-4-[2-(methoxycarbonyl)ethyl]piperidine (J. Med. Chem., 1998, Vol. 41, p. 2492) in a similar manner to the step 1) of Example 83.

$^1$H-NMR (CDCl$_3$) δ: 1.00–1.17(2H,m), 1.30–1.80(11H, m), 1.44(9H,s), 1.80–1.95(1H,m), 2.10–2.23(1H,m), 2.29 (2H,t,J=7.8 Hz), 2.50–2.70(2H,m), 3.90–4.18(3H,m), 4.23 (1H,br.s), 6.05(1H,br,J=6.0 Hz), 6.85(1H,d,J=2.0 Hz), 7.22 (1H,dd,J=8.8, 1.8 Hz), 7.37(1H,d,J=8.8 Hz), 7.62(1H,d,J= 1.8 Hz), 7.89(1H,br.s), 9.59(1H,s). MS (ESI) m/z: 531(M+H)$^+$.

2) The title compound was obtained from the product described above in a similar manner to the step 2) of Example 83.

$^1$H-NMR (DMSO-d$_6$) δ: 1.20–1.90(15H,m), 2.10–2.26 (1H,m), 2.55(3H,s), 2.55–2.70(2H,m), 3.21(2H,t,J=12.0 Hz), 4.00–4.16(2H,m), 7.18(1H,dd,J=8.8, 2.2 Hz), 7.21(1H, s), 7.44(1H,d,J=8.8 Hz), 7.70(1H,d,J=2.2 Hz), 7.82(1H,br, J=6.9 Hz), 8.11(1H,br,J=7.6 Hz), 10.02(1H,br.s), 11.94(1H, s). MS (ESI) m/z: 445(M+H)$^+$.

Example 85

(±)-cis-N$^1$-[(5-Chloroindol-2-yl)carbonyl]-N$^2$-[(1-methylpiperidin-4-yl)propioloyl]-1,2-cyclohexanediamine

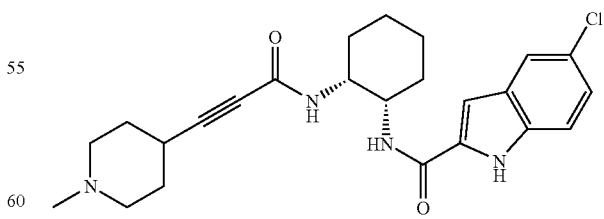

1) (±)-cis-N$^1$-[[1-(tert-Butoxycarbonyl)piperidin-4-yl] propioloyl]-N$^2$-[(5-chloroindol-2-yl)carbonyl]-1,2-cyclohexanediamine was obtained from 1-(tert-butoxycarbonyl)-4-(methoxycarbonylethynyl)piperidine in a similar manner to the step 1) of Example 83.

¹H-NMR (DMSO-d₆) δ: 1.30–1.82(12H,m), 1.38(9H,s), 2.68–2.78(1H,m), 2.96–3.10(2H,m), 3.56–3.66(2H,m), 4.00–4.20(2H,m), 7.16(1H,s), 7.18(1H,dd,J=8.6, 2.0 Hz), 7.43(1H,d,J=8.6 Hz), 7.70(1H,d,J=2.0 Hz), 7.91(1H,br,J=7.3 Hz), 8.25(1H,br,J=7.8 Hz), 11.81(1H,s).

2) The title compound was obtained from the product described above in a similar manner to the step 2) of Example 83.

¹H-NMR (DMSO-d₆) δ: 1.30–1.45(2H,m), 1.45–1.70 (6H,s), 1.70–1.82(4H,m), 1.90–2.03(2H,m), 2.10(3H,s), 2.40–2.52(1H,m), 2.52–2.62(2H,m), 4.04–4.18(2H,m), 7.15 (1H,s), 7.18(1H,dd,J=8.8, 2.0 Hz), 7.43(1H,d,J=8.8 Hz), 7.71(1H,d,J=2.0 Hz), 7.92(1H,br,J=7.3 Hz), 8.25(1H,br,J=7.8 Hz), 11.83(1H,s). MS (FAB) m/z: 441(M+H)⁺.

Example 86

(±)-cis-N¹-[(5-Chloroindol-2-yl)carbonyl]-N²-[(1-methyl-1,2,3,6-tetrahydropyridin-4-yl)propioloyl]-1,2-cyclohexanediamine

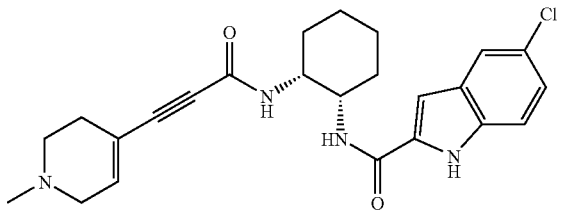

1) (±)-cis-N¹-[[1-(tert-Butoxycarbonyl)-1,2,3,6-tetrahydropyridin-4-yl]propioloyl]-N²-[(5-chloroindol-2-yl)carbonyl]-1,2-cyclohexanediamine was obtained from 1-(tert-butoxycarbonyl)-4-(methoxycarbonylethynyl)-1,2,3,6-tetrahydropyridine in a similar manner to the step 1) of Example 83.

¹H-NMR (DMSO-d₆) δ: 1.35–1.82(8H,m), 1.39(9H,s), 2.15–2.23(2H,m), 3.40(2H,t,J=5.4 Hz), 3.92(2H,br.s), 4.14 (2H,br.s), 6.29(1H,br.s), 7.16(1H,s), 7.18(1H,dd,J=8.7, 2.1 Hz), 7.43(1H,d,J=8.7 Hz), 7.71(1H,d,J=2.1 Hz), 7.92(1H,br,J=7.3 Hz), 8.40(1H,br,J=8.3 Hz), 11.80(1H,s). MS (ESI) m/z: 525(M+H)⁺.

2) The title compound was obtained from the product described above in a similar manner to the step 2) of Example 83.

¹H-NMR (DMSO-d₆) δ: 1.30–1.46(2H,m), 1.46–1.84 (6H,s), 2.15–2.25(2H,m), 2.21(3H,s), 2.42(2H,t,J=5.6 Hz), 2.89–2.97(2H,m), 4.13(2H,br.s), 6.25(1H,br.s), 7.15(1H,s), 7.17(1H,d,J=8.6 Hz), 7.43(1H,d,J=8.6 Hz), 7.70(1H,d,J=7.97 (1H,br,J=7.8 Hz), 8.41(1H,br,J=7.8 Hz), 11.84(1H,s) MS (FAB) m/z: 439(M+H)⁺.

Example 87

(±)-cis-N¹-[(5-Chloroindol-2-yl)carbonyl]-N²-[[1-(4-pyridyl)piperidin-4-yl]carbonyl]-1,2-cyclohexanediamine hydrochloride

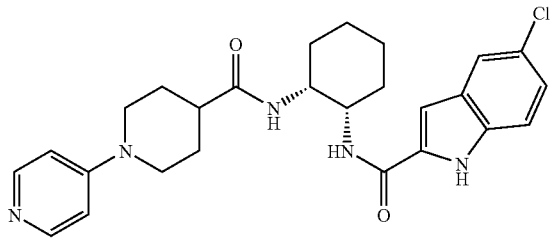

1-(4-Pyridyl)piperidine-4-carboxylic acid (Tetrahedron, 1998, Vol. 44, p. 7095) (206 mg) was suspended in dichloromethane (50 ml), thionyl chloride (144 μl) was added under ice cooling, and the mixture was stirred for 30 minutes. After triethylamine (969 μl) was added to the reaction mixture, (±)-cis-N-[(5-chloroindol-2-yl)carbonyl]-1,2-cyclohexanediamine hydrochloride (328 mg) was added, and the mixture was stirred at room temperature for 30 minutes. After the reaction mixture was concentrated under reduced pressure, and water was added to the residue, the solution was concentrated under reduced pressure, and precipitate deposited was collected by filtration to obtain the title compound (310 mg) as a pale brown solid.

¹H-NMR (DMSO-d₆) δ: 1.30–2.00(10H,m), 2.74(1H, br.s), 3.18(2H,q,J=12.3 Hz), 4.03(1H,br.s), 4.10–4.25(3H, m), 7.15–7.55(4H,m), 7.42(1H,d,J=8.8 Hz), 7.65(1H,s), 7.91(1H,d,J=8.8 Hz), 8.20–8.35(3H,m), 11.91(1H,s), 13.47 (1H,br.s) MS (FAB)m/z: 480(M+H)⁺.

Example 88

(±)-cis-N¹-[(5-Chloroindol-2-yl)carbonyl]-N²-[[4-(morpholinomethyl)thiazol-2-yl]carbonyl]-1,2-cyclohexanediamine hydrochloride

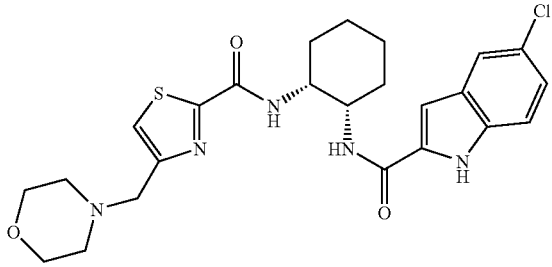

The title compound was obtained from (±)-cis-N-[(5-chloroindol-2-yl)carbonyl]-1,2-cyclohexanediamine hydrochloride and lithium 4-(morpholinomethyl)thiazole-2-carboxylate in a similar manner to Example 2.

¹H-NMR (DMSO-d₆) δ: 1.35–1.55(2H,m), 1.55–1.80 (4H,m), 1.95–2.15(2H,m), 3.00–3.60(4H,m), 3.85–4.00(4H, m), 4.15–4.35(2H,m), 4.40–4.65(2H,m), 7.18(1H,dd,J=8.8, 2.1 Hz), 7.30(1H,s), 7.41(1H,d,J=8.8 Hz), 7.65(1H,d,J=2.1 Hz), 8.19(1H,s), 8.35–8.50(2H,m), 11.01(1H,br.s), 11.94 (1H,br.s). MS (FAB) m/z: 502(M+H)⁺.

Example 89

(±)-cis-N¹-[(5-Chloroindol-2-yl)carbonyl]-N²-[[5-[(N,N-dimethylamino)methyl]thiazol-2-yl]carbonyl]-1,2-cyclohexanediamine hydrochloride

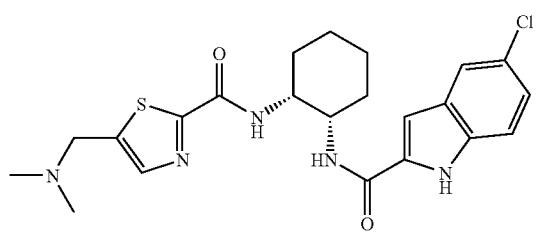

The title compound was obtained from (±)-cis-N-[(5-chloroindol-2-yl)carbonyl]-1,2-cyclohexanediamine hydrochloride and lithium 5-[(N,N-dimethylamino)-methyl]thiazole-2-carboxylate in a similar manner to Example 2

$^1$H-NMR (DMSO-$d_6$) δ: 1.35–1.55(2H,m), 1.55–1.80 (4H,m), 1.85–2.10(2H,m), 2.72(6H,br.s), 4.17–4.35(2H,m), 4.62(2H,br.s), 7.16–7.10(2H,m), 7.43(1H,d,J=8.8 Hz), 7.71 (1H,d,J=1.7 Hz), 8.10(1H,s), 8.15(1H,d,J=7.8 Hz), 8.52(1H, d,J=7.8 Hz), 10.70–10.80(1H,br), 11.86(1H,br.s). MS (FAB) m/z: 460(M+H)⁺.

Example 90

(±)-cis-N¹-[(5-Chloroindol-2-yl)carbonyl]-N²-[(4,5,6,7-tetrahydro-5,6-trimethylenethiazolo[4,5-d]pyridazin-2-yl]carbonyl]-1,2-cyclohexanediamine hydrochloride

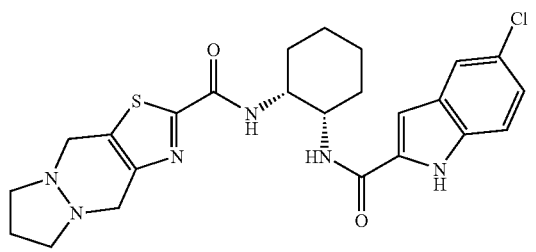

The title compound was obtained from (±)-cis-N-[(5-chloroindol-2-yl)carbonyl]-1,2-cyclohexanediamine hydrochloride and lithium 4,5,6,7-tetrahydro-5,6-trimethylenethiazolo[4,5-d]pyridazine-2-carboxylate in a similar manner to Example 2.

$^1$H-NMR (DMSO-$d_6$) δ: 1.35–1.50(2H,m), 1.61(4H,br.s), 1.80–2.00(2H,m), 2.27(2H,br.s), 2.80–4.80(10H,m), 7.14 (1H,d,J=1.5 Hz), 7.17(1H,dd,J=8.5, 2.0 Hz), 7.41(1H,d,J= 8.5 Hz), 7.70(1H,d,J=2.0 Hz), 8.09(1H,d,J=7.3 Hz), 8.44 (1H,br.s), 11.81(1H,br.s). MS (FAB) m/z: 499(M+H)⁺.

Example 91

(±)-cis-N¹-[(5-Chloroindol-2-yl)carbonyl]-N²-[(4,5,6,7-tetrahydro-5,6-tetramethylenethiazolo[4,5-d]pyridazin-2-yl]carbonyl]-1,2-cyclohexanediamine hydrochloride

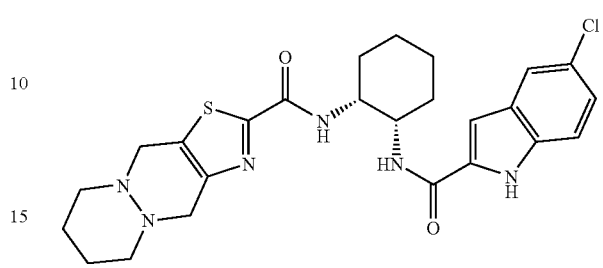

The title compound was obtained from lithium 4,5,6,7-tetrahydro-5,6-tetramethylenethiazolo[4,5-d]-pyridazine-2-carboxylate and (±)-cis-N-[(5-chloroindol-2-yl)carbonyl]-1,2-cyclohexanediamine hydrochloride in a similar manner to Example 2.

$^1$H-NMR (DMSO-$d_6$) δ: 1.35–1.55(2H,m), 1.55–2.10 (10H,m), 2.80–4.80(10H,m), 7.10–7.25(2H,m), 7.42(1H,d, J=8.8 Hz), 7.72(1H,d,J=1.7 Hz), 8.12(1H,br.s), 8.41(1H, br.s), 11.83(1H,br.s). MS (FAB) m/z: 513(M+H)⁺.

Example 92

(±)-cis-N¹-[(5-Chloroindol-2-yl)carbonyl]-N²-[(4,6-dihydro-5H-pyrrolo[3,4-d]thiazol-2-yl)carbonyl]-1,2-cyclohexanediamine hydrochloride

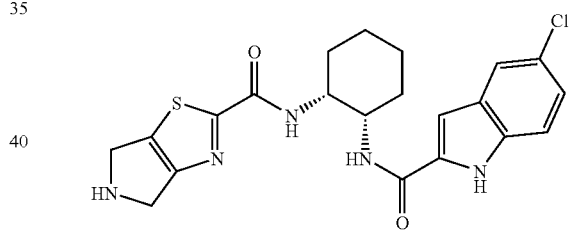

2-Bromo-5-tert-butoxycarbonyl-4,6-dihydro-5H-pyrrolo [3,4-d]thiazole (171 mg) was dissolved in diethyl ether (5 ml) in an argon atmosphere, and the solution was cooled to −78° C., to which n-butyllithium (1.60N hexane solution, 385 μl) was added dropwise. After the reaction mixture was stirred for 10 minutes at −78° C., and carbon dioxide was blown into the reaction mixture for 20 minutes, it was allowed to room temperature. After the reaction mixture was concentrated under reduced pressure, the residue was dissolved in N,N-dimethylformamide (10 ml) To the solution, were added (±)-cis-N-[(5-chloroindol-2-yl)carbonyl]-1,2-cyclohexanediamine hydrochloride (184 mg), 1-hydroxybenzotriazole monohydrate (76 mg) and 1-(3-dimethylaminopropyl)-3-ethylcarbodiimide hydrochloride (215 mg). The resultant mixture was stirred for 3 days. The reaction mixture was concentrated, and dichloromethane and a saturated aqueous solution of sodium hydrogencarbonate were added to the residue to separate an organic layer. The organic layer was dried over anhydrous sodium sulfate, and the solvent was then distilled off under reduced pressure. The resultant residue was purified by column chromatography on silica gel (methanol:dichloromethane=

3:97) to obtain (±)-cis-$N^1$-[(5-tert-butoxycarbonyl-4,6-dihydro-5H-pyrrolo[3,4-d]-thiazol-2-yl)carbonyl]-$N^2$-[(5-chloroindol-2-yl)carbonyl]-1,2-cyclohexanediamine (44 mg). After a saturated ethanol solution (5 ml) of hydrochloric acid was added to the thus-obtained product, the mixture was stirred at room temperature for 1 hour, and the reaction mixture was concentrated, ethyl acetate was added to the residue to solidify it. The resultant powder was collected by filtration to obtain the title compound (31 mg) as colorless powder.

$^1$H-NMR (DMSO-$d_6$) δ: 1.35–1.52(2H,m),1.55–1.80(4H, m), 1.82–2.05(2H,m), 4.22(1H,br.s), 4.28(1H,br.s), 4.38(2H, s), 4.56(2H,s),7.14–7.20(2H,m), 7.42(1H,d,J=8.6 Hz), 7.71 (1H,d,J=1.7 Hz), 8.10(1H,d,J=7.1 Hz), 8.45(1H,d,J=7.8 Hz), 10.10–10.50(2H,br), 11.83(1H,br.s). MS (FAB) m/z: 444 (M+H)$^+$.

Example 93

(1S,2R)-$N^1$-[(5-Chloroindol-2-yl)carbonyl]-$N^2$-[(5-methyl-4,6-dihydro-5H-pyrrolo[3,4-d]thiazol-2-yl)carbonyl]-1,2-cyclohexanediamine hydrochloride

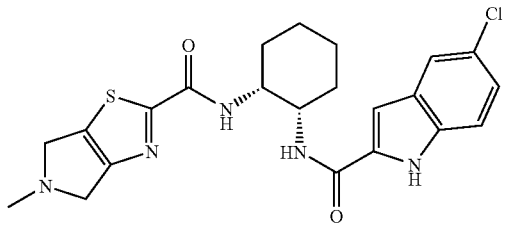

The title compound was obtained from (1S,2R)-$N^1$-[(5-chloroindol-2-yl)carbonyl]-1,2-cyclohexanediamine and lithium 5-methyl-4,6-dihydro-5H-pyrrolo[3,4-d]-thiazole-2-carboxylate in a similar manner to Example 2.

$[α]_D$+110° (24.8°, c=1.20, DMSO). $^1$H-NMR (DMSO-$d_6$) δ: 1.35–1.50(2H,m), 1.63(4H,br.s), 1.85–2.10(2H,m), 3.02 (3H,br.s), 4.15–4.80(6H,m), 7.10–7.22(2H,m), 7.42(1H,d,J= 8.8 Hz), 7.71(1H,d,J=1.7 Hz), 8.10(1H,d,J=6.8 Hz), 8.46 (1H,d,J=7.8 Hz), 11.83(1H,br.s), 11.97(1H,br.s). MS (FAB) m/z: 458(M+H)$^+$.

Example 94

(±)-cis-$N^1$-[[6-(tert-Butoxycarbonyl)-5,7-dihydropyrrolo-[3,4-d]pyrimidin-2-yl]carbonyl]-$N^2$-[(5-chloroindol-2-yl)carbonyl]-1,2-cyclohexanediamine

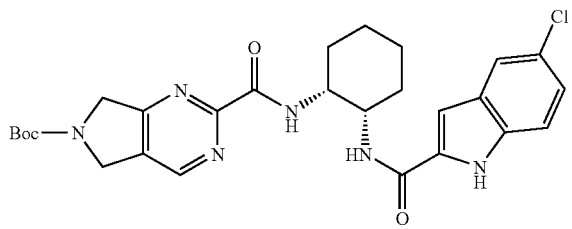

After 6-(tert-Butoxycarbonyl)-5,7-dihydro-2-methoxycarbonylpyrrolo[3,4-d]pyrimidine was hydrolyzed with lithium hydroxide, it was reacted with (±)-cis-N-[(5-chloroindol-2-yl)carbonyl]-1,2-cyclohexanediamine hydrochloride in a similar manner to Example 2 to obtain the title compound.

$^1$H-NMR (CDCl$_3$) δ: 1.54(9H,s), 1.55–2.30(8H,m), 4.23 (1H,br.s), 4.53(1H,br.s), 4.74–4.83(4H,m), 6.99(1H,d,J=1.5 Hz), 7.19(1H,dd,J=8.8, 2.1 Hz), 7.34(1H,d,J=8.8 Hz), 7.62 (1H,d,J=2.1 Hz), 8.11(1H,br.s), 8.48–8.53(1H,br), 8.70–8.76(1H,br), 9.60–9.70(1H,br). MS (ESI) m/z: 539 (M+H)$^+$.

Example 95

(±)-cis-$N^1$-[(5-Chloroindol-2-yl)carbonyl]-$N^2$-[[5,7-dihydro-6-methylpyrrolo[3,4-d]pyrimidin-2-yl] carbonyl]-1,2-cyclohexanediamine hydrochloride

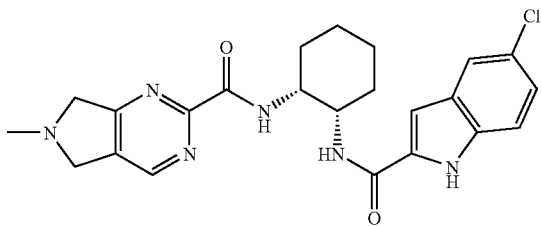

The title compound was obtained from (±)-cis-$N^1$-[[6-(tert-butoxycarbonyl)-5,7-dihydropyrrolo[3,4-d]-pyrimidin-2-yl]carbonyl]-$N^2$-[(5-chloroindol-2-yl)carbonyl]-1,2-cyclohexanediamine in a similar manner to Example 83.

$^1$H-NMR (DMSO-$d_6$) δ: 1.40–1.55(2H,m), 1.55–1.75 (4H,m), 1.80–2.05(2H,m), 2.98(3H,br.s), 4.28(2H,br.s), 4.65 (4H,br.s), 7.14–7.20(2H,m), 7.41(1H,d,J=8.8 Hz), 7.69(1H, d,J=2.0 Hz), 8.17(1H,d,J=6.9 Hz), 8.65(1H,d,J=8.3 Hz), 8.93(1H,s), 11.73(1H,br.s), 11.82(1H,br.s) MS (FAB) m/z: 453(M+H)$^+$.

Example 96

(±)-cis-$N^1$-[(5-Chloroindol-2-yl)carbonyl]-$N^1$,$N^2$-dimethyl-$N^2$-[[5-methyl-4,5,6,7-tetrahydrothiazolo [5,4-c]pyridin-2-yl]carbonyl]-1,2-cyclohexanediamine

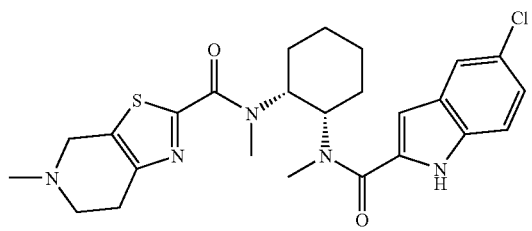

Lithium 5-methyl-4,5,6,7-tetrahydrothiazolo[5,4-c] pyridine-2-carboxylate (653 mg) was suspended in dichloromethane (10 ml), a 1N ethanol solution (3.2 ml) of hydrochloric acid was added, and the mixture was stirred for several minutes. The solvent was then distilled off under reduced pressure. Chloroform (15 ml) was added to the residue, and thionyl chloride (7 ml) and N,N-dimethylformamide (one drop) were added to stir the mixture at 65° C. for 4 hours. The solvent was distilled off under reduced pressure, and a solution (14 ml) of (±)-cis-$N^1$-[(1-benzenesulfonyl-5-chloroindol-2-yl)carbonyl]-$N^1$,$N^2$-dimethyl-1,2-cyclohexanediamine (847 mg) in a 1:1 mixed solvent (14 ml) of dichloromethane and pyridine was added to the residue to stir the mixture overnight at room temperature. Water was added to the reaction mixture to separate an organic layer. The organic layer was washed with water and

Example 97

(±)-cis-N¹-[(5-Chloroindol-2-yl)carbonyl]-N²-[(4,5,6,7-tetrahydrothiazolo[5,4-c]pyridin-2-yl)carbonyl]-1,2-cyclohexanediamine hydrochloride

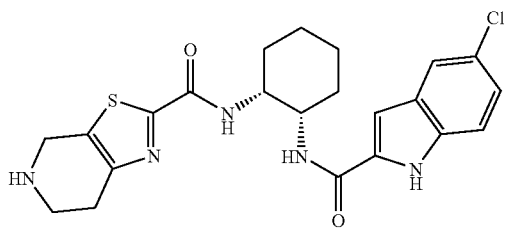

The title compound was obtained from (±)-cis-N-[(5-chloroindol-2-yl)carbonyl]-1,2-cyclohexanediamine hydrochloride and lithium 5-tert-butoxycarbonyl-4,5,6,7-tetrahydrothiazolo[5,4-c]pyridine-2-carboxylate in a similar manner to Example 2.

$^1$H-NMR (DMSO-$d_6$) δ: 1.39–1.52(2H,m), 1.62(4H,br.s), 1.86–2.09(2H,m), 3.03(2H,br.s), 3.40–3.47(2H,m), 4.17–4.32(2H,m), 4.44(2H,s), 7.15(1H,s), 7.17(1H,dd,J=8.6, 2.0 Hz), 7.41(1H,d,J=8.6 Hz), 7.71(1H,s), 8.10–8.15 (1H,m), 8.40–8.47(1H,m), 9.69(2H,br.s), 11.85(1H,s). MS (FAB) m/z: 458(M+H)$^+$.

Then dried over anhydrous sodium sulfate. The solvent was distilled off under reduced pressure, and the residue was purified by flash column chromatography on silica gal (dichloromethane:methanol=47:3). The resultant pale yellow solid was dissolved in methanol (10 ml), and potassium hydroxide (98 mg) was added to stir the mixture at room temperature for 10 hours. The solvent was distilled off under reduced pressure, and a saturated aqueous solution of sodium hydrogencarbonate was added to conduct extraction with dichloromethane. The resultant organic layer was dried over anhydrous sodium sulfate. After the residue was purified by flash column chromatography on silica gal (dichloromethane:methanol=47:3), the resultant pale yellow solid was dissolved in dichloromethane (5 ml), and a 1N ethanol solution (528 μl) of hydrochloric acid was added. Ethyl acetate was added and the solvent was distilled off under reduced pressure to obtain the title compound (267 mg) as a white solid.

$^1$H-NMR (DMSO-$d_6$) δ: 1.59–2.07(8H,m), 2.82(3H,m), 3.07–3.48(10H,m), 4.26–4.50(2H,m), 4.94(1H,s), 5.27(1H, br.s), 6.61(1H,s), 7.13(1H,d,J=8.6 Hz), 7.43(1H,br.s), 7.57 (1H,s), 11.25(1H,br.s), 12.90(1H,br.s). MS (ESI) m/z: 500 (M+H)$^+$.

Example 98

(±)-cis-N¹-[(5-Chloroindol-2-yl)carbonyl]-N²-[(5-ethyl-4,5,6,7-tetrahydrothiazolo[5,4-c]pyridin-2-yl)carbonyl]-1,2-cyclohexanediamine hydrochloride

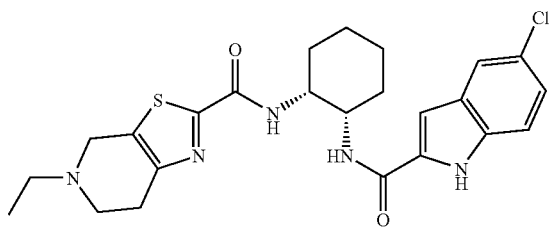

The title compound was obtained by ethylating (±)-cis-N¹-[(5-chloroindol-2-yl)carbonyl]-N²-[(4,5,6,7-tetrahydrothiazolo[5,4-c]pyridin-2-yl)carbonyl]-1,2-cyclohexanediamine hydrochloride with ethyl iodide in a similar manner to Example 52.

$^1$H-NMR (DMSO-$d_6$) δ: 1.31(3H,t,J=7.1 Hz), 1.45(2H, br.s), 1.62(4H,br.s), 1.82–2.10(2H,m), 3.00–3.52(5H,m), 3.71(1H,br.s), 4.15–4.50(3H,m), 4.68–4.82(1H,m), 7.15 (1H,s), 7.17(1H,dd,J=8.8, 2.0 Hz), 7.41(1H,d,J=8.8 Hz), 7.71(1H,d,J=2.0 Hz), 8.14(1H,br.s), 8.36–8.55(1H,m), 11.32 (1H,br.s), 11.86(1H,s). MS (FAB) m/z: 486(M+H)$^+$.

Example 99

(±)-cis-N¹-[(5-Chloroindol-2-yl)carbonyl]-N²-[[5-(2-methoxyethyl)-4,5,6,7-tetrahydrothiazolo[5,4-c]pyridin-2-yl]carbonyl]-1,2-cyclohexanediamine hydrochloride

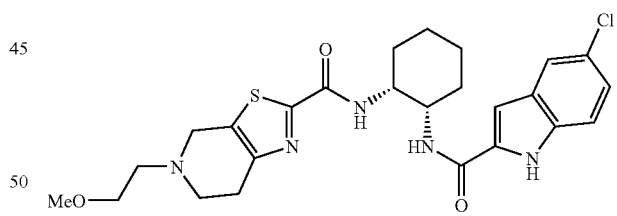

The title compound was obtained from (±)-cis-N¹-[(5-chloroindol-2-yl)carbonyl]-N²-[(4,5,6,7-tetrahydrothiazolo[5,4-c]pyridin-2-yl)carbonyl]-1,2-cyclohexanediamine hydrochloride and 2-methoxyethyl bromide in a similar manner to Example 52.

$^1$H-NMR (DMSO-$d_6$) δ: 1.44(2H,br.s), 1.62(4H,br.s), 1.85–2.10(2H,m), 2.76–3.21(6H,m), 3.28(3H,s), 3.64(2H, br.s), 4.00–4.52(4H,m), 7.14(1H,s), 7.17(1H,dd,J=8.8, 2.0 Hz), 7.41(1H,d,J=8.8 Hz), 7.70(1H,d,J=2.0 Hz), 8.08–8.20 (1H,m), 8.36–8.48(1H,m), 11.84(1H,s). MS (FAB) m/z: 516(M+H)$^+$.

Example 100

(±)-cis-N¹-[(5-Chloroindol-2-yl)carbonyl]-N²-[(5-methoxycarbonylmethyl-4,5,6,7-tetrahydrothiazolo[5,4-c]-pyridin-2-yl)carbonyl]-1,2-cyclohexanediamine

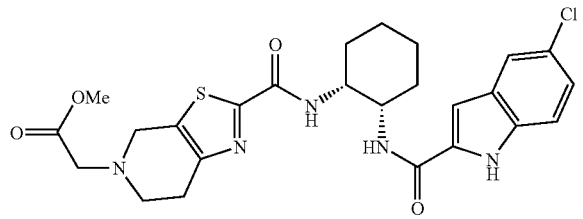

The title compound was obtained from (±)-cis-N¹-[(5-chloroindol-2-yl)carbonyl]-N²-[(4,5,6,7-tetrahydrothiazolo[5,4-c]pyridin-2-yl)carbonyl]-1,2-cyclohexanediamine hydrochloride and methyl bromoacetate in a similar manner to Example 52.

¹H-NMR (CDCl$_3$) δ: 1.52–1.98(7H,m), 2.17(1H,br.s), 2.87–3.10(4H,m), 3.49(2H,s), 3.76(3H,s), 3.93(1H,d,J=15.4 Hz), 3.99(1H,d,J=15.4 Hz), 4.22(1H,br.s), 4.45(1H,br.s), 6.86(1H,d,J=1.2 Hz), 7.18(1H,dd,J=8.8, 2.0 Hz), 7.33(1H, d,J=8.8 Hz), 7.58–7.63(2H,m), 7.87(1H,br.s), 9.88 (1H,br.s). MS (FAB) m/z: 530(M+H)⁺.

Example 101

(±)-cis-N¹-[(5-Chloroindol-2-yl)carbonyl]-N²-[(5-isopropyl-4,5,6,7-tetrahydrothiazolo[5,4-c]pyridin-2-yl)carbonyl]-1,2-cyclohexanediamine hydrochloride

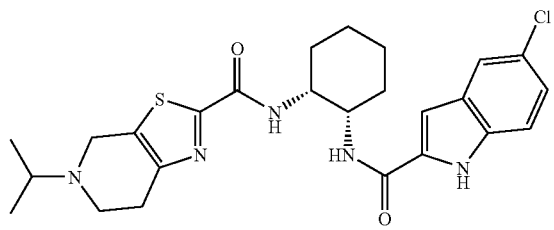

The title compound was obtained from (±)-cis-N¹-[(5-chloroindol-2-yl)carbonyl]-N²-[(4,5,6,7-tetrahydrothiazolo[5,4-c]pyridin-2-yl)carbonyl]-1,2-cyclohexanediamine hydrochloride and acetone in a similar manner to Example 45.

¹H-NMR (DMSO-d$_6$) δ: 1.18–1.73(8H,m), 1.81–2.10 (2H,m), 2.97–3.16(1H,m), 3.20–3.41(2H,m), 3.52–3.80(2H, m), 4.19–4.31(2H,m), 4.34–4.77(2H,m), 7.17(1H,s), 7.18 (1H,dd,J=8.8, 2.0 Hz), 7.42(1H,d,J=8.8 Hz), 7.71(1H,d,J= 2.0 Hz), 8.15(1H,br.s), 8.28–8.51(1H,m), 11.31(1H,br.s), 11.86(1H,s). MS (FAB) m/z: 500(M+H)⁺.

Example 102

(±)-cis-N¹-[(5-Chloroindol-2-yl)carbonyl]-N²-[[5-(2,3,5,6-tetrahydro-4H-pyran-4-yl)-4,5,6,7-tetrahydrothiazolo[5,4-c]pyridin-2-yl]carbonyl]-1,2-cyclohexanediamine hydrochloride

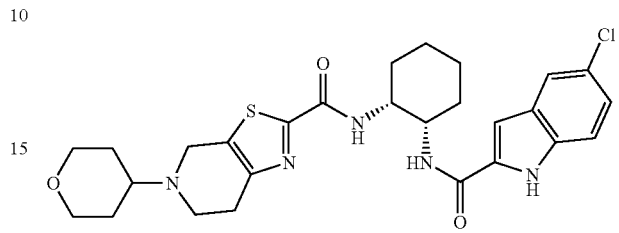

The title compound was obtained from (±)-cis-N¹-[(5-chloroindol-2-yl)carbonyl]-N²-[(4,5,6,7-tetrahydrothiazolo[5,4-c]pyridin-2-yl)carbonyl]-1,2-cyclohexanediamine hydrochloride and tetrahydro-4H-pyran-4-one in a similar manner to Example 45.

¹H-NMR (DMSO-d$_6$) δ: 1.30–3.56(19H,m), 3.70–4.01 (3H,m), 4.17–4.30(2H,m), 4.32–4.80(1H,m), 7.15(1H,s), 7.17(1H,dd,J=8.6, 2.0 Hz), 7.41(1H,d,J=8.6 Hz), 7.71(1H, d,J=2.0 Hz), 8.14(1H,br.s), 8.39(1H,br.s), 11.84(1H,s) MS (FAB) m/z: 542(M+H)⁺.

Example 103

(±)-cis-N¹-[[5-[2-(tert-Butoxycarbonylamino)ethyl]-4,5,6,7-tetrahydrothiazolo[5,4-c]-pyridin-2-yl]carbonyl]-N²-[(5-chloroindol-2-yl)carbonyl]-1,2-cyclohexane-diamine

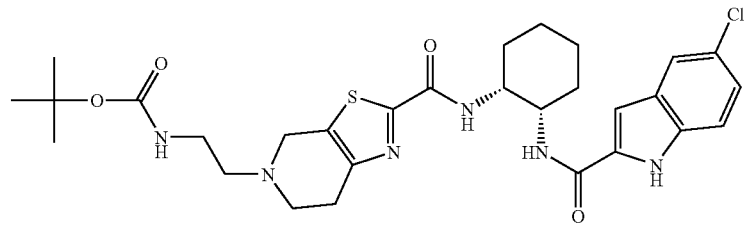

The title compound was obtained from (±)-cis-N¹-[(5-chloroindol-2-yl)carbonyl]-N²-[(4,5,6,7-tetrahydrothiazolo[5,4-c]pyridin-2-yl)carbonyl]-1,2-cyclohexanediamine hydrochloride and N-(tert-butoxycarbonyl)aminoacetoaldehyde (J. Org. Chem., 1988, Vol. 53, p. 3457) in a similar manner to Example 45.

$^1$H-NMR (CDCl$_3$) δ: 1.44(9H,s), 1.54–1.98(7H,m), 2.10–2.20(1H,m), 2.74(2H,br.s), 2.92(4H,br.s), 3.34(2H, br.s), 3.84(2H,br.s),4.21(1H,br.s), 4.45(1H,br.s), 6.86(1H,s), 7.19(1H,dd,J=8.8, 2.0 Hz), 7.33(1H,d,J=8.8 Hz), 7.57–7.63 (2H,m), 7.81(1H,br.s), 9.66(1H,br.s). MS (FAB) m/z: 601 (M+H)$^+$.

Example 104

(±)-cis-N$^1$-[[5-(2-Aminoethyl)-4,5,6,7-tetrahydrothiazolo-[5,4-c]pyridin-2-yl]carbonyl]-N$^2$-[(5-chloroindol-2-yl)carbonyl]-1,2-cyclohexanediamine hydrochloride

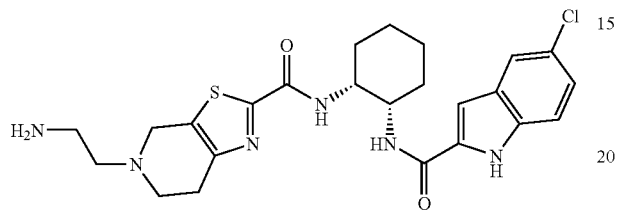

(±)-cis-N$^1$-[[5-[2-(tert-Butoxycarbonylamino)-ethyl]-4,5, 6,7-tetrahydrothiazolo[5,4-c]pyridin-2-yl]carbonyl]-N$^2$-[(5-chloroindol-2-yl)carbonyl]-1,2-cyclohexanediamine (450 mg) was dissolved in dichloromethane (5 ml), and a saturated ethanol solution (30 ml) of hydrochloric acid was added to stir the mixture at room temperature for 1 minute. The reaction mixture was concentrated under reduced pressure, ethyl acetate was added to the residue, and solids deposited were collected by filtration to obtain the title compound (367 mg) as a pale yellow amorphous solid.

$^1$H-NMR (DMSO-d$_6$) δ: 1.38–1.50(2H,m), 1.61(4H,br.s), 1.85–2.08(2H,m), 3.00–4.62(12H,m), 7.14(1H,s), 7.16(1H, dd,J=8.8, 2.0 Hz), 7.41(1H,d,J=8.8 Hz), 7.69(1H,d,J=2.0 Hz), 8.12(1H,d,J=6.6 Hz), 8.15–8.68(4H,m), 11.85(1H,s). MS (FAB) m/z: 501(M+H)$^+$.

Example 105

(±)-cis-N$^1$-[(5-Chloroindol-2-yl)carbonyl]-N$^2$-[[5-[2-(methanesulfonylamino)ethyl]-4,5,6,7-tetrahydrothiazolo[5,4-c]pyridin-2-yl]carbonyl]-1,2-cyclohexane-diamine hydrochloride

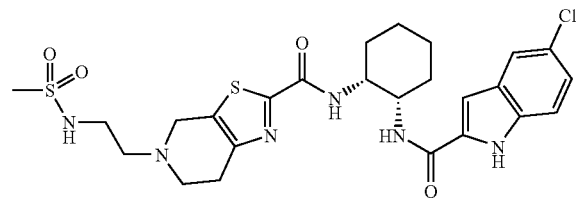

(±)-cis-N$^1$-[[5-(2-Aminoethyl)-4,5,6,7-tetrahydrothiazolo [5,4-c]pyridin-2-yl]carbonyl]-N$^2$-[(5-chloroindol-2-yl) carbonyl]-1,2-cyclohexanediamine hydrochloride (110 mg) was dissolved in pyridine (3 ml), methanesulfonyl chloride (30 μl) was added, and the mixture was stirred overnight at room temperature. The reaction mixture was concentrated under reduced pressure, and a 85:15 mixed solvent of dichloromethane and methanol, and water were added to conduct liquid separation. The resultant organic layer was dried over anhydrous sodium sulfate. The solvent was distilled off under reduced pressure, and the residue was purified by column chromatography on silica gel (dichloromethane:methanol=100:3) to obtain a pale yellow foamy substance. This product was suspended in 1N hydrochloric acid (0.3 ml), and the suspension was concentrated under reduced pressure to obtain the title compound (63 mg) as a pale yellow foamy substance.

$^1$H-NMR (DMSO-d$_6$) δ: 1.38–1.50(2H,m), 1.55–1.70 (4H,m), 1.86–2.05(2H,m), 2.97(3H,s), 3.02–3.25(2H,m), 3.30–3.60(5H,m), 3.78(1H,br.s), 4.18–4.30(2H,m), 4.45–4.86(2H,m), 7.14(1H,s), 7.16(1H,dd,J=8.8, 2.0 Hz), 7.40(1H,d,J=8.8 Hz), 7.41(1H,br.s), 7.69(1H,d,J=2.0 Hz), 8.09(1H,br.s), 8.43(1H,br.s), 11.18(1H,br.s), 11.82(1H,s). MS (FAB) m/z: 579(M+H)$^+$.

Example 106

(±)-cis-N$^1$-[(5-Chloroindol-2-yl)carbonyl]-N$^2$-[[5-[2-(methoxycarbonylamino)ethyl]-4,5,6,7-tetrahydrothiazolo[5,4-c]pyridin-2-yl]carbonyl]-1,2-cyclohexane-diamine hydrochloride

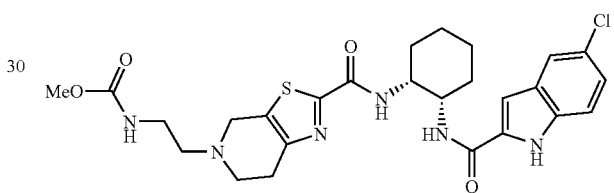

(±)-cis-N$^1$-[[5-(2-Aminoethyl)-4,5,6,7-tetrahydrothiazolo [5,4-c]pyridin-2-yl]carbonyl]-N$^2$-[(5-chloroindol-2-yl) carbonyl]-1,2-cyclohexanediamine hydrochloride (144 mg) was dissolved in pyridine (3 ml), triethylamine (138 μl) was added, and the mixture was stirred at room temperature for 5 minutes. A solution prepared by adding triphosgene (49 mg) to tetrahydrofuran (1 ml) containing methanol (20 μl) was added dropwise to this solution. The reaction mixture was stirred at room temperature for 1 hour, then concentrated under reduced pressure, and the residue was dissolved in a 9:1 mixed solvent of dichloromethane and methanol. Water was added to the solution to conduct liquid separation. The resultant organic layer was dried over anhydrous sodium sulfate. The solvent was distilled off under reduced pressure, and the residue was purified by column chromatography on silica gel (dichloromethane:methanol=100:3) to obtain a colorless foamy substance. This product was suspended in 1N hydrochloric acid (0.2 ml), and the suspension was concentrated under reduced pressure to obtain the title compound (60 mg) as a pale yellow foamy substance.

$^1$H-NMR (DMSO-d$_6$) δ: 1.38–1.50(2H,m), 1.61(4H,br.s), 1.85–2.04(2H,m), 2.80–3.49(8H,m), 3.52(3H,s), 3.62–4.91 (4H,m), 7.14(1H,s), 7.16(1H,dd,J=8.8, 2.0 Hz), 7.37(1H, br.s), 7.40(1H,d,J=8.8 Hz), 7.70(1H,s), 8.11(1H,d,J=6.8 Hz), 8.40(1H,br.s.), 11.05(1H,br.s), 11.82(1H,br.s). MS (FAB) m/z: 559(M+H)$^+$.

Example 107

(±)-cis-N¹-[[5-[2-(Acetylamino)ethyl]-4,5,6,7-tetrahydrothiazolo[5,4-c]pyridin-2-yl]carbonyl]-N²-[(5-chloroindol-2-yl)carbonyl]-1,2-cyclohexanediamine hydrochloride

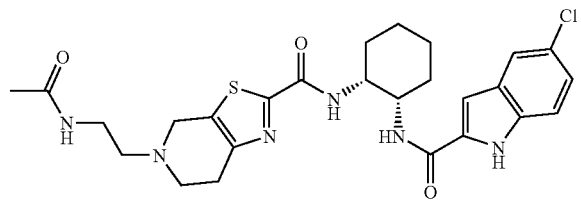

(±)-cis-N¹-[[5-(2-Aminoethyl)-4,5,6,7-tetrahydrothiazolo[5,4-c]pyridin-2-yl]carbonyl]-N²-[(5-chloroindol-2-yl)carbonyl]-1,2-cyclohexanediamine hydrochloride (90 mg) was dissolved in N,N-dimethylformamide (3 ml), triethylamine (65 μl) and acetic anhydride (22 μl) were added, and the mixture was stirred overnight at room temperature. The reaction mixture was concentrated under reduced pressure, and dichloromethane and a 0.3N aqueous solution of sodium hydroxide were added to the residue to conduct liquid separation. The resultant organic layer was dried over anhydrous sodium sulfate. The solvent was distilled off under reduced pressure, and the residue was purified by column chromatography on silica gel (dichloromethane:methanol= 100:3) to obtain a colorless foamy substance. This product was suspended in 1N hydrochloric acid (0.3 ml), and the suspension was concentrated under reduced pressure to obtain the title compound (73 mg) as a pale yellow foamy substance.

¹H-NMR (DMSO-$d_6$) δ: 1.39–1.52(2H,m), 1.54–1.70 (4H,m), 1.83(3H,s), 1.84–2.06(2H,m), 3.02–3.87(8H,m), 4.16–4.32(2H,m), 4.40–4.52(1H,m), 4.78–4.88(1H,m), 7.14 (1H,s), 7.16(1H,d,J=8.6 Hz), 7.40(1H,d,J=8.6 Hz), 7.70(1H, s), 8.07–8.17(1H,m), 8.22–8.30(1H,m), 8.38–8.52(1H,m), 11.14(1H,br.s), 11.83(1H,s). MS (FAB) m/z: 543(M+H)⁺.

Example 108

(±)-cis-N¹-[(5-Chloroindol-2-yl)carbonyl]-N²-[[5-(2-hydroxyethyl)-4,5,6,7-tetrahydrothiazolo[5,4-c]pyridin-2-yl]carbonyl]-1,2-cyclohexanediamine

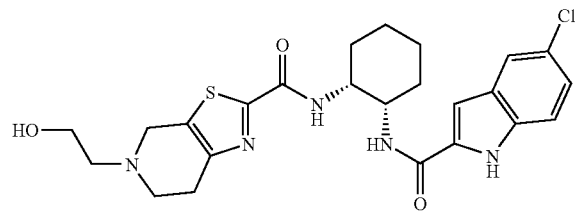

The title compound was obtained from (±)-cis-N¹-[(5-chloroindol-2-yl)carbonyl]-N²-[(4,5,6,7-tetrahydrothiazolo[5,4-c]pyridin-2-yl)carbonyl]-1,2-cyclohexanediamine hydrochloride and 2-bromoethanol in a similar manner to Example 52.

¹H-NMR (DMSO-$d_6$) δ: 1.37–1.69(6H,m), 1.86–2.03 (2H,m), 2.54–2.61(2H,m), 2.75–2.86(4H,m), 3.52–3.59(2H, m), 3.75(2H,s), 4.47(1H,t,J=5.4 Hz), 7.12(1H,s), 7.16(1H, dd,J=8.8, 2.0 Hz), 7.40(1H,d,J=8.8 Hz), 7.70(1H,s), 8.05–8.13(1H,m), 8.28–8.35(1H,m), 11.78(1H,s). MS (FAB) m/z: 502(M+H)⁺.

Example 109

(±)-cis-N¹-[(5-Chloroindol-2-yl)carbonyl]-N²-[[5-(3-hydroxypropyl)-4,5,6,7-tetrahydrothiazolo[5,4-c]pyridin-2-yl]carbonyl]-1,2-cyclohexanediamine hydrochloride

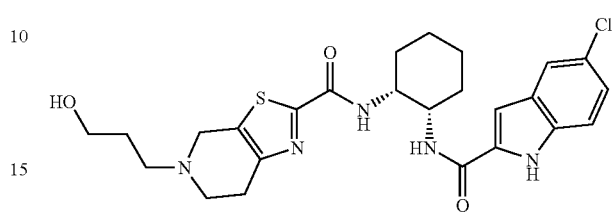

The title compound was obtained from (±)-cis-N¹-[(5-chloroindol-2-yl)carbonyl]-N²-[(4,5,6,7-tetrahydrothiazolo[5,4-c]pyridin-2-yl)carbonyl]-1,2-cyclohexanediamine hydrochloride and 3-bromopropanol in a similar manner to Example 52.

¹H-NMR (DMSO-$d_6$) δ: 1.45(2H,br.s), 1.56–1.71(4H,m) 1.87–2.10(4H,m), 3.05–3.55(7H,m), 3.70–3.80(1H,m), 4.19–4.32(2H,m), 4.40–4.50(1H,m), 4.74–4.84(1H,m), 7.12–7.20(2H,m), 7.41(1H,d,J=8.8 Hz), 7.70(1H,s), 8.08–8.16(1H,m), 8.40–8.51(1H,m), 10.98(1H,br.s), 11.82 (1H,s) MS (FAB) m/z: 516(M+H)⁺.

Example 110

(±)-cis-N¹-[(5-Chloroindol-2-yl)carbonyl]-N²-[[5-butyl-4,5,6,7-tetrahydrothiazolo[5,4-c]pyridin-2-yl)carbonyl]-1,2-cyclohexanediamine hydrochloride

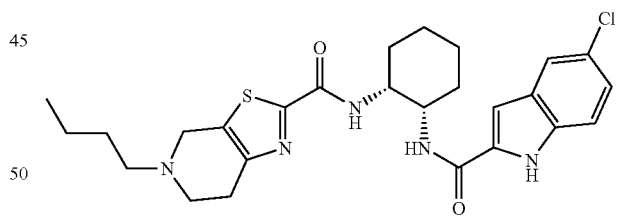

The title compound was obtained from (±)-cis-N¹-[(5-chloroindol-2-yl)carbonyl]-N²-[(4,5,6,7-tetrahydrothiazolo[5,4-c]pyridin-2-yl)carbonyl]-1,2-cyclohexanediamine hydrochloride and n-butyl bromide in a similar manner to Example 52.

¹H-NMR (DMSO-$d_6$) δ: 0.88(3H,t,J=7.2 Hz), 1.20–1.70 (10H,m), 1.87–2.05(2H,m), 2.55–3.40(8H,m), 4.16–4.30 (2H,m), 7.13(1H,s), 7.16(1H,d,J=8.8 Hz), 7.40(1H,d,J=8.8 Hz), 7.69(1H,s), 8.05–8.14(1H,m), 8.35(1H,br.s), 11.81(1H, s). MS (FAB) m/z: 514(M+H)⁺.

Example 111

(±)-cis-N$^1$-[(5-Chloroindol-2-yl)carbonyl]-N$^2$-[(5-isobutyl-4,5,6,7-tetrahydrothiazolo[5,4-c]pyridin-2-yl)carbonyl]-1,2-cyclohexanediamine hydrochloride

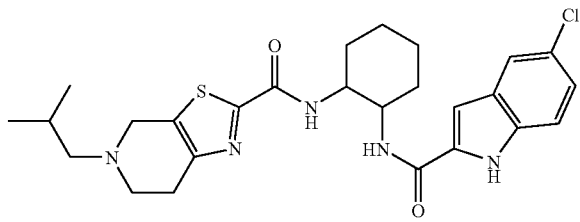

The title compound was obtained from (±)-cis-N$^1$-[(5-chloroindol-2-yl)carbonyl]-N$^2$-[(4,5,6,7-tetrahydrothiazolo[5,4-c]pyridin-2-yl)carbonyl]-1,2-cyclohexanediamine hydrochloride and isobutyl iodide in a similar manner to Example 52.

$^1$H-NMR (DMSO-d$_6$) δ: 0.80–1.05(7H,m), 1.38–1.50 (2H,m), 1.54–1.70(4H,m), 1.89–2.02(2H,m), 2.52–3.77(8H, m), 4.18–4.31(2H,m), 7.17(1H,dd,J=8.8, 2.0 Hz), 7.40(1H, d,J=8.8 Hz), 7.69(1H,s), 8.05–8.13(1H,m), 8.27–8.53(1H, m), 11.81(1H,s). MS (FAB) m/z: 514(M+H)$^+$.

Example 112

(±)-cis-N$^1$-[(5-Acetyl-4,5,6,7-tetrahydrothiazolo[5,4-c]-pyridin-2-yl]carbonyl]-N$^2$-[(5-chloroindol-2-yl)carbonyl]-1,2-cyclohexanediamine

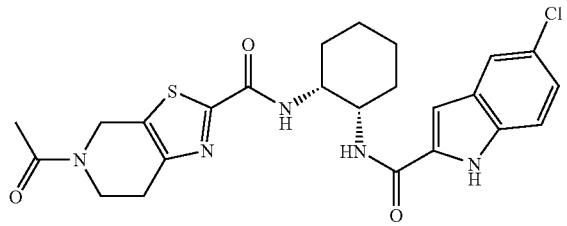

(±)-cis-N$^1$-[(5-Chloroindol-2-yl)carbonyl]-N$^2$-[(4,5,6,7-tetrahydrothiazolo[5,4-c]pyridin-2-yl]carbonyl]-1,2-cyclohexanediamine hydrochloride (100 mg) was dissolved in N,N-dimethylformamide (3 ml), triethylamine (84 µl) and acetic anhydride (29 µl) were added, and the mixture was stirred at room temperature for 3 hours. The reaction mixture was concentrated under reduced pressure, and dichloromethane and 1N hydrochloric acid were added to the residue to conduct liquid separation. The resultant organic layer was dried over anhydrous sodium sulfate. The solvent was distilled off under reduced pressure, and the residue was purified by column chromatography on silica gel (dichloromethane:methanol=100:3) to obtain the title compound (86 mg) as a pale yellow foamy substance.

$^1$H-NMR (CDCl$_3$) δ: 1.52–1.85(5H,m), 1.91(2H,br.s), 2.10–2.28(4H,m), 2.77–3.00(2H,m), 3.70–4.00(2H,m), 4.19–4.38(1H,m), 4.45(1H,br.s), 4.68–4.99(2H,m), 6.85 (1H,s), 7.17–7.22(1H,m), 7.30–7.39(1H,m), 7.50–7.84(3H, m), 9.72–10.05(1H,m). MS (FAB) m/z: 500(M+H)$^+$.

Example 113

(±)-cis-N$^1$-[(5-Chloroindol-2-yl)carbonyl]-N$^2$-[(5-methanesulfonyl-4,5,6,7-tetrahydrothiazolo[5,4-c]-pyridin-2-yl)carbonyl]-1,2-cyclohexanediamine

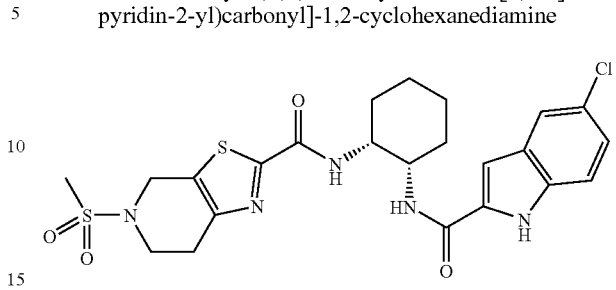

(±)-cis-N$^1$-[(5-chloroindol-2-yl)carbonyl]-N$^2$-[(4,5,6,7-tetrahydrothiazolo[5,4-c]pyridin-2-yl)-carbonyl]-1,2-cyclohexanediamine hydrochloride (100 mg) was dissolved in pyridine (3 ml), triethylamine (168 µl) and methanesulfonyl chloride (48 µl) were added, and the mixture was stirred overnight at room temperature. The reaction mixture was concentrated under reduced pressure, and dichloromethane and 1N hydrochloric acid were added to the residue to separate an organic layer. The resultant organic layer was dried over anhydrous sodium sulfate. The solvent was distilled off under reduced pressure, and the residue was purified by column chromatography on silica gel (dichloromethane:methanol=100:1) to obtain the title compound (79 mg) as a pale yellow foamy substance.

$^1$H-NMR (CDCl$_3$) δ: 1.50–1.82(5H,m), 1.90(2H,br.s), 2.13(1H,br.s), 2.89(3H,s), 2.91–2.98(2H,m), 3.60–3.70(2H, m), 4.30(1H,br.s), 4.44(1H,br.s),4.58(2H,s), 6.87(1H,s), 7.19(1H,d,J=8.8 Hz), 7.34(1H,d,J=8.8 Hz), 7.61(3H,br.s), 9.91(1H,br.s). MS (FAB) m/z: 536(M+H)$^+$.

Example 114

(±)-cis-N$^1$-[(5-Methylindol-2-yl)carbonyl]-N$^2$-[(5-methyl-4,5,6,7-tetrahydrothiazolo[5,4-c]-pyridin-2-yl)carbonyl]-1,2-cyclohexanediamine hydrochloride

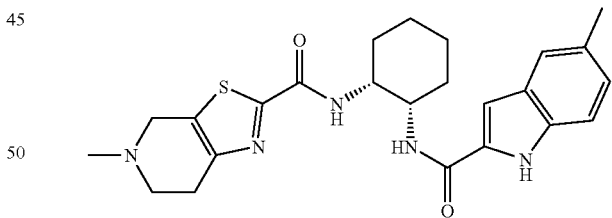

The title compound was obtained from (±)-cis-N-[(5-methyl-4,5,6,7-tetrahydrothiazolo[5,4-c]pyridin-2-yl) carbonyl]-1,2-cyclohexanediamine hydrochloride and 5-methylindole-2-carboxylic acid in a similar manner to Example 6.

$^1$H-NMR (DMSO-d$_6$) δ: 1.35–1.50(2H,m), 1.50–1.80 (4H,m), 1.85–2.07(2H,m), 2.36(3H,s),2.88(3H,s), 3.12(2H, br.s), 3.53(2H,br.s), 4.15–4.30(2H,m), 4.30–4.80(2H,br), 7.00(1H,dd,J=8.4, 1.5 Hz), 7.05(1H,d,J=1.5 Hz), 7.30(1H, d,J=8.4 Hz), 7.38(1H,s), 8.00(1H,d,J=7.3 Hz), 8.43(1H, br.s), 11.45(1H,br.s), 11.49(1H,br.s). MS (FAB) m/z: 452 (M+H)$^+$.

Example 115

(±)-cis-N¹-[(6-Chloro-4-hydroxynaphthalen-2-yl)carbonyl]-N²-[(5-methyl-4,5,6,7-tetrahydrothiazolo[5,4-c]pyridin-2-yl)carbonyl]-1,2-cyclohexanediamine hydrochloride

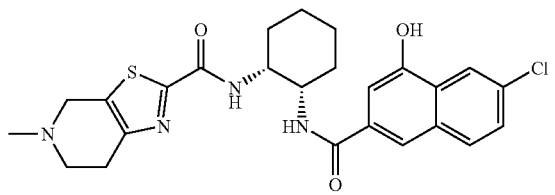

The title compound was obtained from (±)-cis-N-[(5-methyl-4,5,6,7-tetrahydrothiazolo[5,4-c]pyridin-2-yl)carbonyl]-1,2-cyclohexanediamine hydrochloride and 6-chloro-4-hydroxynaphthalene-2-carboxylic acid in a similar manner to Example 6.

$^1$H-NMR (DMSO-$d_6$) δ: 1.44–1.63(6H,m), 1.98–1.99 (2H,m), 2.87(3H,s), 3.08(2H,br.s), 3.52(2H,br.s), 4.22(2H,br.s), 4.74(2H,br.s), 7.26(1H,s), 7.55–7.57(1H,m), 7.82(1H,s), 7.99(1H,d,J=9.0 Hz), 8.10(1H,s), 8.22(1H,d,J=5.9 Hz), 8.49(1H,br.s), 10.65(1H,s), 11.33(1H,br.s). MS (FAB) m/z: 485(M+H)⁺.

Example 116

(±)-cis-N¹-[(6-Chloroimidazo[1,2-a]pyridin-2-yl)carbonyl]-N²-[(5-methyl-4,5,6,7-tetrahydrothiazolo-[5,4-c]pyridin-2-yl)carbonyl]-1,2-cyclohexanediamine hydrochloride

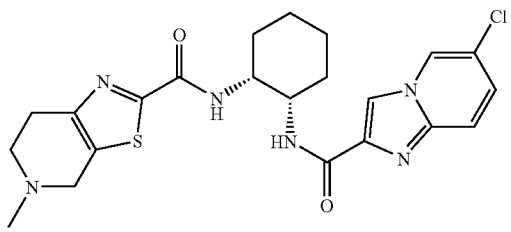

Ethyl 6-chloroimidazo[1,2-a]pyridine-2-carboxylate (Japanese Patent Application Laid-Open No. 11-500123 through PCT route) (150 mg) was dissolved in tetrahydrofuran (4 ml), and water (1 ml) and lithium hydroxide (18 mg) were added at room temperature to stir the mixture for 1 hour. The reaction mixture was concentrated under reduced pressure to obtain crude lithium 6-chloroimidazo[1,2-a]pyridine-2-carboxylate. This product was dissolved in N,N-dimethylformamide (4.0 ml), and (±)-cis-N-[(5-methyl-4,5,6,7-tetrahydrothiazolo[5,4-c]pyridin-2-yl)carbonyl]-1,2-cyclohexane-diamine hydrochloride (232 mg), 1-hydroxybenzotriazole monohydrate (180 mg), 1-(3-dimethylaminopropyl)-3-ethylcarbodiimide hydrochloride (256 mg) and triethylamine (371 µl) were added to this solution to stir the mixture at room temperature for 3 days. The reaction mixture was concentrated under reduced pressure, and water and a saturated aqueous solution of sodium hydrogencarbonate were added to the residue to conduct extraction with dichloromethane. The resultant organic layer was then dried over anhydrous sodium sulfate, and the solvent was distilled off under reduced pressure. The resultant residue was purified by column chromatography on silica gel (dichloromethane:acetone=1:1→dichloromethane:acetone:methanol=5:5:1) to obtain a white solid. To this solid, were added dichloromethane, methanol and 1N hydrochloric acid, and the resultant mixture was concentrated to obtain the title compound (224 mg) as a pale brown solid.

$^1$H-NMR (DMSO-$d_6$) δ: 1.35–1.51(2H,m), 1.51–1.70 (4H,m), 1.86–2.05(2H,m), 2.87(3H,s), 3.00–3.15(1H,m), 3.15–3.30(1H,m), 3.35–3.50(1H,m), 3.44(1H,br.s), 3.65 (1H,br.s), 4.10–4.32(2H,m), 4.32–4.45(1H,m), 4.58–4.70 (1H,m), 7.60–7.70(1H,m), 7.75(1H,d,J=9.5 Hz), 8.50–8.60 (2H,m), 8.60–8.70(1H,m), 9.08(1H,d,J=15.9 Hz), 11.75–11.98(1H,br). MS (FAB) m/z: 473(M+H)⁺.

Example 117

(±)-cis-N¹-[(5-Chloroindol-2-yl)carbonyl]-N²-[(5-methyl-4,5,6,7-tetrahydrothiazolo[5,4-c]pyridin-2-yl)carbonyl]-4-cyclohexene-1,2-diamine hydrochloride

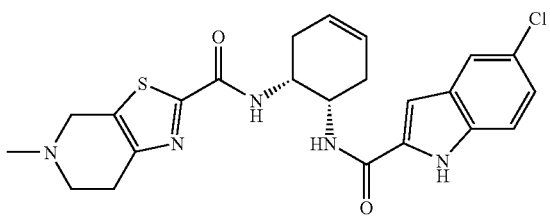

The title compound was obtained from (±)-cis-N-[(5-chloroindol-2-yl)carbonyl]-4-cyclohexene-1,2-diamine and lithium 5-methyl-4,5,6,7-tetrahydrothiazolo[5,4-c]-pyridine-2-carboxylate in a similar manner to Example 2.

$^1$H-NMR (DMSO-$d_6$) δ: 2.43–2.34(m,4H), 2.50(s,3H), 3.11(m,2H), 3.42(m,1H), 3.65(m,1H), 4.20(m,1H), 4.30(m,2H), 4.64(m,1H), 5.66(s,2H), 7.02(s,1H), 7.15(dd,1H,J=1.5, 8.8 Hz), 7.39(d,1H,J=8.5 Hz), 7.68(s,1H), 8.34(d,1H,J=8.5 Hz), 8.69(d,1H,J=8.8 Hz), 11.72(s,1H). MS (ESI) m/z: 470 (M+H)⁺.

Example 118

(1R*,2S*,4R*)-N¹-[(5-chloroindol-2-yl)carbonyl]-4-ethoxycarbonyl-N²-[(5-methyl-4,5,6,7-tetrahydrothiazolo[5,4-c]pyridin-2-yl)carbonyl]-1,2-cyclohexanediamine

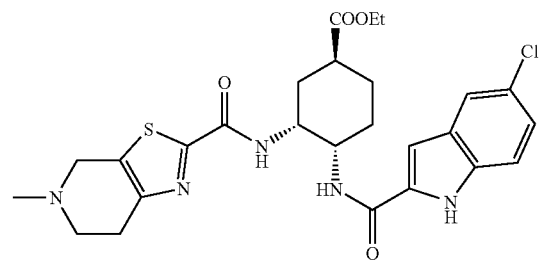

(1R*,2S*,4R*)-N²-tert-Butoxycarbonyl-N¹-[(5-chloroindol-2-yl)carbonyl]-4-ethoxycarbonyl-1,2- cyclohexanediamine (1.40 g) was suspended in ethanol (8 ml), and a saturated ethanol solution (10 ml) of hydrochloric acid was added at room temperature to stir the mixture for 12 hours. The solvent was distilled off under reduced pressure to obtain (1R*,2S*,4R*)-N¹-[(5-chloroindol-2-yl) carbonyl]-4-ethoxycarbonyl-1,2-cyclohexanediamine hydrochloride (1.25 g) as a colorless solid.

The title compound was obtained from the above-described product and lithium 5-methyl-4,5,6,7-tetrahydrothiazolo[5,4-c]pyridine-2-carboxylate in a similar manner to Example 2.

$^1$H-NMR (CDCl$_3$) δ: 1.29(3H,t,J=7.1 Hz), 1.52–1.80(2H, m), 2.03–2.37(4H,m), 2.53(3H,s), 2.57–2.71(1H,m), 3.73 and 3.78(each 1H,each d,J=14.4 Hz), 4.08–4.17(1H,m), 4.18(2H,q,J=7.2 Hz), 4.55–4.65(1H,m), 6.85(1H,br.s), 7.21 (1H,dd,J=8.8, 2.0 Hz), 7.33(1H,d,J=8.8 Hz), 7.48(1H,d,J=7.6 Hz), 7.63(1H,d,J=2.0 Hz), 7.98(1H,d,J=7.6 Hz), 9.30 (1H,s). MS (ESI) m/z: 544(M+H)$^+$.

Example 119

(1S,2R,4S)-N¹-[(5-Chloroindol-2-yl)carbonyl]-4-ethoxycarbonyl-N²-[(5-methyl-4,5,6,7-tetrahydrothiazolo[5,4-c]pyridin-2-yl)carbonyl]-1,2-cyclohexanediamine (1S,2R,4S)-N²-tert-Butoxycarbonyl-N¹-[(5-chloroindol-2-yl)carbonyl]-4-ethoxycarbonyl-1,2-cyclohexanediamine (4.2 g) was suspended in ethanol (25 ml), and a saturated ethanol solution (55 ml) of hydrochloric acid was added at room temperature to stir the mixture for 11 hours. The solvent was distilled off under reduced pressure to obtain (1S,3R,4S)-N¹-[(5-chloroindol-2-yl)carbonyl]-4-ethoxycarbonyl-1,2-cyclohexanediamine hydrochloride (4.15 g) as a colorless solid.

(1S,2R,4S)-N¹-[(5-Chloroindol-2-yl)carbonyl]-4-ethoxycarbonyl-1,2-cyclohexanediamine hydrochloride (4.15 g) was dissolved in N,N-dimethylformamide (40 ml), and lithium 5-methyl-4,5,6,7-tetrahydrothiazolo[5,4-c]-pyridine-2-carboxylate (2.86 g), 1-hydroxybenzotriazole monohydrate (1.72 g) and 1-(3-dimethylaminopropyl)-3-ethylcarbodiimide hydrochloride (2.15 g) were added to this solution at room temperature to stir the mixture for 39 hours. The reaction mixture was concentrated under reduced pressure, and water was added to the residue to conduct extraction with chloroform. The resultant organic layer was washed with saturated saline and dried over anhydrous magnesium sulfate. The solvent was distilled off under reduced pressure, and the resultant residue was purified by column chromatography on silica gel (chloroform:methanol=100:1) to obtain the title compound (1.71 g) as a colorless amorphous substance.

[α]$_D$ –94° (C=1.0, chloroform).

Example 120

(1R*,2R*,4S*)-N¹-[(5-Chloroindol-2-yl)carbonyl]-4-ethoxycarbonyl-N²-[(5-methyl-4,5,6,7-tetrahydrothiazolo[5,4-c]pyridin-2-yl)carbonyl]-1,2-cyclohexanediamine

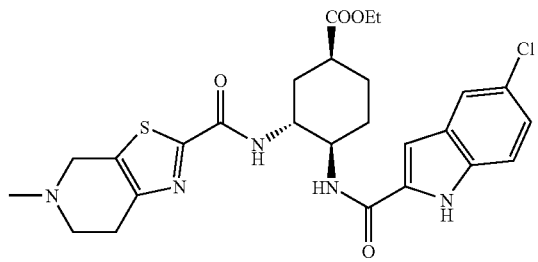

(1R*,2R*,4S*)-N²-tert-Butoxycarbonyl-N¹-[(5-chloroindol-2-yl)carbonyl]-4-ethoxycarbonyl-1,2-cyclohexanediamine was treated with a saturated ethanol solution of hydrochloric acid and then condensed with lithium 5-methyl-4,5,6,7-tetrahydrothiazolo[5,4-c]-pyridine-2-carboxylate in a similar manner to Example 118 to obtain the title compound.

$^1$H-NMR (CDCl$_3$) δ: 1.29(3H,t,J=7.10 Hz), 1.43–1.86 (3H,m), 1.19–2.35(2H,m), 2.46(3H,s), 2.45–2.60(1H,m), 2.67–2.80(1H,m), 2.80–2.98(4H,m), 3.58 and 3.71(each 1H,each d,J=15.2 Hz), 3.80–3.95(1H,m), 4.10–4.40(3H,m), 6.86(1H,br.s), 7.14–7.22(1H,m), 7.22–7.34(2H,m), 7.47 (1H,d,J=6.8 Hz), 7.60(1H,s), 9.35(1H,s). MS (ESI) m/z: 544(M+H)$^+$.

Example 121

(1R*,2S*,4S*)-N²-[(5-Chloroindol-2-yl)carbonyl]-4-methoxycarbonyl-N¹-[(5-methyl-4,5,6,7-tetrahydrothiazolo[5,4-c]pyridin-2-yl)carbonyl]-1,2-cyclohexanediamine

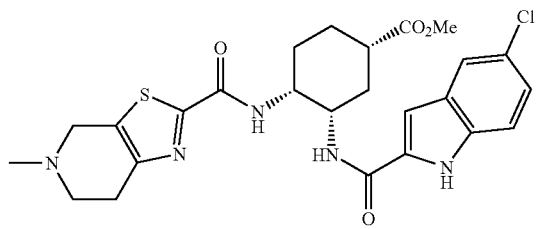

(1R*,2S*,4S*)-N¹-tert-Butoxycarbonyl-N²-[(5-chloroindol-2-yl)carbonyl]-4-methoxycarbonyl-1,2-cyclohexanediamine was treated with a saturated ethanol solution of hydrochloric acid and then condensed with lithium 5-methyl-4,5,6,7-tetrahydrothiazolo[5,4-c]-pyridine-2-carboxylate in a similar manner to Example 118 to obtain the title compound.

$^1$H-NMR (DMSO-d$_6$) δ: 1.55–1.80(3H,m), 1.80–2.20 (3H,m), 2.60–2.75(1H,m), 2.92(3H,s), 3.15–3.30(1H,m), 3.30–3.50(4H,m), 3.57(3H,s), 3.55–3.70(1H,m), 4.20–4.30 (1H,m), 4.30–4.40(1H,m), 7.02(1H,s), 7.17(1H,dd,J=8.5, 2.0 Hz), 7.41(1H,d,J=8.5 Hz), 7.71(1H,s), 8.20–8.35(1H,m), 8.35–8.45(1H,m), 11.82(1H,br). MS (FAB) m/z: 530(M+ H)$^+$.

Example 122

(1R*,2S*,4R*)-N²-[(5-Chloroindol-2-yl)carbonyl]-4-ethoxycarbonyl-N¹-[(5-methyl-4,5,6,7-tetrahydrothiazolo[5,4-c]pyridin-2-yl)carbonyl]-1,2-cyclohexanediamine

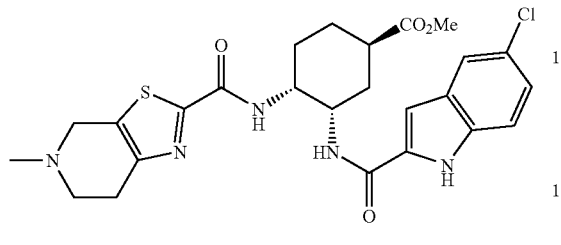

(1R*,2S*,4R*)-N²-tert-Butoxycarbonyl-4-ethoxycarbonyl-N¹-[(5-methyl-4,5,6,7-tetrahydrothiazolo[5,4-c]pyridin-2-yl)carbonyl]-1,2-cyclohexanediamine was treated with a saturated ethanol solution of hydrochloric acid and then condensed with 5-chloroindole-2-carboxylic acid in a similar manner to Example 118 to obtain the title compound.

$^1$H-NMR (CDCl$_3$) δ: 1.29(3H,t,J=7.1 Hz), 1.82–2.30(6H, m), 2.49(3H,s), 2.62–2.73(1H,m), 3.74–3.85(2H,m), 3.85–3.93(2H,m), 3.71(2H,s), 4.12–4.29(3H,m), 4.49–4.59 (1H,m), 6.89(1H,br.s), 7.21(1H,dd,J=8.8 and 2.0 Hz), 7.32 (1H,d,J=8.8 Hz), 7.33(1H,br.s), 7.41(1H,br.s), 7.62(1H,br.s), 9.37(1H,s). MS (ESI) m/z: 544(M+H)$^+$.

Example 123

(1R*,2S*,4S*)-N¹-[(5-Chloroindol-2-yl)carbonyl]-4-methoxycarbonyl-N²-[(5-methyl-4,5,6,7-tetrahydrothiazolo[5,4-c]pyridin-2-yl)carbonyl]-1,2-cyclohexanediamine hydrochloride

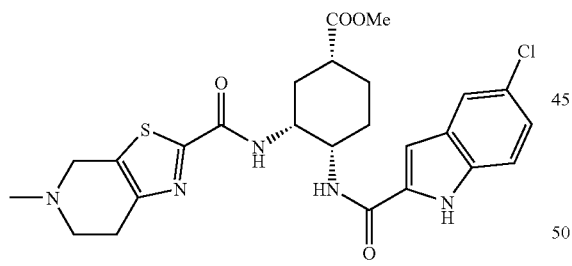

(1R*,2S*,4S*)-N¹-tert-Butoxycarbonyl-4-methoxycarbonyl-N²-[(5-methyl-4,5,6,7-tetrahydrothiazolo[5,4-c]pyridin-2-yl)carbonyl]-1,2-cyclohexanediamine was treated with a 4N dioxane solution of hydrochloric acid and then condensed with 5-chloroindole-2-carboxylic acid in a similar manner to Example 118 to obtain the title compound.

$^1$H-NMR (DMSO-d$_6$) δ: 1.65–1.80(3H,m), 1.80–2.10 (2H,m), 2.15–2.25(1H,m), 2.55–2.70(1H,m), 2.89(3H,s), 3.05–3.20(1H,m), 3.30–3.50(4H,m), 3.55–3.65(1H,m), 3.62 (3H,s), 4.20–4.30(1H,m), 4.35–4.45(1H,m), 7.19(1H,dd,J= 8.8, 1.2 Hz), 7.23(1H,s), 7.43(1H,d,J=8.8 Hz), 7.73(1H,s), 8.03(1H,d,J=6.8 Hz), 8.73(1H,d,J=8.5 Hz), 11.85(1H,s). MS (FAB) m/z: 530(M+H)$^+$.

Example 124

(1S,2R,4R)-N¹-[(5-Chloroindol-2-yl)carbonyl]-4-methoxycarbonyl-N²-[(5-methyl-4,5,6,7-tetrahydrothiazolo[5,4-c]pyridin-2-yl)carbonyl]-1,2-cyclohexanediamine hydrochloride

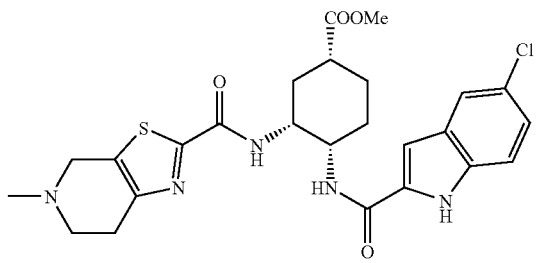

(1S,2R,4R)-N¹-tert-Butoxycarbonyl-4-methoxycarbonyl-N²-[(5-methyl-4,5,6,7-tetrahydrothiazolo[5,4-c]pyridin-2-yl)carbonyl]-1,2-cyclohexanediamine was treated with a 4N dioxane solution of hydrochloric acid and then condensed with 5-chloroindole-2-carboxylic acid in a similar manner to Example 118 to obtain the title compound.

$^1$H-NMR (DMSO-d$_6$) δ: 1.67–1.76(3H,m), 1.88–1.91 (1H,m), 2.01(1H,br.s), 2.13–2.22(1H,m), 2.52–2.67(4H,m), 2.86(2H,br.s), 3.04(2H,br.s), 3.33–3.41(1H,m), 3.61(3H,s), 4.22–4.36(3H,m), 7.17–7.22(2H,m), 7.42(1H,d,J=8.8 Hz), 7.72(1H,s), 8.00(1H,d,J=6.9 Hz), 8.68(1H,d,J=8.6 Hz), 11.80(1H,s). MS (FAB) m/z: 530(M+H)$^+$.

Example 125

(1S,2R,4R)-N¹-[(5-Fluoroindol-2-yl)carbonyl]-4-methoxycarbonyl-N²-[(5-methyl-4,5,6,7-tetrahydrothiazolo[5,4-c]pyridin-2-yl)carbonyl]-1,2-cyclohexanediamine hydrochloride

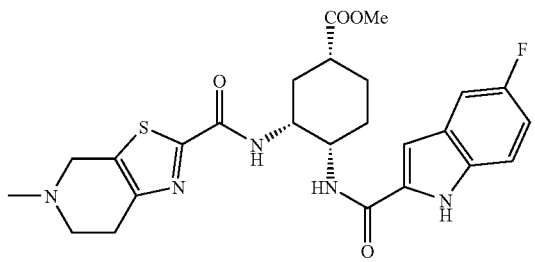

(1S,2R,4R)-N¹-tert-Butoxycarbonyl-4-methoxycarbonyl-N²-[(5-methyl-4,5,6,7-tetrahydrothiazolo[5,4-c]pyridin-2-yl)carbonyl]-1,2-cyclohexanediamine was treated with a 4N dioxane solution of hydrochloric acid and then condensed with 5-fluoroindole-2-carboxylic acid in a similar manner to Example 118 to obtain the title compound.

$^1$H-NMR (CD$_3$OD) δ: 1.81–1.90(3H,m), 2.09–2.17(3H, m), 2.61(3H,s), 2.60–2.63(1H,m), 2.95(2H,br.s), 3.10–3.12 (2H,m), 3.45–3.49(1H,m), 3.69(3H,s), 4.28–4.69(3H,m), 6.99–7.04(1H,m), 7.16(1H,s), 7.29(1H,dd,J=9.8, 2.5 Hz), 7.41(1H,dd,J=8.8, 4.6 Hz). MS (FAB) m/z: 514(M+H)$^+$.

Example 126

(1S,2R,4S)-4-Ethoxycarbonyl-N¹-[(5-fluoroindol-2-yl)carbonyl]-N²-[(5-methyl-4,5,6,7-tetrahydrothiazolo[5,4-c]pyridin-2-yl)carbonyl]-1,2-cyclohexanediamine

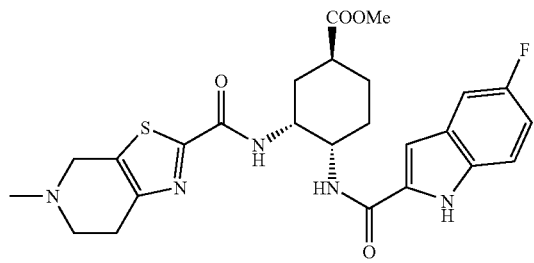

(1S,2R,4S)-N²-tert-Butoxycarbonyl-4-ethoxycarbonyl-N¹-[(5-fluoroindol-2-yl)carbonyl]-1,2-cyclohexanediamine was treated with a 4N dioxane solution of hydrochloric acid and then condensed with lithium 5-methyl-4,5,6,7-tetrahydrothiazolo-[5,4-c]pyridine-2-carboxylate in a similar manner to Example 118 to obtain the title compound.

$^1$H-NMR (CD$_3$OD) δ: 1.29(3H,t,J=7.1 Hz), 1.60–2.34 (6H,m), 2.53(3H,s), 2.61–2.68(1H,m), 2.80–2.88(2H,m), 2.96–2.99(2H,m), 3.75(2H,s), 4.12–4.14(1H,m), 4.18(2H,q, J=7.1 Hz), 4.59–4.60(1H,m), 6.86(1H,s), 6.99–7.04(1H,m), 7.27–7.34(2H,m), 7.47(1H,d,J=7.1 Hz), 7.92(1H,d,J=5.6 Hz), 9.13(1H,s). MS (FAB) m/z: 528(M+H)$^+$.

Example 127

(1R*,2S*,4R*,5S* or 1R*,2S*,4S*,5R*)-4,5-Bis(methoxycarbonyl)-N¹(or N²)-[(5-chloroindol-2-yl)carbonyl]-N²(or N¹)-[(5-methyl-4,5,6,7-tetrahydrothiazolo[5,4-c]pyridin-2-yl)-1,2-cyclohexanediamine

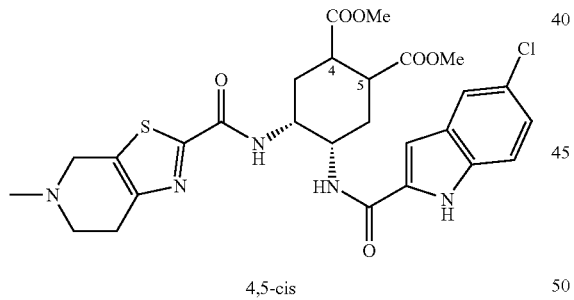

4,5-cis

Dimethyl (1R*,2S*,4R*,5S* or 1R*,2S*,4S*,5R*)-4,5-bis(tert-butoxycarbonylamino)-1,2-cyclohexanedicarboxylate (350 mg) was dissolved in methanol (30 ml), and a saturated methanol solution of hydrochloric acid was added to stir the mixture at room temperature for 9 hours. The solvent was distilled off under reduced pressure to obtain crude dimethyl 4,5-diamino-1,2-cyclohexanedicarboxylate. This product was dissolved in N,N-dimethylformamide (50 ml), and 5-chloroindole-2-carboxylic acid (120 mg), 1-(3-dimethylaminopropyl)-3-ethylcarbodiimide hydrochloride (120 mg), 1-hydroxybenzotriazole monohydrate (140 mg) and N-methylmorpholine (0.13 ml) were added to the solution to stir the mixture at room temperature for 17 hours. The solvent was distilled off under reduced pressure, and water was added to the residue to conduct extraction with dichloromethane. The resultant organic layer was washed with saturated aqueous solution of sodium chloride and dried over anhydrous sodium sulfate. The solvent was distilled off under reduced pressure, and the resultant residue was purified by column chromatography on silica gel (methanol:dichloromethane=1:9) to obtain crude(1R*,2S*,4R*,5S* or 1R*,2S*,4S*,5R*)-4,5-bis(methoxycarbonyl)-N¹(or N²)-[(5-chloroindol-2-yl)carbonyl]-1,2-cyclohexanediamine (190 mg). This product was dissolved in N,N-dimethylformamide (50 ml), and lithium 5-methyl-4,5,6,7-tetrahydrothiazolo-[5,4-c]pyridine-2-carboxylate (280 mg), 1-(3-dimethylaminopropyl)-3-ethylcarbodiimide hydrochloride (130 mg) and 1-hydroxybenzotriazole monohydrate (210 mg) were added to stir the mixture at room temperature for 17 hours. The solvent was distilled off under reduced pressure, and water was added to the residue to conduct extraction with dichloromethane. The resultant organic layer was washed with saturated aqueous solutiono of sodium chloride and dried over anhydrous sodium sulfate. The solvent was distilled off under reduced pressure, and the resultant residue was purified by column chromatography on silica gel (methanol:dichloromethane=1:9) and preparative chromatography to obtain the title compound (22 mg) as white powder.

$^1$H-NMR (DMSO-d$_6$) δ: 1.97–1.99(2H,m), 2.33–2.36 (2H,m), 2.39(3H,s), 2.68–3.69(8H,m), 3.88(3H,s), 3.89(3H, s), 4.18(1H,br), 4.28(1H,br), 7.01(1H,s), 7.16–7.19(2H,m), 7.40–7.42(2H,m), 7.74(1H,s), 11.81(1H,s) MS (FAB) m/z: 588(M+H)$^+$.

Example 128

(1R*,2S*,4R*)-4-Carboxy-N¹-[(5-chloroindol-2-yl)-carbonyl]-N²-[(5-methyl-4,5,6,7-tetrahydrothiazolo-[5,4-c]pyridin-2-yl)carbonyl]-1,2-cyclohexanediamine

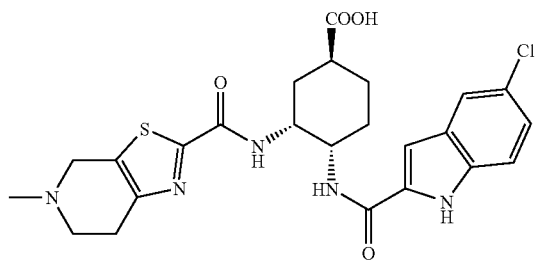

(1R*,2S*,4R*)-N¹-[(5-Chloroindol-2-yl)carbonyl]-4-ethoxycarbonyl-N²-[(5-methyl-4,5,6,7-tetrahydrothiazolo[5,4-c]pyridin-2-yl)carbonyl]-1,2-cyclohexane-diamine (916 mg) was suspended in a mixed solvent of ethanol (10 ml) and tetrahydrofuran (8 ml), and a 1N aqueous solution (3.3 ml) of sodium hydroxide was added at room temperature to stir the mixture for 12 hours at the same temperature. After adding 1N hydrochloric acid (3.3 ml), the solvent was distilled off under reduced pressure, and the residue was washed with water and ether to obtain the title compound (712 mg) as a colorless solid.

Example 129

(1R,2R,4S)-4-Carboxy-N¹-[(5-chloroindol-2-yl)-carbonyl]-N²-[(5-methyl-4,5,6,7-tetrahydrothiazolo[5,4-c]pyridin-2-yl)carbonyl]-1,2-cyclohexanediamine

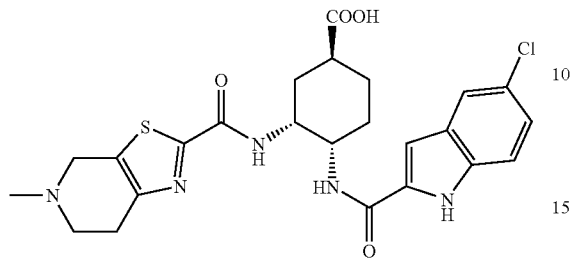

(1R,2R,4S)-N¹-[(5-Chloroindol-2-yl)carbonyl]-4-ethoxycarbonyl-N²-[(5-methyl-4,5,6,7-tetrahydrothiazolo[5,4-c]pyridin-2-yl)carbonyl]-1,2-cyclohexane-diamine (1.6 g) was suspended in a mixed solvent of ethanol (20 ml) and tetrahydrofuran (15 ml), and a 1N aqueous solution (5.9 ml) of sodium hydroxide was added at room temperature to stir the mixture for 12 hours at the same temperature. After adding 1N hydrochloric acid (5.9 ml), the solvent was distilled off under reduced pressure, and the residue was washed with water and ether to obtain the title compound (1.19 g) as a colorless solid.

m.p. 234–236° C. $[\alpha]_D$ –57° (C=1.0, methanol).

Example 130

(1R*,2S*,4S*)-4-Carboxy-N¹-[(5-chloroindol-2-yl)-carbonyl]-N²-[(5-methyl-4,5,6,7-tetrahydrothiazolo[5,4-c]pyridin-2-yl)carbonyl]-1,2-cyclohexanediamine hydrochloride

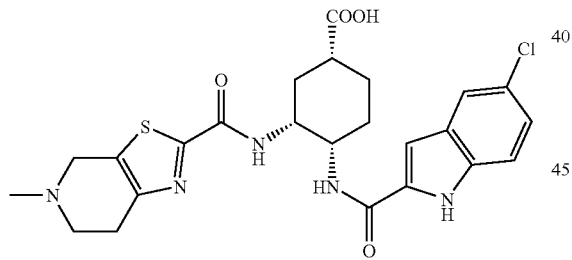

(1R*,2S*,4S*)-N¹-[(5-Chloroindol-2-yl)carbonyl]-4-methoxycarbonyl-N²-[(5-methyl-4,5,6,7-tetrahydrothiazolo[5,4-c]pyridin-2-yl)carbonyl]-1,2-cyclohexane-diamine (180 mg) was dissolved in a mixed solvent of tetrahydrofuran (8 ml) and water (2 ml), and lithium hydroxide (17 mg) was added to stir the mixture at room temperature for 45 minutes. After adding 1N hydrochloric acid, the reaction mixture was concentrated under reduced pressure, a small amount of water was added to the residue, and solids deposited were collected by filtration to obtain the title compound (140 mg) as a pale yellow solid.

¹H-NMR (DMSO-$d_6$) δ: 1.60–1.80(3H,m), 1.80–1.95(1H,m), 1.95–2.20(2H,m), 2.41(3H,s), 2.70–2.90(4H,m), 3.70–3.85(2H,m), 4.15–4.30(1H,m), 4.30–4.40(1H,m), 7.19(1H,dd,J=8.8, 2.2 Hz), 7.22(1H,d,J=1.5 Hz), 7.43(1H,d,J=8.8 Hz), 7.72(1H,d,J=2.2 Hz), 8.00(1H,d,J=6.8 Hz), 8.64(1H,d,J=8.5 Hz), 11.82(1H,s). MS (FAB) m/z: 516(M+H)⁺.

Example 131

(1R*,2R*,4S*)-4-Carboxy-N¹-[(5-chloroindol-2-yl)-carbonyl]-N²-[(5-methyl-4,5,6,7-tetrahydrothiazolo[5,4-c]pyridin-2-yl)carbonyl]-1,2-cyclohexanediamine

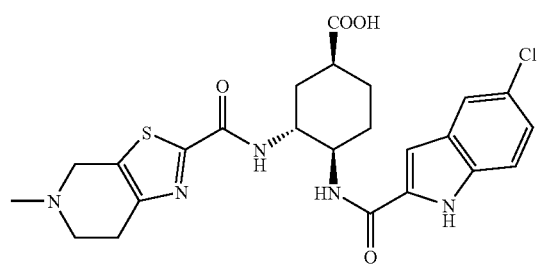

(1R*,2R*,4S*)-N¹-[(5-Chloroindol-2-yl)carbonyl]-4-ethoxycarbonyl-N²-[(5-methyl-4,5,6,7-tetrahydrothiazolo[5,4-c]pyridin-2-yl)carbonyl]-1,2-cyclohexane-diamine (244 mg) was suspended in a mixed solvent of ethanol (8 ml) and tetrahydrofuran (5 ml), and a 1N aqueous solution (0.9 ml) of sodium hydroxide was added at room temperature to stir the mixture for 12 hours. After adding 1N hydrochloric acid (0.9 ml), the solvent was distilled off under reduced pressure, and the residue was washed with water and ether to obtain the title compound (152 mg) as a colorless solid.

¹H-NMR (DMSO-$d_6$) δ: 1.44–2.23(6H,m), 2.34(3H,s), 2.60–2.90(5H,m), 3.53 and 3.62(each 1H,each d,J=5.65 Hz), 3.95–4.25(2H,m), 7.02(1H,s), 7.12(1H,br,J=8.8 Hz), 7.36(1H,d,J=8.8 Hz), 8.29(1H,d,J=8.8 Hz), 8.40(1H,d,J=8.8 Hz), 11.65(1H,s). MS (ESI) m/z: 516(M+H)⁺.

Example 132

(1R*,2S*,4S*)-4-Carboxy-N²-[(5-Chloroindol-2-yl)-carbonyl]-N¹-[(5-methyl-4,5,6,7-tetrahydrothiazolo[5,4-c]pyridin-2-yl)carbonyl]-1,2-cyclohexanediamine lithium salt

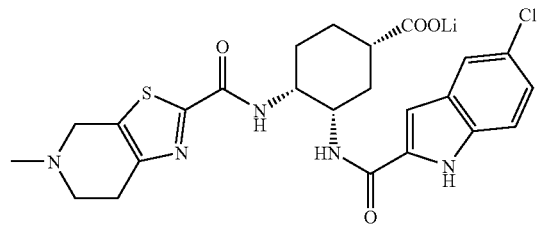

(1R*,2S*,4S*)-N²-[(5-Chloroindol-2-yl)carbonyl]-4-methoxycarbonyl-N¹-[(5-methyl-4,5,6,7-tetrahydrothiazolo[5,4-c]pyridin-2-yl)carbonyl]-1,2-cyclohexane-diamine (1.2 g) was dissolved in tetrahydrofuran (32 ml), and lithium hydroxide (60.8 mg) and water (4 ml) were successively added under ice cooling to stir the mixture at room temperature for 14 hours. The solvent was distilled off under reduced pressure to obtain the title compound (1.12 g).

¹H-NMR (DMSO-$d_6$) δ: 1.55–1.70(2H,m), 1.70–2.05(4H,m), 2.10–2.20(1H,m), 2.25–2.40(4H,m), 2.50–2.80(4H,m), 3.45–3.65(3H,m), 4.10–4.30(2H,m), 7.00–7.20(2H,m), 7.50–7.65(2H,m).

Example 133

(1R*,2S*,4R*)-4-Carbamoyl-N¹-[(5-chloroindol-2-yl)-carbonyl]-N²-[(5-methyl-4,5,6,7-tetrahydrothiazolo-[5,4-c]pyridin-2-yl)carbonyl]-1,2-cyclohexanediamine

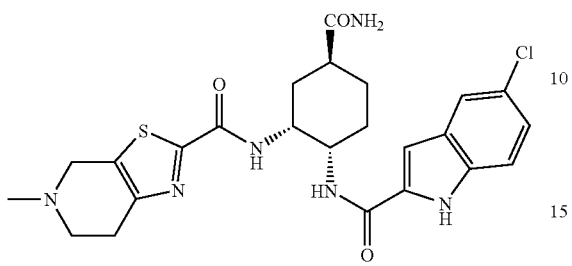

(1R*,2S*,4R*)-N²-(tert-Butoxycarbonyl)-4-carbamoyl-N¹-[(5-chloroindol-2-yl)carbonyl]-1,2-cyclohexanediamine was treated with a 4N dioxane solution of hydrochloric acid and then condensed with lithium 5-methyl-4,5,6,7-tetrahydrothiazolo-[5,4-c]pyridine-2-carboxylate in a similar manner to Example 118 to obtain the title compound.

¹H-NMR (CDCl$_3$) δ: 0.78–2.40(7H,m), 2.53(3H, s), 2.80–2.89(1H,m), 2.91–3.00(1H,m), 3.68–3.76(2H,m), 4.08–4.19(1H,m), 4.54–4.65(1H,m), 6.80(1H,br.s), 7.21 (1H,dd,J=8.4 and 1.6 Hz), 7.33(1H,d,J=8.4 Hz), 7.38–7.43 (1H,m), 7.49–7.55(1H,m), 7.63(1H,br.s), 9.14(1H,br.s). MS (ESI) m/z: 515(M+H)⁺.

Example 134

(1R*,2S*,4R*)-N¹-[(5-Chloroindol-2-yl)carbonyl]-4-(N,N-dimethylcarbamoyl)-N²-[(5-methyl-4,5,6,7-tetrahydrothiazolo[5,4-c]pyridin-2-yl)carbonyl]-1,2-cyclohexanediamine hydrochloride

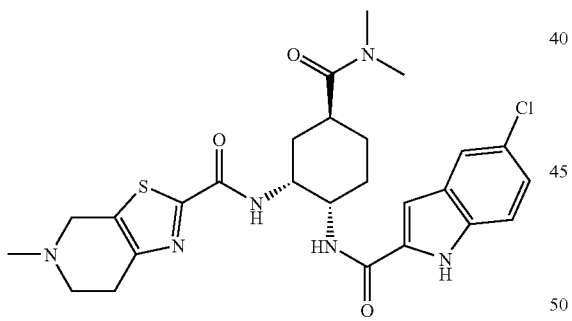

Triethylamine (0.25 ml), dimethylamine hydrochloride (133 mg), 1-hydroxybenzotriazole monohydrate (53 mg) and 1-(3-dimethylaminopropyl)-3-ethylcarbodiimide hydrochloride (75 mg) were added to a chloroform suspension (10 ml) of (1R*,2S*,4R*)-4-carboxy-N¹-[(5-chloroindol-2-yl)carbonyl]-N²-[(5-methyl-4,5,6,7-tetrahydrothiazolo[5,4-c]pyridin-2-yl)carbonyl]-1,2-cyclohexanediamine (168 mg), and the mixture was stirred for 72 hours. The solvent was distilled off under reduced pressure, and water was added to the residue to conduct extraction with chloroform. The resultant organic layer was washed with saturated aqueous solution of sodium chloride and dried over anhydrous magnesium sulfate. The solvent was distilled off under reduced pressure, and the resultant residue was purified by column chromatography on silica gel (dichloromethane:methanol= 93:7). The thus-obtained colorless solid (135 mg) was suspended in ethanol (5 ml), to which 1N hydrochloric acid (0.5 ml) was added. The mixture was stirred for 2 hours, and the solvent was distilled off to obtain the title compound (112 mg) as colorless powder.

¹H-NMR (DMSO-d$_6$) δ: 1.42–2.07(6H,m), 2.73–3.70 (10H,m), 2.88(3H,s), 2.97(3H,s), 4.03–4.20(1H,m), 4.51–4.67(1H,m), 7.04(1H,br.s), 7.16(1H,br,J=8.8 Hz), 7.41 (1H,d,J=8.8 Hz), 7.68(1H,br.s), 8.32–8.47(2H,m), 10.76 (1H,br.s). MS (ESI) m/z: 543(M+H)⁺.

Example 135

(1R*,2R*,4S*)-N¹-[(5-Chloroindol-2-yl)carbonyl]-4-(N,N-dimethylcarbamoyl)-N²-[(5-methyl-4,5,6,7-tetrahydrothiazolo[5,4-c]pyridin-2-yl)carbonyl]-1,2-cyclohexanediamine hydrochloride

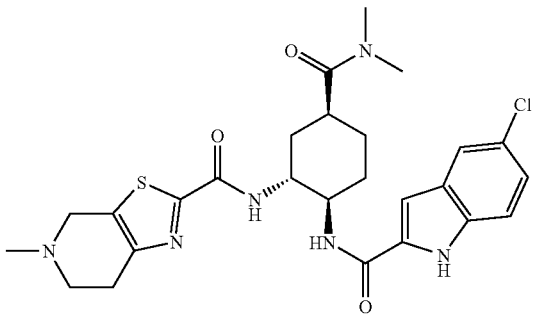

The title compound was obtained from (1R*,2R*,4S*)-4-carboxy-N¹-[(5-chloroindol-2-yl)-carbonyl]-N²-[(5-methyl-4,5,6,7-tetrahydrothiazolo-[5,4-c]pyridin-2-yl) carbonyl]-1,2-cyclohexanediamine and dimethylamine hydrochloride in a similar manner to Example 134.

¹H-NMR (DMSO-d$_6$) δ: 1.00–2.05(7H,m), 2.50(3H,s), 2.81(3H,s), 2.92–3.65(9H,m), 3.95–4.10(1H,m), 4.50–4.68 (1H,m), 7.08(1H,s), 7.13(1H,dd,J=8.8, 2.0 Hz), 7.37(1H,d, J=8.8 Hz), 7.66(1H,br.s), 8.31(1H,d,J=8.4 Hz), 8.50(1H,d, J=9.2 Hz), 11.67(1H,s). MS (ESI) m/z: 543(M+H)⁺.

Example 136

(1R*,2S*,4S*)-N¹-[(5-Chloroindol-2-yl)carbonyl]-4-(N,N-dimethylcarbamoyl)-N²-[(5-methyl-4,5,6,7-tetrahydrothiazolo[5,4-c]pyridin-2-yl)carbonyl]-1,2-cyclohexanediamine hydrochloride

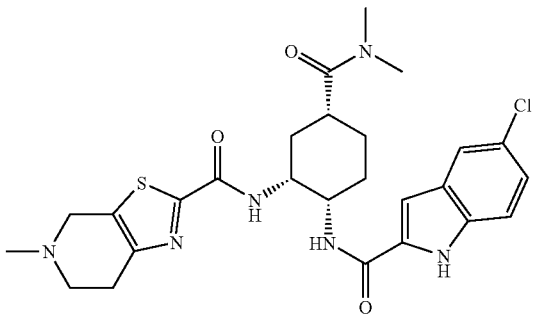

The title compound was obtained from (1R*,2S*,4S*)-4-carboxy-N¹-[(5-chloroindol-2-yl)-carbonyl]-N²-[(5-methyl-4,5,6,7-tetrahydrothiazolo-[5,4-c]pyridin-2-yl)carbonyl]-1,2-cyclohexanediamine and dimethylamine hydrochloride in a similar manner to Example 134.

¹H-NMR (DMSO-d₆) δ: 1.42–2.25(7H,m), 2.80–3.12(4H,m), 2.82(3H,s), 2.88(3H,s), 3.04(3H,s), 3.32–3.68(2H,m), 4.29–4.61(2H,m), 7.16–7.24(2H,m), 7.42(1H,d,J=8.8 Hz), 7.74(1H,s), 8.01(1H,d,J=5.6 Hz), 8.91(1H,d,J=8.4 Hz), 11.85(1H,br.s). MS (ESI) m/z: 543(M+H)⁺.

Example 137

(1R*,2S*,4R*)-N¹-[(5-Chloroindol-2-yl)carbonyl]-4-(N-methylcarbamoyl)-N²-[(5-methyl-4,5,6,7-tetrahydrothiazolo[5,4-c]pyridin-2-yl)carbonyl]-1,2-cyclohexane-diamine hydrochloride

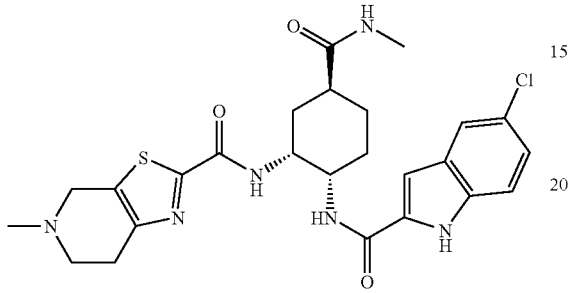

The title compound was obtained from (1R*,2S*,4R*)-4-carboxy-N¹-[(5-chloroindol-2-yl)-carbonyl]-N²-[(5-methyl-4,5,6,7-tetrahydrothiazolo-[5,4-c]pyridin-2-yl)carbonyl]-1,2-cyclohexanediamine and methylamine hydrochloride in a similar manner to Example 134.

¹H-NMR (DMSO-d₆) δ: 1.50–2.70(7H,m), 2.90(3H,s), 3.05–3.75(9H,m), 4.05–4.20(1H,m), 4.38–4.53(1H,m), 7.03(1H,br.s), 7.16(1H,br,J=8.8 Hz), 7.41(1H,d,J=8.8 Hz), 7.69(1H,br.s), 8.11(1H,br.s), 8.39(1H,d,J=7.6 Hz), 11.78(1H,br.s). MS (ESI) m/z: 529(M+H)⁺.

Example 138

(1S,2R,4S)-N¹-[(5-Chloroindol-2-yl)carbonyl]-4-(N-isopropylcarbamoyl)-N²-[(5-methyl-4,5,6,7-tetrahydrothiazolo[5,4-c]pyridin-2-yl)carbonyl]-1,2-cyclohexane-diamine hydrochloride

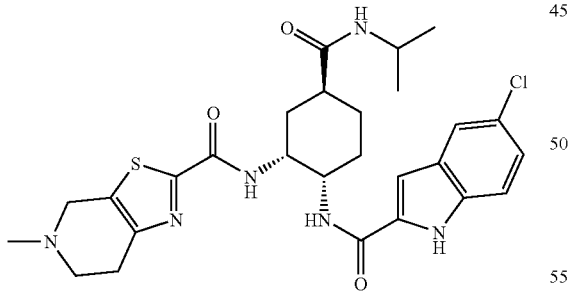

The title compound was obtained from (1S,2R,4S)-4-carboxy-N¹-[(5-chloroindol-2-yl)-carbonyl]-N²-[(5-methyl-4,5,6,7-tetrahydrothiazolo-[5,4-c]pyridin-2-yl)carbonyl]-1,2-cyclohexanediamine and isopropylamine in a similar manner to Example 134.

¹H-NMR (DMSO-d₆) δ: 1.02(6H,dd,J=6.5, 2.5 Hz), 1.50–2.10(6H,m), 2.30(1H,t,J=12.0 Hz), 2.91(3H,s), 3.10–3.75(4H,m), 3.75–3.90(1H,m), 4.07–4.20(1H,m), 4.30–4.57(2H,br.s), 4.57–4.83(1H,br.s), 7.03(1H,d,J=1.5 Hz), 7.16(1H,dd,J=8.8, 2.1 Hz), 7.41(1H,d,J=8.8 Hz), 7.60–7.75(2H,m), 8.05(1H,br.s), 8.43(1H,br,J=7.8 Hz), 11.63(1H,br.s), 11.79(1H,s). MS (FAB) m/z: 557(M+H)⁺.

Example 139

(1S,2R,4S)-N¹-[(5-Chloroindol-2-yl)carbonyl]-4-(N-cyclopropylcarbamoyl)-N²-[(5-methyl-4,5,6,7-tetrahydrothiazolo[5,4-c]pyridin-2-yl)carbonyl]-1,2-cyclohexanediamine hydrochloride

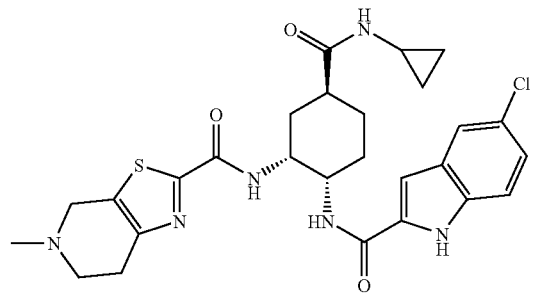

The title compound was obtained from (1S,2R,4S)-4-carboxy-N¹-[(5-chloroindol-2-yl)-carbonyl]-N²-[(5-methyl-4,5,6,7-tetrahydrothiazolo-[5,4-c]pyridin-2-yl)carbonyl]-1,2-cyclohexanediamine and cyclopropylamine in a similar manner to Example 134.

¹H-NMR (DMSO-d₆) δ: 0.32–0.40(2H,m), 0.53–0.63(2H,m), 1.50–2.10(6H,m), 2.25–2.40(1H,m), 2.45–2.70(2H,m), 2.91(3H,s), 3.05–3.80(3H,m), 4.05–4.17(1H,m), 4.30–4.55(2H,m), 4.55–4.80(1H,m), 7.03(1H,d,J=1.5 Hz), 7.16(1H,dd,J=8.8, 2.0 Hz), 7.41(1H,d,J=8.8 Hz), 7.68(1H,d,J=2.0 Hz), 7.86(1H,br,J=3.4 Hz), 8.06(1H,br.s), 8.40(1H,br,J=7.6 Hz), 11.20–11.60(1H,br), 11.79(1H,s). MS (FAB) m/z: 555(M+H)⁺.

Example 140

(1S,2R,4S)-N¹-[(5-Chloroindol-2-yl)carbonyl]-4-(N-ethyl-N-methylcarbamoyl)-N²-[(5-methyl-4,5,6,7-tetrahydrothiazolo[5,4-c]pyridin-2-yl)carbonyl]-1,2-cyclohexanediamine hydrochloride

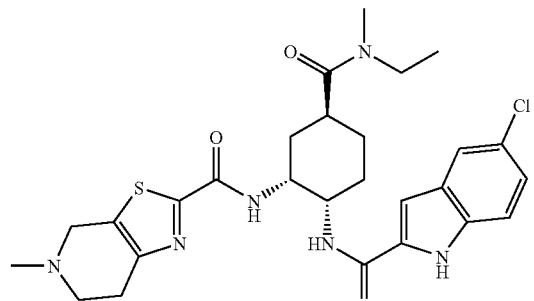

The title compound was obtained from (1S,2R,4S)-4-carboxy-N¹-[(5-chloroindol-2-yl)-carbonyl]-N²-[(5-methyl-4,5,6,7-tetrahydrothiazolo-[5,4-c]pyridin-2-yl)carbonyl]-1,2-cyclohexanediamine and ethylmethylamine in a similar manner to Example 134.

¹H-NMR (DMSO-d₆) δ: 0.93–1.13(3H,m), 1.40–1.64(1H,m), 1.64–1.88(3H,m), 1.88–2.10(2H,m), 2.76(½ of 3H,s), 2.90(3H,s), 2.93(½ of 3H,s), 3.10–3.80(7H,m), 4.05–4.17(1H,m), 4.30–4.85(3H,m), 7.04(1H,s), 7.15(1H, dd,J=8.8, 1.7 Hz), 7.40(1H,d,J=8.8 Hz), 7.67(1H,s), 8.30–8.50(2H,m), 11.29(1H,br.s), 11.77(1H,s). MS (FAB) m/z: 557(M+H)+.

Example 141

(1S,2R,4S)-N¹-[(5-Chloroindol-2-yl)carbonyl]-N²-[(5-methyl-4,5,6,7-tetrahydrothiazolo[5,4-c]pyridin-2-yl)carbonyl]-4-(pyrrolidinocarbonyl)-1,2-cyclohexane-diamine hydrochloride

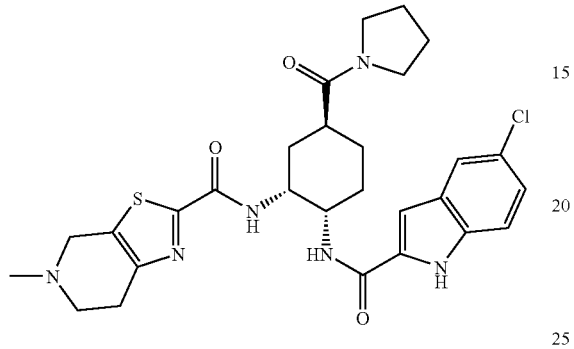

The title compound was obtained from (1S,2R,4S)-4-carboxy-N¹-[(5-chloroindol-2-yl)-carbonyl]-N²-[(5-methyl-4,5,6,7-tetrahydrothiazolo-[5,4-c]pyridin-2-yl)carbonyl]-1,2-cyclohexanediamine and pyrrolidine in a similar manner to Example 134.

¹H-NMR (DMSO-d₆) δ: 1.45–2.10(10H,m), 2.75–2.90 (2H,m), 2.90(3H,s), 3.10–3.70(H,m), 4.05–4.20(1H,m), 4.25–4.80(3H,m), 7.05(1H,s), 7.17(1H,d,J=8.7 Hz), 7.41 (1H,d,J=8.7 Hz), 7.69(1H,s), 8.32(1H,br,J=7.6 Hz), 8.38 (1H,br,J=7.1 Hz), 11.22(1H,br.s), 11.78(1H,s). MS (FAB) m/z: 569(M+H)+.

Example 142

(1R*,2S*,4R*)-N¹-[(5-Chloroindol-2-yl)carbonyl]-N²-[(5-methyl-4,5,6,7-tetrahydrothiazolo[5,4-c]pyridin-2-yl)carbonyl]-4-(4-morpholinocarbonyl)-1,2-cyclohexane-diamine hydrochloride

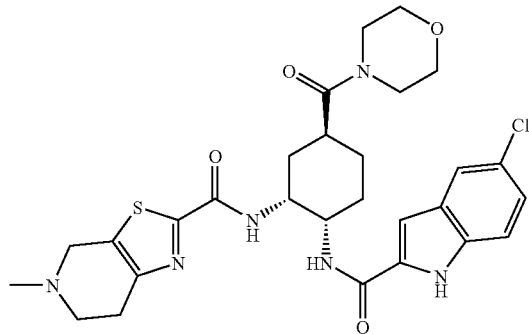

The title compound was obtained from (1R*,2S*,4R*)-4-carboxy-N¹-[(5-chloroindol-2-yl)-carbonyl]-N²-[(5-methyl-4,5,6,7-tetrahydrothiazolo-[5,4-c]pyridin-2-yl)carbonyl]-1,2-cyclohexanediamine and morpholine in a similar manner to Example 134.

¹H-NMR (DMSO-d₆) δ: 1.40–2.05(6H,m), 2.75–3.70 (18H,m) 4.02–4.17(1H,m), 4.55–4.69(1H,m), 7.05(1H,br.s), 7.17(1H,br,J=8.8 Hz), 7.41(1H,d,J=8.8 Hz), 7.67(1H,br.s), 8.35(1H,d,J=7.6 Hz), 8.40(1H,d,J=7.6 Hz), 10.79(1H,br.s). MS (ESI) m/z: 585(M+H)+.

Example 143

(1S,2R,4S)-N¹-[(5-Chloroindol-2-yl)carbonyl]-4-(N-ethylcarbamoyl)-N²-[(5-methyl-4,5,6,7-tetrahydrothiazolo[5,4-c]pyridin-2-yl)carbonyl]-1,2-cyclohexanediamine hydrochloride

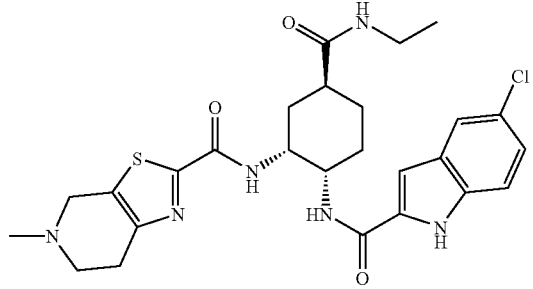

(1S,2R,4S)-4-Carboxy-N¹-[(5-chloroindol-2-yl)carbonyl]-N²-[(5-methyl-4,5,6,7-tetrahydrothiazolo-[5,4-c]pyridin-2-yl)carbonyl]-1,2-cyclohexanediamine (150 mg) was dissolved in N,N-dimethylformamide (3 ml), to which N-ethylamine hydrochloride (119 mg), 1-hydroxybenzotriazole monohydrate (79 mg), 1-(3-dimethylaminopropyl)-3-ethylcarbodiimide hydrochloride (112 mg) and triethylamine (326 μl) were added, and the mixture was stirred at room temperature for 4 days. The solvent was distilled off under reduced pressure, and a saturated aqueous solution of sodium hydrogencarbonate was added to the residue to conduct extraction with dichloromethane. The resultant organic layer was dried over anhydrous sodium sulfate. The solvent was distilled off under reduced pressure, and the resultant residue was purified by flash column chromatography on silica gel (dichloromethane:methanol=47:3). The thus-obtained white solid was dissolved in dichloromethane, to which 1N ethanol solution (171 μl) of hydrochloric acid was added. The solvent was distilled off under reduced pressure, and methanol and diethyl ether were added to the residue to collect precipitate formed by filtration, thereby obtaining the title compound (74 mg) as white solid.

¹H-NMR (DMSO-d₆) δ: 0.99(3H,t,J=7.2 Hz), 1.57–2.02 (6H,m), 2.33–2.38(1H,m), 2.92(3H,s), 3.01–3.08(2H,m), 3.17–3.20(2H,s), 3.45–3.70(2H,m), 4.10–4.17(1H,m), 4.40–4.69(3H,m), 7.04(1H,d,J=2.0 Hz), 7.17(1H,dd,J=8.8, 2.0 Hz), 7.41(1H,d,J=8.8 Hz), 7.69(1H,d,J=2.0 Hz), 7.78–7.81(1H,m), 8.08–8.12(1H,m), 8.40(1H,d,J=8.1 Hz), 11.23(1H,br.s), 11.79(1H,br.s). MS (FAB) m/z: 543(M+H)+.

Example 144

(1S,2R,4S)-N$^1$-[(5-Chloroindol-2-yl)carbonyl]-4-(N,N-dimethylcarbamoyl)-N$^2$-[(5-methyl-4,5,6,7-tetrahydrothiazolo[5,4-c]pyridin-2-yl)carbonyl]-1,2-cyclohexanediamine hydrochloride

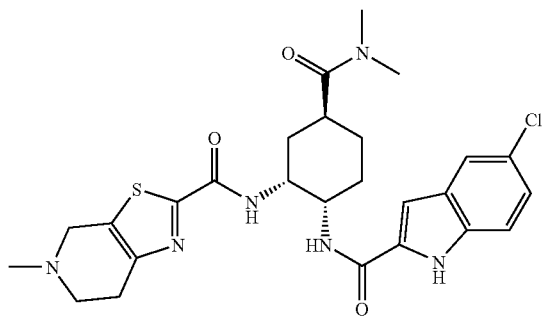

(1S,2R,4S)-4-Carboxy-N$^1$-[(5-chloroindol-2-yl)carbonyl]-N$^2$-[(5-methyl-4,5,6,7-tetrahydrothiazolo-[5,4-c]pyridin-2-yl)carbonyl]-1,2-cyclohexanediamine (900 mg) was dissolved in N,N-dimethylformamide (50 ml), to which dimethylamine hydrochloride (304 mg), 1-hydroxybenzotriazole monohydrate (262 mg), 1-(3-dimethylaminopropyl)-3-ethylcarbodiimide hydrochloride (369 mg) and diisopropylethylamine (1.83 ml) were added, and the mixture was stirred at room temperature for 12 hours. The solvent was distilled off under reduced pressure, and a saturated aqueous solution of sodium hydrogencarbonate was added to the residue to conduct extraction with dichloromethane. The resultant organic layer was dried over anhydrous sodium sulfate. The solvent was distilled off under reduced pressure, and the resultant residue was purified by flash column chromatography on silica gel (dichloromethane:methanol=47:3). The thus-obtained white solid was dissolved in dichloromethane, to which 1N ethanol solution (1.49 ml) of hydrochloric acid was added. The solvent was distilled off under reduced pressure, and methanol and diethyl ether were added to the residue to collect precipitate formed by filtration, thereby obtaining the title compound (777 mg) as white solid.

$[\alpha]_D$=−53.9° (18° C., c=0.505, methanol). $^1$H-NMR (DMSO-d$_6$) δ: 1.45–1.60(1H,m), 1.70–1.85(3H,m), 2.80 (3H,s), 2.91(3H,s), 2.95–3.10(1H,m), 2.97(3H,s), 3.10–3.75 (4H,m), 4.05–4.15(1H,m), 4.35–4.75(3H,m), 7.05(1H,s), 7.16(1H,dd,J=8.7, 2.1 Hz), 7.41(1H,d,J=8.6 Hz), 7.67(1H, s), 8.30–8.45(2H,m), 11.63(1H,br), 11.78(1H,s). MS (FAB) m/z: 543(M+H)$^+$.

Example 145

(1S,2R,4S)-N$^1$-[(5-Chloroindol-2-yl)carbonyl]-4-(N,N-diethylcarbamoyl)-N$^2$-[(5-methyl-4,5,6,7-tetrahydrothiazolo[5,4-c]pyridin-2-yl)carbonyl]-1,2-cyclohexanediamine hydrochloride

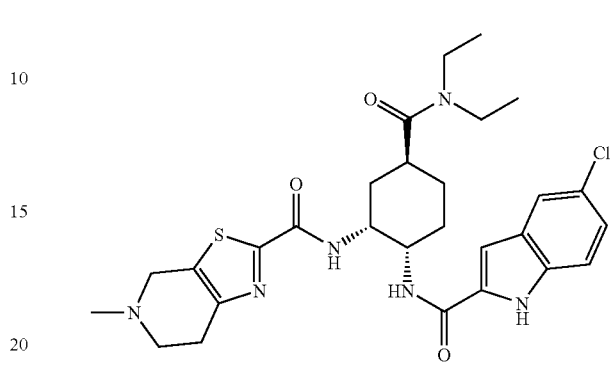

The title compound was obtained from (1S,2R,4S)-4-carboxy-N$^1$-[(5-chloroindol-2-yl)-carbonyl]-N$^2$-[(5-methyl-4,5,6,7-tetrahydrothiazolo-[5,4-c]pyridin-2-yl)carbonyl]-1,2-cyclohexanediamine and diethylamine in a similar manner to Example 134.

$^1$H-NMR (DMSO-d$_6$) δ: 0.99,1.05(6H, each t, J=7.1 Hz), 1.53–1.61(1H,m), 1.74–1.80(3H,m), 1.96–2.05(2H,m), 2.88–2.95(4H,m), 3.17–3.67(8H,m), 4.11–4.16(1H,m), 4.45 (1H,br.s), 4.55–4.58(1H,m), 4.66(1H,br.s), 7.06(1H,d,J=2.0 Hz), 7.16(1H,dd,J=8.9, 1.9 Hz), 7.42(1H,d,J=8.9 Hz), 7.69 (1H,d,J=1.9 Hz), 8.41(2H,d,J=7.8 Hz), 11.65(1H,br.s), 11.81 (1H,br.s). MS (FAB) m/z: 571(M+H)$^+$.

Example 146

(1S,2R,4S)-N$^1$-[(5-Chloroindol-2-yl)carbonyl]-4-(N-methyl-N-propylcarbamoyl)-N$^2$-[(5-methyl-4,5,6,7-tetrahydrothiazolo[5,4-c]pyridin-2-yl)carbonyl]-1,2-cyclohexanediamine hydrochloride

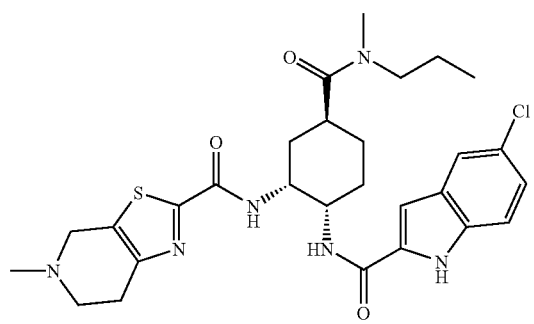

The title compound was obtained from (1S,2R,4S)-4-carboxy-N$^1$-[(5-chloroindol-2-yl)-carbonyl]-N$^2$-[(5-methyl-4,5,6,7-tetrahydrothiazolo-[5,4-c]pyridin-2-yl)carbonyl]-1,2-cyclohexanediamine and N-methyl-N-propylamine in a similar manner to Example 134.

$^1$H-NMR (DMSO-d$_6$) δ: 0.71,0.79(3H,each t,J=7.3 Hz) 1.41–1.75(6H,m), 1.99(2H,br.s), 2.67–3.02(7H,m), 3.11–3.40(4H,m), 3.47(1H,br.s), 3.67(1H,br.s), 4.12(1H, br.s), 4.44–4.68(3H,m), 7.05(1H,s), 7.16(1H,dd,J=8.8, 1.7 Hz), 7.41(1H,d,J=8.8 Hz), 7.69(1H,d,J=1.7 Hz), 8.35–8.42 (2H,m), 11.45(1H,br.s), 11.79, 11.81(1H,each s). MS (FAB) m/z: 571(M+H)+.

Example 147

(1S,2R,4S)-N¹-[(5-Chloroindol-2-yl)carbonyl]-4-(N, N-dipropylcarbamoyl)-N²-[(5-methyl-4,5,6,7-tetrahydrothiazolo[5,4-c]pyridin-2-yl)carbonyl]-1,2-cyclohexanediamine hydrochloride

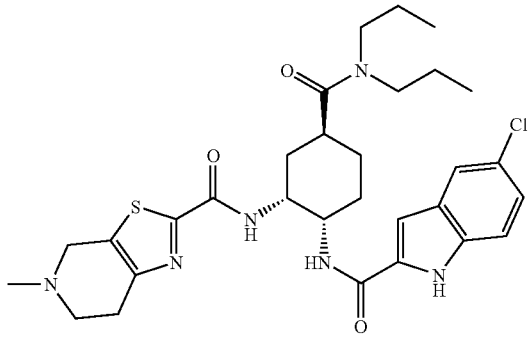

The title compound was obtained from (1S,2R,4S)-4-carboxy-N¹-[(5-chloroindol-2-yl)-carbonyl]-N²-[(5-methyl-4,5,6,7-tetrahydrothiazolo-[5,4-c]pyridin-2-yl)carbonyl]-1,2-cyclohexanediamine and dipropylamine in a similar manner to Example 134.

¹H-NMR (DMSO-d₆) δ: 0.69(3H,t,J=7.3 Hz), 0.79(3H,t, J=7.3 Hz), 1.38–1.47(4H,m), 1.57–1.78(4H,m), 1.98–2.01 (2H,m), 2.80(1H,t,J=11.5 Hz), 3.01–3.39(6H,m), 3.48(1H, br.s), 3.68(1H,br.s), 4.13–4.16(1H,m), 4.43(1H,br.s), 4.48–4.50(1H,m), 4.68(1H,br.s), 7.04(1H,d,J=2.0 Hz), 7.16 (1H,dd,J=8.8, 2.2 Hz), 7.41(1H,d,J=8.8 Hz), 7.70(1H,d,J= 2.2 Hz), 8.33(1H,d,J=7.6 Hz), 11.27–11.40(1H,m), 11.80 (1H,br.s). MS (FAB) m/z: 599(M+H)+.

Example 148

(1S,2R,4S)-N¹-[(5-Chloroindol-2-yl)carbonyl]-4-(N-isopropyl-N-methylcarbamoyl)-N²-[(5-methyl-4,5,6,7-tetrahydrothiazolo[5,4-c]pyridin-2-yl)carbonyl]-1,2-cyclohexanediamine hydrochloride

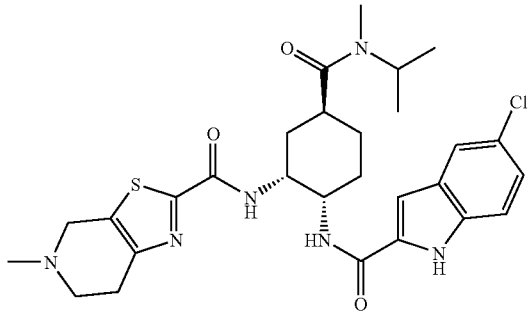

The title compound was obtained from (1S,2R,4S)-4-carboxy-N¹-[(5-chloroindol-2-yl)-carbonyl]-N²-[(5-methyl-4,5,6,7-tetrahydrothiazolo-[5,4-c]pyridin-2-yl)carbonyl]-1,2-cyclohexanediamine and N-isopropyl-N-methylamine in a similar manner to Example 134.

¹H-NMR (DMSO-d₆) δ: 0.99–1.15(6H,m), 1.50–1.99 (6H,m), 2.64,2.78(3H,each s), 2.92(3H,s), 2.96–3.39(4H, m), 3.47(1H,br.s), 3.68(1H,br.s), 4.12–4.13(1H,m), 4.45(1H, br.s), 4.58–4.70(2H,m), 7.05(1H,s), 7.16(1H,dd,J=8.8, 2.0 Hz), 7.41(1H,d,J=8.8 Hz), 7.69(1H,d,J=2.0 Hz), 8.38–8.46 (2H,m), 11.27(1H,br.s), 11.79(1H,br.s). MS (FAB) m/z: 571 (M+H)+.

Example 149

(1S,2R,4S)-N¹-[(5-Chloroindol-2-yl)carbonyl]-4-[N-(2-methoxyethyl)-N-methylcarbamoyl]-N²-[(5-methyl-4,5,6,7-tetrahydrothiazolo[5,4-c]pyridin-2-yl)carbonyl]-1,2-cyclohexanediamine hydrochloride:

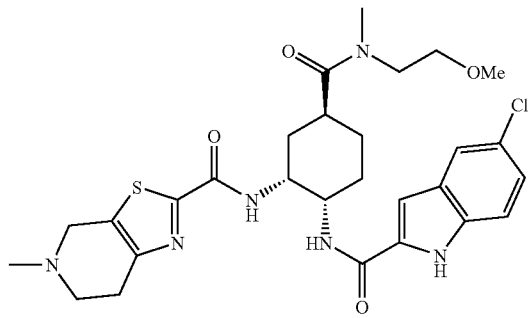

The title compound was obtained from (1S,2R,4S)-4-carboxy-N¹-[(5-chloroindol-2-yl)-carbonyl]-N²-[(5-methyl-4,5,6,7-tetrahydrothiazolo-[5,4-c]pyridin-2-yl)carbonyl]-1,2-cyclohexanediamine and N-(2-methoxyethyl)-N-methylamine in a similar manner to Example 134.

¹H-NMR (DMSO-d₆) δ: 1.50–1.99(6H,m), 2.80, 3.01(3H, each s), 2.91(3H,s), 3.03(1H,br.s), 3.16(2H,s), 3.23(3H,s), 3.35–3.67(6H,m), 4.09–4.16(1H,m), 4.43–4.67(3H,m), 7.04–7.06(1H,m), 7.16(1H,dd,J=8.8, 2.0 Hz), 7.42(1H,d,J= 8.8 Hz), 7.69(1H,br.s), 8.29–8.41(2H,m), 11.59(1H,br.s), 11.80(1H,br.s). MS (FAB) m/z: 587(M+H)+.

Example 150

(1S,2R,4S)-N¹-[(5-Chloroindol-2-yl)carbonyl]-4-[N-(2-hydroxyethyl)-N-methylcarbamoyl]-N²-[(5-methyl-4,5,6,7-tetrahydrothiazolo[5,4-c]pyridin-2-yl)carbonyl]-1,2-cyclohexanediamine hydrochloride

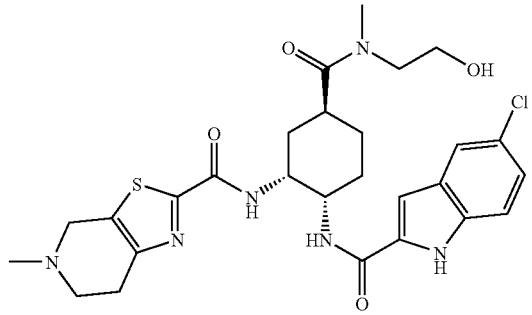

The title compound was obtained from (1S,2R,4S)-4-carboxy-N¹-[(5-chloroindol-2-yl)-carbonyl]-N²-[(5-methyl-4,5,6,7-tetrahydrothiazolo-[5,4-c]pyridin-2-yl)carbonyl]-1,2-cyclohexanediamine and N-(2-hydroxyethyl)-N-methylamine in a similar manner to Example 134.

¹H-NMR (DMSO-d₆) δ: 1.50–1.55(1H,m), 1.74–1.84 (3H,m), 1.94–1.97(2H,m), 2.67,3.02(3H,each s), 2.91(3H, s), 3.10–3.68(9H,m), 4.11–4.13(1H,m), 4.43–4.66(4H,m), 7.05(1H,s), 7.16(1H,dd,J=8.7, 2.0 Hz), 7.41(1H,d,J=8.7 Hz), 7.68(1H,s), 8.34–8.40(2H,m), 11.47(1H,br.s), 11.79 (1H,s). MS (FAB) m/z: 573(M+H)⁺.

Example 151

(1S,2R,4S)-4-[(Azetidin-1-yl)carbonyl]-N¹-[(5-chloroindol-2-yl)carbonyl]-N²-[(5-methyl-4,5,6,7-tetrahydrothiazolo[5,4-c]pyridin-2-yl)carbonyl]-1,2-cyclohexanediamine hydrochloride

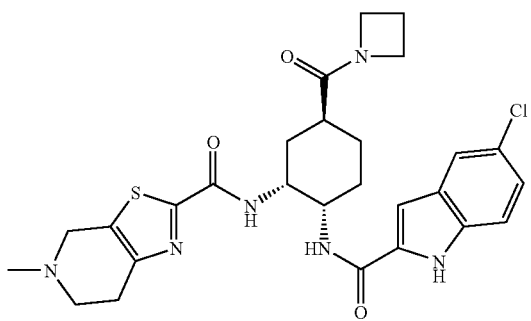

The title compound was obtained from (1S,2R,4S)-4-carboxy-N¹-[(5-chloroindol-2-yl)-carbonyl]-N²-[(5-methyl-4,5,6,7-tetrahydrothiazolo-[5,4-c]pyridin-2-yl)carbonyl]-1,2-cyclohexanediamine and azetidine hydrochloride in a similar manner to Example 134.

¹H-NMR (DMSO-d₆) δ: 1.47–1.55(1H,m), 1.65–1.82 (3H,m), 1.88–2.01(2H,m), 2.16(2H,quint.,J=7.6 Hz), 3.17–3.67(5H,m), 3.82(2H,t,J=7.6 Hz), 4.02–4.14(3H,m), 4.43–4.67(3H,m), 7.06(1H,s), 7.17(1H,dd,J=8.7, 1.7 Hz), 7.41(1H,d,J=8.7 Hz), 7.69(1H,br.s), 8.31(1H,d,J=7.6 Hz), 8.38(1H,d,J=7.6 Hz), 11.41(1H,br.s), 11.80(1H,s). MS (FAB) m/z: 555(M+H)⁺.

Example 152

(1S,2R,4S)-N¹-[(5-Chloroindol-2-yl)carbonyl]-4-[[(3S)-3-fluoropyrrolidin-1-yl]carbonyl]-N²-[(5-methyl-4,5,6,7-tetrahydrothiazolo[5,4-c]pyridin-2-yl)carbonyl]-1,2-cyclohexanediamine hydrochloride

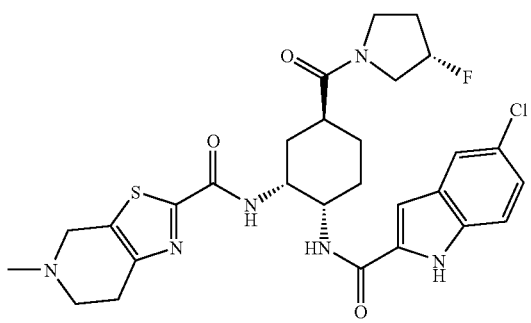

The title compound was obtained from (1S,2R,4S)-4-carboxy-N¹-[(5-chloroindol-2-yl)-carbonyl]-N²-[(5-methyl-4,5,6,7-tetrahydrothiazolo-[5,4-c]pyridin-2-yl)carbonyl]-1,2-cyclohexanediamine and (S)-3-fluoropyrrolidine (Synlett., 1995, p. 55) in a similar manner to Example 134.

¹H-NMR (DMSO-d₆) δ: 1.23–3.77(22H,m), 4.11–4.16 (1H,m) 4.58–4.51(1H,m), 5.23–5.42(1H,m), 7.05(1H,s), 7.16(1H,d,J=8.3 Hz), 7.42(1H,d,J=8.3 Hz), 7.68(1H,s), 8.34–8.37(2H,m), 11.78(1H,s). MS (FAB) m/z: 587(M+H)⁺.

Example 153

(1R*,2S*,4S*)-N²-[(5-Chloroindol-2-yl)carbonyl]-4-(N-methylcarbamoyl)-N¹-[(5-methyl-4,5,6,7-tetrahydrothiazolo[5,4-c]pyridin-2-yl)carbonyl]-1,2-cyclohexanediamine

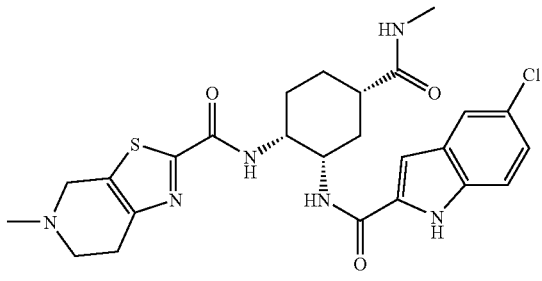

The title compound was obtained from (1R*,2S*,4S*)-4-carboxy-N²-[(5-chloroindol-2-yl)carbonyl]-N¹-[(5-methyl-4,5,6,7-tetrahydrothiazolo-[5,4-c]pyridin-2-yl)carbonyl]-1,2-cyclohexanediamine lithium salt and methylamine in a similar manner to Example 134.

¹H-NMR (DMSO-d₆) δ: 1.50–1.80(4H,m), 1.90–2.05 (2H,m), 2.35–2.45(4H,m), 2.59(3H,d,J=4.4 Hz), 2.70–2.80 (2H,m), 2.85–2.95(2H,m), 3.64(2H,s), 4.20–4.35(2H,m), 7.02(1H,s), 7.16(1H,d,J=8.6 Hz), 7.41(1H,d,J=8.8 Hz), 7.68 (1H,s), 7.85(1H,d,J=4.4 Hz), 7.98(1H,d,J=7.6 Hz), 8.67(1H, d,J=7.6 Hz), 11.76(1H, s). MS (FAB) m/z: 529(M+H)⁺.

Example 154

(1R*,2S*,4S*)-N²-[(5-Chloroindol-2-yl)carbonyl]-4-[N-(2-methoxyethyl)carbamoyl]-N¹-[(5-methyl-4,5,6,7-tetrahydrothiazolo[5,4-c]pyridin-2-yl)carbonyl]-1,2-cyclohexanediamine hydrochloride

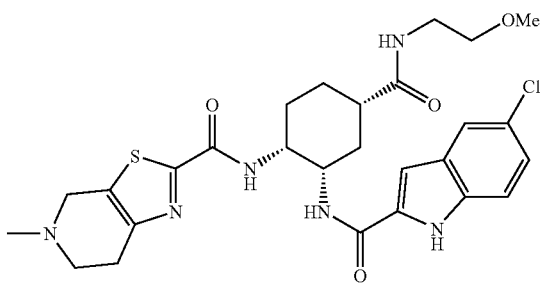

The title compound was obtained from (1R*,2S*,4S*)-4-carboxy-N²-[(5-chloroindol-2-yl)carbonyl]-N¹-[(5-methyl-4,5,6,7-tetrahydrothiazolo-[5,4-c]pyridin-2-yl)carbonyl]-1,2-cyclohexanediamine lithium salt and 2-methoxyethylamine in a similar manner to Example 134.

¹H-NMR (DMSO-d₆) δ: 1.50–1.80(4H,m), 1.95–2.05 (2H,m), 2.85–2.95(4H,m), 3.10–3.40(10H,m), 3.40–3.70 (2H,m), 4.15–4.70(4H,m), 7.02(1H,s), 7.16(1H,d,J=8.8 Hz), 7.41(1H,d,J=8.8 Hz), 7.69(1H,s), 7.95–8.05(1H,m), 8.08 (1H,d,J=7.6 Hz), 8.67(1H,d,J=7.8 Hz), 11.20–11.90(2H,m). MS (FAB) m/z: 573(M+H)⁺.

Example 155

(1R*,2S*,4S*)-N²-[(5-Chloroindol-2-yl)carbonyl]-4-(N-isopropylcarbamoyl)-N¹-[(5-methyl-4,5,6,7-tetrahydrothiazolo[5,4-c]pyridin-2-yl)carbonyl]-1,2-cyclohexanediamine hydrochloride

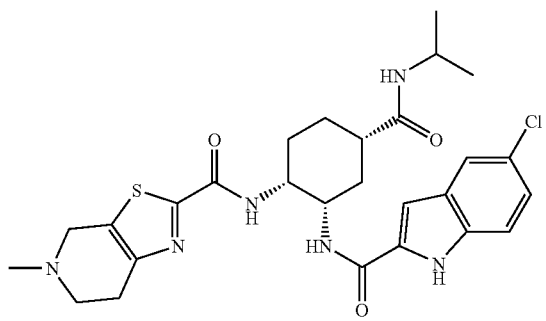

The title compound was obtained from (1R*,2S*,4S*)-4-carboxy-N²-[(5-chloroindol-2-yl)carbonyl]-N¹-[(5-methyl-4,5,6,7-tetrahydrothiazolo-[5,4-c]pyridin-2-yl)carbonyl]-1,2-cyclohexanediamine lithium salt and isopropylamine in a similar manner to Example 134.

¹H-NMR (DMSO-$d_6$) δ: 1.00–1.10(6H,m), 1.50–1.80 (4H,m), 1.95–2.05(2H,m), 2.35–2.45(1H,m), 2.91(3H,s), 3.15–3.25(2H,m), 3.45–3.70(2H,m), 3.80–3.90(1H,m), 4.20–4.70(4H,m), 7.02(1H,d,J=1.5 Hz), 7.16(1H,dd,J=8.8, 2.2 Hz), 7.41(1H,d,J=8.8 Hz), 7.68(1H,d,J=1.7 Hz), 7.76 (1H,d,J=7.6 Hz), 8.04(1H,d,J=8.8 Hz), 8.68(1H,d,J=7.8 Hz), 11.39(1H,br), 11.76(1H,s). MS (FAB) m/z: 557(M+H)⁺.

Example 156

(1R*,2S*,4S*)-N²-[(5-Chloroindol-2-yl)carbonyl]-4-(N,N-dimethylcarbamoyl)-N¹-[(5-methyl-4,5,6,7-tetrahydrothiazolo[5,4-c]pyridin-2-yl)carbonyl]-1,2-cyclohexanediamine hydrochloride

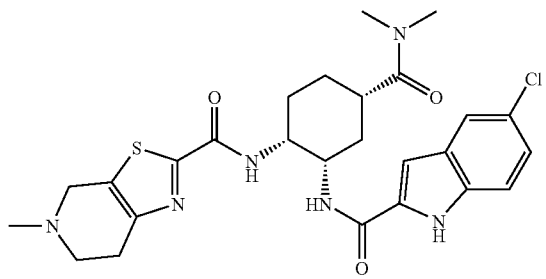

The title compound was obtained from (1R*,2S*,4S*)-4-carboxy-N²-[(5-chloroindol-2-yl)carbonyl]-N¹-[(5-methyl-4,5,6,7-tetrahydrothiazolo-[5,4-c]pyridin-2-yl)carbonyl]-1,2-cyclohexanediamine lithium salt and dimethylamine hydrochloride in a similar manner to Example 134.

¹H-NMR (DMSO-$d_6$) δ: 1.40–1.60(2H,m), 1.65–1.80 (2H,m) 1.95–2.10(2H,m), 2.84(3H,s), 2.90–3.05(1H,m), 2.92(3H,s), 3.06(3H,s), 3.15–3.75(4H,m), 4.25–4.75(4H,m), 7.02(1H,d,J=1.5 Hz), 7.15(1H,dd,J=8.8, 2.1 Hz), 7.41(1H, d,J=8.8 Hz), 7.69(1H,d,J=2.1 Hz), 8.05(1H,d, J=7.7 Hz), 8.63(1H,d,J=7.7 Hz), 11.20(1H,br), 11.79(1H,s). MS (FAB) m/z: 543(M+H)⁺.

Example 157

(1S,2R,4R)-N¹-[(5-Chloroindol-2-yl)carbonyl]-N²-[(5-methyl-4,5,6,7-tetrahydrothiazolo[5,4-c]pyridin-2-yl)carbonyl]-4-(piperidin-1-yl)carbonyl-1,2-cyclohexanediamine hydrochloride

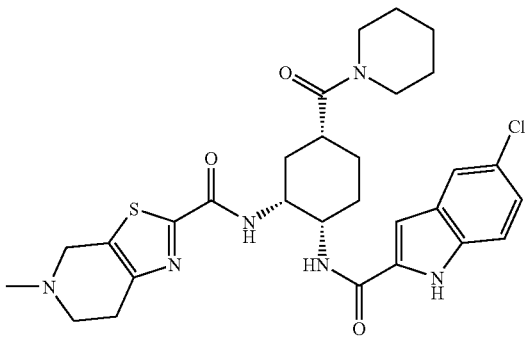

(1S,2R,4R)-N¹-[(5-Chloroindol-2-yl)carbonyl]-4-methoxycarbonyl-N²-[(5-methyl-4,5,6,7-tetrahydrothiazolo [5,4-c]pyridin-2-yl)carbonyl]-1,2-cyclohexanediamine (200 mg) was dissolved in tetrahydrofuran (5 ml) and water (0.6 ml), and lithium hydroxide (12 mg) was added to stir the mixture at room temperature. After 3 hours, the reaction was stopped, the solvent was concentrated under reduced pressure, and the residue was then dissolved in N,N-dimethylformamide (10 ml), to which piperidine (65 mg), 1-(3-dimethyl-aminopropyl)-3-ethylcarbodiimide hydrochloride (110 mg), 1-hydroxybenzotriazole (77 mg) and diisopropylethylamine (390 mg) were added, and the mixture was stirred at room temperature for 3 days. The solvent was distilled off under reduced pressure, dichloromethane was added to the residue, and the resultant mixture was washed with a saturated aqueous solution of sodium hydrogencarbonate. The resultant organic layer was dried over anhydrous magnesium sulfate. The solvent was distilled off under reduced pressure, and the resultant residue was purified by column chromatography on silica gel (methanol:dichloromethane=1:10) to obtain a product (132 mg) in a free form. This product was dissolved in methanol, to which 1N ethanol solution (230 μl) of hydrochloric acid was added. The mixture was dried to solid. Ether was added to the residue to solidify it. This solid was collected by filtration to obtain the title compound (127 mg) as a colorless solid.

¹H-NMR (CD₃OD) δ: 1.55–2.10(12H,m), 3.06(3H,s), 3.07–3.16(3H,m), 3.59–3.70(7H,m), 4.35(1H,br.s), 4.61 (2H,br.s), 7.13–7.21(2H,m), 7.41(1H,d,J=8.8 Hz), 7.60(1H, s),7.86(0.5H,d,J=7.6 Hz), 8.84(0.5H,d,J=7.6 Hz). MS (FAB) m/z: 583(M+H)⁺.

Example 158

(1S,2R,4S)-N¹-[(5-Fluoroindol-2-yl)carbonyl]-4-(N,N-dimethylcarbamoyl)-N²-[(5-methyl-4,5,6,7-tetrahydrothiazolo[5,4-c]pyridin-2-yl)carbonyl]-1,2-cyclohexanediamine hydrochloride

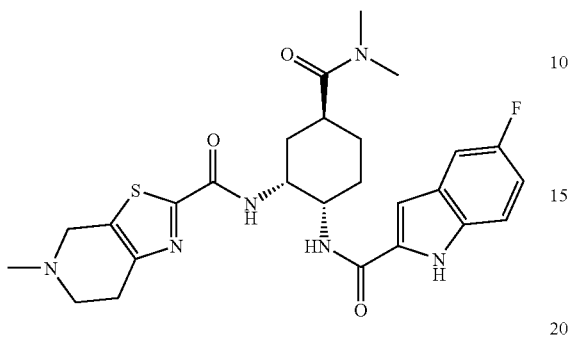

(1S,2R,4S)-4-Ethoxycarbonyl-N¹-[(5-fluoroindol-2-yl)carbonyl]-N²-[(5-methyl-4,5,6,7-tetrahydrothiazolo[5,4-c]pyridin-2-yl)carbonyl]-1,2-cyclohexanediamine was hydrolyzed and then subjected to a condensation reaction with dimethylamine hydrochloride in a similar manner to Example 157 to obtain the title compound.

¹H-NMR (DMSO-d₆) δ: 1.48–2.00(6H,m), 2.60–3.30 (5H,m), 2.80(3H,s), 2.91(3H,s), 2.98(3H,s), 3.70–4.68(4H,m), 7.00–7.06(2H,m), 7.37–7.42(2H,m), 8.36–8.41(2H,m), 11.69(1H,s). MS (FAB) m/z: 527(M+H)⁺.

Example 159

(1S,2R,4S)-N¹-[(5-Fluoroindol-2-yl)carbonyl]-4-(N-methylcarbamoyl)-N²-[(5-methyl-4,5,6,7-tetrahydrothiazolo[5,4-c]pyridin-2-yl)carbonyl]-1,2-cyclohexanediamine hydrochloride

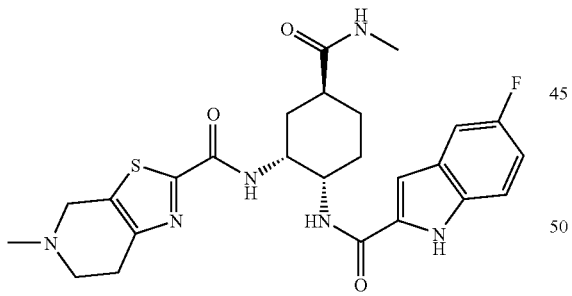

(1S,2R,4S)-4-Ethoxycarbonyl-N¹-[(5-fluoroindol-2-yl)carbonyl]-N²-[(5-methyl-4,5,6,7-tetrahydrothiazolo[5,4-c]pyridin-2-yl)carbonyl]-1,2-cyclohexahediamine was hydrolyzed and then subjected to a condensation reaction with monomethylamine hydrochloride in a similar manner to Example 157 to obtain the title compound.

¹H-NMR (DMSO-d₆) δ: 1.57–2.04(6H,m), 2.33–2.41(1H,m), 2.55(3H,s), 2.92(3H,s), 3.17–3.71(4H,m), 4.13–4.14(1H,m), 4.46(2H,br.s), 4.69–4.73(1H,m), 7.00–7.05(2H,m), 7.38–7.42(2H,m), 7.77(1H,s), 8.09–8.15(1H,m), 8.39(1H,d,J=7.6 Hz), 11.70(1H,s). MS (FAB) m/z: 513(M+H)⁺.

Example 160

(1S,2R,4S)-4-[N-(tert-Butyl)carbamoyl]-N¹-[(5-chloroindol-2-yl)carbonyl]-N²-[(5-methyl-4,5,6,7-tetrahydrothiazolo[5,4-c]pyridin-2-yl)carbonyl]-1,2-cyclohexanediamine hydrochloride

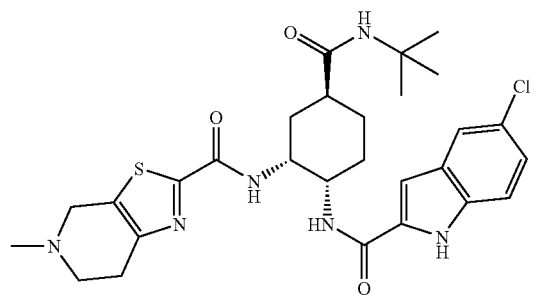

(1S,2R,4S)-N²-(tert-Butoxycarbonyl)-4-[N-(tert-butyl)carbamoyl]-N¹-[(5-chloroindol-2-yl)carbonyl]-1,2-cyclohexanediamine was treated with a 4N dioxane solution of hydrochloric acid and then condensed with lithium 5-methyl-4,5,6,7-tetrahydrothiazolo[5,4-c]pyridine-2-carboxylate in a similar manner to Example 118 to obtain the title compound.

¹H-NMR (DMSO-d₆) δ: 1.23(9H,s), 1.50–2.00(6H,m), 2.30–2.50(1H,m), 2.93(3H,s), 3.10–3.80(4H,m), 4.05–4.80 (4H,m), 7.03(1H,d,J=1.5 Hz), 7.16(1H,dd,J=8.8, 2.0 Hz), 7.35–7.45(2H,m), 7.68(1H,d,J=2.0 Hz), 7.90–8.10(1H,m), 8.42(1H,d,J=8.1 Hz), 11.30–11.45(1H,m), 11.79(1H,s). MS (FAB) m/z: 571(M+H)⁺.

Example 161

(1S,2R,4S)-N¹-[(5-Chloroindol-2-yl)carbonyl]-4-[[(3R)-3-hydroxypyrrolidin-1-yl]carbonyl]-N²-[(5-methyl-4,5,6,7-tetrahydrothiazolo[5,4-c]pyridin-2-yl)carbonyl]-1,2-cyclohexanediamine hydrochloride

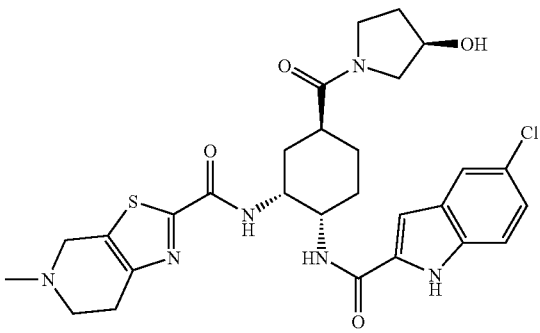

1) (3R)-1-Benzyl-3-(tert-butyldiphenyl-silyloxy)pyrrolidine (1.18 g) was dissolved in methanol (12 ml), 1N

245 hydrochloric acid (240 μl) and palladium hydride (221 mg) were added, and hydrogen was introduced to conduct catalytic reduction under normal pressure at room temperature for 4.5 hours. The catalyst was removed by filtration, and the filtrate was concentrated to solid under reduced pressure to obtain crude (3R)-3-(tert-butyldiphenyl-silyloxy)pyrrolidine hydrochloride (984 mg).

The thus-obtained product (249 mg), (1S,2R,4S)-4-carboxy-N$^1$-[(5-chloroindol-2-yl)carbonyl]-N$^2$-[(5-methyl-4,5,6,7-tetrahydrothiazolo[5,4-c]pyridin-2-yl)carbonyl]-1,2-cyclohexanediamine (295 mg), 1-(3-dimethylaminopropyl)-3-ethylcarbodiimide hydrochloride (126 mg) and 1-hydroxybenzotriazole (87 mg) were dissolved in N,N-dimethylformamide (10 ml). Diisopropylethylamine (450 μl) was added dropwise to the solution under ice cooling, and the mixture was stirred at room temperature for 12 hours. The solvent was distilled off under reduced pressure, dichloromethane and a saturated aqueous solution of sodium hydrogencarbonate were added to the residue to conduct liquid separation. The resultant organic layer was dried over anhydrous sodium sulfate, and the solvent was distilled off under reduced pressure. The residue was subjected to flash column chromatography on silica gel (methanol:dichloromethane=3:97) to obtain (1S,2R,4S)-4-[[(3R)-3-(tert-butyldiphenylsilyloxy)pyrrolidin-1-yl]carbonyl]-N$^1$-[(5-chloroindol-2-yl)carbonyl]-N$^2$-[(5-methyl-4,5,6,7-tetrahydrothiazolo[5,4-c]pyridin-2-yl)carbonyl]-1,2-cyclohexanediamine (248 mg) as a pale yellow amorphous substance.

$^1$H-NMR (CDCl$_3$) δ: 1.06(9H,s), 1.50–1.60(1H,m), 1.75–2.10(5H,m), 2.20–2.50(2H,m), 2.54(3H,d,J=2.8 Hz), 2.60–3.00(5H,m), 3.30–3.80(6H,m), 4.10–4.20(1H,m), 4.40–4.70(2H,m), 6.85(1H,s), 7.15–7.25(1H,m), 7.30–7.50 (8H,m), 7.60–7.70(5H,m), 7.90–8.00(1H,m), 9.38(1H,s). MS (FAB) m/z: 823(M+H)$^+$.

2) The above product (240 mg) was dissolved in pyridine (10 ml), and hydrogen fluoride-pyridine complex (3.0 ml) was added dropwise under ice cooling to stir the mixture at 0° C. for 4.5 hours. Ethyl acetate (80 ml) was added to the reaction mixture under ice cooling to dilute it. The diluted reaction mixture was poured into ice. After sodium hydrogencarbonate was added to this solution to alkalify it, liquid separation was conducted. The resultant organic layer was dried over anhydrous sodium sulfate. The solvent was distilled under reduced pressure, and the residue was purified by column chromatography on silica gel (methanol:dichloromethane=1:19→1:9). The resultant crude purified product was dissolved in dichloromethane and methanol, to which 1N ethanol solution (225 μl) of hydrochloric acid was added, then dry it once. Methanol and ether were added to the residue to solidify it, thereby obtaining the hydrochloride (114 mg) of the title compound as colorless powder.

1H-NMR (DMSO-d$_6$) δ: 1.50–1.60(1H,m), 1.70–2.10 (6H,m), 2.75–2.85(1H,m), 2.92(3H,s), 3.10–3.80(8H,m), 4.10–5.10(6H,m), 7.05(1H,d,J=1.7 Hz), 7.16(1H,dd,J=8.8, 2.7 Hz), 7.42(1H,d,J=8.8 Hz), 7.68(1H,s), 8.30–8.45(2H,m), 11.10–11.40(1H,m), 11.78(1H,s). MS (FAB) m/z: 585(M+H)$^+$.

246

Example 162

(1S,2R,4S)-N$^1$-[(5-Chloroindol-2-yl)carbonyl]-4-[(3-hydroxyazetidin-1-yl)carbonyl]-N$^2$-[(5-methyl-4,5,6,7-tetrahydrothiazolo[5,4-c]pyridin-2-yl)carbonyl]-1,2-cyclohexanediamine hydrochloride

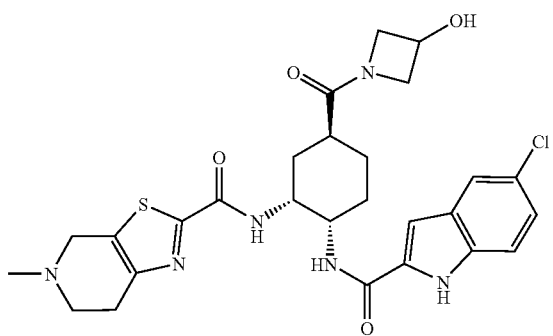

1) After 1-benzhydryl-3-(tert-butyldiphenyl-silyloxy) azetidine was catalytically reduced in the same manner as in the step 1) of Example 161 to obtain 3-(tert-butyldiphenylsilyloxy)azetidine hydrochloride, the resultant was condensed with (1S,2R,4S)-4-carboxy-N$^1$-[(5-chloroindol-2-yl)carbonyl]-N$^2$-[(5-methyl-4,5,6,7-tetrahydrothiazolo[5,4-c]pyridin-2-yl)carbonyl]-1,2-cyclohexanediamine to obtain (1S,2R,4S)-4-[[3-(tert-butyldiphenylsilyloxy)-azetidin-1-yl]carbonyl]-N$^1$-[(5-chloroindol-2-yl)carbonyl]-N$^2$-[(5-methyl-4,5,6,7-tetrahydrothiazolo-[5,4-c]pyridin-2-yl)carbonyl]-1,2-cyclohexanediamine.

$^1$H-NMR (CDCl$_3$) δ: 1.07(9H,s),1.50–2.50(5H,m), 2.55 (3H,d,J=2.0 Hz), 2.80–3.00(6H,m), 3.70–3.80(2H,m), 3.90–4.30(5H,m), 4.55–4.65(2H,m), 6.84(1H,br), 7.15–7.25 (1H,m), 7.30–7.50(8H,m), 7.60–7.70(5H,m), 7.90–8.10(1H, m), 9.30(1H,br). MS (FAB) m/z: 809(M+H)$^+$.

2) The title compound was obtained from the above-described product in the same manner as in the step 2) of Example 161.

$^1$H-NMR (DMSO-d$_6$) δ: 1.45–1.55(1H,m), 1.60–2.10 (5H,m), 2.55–2.65(1H,m), 2.91(3H,s), 3.10–3.90(6H,m), 4.00–4.30(3H,m), 4.40–5.80(5H,m), 7.06(1H,d,J=1.5 Hz), 7.16(1H,dd,J=8.8, 2.2 Hz), 7.42(1H,d,J=8.8 Hz), 7.69(1H, d,J=1.7 Hz), 8.30–8.45(2H,m), 11.40–11.60(1H,m), 11.80 (1H,s). MS (FAB) m/z: 571(M+H)$^+$.

Example 163

(1S,2R,4S)-$N^1$-[(5-Chloroindol-2-yl)carbonyl]-4-(N,N-dimethylcarbamoyl)-$N^2$-[5-(1,1-dimethyl-2-hydroxyethyl)-4,5,6,7-tetrahydrothiazolo[5,4-c]pyridin-2-yl)carbonyl]-1,2-cyclohexanediamine

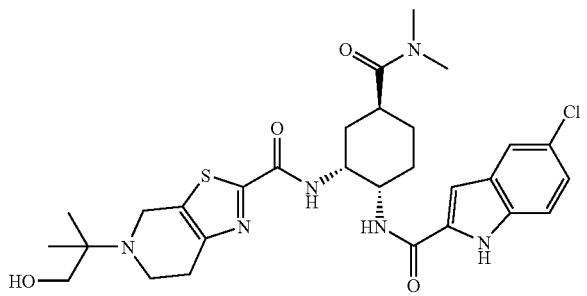

1) (1S,2R,4S)-$N^2$-(tert-Butoxycarbonyl)-$N^1$-[(5-chloroindol-2-yl)carbonyl]-4-(N,N-dimethylcarbamoyl)-1,2-cyclohexanediamine (200 mg) was dissolved in dichloromethane (6 ml), trifluoroacetic acid (2 ml) was added, and the mixture was stirred at room temperature for 2.5 hours. The solvent was distilled off under reduced pressure to obtain (1S,2R,4S)-$N^1$-[(5-chloroindol-2-yl)carbonyl]-4-(N,N-dimethylcarbamoyl)-1,2-cyclohexanediamine trifluoroacetate.

The trifluoroacetate, lithium 5-[1,1-dimethyl-2-(tert-butyldiphenylsilyloxy)ethyl]-4,5,6,7-tetrahydrothiazolo-[5,4-c]pyridine-2-carboxylate (324 mg), N-methylmorpholine (143 µl) and 1-hydroxybenzotriazole monohydrate (86 mg) were dissolved in N,N-dimethylformamide (5 ml), and the solution was reacted with 1-(3-dimethylaminopropyl)-3-ethylcarbodiimide hydrochloride (108 mg) as a condensing agent, thereby obtaining (1S,2R,4S)-$N^1$-[(5-Chloroindol-2-yl)carbonyl]-4-(N,N-dimethylcarbamoyl)-$N^{2-5}$-[1,1-dimethyl-2-(tert-butyldiphenylsilyloxy)ethyl]-4,5,6,7-tetrahydrothiazolo[5,4-c]pyridin-2-yl)carbonyl]-1,2-cyclohexanediamine (363 mg) as an amorphous solid.

$^1$H-NMR (CDCl$_3$) δ: 1.07(s,9H), 1.66(m,2H), 1.77(m,1H), 1.84(m,1H), 2.04(m,1H), 2.23(m,1H), 2.34(m,1H), 2.84–3.06(8H), 2.97(s,3H), 3.10(s,3H), 3.58(m,1H), 3.62(s,2H), 3.98(s,1H), 4.03(s,2H), 4.17(m,1H), 4.63(m,1H), 6.84 (s,1H), 7.20(dd,1H,J=8.8, 2.0 Hz), 7.33(d,1H,J=8.8 Hz), 7.39–7.66(12H), 7.89(1H,d,J=5.9 Hz), 9.34(1H,s).

2) The title compound was obtained from the above product in the same manner as in the step 3) of Example 69.

$^1$H-NMR (DMSO-d$_6$) δ: 1.54(1H,m), 1.74(3H,m), 1.97 (2H,m), 2.76(1H,m), 2.80(3H,s), 2.91(3H,s), 2.98(3H,s), 3.00–3.76(3H), 3.04(2H,m), 3.18(2H,m), 3.49(1H,m), 3.68 (1H,m), 4.12(1H,br,J=3.6 Hz), 4.43(1H,m), 4.59(1H,d,J=3.6 Hz), 4.67(1H,m), 7.05(1H,s), 7.17(1H,d,J=8.8 Hz), 7.41(1H, d,J=8.8 Hz), 11.78(1H,s), 7.68(1H,s), 8.38(1H,s), 8.40(1H, s), 11.35(1H,br.s). MS (ESI) m/z: 601(M+H)$^+$.

Example 164

(±)-cis-$N^1$ (or $N^2$)-[(5-Chloroindol-2-yl)carbonyl]-4,4-dimethoxy-$N^2$(or $N^1$)-[(5-methyl-4,5,6,7-tetrahydrothiazolo[5,4-c]pyridin-2-yl)carbonyl]-1,2-cyclohexanediamine The title compound was obtained from (±)-cis-$N^1$(or $N^2$)-[(5-chloroindol-2-yl)carbonyl]-4,4-dimethoxy-1,2-cyclohexanediamine and lithium 5-methyl-4,5,6,7-tetrahydrothiazolo[5,4-c]pyridine-2-carboxylate in a similar manner to Example 2.

$^1$H-NMR (CDCl$_3$) δ: 2.13(1H,m), 2.23(1H,m), 2.42(1H, m), 2.46(3H,s), 2.72(1H,m), 2.84(1H,m),3.21(3H,s), 3.24 (3H,s), 3.49(1H,s), 3.58(1H,d,J=15.6 Hz), 3.71(1H,d,J=15.6 Hz), 3.89(1H,m),4.28(1H,m), 6.85(1H,d,J=2.0 Hz), 7.19 (1H,dd,J=8.5, 2.0 Hz), 7.30(1H,d,J=8.5 Hz), 7.62(1H,s), 9.21(1H,s).

Example 165

(±)-cis-$N^1$(or $N^2$)-[(5-Chloroindol-2-yl)carbonyl]-$N^2$ (or $N^1$)-[(5-methyl-4,5,6,7-tetrahydrothiazolo[5,4-c]pyridin-2-yl)carbonyl]-4-oxo-1,2-cyclohexanediamine (±)-cis-$N^1$(or $N^2$)-[(5-Chloroindol-2-yl)carbonyl]-4,4-dimethoxy-$N^2$(or $N^1$)-[(5-methyl-4,5,6,7-tetrahydrothiazolo[5,4-c]pyridin-2-yl)carbonyl]-1,2-cyclohexanediamine (100 mg) was dissolved in chloroform (2 ml), and trifluoroacetic acid (0.5 ml) and water (0.5 ml) were added to stir the mixture at room temperature for 3.5 hours. A saturated aqueous solution of sodium hydrogencarbonate was added to the reaction mixture to conduct extraction with ethyl acetate. The resultant organic layer was washed with saturated saline and dried over anhydrous sodium sulfate. The solvent was distilled off under reduced pressure, and the resultant residue was purified by preparative thin-layer chromatography on silica gel (dichloromethane:methanol=19:1). The thus-obtained white solid was dissolved in methanol (4 ml), to which a 1N ethanol solution (0.38 ml) of hydrochloric acid was added. The solvent was distilled off under reduced pressure to obtain the title compound (35 mg) as white powder.

$^1$H-NMR (DMSO-d$_6$) δ: 1.86(1H,m), 2.09(1H,m), 2.30 (1H,m), 2.54(1H,m), 2.87(3H,s), 2.96(1H,t,J=13.0 Hz), 3.08 (2H,m), 3.35(3H,m), 4.03(2H,m), 4.56(2H,m), 7.03(1H,s), 7.15(1H,d,J=8.8 Hz), 7.38(1H,d,J=8.8 Hz), 7.69(1H,s), 8.43 (1H,d,J=8.8 Hz), 8.91(1H,d,J=8.8 Hz), 11.75(1H,s).

Example 166

(±)-cis-$N^1$(or $N^2$)-[(5-Chloroindol-2-yl)carbonyl]-4-hydroxyimino-$N^2$ (or $N^1$)-[(5-methyl-4,5,6,7-tetrahydrothiazolo[5,4-c]pyridin-2-yl)carbonyl]-1,2-cyclohexanediamine (±)-cis-$N^1$ (or $N^2$)-[(5-Chloroindol-2-yl)carbonyl]-$N^2$ (or $N^1$)-[(5-methyl-4,5,6,7-tetrahydrothiazolo[5,4-c]pyridin-2-yl)carbonyl]-4-oxo-1,2-cyclohexanediamine (133 mg) was dissolved in a mixed solvent of pyridine (8 ml) and methanol (8 ml), and hydroxylamine hydrochloride (30 mg) was added to stir the mixture at room temperature for 3 days. The reaction mixture was concentrated, and water was added to the residue to conduct extraction with ethyl acetate. The resultant organic layer was washed with saturated saline and dried over anhydrous magnesium sulfate. The solvent was distilled off under reduced pressure, and the resultant residue was purified by column chromatography on silica gel (dichloromethane:methanol=97:3→17:3) to obtain the title compound (131 mg) as a colorless solid.

$^1$H-NMR (CDCl$_3$) δ: 1.43–1.86(3H), 2.01(1H,m), 2.28 (1H,m), 2.45(3H,s), 2.51(1H,m), 2.69(1H,m), 2.82(3H,m), 3.86–3.43(2H,m), 4.20(2H,m), 6.85(1H,s), 7.16–7.13(1H, m), 7.22(1H,m), 7.46,7.50(total 1H,s), 7.56–7.64(2H), 9.59, 9.62(total 1H,s).

Example 167

(±)-cis-$N^1$ (or $N^2$)-[(5-Chloroindol-2-yl)carbonyl]-4,4-(1,2-ethylenedioxy)-$N^2$ (or $N^1$)-[(5-methyl-4,5,6,7-tetrahydrothiazolo[5,4-c]pyridin-2-yl)carbonyl]-1,2-cyclohexanediamine The title compound was obtained from (±)-cis-$N^1$(or $N^2$)-[(5-chloroindol-2-yl)carbonyl]-4,4-(1,2-ethylenedioxy)-1,2-cyclohexanediamine and lithium 5-methyl-4,5,6,7-tetrahydrothiazolo[5,4-c]pyridine-2-carboxylate in a similar manner to Example 2.

$^1$H-NMR (CDCl$_3$) δ: 1.69–1.87(6H,m), 2.31(1H,m), 2.47 (3H,s), 2.73(1H,m), 2.86(2H,m), 3.58(1H,d,J=15.4 Hz), 3.72(1H,d,J=15.4 Hz), 3.91(1H,m),3.99(4H,s), 4.38(1H,m), 6.86(1H,d,J=2.0 Hz), 7.19(1H,dd,J=8.8, 2.0 Hz), 7.30(1H,d,J=8.8 Hz), 7.38(1H,d,J=7.3 Hz), 7.62(1H,d,J=2.0 Hz), 9.15(1H,s).

Example 168

(±)-cis-$N^2$(or $N^1$)-[(5-Chloroindol-2-yl)carbonyl]-4,4-(1,2-ethylenedioxy)-$N^1$ (or $N^2$)-[(5-methyl-4,5,6,7-tetrahydrothiazolo[5,4-c]pyridin-2-yl)carbonyl]-1,2-cyclohexanediamine The title compound was obtained from (±)-cis-$N^2$(or $N^1$)-[(5-chloroindol-2-yl)carbonyl]-4,4-(1,2-ethylenedioxy)-1,2-cyclohexanediamine and lithium 5-methyl-4,5,6,7-tetrahydrothiazolo[5,4-c]pyridine-2-carboxylate in a similar manner to Example 2.

$^1$H-NMR (CDCl$_3$) δ: 1.71–1.93(5H,m), 2.07(1H,m), 2.45 (1H,m), 2.47(3H,s), 2.72(1H,m), 2.86(2H,m), 3.59(1H,d,J=15.4 Hz), 3.72(1H,d,J=15.4 Hz), 3.98(4H,s), 4.05(1H,m), 4.16(1H,m), 4.25(1H,m), 6.85(1H,s) 7.18(1H,dd,J=8.8, 2.0 Hz), 7.34(1H,d,J=8.8 Hz), 7.39(1H,d,J=7.1 Hz), 7.61(1H,s), 9.47(1H,s).

Example 169

(±)-cis-$N^1$(or $N^2$)-[(5-Chloroindol-2-yl)carbonyl]-4-methoxyimino-$N^2$(or $N^1$)-[(5-methyl-4,5,6,7-tetrahydrothiazolo[5,4-c]pyridin-2-yl)carbonyl]-1,2-cyclohexanediamine 1) (±)-cis-$N^1$,$N^2$-bis(tert-Butoxycarbonyl)-4-methoxyimino-1,2-cyclohexanediamine (2.21 g) was dissolved in dichloromethane (30 ml), and trifluoroacetic acid (6 ml) was added to stir the mixture at room temperature for 1.5 hours. The reaction mixture was concentrated, dried with a vacuum pump and then dissolved in N,N-dimethylformamide (20 ml), to which 5-chloroindole-2-carboxylic acid (500 mg), 1-(3-dimethylaminopropyl)-3-ethylcarbodiimide hydrochloride (593 mg), 1-hydroxybenzotriazole monohydrate (473 mg) and N-methylmorpholine (2.8 ml) were added. The mixture was stirred at room temperature for 10 hours. Additionally, 5-chloroindole-2-carboxylic acid (242 mg), 1-(3-dimethylaminopropyl)-3-ethylcarbodiimide hydrochloride (237 mg) and 1-hydroxybenzotriazole monohydrate (189 mg) were added to stir the mixture for 4 hours. A saturated aqueous solution of sodium hydrogencarbonate was added to the reaction mixture to conduct extraction with ethyl acetate and with a mixed solvent of ethyl acetate and tetrahydrofuran. The resultant organic layer was washed with saturated saline and dried over anhydrous sodium sulfate. The solvent was distilled off under reduced pressure, and the resultant residue was purified by column chromatography on silica gel (dichloromethane:methanol= 97:3→4:1) to obtain (±)-cis-$N^1$(or $N^2$)-[(5-chloroindol-2-yl)carbonyl]-4-methoxyimino-1,2-cyclohexanediamine (368 mg) and (±)-cis-$N^2$ (or $N^1$)-[(5-chloroindol-2-yl)carbonyl]-4-methoxyimino-1,2-cyclohexanediamine (300 mg).

2) The title compound (mixture of syn and anti isomers at the methoxyimino group portion) from the above-obtained (±)-cis-$N^1$ (or $N^2$)-[(5-chloroindol-2-yl)carbonyl]-4-methoxyimino-1,2-cyclohexanediamine and lithium 5-methyl-4,5,6,7-tetrahydrothiazolo[5,4-c]-pyridine-2-carboxylate in a similar manner to Example 2.

$^1$H-NMR (CDCl$_3$) δ: 1.84–2.00(3H,m), 2.26–2.56(3H, m), 2.46(3H,s), 2.81(4H,m), 3.57(1H,q,J=15.4 Hz), 3.70 (1H,q,J=15.4 Hz), 3.84,3.85(total 3H,s), 4.11(1H,m), 4.28 (1H,m), 6.84(1H,s), 7.17(1H,d,J=8.8 Hz), 7.27(1H,d,J=8.8 Hz), 7.46(2H,m), 7.56(1H,m), 9.42,9.55(total 1H,s).

Example 170

(1R*,2S*)-$N^1$ (or $N^2$)-[(5-Chloroindol-2-yl)carbonyl]-4-hydroxy-$N^2$ (or $N^1$)-[(5-methyl-4,5,6,7-tetrahydrothiazolo[5,4-c]pyridin-2-yl)carbonyl]-1,2-cyclohexanediamine (Stereoisomer A)

1) (1R*,2S*)-$N^1$,$N^2$-Bis(tert-butoxycarbonyl)-4-(tert-butyldiphenylsilyloxy)-1,2-cyclohexanediamine (Stereoisomer A) was subjected to de(tert-butoxycarbonylation) in the same manner as in the step 1) of Example 169 and reacted with 5-chloroindole-2-carboxylic acid, thereby obtaining (1R*,2S*)-4-(tert-butyldiphenylsilyloxy)-$N^1$ (or $N^2$)-[(5-chloroindol-2-yl)carbonyl]-1,2-cyclohexanediamine (Stereoisomer A) and (1R*,2S*)-4-(tert-butyldiphenylsilyloxy)-$N^2$ (or $N^1$)-[(5-chloroindol-2-yl)carbonyl]-1,2-cyclohexanediamine (Stereoisomer A).

2) (1R*,2S*)-4-(tert-Butyldiphenylsilyloxy)-$N^1$ (or $N^2$)-[(5-chloroindol-2-yl)carbonyl]-$N^2$(or $N^1$)-[(5-methyl-4,5,6,7-tetrahydrothiazolo[5,4-c]pyridin-2-yl)carbonyl]-1,2-cyclohexanediamine (Stereoisomer A) was obtained from (1R*,2S*)-4-(tert-butyldiphenylsilyloxy)-$N^1$ (or $N^2$)-[(5-chloroindol-2-yl)carbonyl]-1,2-cyclohexanediamine (Stereoisomer A) obtained by the above reaction and lithium 5-methyl-4,5,6,7-tetrahydrothiazolo[5,4-c]-pyridine-2-carboxylate in a similar manner to Example 2.

$^1$H-NMR (CDCl$_3$) δ: 1.06(9H,s), 1.58(1H,m), 1.87(1H, m), 2.21(1H,m), 2.46(3H,s), 2.51(2H,d,J=7.6 Hz), 2.72(1H, m), 3.56(1H,s), 3.57(1H,d,J=15.3 Hz), 3.72(1H,d,J=15.3 Hz), 3.76(1H,m), 3.92(1H,m), 6.78(1H,s), 7.17(1H,dd,J= 2.0, 8.8 Hz), 7.40(7H,m), 7.59(1H,s), 7.66(6H,m), 9.30(1H, s).

3) The title compound was obtained from the compound obtained by the above-described reaction in the same manner as in the step 1) of Example 69.

$^1$H-NMR (DMSO-d$_6$) δ: 1.28(2H,m), 1.45–1.64(2H,m) 1.86(1H,d,J=9.0 Hz), 2.02(1H,m), 2.33(3H,s), 2.69(2H,m), 2.77(2H,m), 3.54(1H,d,J=15.6 Hz), 3.62(1H,d,J=15.6 Hz), 3.99(2H,m), 4.78(1H,d,J=4.2 Hz), 7.00(1H,s), 7.14(1H,dd, J=2.0, 8.8 Hz), 7.38(1H,d,J=8.8 Hz), 7.66(1H,s), 8.20(1H, d,J=7.8 Hz), 8.54(1H,d,J=7.8 Hz), 11.69(1H,s).

Example 171

(1R*,2S*)-$N^2$ (or $N^1$)-[(5-Chloroindol-2-yl)carbonyl]-4-hydroxy-$N^1$ (or $N^2$)-[(5-methyl-4,5,6,7-tetrahydrothiazolo[5,4-c]pyridin-2-yl)carbonyl]-1,2-cyclohexanediamine (Stereoisomer B)

1) (1R*,2S*)-4-Acetoxy-$N^1$,$N^2$-bis(tert-butoxycarbonyl)-1,2-cyclohexanediamine (Stereoisomer B) was subjected to de(tert-butoxycarbonylation) in the same manner as in the step 1) of Example 169 and reacted with 5-chloroindole-2-carboxylic acid. The reaction mixture was subjected to chromatography on silica gel, thereby obtaining (1R*,2S*)-4-acetoxy-$N^1$ (or $N^2$)-[(5-chloroindol-2-yl)carbonyl]-1,2-cyclohexanediamine (Stereoisomer B) and (1R*,2S*)-4-acetoxy-$N^2$ (or $N^1$)-[(5-chloroindol-2-yl)carbonyl]-1,2-cyclohexanediamine (Stereoisomer B).

2) (1R*,2S*)-4-Acetoxy-$N^2$(or $N^1$)-[(5-chloroindol-2-yl)carbonyl]-$N^1$ (or $N^2$)-[(5-methyl-4,5,6,7-tetrahydrothiazolo[5,4-c]pyridin-2-yl)carbonyl]-1,2-cyclobutanediamine (Stereoisomer B) was obtained from (1R*,2S*)-4-acetoxy-$N^2$(or $N^1$)-[(5-chloroindol-2-yl)carbonyl]-1,2-cyclohexanediamine (Stereoisomer B) obtained by the above reaction and lithium 5-methyl-4,5,6,7-tetrahydrothiazolo[5,4-c]pyridine-2-carboxylate in a similar manner to Example 2.

$^1$H-NMR (CDCl$_3$) δ: 1.74(2H,m), 2.09(2H,m), 2.11(3H, s), 2.29(2H,m), 2.47(3H,s), 2.73(1H,m), 2.84(3H,m), 3.59 (1H,d,J=15.4 Hz), 3.72(1H,d,J=15.4 Hz), 3.89(1H,m), 4.41 (1H,m), 5.24(1H,s), 6.87(1H,s), 7.20(1H,dd,J=8.8, 2.0 Hz), 7.26(1H), 7.30(1H,d,J=8.8 Hz), 7.43(1H,d,J=6.8 Hz), 7.64 (1H,s), 9.13(1H,s). MS (ESI) m/z: 530(M+H)$^+$.

3) The above-obtained product (82 mg) was dissolved in tetrahydrofuran (2 ml)-methanol (2 ml), to which 1N lithium hydroxide (232 ml) was added, and the mixture was stirred at room temperature for 4 hours. Water was added to the reaction mixture to conduct extraction with ethyl acetate. The resultant organic layer was washed with saturated saline and dried over anhydrous magnesium sulfate. The solvent was distilled off under reduced pressure, and the resultant residue was purified by preparative thin-layer chromatography (dichloromethane:methanol=47:3) to obtain the title compound (53 mg) as a pale yellow solid.

$^1$H-NMR (CDCl$_3$) δ: 1.75(4H,m), 1.92(3H,m), 2.15(1H, m), 2.23(1H,m), 2.46(3H,s), 2.72(1H,m), 2.85(2H,m), 3.58 (1H,d,J=15.6 Hz), 3.70(1H,d,J=15.6 Hz), 4.33(1H,s), 3.93 (1H,m), 4.56(1H,m), 6.89(1H,d,J=2.0 Hz), 7.18(1H,dd,J= 8.8, 2.0 Hz), 7.27(1H), 7.31(1H,d,J=8.8 Hz), 7.46(1H,d,J= 7.1 Hz), 7.58(1H,s), 9.16(1H,s).

Example 172

(1R*,2S*)-$N^1$ (or $N^2$)-[(5-Chloroindol-2-yl)carbonyl]-4-hydroxy-4-methyl-$N^2$ (or $N^1$)-[(5-methyl-4,5,6,7-tetrahydrothiazolo[5,4-c]pyridin-2-yl)carbonyl]-1,2-cyclohexanediamine (Stereoisomer A1) and (1R*,2S*)-$N^2$ (or $N^1$)-[(5-chloroindol-2-yl)carbonyl]-4-hydroxy-4-methyl-$N^1$ (or $N^2$)-[(5-methyl-4,5,6,7-tetrahydrothiazolo[5,4-c]pyridin-2-yl)carbonyl]-1,2-cyclohexanediamine (Stereoisomer A2):

The title compounds were obtained by reacting a mixture of (1R*,2S*)-$N^1$-[(5-chloroindol-2-yl)carbonyl]-4-hydroxy-4-methyl-1,2-cyclohexanediamine (Stereoisomer A) and (1R*,2S*)-$N^2$-[(5-chloroindol-2-yl)carbonyl]-4-hydroxy-4-methyl-1,2-cyclohexanediamine (Stereoisomer A) with lithium 5-methyl-4,5,6,7-tetrahydrothiazolo[5,4-c]pyridine-2-carboxylate in a similar manner to Example 2.
Stereoisomer A1:

$^1$H-NMR (DMSO-d$_6$) δ: 1.24(3H,s), 1.33–1.82(4H,m), 2.34(3H,s), 2.67–3.64(8H,m), 4.06(2H,br), 4.67(1H,br), 7.02(1H,s), 7.13(1H,d,J=8.6 Hz), 7.38(1H,d,J=8.6 Hz), 7.66 (1H,d,J=2.0 Hz), 8.23(1H,br), 8.59(1H,d,J=8.1 Hz), 11.73 (1H,br) MS (FAB) m/z: 502(M+H)$^+$.
Stereoisomer A2:

$^1$H-NMR (DMSO-d$_6$) δ: 1.25(3H,s), 1.33–1.79(4H,m), 2.33(3H,s), 2.65–3.63(8H,m), 3.88–3.94(1H,m), 4.23(1H, m), 4.59(1H,br), 7.01(1H,s), 7.13(1H,d, J=7.8 Hz), 7.38(1H, d,J=8.6 Hz), 7.67(1H,s), 8.29(1H,br), 8.43(1H,d,J=9.3 Hz), 11.67(1H,br) MS (FAB) m/z: 502(M+H)$^+$.

Example 173

(1R*,2S*)-$N^1$ (or $N^2$)-[(5-Chloroindol-2-yl)carbonyl]-4-hydroxy-4-methyl-$N^2$ (or $N^1$)-[(5-methyl-4,5,6,7-tetrahydrothiazolo[5,4-c]pyridin-2-yl)carbonyl]-1,2-cyclohexanediamine (Stereoisomer B)

The title compound was obtained from (1R*,2S*)-$N^1$ (or $N^2$)-[(5-chloroindol-2-yl)carbonyl]-4-hydroxy-4-methyl-1,2-cyclohexanediamine (Stereoisomer B) and lithium 5-methyl-4,5,6,7-tetrahydrothiazolo[5,4-c]pyridine-2-carboxylate in a similar manner to Example 2.

$^1$H-NMR (DMSO-d$_6$) δ: 1.16(3H,s), 1.24(1H,br), 1.39–1.42(1H,m), 1.57–1.79(3H,m), 1.92–1.94(1H,m), 2.33 (3H,s), 2.66–2.78(4H,m), 3.53(1H,d,J=15.7 Hz), 3.60(1H,d, J=15.7 Hz), 4.01(1H,br), 4.32(1H,br), 7.04(1H,s), 7.13(1H, dd,J=8.8, 2.0 Hz), 7.37(1H,d,J=8.8 Hz), 7.65(1H,d,J=2.0 Hz), 8.24(1H,d,J=8.8 Hz), 8.28(1H,d,J=9.0 Hz), 11.65(1H, br) MS (FAB) m/z: 502(M+H)$^+$.

Example 174

(1R*,2S*)-$N^1$-[(5-Chloroindol-2-yl)carbonyl]-4-hydroxymethyl-$N^2$-[(5-methyl-4,5,6,7-tetrahydrothiazolo[5,4-c]pyridin-2-yl)carbonyl]-1,2-cyclohexanediamine (Stereoisomer A)

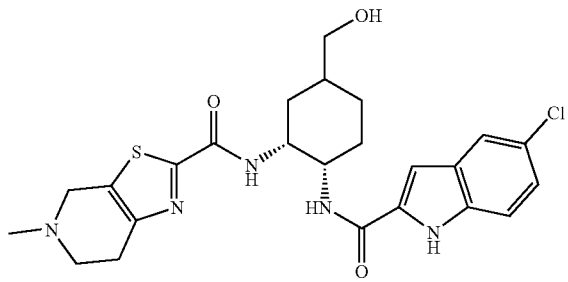

1) (1R*,2S*)-4-(tert-Butyldiphenylsilyloxy-methyl)-$N^1$-[(5-chloroindol-2-yl)carbonyl]-1,2-cyclohexanediamine (Stereoisomer A) was obtained from (1R*,2S*)-4-(tert-butyldiphenylsilyloxymethyl)-1,2-cyclobutanediamine (Stereoisomer A) and 5-chloroindole-2-carboxylic acid in a similar manner to Referential Example 30.

2) (1R*,2S*)-4-(tert-butyldiphenylsilyloxymethyl)-$N^1$-[(5-chloroindol-2-yl)carbonyl]-$N^2$-[(5-methyl-4,5,6,7-tetrahydrothiazolo[5,4-c]pyridin-2-yl)carbonyl]-1,2-cyclohexanediamine hydrochloride (Stereoisomer A) was obtained from the compound obtained above and lithium 5-methyl-4,5,6,7-tetrahydrothiazolo[5,4-c]pyridine-2-carboxylate in a similar manner to Example 2.

$^1$H-NMR (DMSO-d$_6$) δ: 1.04(9H,s), 1.23–2.07(7H,m), 2.35(3H,s), 2.73–2.89(4H,m), 3.58–3.59(2H,m), 3.63(2H, br.s), 4.20(1H,m), 4.31(1H,br.s), 7.16(1H,s), 7.19(1H,dd,J= 8.8, 2.2 Hz), 7.42–7.46(6H,m), 7.63–7.65(4H,m), 7.69(1H, br.s), 7.88(1H,d,J=6.6 Hz), 7.95(1H,s), 8.71(1H,d,J=8.5 Hz), 11.82(1H,s). MS (FAB) m/z: 741(M+H)$^+$.

The title compound was obtained by treating the above product in a similar manner to the step 3) of Example 69.

¹H-NMR (DMSO-d₆) δ: 1.21–1.23(1H,m), 1.49–1.72 (5H,m), 2.00–2.04(1H,m), 2.34(3H,s), 2.67–2.69(2H,m), 2.74–2.75(2H,m), 3.62(2H,s), 4.10–4.13(2H,m), 4.31(1H, br.s), 4.53(1H,m),7.17–7.20(2H,m), 7.43(1H,d,J=8.6 Hz), 7.73(1H,d,J=2.0 Hz), 7.91(1H,d,J=6.9 Hz), 8.64(1H,d,J=8.6 Hz), 11.83(1H,s) MS (FAB) m/z: 502(M+H)⁺.

Example 175

(1R*,2R*,4S*)-N¹-[(5-Chloroindol-2-yl)carbonyl]-4-hydroxymethyl-N²-[(5-methyl-4,5,6,7-tetrahydrothiazolo[5,4-c]pyridin-2-yl)carbonyl]-1,2-cyclohexanediamine

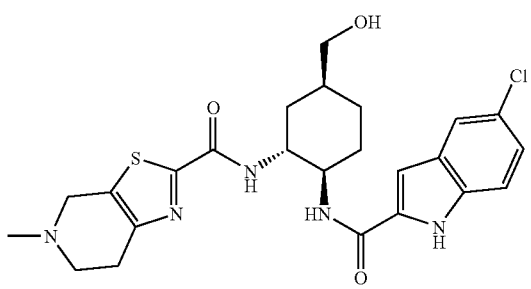

The title compound was obtained by treating (1R*,2R*,4S*)-N²-(tert-butoxycarbonyl)-N¹-[(5-chloroindol-2-yl)carbonyl]-4-hydroxymethyl-1,2-cyclohexanediamine with a saturated ethanol solution of hydrochloric acid and then condensing it with lithium 5-methyl-4,5,6,7-tetrahydrothiazolo[5,4-c]pyridine-2-carboxylate in a similar manner to Example 118.

¹H-NMR (DMSO-d₆) δ: 1.42–1.90(5H,m), 2.07–2.26 (3H,m), 2.46(3H,s), 2.67–2.95(4H,m), 3.55–3.80(4H,m), 3.80–3.95(1H,m), 4.13–4.25(1H,m), 6.84(1H,br.s), 7.17 (1H,dd,J=8.8, 2.0 Hz), 7.23–7.35(2H,m), 7.43(1H,d,J=7.2 Hz), 7.58(1H,br.s), 9.29(1H,s). MS (ESI) m/z: 502(M+H)⁺.

Example 176

(1R,2R,4S)-N¹-[(5-Chloroindol-2-yl)carbonyl]-4-hydroxymethyl-N²-[(5-methyl-4,5,6,7-tetrahydrothiazolo[5,4-c]pyridin-2-yl)carbonyl]-1,2-cyclohexanediamine

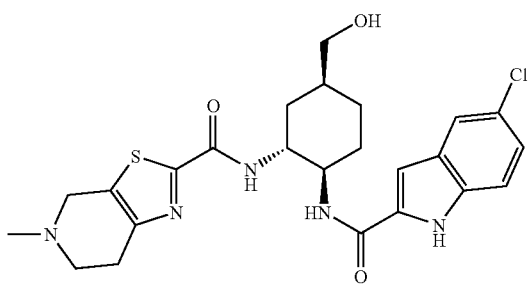

The title compound was obtained by treating (1R,2R,4S)-N²-(tert-butoxycarbonyl)-N¹-[(5-chloroindol-2-yl)carbonyl]-4-hydroxymethyl-1,2-cyclohexanediamine with a saturated ethanol solution of hydrochloric acid and then condensing it with lithium 5-methyl-4,5,6,7-tetrahydrothiazolo[5,4-c]-pyridine-2-carboxylate in a similar manner to Example 118.

¹H-NMR (DMSO-d₆) δ: 1.42–1.90(5H,m), 2.07–2.26 (3H,m), 2.46(3H,s), 2.67–2.95(4H,m), 3.55–3.80(4H,m), 3.80–3.95(1H,m), 4.13–4.25(1H,m), 6.84(1H,br.s), 7.17 (1H,dd,J=8.8, 2.0 Hz), 7.23–7.35(2H,m), 7.43(1H,d,J=7.2 Hz), 7.58(1H,br.s), 9.29(1H,s). MS (ESI) m/z: 502(M+H)⁺.

Example 177

(1R*,2S*,4R*)-N¹-[(5-Chloroindol-2-yl)carbonyl]-4-(1-hydroxy-1-methylethyl)-N²-[(5-methyl-4,5,6,7-tetrahydrothiazolo[5,4-c]pyridin-2-yl)carbonyl]-1,2-cyclohexanediamine hydrochloride

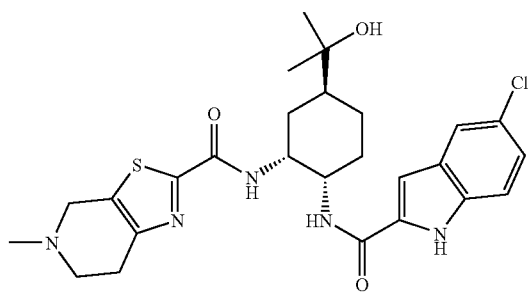

The title compound was obtained from (1R*,2S*,4R*)-N¹-[(5-chloroindol-2-yl)carbonyl]-4-(1-hydroxy-1-methylethyl)-1,2-cyclohexanediamine hydrochloride and lithium 5-methyl-4,5,6,7-tetrahydrothiazolo[5,4-c]pyridine-2-carboxylate in a similar manner to Example 2.

¹H-NMR (CD₃OD) δ: 1.17(3H,s), 1.20(3H,s), 1.24–2.22 (7H,m), 3.02(3H,s), 3.18–3.41(4H,m), 3.52–3.68(2H,m), 4.08–4.21(1H,m), 4.50–4.65(1H,m), 6.92(1H,br.s), 7.13–7.19(1H,m), 7.39(1H,br,J=8.0 Hz), 7.84–7.93(1H,m), 8.22–8.32(1H,m). MS (FAB) m/z: 530(M+H)⁺.

Example 178

(1R*,2S*,4R*)-N¹-[(5-Chloroindol-2-yl)carbonyl]-4-methoxymethyl-N²-[(5-methyl-4,5,6,7-tetrahydrothiazolo[5,4-c]pyridin-2-yl)carbonyl]-1,2-cyclohexanediamine

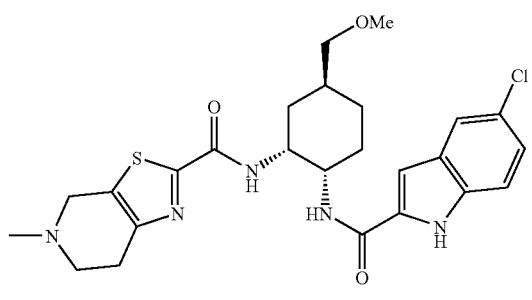

The title compound was obtained by treating (1R*,2S*,4R*)-N²-(tert-butoxycarbonyl)-N¹-[(5-chloroindol-2-yl)carbonyl]-4-methoxymethyl-1,2-cyclohexanediamine with a saturated ethanol solution of hydrochloric acid and then condensing it with lithium 5-methyl-4,5,6,7-tetrahydrothiazolo[5,4-c]-pyridine-2-carboxylate in a similar manner to Example 118.

¹H-NMR (CDCl₃) δ: 1.20–1.38(1H,m), 1.50–1.67(2H, m), 1.88–2.03(2H,m), 2.03–2.14(1H,m), 2.21–2.32(1H,m), 2.53(3H,s), 2.75–2.95(2H,m), 3.20–3.35(2H,m), 3.37(3H,s), 3.71 and 3.78(each 1H,each d,J=11.2 Hz), 4.04–4.13(1H,m), 4.53–4.62(1H,m), 6.85(1H,d,J=2.0 Hz), 7.19(1H,dd,J=8.8, 2.0 Hz), 7.33(1H,d,J=8.8 Hz), 7.54(1H,d,J=7.2 Hz), 7.63 (1H,d,J=2.0 Hz), 8.07(1H,d,J=5.6 Hz), 9.49(1H,br.s).

Example 179

Mixture of (1R*,2S*,4R*,5S*)-N¹-[(5-chloroindol-2-yl)carbonyl]-4,5-dihydroxy-N²-[(5-methyl-4,5,6,7-tetrahydrothiazolo[5,4-c]pyridin-2-yl)carbonyl]-1,2-cyclohexanediamine hydrochloride and (1R*,2S*,4S*,5R*)-N¹-[(5-chloroindol-2-yl)carbonyl]-4,5-dihydroxy-N²-[(5-methyl-4,5,6,7-tetrahydrothiazolo[5,4-c]pyridin-2-yl)carbonyl]-1,2-cyclohexanediamine hydrochloride

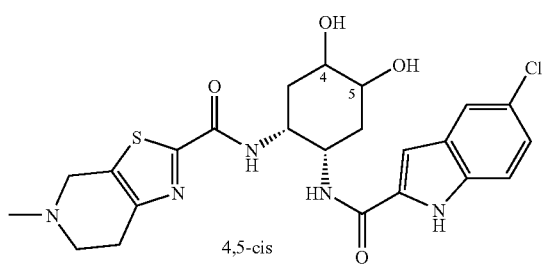

4,5-cis (±)-cis-N¹-[(5-Chloroindol-2-yl)carbonyl]-N²-[(5-methyl-4,5,6,7-tetrahydrothiazolo[5,4-c]pyridin-2-yl)carbonyl]-4-cyclohexene-1,2-diamine (2.85 g) was dissolved in a mixed solvent of tetrahydrofuran (10 ml), acetone (10 ml) and water (10 ml), and osmium tetroxide (31 mg) and N-methylmorpholine-N-oxide (1.23 g) were added to stir the mixture at room temperature for 14 hours. Further, osmium tetroxide (16 mg) and N-methylmorpholine-N-oxide (613 mg) were added to stir the mixture at 40° C. for 5 days. The reaction mixture was poured into a 10% aqueous solution of sodium thiosulfate and extracted with ethyl acetate. The resultant organic layer was washed with saturated saline and dried over anhydrous magnesium sulfate. The solvent was distilled off under reduced pressure, and the residue was purified by column chromatography on silica gel (dichloromethane:methanol=49:1→17:3) to obtain a crude diol derivative (811 mg). A part (200 mg) thereof was purified by preparative thin-layer chromatography (dichloromethane:methanol=93:7) and then dissolved in methanol. A 1N ethanol solution of hydrochloric acid was added to the solution to obtain the title compound (811 mg).

¹H-NMR (DMSO-d₆) δ: 2.02–1.79(3H,m), 2.33(3H,s), 2.76–2.64(4H,m), 3.57(4H,m), 3.82(1H,br.s), 3.96,4.13(1H,m), 4.32(1H,m), 4.49,4.52(1H,each d,J=16.4 Hz), 4.66,4.67(1H,each d,J=17.4 Hz), 7.02,7.06(1H,each s), 7.14(1H,m), 7.37,7.39(1H,each s), 7.66,7.67(1H,each d,J=2.4 Hz), 8.18, 8.28(1H,each d,J=8.5 Hz), 8.33,8.41(1H,each d,J=8.8 Hz), 11.67,11.71(1H,each s).

Example 180

Mixture of (1R*,2S*,4R*,5S*)-N¹-[(5-chloroindol-2-yl)carbonyl]-4,5-diacetoxy-N²-[(5-methyl-4,5,6,7-tetrahydrothiazolo[5,4-c]pyridin-2-yl)carbonyl]-1,2-cyclohexanediamine and (1R*,2S*,4S*,5R*)-N¹-[(5-chloroindol-2-yl)carbonyl]-4,5-diacetoxy-N²-[(5-methyl-4,5,6,7-tetrahydrothiazolo[5,4-c]pyridin-2-yl)carbonyl]-1,2-cyclohexanediamine

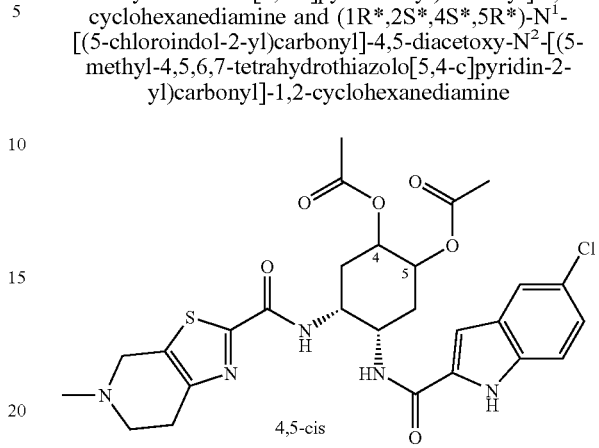

4,5-cis

A mixture (200 mg) of (1R*,2S*,4R*,5S*)-N¹-[(5-chloroindol-2-yl)carbonyl]-4,5-dihydroxy-N²-[(5-methyl-4,5,6,7-tetrahydrothiazolo[5,4-c]pyridin-2-yl)carbonyl]-1,2-cyclohexanediamine and (1R*,2S*,4S*,5R*)-N¹-[(5-chloroindol-2-yl)carbonyl]-4,5-dihydroxy-N²-[(5-methyl-4,5,6,7-tetrahydrothiazolo[5,4-c]pyridin-2-yl)carbonyl]-1,2-cyclohexanediamine was dissolved in pyridine (8 ml), and acetic anhydride (745 µl) was added to stir the mixture at room temperature for 2 days. The reaction mixture was concentrated and purified by preparative thin-layer chromatography (dichloromethane:methanol=97:3) to obtain the title compound (132 mg) as a pale yellow solid. This product was dissolved in methanol (2 ml). A 1N ethanol solution (1 ml) of hydrochloric acid was added to the solution, and the mixture was concentrated under reduced pressure to convert the compound into the hydrochloride.

¹H-NMR (DMSO-d₆) δ: 1.96(4H,m), 2.08(3H,s), 2.09(3H,s), 2.14.(3H,s), 2.33(3H,s), 2.70(4H,m), 4.31(1H,m), 4.84(1H,m), 5.26(1H,s), 7.05(1H,s), 7.15(1H,d,J=8.5 Hz), 7.38(1H,d,J=8.5 Hz), 7.68(1H,s), 8.49(1H,d,J=8.8 Hz), 8.54(1H,d,J=8.8 Hz),11.71(1H,s).

Example 181

(1R*,2S*,4R*,5S*)-4,5-Carbonyldioxy-N¹-[(5-chloroindol-2-yl)carbonyl]-N²-[(5-methyl-4,5,6,7-tetrahydrothiazolo[5,4-c]pyridin-2-yl)carbonyl]-1,2-cyclohexanediamine hydrochloride and (1R*,2S*,4S*,5R*)-4,5-Carbonyldioxy-N¹-[(5-chloroindol-2-yl)carbonyl]-N²-[(5-methyl-4,5,6,7-tetrahydrothiazolo[5,4-c]pyridin-2-yl)carbonyl]-1,2-cyclohexanediamine hydrochloride:

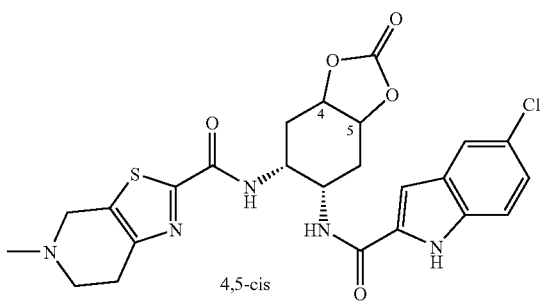

4,5-cis

A mixture (253 mg) of (1R*,2S*,4R*,5S*)-N¹-[(5-chloroindol-2-yl)carbonyl]-4,5-dihydroxy-N²-[(5-methyl-4,5,6,7-tetrahydrothiazolo[5,4-c]pyridin-2-yl)carbonyl]-1,2-cyclohexanediamine and (1R*,2S*,4S*,5R*)-N¹-[(5-chloroindol-2-yl)carbonyl]-4,5-dihydroxy-N²-[(5-methyl-4,5,6,7-tetrahydro-thiazolo[5,4-c]pyridin-2-yl)carbonyl]-1,2-cyclohexanediamine and N,N'-carbonyldiimidazole (122 mg) were dissolved in tetrahydrofuran (6 ml), and the mixture was stirred overnight at room temperature. Thereafter, N,N'-carbonyldiimidazole (122 mg) was additionally added to stir teh mixture at 60° C. for 10 hours. Further, N,N'-carbonyldiimidazole (81 mg) was added to stir the mixture overnight. The reaction mixture was concentrated, and water was added to the residue to conduct extraction with ethyl acetate. The resultant organic layer was washed with saturated saline and dried over anhydrous sodium sulfate. The solvent was distilled off under reduced pressure, and the residue was purified by preparative thin-layer chromatography (dichloromethane:methanol=19:1) to separate stereoisomers. The products were respectively dissolved in methnol and tetrahydrofuran, and a 1N ethanol solution of hydrochloric acid was added to the solutions to obtain one title compound (Stereoisomer A) (91 mg), and the other title compound (Stereoisomer B) (93 mg) as colorless powder.

Stereoisomer A:

¹H-NMR (DMSO-$d_6$) δ: 2.08(2H,m), 2.34(2H,m), 2.88 (3H,s), 3.11(2H,m), 3.68(1H,m), 3.73(1H,d,J=16.7 Hz), 4.02(1H,m), 4.37(1H,m), 5.02(1H,s), 5.08(1H,m), 7.01(1H, s), 7.15(1H,dd,J=8.8, 2.0 Hz), 7.38(1H,d,J=8.8 Hz), 8.83 (1H,d,J=8.8 Hz), 11.75(1H,s).

Stereoisomer B:

¹H-NMR (DMSO-$d_6$) δ: 1.85(1H,m), 2.22(1H,m), 2.33 (2H,m), 2.87(3H,s), 3.10(2H,m), 3.53(2H,m), 3.72(1H,d,J=17.9 Hz), 4.23(1H,m), 4.49(1H,m), 5.03(1H,br.s), 5.08(1H, m), 7.00(1H,m), 7.15(1H,dd,J=8.8, 2.0 Hz), 7.37(1H,d,J=8.8 Hz), 7.69(1H,s), 8.42(1H,d,J=7.8 Hz), 8.85(1H,d,J=8.3 Hz), 11.74(1H,s).

Example 182

(1R*,2S*,4R*,5S*)-N¹-[(5-Chloroindol-2-yl)carbonyl]-4,5-isopropylidenedioxy-N²-[(5-methyl-4,5,6,7-tetrahydrothiazolo[5,4-c]pyridin-2-yl)carbonyl]-1,2-cyclohexanediamine and (1R*,2S*,4S*,5R*)-N¹-[(5-chloroindol-2-yl)carbonyl]-4,5-isopropylidenedioxy-N²-[(5-methyl-4,5,6,7-tetrahydrothiazolo[5,4-c]-pyridin-2-yl)carbonyl]-1,2-cyclohexanediamine

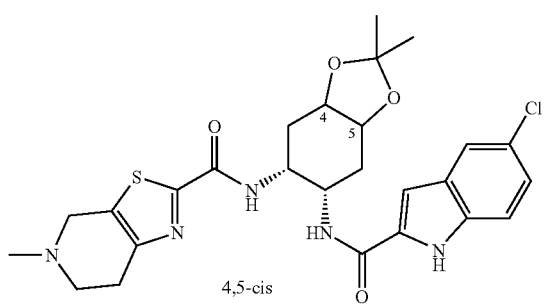

The title compounds were obtained by reacting a mixture of (1R*,2S*,4R*,5S*)-N¹-[(5-chloroindol-2-yl)carbonyl]-4,5-isopropylidenedioxy-1,2-cyclohexanediamine and (1R*,2S*,4S*,5R*)-N¹-[(5-chloroindol-2-yl)carbonyl]-4,5-isopropylidenedioxy-1,2-cyclohexanediamine with lithium 5-methyl-4,5,6,7-tetrahydrothiazolo[5,4-c]pyridine-2-carboxylate in a similar manner to Example 2.

One compound:

¹H-MNR (CDCl₃) δ: 1.39(3H,s), 1.58(3H,s), 1.78(1H,m), 1.90(1H,m), 2.27(1H,m), 2.46(3H,s), 2.84–2.69(5H,m), 3.58(1H,d,J=16.6 Hz), 3.70(1H,d,J=15.6 Hz), 4.10(1H,m), 4.29(1H,m), 4.35(2H,br.s), 6.81(1H,s), 7.17(1H,dd,J=8.5, 2.0 Hz), 7.26(1H,d,J=7.6 Hz), 7.36(1H,d,J=8.5 Hz), 7.40 (1H,s), 7.57(1H,s), 9.70(1H,s).

The other compound:

¹H-MNR (CDCl₃) δ: 1.37(3H,s), 1.56(3H,s), 1.83(2H,m), 1.93(1H,dt,J=11.3, 3.9 Hz), 2.45(2H,m), 2.46(3H,s), 2.72 (1H,m), 2.82(3H,m), 3.58(1H,d,J=15.4 Hz), 3.70(1H,d,J= 15.4 Hz), 3.98(1H,m), 4.32(1H,m), 4.37(1H,br.s), 4.45(1H, s), 6.84(1H,s), 7.18(1H,d,J=8.8 Hz), 7.30(1H,d,J=7.6 Hz), 7.43(1H,d,J=7.6 Hz), 7.59(1H,s), 9.33(1H,s).

Example 183

(1R*,2S*,4R*,5R*)-N¹-[(5-Chloroindol-2-yl)carbonyl]-4,5-dimethoxy-N²-[(5-methyl-4,5,6,7-tetrahydrothiazolo[5,4-c]pyridin-2-yl)carbonyl]-1,2-cyclohexanediamine hydrochloride and (1R*,2S*,4S*,5R*)-N¹-[(5-chloroindol-2-yl)carbonyl]-4,5-dimethoxy-N²-[(5-methyl-4,5,6,7-tetrahydrothiazolo[5,4-c]pyridin-2-yl)carbonyl]-1,2-cyclohexanediamine hydrochloride

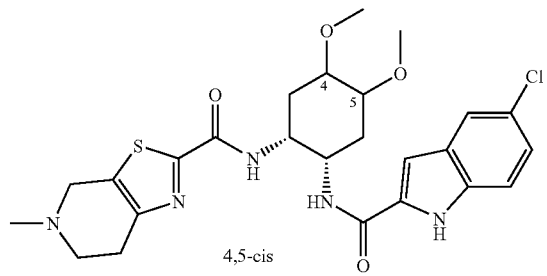

A mixture (645 mg) of (1R*,2S*,4R*,5S*)-4,5-dimethoxy-1,2-cyclohexanediamine hydrochloride and (1R*,2S*,4S*,5R*)-4,5-dimethoxy-1,2-cyclohexanediamine hydrochloride was suspended in N,N-dimethylformamide (50 ml), and triethylamine (1.10 ml) and p-nitrophenyl 5-chloroindole-2-carboxylate (920 mg) were added to stir the mixture overnight at room temperature. The reaction mixture was concentrated under reduced pressure, and a saturated aqueous solution of sodium hydrogencarbonate was added to the residue to conduct extraction with dichloromethane. The resultant organic layer was dried over anhydrous sodium sulfate. The solvent was distilled off under reduced pressure, and the residue was purified by column chromatography on silica gel (methanol:dichloromethane=1:9) to obtain a mixture (330 mg) of (1R*,2S*,4R*,5S*)-N¹-[(5-chloroindol-2-yl)carbonyl]-4,5-dimethoxy-1,2-cyclohexanediamine and (1R*,2S*,4S*,5R*)-N¹-[(5-chloroindol-2-yl)carbonyl]-4,5-dimethoxy-1,2-cyclohexanediamine as pale yellow powder.

Products obtained from the above products and lithium 5-methyl-4,5,6,7-tetrahydrothiazolo[5,4-c]-pyridine-2-carboxylate in a similar manner to Example 2 were separated by column chromatography on silica gel to obtain the title compounds.

One Compound:

¹H-NMR (DMSO-$d_6$) δ: 1.52–1.63(1H,m), 1.85–2.20 (3H,m), 2.88(3H,br.s), 3.10(2H,br.s), 3.25–3.50(8H,m), 3.60–3.72(1H,br), 3.75(1H,br.s), 3.95–4.10(1H,m), 4.20–4.72(3H,m), 7.02(1H,s), 7.14(1H,d,J=8.8 Hz), 7.37

(1H,d,J=8.8 Hz), 7.68(1H,s), 8.30(1H,d,J=8.8 Hz), 8.73(1H, d,J=8.8 Hz), 11.00–11.30(1H,br), 11.74(1H,br.s). MS (FAB) m/z: 532(M+H)⁺.

The Other Compound:
¹H-NMR (DMSO-d₆) δ: 1.63–1.77(1H,m), 1.82–2.02 (2H,m), 2.05–2.18(1H,m), 2.86(3H,br.s), 2.95–3.80(12H, m), 4.10–4.70(4H,m), 7.07(1H,s), 7.14(1H,dd,J=8.8, 2.0 Hz), 7.37(1H,d,J=8.8 Hz), 7.67(1H,d,J=2.0 Hz), 8.45(1H,d, J=8.1 Hz), 8.57(1H,d,J=8.6 Hz), 11.30–11.65(1H,br), 11.70 (1H,br.s). MS (FAB) m/z: 532(M+H)⁺.

Example 184

(1R*,2S*,4R*)-N¹-[(5-Chloroindol-2-yl)carbonyl]-4-methanesulfonylaminomethyl-N²-[(5-methyl-4,5,6,7-tetrahydrothiazolo[5,4-c]pyridin-2-yl)carbonyl]-1,2-cyclohexanediamine

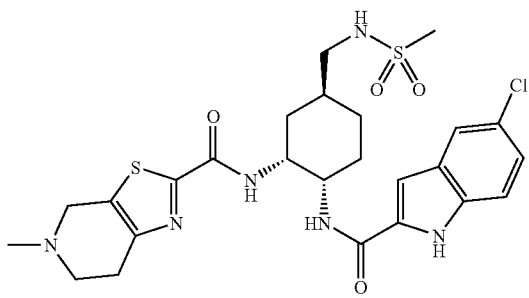

1) (1R*,2S*,4R*)-4-Azidomethyl-N²-(tert-butoxycarbonyl)-N¹-[(5-chloroindol-2-yl)carbonyl]-1,2-cyclohexanediamine (437 mg) was dissolved in ethanol (5 ml), and a 4N dioxane solution (5 ml) of hydrochloric acid was added at room temperature to stir the mixture for 13 hours. The solvent was distilled off, and the residue was dissolved in N,N-dimethylformamide (10 ml) to which triethylamine (0.7 ml), lithium 5-methyl-4,5,6,7-tetrahydrothiazolo[5,4-c]-pyridine-2-carboxylate (300 mg), 1-hydroxybenzotriazole monohydrate (162 mg) and 1-(3-dimethylaminopropyl)-3-ethylcarbodiimide hydrochloride (230 mg) were added. The mixture was stirred for 13 hours, and water was added to the reaction mixture to conduct extraction with chloroform. The resultant organic layer was washed with a saturated aqueous solution of sodium hydrogencarbonate and saturated saline and dried over anhydrous magnesium sulfate. The solvent was distilled off under reduced pressure, and the resultant residue was purified by column chromatography on silica gel (dichloromethane:methanol=97:3) to obtain (1R*,2S*,4R*)-4-azidomethyl-N¹-[(5-chloroindol-2-yl)carbonyl]-N²-[(5-methyl-4,5,6,7-tetrahydrothiazolo[5,4-c]pyridin-2-yl)carbonyl]-1,2-cyclohexanediamine (330 mg) as a pale yellow solid.

¹H-NMR (DMSO-d₆) δ: 1.15–2.08(7H,m), 2.33(3H,s), 2.34–2.95(6H,m), 3.64(2H,s), 4.05–4.17(1H,m), 4.36–4.47 (1H,m), 7.02(1H,s), 7.15(1H,dd,J=8.8, 2.0 Hz), 7.40(1H,d, J=8.8 Hz), 7.67(1H,d,J=2.0 Hz), 8.02(1H,d,J=7.6 Hz), 8.44 (1H,d,J=7.6 Hz), 11.8(1H,s).

2) The compound (300 mg) obtained by the above reaction was dissolved in ethanol (8 ml), and a catalytic amount of 10% palladium on carbon was added to stir the mixture at room temperature for 168 hours in a hydrogen atmosphere. Insoluble matter was filtered, and the solvent was distilled off to obtain crude (1R*,2S*,4R*)-4-aminomethyl-N¹-[(5-chloroindol-2-yl)carbonyl]-N²-[(5-methyl-4,5,6,7-tetrahydrothiazolo[5,4-c]pyridin-2-yl)carbonyl]-1,2-cyclohexanediamine (150 mg).

3) The product described above was dissolved in chloroform (6 ml), and triethylamine (0.2 ml) and methanesulfonyl chloride (0.035 ml) were added to stir the mixture for 13 hours. The reaction mixture was concentrated under reduced pressure, and water was added to the residue to conduct extraction with chloroform. The resultant organic layer was washed with a saturated aqueous solution of sodium hydrogencarbonate and saturated saline and dried over anhydrous magnesium sulfate. The solvent was distilled off under reduced pressure, and the resultant residue was purified by column chromatography on silica gel (dichloromethane:methanol=24:1) to obtain the title compound (56 mg) as a pale yellow solid.

¹H-NMR (CDCl₃) δ: 1.18–1.34(2H,m), 1.50–1.75(4H, m), 1.90–2.30(4H,m), 2.53(3H,s), 2.78–2.90(2H,m), 2.90–3.05(6H,m), 3.20–3.30(1H,m), 3.68–3.81(2H,m), 3.98–4.08(1H,m), 4.54–4.62(1H,m), 6.10–6.19(1H,m), 6.86 (1H,s), 7.19(1H,dd,J=8.8, 2.0 Hz), 7.35(1H,d,J=8.8 Hz), 7.52(1H,d,J=7.6 Hz), 7.62(1H,d,J=2.0 Hz), 8.21(1H,d,J=5.6 Hz), 9.89(1H,s). MS (ESI) m/z: 579(M+H)⁺.

Example 185

(1R*,2S*,4R*)-N¹-[(5-Chloroindol-2-yl)carbonyl]-4-(N,N-dimethylaminomethyl)-N²-[(5-methyl-4,5,6,7-tetrahydrothiazolo[5,4-c]pyridin-2-yl)carbonyl]-1,2-cyclohexanediamine trifluoroacetate

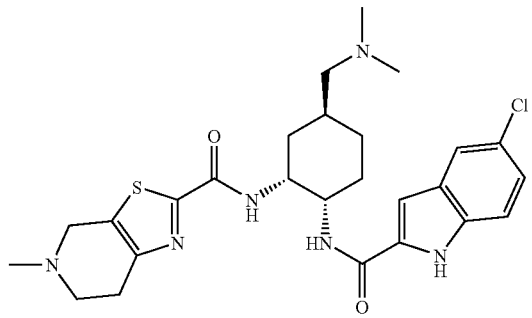

The title compound was obtained from (1R*,2S*,4R*)-4-aminomethyl-N¹-[(5-chloroindol-2-yl)carbonyl]-N²-[(5-methyl-4,5,6,7-tetrahydrothiazolo[5,4-c]pyridin-2-yl) carbonyl]-1,2-cyclohexanediamine and formalin in a similar manner to Example 45.

¹H-NMR (DMSO-d₆) δ: 1.15–2.22(7H,m), 2.40–2.65 (2H,m), 2.68–2.85(6H,m), 2.92–3.08(5H,m), 3.10–3.18(2H, m), 4.08–4.20(1H,m), 4.35–4.51(2H,m), 7.04(1H,s), 7.14–7.20(1H,m), 7.41(1H,d,J=8.8 Hz), 7.67(1H,s), 8.25–8.42(2H,m), 9.11(1H,br.s), 9.89(1H,s). MS (ESI) m/z: 529(M+H)⁺.

Example 186

(1R*,2S*)-N² (or N¹)-[(5-Chloroindol-2-yl)carbonyl]-4-[1-(ethoxycarbonyl)cyclopropan-1-yl]amino-N¹ (or N²)-[(5-methyl-4,5,6,7-tetrahydrothiazolo[5,4-c]pyridin-2-yl)carbonyl]-1,2-cyclohexanediamine (Stereoisomer A)

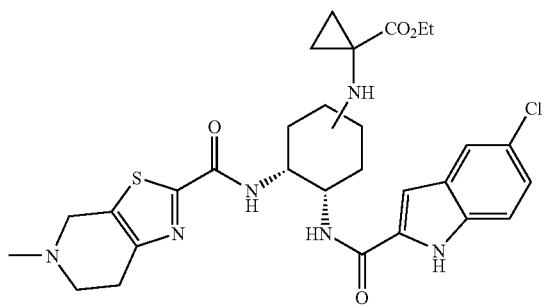

The title compound was obtained from (1R*,2S*)-N² (or N¹)-[(5-chloroindol-2-yl)carbonyl]-4-[1-(ethoxycarbonyl)cyclopropan-1-yl]amino-1,2-cyclohexanediamine (Stereoisomer A) and lithium 5-methyl-4,5,6,7-tetrahydrothiazolo[5,4-c]pyridine-2-carboxylate in a similar manner to Example 2.

¹H-NMR (DMSO-d₆) δ: 0.93(1H,m), 1.05–1.30(6H,m), 1.45–2.10(6H,m), 2.33(3H,s), 2.65–2.85(5H,m), 3.30–3.40(1H,m), 3.54(1H,d,J=15.9 Hz), 3.62(1H,d,J=15.9 Hz), 4.00–4.15(3H,m), 4.25(1H,m), 7.06(1H,s), 7.14(1H,dd,J=8.8, 2.0 Hz), 7.38(1H,d,J=8.8 Hz), 7.65(1H,d,J=2.0 Hz), 8.28(1H,d,J=9.0 Hz), 8.32(1H,d,J=8.5 Hz), 11.67(1H,s). MS (FAB) m/z: 599(M+H)⁺.

Example 187

(1R*,2S*)-4-(tert-Butoxycarbonylamino)-N¹-[(5-chloroindol-2-yl)carbonyl]-N²-[(5-methyl-4,5,6,7-tetrahydrothiazolo[5,4-c]pyridin-2-yl)carbonyl]-1,2-cyclohexanediamine (Isomer B) and (1R*,2S*)-4-(tert-butoxycarbonylamino)-N²-[(5-chloroindol-2-yl)carbonyl]-N¹-[(5-methyl-4,5,6,7-tetrahydrothiazolo-[5,4-c]pyridin-2-yl)carbonyl]-1,2-cyclohexanediamine (Isomer B)

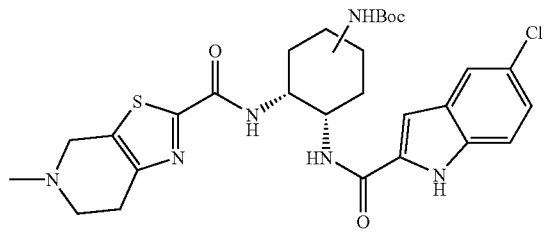

(1R*,2S*)-4-(tert-Butoxycarbonylamino-1,2-diazidocyclohexane (Stereoisomer B) (1.79 g) was dissolved in tetrahydrofuran (36 ml), and 10% palladium on carbon (0.40 g) was added to stir the mixture at room temperature for 20 hours in a hydrogen atmosphere. After the catalyst was removed by filtration, the filtrate was concentrated under reduced pressure, and the residue was dissolved in N,N-dimethylformamide (36 ml), to which p-nitrophenyl 5-chloroindole-2-carboxylate (2.02 g) was added to stir the mixture for 16 hours. The reaction mixture was concentrated under reduced pressure, and ethyl acetate and water were added to the residue to collect insoluble matter by filtration. The product was washed with ethyl acetate to obtain crude (1R*,2S*)-4-(tert-butoxycarbonylamino)-N¹ (or N²)-[(5-chloroindol-2-yl)carbonyl]-1,2-cyclohexanediamine (Isomer B1) (1.49 g) as a colorless solid. The organic layer of the filtrate was washed with water and dried over anhydrous sodium sulfate. The solvent was distilled off under reduced pressure, and the residue was purified by column chromatography on silica gel (dichloromethane:methanol= 30:1→10:1) to obtain (1R*,2S*)-4-(tert-butoxycarbonylamino)-N² (or N¹)-[(5-chloroindol-2-yl)carbonyl]-1,2-cyclohexanediamine (Isomer B2) (0.37 g) as a brown amorphous solid.

One of the title compounds was obtained from the Isomer B1 and lithium 5-methyl-4,5,6,7-tetrahydrothiazolo[5,4-c]pyridine-2-carboxylate in a similar manner to Example 2.

¹H-NMR (DMSO-d₆) δ: 1.25–1.50(1H,m), 1.37(9H,s), 1.50–1.65(1H,m), 1.75–2.20(4H,m),2.37(3H,s), 2.70–3.00(4H,m), 3.60–3.80(3H,m), 4.13(1H,m), 4.43(1H,m), 6.92(1H,d,J=7.1 Hz), 7.05(1H,s), 7.17(1H,dd,J=8.8, 2.2 Hz), 7.41(1H,d,J=8.8 Hz), 7.69(1H,s), 8.15(1H,d,J=7.8 Hz), 8.37(1H,d,J=7.1 Hz), 11.78(1H,s). MS (FAB) m/z: 587(M+H)⁺.

The other title compound was obtained from the Isomer B2 in the same manner.

¹H-NMR (DMSO-d₆) δ: 1.15–1.30(1H,m), 1.35(9H,s), 1.45–1.60(1H,m), 1.65–1.75(1H,m), 1.85–1.95(1H,m), 2.05–2.20(2H,m), 2.34(3H,s), 2.65–2.85(4H,m), 3.55–3.70(3H,m), 4.09(1H,m),4.40(1H,m), 6.80(1H,d,J=7.3 Hz), 7.15–7.25(2H,m), 7.43(1H,d,J=8.8 Hz), 7.73(1H,d,J=2.0 Hz), 8.05(1H,d,J=6.6 Hz), 8.51(1H,d,J=8.8 Hz), 11.82(1H,s). MS (FAB) m/z: 587(M+H)⁺.

Example 188

(1R*,2S*)-4-Amino-N¹ (or N²)-[(5-chloroindol-2-yl)-carbonyl]-N² (or N¹)-[(5-methyl-4,5,6,7-tetrahydrothiazolo[5,4-c]pyridin-2-yl)carbonyl]-1,2-cyclohexanediamine hydrochloride (Stereoisomer B)

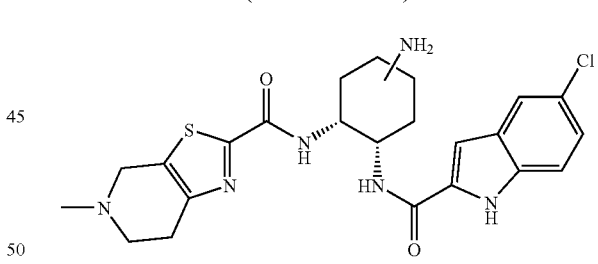

(1R*,2S*)-4-(tert-Butoxycarbonylamino)-N¹ (or N²)-[(5-chloroindol-2-yl)carbonyl]-N² (or N¹)-[(5-methyl-4,5,6,7-tetrahydrothiazolo[5,4-c]pyridin-2-yl)carbonyl]-1,2-cyclohexanediamine (Stereoisomer B) (1.11 g) was suspended in dichloromethane (20 ml), and a saturated ethanol solution (20 ml) of hydrochloric acid was added to stir the mixture at room temperature for 2 hours. The solvent was distilled off under reduced pressure, and the residue was purified by gel filtration (Sephadex LH-20, methanol) to obtain the title compound (1.05 g) as a yellow amorphous solid.

¹H-NMR (DMSO-d₆) δ: 1.55–1.65(1H,m), 1.75–1.90(2H,m), 1.95–2.20(2H,m), 2.20–2.40(1H,m), 2.90(3H,s), 3.10–3.20(1H,m), 3.20–3.50(3H,m), 3.65–3.75(1H,m), 4.10–4.20(1H,m), 4.35–4.50(1H,m), 4.55–4.65(1H,m), 4.65–4.75(1H,m), 7.07(1H,s), 7.17(1H,dd,J=8.8, 2.0 Hz), 7.42(1H,d,J=8.8 Hz), 7.69(1H,s), 8.05–8.30(3H,br), 8.40–8.50(2H,m), 11.70–11.90(2H,m). MS (FAB) m/z: 487 (M+H)⁺.

Example 189

(1R*,2S*)-N$^1$ (or N$^2$)-[(5-Chloroindol-2-yl)carbonyl]-4-methanesulfonylamino-N$^2$ (or N$^1$)-[(5-methyl-4,5,6,7-tetrahydrothiazolo[5,4-c]pyridin-2-yl)carbonyl]-1,2-cyclohexanediamine (Stereoisomer B)

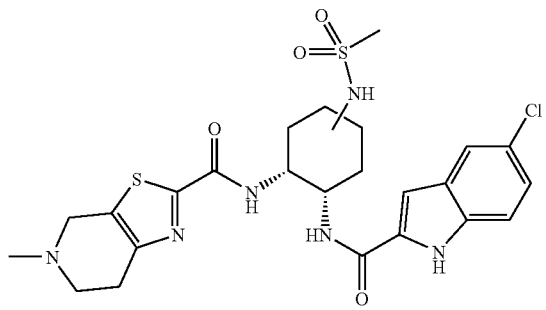

(1R*,2S*)-4-Amino-N$^1$ (or N$^2$)-[(5-chloroindol-2-yl)carbonyl]-N$^2$ (or N$^1$)-[(5-methyl-4,5,6,7-tetrahydrothiazolo[5,4-c]pyridin-2-yl)carbonyl]-1,2-cyclohexanediamine hydrochloride (Stereoisomer B) (0.20 g) was suspended in dichloromethane (7 ml), and triethylamine (0.16 ml) and methanesulfonyl chloride (28 μl) were added to stir the mixture at room temperature for 20 hours. After the reaction mixture was diluted with dichloromethane, it was washed with an aqueous solution of sodium hydroxide and dried over anhydrous sodium sulfate. The solvent was distilled off under reduced pressure, and the residue was purified by column chromatography on silica gel (dichloromethane:methanol=30:1→15:1) to obtain the title compound (67.9 mg) as a colorless amorphous solid.

$^1$H-NMR (DMSO-d$_6$) δ: 1.40–1.55(1H,m), 1.65–1.85 (2H,m), 1.90–2.05(2H,m), 2.15–2.25(1H,m), 2.41(3H,s), 2.75–2.95(4H,m), 2.92(3H,s), 3.55–3.80(3H,m), 4.10–4.20 (1H,m), 4.45–4.55(1H,m), 7.08(1H,s), 7.15–7.20(2H,m), 7.41(1H,d,J=8.8 Hz), 7.69(1H,s), 8.27(1H,d,J=7.3 Hz), 8.33 (1H,d,J=8.1 Hz), 11.77(1H,s). MS (FAB) m/z: 565[(M+H)⁺.

Example 190

(1R*,2S*)-4-Acetylamino-N$^1$ (or N$^2$)-[(5-chloroindol-2-yl)carbonyl]-N$^2$ (or N$^1$)-[(5-methyl-4,5,6,7-tetrahydrothiazolo[5,4-c]pyridin-2-yl)carbonyl]-1,2-cyclohexanediamine (Stereoisomer B)

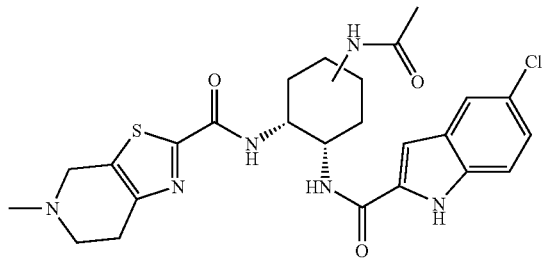

(1R*,2S*)-4-Amino-N$^1$ (or N$^2$)-[(5-chloroindol-2-yl)carbonyl]-N$^2$ (or N$^1$)-[(5-methyl-4,5,6,7-tetrahydrothiazolo[5,4-c]pyridin-2-yl)carbonyl]-1,2-cyclohexanediamine hydrochloride (Stereoisomer B) (0.20 g) was suspended in dichloromethane (7 ml), and triethylamine (0.16 ml) and acetic anhydride (34 μl) were added to stir the mixture at room temperature for 20 hours. Dichloromethane and an aqueous solution of sodium hydroxide were added to the reaction mixture to separate insoluble matter by filtration. The organic layer of the filtrate was separated and dried over anhydrous sodium sulfate, and the solvent was then distilled off under reduced pressure. The residue was purified by column chromatography on silica gel (dichloromethane:methanol=15:1→10:1) to obtain the title compound (0.12 g) as a colorless solid.

$^1$H-NMR (DMSO-d$_6$) δ: 1.35–1.50(1H,m), 1.55–1.70 (1H,m), 1.80(3H,s), 1.80–2.05(3H,m), 2.05–2.20(1H,m), 2.47(3H,s), 2.80–3.00(4H,m), 3.75–4.00(3H,m), 4.15–4.30 (1H,m), 4.45–4.55(1H,m), 7.07(1H,s), 7.17(1H,dd,J=8.8, 1.0 Hz), 7.41(1H,d,J=8.8 Hz), 7.69(1H,s), 7.89(1H,d,J=7.3 Hz), 8.24(1H,d,J=8.1 Hz), 8.31(1H,d,J=7.3 Hz), 11.77(1H, s). MS (FAB) m/z: 528(M+H)⁺.

Example 191

(1S,2R,4S)-N$^1$-[(5-Chloroindol-2-yl)carbonyl]-4-(N-methoxy-N-methylcarbamoyl)-N$^2$-[(5-methyl-4,5,6,7-tetrahydrothiazolo[5,4-c]pyridin-2-yl)carbonyl]-1,2-cyclohexanediamine hydrochloride

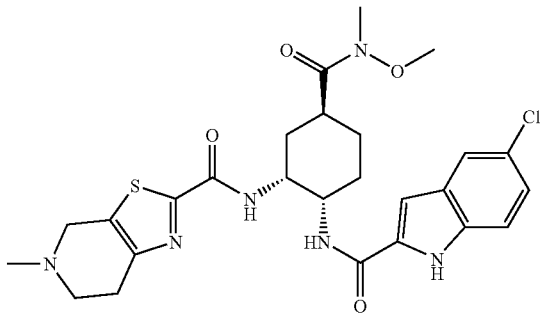

(1S,2R,4S)-4-Carboxy-N-$^1$-[(5-chloroindol-2-yl)-carbonyl]-N$^2$-[(5-methyl-4,5,6,7-tetrahydrothiazolo-[5,4-c]pyridin-2-yl)carbonyl]-1,2-cyclohexanediamine (250 mg) was dissolved in N,N-dimethylformamide (5 ml), and N,O-dimethylhydroxylamine hydrochloride (142 mg), 1-(3-dimethylaminopropyl)-3-ethylcarbodiimide hydrochloride (111 mg), 1-hydroxybenzotriazole monohydrate (89 mg) and N-methylmorpholine (213 ml) were added to stir the mixture at room temperature for 19 hours. After the reaction mixture was concentrated, an aqueous solution of sodium hydrogencarbonate was added to the residue to conduct extraction with ethyl acetate. After the resultant organic layer was washed with saturated saline and dried over anhydrous sodium sulfate, the solvent was distilled off under reduced pressure. The residue was purified by column chromatography on silica gel (dichloromethane:methanol= 47:3→23:2) to obtain a colorless amorphous solid (179 mg). This prodcut was dissolved in methanol-tetrahydrofuran, and 1N ethanol solution (960 ml) of hydrochloric acid was added to obtain the title compound.

$^1$H-NMR (DMSO-d$_6$) δ: 1.57–1.91(4H,m), 1.96–2.00 (1H,m), 2.10–2.21(1H,m), 2.92(3H,s), 2.93–3.03(2H,m), 3.08(3H,s), 3.10–3.28(2H,m), 4.16–4.19(1H,m), 4.50–4.52 (1H,m), 4.69(1H,br.s), 7.06(s,1H), 7.17(1H,dd,J=1.5, 8.8 Hz), 7.42(1H,d,J=8.8 Hz), 7.70(1H,s), 8.33(1H,br.s), 8.41 (1H,d,J=7.8 Hz), 11.81(1H,br.s). MS (ESI) m/z: 559(M+H)⁺.

Example 192

(1S,2R,4S)-N$^1$-[(5-Chloroindol-2-yl)carbonyl]-4-(N$^2$,N$^2$-dimethylcarbamoyl)-N$^2$-[(5-methyl-4,5,6,7-tetrahydrothiazolo[5,4-c]pyridin-2-yl)carbonyl]-1,2-cyclohexanediamine hydrochloride

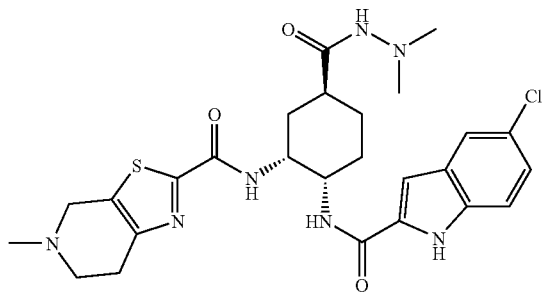

The title compound was obtained from (1S,2R,4S)-4-carboxy-N$^1$-[(5-chloroindol-2-yl)-carbonyl]-N$^2$-[(5-methyl-4,5,6,7-tetrahydrothiazolo-[5,4-c]pyridin-2-yl)carbonyl]-1,2-cyclohexanediamine and N,N-dimethylhydrazine in a similar manner to Example 134.

$^1$H-NMR (DMSO-d$_6$) δ: 1.49–1.54(1H,m), 1.76–1.81 (2H,m), 1.89–1.93(2H,m), 2.07–2.17(1H,m), 2.33–3.60 (14H,m), 4.15–4.19(1H,m), 4.40–4.47(2H,m), 4.70–4.72 (1H,m), 7.04(1H,s), 7.17(1H,dd,J=2.0, 8.5 Hz), 7.42(1H,d, J=8.5 Hz), 7.70(1H,s), 8.17–8.22(1H,m), 8.41–8.43(1H,m), 11.80(1H,br.s). MS (ESI) m/z: 558(M+H)$^+$.

Example 193

(1S,2R,4S)-N$^1$-[(6-Chloroquinolin-2-yl)carbonyl]-4-(N,N-dimethylcarbamoyl)-N$^2$-[(5-methyl-4,5,6,7-tetrahydrothiazolo[5,4-c]pyridin-2-yl)carbonyl]-1,2-cyclohexanediamine hydrochloride

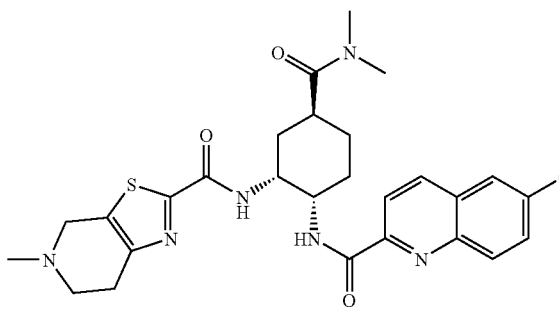

(1S,2R,4S)-N$^2$-(tert-Butoxycarbonyl)-N$^1$-[(6-chloroquinolin-2-yl)carbonyl]-4-(N,N-dimethylcarbamoyl)-1,2-cyclohexanediamine was treated with a saturated ethanol solution of hydrochloric acid and then condensed with lithium 5-methyl-4,5,6,7-tetrahydrothiazolo[5,4-c]pyridine-2-carboxylate in a similar manner to Example 118 to obtain the title compound.

$^1$H-NMR (DMSO-d$_6$) δ: 1.45–1.60(1H,m), 1.75–1.90 (3H,m), 1.90–2.00(1H,m), 2.00–2.20(1H,m), 2.80(3H,s), 2.90(3H,s), 2.99(3H,s), 3.10–3.30(5H,m), 3.56(1H,br), 4.10–4.20(1H,m), 4.40–4.70(2H,m), 7.88(2H,s), 8.15(1H,d, J=8.6 Hz), 8.22(1H,s), 8.52(1H,d,J=8.6 Hz), 8.72(1H,d,J= 8.3 Hz), 8.89(1H,d,J=8.3 Hz). MS (FAB) m/z: 555(M+H)$^+$.

Example 194

(1S,2R,4S)-N$^1$-[(5-Chloro-4-fluoroindol-2-yl)carbonyl]-4-(N,N-dimethylcarbamoyl)-N$^2$-[(5-methyl-4,5,6,7-tetrahydrothiazolo[5,4-c]pyridin-2-yl)carbonyl]-1,2-cyclohexanediamine hydrochloride

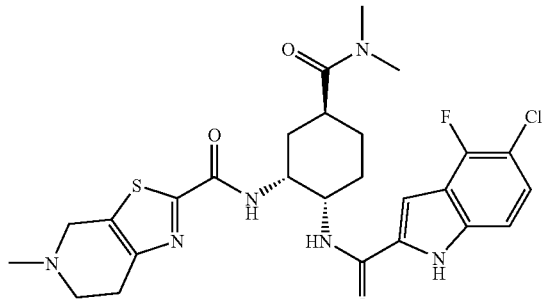

1) (1S,2R,4S)-N$^2$-(tert-Butoxycarbonyl)-N$^1$-[(6-chloro-4-fluoroindol-2-yl)carbonyl]-4-(N,N-dimethylcarbamoyl)-1,2-cyclohexanediamine was obtained from (1S,2R,4S)-N$^2$-(tert-butoxycarbonyl)-4-(N,N-dimethylcarbamoyl)-1,2-cyclohexanediamine and 5-chloroindole-2-carboxylic acid in a similar manner to Referential Example 159.

2) (1S,2R,4S)-N$^2$-(tert-Butoxycarbonyl)-N$^1$-[(6-chloro-4-fluoroindol-2-yl)carbonyl]-4-(N,N-dimethylcarbamoyl)-1,2-cyclohexanediamine was treated with a 4N dioxane solution of hydrochloric acid and then condensed with lithium 5-methyl-4,5,6,7-tetrahydrothiazolo[5,4-c]pyridine-2-carboxylate in a similar manner to Example 118 to obtain the title compound.

$^1$H-NMR (DMSO-d$_6$) δ: 1.24–1.98(6H,m), 2.33–3.33 (6H,m), 2.81(3H,s), 2.90(3H,s), 2.99(3H,s), 4.12(1H,br.s), 4.30–4.70(1H,m), 4.60(1H,br.s), 7.21(1H,s), 7.27(2H,br.s), 8.37(1H,d,J=8.1 Hz), 8.43(1H,d,J=7.6 Hz), 12.11(1H,s). MS (FAB) m/z: 561(M+H)$^+$.

Example 195

(1S,2R,4S)-N$^1$-[(7-Chloroisoquinolin-3-yl)carbonyl]-4-(N,N-dimethylcarbamoyl)-N$^2$-[(5-methyl-4,5,6,7-tetrahydrothiazolo[5,4-c]pyridin-2-yl)carbonyl]-1,2-cyclohexanediamine hydrochloride

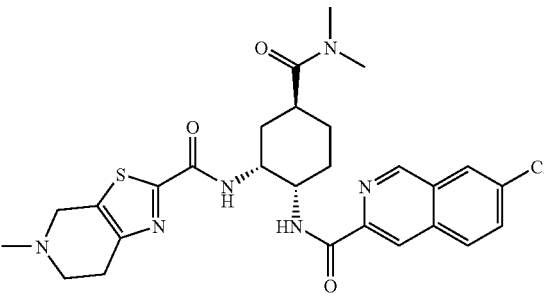

(1S,2R,4S)-N$^2$-(tert-Butoxycarbonyl)-N$^1$-[(7-chloroisoquinolin-3-yl)carbonyl]-4-(N,N-dimethylcarbamoyl)-1,2-cyclohexanediamine was treated with a saturated ethanol solution of hydrochloric acid and then condensed with lithium 5-methyl-4,5,6,7-tetrahydrothiazolo[5,4-c]pyridine-2-carboxylate in a similar manner to Example 118 to obtain the title compound.

$^1$H-NMR (DMSO-d$_6$) δ: 1.45–1.65(1H,m), 1.70–1.85 (3H,m), 1.95–2.10(1H,m), 2.10–2.20(1H,m), 2.80(3H,s), 2.92(3H,s), 2.96(3H,s), 2.95–3.10(1H,m), 3.10–3.40(3H,m), 3.70–3.80(1H,m), 4.20–4.30(1H,m), 4.40–4.60(2H,m), 4.65–4.80(1H,m), 7.89(1H,m), 8.26(1H,d,J=8.8 Hz), 8.38 (1H,s), 8.60(1H,s), 8.85–9.00(2H,m), 9.33(1H,m). MS (FAB) m/z: 555(M+H)$^+$.

Test Example 1

Determination of FXa-Inhibiting Effect (IC$_{50}$ Value)

Each specimen solution (10 μl), 100 mM Tris.200 mM sodium chloride.0.2% BSA (pH 7.4) buffer (40 μl) and 0.05 U/ml human FXa (Cosmobio ERL HFXa-1011, dissolved and diluted with buffer for measurement) (10 μl) were put on a 96-well microplate, and 750 μM S2222 (Chromogenix Co.) (40 ml) was added to determine an increase (mOD/min) in absorbance at 405 nm at room temperature. The percent inhibition of each specimen was found in accordance with the following equation. The final concentration of the specimen and the percent inhibition thereof were plotted on the axis of abscissa and the axis of ordinate of logarithmic normal probability paper, respectively, to determine the median inhibition dose (IC$_{50}$).

Percent inhibition (%)=[1−(OD of specimen)÷(OD of control)]×100

<Result>

In the following table, it is demonstrated that the compounds according to the present invention have a strong FXa-inhibiting effect.

| Compound | FXa-inhibiting effect (IC$_{50}$) |
| --- | --- |
| Example 3 | 86 nM |
| Example 8 | 16 nM |
| Example 10 | 83 nM |
| Example 15 | 92 nM |
| Example 41 | 36 nM |
| Example 68 | 4.1 nM |
| Example 70 | 2.7 nM |
| Example 124 | 4.2 nM |
| Example 143 | 3.5 nM |
| Example 144 | 2.5 nM |
| Example 167 | 1.4 nM |
| Example 176 | 3.3 nM |

INDUSTRIAL APPLICABILITY

The ethylenediamine derivatives according to the present invention exhibit a strong inhibitory effect on activated blood coagulation factor X and are useful as agents for preventing and/or treating thrombotic diseases.

What is claimed is:

1. A compound represented by the general formula (1):

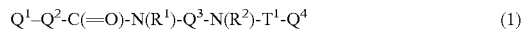

wherein

R$^1$ and R$^2$, independently of each other, represent a hydrogen atom, hydroxyl group, alkyl group or alkoxy group;

Q$^1$ represents a thienopyridyl group which may be substituted, tetrahydrothienopyridyl group which may be substituted, thiazolopyridyl group which may be substituted, tetrahydrothiazolopyridyl group which may be substituted, thiazolopyridazinyl group which may be substituted, tetrahydrothiazolopyridazinyl group which may be substituted, pyranothiazolyl group which may be substituted, dihydropyranothiazolyl group which may be substituted, furopyridyl group which may be substituted, tetrahydrofuropyridyl group which may be substituted, oxazolopyridyl group which may be substituted, tetrahydrooxazolopyridyl group which may be substituted, pyrrolopyridyl group which may be substituted, dihydropyrrolopyridyl group which may be substituted, tetrahydropyrrolopyridyl group which may be substituted, pyrrolopyrimidinyl group which may be substituted, dihydropyrrolopyrimidinyl group which may be substituted, oxazolopyridazinyl group which may be substituted, tetrahydrooxazolopyridazinyl group which may be substituted, pyrrolothiazolyl group which maybe substituted, dihydropyrrolothiazolyl group which may be substituted, pyrrolooxazolyl group which may be substituted, dihydropyrrolooxazolyl group which may be substituted, benzothiazolyl group which may be substituted, tetrahydrobenzothiazolyl group which may be substituted, 4,5,6,7-tetrahydro-5,6-tetramethylenethiazolopyridazinyl group which may be substituted, or 5,6-trimethylene-4,5,6,7-tetrahydrothiazolopyridazinyl group which may be substituted;

Q$^2$ represents a single bond;

Q$^3$ represents

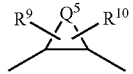

in which Q$^5$ represents an alkylene group having 1 to 8 carbon atoms or an alkenylene group having 2 to 8 carbon atoms, and R$^9$ is a hydrogen atom, and R$^{10}$ is a hydrogen atom, hydroxyl group, alkyl group, halogen atom, hydroxyimino group, N-alkylaminoalkyl group, N,N-dialkylaminoalkyl group, acyl group, acylamino group which may be substituted, acylaminoalkyl group, alkoxy group, alkoxyalkyl group, hydroxyalkyl group, carboxyl group, alkoxycarbonyl group, alkoxycarbonylalkyl group, alkoxycarbonylamino group, carbamoyl group, N-alkylcarbamoyl group which may have a substituent on the alkyl group, N,N-dialkylcarbamoyl group which may have a substituent on the alkyl group, N-alkenylcarbamoyl group, N-alkenylcarbamoylalkyl group, N-alkenyl-N-alkylcarbamoyl group, N-alkenyl-N-alkylcarbamoylalkyl group, N-alkoxycarbamoyl group, N-alkyl-N-alkoxycarbamoyl group, N-alkyl-N-alkoxy-carbamoylalkyl group, carbazoyl group which may be substituted by 1 to 3 alkyl groups, alkylsulfonyl group, alkylsulfonylalkyl group, 3- to 6-membered nitrogen-containing heterocyclic carbonyl group which may be substituted, 3- to 6-membered nitrogen-containing heterocyclic carbonyloxyalkyl group which may be substituted, carbamoylalkyl group, N,N-dialkylcarbamoyloxyalkyl group, N-alkylcarbamoylalkyl group which may have a substituent on the alkyl group, N,N-dialkylcarbamoylalkyl group which may have a substituent on the alkyl groups, alkylsulfonylamino group, alkylsulfonylaminoalkyl group, oxo group or acyloxy group;

Q⁴ represents any one of the following groups:

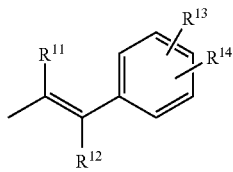

wherein R¹¹ and R¹², independently of each other, represent a hydrogen atom, cyano group, halogen atom, alkyl group, hydroxyalkyl group, alkoxy group, alkoxyalkyl group, carboxyl group, carboxyalkyl group, acyl group, alkoxycarbonyl group, alkoxycarbonylalkyl group, or phenyl group which may be substituted by a cyano group, hydroxyl group, halogen atom, alkyl group or alkoxy group; and R¹³ and R¹⁴, independently of each other, represent a hydrogen atom, hydroxyl group, nitro group, cyano group, halogen atom, alkyl group, alkenyl group, alkynyl group, halogenoalkyl group, hydroxyalkyl group, alkoxy group, alkoxyalkyl group, carboxyl group, carboxyalkyl group, carbamoyl group, alkoxycarbonyl group, amidino group or alkoxycarbonylalkyl group;

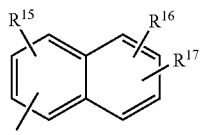

wherein R¹⁵, R¹⁶ and R¹⁷, independently of one another, represent a hydrogen atom, hydroxyl group, nitro group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, alkoxycarbonyl group, amidino group or alkoxycarbonylalkyl group;

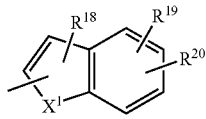

wherein X¹ represents CH₂, CH, NH, NOH, N, O or S; and

R¹⁸, R¹⁹ and R²⁰, independently of one another, represent a hydrogen atom, hydroxyl group, nitro group, a cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, alkoxycarbonyl group, amidino group or alkoxycarbonylalkyl group;

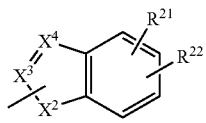

wherein X² represents NH, N, O or S;
X³ represents N, C or CH;
X⁴ represents N, C or CH; and
R²¹ and R²², independently of each other, represent a hydrogen atom, hydroxyl group, nitro group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, alkoxycarbonyl group, amidino group or alkoxycarbonylalkyl group; and

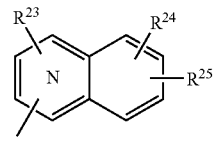

wherein N indicates that any one of carbon atoms of the ring substituted by R²³ has been substituted by a nitrogen atom; and R²³, R²⁴ and R²⁵, independently of one another, represent a hydrogen atom, hydroxyl group, nitro group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, alkoxycarbonyl group, amidino group or alkoxycarbonylalkyl group; and T¹ represents a carbonyl group, or a salt thereof, a solvate thereof, or an N-oxide thereof.

2. The compound, the salt thereof, the solvate thereof, or the N-oxide thereof according to claim 1, wherein the group Q⁴ in the formula (1) is

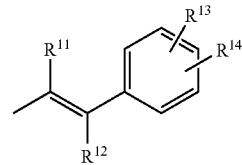

wherein R¹¹, R¹² and R¹³ are all hydrogen atoms, and R¹⁴ is a halogen atom or ethynyl group;

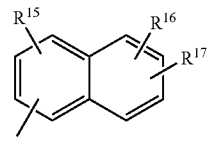

wherein R¹⁵ is a hydrogen atom and R¹⁶ is a hydrogen atom or a hydroxyl group, and R¹⁷ is a halogen atom or ethynyl group;

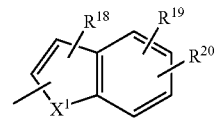

wherein X¹ is NH, NOH, N, O or S, R¹⁸ is a hydrogen atom, R¹⁹ is a hydrogen or halogen atom, and R²⁰ is a halogen atom, alkyl or ethynyl group;

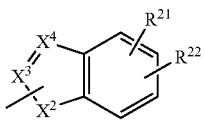

wherein $X^2$ is NH, O or S, $X^3$ is N, C or CH, $X^4$ is N, C or CH, $R^{21}$ is a hydrogen atom, and $R^{22}$ is a halogen atom or ethynyl group; or

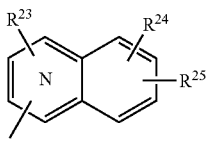

wherein N indicates that any one of carbon atoms of the ring substituted by $R^{23}$ has been substituted by a nitrogen atom, and $R^{23}$ and $R^{24}$ are both hydrogen atoms, and $R^{25}$ is a cyano group, halogen atom, alkyl group, alkenyl group, alkynyl group or halogenoalkyl group.

3. The compound, the salt thereof, the solvate thereof, or the N-oxide thereof according to claim 1, wherein the group $Q^4$ in the formula (1) is a 4-chlorostyryl, 4-fluorostyryl, 4-bromostyryl, 4-ethynylstyryl, 6-chloro-2-naphthyl, 6-fluoro-2-naphthyl, 6-bromo-2-naphthyl, 6-ethynyl-2-naphthyl, 7-chloro-2-naphthyl, 7-fluoro-2-naphthyl, 7-bromo-2-naphthyl, 7-ethynyl-2-naphthyl, 5-chloroindol-2-yl, 5-fluoroindol-2-yl, 5-bromoindol-2-yl, 5-ethynylindol-2-yl, 5-methylindol-2-yl, 5-chloro-4-fluoroindol-2-yl, 6-chloroindol-2-yl, 6-fluoroindol-2-yl, 6-bromoindol-2-yl, 6-ethynylindol-2-yl, 6-methylindol-2-yl, 5-chlorobenzothiophen-2-yl, 5-fluorobenzothiophen-2-yl, 5-bromobenzothiophen-2-yl, 5-ethynylbenzothiophen-2-yl, 5-methylbenzothiophen-2-yl, 5-chloro-4-fluoro-benzothiophen-2-yl, 6-chlorobenzothiophen-2-yl, 6-fluorobenzothiophen-2-yl, 6-bromobenzothiophen-2-yl, 6-ethynylbenzothiophen-2-yl, 6-methylbenzothiophen-2-yl, 5-chlorobenzofuran-2-yl, 5- fluorobenzofuran-2-yl, 5-bromobenzofuran-2-yl, 5-ethynylbenzofuran-2-yl, 5-methylbenzofuran-2-yl, 5-chloro-4-fluorobenzofuran-2-yl, 6-chlorobenzofuran-2-yl, 6-fluorobenzofuran-2-yl,6-bromobenzofuran-2-yl, 6-ethynylbenzofuran-2-yl, 6-methylbenzofuran-2-yl, 6-chloroquinolin-2-yl, 6-fluoroquinolin-2-yl, 6-bromoquinolin-2-yl, 6-ethynylquinolin-2-yl, 7-chloroquinolin-3-yl, 7-fluoroquinolin-3-yl, 7-bromoquinolin-3-yl, 7-ethynylquinolin-3-yl, 7-chloroisoquinolin-3-yl, 7-fluoroisoquinolin-3-yl, 7-bromoisquinolin-3-yl or 7-ethynylisoquinolin-3-yl group.

4. The compound, the salt thereof, the solvate thereof, or the N-oxide thereof according to claim 2, wherein the group $Q^4$ in the formula (1) is a 4-chlorostyryl, 4-fluorostyryl, 4-bromostyryl, 4-ethynylstyryl, 6-chloro-2-naphthyl, 6-fluoro-2-naphthyl, 6-bromo-2-naphthyl, 6-ethynyl-2-naphthyl, 7-chloro-2-naphthyl, 7-fluoro-2-naphthyl, 7-bromo-2-naphthyl, 7-ethynyl-2-naphthyl, 5-chloroindol-2-yl, 5-fluoroindol-2-yl, 5-bromoindol-2-yl, 5-ethynylindol-2-yl, 5-methylindol-2-yl, 5-chloro-4-fluoroindol-2-yl, 6-chloroindol-2-yl, 6-fluoroindol-2-yl, 6-bromoindol-2-yl, 6-ethynylindol-2-yl, 6-methylindol-2-yl, 5-chlorobenzothiophen-2-yl, 5-fluorobenzothiophen-2-yl, 5-bromobenzothiophen-2-yl, 5-ethynylbenzothiophen-2-yl, 5-methylbenzothiophen-2-yl, 5-chloro-4-fluoro-benzothiophen-2-yl, 6-chlorobenzothiophen-2-yl, 6-fluorobenzothiophen-2-yl, 6-bromobenzothiophen-2-yl, 6-ethynylbenzothiophen-2-yl, 6-methylbenzothiophen-2-yl, 5-chlorobenzofuran-2-yl, 5-fluorobenzofuran-2-yl, 5-bromobenzofuran-2-yl, 5-ethynylbenzofuran-2-yl, 5-methylbenzofuran-2-yl, 5-chloro-4-fluorobenzofuran-2-yl, 6-chlorobenzofuran-2-yl, 6-fluorobenzofuran-2-yl, 6-bromobenzofuran-2-yl, 6-ethynylbenzofuran-2-yl, 6-methylbenzofuran-2-yl, 6-chloroquinolin-2-yl, 6-fluoroquinolin-2-yl, 6-bromoquinolin-2-yl, 6-ethynylquinolin-2-yl, 7-chloroquinolin-3-yl, 7-fluoroquinolin-3-yl, 7-bromoquinolin-3-yl, 7-ethynylquinolin-3-yl, 7-chloroisoquinolin-3-yl, 7-fluoroisoquinolin-3-yl, 7-bromoisoquinolin-3-yl or 7-ethynylisoquinolin-3-yl group.

5. The compound, the salt thereof, the solvate thereof, or the N-oxide thereof according to claim 1, wherein the group $Q^3$ in the formula (1) is

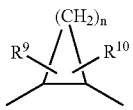

wherein n is an integer of 1 to 8.

6. The compound, the salt thereof, the solvate thereof, or the N-oxide thereof according to claim 2, wherein the group $Q^3$ in the formula (1) is

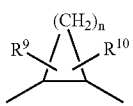

wherein n is an integer of 1 to 8.

7. The compound, the salt thereof, the solvate thereof, or the N-oxide thereof according to claim 3 wherein group $Q^3$ formula (1) is

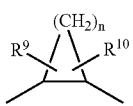

wherein n is an integer of 1 to 8.

8. The compound, the salt thereof, the solvate thereof, or the N-oxide thereof according to claim 4, wherein the group $Q^3$ in the formula (1) is

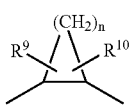

wherein n is an integer of 1 to 8.

9. The compound, the salt thereof, the solvate thereof, or the N-oxide thereof according to claim 1, wherein $R^1$ and $R^2$, independently of each other, represent a hydrogen atom or an alkyl group.

10. The compound, the salt thereof, the solvate thereof, or the N-oxide thereof according to claim 1, wherein $R^1$ and $R^2$ each represent a hydrogen atom.

11. The compound, the salt thereof, the solvate thereof, or the N-oxide thereof according to claim 1, wherein $Q^4$ represents:

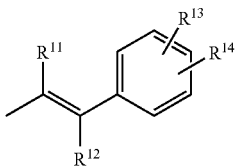

wherein $R^{11}$, $R^{12}$, $R^{13}$ and $R^{14}$ are as defined in claim 1.

12. The compound, the salt thereof, the solvate thereof, or the N-oxide thereof according to claim 1, wherein $Q^4$ represents:

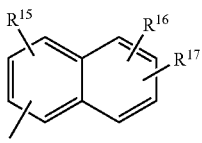

wherein $R^{15}$, $R^{16}$ and $R^{17}$ are as defined in claim 1.

13. The compound, the salt thereof, the solvate thereof, or the N-oxide thereof according to claim 1, wherein $Q^4$ represents:

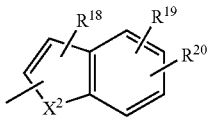

wherein $X^1$, $R^{18}$, $R^{19}$ and $R^{20}$ are as defined in claim 1.

14. The compound, the salt thereof, the solvate thereof, or the N-oxide thereof according to claim 1, wherein $Q^4$ represents:

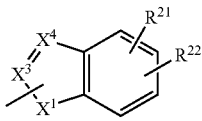

wherein $X^2$, $X^3$, $X^4$, $R^{21}$ and $R^{22}$ are as defined in claim 1.

15. The compound, the salt thereof, the solvate thereof, or the N-oxide thereof according to claim 1, wherein $Q^4$ represents:

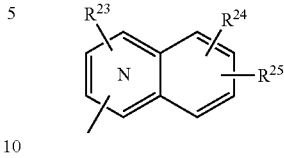

wherein N, $R^{23}$, $R^{24}$ and $R^{25}$ are as defined in claim 1.

16. The compound, the salt thereof, the solvate thereof, or the N-oxide thereof according to claim 1, which is said salt thereof.

17. The compound, the salt thereof, the solvate thereof, or the N-oxide thereof according to claim 1, which is said solvate thereof.

18. The compound, the salt thereof, the solvate thereof, or the N-oxide thereof according to claim 1, which is said N-oxide thereof.

19. A method for treating thrombosis or embolism, which comprises administering the compound, the salt thereof, the solvate thereof, or the N-oxide thereof according to claim 1.

20. The compound, the salt thereof, the solvate thereof, or the N-oxide thereof according to claim 1, wherein the substituents for the $Q^1$ group are selected from the group consisting of a hydroxyl group, halogen atoms, halogenomethyl groups having 1 to 3 halogen substituents, an amino group, a cyano group, an amidino group, a hydroxyamidino group, linear, branched or cyclic alkyl groups having 1 to 6 carbon atoms, hydroxy-$C_1$–$C_6$ alkyl groups, $C_1$–$C_6$ alkoxy groups, $C_2$–$C_6$ alkoxycarbonyl-$C_1$–$C_6$ alkyl groups, amidino groups substituted by a $C_2$–$C_6$ alkoxycarbonyl group, $C_2$–$C_6$ alkenyl groups, $C_2$–$C_6$ alkynyl groups, $C_2$–$C_6$ alkoxycarbonyl groups, amino $C_1$–$C_6$ alkyl groups, $C_1$–$C_6$ alkylamino-$C_1$–$C_6$ alkyl groups, $C_1$–$C_6$ dialkylamino $C_1$–$C_6$ alkyl groups, $C_2$–$C_6$ alkoxycarbonylamino-$C_1$–$C_6$ alkyl groups, $C_1$–$C_6$ alkanoyl groups, $C_1$–$C_6$ alkanoylamino-$C_1$–$C_6$ alkyl groups, $C_1$–$C_6$ alkylsulfonyl groups, $C_1$–$C_6$ alkylsulfonylamino-$C_1$–$C_6$ alkyl groups, a carbamoyl group; $C_1$–$C_6$ alkylcarbamoyl groups, N,N-di($C_1$–$C_6$ alkyl) carbamoyl groups, $C_1$–$C_6$ alkylamino groups, $C_1$–$C_6$ dialklamino groups, 5- or 6-membered heterocyclic groups containing one of nitrogen, oxygen and sulfur or the same or different two atoms thereof, and groups composed of a 5- or 6-membered heterocyclic groups containing one of nitrogen, oxygen and sulfur or the same or different two atoms thereof and a $C_1$–$C_4$ alkyl group.

* * * * *

UNITED STATES PATENT AND TRADEMARK OFFICE
CERTIFICATE OF CORRECTION

PATENT NO. : 7,192,968 B2  
APPLICATION NO. : 10/240725  
DATED : March 20, 2007  
INVENTOR(S) : Toshiharu Yoshino et al.

Page 1 of 1

It is certified that error appears in the above-identified patent and that said Letters Patent is hereby corrected as shown below:

<u>Column 274, Lines 32-33</u>:
"$C_1$-$C_6$ alkoxy groups, $C_2$-$C_6$ alkoxycarbonyl- $C_1$-$C_6$ alkyl groups" should read -- $C_1$-$C_6$ alkoxy-$C_1$-$C_6$ alkyl groups, a carboxyl group, $C_2$-$C_6$ carboxalkyl groups--.

Signed and Sealed this

Nineteenth Day of June, 2007

JON W. DUDAS  
*Director of the United States Patent and Trademark Office*